(12) United States Patent
Lewis et al.

(10) Patent No.: US 11,173,145 B2
(45) Date of Patent: *Nov. 16, 2021

(54) COMPOUNDS USEFUL AS INHIBITORS OF INDOLEAMINE 2,3-DIOXYGENASE AND/OR TRYPTOPHAN DIOXYGENASE

(71) Applicant: Board of Regents, The University of Texas System, Austin, TX (US)

(72) Inventors: Richard T. Lewis, Missouri City, TX (US); Matthew Hamilton, Missouri City, TX (US); Philip Jones, Houston, TX (US); Alessia Petrocchi, Houston, TX (US); Naphtali Reyna, Arlington, TX (US); Jason Cross, Pearland, TX (US); Michelle Han, Houston, TX (US); Michael Soth, Sugar Land, TX (US); Timothy McAfoos, Pearland, TX (US); Martin Tremblay, Waltham, MA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/478,076

(22) PCT Filed: Jan. 16, 2018

(86) PCT No.: PCT/US2018/013914
§ 371 (c)(1),
(2) Date: Jul. 15, 2019

(87) PCT Pub. No.: WO2018/136437
PCT Pub. Date: Jul. 26, 2018

(65) Prior Publication Data
US 2019/0365718 A1    Dec. 5, 2019

Related U.S. Application Data

(60) Provisional application No. 62/528,366, filed on Jul. 3, 2017, provisional application No. 62/458,777, filed (Continued)

(51) Int. Cl.
| | |
|---|---|
| C07D 231/14 | (2006.01) |
| A61K 31/4192 | (2006.01) |
| A61P 35/00 | (2006.01) |
| A61K 31/166 | (2006.01) |
| A61K 31/18 | (2006.01) |
| A61K 31/351 | (2006.01) |
| A61K 31/4015 | (2006.01) |
| A61K 31/4184 | (2006.01) |
| A61K 31/4196 | (2006.01) |
| A61K 31/421 | (2006.01) |
| A61K 31/4245 | (2006.01) |

(Continued)

(52) U.S. Cl.
CPC ........ *A61K 31/4192* (2013.01); *A61K 31/166* (2013.01); *A61K 31/18* (2013.01); *A61K 31/351* (2013.01); *A61K 31/4015* (2013.01); *A61K 31/4184* (2013.01); *A61K 31/4196* (2013.01); *A61K 31/421* (2013.01); *A61K 31/4245* (2013.01); *A61K 31/437* (2013.01); *A61K 31/4402* (2013.01); *A61K 31/47* (2013.01); *A61K 31/4706* (2013.01); *A61K 31/4965* (2013.01); *A61K 31/50* (2013.01); *A61K 31/502* (2013.01); *A61K 31/517* (2013.01); *A61K 31/5375* (2013.01); *A61P 35/00* (2018.01); *C07C 231/14* (2013.01); *C07C 307/02* (2013.01); *C07D 209/38* (2013.01); *C07D 215/42* (2013.01); *C07D 235/08* (2013.01); *C07D 237/24* (2013.01); *C07D 237/28* (2013.01); *C07D 239/88* (2013.01); *C07D 241/24* (2013.01); *C07D 249/04* (2013.01); *C07D 249/08* (2013.01); *C07D 263/22* (2013.01); *C07D 295/195* (2013.01); *C07D 309/12* (2013.01); *C07D 401/04* (2013.01); *C07D 401/12* (2013.01); *C07D 403/04* (2013.01); *C07D 403/06* (2013.01); *C07D 413/12* (2013.01); *C07D 471/04* (2013.01)

(58) Field of Classification Search
CPC .................................................. C07D 215/233
See application file for complete search history.

(56) References Cited

U.S. PATENT DOCUMENTS

| | | | |
|---|---|---|---|
| 4,177,280 A | 12/1979 | Berkoz | |
| 5,705,511 A | 1/1998 | Hudkins | |

(Continued)

FOREIGN PATENT DOCUMENTS

| | | |
|---|---|---|
| CN | 102532144 | 7/2012 |
| WO | 2000018770 | 4/2000 |

(Continued)

OTHER PUBLICATIONS

McMahon et al. (2000).*

(Continued)

*Primary Examiner* — Paul V Ward
(74) *Attorney, Agent, or Firm* — Dennis A. Bennett; Lauren L. Stevens; Cynthia Hathaway

(57) ABSTRACT

Compounds of formula (VII), which are useful as inhibitors of indoleamine 2,3-dioxygenase and/or tryptophan dioxygenase, are provided. Also provided are pharmaceutical compositions, kits comprising said compounds, and methods and uses pertaining to said compounds.

27 Claims, No Drawings

Related U.S. Application Data on Feb. 14, 2017, provisional application No. 62/447,368, filed on Jan. 17, 2017.

(51) Int. Cl.

| | |
|---|---|
| *A61K 31/437* | (2006.01) |
| *A61K 31/4402* | (2006.01) |
| *A61K 31/47* | (2006.01) |
| *A61K 31/4706* | (2006.01) |
| *A61K 31/4965* | (2006.01) |
| *A61K 31/50* | (2006.01) |
| *A61K 31/502* | (2006.01) |
| *A61K 31/517* | (2006.01) |
| *A61K 31/5375* | (2006.01) |
| *C07C 231/14* | (2006.01) |
| *C07C 307/02* | (2006.01) |
| *C07D 209/38* | (2006.01) |
| *C07D 215/42* | (2006.01) |
| *C07D 235/08* | (2006.01) |
| *C07D 237/24* | (2006.01) |
| *C07D 237/28* | (2006.01) |
| *C07D 239/88* | (2006.01) |
| *C07D 241/24* | (2006.01) |
| *C07D 249/04* | (2006.01) |
| *C07D 249/08* | (2006.01) |
| *C07D 263/22* | (2006.01) |
| *C07D 295/195* | (2006.01) |
| *C07D 309/12* | (2006.01) |
| *C07D 401/04* | (2006.01) |
| *C07D 401/12* | (2006.01) |
| *C07D 403/04* | (2006.01) |
| *C07D 403/06* | (2006.01) |
| *C07D 413/12* | (2006.01) |
| *C07D 471/04* | (2006.01) |

(56) References Cited

U.S. PATENT DOCUMENTS

| | | |
|---|---|---|
| 2004/0077617 A1 | 4/2004 | Bennani |
| 2007/0078156 A1 | 4/2007 | Fletcher |
| 2009/0306408 A1 | 12/2009 | Yasuhara |
| 2012/0046292 A1 | 2/2012 | Kawano |
| 2020/0024236 A1 | 1/2020 | Lewis |

FOREIGN PATENT DOCUMENTS

| | | |
|---|---|---|
| WO | 2004005252 | 1/2004 |
| WO | 2006005185 | 1/2006 |
| WO | 2006091905 | 8/2006 |
| WO | 2006122150 | 11/2006 |
| WO | 2007075598 | 7/2007 |
| WO | 2007095050 | 8/2007 |
| WO | 2008036642 | 3/2008 |
| WO | 2008036643 | 3/2008 |
| WO | 2008036652 | 3/2008 |
| WO | 2008036653 | 3/2008 |
| WO | 2008058178 | 5/2008 |
| WO | 2009073620 | 6/2009 |
| WO | 2009127669 | 10/2009 |
| WO | 2009132238 | 10/2009 |
| WO | 2010005958 | 1/2010 |
| WO | 2011056652 | 5/2011 |
| WO | 2012064943 | 5/2012 |
| WO | 2012068067 | 5/2012 |
| WO | 2012142237 | 10/2012 |
| WO | 2013062680 | 5/2013 |
| WO | 2013069765 | 5/2013 |
| WO | 2013107164 | 7/2013 |
| WO | 2014009295 | 1/2014 |
| WO | 2014081689 | 5/2014 |
| WO | 2014150646 | 9/2014 |
| WO | 2014150677 | 9/2014 |
| WO | 2014159248 | 10/2014 |
| WO | 2015002918 | 1/2015 |
| WO | 2015007249 | 1/2015 |
| WO | 2015031295 | 3/2015 |
| WO | 2015070766 | 5/2015 |
| WO | 2015082499 | 6/2015 |
| WO | 2015086512 | 6/2015 |
| WO | 2015086526 | 6/2015 |
| WO | 2015091889 | 6/2015 |
| WO | 2015119944 | 8/2015 |
| WO | 2015150097 | 10/2015 |
| WO | 2015173764 | 11/2015 |
| WO | 2015188085 | 12/2015 |
| WO | 2016024233 | 2/2016 |
| WO | 2016026772 | 2/2016 |
| WO | 2016027241 | 2/2016 |
| WO | 2016037026 | 3/2016 |
| WO | 2016041489 | 3/2016 |
| WO | 2016051181 | 4/2016 |
| WO | 2016059412 | 4/2016 |
| WO | 2016071283 | 5/2016 |
| WO | 2016071293 | 5/2016 |
| WO | 2016073738 | 5/2016 |
| WO | 2016073770 | 5/2016 |
| WO | 2016073774 | 5/2016 |
| WO | 2016161269 | 10/2016 |
| WO | 2016161279 | 10/2016 |
| WO | 2016161286 | 10/2016 |
| WO | 2016161960 | 10/2016 |
| WO | 2016210414 | 12/2016 |
| WO | 2017051353 | 3/2017 |
| WO | 2017051354 | 3/2017 |
| WO | 2017139414 | 8/2017 |
| WO | 2017192811 | 11/2017 |
| WO | 2017192815 | 11/2017 |
| WO | 2017192844 | 11/2017 |
| WO | 2018039512 | 3/2018 |
| WO | 2018136437 | 7/2018 |
| WO | 2018136887 | 7/2018 |
| WO | 2020018670 | 1/2020 |

OTHER PUBLICATIONS

Pinedo et al. (2000).*
Vlppagunta et al. (2001).*
U.S. Appl. No. 16/514,282, filed Jul. 17, 18.*
Arai, S. et al., "Asymmetric Cyclopropanation Reaction Under Phase-Transfer Catalyzed Conditions", Tetrahedron Lett., 40(22):4215-8, (1999).
Horie, H. et al., "Nickel-catalyzed Cycloaddition of α,β,γ,δ-unsaturated Ketones With Alkynes", Angew Chem Int Ed Engl., 50(38):8956-9, (2011).
Reutrakul, V. et al., "A Rapid Entry to Functionalized Cyclohexanes and Cyclopentanes via a One-Pot Multicomponent Annulations", J Sci Soc Thailand, 22(1):83-7, (1996).
Wessig, P. et al., "A New Photochemical Route to Cyclopropanes", Angew Chem Int Ed Engl., 40(6):1064-5, (2001).
Zhao, G. et al., "Photochemical Studies on Exo-bicyclo[2.1.1]hexyl and Bicyclo[3.1.0]hexyl Aryl Ketones: Two Approaches for Synthesis of Enantiomerically Enriched Cyclopentene Derivatives", Tetrahedron, 65(48):9952-5, (2009).
Creary, X., "Cyclopropyl Inflates. Neighboring-Group and Solvent Effects", J Am Chem Soc., 98 (21):6608-13, (1976).
Dounay, A. et al., "Challenges and Opportunities in the Discovery of New Therapeutics Targeting the Kynurenine Pathway", J Med Chem., 58(22):8762-82, (2015).
Guillemin, G. et al., "Accumulation of an Endogenous Tryptophan-Derived Metabolite in Colorectal and Breast Cancers", PLoS One, 10(4):e0122046/1-e0122046/9, (2015).
International Application No. PCT/US2018/013914; International Preliminary Report on Patentability, dated Aug. 1, 2019; 14 pages.
International Application No. PCT/US2018/013914; International Search Report and Written Opinion of the International Searching Authority, dated Jul. 6, 2018; 9 pages.

(56) References Cited

OTHER PUBLICATIONS

International Application No. PCT/US2019/046449; International Search Report and Written Opinion of the International Searching Authority, dated Sep. 10, 2019; 10 pages.

Jendralla, H., "Desaminierung von N□(6□endo□Methylbicyclo[3.1.0]hex□6□exo□yl)□und N□(6□endo□Methylbicyclo[3.1.0]hex□2□en□6□exo□yl)□N□nitrosoharnstoff. Versuchte nicht□photochemische Erzeugung von trans□Cyclohexen□Derivaten", Chemische Berichte, 113(11):3585-96, (1980).

Kaplan, L. et al., "Photosolvation of Benzene. Mechanism of Formation of Bicyclo[3.1.0]hex-3-en-2-yl and of bicyclo[3.1.0]hex-2-en-6-yl Derivatives", J Am Chem Soc., 94(24):8638-40, (1972).

Koblish, H. et al., "Hydroxyamidine Inhibitors of Indoleamine-2,3-dioxygenase Potently Suppress Systemic Tryptophan Catabolism and the Growth of IDO-Expressing Tumors", Molecular Cancer Therapeutics, 9(2):489-98, (2010).

Lim, C. et al., "Involvement of the Kynurenine Pathway in the Pathogenesis of Parkinson's Disease", Progress in Neurobiology, 155:76-95, (2017).

Liu, X. et al., "Selective Inhibition of IDO1 Effectively Regulates Mediators of Antitumor Immunity", Blood, 115(17):3520-30, (2010).

Maleki Vareki, S. et al., "IDO Downregulation Induces Sensitivity to Pemetrexed, Gemcitabine, FK866, and Methoxyamine in Human Cancer Cells", PLoS One, 10(11):e0143435/1-e0143435/22, (2015).

PubChem Substance record for SID 103905401, Kinome_3406 (5-Phenylimidazo[1,5-a]pyridin-3-amine), Available date: Jan. 6, 2011, pp. 1-6., https://pubchem.ncbi.nlm.nih.gov/substance/103905401.

Pubchem. CID 280183. Mar. 26, 2005, pp. 1-7. Retrieved from the Internet <URL: https://pubchem.ncbi.nlm.nih.gov/compound/280183>; p. 2, formula.

Pubchem. CID 57266349. Jun. 15, 2012, pp. 1-8. Retrieved from the Internet <URL: https:IIpubchem.ncbi.nlm.nih.gov/compound/57266349>; p. 2, formula.

Pubmed Compound Summary for CID 12013505, [(1S,5R)-6-Bicyclo[3.1.0]hexanyl]-phenylmethanone, US National Library of Medecine, Feb. 7, 2007, p. 1-10; https://pubchem.ncbi.nlm.nih.gov/compound/12013505.

Qian, S. et al., "IDO as a Drug Target for Cancer Immunotherapy: Recent Developments in IDO Inhibitors Discovery", RSC Advances, 6(9):7575-81, (2016).

Röhrig, U. et al., "Challenges in the Discovery of Indoleamine 2,3-Dioxygenase 1 (IDO1) Inhibitors", J Med Chem., 58(24):9421-37, (2015).

Yeung, A. et al., "Role of Indoleamine 2,3-Dioxygenase in Health and Disease", Clinical Science, 129(7):601-72, (2015).

Zhai, L. et al., "Molecular Pathways: Targeting IDO1 and Other Tryptophan Dioxygenases for Cancer Immunotherapy", Clin Cancer Res, 21(24):5427-33, (2015).

Zhai, L. et al., "The Role of IDO in Brain Tumor Immunotherapy", A Journal of Neuro-Oncology, 123(3): 395-403, (2015).

International Application No. PCT/US2019/042211; International Preliminary Report on Patentability, dated Jan. 28, 2021; 8 pages.

U.S. Appl. No. 16/514,382; Non-Final Office Action, dated Nov. 25, 2020; 20 pages.

* cited by examiner

COMPOUNDS USEFUL AS INHIBITORS OF INDOLEAMINE 2,3-DIOXYGENASE AND/OR TRYPTOPHAN DIOXYGENASE

This disclosure relates to compounds useful as inhibitors of indoleamine 2,3-dioxygenase and/or tryptophan dioxygenase, in particular to compounds having favourable activity and/or selectivity for use in the treatment of conditions such as cancers.

SUMMARY OF THE INVENTION

Indoleamine 2,3-dioxygenase (IDO1 and IDO2) and tryptophan dioxygenase (TDO) belong to a family of heme-containing enzymes that mediate the degradation of the essential amino acid L-tryptophan (L-TRP) to N-formylkynurenine. This is the first and rate-limiting step of L-TRP oxidation in the kynurenine (KYN) pathway. Although IDO1, IDO2 and TDO all catalyse the same biochemical reaction, they share limited structural similarity. TDO is a homotetrameric enzyme with high substrate specificity for L-TRP, whilst IDO1 is a monomeric enzyme which recognises a broader range of substrates including L- and D-TRP, serotonin and tryptamine. IDO2 shares 43% sequence identity with IDO1 but is much less effective in catabolising L-TRP. In healthy patients, TDO is primarily expressed in the liver, and lower levels of the enzyme are also present in the brain. In contrast, IDO1 is ubiquitous in the body, including in the placenta, lung, small and large intestines, colon, spleen, liver, kidney, stomach and brain. IDO2 is expressed in a subset of the tissues that express IDO1, primarily in the kidney, as well as in the epididymis, testis, liver, ovary, uterus, and placenta (Dounay et al., J. Med. Chem. (2015) 58:8762-8782).

The KYN pathway is thought to regulate immune responses to prevent excessive immune activity and immunopathology. For example, IDO1 is believed to play a role in the protection of the foetus from rejection by the mother's immune system (Munn et al., Science (1998) 281:1191-1193), and is implicated in allergies, in autoimmunity, and in tolerance to allografts (Lovelace et al., Neuropharmacology (2017) 112:373-388).

The catabolism of L-TRP by IDO1, IDO2 and/or TDO, and the production of L-TRP derived metabolites such as KYN, has also been identified as an important immune effector pathway in tumour cells to escape potential immune responses, for example by suppressing antigen-specific T-cells and natural killer T-cells, while inducing the formation of regulatory T-cells which suppress immune cells (Qian et al., RSC Adv. (2016) 6:7575-7581). The generation of KYN and its metabolites, including quinolic acid (QUIN), also affects the synthesis of the coenzyme nicotinamide adenine dinucleotide (NAD$^+$). NAD$^+$ plays an important role in DNA replication, and hence cell division, as well as in DNA repair, redox signalling, and mitochondrial function, all of which may be involved in cancer cell proliferation (Bostian et al., Chem. Res. Toxicol. (2016) 29:1369-1380).

IDO1, IDO2 and/or TDO are expressed by many human tumours. The degree of IDO1 expression in tumour cells is known to correlate with clinical prognosis (e.g. overall survival and progression-free survival) and increased IDO1 levels have been linked with tumour cell resistance to immunotherapy, radiation therapy, and chemotherapy agents. Tumour cell resistance is often accompanied by increased metastasis, due to the suppression of the patient's immune response to the invading cancer cells. In particular, in vitro experiments have demonstrated the role of IDO1 in tumour chemoresistance to a variety of agents including cisplatin, olaparib, paclitaxel, pemetrexed, gemcitabine, and gamma radiation (Vareki et al., PLOS ONE (2015) 10(11), e0143435/1-22).

Aberrant KYN signalling has also been associated with a number of neurological diseases or disorders such as Alzheimer's disease, amyotrophic lateral sclerosis, Huntington's disease, multiple sclerosis and Parkinson's disease (Bostian, 2016). The interaction between immune activation and the metabolism of L-TRP via the kynurenine pathway has also been shown to be involved in neuropsychological diseases or disorders such as schizophrenia, anorexia and depression, including depressive and anxiety symptoms in the early puerperium (Lovelace, 2017).

Inhibitors of IDO1, IDO2 and/or TDO are also believed to have utility in the treatment of cataracts; infectious diseases where the immune system is compromised (e.g. influenza virus, peritonitis, sepsis, *Chlamydia trachomatis*, human immunodeficiency virus (HIV) and HIV-associated neurological disorders (HAND)); and autoimmune disorders such as arthritis, rheumatoid arthritis or multiple sclerosis (Lovelace, 2017).

A number of structurally-diverse inhibitors of IDO1, IDO2 and/or TDO have recently been developed. These include indoximod (NLG8189), which is being evaluated clinical studies for metastatic breast cancer, metastatic melanoma, non-small cell lung cancer, primary malignant brain tumours, metastatic pancreatic cancer, as well as metastatic prostate cancer; epacadostat (INCB024360), which is being evaluated in clinical studies in gynaecological and peritoneal cancers, melanoma, malignant solid tumour, lymphoma, breast, lung, and renal cell cancers; and GDC-0919 (NLG919), which is being evaluated in trials for the treatment of advanced-stage solid tumours.

However, there remains a need for new inhibitors of IDO1, IDO2 and/or TDO, especially inhibitors having high potency, high selectivity and/or beneficial in vivo properties such as pharmacokinetic properties. This need is met by the present invention.

The present inventors have discovered a family of compounds which are useful as inhibitors of IDO1, IDO2 and/or TDO, especially IDO1. These compounds are suitable for use in pharmaceutical compositions as well as in medical treatments in which the KYN pathway needs to be modulated. In particular, the compounds of the invention are suitable for use in the treatment of cancers, immune system regulatory disorders and neurological disorders.

Without wishing to be bound by theory, the inventors postulate that compounds of the present disclosure may inhibit IDO1, IDO2 and/or TDO apoprotein, i.e. before incorporation of the heme cofactor. Such inhibition may prevent the formation of functional protein and offer advantages over other classes of inhibitors which bind directly to the heme moiety in the holoprotein.

In a first aspect, the invention provides a compound characterised by formula (VII),

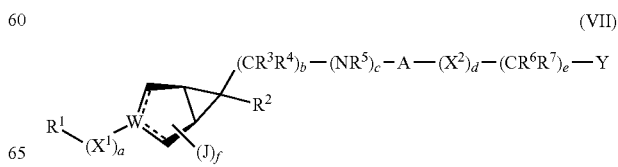

(VII)

or a pharmaceutically acceptable salt or prodrug thereof, wherein one but not both of the dashed bonds may optionally be a carbon-carbon double bond, and wherein:
W is selected from C, CH, and N;
a is 0 or 1;
b is 0, 1 or 2;
c is 0 or 1;
d is 0 or 1;
e is 0 or 1;
f is 0, 1 or 2;
A is selected from O, C(O), and $S(O)_2$;
J is in each case independently selected from oxo, OH, CN, halogen, and $C_{1-3}$-alkyl;
$X^1$ is selected from $C(R^8)(R^9)$, $N(R^{10})$, O, and S;
$X^2$ is selected from $C(R^{11})(R^{12})$, $N(R^{13})$, and O;
Y is selected from
  $C_{6-10}$-aryl, and
  5- to 10-membered heteroaryl comprising 1, 2, 3 or 4 ring heteroatoms selected from N, S and O,
  wherein said aryl and heteroaryl are optionally substituted by one or more groups independently selected from $R^{14}$;
$R^1$ is selected from
  H,
  $(G)_n$-($C_{1-6}$-alkyl),
  $(G)_n$-($C_{3-8}$-cycloalkyl),
  $N_3$,
  $(G)_n$-heterocycloalkyl, wherein said heterocycloalkyl is a 3- to 6-membered heterocycloalkyl comprising 1, 2 or 3 ring heteroatoms selected from N, S and O,
  $(G)_n$-($C_{5-8}$-cycloalkenyl),
  $(G)_n$-heterocycloalkenyl, wherein said heterocycloalkenyl is a 5- to 6-membered heterocycloalkenyl comprising 1, 2 or 3 ring heteroatoms selected from N, S and O,
  $(G)_n$-($C_{6-10}$-aryl), and
  $(G)_n$-heteroaryl, wherein said heteroaryl is a 5- to 10-membered heteroaryl comprising 1, 2, 3 or 4 ring heteroatoms selected from N, S and O,
  wherein G in each case is independently selected from $C(R^8)(R^9)$, C(O), $S(O)_2$, $C(O)NR^{10}$, and $S(O)_2NR^{10}$; and wherein n in each case is either 0 or 1, and
  wherein said alkyl, cycloalkyl, heterocycloalkyl, cycloalkenyl, heterocycloalkenyl, aryl and heteroaryl are optionally substituted by one or more groups independently selected from $R^{15}$;
$R^2$, $R^3$, $R^4$, $R^6$, $R^7$, $R^8$, $R^9$, $R^{11}$ and $R^{12}$ are in each case independently selected from
  H,
  halogen,
  CN,
  OH,
  ($C_{0-4}$-alkyl)-$SO_2R^{17}$,
  ($C_{0-4}$-alkyl)-$N(R^{18})_2$,
  ($C_{0-4}$-alkyl)-$NHCOR^{19}$,
  ($C_{0-4}$-alkyl)-$NHSO_2R^{20}$,
  ($C_{0-4}$-alkyl)-$CON(R^{21})_2$,
  ($C_{0-4}$-alkyl)-$CO_2R^{22}$,
  ($C_{0-4}$-alkyl)-$SO_2N(R^{23})_2$,
  $C_{1-6}$-alkyl,
  O—($C_{1-6}$-alkyl),
  $C_{3-8}$-cycloalkyl,
  3- to 6-membered heterocycloalkyl comprising 1, 2 or 3 ring heteroatoms selected from N, S and O,
  $C_{5-8}$-cycloalkenyl,
  5- to 6-membered heterocycloalkenyl comprising 1, 2 or 3 ring heteroatoms selected from N, S and O,
  $C_{6-10}$-aryl, and
  5- to 10-membered heteroaryl comprising 1, 2, 3 or 4 ring heteroatoms selected from N, S and O, or
  one or both geminal $R^3$ and $R^4$ pairs, taken together with the carbon atom to which they are attached, independently forms a 3- to 6-membered cycloalkyl group or a 3- to 6-membered heterocycloalkyl group which comprises 1, 2 or 3 ring heteroatoms selected from N, S and O,
  wherein said alkyl, cycloalkyl, heterocycloalkyl, cycloalkenyl, heterocycloalkenyl, aryl and heteroaryl are optionally substituted by one or more groups independently selected from $R^{16}$;
$R^5$, $R^{10}$ and $R^{13}$ are in each case independently selected from
  H,
  $C_{1-6}$-alkyl,
  $C_{3-8}$-cycloalkyl,
  3- to 6-membered heterocycloalkyl comprising 1, 2 or 3 ring heteroatoms selected from N, S and O,
  $C_{5-8}$-cycloalkenyl,
  5- to 6-membered heterocycloalkenyl comprising 1, 2 or 3 ring heteroatoms selected from N, S and O,
  $C_{6-10}$-aryl, and
  5- to 10-membered heteroaryl comprising 1, 2, 3 or 4 ring heteroatoms selected from N, S and O,
  optionally wherein one of $R^3$ and $R^5$, together with one of $R^{11}$ and $R^{13}$ and the atoms intervening between them, may form a 5- or 6-membered cycloalkyl, cycloalkenyl or aryl group, or a 5- or 6-membered heterocycloalkyl, heterocycloalkenyl or heteroaryl group which comprises 1, 2, 3 or 4 ring heteroatoms selected from N, S and O;
  wherein said alkyl, cycloalkyl, heterocycloalkyl, cycloalkenyl, heterocycloalkenyl, aryl and heteroaryl are optionally substituted by one or more groups independently selected from $R^{24}$;
any two $R^{14}$ substituents on adjacent ring atoms may, together with the ring atoms to which they are attached, independently form a 5- or 6-membered cyclic group optionally comprising 1, 2 or 3 ring heteroatoms selected from N, S and O, which cyclic group is optionally substituted by one or more groups independently selected from halogen, $C_{1-4}$-alkyl and $C_{1-4}$-haloalkyl, and
any remaining $R^{14}$ is in each case independently selected from
  halogen,
  CN,
  OH,
  $C_{1-6}$-alkyl,
  O—($C_{1-6}$-alkyl),
  O—($C_{1-16}$-haloalkyl),
  O—($C_{1-6}$-alkyl-$C_{3-6}$-cycloalkyl),
  ($C_{0-4}$-alkyl)-$SO_2R^{17}$,
  ($C_{0-4}$-alkyl)-$N(R^{18})_2$,
  ($C_{0-4}$-alkyl)-$NHCOR^{19}$,
  ($C_{0-4}$-alkyl)-$NHSO_2R^{20}$,
  ($C_{0-4}$-alkyl)-$CON(R^{21})_2$,
  ($C_{0-4}$-alkyl)-$CO_2R^{22}$,
  ($C_{0-4}$-alkyl)-$SO_2N(R^{23})_2$, and
  ($C_{0-4}$-alkyl)-heteroaryl,
  wherein said heteroaryl is a 5- to 10-membered heteroaryl comprising 1, 2, 3 or 4 ring heteroatoms selected from N, S and O;

$R^{15}$ is in each case independently selected from
- halogen,
- CN,
- OH,
- oxo,
- $NO_2$,
- $C_{1-6}$-alkyl,
- $C_{2-6}$-alkenyl,
- $C_{2-6}$-alkynyl,
- $(C_{0-4}$-alkyl$)$-O—$(C_{1-6}$-alkyl$)$,
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$,
- $(C_{0-4}$-alkyl$)$-heteroaryl, wherein said heteroaryl is a 5- to 10-membered heteroaryl comprising 1, 2, 3 or 4 ring heteroatoms selected from N, S and O,
- $(C_{0-4}$-alkyl$)$-heterocycloalkenyl, wherein said heterocycloalkenyl is a 5- to 10-membered heterocycloalkenyl comprising 1 or 2 ring heteroatoms selected from N and O,
- $(C_{0-4}$-alkyl$)$-heterocycloalkyl, wherein said heterocycloalkyl is a 4- to 6-membered heterocycloalkyl comprising 1 or 2 ring heteroatoms selected from N and O,
- $(C_{0-4}$-alkyl$)$-aryl, wherein said aryl is a 6- to 10-membered aryl,
- $(C_{0-4}$-alkyl$)$-cycloalkenyl, wherein said cycloalkenyl is a 5- to 8-membered cycloalkenyl, and
- $(C_{0-4}$-alkyl$)$-cycloalkyl, wherein said cycloalkyl is a 3- to 8-membered cycloalkyl, wherein said alkyl, alkenyl, alkynyl, heteroaryl, heterocycloalkenyl, heterocycloalkyl, aryl, cycloalkenyl and cycloalkyl are optionally substituted by one or more groups independently selected from halogen, OH, O—$(C_{1-4}$-alkyl$)$, oxo, C(O)—$(C_{1-4}$-alkyl$)$, C(O)O—$(C_{1-4}$-alkyl$)$, and $NH_2$;

$R^{16}$ and $R^{24}$ are in each case independently selected from
- halogen,
- CN,
- OH,
- $C_{1-6}$-alkyl,
- O—$(C_{1-6}$-alkyl$)$,
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$,
- $(C_{0-4}$-alkyl$)$-heteroaryl, wherein said heteroaryl is a 5- to 10-membered heteroaryl comprising 1, 2, 3 or 4 ring heteroatoms selected from N, S and O,
- $(C_{0-4}$-alkyl$)$-heterocycloalkenyl, wherein said heterocycloalkenyl is a 5- to 6-membered heterocycloalkenyl comprising 1 or 2 ring heteroatoms selected from N and O,
- $(C_{0-4}$-alkyl$)$-heterocycloalkyl, wherein said heterocycloalkyl is a 4- to 6-membered heterocycloalkyl comprising 1 or 2 ring heteroatoms selected from N and O,
- $(C_{0-4}$-alkyl$)$-aryl, wherein said aryl is a 6- to 10-membered aryl,
- $(C_{0-4}$-alkyl$)$-cycloalkenyl, wherein said cycloalkenyl is a 5- to 8-membered cycloalkenyl, and
- $(C_{0-4}$-alkyl$)$-cycloalkyl, wherein said cycloalkyl is a 3- to 8-membered cycloalkyl, wherein said alkyl, heteroaryl, heterocycloalkenyl, heterocycloalkyl, aryl, cycloalkenyl and cycloalkyl are optionally substituted by one or more groups independently selected from halogen; and $R^{17}$ to $R^{23}$ are in each case independently selected from
- H,
- $C_{1-6}$-alkyl,
- $C_{3-8}$-cycloalkyl,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O, wherein any pair of $R^{18}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O, wherein any pair of $R^{21}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O, wherein any pair of $R^{23}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O, wherein each said alkyl, cycloalkyl, heterocycloalkyl, cycloalkenyl, heterocycloalkenyl, aryl and heteroaryl is optionally and independently substituted by one or more groups independently selected from halogen, OH, $C_{1-6}$-alkyl and $C_{1-6}$-haloalkyl.

In embodiments, the compound is characterised by formula (VI), $$R^1\text{—}(X^1)_a\text{—}W\underset{(J)_f}{\overset{R^2}{\diagdown}}\text{—}(CR^3R^4)_b\text{—}(NR^5)_c\text{—}A\text{—}(X^2)_d\text{—}(CR^6R^7)_e\text{—}Y \quad \text{(VI)}$$

or a pharmaceutically acceptable salt or prodrug thereof, wherein:

W is selected from CH, and N; and a, b, c, d, e, f, A, J, $X^1$, $X^2$, Y, and $R^1$ to $R^7$ are as defined hereinabove.

In embodiments, the compound is characterised by formula (I),

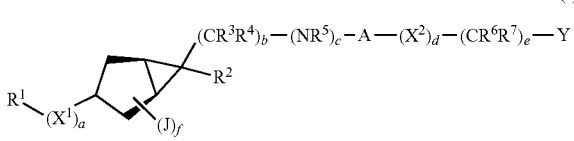

(I)

or a pharmaceutically acceptable salt or prodrug thereof, wherein a, b, c, d, e, f, A, J, $X^1$, $X^2$, Y, and $R^1$ to $R^7$ are as defined hereinabove.

In embodiments, A is C(O) or $S(O)_2$, preferably wherein A is C(O).

In embodiments, f is 0.

In embodiments, the compound is characterised by formula (III),

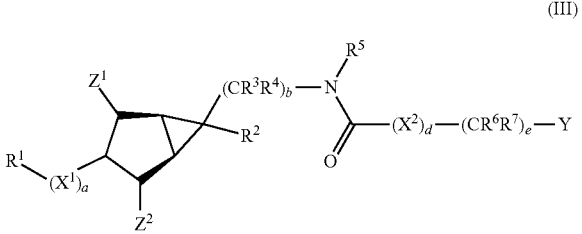

(III)

or a pharmaceutically acceptable salt or prodrug thereof, wherein:
$Z^1$ and $Z^2$ are each independently selected from H and J,
b is 0 or 1, and
a, d, e, J, $X^1$, $X^2$, Y, and $R^1$ to $R^7$ are as defined hereinabove.

In embodiments, $Z^1$ and $Z^2$ are each independently selected from H.

In embodiments, d is 0.

In embodiments, the compound is characterised by formula (IV),

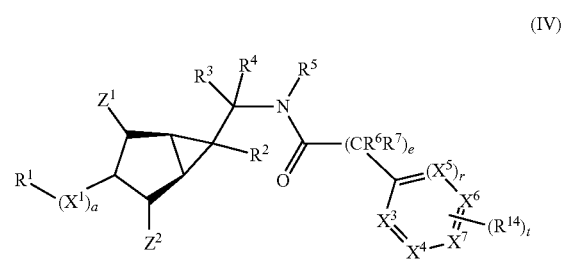

(IV)

or a pharmaceutically acceptable salt or prodrug thereof, wherein:
r is 0 or 1;
t is 0, 1, 2 or 3;
$X^3$ to $X^7$ are independently selected from CH, $CR^{14}$ and N, wherein no more than three of $X^3$ to $X^7$ may be N, and
a, e, $X^1$, $Z^1$, $Z^2$, $R^1$ to $R^7$, and $R^{14}$ are as defined hereinabove.

In embodiments, r is 1, and/or wherein t is 1, 2 or 3.

In embodiments, $X^7$ is CH or $CR^{14}$, wherein $R^{14}$ is as defined hereinabove.

In embodiments, the compound is characterised by formula (IVa),

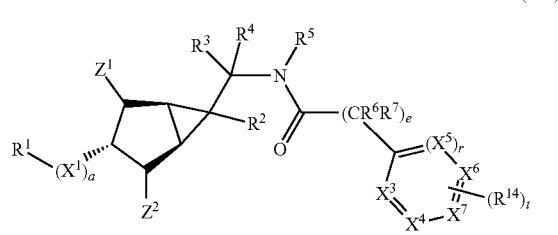

(IVa)

or a pharmaceutically acceptable salt or prodrug thereof, wherein a, e, r, t, $X^1$, $X^3$ to $X^7$, $Z^1$, $Z^2$, $R^1$ to $R^7$, and $R^{14}$ are as defined hereinabove.

In embodiments, the compound is characterised by formula (IVac) or formula (IVbc),

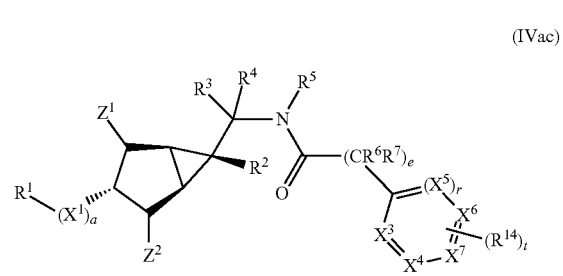

(IVac)

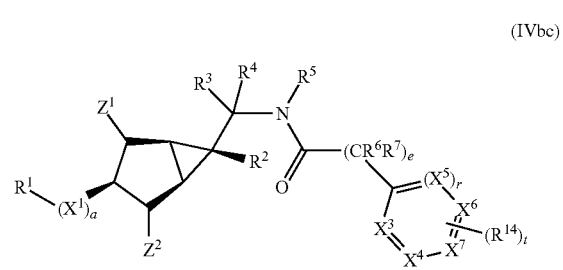

(IVbc)

or a pharmaceutically acceptable salt or prodrug thereof, wherein a, e, r, t, $X^1$, $X^3$ to $X^7$, $Z^1$, $Z^2$, $R^1$ to $R^7$, and $R^{14}$ are as defined hereinabove.

In embodiments, the compound is characterised by formula (VIII) or formula (IX),

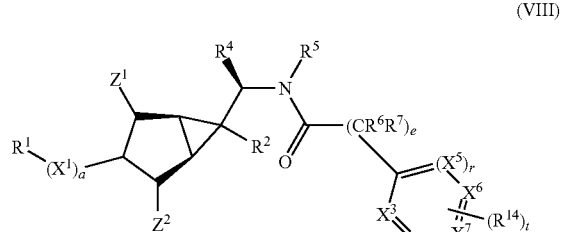

(VIII)

-continued (IX)

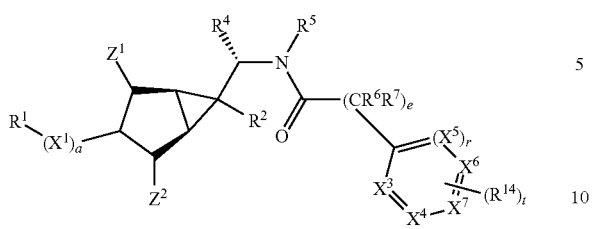

or a pharmaceutically acceptable salt or prodrug thereof, wherein a, e, r, t, $X^1$, $X^3$ to $X^7$, $Z^1$, $Z^2$, $R^1$, $R^2$, $R^4$ to $R^7$, and $R^{14}$ are as defined hereinabove.

In embodiments, the compound is characterised by formula (VIIIa), (VIIIa)

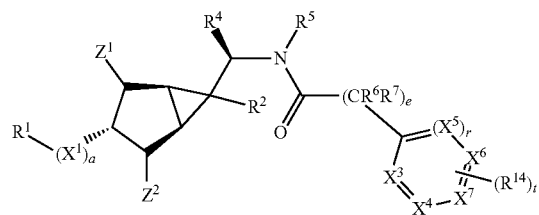

or a pharmaceutically acceptable salt or prodrug thereof, wherein a, e, r, t, $X^1$, $X^3$ to $X^7$, $Z^1$, $Z^2$, $R^1$, $R^2$, $R^4$ to $R^7$, and $R^{14}$ are as defined hereinabove.

In embodiments, the compound is characterised by formula (VIIIac), (VIIIac)

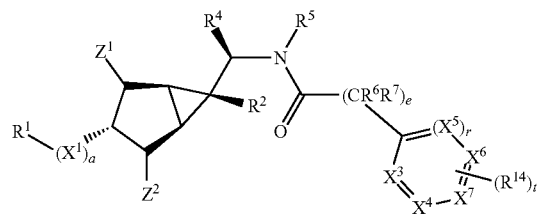

or a pharmaceutically acceptable salt or prodrug thereof, wherein a, e, r, t, $X^1$, $X^3$ to $X^7$, $Z^1$, $Z^2$, $R^1$, $R^2$, $R^4$ to $R^7$, and $R^{14}$ are as defined hereinabove.

In embodiments, the compound is characterised by formula (XII), (XII)

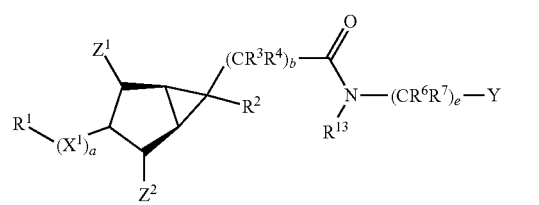

or a pharmaceutically acceptable salt or prodrug thereof, wherein:

b is 1 or 2, and a, e, $X^1$, Y, $Z^1$, $Z^2$ and $R^1$ to $R^4$, $R^6$, $R^7$, and $R^{13}$ are as defined hereinabove.

In embodiments, $Z^1$ and $Z^2$ are each independently selected from H.

In embodiments, the compound is characterised by formula (XIII), (XIII)

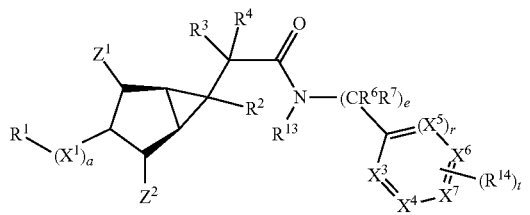

or a pharmaceutically acceptable salt or prodrug thereof, wherein a, e, r, t, $X^1$, $X^3$ to $X^7$, $Z^1$, $Z^2$, $R^1$ to $R^4$, $R^6$, $R^7$, $R^{13}$, and $R^{14}$ are as defined hereinabove.

In embodiments, the compound is characterised by formula (XIIIa), (XIIIa)

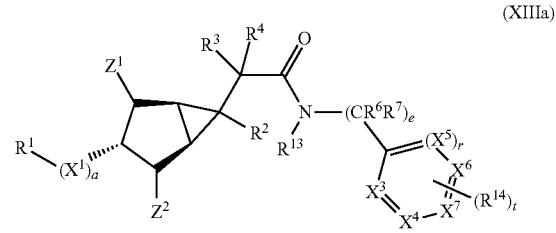

or a pharmaceutically acceptable salt or prodrug thereof, wherein a, e, r, t, $X^1$, $X^3$ to $X^7$, $Z^1$, $Z^2$, $R^1$ to $R^4$, $R^6$, $R^7$, $R^{13}$, and $R^{14}$ are as defined hereinabove.

In embodiments, the compound is characterised by formula (XIIIac), (XIIIac)

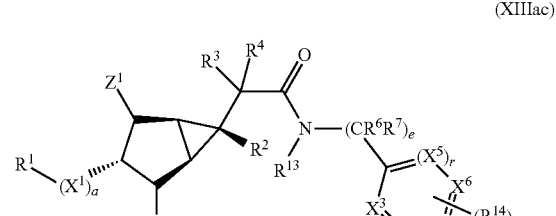

or a pharmaceutically acceptable salt or prodrug thereof, wherein a, e, r, t, $X^1$, $X^3$ to $X^7$, $Z^1$, $Z^2$, $R^1$ to $R^4$, $R^6$, $R^7$, $R^{13}$, and $R^{14}$ are as defined hereinabove.

In embodiments, the compound is characterised by formula (XIV) or formula (XV), (XIV)

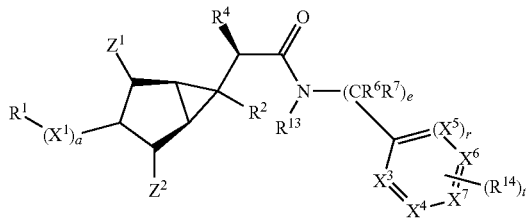

(XV)

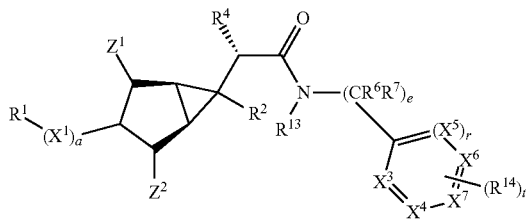

or a pharmaceutically acceptable salt or prodrug thereof, wherein a, e, r, t, $X^1$, $X^3$ to $X^7$, $Z^1$, $Z^2$, R, $R^2$, $R^4$, $R^6$, $R^7$, $R^{13}$, and $R^{14}$ are as defined hereinabove.

In embodiments, the compound is characterised by formula (XIVac), (XIVac)

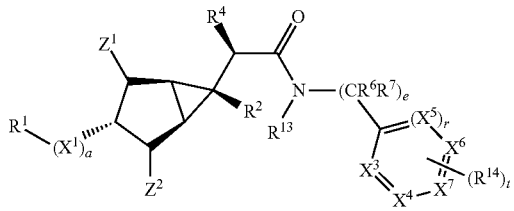

or a pharmaceutically acceptable salt or prodrug thereof, wherein a, e, r, t, $X^1$, $X^3$ to $X^7$, $Z^1$, $Z^2$, R, $R^2$, $R^4$, $R^6$, $R^7$, $R^{13}$, and $R^{14}$ are as defined hereinabove.

In embodiments, the compound is characterised by formula (V), (V)

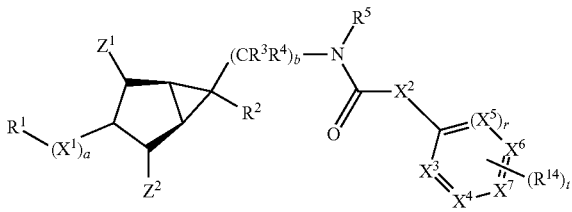

or a pharmaceutically acceptable salt or prodrug thereof, wherein a, b, r, t, $X^1$ to $X^7$, $Z^1$, $Z^2$, $R^1$ to $R^5$, and $R^{14}$ are as defined hereinabove.

In embodiments, the compound is characterised by formula (Vac), (Vac)

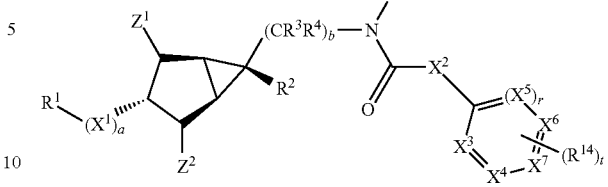

or a pharmaceutically acceptable salt or prodrug thereof, wherein a, b, r, t, $X^1$ to $X^7$, $Z^1$, $Z^2$, $R^1$ to $R^5$, and $R^{14}$ are as defined hereinabove.

In embodiments, $X^2$ is $NR^{13}$.

In embodiments, $R^1$ is selected from $C_{3-8}$-cycloalkyl; 3- to 6-membered heterocycloalkyl comprising 1, 2 or 3 ring heteroatoms selected from N, S and O; $C_{5-8}$-cycloalkenyl; 5- to 6-membered heterocycloalkenyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said cycloalkyl, heterocycloalkyl, cycloalkenyl, heterocycloalkenyl, aryl and heteroaryl are optionally substituted by one or more groups independently selected from $R^{15}$ as defined hereinabove.

In embodiments, $R^1$ is selected from phenyl, quinolinyl, pyridyl, cinnolinyl, quinazolinyl, pyrimidinyl, benzimidazolyl, pyrazolyl, triazolyl and imidazolyl, each of which is optionally substituted by one or more groups independently selected from $R^{15}$ as defined hereinabove.

In embodiments, $R^1$ is selected from N-morpholinylcarbonyl, pyrazolylcarbonyl, pyridinylcarbonyl, pyrimidinylcarbonyl, pyrazinylcarbonyl, pyridazinylcarbonyl, quinolonylcarbonyl, and N-(pyridinyl)aminocarbonyl, each of which is optionally substituted by one or more groups independently selected from $R^{15}$ as defined hereinabove.

In embodiments, $R^1$ is substituted by 1 or 2 groups independently selected from $R^{15}$ as defined hereinabove.

In embodiments, $R^{15}$ is in each case independently selected from halogen, CN, oxo, OH, $NO_2$, $C_{1-6}$-alkyl, $C_{2-6}$-alkenyl, $C_{2-6}$-alkynyl, ($C_{0-4}$-alkyl)-O—($C_{1-6}$-alkyl), and ($C_{0-4}$-alkyl)-cycloalkyl, wherein said cycloalkyl is a 3- to 8-membered cycloalkyl, and wherein each said alkyl, alkenyl, alkynyl and cycloalkyl is optionally and independently substituted by one or more groups independently selected from halogen, OH, and $NH_2$.

In embodiments, a is 1; and $X^1$ is selected from O and NH.

In embodiments, a is 0; and $R^1$ is attached to the rest of the molecule via a nitrogen atom of the said $R^1$.

In embodiments, $R^2$ is selected from H.

In embodiments, b is 1; $R^3$ is independently selected from H, halogen, and $C_{1-6}$-alkyl; and $R^4$ is independently selected from H, halogen, CN, and $C_{1-6}$-alkyl, wherein said alkyl is optionally substituted by one or more groups independently selected from $R^{16}$ as defined hereinabove.

In embodiments, c is 1; and $R^5$ is selected from H, and $C_{1-6}$-alkyl.

In embodiments, e is 0.

In embodiments, Y is selected from:

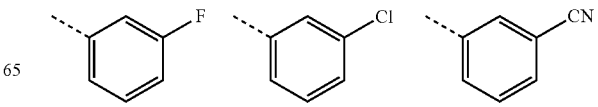

-continued

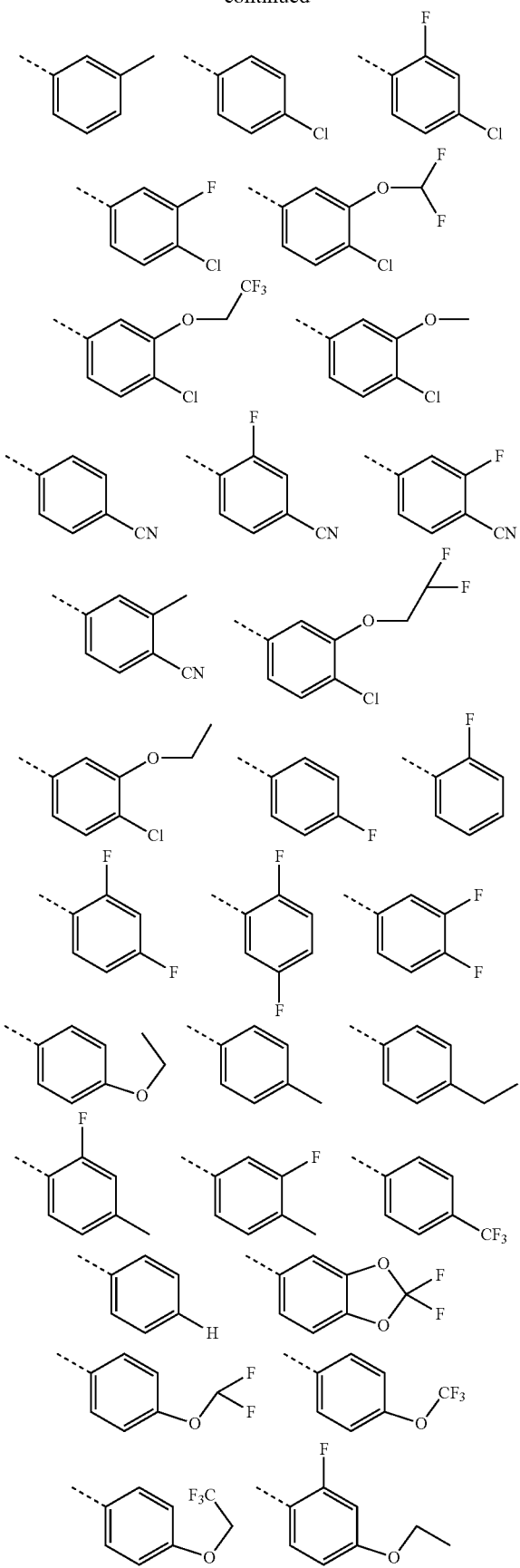

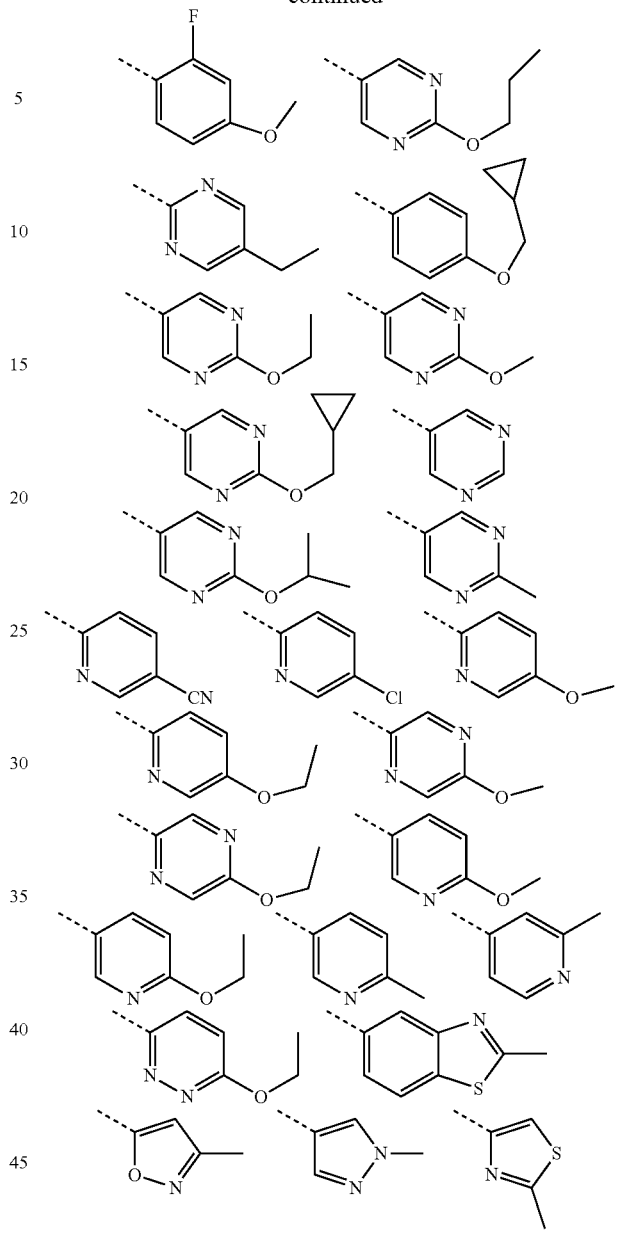

wherein the dashed bonds denotes the point of attachment of Y to the rest of the molecule.

In embodiments, $R^{16}$ is in each case independently selected from halogen; CN; OH; $C_{1-6}$-alkyl; O—($C_{1-6}$-alkyl); and ($C_{0-4}$-alkyl)-heterocycloalkyl, wherein said heterocycloalkyl is a 4- to 6-membered heterocycloalkyl comprising 1 or 2 ring heteroatoms selected from N and O.

In embodiments, $R^{24}$ is in each case independently selected from CN, OH, $C_{1-6}$-alkyl, O—($C_{1-6}$-alkyl), and ($C_{0-4}$-alkyl)-heterocycloalkyl, wherein said heterocycloalkyl is a 4- to 6-membered heterocycloalkyl comprising 1 or 2 ring heteroatoms selected from N and O.

The invention further provides a compound selected from the group consisting of Compounds 1 to 363 and the pharmaceutically acceptable salts and prodrugs thereof as defined hereinafter.

In embodiments, the compound of the invention has an inhibitory activity (measured as $IC_{50}$ value) against IDO1 of less than 200 nM.

The invention further provides a pharmaceutical composition comprising a compound of the invention, and at least one pharmaceutically acceptable excipient.

In embodiments, the pharmaceutical composition comprises a further active agent selected from the group consisting of chemotherapeutic agents and immunotherapeutic agents.

The invention further provides a compound, or a pharmaceutical composition, of the invention for use in therapy.

The invention further provides a method for treating an IDO1, IDO2 and/or TDO mediated condition in a subject, the method comprising administering to the subject an effective amount of a compound of the invention.

In embodiments, the IDO1, IDO2 and/or TDO mediated condition is selected from a cancer; a neurological or neuropsychological disease or disorder; an autoimmune disease or disorder; an infection; a cataract; and a vascular disease.

In embodiments, the IDO1, IDO2 and/or TDO mediated condition is characterised by the overexpression of IDO1, IDO2 and/or TDO, respectively.

In embodiments, the IDO1, IDO2 and/or TDO mediated condition is a cancer is selected from head and neck cancer, breast cancer (e.g. metastatic breast cancer), prostate cancer (e.g. metastatic prostate cancer), ovarian cancer, endometrial cancer, colon cancer, lung cancer (e.g. non-small cell lung cancer), bladder cancer, pancreatic cancer (e.g. metastatic pancreatic cancer), brain tumour (e.g. primary malignant brain tumour), gynaecological cancer, peritoneal cancer, skin cancer, thyroid cancer, oesophageal cancer, cervical cancer, gastric cancer, liver cancer, stomach cancer, renal cell cancer, biliary tract cancer, hematologic cancer, and blood cancer.

In embodiments, the cancer is associated with low levels of L-TRP and/or the cancer is associated with high levels of L-TRP metabolites.

In embodiments, the IDO1, IDO2 and/or TDO mediated condition is a cancer, and the method comprises administering said compound in combination with another therapeutic intervention for said cancer.

In embodiments, said another therapeutic intervention is immunotherapy, radiation therapy and/or chemotherapy.

In embodiments, the method is for treating a subject diagnosed as having a cancer or being at risk of developing a cancer.

In embodiments, the IDO1, IDO2 and/or TDO mediated condition is a neurological disease or disorder selected from Alzheimer's disease, amyotrophic lateral sclerosis, Huntington's disease, multiple sclerosis, Parkinson's disease, and HIV-associated neurological disorders (HAND).

In embodiments, the IDO1, IDO2 and/or TDO mediated condition is a neuropsychological disease or disorder selected from schizophrenia, anorexia, depression, and anxiety.

In embodiments, the IDO1, IDO2 and/or TDO mediated condition is an autoimmune disease or disorder selected from arthritis, rheumatoid arthritis, and multiple sclerosis.

In embodiments, the IDO1, IDO2 and/or TDO mediated condition is an infection selected from influenza virus infection, peritonitis, sepsis, *Chlamydia trachomatis* infection, and human immunodeficiency virus (HIV).

In embodiments, the IDO1, IDO2 and/or TDO mediated condition is a cataract.

In embodiments, the IDO1, IDO2 and/or TDO mediated condition is a cardiovascular disease.

The invention further provides a compound of the invention for use in a method as defined hereinbefore.

The invention further provides the use of a compound of the invention in the manufacture of a medicament for use in a method as defined hereinbefore.

DETAILED DESCRIPTION

Although specific embodiments of the present disclosure will now be described with reference to the description and examples, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure.

Definitions

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, exemplary methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present disclosure will employ, unless otherwise indicated, conventional techniques of chemical synthesis, tissue culture, immunology, molecular biology, microbiology, cell biology and recombinant DNA, which are within the skill of the art. See, e.g., Michael R. Green and Joseph Sambrook, Molecular Cloning ($4^{th}$ ed., Cold Spring Harbor Laboratory Press 2012); the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)); Sohail (ed.) (2004) Gene Silencing by RNA Interference: Technology and Application (CRC Press).

Numerical designations, e.g. pH, temperature, time, concentration, molecular weight, etc., including ranges, are approximations which are varied (+) or (−) by increments of 0.1 or 1.0, where appropriate. It is to be understood, although not always explicitly stated that all numerical designations are preceded by the term "about". It also is to be understood, although not always explicitly stated, that the reagents described herein are merely exemplary and that equivalents of such may be known in the art.

As used in the specification and claims, the singular forms "a", "an" and "the" include plural references unless the context clearly dictates otherwise. For example, the term "a cell" includes a plurality of cells, including mixtures thereof. Unless specifically stated or obvious from context, as used herein, the term "or" is understood to be inclusive. The term "including" is used herein to mean, and is used interchangeably with, the phrase "including but not limited to".

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure or process steps to produce a composition or achieve an intended result. Embodiments defined by each of these transition terms are within the scope of this invention. Use of the term "comprising" herein is intended to encompass, and to disclose, the corresponding statements in which the term "comprising" is replaced by "consisting essentially of" or "consisting of".

A "subject," "individual" or "patient" is used interchangeably herein, and refers to a vertebrate, such as a mammal. Mammals include, but are not limited to, rodents, farm animals, sport animals, pets and primates; for example murines, rats, rabbit, simians, bovines, ovines, porcines, canines, felines, equines, and humans. In one embodiment, the mammals include horses, dogs, and cats. In a preferred embodiment, the mammal is a human.

"Administering" is defined herein as a means of providing an agent or a composition containing the agent to a subject in a manner that results in the agent being inside the subject's body. Such an administration can be by any route including, without limitation, oral, transdermal (e.g. by the vagina, rectum, or oral mucosa), by injection (e.g. subcutaneous, intravenous, parenteral, intraperitoneal, or into the central nervous system), or by inhalation (e.g. oral or nasal). Pharmaceutical preparations are, of course, given by forms suitable for each administration route.

"Treating" or "treatment" of a disease includes: (1) preventing the disease, i.e. causing the clinical symptoms of the disease not to develop in a patient that may be predisposed to the disease but does not yet experience or display symptoms of the disease; (2) inhibiting the disease, i.e. arresting or reducing the development of the disease or its clinical symptoms; and/or (3) relieving the disease, i.e. causing regression of the disease or its clinical symptoms.

The term "suffering" as it relates to the term "treatment" refers to a patient or individual who has been diagnosed with or is predisposed to the disease. A patient may also be referred to being "at risk of suffering" from a disease because of a history of disease in their family lineage or because of the presence of genetic mutations associated with the disease. A patient at risk of a disease has not yet developed all or some of the characteristic pathologies of the disease.

An "effective amount" or "therapeutically effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including, for example, the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks.

As used herein, the term "pharmaceutically acceptable excipient" encompasses any of the standard pharmaceutical excipients, including carriers such as a phosphate buffered saline solution, water, and emulsions, such as an oil/water or water/oil emulsion, and various types of wetting agents. Pharmaceutical compositions also can include stabilizers and preservatives. For examples of carriers, stabilizers and adjuvants, see Remington's Pharmaceutical Sciences (20th ed., Mack Publishing Co. 2000).

As used herein, the term "prodrug" means a pharmacological derivative of a parent drug molecule that requires biotransformation, either spontaneous or enzymatic, within the organism to release the active drug. For example, prodrugs are variations or derivatives of the compounds described herein that have groups cleavable under certain metabolic conditions, which when cleaved, become the compounds described herein, e.g. a compound of formula (I). Such prodrugs then are pharmaceutically active in vivo when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (Bundgard, Design of Prodrugs, pp. 7-9, 21-24, Elsevier, Amsterdam 1985 and Silverman, "The Organic Chemistry of Drug Design and Drug Action" pp. 352-401, Academic Press, San Diego, Calif., 1992).

Prodrugs commonly known in the art include well-known acid derivatives, such as, for example, esters prepared by reaction of acid compounds with a suitable alcohol, amides prepared by reaction of acid compounds with an amine, basic groups reacted to form an acylated base derivative, etc. Other prodrug derivatives may be combined with other features disclosed herein to enhance bioavailability. As such, those of skill in the art will appreciate that certain of the presently disclosed compounds having, for example, free amino or hydroxyl groups can be converted into prodrugs. Prodrugs also include compounds having a carbonate, carbamate, amide or alkyl ester moiety covalently bonded to any of the above substituents disclosed herein.

As used herein, the term "pharmaceutically acceptable salt" means a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

As used herein, the term "alkyl" means a saturated linear or branched free radical consisting essentially of carbon atoms and a corresponding number of hydrogen atoms. Exemplary alkyl groups include methyl, ethyl, n-propyl, isopropyl, n-butyl, isobutyl, etc. Other alkyl groups will be readily apparent to those of skill in the art given the benefit of the present disclosure. The terms "$C_{1-3}$-alkyl", "$C_{4-8}$-alkyl", etc., have equivalent meanings, i.e. a saturated linear or branched free radical consisting essentially of 1 to 3 (or 4 or 8) carbon atoms and a corresponding number of hydrogen atoms. As used herein, the term "haloalkyl" means an alkyl group which is substituted by one or more halogens. Exemplary haloalkyl groups include chloromethyl, dichloromethyl, trichloroethyl, etc. The term "fluoroalkyl" is to be construed accordingly, i.e. to encompass fluoromethyl, difluoromethyl, trifluoroethyl, etc.

As used herein, the term "cyclic group" means a saturated, partially or fully unsaturated, or aromatic group having at least 3 to 9 atoms (i.e. ring atoms) that form a ring. The term is intended to encompass both carbocyclic groups, which are groups having at least 3 to 9 carbon atoms that form a ring, as well as heterocyclic groups, which are groups having at least 3 to 6 atoms that form a ring, wherein 1 to 5 of said ring atoms are carbon and the remaining 1 to 5 ring atom(s) (i.e. hetero ring atom(s)) are selected independently from the group consisting of nitrogen, sulphur and oxygen. Where a cyclic group is defined as having a certain number of members, the term "members", "membered" and the like is used to denote the number of ring atoms in said cyclic group. For example, a 5-membered cyclic group (e.g. a 5-membered heterocyclic group) contains 5 ring atoms.

As used herein, the term "cycloaliphatic" means a non-aromatic cyclic group. The term is intended to encompass both carbocyclic and heterocyclic groups having at least 3 to 10 atoms (i.e. ring atoms) that form a ring. Where a cycloaliphatic is defined as having a certain number of members, the term "members", "membered" and the like is used to denote the number of ring atoms in said cycloaliphatic. For example, a 5-membered cycloaliphatic contains 5 ring atoms.

As used herein, the term "cycloalkyl" means a saturated free radical having at least 3 to 9 carbon atoms (i.e. ring atoms) that form a ring. Exemplary cycloalkyl groups include cyclopropyl, cyclobutyl, cyclopentyl and cyclohexyl. It will be appreciated that the cycloalkyl group may be monocyclic or multicyclic (e.g. fused, bridged or spirocyclic systems). In the case of multicyclic cycloalkyl groups, there are further rings, e.g. 1, 2, 3, or more, further rings, all of which contain from 3 to 9 carbon atoms (i.e. ring atoms). Exemplary cycloalkyl groups having such further rings include decalinyl (bicyclo[4.4.0]decanyl) and spiro[5.5]undecanyl.

As used herein, the term "cycloalkenyl" means a partially or fully unsaturated free radical having at least 3 to 9 carbon atoms (i.e. ring atoms) that form a ring. The term "cycloalkenyl" is not intended to encompass cyclic groups having significant aromatic character. Exemplary cycloalkenyl groups include cyclobutenyl, cyclopentenyl, cyclohexenyl and cycloheptenyl. It will be appreciated that the cycloalkenyl group may be monocyclic or multicyclic (e.g. fused, bridged or spirocyclic systems). In the case of multicyclic cycloalkenyl groups, there are further rings, e.g. 1, 2, 3, or more, further rings, all of which contain from 3 to 9 carbon atoms (i.e. ring atoms) and which may themselves be saturated or partially or fully unsaturated. Exemplary cycloalkenyl groups having such further rings include spiro [5.5]undecenyl and octahydronaphthalenyl.

As used herein, the term "aryl" means an aromatic free radical having at least 6 carbon atoms (i.e. ring atoms) that form a ring. It will be appreciated that the aryl group may be monocyclic or multicyclic (e.g. fused, bridged or spirocyclic systems). In the case of multicyclic aryl groups, there are further rings, e.g. 1, 2, 3, or more, further rings, all of which contain at least 3 carbon atoms (i.e. ring atoms), which further rings may optionally be aromatic. Examples of aryl groups include phenyl and naphthalenyl, as well as indenyl and indanyl groups.

As used herein, the term "heterocycloalkyl" means a saturated free radical having at least 3 to 6 atoms (i.e. ring atoms) that form a ring, wherein 1 to 5 of said ring atoms are carbon and the remaining 1 to 5 ring atom(s) (i.e. hetero ring atom(s)) are selected independently from the group consisting of nitrogen, sulphur and oxygen. Exemplary heterocycloalkyl groups include aziridinyl, pyrrolidinyl, piperidinyl, morpholinyl and piperazinyl. In the case of multicyclic heterocycloalkyl groups, there are further rings, e.g. 1, 2, 3, or more, further rings, all of which contain from 3 to 6 ring atoms selected from carbon, nitrogen, sulphur and oxygen. Multicyclic heterocycloalkyl rings include fused, bridged and spirocyclic ring systems. Exemplary heterocycloalkyl groups having such further rings include 2-azabicyclo[3.3.0] octanyl and 3,9-diazaspiro[5.5]undecanyl.

As used herein, the term "heterocycloalkenyl" means a partially or fully unsaturated free radical having at least 3 to 6 atoms (i.e. ring atoms) that form a ring, wherein 1 to 5 of said ring atoms are carbon and the remaining 1 to 5 ring atom(s) (i.e. hetero ring atom(s)) are selected independently from the group consisting of nitrogen, sulphur and oxygen. Exemplary heterocycloalkenyl groups include tetrahydropyridyl. In the case of multicyclic heterocycloalkenyl groups, there are further rings, e.g. 1, 2, 3, or more, further rings, all of which contain from 3 to 6 ring atoms selected from carbon, nitrogen, sulphur and oxygen. Said further rings may be saturated, or partially or fully unsaturated. Multicyclic heterocycloalkenyl groups include fused, bridged and spirocyclic ring systems. Exemplary heterocycloalkenyl groups having such further rings include 2,3-dihydroindolyl and 5,6-dihydroindolyl.

As used herein, the term "heteroaryl" means an aromatic free radical typically containing from 6 to 10 ring atoms, wherein 1 to 9 of said ring atoms are carbon and the remaining 1 to 9 ring atom(s) (i.e. hetero ring atom(s)) are selected independently from the group consisting of nitrogen, sulphur and oxygen. It will be appreciated that the heteroaryl group may be monocyclic or multicyclic (e.g. fused, bridged or spirocyclic systems). In the case of multicyclic heteroaryl groups, there are further rings, e.g. 1, 2, 3, or more, further rings, all of which contain at least 3 atoms (i.e. ring atoms), which further rings may optionally be aromatic. Examples of heteroaryl groups include monocyclic groups such as pyrrolyl, pyridyl, pyrazinyl, pyridazinyl, imidazolyl and N-pyridin-4-onyl, as well as multicyclic groups such as benzofuranyl, benzothiophenyl, benzoxazolyl, indolyl, pyrrolopyridinyl, quinolinyl, pteridinyl and 2-oxobenzimidazolyl.

As used herein, the terms "halo" and "halogen" mean fluorine, chlorine, bromine, or iodine. These terms are used interchangeably and may refer to a halogen free radical group or to a halogen atom as such. Those of skill in the art will readily be able to ascertain the identification of which in view of the context in which this term is used in the present disclosure.

As used herein, the term "CN" mean a free radical having a carbon atom linked to a nitrogen atom via a triple bond. The CN radical is attached via its carbon atom.

As used herein, the term "oxo" means a free radical wherein an oxygen atom is connected to the atom bearing this radical via a double bond. For example, where a carbon atom carries an oxo radical it forms a carbon-oxygen double bond. It will be appreciated that not all atoms within a given structure can be substituted by oxo, and that this will depend on the free valency of the atom to be substituted. For example, in the compounds of formula (I) disclosed herein, the 1-, 3- and 5-positions of the bicyclo[3.1.0]hexane moiety, each of which has one free valency, cannot be substituted by oxo, whereas the 2- and 4-positions of the bicyclo [3.1.0]hexane moiety, each of which has two free valencies, can be substituted by oxo.

As used herein, the term "amide" generally means a free radical having a nitrogen atom bonded directly to a carbonyl (C=O) group. The term is intended, generally, to encompass primary, secondary and tertiary amide radicals. "amide" radicals are attached via their carbonyl carbon atom.

As used herein, the term "sulfonamide" means an amino group which is directly bonded to a sulfonyl group, e.g. —NHS(O)$_2$—. As used herein, the term "sulfonyl" means a free radical containing a sulphur atom which participates in two double bonds with oxygen atoms, i.e. it contains a group —S(=O)$_2$—. The "sulfonyl" radical is attached via the said sulphur atom.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Compositions and methods provided herein may be combined with one or more of any of the other compositions and methods provided herein.

The following abbreviations are used herein:
° C.=Celsius
$^1$H-NMR=proton nuclear magnetic resonance
ACN=acetonitrile
ADDP=1,1'-(azodicarbonyl)dipiperidine
Pd$_2$(dba)$_3$=tris(dibenzylideneacetone)dipalladium(0)
DCM=dichloromethane
DEAD=diethyl azodicarboxylate
DIAD=diisopropyl azodicarboxylate
DIBAL=diisobutylaluminum hydride
DIEA=N,N-diisopropylethylamine
DMEM=Dulbecco's Modified Eagle's Medium
DMF=dimethylformamide
DMP=Dess-Martin periodinane
DMSO=dimethyl sulfoxide
dppf=1,1'-ferrocenediyl-bis(diphenylphosphine)
DTBAD=(E)-di-tert-butyl diazene-1,2-dicarboxylate
EDC=1-Ethyl-3-(3-dimethylaminopropyl)carbodiimide
ES$^+$=electrospray positive ionization
EtOAc=ethyl acetate
FBS=Fetal Bovine Serum
h=hour
HAND=HIV-associated neurological disorders
HATU=1-[bis(dimethylamino)methylene]-1H-1,2,3-triazolo[4,5-b]pyridinium 3-oxide hexafluorophosphate
HIV=human immunodeficiency virus
HOAt=3-hydroxy-1,2,3-triazolo[4,5-b]pyridine
HOBt=hydroxybenzotriazole
HPLC=high pressure liquid chromatography
Hz=hertz
IDO1/IDO2=indoleamine 2,3-dioxygenase
IFN=interferon
KYN=kynurenine
LAH=Lithium aluminium hydride (LiAlH$_4$)
LiHMDS/LHDMS=Lithium bis(trimethylsilyl)amide
L-TRP=L-tryptophan
M=molar
MeCN=acetonitrile
MHz=megahertz;
min=minute
MS=mass spectrometry
PPTS=pyridinium p-toluenesulfonate
PTSA=p-toluenesulfonic acid
QUIN=quinolic acid
rt/RT=room temperature
SFC=supercritical fluid chromatography
TBAF=tetra-n-butylammonium fluoride
TBDPS=tert-butyldiphenylsilyl
TDO=tryptophan dioxygenase
TEA=triethylamine
TEMPO=2,2,6,6-tetramethylpiperidine 1-oxyl
TFA=trifluoroacetic acid
THF=tetrahydrofuran
TMS-CN=trimethylsilyl cyanide
TMZ=temozolomide Compounds The present invention relates to compounds useful as inhibitors of IDO1, IDO2 and/or TDO. In one aspect, the invention provides a compound characterised by formula (VII),

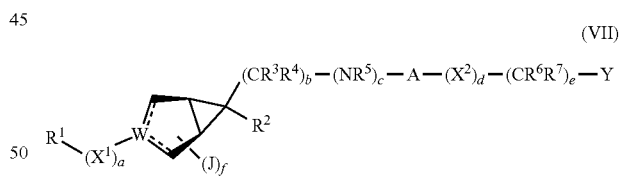

(VII)

or a pharmaceutically acceptable salt or prodrug thereof, wherein one but not both of the dashed bonds may optionally be a carbon-carbon double bond, and wherein:

W is selected from C, CH, and N;
a is 0 or 1;
b is 0, 1 or 2;
c is 0 or 1;
d is 0 or 1;
e is 0 or 1;
f is 0, 1 or 2;
A is selected from O, C(O), S(O)$_2$, and NH;
J is in each case independently selected from oxo, OH, CN, halogen, and C$_{1-3}$-alkyl;
$X^1$ is selected from C($R^8$)($R^9$), N($R^{10}$), O, and S;
$X^2$ is selected from C($R^{11}$)($R^{12}$), N($R^{13}$), and O;

Y is selected from
- $C_{6-10}$-aryl,
- 5- to 10-membered heteroaryl comprising 1, 2, 3 or 4 ring heteroatoms selected from N, S and O, and
- 3- to 10-membered cycloaliphatic,
- wherein said aryl, heteroaryl, and cycloaliphatic are optionally substituted by one or more groups independently selected from $R^{14}$;

$R^1$ is selected from
- H,
- $(G)_n$-$(C_{1-6}$-alkyl),
- $(G)_n$-$(C_{3-8}$-cycloalkyl),
- $N_3$,
- $(G)_n$-heterocycloalkyl, wherein said heterocycloalkyl is a 3- to 6-membered heterocycloalkyl comprising 1, 2 or 3 ring heteroatoms selected from N, S and O,
- $(G)_n$-$(C_{5-8}$-cycloalkenyl),
- $(G)_n$-heterocycloalkenyl, wherein said heterocycloalkenyl is a 5- to 6-membered heterocycloalkenyl comprising 1, 2 or 3 ring heteroatoms selected from N, S and O,
- $(G)_n$-$(C_{6-10}$-aryl), and
- $(G)_n$-heteroaryl, wherein said heteroaryl is a 5- to 10-membered heteroaryl comprising 1, 2, 3 or 4 ring heteroatoms selected from N, S and O,
- wherein G in each case is independently selected from $C(R^8)(R^9)$, $C(O)$, $S(O)_2$, $C(O)NR^{10}$, and $S(O)_2NR^{10}$; and wherein n in each case is either 0 or 1, and
- wherein said alkyl, cycloalkyl, heterocycloalkyl, cycloalkenyl, heterocycloalkenyl, aryl and heteroaryl are optionally substituted by one or more groups independently selected from $R^{15}$;

$R^2$, $R^3$, $R^4$, $R^6$, $R^7$, R, $R^9$, $R^{11}$ and $R^{12}$ are in each case independently selected from
- H,
- halogen,
- CN,
- OH,
- $(C_{0-4}$-alkyl)-$SO_2R^{17}$,
- $(C_{0-4}$-alkyl)-$N(R^{18})_2$,
- $(C_{0-4}$-alkyl)-$NHCOR^{19}$,
- $(C_{0-4}$-alkyl)-$NHSO_2R^{20}$,
- $(C_{0-4}$-alkyl)-$CON(R^{21})_2$,
- $(C_{0-4}$-alkyl)-$CO_2R^{22}$,
- $(C_{0-4}$-alkyl)-$SO_2N(R^{23})_2$,
- $C_{1-6}$-alkyl,
- O—$(C_{1-6}$-alkyl),
- $C_{3-8}$-cycloalkyl,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O, or
- one or both geminal $R^3$ and $R^4$ pairs, taken together with the carbon atom to which they are attached, independently forms a 3- to 6-membered cycloalkyl group or a 3- to 6-membered heterocycloalkyl group which comprises 1, 2 or 3 ring heteroatoms selected from N, S and O,
- wherein said alkyl, cycloalkyl, heterocycloalkyl, cycloalkenyl, heterocycloalkenyl, aryl and heteroaryl are optionally substituted by one or more groups independently selected from $R^{16}$;

$R^5$, $R^{10}$ and $R^{13}$ are in each case independently selected from
- H,
- $C_{1-6}$-alkyl,
- $C_{3-8}$-cycloalkyl,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O,
- optionally wherein one of $R^3$ and $R^5$, together with one of $R^{11}$ and $R^{13}$ and the atoms intervening between them, may form a 5- or 6-membered cycloalkyl, cycloalkenyl or aryl group, or a 5- or 6-membered heterocycloalkyl, heterocycloalkenyl or heteroaryl group which comprises 1, 2, 3 or 4 ring heteroatoms selected from N, S and O;
- wherein said alkyl, cycloalkyl, heterocycloalkyl, cycloalkenyl, heterocycloalkenyl, aryl and heteroaryl are optionally substituted by one or more groups independently selected from $R^{24}$;

any two $R^{14}$ substituents on adjacent ring atoms may, together with the ring atoms to which they are attached, independently form a 5- or 6-membered cyclic group optionally comprising 1, 2 or 3 ring heteroatoms selected from N, S and O, which cyclic group is optionally substituted by one or more groups independently selected from halogen, $C_{1-4}$-alkyl and $C_{1-4}$-haloalkyl, and any remaining $R^{14}$ is in each case independently selected from
- halogen,
- CN,
- OH,
- $C_{1-6}$-alkyl,
- O—$(C_{1-6}$-alkyl),
- O—$(C_{1-6}$-haloalkyl),
- O—$(C_{1-6}$-alkyl-$C_{3-6}$-cycloalkyl),
- $(C_{0-4}$-alkyl)-$SO_2R^{17}$,
- $(C_{0-4}$-alkyl)-$N(R^{18})_2$,
- $(C_{0-4}$-alkyl)-$NHCOR^{19}$,
- $(C_{0-4}$-alkyl)-$NHSO_2R^{20}$,
- $(C_{0-4}$-alkyl)-$CON(R^{21})_2$,
- $(C_{0-4}$-alkyl)-$CO_2R^{22}$,
- $(C_{0-4}$-alkyl)-$SO_2N(R^{23})_2$, and
- $(C_{0-4}$-alkyl)-heteroaryl,
- wherein said heteroaryl is a 5- to 10-membered heteroaryl comprising 1, 2, 3 or 4 ring heteroatoms selected from N, S and O;

$R^{15}$ is in each case independently selected from
- halogen,
- CN,
- OH,
- oxo,
- $NO_2$,
- $C_{1-6}$-alkyl,
- $C_{2-6}$-alkenyl,
- $C_{2-6}$-alkynyl,
- $(C_{0-4}$-alkyl)-O—$(C_{1-6}$-alkyl),
- $(C_{0-4}$-alkyl)-$SO_2R^{17}$,
- $(C_{0-4}$-alkyl)-$N(R^{18})_2$,
- $(C_{0-4}$-alkyl)-$NHCOR^{19}$,
- $(C_{0-4}$-alkyl)-$NHSO_2R^{20}$,
- $(C_{0-4}$-alkyl)-$CON(R^{21})_2$,
- $(C_{0-4}$-alkyl)-$CO_2R^{22}$,
- $(C_{0-4}$-alkyl)-$SO_2N(R^{23})_2$, ($C_{0-4}$-alkyl)-heteroaryl, wherein said heteroaryl is a 5- to 10-membered heteroaryl comprising 1, 2, 3 or 4 ring heteroatoms selected from N, S and O,
($C_{0-4}$-alkyl)-heterocycloalkenyl, wherein said heterocycloalkenyl is a 5- to 10-membered heterocycloalkenyl comprising 1 or 2 ring heteroatoms selected from N and O,
($C_{0-4}$-alkyl)-heterocycloalkyl, wherein said heterocycloalkyl is a 4- to 6-membered heterocycloalkyl comprising 1 or 2 ring heteroatoms selected from N and O,
($C_{0-4}$-alkyl)-aryl, wherein said aryl is a 6- to 10-membered aryl,
($C_{0-4}$-alkyl)-cycloalkenyl, wherein said cycloalkenyl is a 5- to 8-membered cycloalkenyl, and
($C_{0-4}$-alkyl)-cycloalkyl, wherein said cycloalkyl is a 3- to 8-membered cycloalkyl,
wherein said alkyl, alkenyl, alkynyl, heteroaryl, heterocycloalkenyl, heterocycloalkyl, aryl, cycloalkenyl and cycloalkyl are optionally substituted by one or more groups independently selected from halogen, OH, O—($C_{1-4}$-alkyl), oxo, C(O)—($C_{1-4}$-alkyl), C(O)O—($C_{1-4}$-alkyl), and $NH_2$;
$R^{16}$ and $R^{24}$ are in each case independently selected from halogen,
CN,
OH,
$C_{1-6}$-alkyl,
O—($C_{1-6}$-alkyl),
($C_{0-4}$-alkyl)-$SO_2R^{17}$,
($C_{0-4}$-alkyl)-N($R^8$)$_2$,
($C_{0-4}$-alkyl)-NHCOR$^{19}$,
($C_{0-4}$-alkyl)-NHSO$_2$R$^{20}$,
($C_{0-4}$-alkyl)-CON($R^{21}$)$_2$,
($C_{0-4}$-alkyl)-CO$_2$R$^{22}$,
($C_{0-4}$-alkyl)-SO$_2$N($R^{23}$)$_2$,
($C_{0-4}$-alkyl)-heteroaryl, wherein said heteroaryl is a 5- to 10-membered heteroaryl comprising 1, 2, 3 or 4 ring heteroatoms selected from N, S and O,
($C_{0-4}$-alkyl)-heterocycloalkenyl, wherein said heterocycloalkenyl is a 5- to 6-membered heterocycloalkenyl comprising 1 or 2 ring heteroatoms selected from N and O,
($C_{0-4}$-alkyl)-heterocycloalkyl, wherein said heterocycloalkyl is a 4- to 6-membered heterocycloalkyl comprising 1 or 2 ring heteroatoms selected from N and O,
($C_{0-4}$-alkyl)-aryl, wherein said aryl is a 6- to 10-membered aryl, ($C_{0-4}$-alkyl)-cycloalkenyl, wherein said cycloalkenyl is a 5- to 8-membered cycloalkenyl, and
($C_{0-4}$-alkyl)-cycloalkyl, wherein said cycloalkyl is a 3- to 8-membered cycloalkyl,
wherein said alkyl, heteroaryl, heterocycloalkenyl, heterocycloalkyl, aryl, cycloalkenyl and cycloalkyl are optionally substituted by one or more groups independently selected from halogen; and
$R^{17}$ to $R^{23}$ are in each case independently selected from H,
$C_{1-6}$-alkyl,
$C_{3-8}$-cycloalkyl,
3- to 6-membered heterocycloalkyl comprising 1, 2 or 3 ring heteroatoms selected from N, S and O,
$C_{5-8}$-cycloalkenyl,
5- to 6-membered heterocycloalkenyl comprising 1, 2 or 3 ring heteroatoms selected from N, S and O,
$C_{6-10}$-aryl, and
5- to 10-membered heteroaryl comprising 1, 2, 3 or 4 ring heteroatoms selected from N, S and O,
wherein any pair of $R^{18}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O,
wherein any pair of $R^{21}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O,
wherein any pair of $R^{23}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O,
wherein each said alkyl, cycloalkyl, heterocycloalkyl, cycloalkenyl, heterocycloalkenyl, aryl and heteroaryl is optionally and independently substituted by one or more groups independently selected from halogen, OH, $C_{1-6}$-alkyl and $C_{1-6}$-haloalkyl.

In embodiments, A is selected from O, C(O), and S(O)$_2$; and Y is selected from $C_{6-10}$-aryl and 5- to 10-membered heteroaryl comprising 1, 2, 3 or 4 ring heteroatoms selected from N, S and O, wherein said aryl and heteroaryl are optionally substituted by one or more groups independently selected from $R^{14}$.

In embodiments, both of the dashed bonds denote single bonds. In this case, W is selected from CH and N. In other embodiments, one of the dashed bonds is a carbon-carbon double bond. In this case, the other dashed bond is a carbon-carbon single bond, and W denotes C.

In other aspects and embodiments, the invention provides a compound characterised by formula (VI),

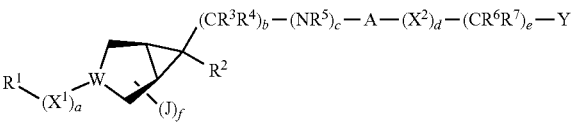

(VI)

or a pharmaceutically acceptable salt or prodrug thereof, wherein:
W is selected from CH, and N;
a is 0 or 1;
b is 0, 1 or 2;
c is 0 or 1;
d is 0 or 1;
e is 0 or 1;
f is 0, 1 or 2;
A is selected from O, C(O), and S(O)$_2$;
J is in each case independently selected from oxo, OH, CN, halogen, and $C_{1-3}$-alkyl;
$X^1$ is selected from C($R^8$)($R^9$), N($R^{10}$), O, and S;
$X^{21}$ is selected from C($R^{11}$)($R^{12}$), N($R^{13}$), and O;
Y is selected from
$C_{6-10}$-aryl, and
5- to 10-membered heteroaryl comprising 1, 2, 3 or 4 ring heteroatoms selected from N, S and O, wherein said aryl and heteroaryl are optionally substituted by one or more groups independently selected from $R^{14}$;

$R^1$ is selected from
- H,
- $(G)_n$-($C_{1-6}$-alkyl),
- $(G)_n$-($C_{3-8}$-cycloalkyl),
- $N_3$,
- $(G)_n$-heterocycloalkyl, wherein said heterocycloalkyl is a 3- to 6-membered heterocycloalkyl comprising 1, 2 or 3 ring heteroatoms selected from N, S and O,
- $(G)_n$-($C_{5-8}$-cycloalkenyl),
- $(G)_n$-heterocycloalkenyl, wherein said heterocycloalkenyl is a 5- to 6-membered heterocycloalkenyl comprising 1, 2 or 3 ring heteroatoms selected from N, S and O,
- $(G)_n$-($C_{6-10}$-aryl), and
- $(G)_n$-heteroaryl, wherein said heteroaryl is a 5- to 10-membered heteroaryl comprising 1, 2, 3 or 4 ring heteroatoms selected from N, S and O,
- wherein G in each case is independently selected from $C(R^8)(R^9)$, $C(O)$, $S(O)_2$, $C(O)NR^{10}$, and $S(O)_2NR^{10}$; and wherein n in each case is either 0 or 1, and
- wherein said alkyl, cycloalkyl, heterocycloalkyl, cycloalkenyl, heterocycloalkenyl, aryl and heteroaryl are optionally substituted by one or more groups independently selected from $R^{15}$;

$R^2$, $R^3$, $R^4$, $R^6$, $R^7$, $R^8$, $R^9$, $R^{11}$ and $R^{12}$ are in each case independently selected from
- H,
- halogen,
- CN,
- OH,
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$,
- $C_{1-6}$-alkyl,
- O—($C_{1-6}$-alkyl),
- $C_{3-8}$-cycloalkyl,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O, or
- one or both geminal $R^3$ and $R^4$ pairs, taken together with the carbon atom to which they are attached, independently forms a 3- to 6-membered cycloalkyl group or a 3- to 6-membered heterocycloalkyl group which comprises 1, 2 or 3 ring heteroatoms selected from N, S and O,
- wherein said alkyl, cycloalkyl, heterocycloalkyl, cycloalkenyl, heterocycloalkenyl, aryl and heteroaryl are optionally substituted by one or more groups independently selected from $R^{16}$;

$R^5$, $R^{10}$ and $R^{13}$ are in each case independently selected from
- H,
- $C_{1-6}$-alkyl,
- $C_{3-8}$-cycloalkyl,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O,
- optionally wherein one of $R^3$ and $R^5$, together with one of $R^{11}$ and $R^{13}$ and the atoms intervening between them, may form a 5- or 6-membered cycloalkyl, cycloalkenyl or aryl group, or a 5- or 6-membered heterocycloalkyl, heterocycloalkenyl or heteroaryl group which comprises 1, 2, 3 or 4 ring heteroatoms selected from N, S and O;
- wherein said alkyl, cycloalkyl, heterocycloalkyl, cycloalkenyl, heterocycloalkenyl, aryl and heteroaryl are optionally substituted by one or more groups independently selected from $R^{24}$;

any two $R^{14}$ substituents on adjacent ring atoms may, together with the ring atoms to which they are attached, independently form a 5- or 6-membered cyclic group optionally comprising 1, 2 or 3 ring heteroatoms selected from N, S and O, which cyclic group is optionally substituted by one or more groups independently selected from halogen, $C_{1-4}$-alkyl and $C_{1-4}$-haloalkyl, and any remaining $R^{14}$ is in each case independently selected from
- halogen,
- CN,
- OH,
- $C_{1-6}$-alkyl,
- O—($C_{1-6}$-alkyl),
- O—($C_{1-6}$-haloalkyl),
- O—($C_{1-6}$-alkyl-$C_{3-6}$-cycloalkyl),
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$, and
- $(C_{0-4}$-alkyl$)$-heteroaryl,
- wherein said heteroaryl is a 5- to 10-membered heteroaryl comprising 1, 2, 3 or 4 ring heteroatoms selected from N, S and O;

$R^{15}$ is in each case independently selected from
- halogen,
- CN,
- OH,
- oxo,
- $NO_2$,
- $C_{1-6}$-alkyl,
- $C_{2-6}$-alkenyl,
- $C_{2-6}$-alkynyl,
- $(C_{0-4}$-alkyl$)$-O—($C_{1-6}$-alkyl),
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$,
- $(C_{0-4}$-alkyl$)$-heteroaryl, wherein said heteroaryl is a 5- to 10-membered heteroaryl comprising 1, 2, 3 or 4 ring heteroatoms selected from N, S and O, ($C_{0-4}$-alkyl)-heterocycloalkenyl, wherein said heterocycloalkenyl is a 5- to 10-membered heterocycloalkenyl comprising 1 or 2 ring heteroatoms selected from N and O, ($C_{0-4}$-alkyl)-heterocycloalkyl, wherein said heterocycloalkyl is a 4- to 6-membered heterocycloalkyl comprising 1 or 2 ring heteroatoms selected from N and O, ($C_{0-4}$-alkyl)-aryl, wherein said aryl is a 6- to 10-membered aryl, ($C_{0-4}$-alkyl)-cycloalkenyl, wherein said cycloalkenyl is a 5- to 8-membered cycloalkenyl, and ($C_{0-4}$-alkyl)-cycloalkyl, wherein said cycloalkyl is a 3- to 8-membered cycloalkyl, wherein said alkyl, alkenyl, alkynyl, heteroaryl, heterocycloalkenyl, heterocycloalkyl, aryl, cycloalkenyl and cycloalkyl are optionally substituted by one or more groups independently selected from halogen, OH, O—($C_{1-4}$-alkyl), oxo, C(O)—($C_{1-4}$-alkyl), C(O)O—($C_{1-4}$-alkyl), and $NH_2$;

$R^{16}$ and $R^{24}$ are in each case independently selected from halogen,
CN,
OH,
$C_{1-6}$-alkyl,
O—($C_{1-6}$-alkyl),
($C_{0-4}$-alkyl)-$SO_2R^{17}$,
($C_{0-4}$-alkyl)-$N(R^{18})_2$,
($C_{0-4}$-alkyl)-$NHCOR^{19}$,
($C_{0-4}$-alkyl)-$NHSO_2R^{20}$,
($C_{0-4}$-alkyl)-$CON(R^{21})_2$,
($C_{0-4}$-alkyl)-$CO_2R^{22}$,
($C_{0-4}$-alkyl)-$SO_2N(R^{23})_2$,
($C_{0-4}$-alkyl)-heteroaryl, wherein said heteroaryl is a 5- to 10-membered heteroaryl comprising 1, 2, 3 or 4 ring heteroatoms selected from N, S and O,
($C_{0-4}$-alkyl)-heterocycloalkenyl, wherein said heterocycloalkenyl is a 5- to 6-membered heterocycloalkenyl comprising 1 or 2 ring heteroatoms selected from N and O,
($C_{0-4}$-alkyl)-heterocycloalkyl, wherein said heterocycloalkyl is a 4- to 6-membered heterocycloalkyl comprising 1 or 2 ring heteroatoms selected from N and O,
($C_{0-4}$-alkyl)-aryl, wherein said aryl is a 6- to 10-membered aryl,
($C_{0-4}$-alkyl)-cycloalkenyl, wherein said cycloalkenyl is a 5- to 8-membered cycloalkenyl, and
($C_{0-4}$-alkyl)-cycloalkyl, wherein said cycloalkyl is a 3- to 8-membered cycloalkyl, wherein said alkyl, heteroaryl, heterocycloalkenyl, heterocycloalkyl, aryl, cycloalkenyl and cycloalkyl are optionally substituted by one or more groups independently selected from halogen; and $R^{17}$ to $R^{23}$ are in each case independently selected from
H,
$C_{1-6}$-alkyl,
$C_{3-8}$-cycloalkyl,
3- to 6-membered heterocycloalkyl comprising 1, 2 or 3 ring heteroatoms selected from N, S and O,
$C_{5-8}$-cycloalkenyl,
5- to 6-membered heterocycloalkenyl comprising 1, 2 or 3 ring heteroatoms selected from N, S and O,
$C_{6-10}$-aryl, and
5- to 10-membered heteroaryl comprising 1, 2, 3 or 4 ring heteroatoms selected from N, S and O, wherein any pair of $R^{18}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O, wherein any pair of $R^{21}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O, wherein any pair of $R^{23}$ groups attached to the same nitrogen atom, taken together with the intervening nitrogen atom, may form a 3- to 10-membered heterocycloalkyl or heterocycloalkenyl group comprising 1, 2 or 3 ring heteroatoms selected from N, S and O, wherein each said alkyl, cycloalkyl, heterocycloalkyl, cycloalkenyl, heterocycloalkenyl, aryl and heteroaryl is optionally and independently substituted by one or more groups independently selected from halogen, OH, $C_{1-6}$-alkyl and $C_{1-6}$-haloalkyl.

In other aspects and embodiments, the invention provides a compound characterised by formula (I),

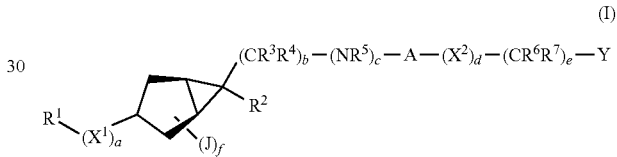

(I)

or a pharmaceutically acceptable salt or prodrug thereof, wherein:
a, b, c, d, e, f, A, J, $X^1$, $X^2$, Y, and $R^1$ to $R^7$ are as defined herein.

In other aspects and embodiments, the invention provides a compound characterised by formula (I),

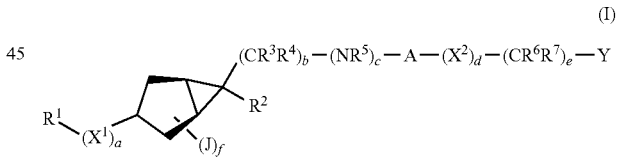

(I)

or a pharmaceutically acceptable salt or prodrug thereof, wherein:
a is 0 or 1;
b is 0, 1 or 2;
c is 0 or 1;
d is 0 or 1;
e is 0 or 1;
f is 0, 1 or 2;
A is selected from O, C(O), and $S(O)_2$;
J is in each case independently selected from oxo, OH, CN, halogen, and $C_{1-3}$-alkyl;
$X^1$ is selected from $C(R^8)(R^9)$, $N(R^{10})$, O, and S;
$X^2$ is selected from $C(R^{11})(R^{12})$, $N(R^{13})$, and O;
Y is selected from
$C_{6-10}$-aryl, and
5- to 10-membered heteroaryl comprising 1, 2 or 3 ring heteroatoms selected from N, S and O, wherein said aryl and heteroaryl are optionally substituted by one or more groups independently selected from $R^{14}$;

$R^1$ is selected from
- H,
- $C_{1-6}$-alkyl,
- $C_{3-8}$-cycloalkyl,
- $N_3$,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O,
- wherein said alkyl, cycloalkyl, heterocycloalkyl, cycloalkenyl, heterocycloalkenyl, aryl and heteroaryl are optionally substituted by one or more groups independently selected from $R^{15}$;

$R^2$, $R^3$, $R^4$, $R^6$, $R^7$, $R^8$, $R^9$, $R^{11}$ and $R^{12}$ are in each case independently selected from
- H,
- halogen,
- CN,
- OH,
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$,
- $C_{1-6}$-alkyl, O—$(C_{1-6}$-alkyl$)$,
- $C_{3-8}$-cycloalkyl,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O, or
- one or both geminal $R^3$ and $R^4$ pairs, taken together with the carbon atom to which they are attached, independently forms a 3- to 6-membered cycloalkyl group or a 3- to 6-membered heterocycloalkyl group which comprises 1, 2 or 3 ring heteroatoms selected from N, S and O,
- wherein said alkyl, cycloalkyl, heterocycloalkyl, cycloalkenyl, heterocycloalkenyl, aryl and heteroaryl are optionally substituted by one or more groups independently selected from $R^{16}$;

$R^5$, $R^{10}$ and $R^{13}$ are in each case independently selected from
- H,
- $C_{1-6}$-alkyl,
- $C_{3-8}$-cycloalkyl,
- 3- to 6-membered heterocycloalkyl comprising 1, 2 or 3 ring heteroatoms selected from N, S and O,
- $C_{5-8}$-cycloalkenyl,
- 5- to 6-membered heterocycloalkenyl comprising 1, 2 or 3 ring heteroatoms selected from N, S and O,
- $C_{6-10}$-aryl, and
- 5- to 10-membered heteroaryl comprising 1, 2, 3 or 4 ring heteroatoms selected from N, S and O, optionally wherein one of $R^3$ and $R^5$, together with one of $R^{11}$ and $R^{13}$ and the atoms intervening between them, may form a 5- or 6-membered cycloalkyl, cycloalkenyl or aryl group, or a 5- or 6-membered heterocycloalkyl, heterocycloalkenyl or heteroaryl group which comprises 1, 2, 3 or 4 ring heteroatoms selected from N, S and O;

wherein said alkyl, cycloalkyl, heterocycloalkyl, cycloalkenyl, heterocycloalkenyl, aryl and heteroaryl are optionally substituted by one or more groups independently selected from $R^{24}$;

any two $R^{14}$ substituents on adjacent ring atoms may, together with the ring atoms to which they are attached, independently form a 5- or 6-membered cyclic group optionally comprising 1, 2 or 3 ring heteroatoms selected from N, S and O, which cyclic group is optionally substituted by one or more groups independently selected from halogen, $C_{1-4}$-alkyl and $C_{1-4}$-haloalkyl, and any remaining $R^{14}$ is in each case independently selected from
- halogen,
- CN,
- OH,
- $C_{1-6}$-alkyl,
- O—$(C_{1-6}$-alkyl$)$,
- O—$(C_{1-6}$-haloalkyl$)$,
- O—$(C_{1-6}$-alkyl-$C_{3-6}$-cycloalkyl$)$,
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$, and
- $(C_{0-4}$-alkyl$)$-heteroaryl,
- wherein said heteroaryl is a 5- to 10-membered heteroaryl comprising 1, 2, 3 or 4 ring heteroatoms selected from N, S and O;

$R^{15}$ is in each case independently selected from
- halogen,
- CN,
- OH,
- oxo,
- $C_{1-6}$-alkyl,
- O—$(C_{1-6}$-alkyl$)$,
- $(C_{0-4}$-alkyl$)$-$SO_2R^{17}$,
- $(C_{0-4}$-alkyl$)$-$N(R^8)_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$,
- $(C_{0-4}$-alkyl$)$-heteroaryl, wherein said heteroaryl is a 5- to 10-membered heteroaryl comprising 1, 2, 3 or 4 ring heteroatoms selected from N, S and O,
- $(C_{0-4}$-alkyl$)$-heterocycloalkenyl, wherein said heterocycloalkenyl is a 5- to 6-membered heterocycloalkenyl comprising 1 or 2 ring heteroatoms selected from N and O,
- $(C_{0-4}$-alkyl$)$-heterocycloalkyl, wherein said heterocycloalkyl is a 4- to 6-membered heterocycloalkyl comprising 1 or 2 ring heteroatoms selected from N and O,
- $(C_{0-4}$-alkyl$)$-aryl, wherein said aryl is a 6- to 10-membered aryl, ($C_{0-4}$-alkyl)-cycloalkenyl, wherein said cycloalkenyl is a 5- to 8-membered cycloalkenyl, and ($C_{0-4}$-alkyl)-cycloalkyl, wherein said cycloalkyl is a 3- to 8-membered cycloalkyl, wherein said alkyl, heteroaryl, heterocycloalkenyl, heterocycloalkyl, aryl, cycloalkenyl and cycloalkyl are optionally substituted by one or more groups independently selected from halogen, OH and $NH_2$;

$R^{16}$ and $R^{24}$ are in each case independently selected from
halogen,
CN,
OH,
$C_{1-6}$-alkyl,
O—($C_{1-6}$-alkyl),
($C_{0-4}$-alkyl)-$SO_2R^{17}$,
($C_{0-4}$-alkyl)-$N(R^{18})_2$,
($C_{0-4}$-alkyl)-$NHCOR^{19}$,
($C_{0-4}$-alkyl)-$NHSO_2R^{20}$,
($C_{0-4}$-alkyl)-$CON(R^{21})_2$,
($C_{0-4}$-alkyl)-$CO_2R^{22}$,
($C_{0-4}$-alkyl)-$SO_2N(R^{23})_2$,
($C_{0-4}$-alkyl)-heteroaryl, wherein said heteroaryl is a 5- to 10-membered heteroaryl comprising 1, 2, 3 or 4 ring heteroatoms selected from N, S and O,
($C_{0-4}$-alkyl)-heterocycloalkenyl, wherein said heterocycloalkenyl is a 5- to 6-membered heterocycloalkenyl comprising 1 or 2 ring heteroatoms selected from N and O,
($C_{0-4}$-alkyl)-heterocycloalkyl, wherein said heterocycloalkyl is a 4- to 6-membered heterocycloalkyl comprising 1 or 2 ring heteroatoms selected from N and O,
($C_{0-4}$-alkyl)-aryl, wherein said aryl is a 6- to 10-membered aryl,
($C_{0-4}$-alkyl)-cycloalkenyl, wherein said cycloalkenyl is a 5- to 8-membered cycloalkenyl, and
($C_{0-4}$-alkyl)-cycloalkyl, wherein said cycloalkyl is a 3- to 8-membered cycloalkyl, wherein said alkyl, heteroaryl, heterocycloalkenyl, heterocycloalkyl, aryl, cycloalkenyl and cycloalkyl are optionally substituted by one or more groups independently selected from halogen; and $R^{17}$ to $R^{23}$ are in each case independently selected from
H,
$C_{1-6}$-alkyl,
$C_{3-8}$-cycloalkyl,
3- to 6-membered heterocycloalkyl comprising 1, 2 or 3 ring heteroatoms selected from N, S and O,
$C_{5-8}$-cycloalkenyl,
5- to 6-membered heterocycloalkenyl comprising 1, 2 or 3 ring heteroatoms selected from N, S and O,
$C_{6-10}$-aryl, and
5- to 10-membered heteroaryl comprising 1, 2, 3 or 4 ring heteroatoms selected from N, S and O,
wherein said alkyl, cycloalkyl, heterocycloalkyl, cycloalkenyl, heterocycloalkenyl, aryl and heteroaryl are optionally substituted by one or more groups independently selected from halogen, OH, $C_{1-6}$-alkyl and $C_{1-6}$-haloalkyl.

In one embodiment, a is 0. In another embodiment, a is 1.

In embodiments, b is 0. In other embodiments, b is 1 or 2. In one embodiment, b is 2. In another embodiment, b is 1.

In one embodiment, c is 0. In another embodiment, c is 1.

In one embodiment, d is 0. In another embodiment, d is 1.

In one embodiment, e is 0. In another embodiment, e is 1.

In one embodiment, f is 0. In other embodiments, f is 1 or 2. In one embodiment, f is 1. In another embodiment, f is 2.

In embodiments, W is CH and a is 0 or 1. In other embodiments, W is N and a is 0. In other embodiments, W is N, a is 1, and $X^1$ is $C(R^8)(R^9)$.

As will be appreciated, e.g. on inspection of formula (VI), W may optionally be substituted by a group J as defined herein. Accordingly, in embodiments: W is CH substituted by J, wherein J is selected from OH, CN, halogen, and $C_{1-3}$-alkyl; and a is 0. In other embodiments: W is CH substituted by J, wherein J is selected from OH, CN, halogen, and $C_{1-3}$-alkyl; a is 1; and $X^1$ is $C(R^8)(R^9)$. In other embodiments: W is CH substituted by J, wherein J is selected from CN and $C_{1-3}$-alkyl; a is 1; and $X^1$ is selected from $N(R^{10})$, O, and S. In other embodiments, W is CH which is not substituted by J.

In embodiments, A is selected from C(O), and $S(O)_2$. In one embodiment, A is C(O). In another embodiment, A is $S(O)_2$. In another embodiment, A is O.

In embodiments, J is in each case independently selected from OH, CN, halogen, and $C_{1-3}$-alkyl. In other embodiments, J is in each case independently selected from OH, halogen, and $C_{1-3}$-alkyl.

In embodiments, f is 1 or 2; and J is in each case independently selected from F, Cl, and OH. In other embodiments, f is 1 or 2; and J is in each case independently selected from F, and OH. In embodiments, f is 1 or 2; and J is in each case independently selected from F, and Cl. In other embodiments, f is 1 or 2; and J is F. In other embodiments, f is 1 or 2; and J is in each case independently selected from $C_{1-3}$-alkyl. In embodiments, f is 1 or 2; and J is methyl.

In embodiments, f is 1; and J is selected from F, Cl, and OH. In other embodiments, f is 1; and J is selected from F, and OH. In embodiments, f is 1; and J is selected from F, and Cl. In other embodiments, f is 1; and J is F. In other embodiments, f is 1; and J is selected from $C_{1-3}$-alkyl. In embodiments, f is 1; and J is methyl.

In one embodiment, a is 1; and $X^1$ is $C(R^8)(R^9)$. In another embodiment, a is 1; and $X^1$ is $N(R^{10})$. In one embodiment, a is 1; and $X^1$ is NH. In embodiments, a is 1; and $X^1$ is selected from O, and S. In one embodiment, a is 1; and $X^1$ is O.

In one embodiment, d is 1; and $X^2$ is $C(R^{11})(R^{12})$. In one embodiment, d is 1; and $X^2$ is $N(R^{13})$. In embodiments, d is 1; and $X^2$ is selected from O, and S. In one embodiment, d is 1; and $X^2$ is O.

In embodiments, Y is selected from
phenyl, and
5- to 10-membered heteroaryl comprising 1 or 2 ring heteroatoms selected from N, S and O,
wherein said phenyl and heteroaryl are optionally substituted by one or more groups independently selected from $R^{14}$.

In embodiments, Y is selected from phenyl, pyridyl, pyrimidinyl, pyrazinyl, pyradizinyl, isoxazolyl, benzodioxalyl, and benzothiazolyl, each of which is optionally substituted by one or more groups independently selected from $R^{14}$.

In embodiments, Y is selected from phenyl, pyridyl, pyrimidinyl, pyrazinyl, and pyradizinyl, each of which is optionally substituted by one or more groups independently selected from $R^{14}$.

In embodiments, Y is selected from phenyl, pyridyl, pyrimidinyl, pyrazinyl, and pyradizinyl, each of which is optionally substituted by one or more groups independently selected from $R^{14}$.

In one embodiment, Y is phenyl optionally substituted by one or more groups independently selected from $R^{14}$. In embodiments where said phenyl is substituted, there is a substituent at the 3-position of the phenyl (i.e. at the position meta to the bond which joins Y to the rest of the molecule). In embodiments where said phenyl is substituted, there is preferably a substituent at the 4-position of the phenyl (i.e. at the position para to the bond which joins Y to the rest of the molecule). In embodiments, Y is phenyl substituted at the 4-position by halogen and further optionally substituted at the 3-position by a group independently selected from $R^{14}$. In embodiments, Y is phenyl substituted at the 4-position by chlorine and further optionally substituted at the 3-position by a halogen (e.g. chlorine or fluorine).

In embodiments, Y is selected from 4-bromophenyl, 4-chlorophenyl, 4-fluorophenyl, 4-cyanophenyl, 4-methylphenyl, 3-chlorophenyl, 3-fluorophenyl, 3-cyanophenyl, and 3-fluoro-4-chlorophenyl. In embodiments, Y is selected from 4-bromophenyl, 4-chlorophenyl, 4-fluorophenyl, 4-cyanophenyl, and 3-fluoro-4-chlorophenyl. In embodiments, Y is selected from 4-chlorophenyl, 4-fluorophenyl, 4-cyanophenyl, and 3-fluoro-4-chlorophenyl. In embodiments, Y is selected from 4-bromophenyl, and 4-chlorophenyl. In one embodiment, Y is 4-chlorophenyl.

In embodiments, Y is selected from:

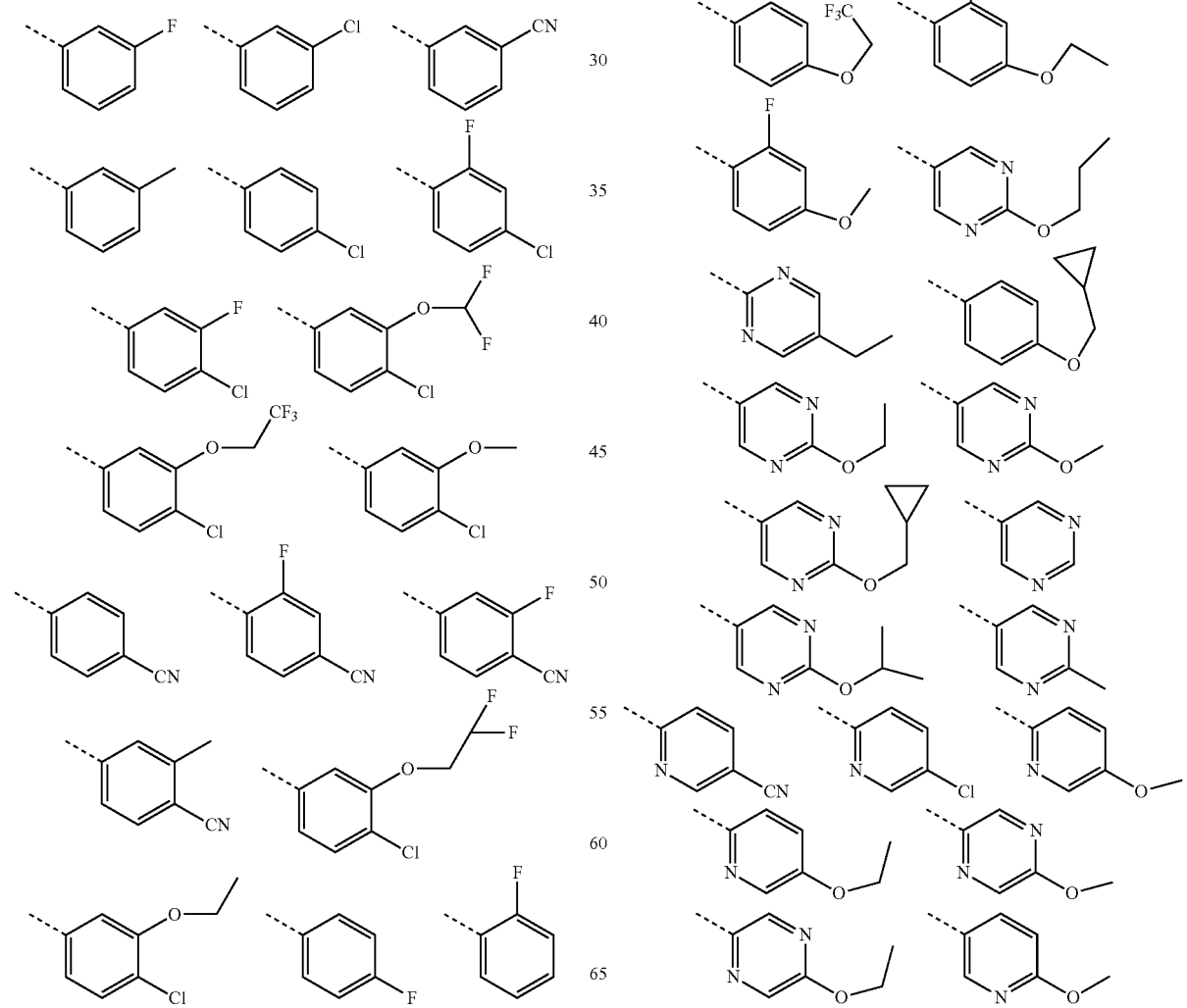

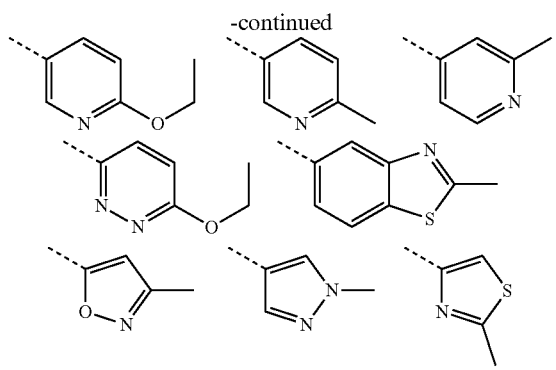
wherein the dashed bonds denotes the point of attachment of Y to the rest of the molecule.
In embodiments, Y is selected from:
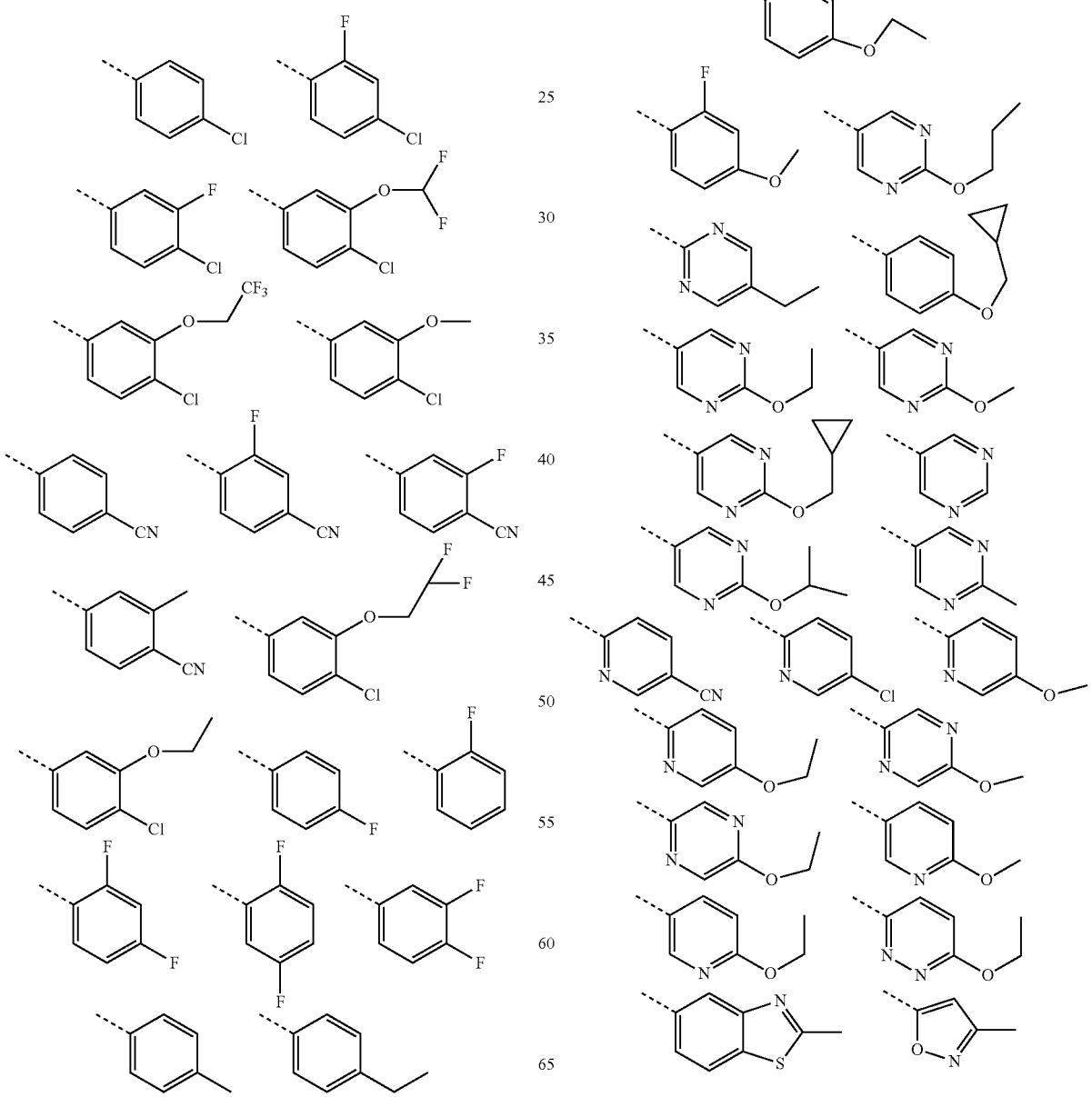
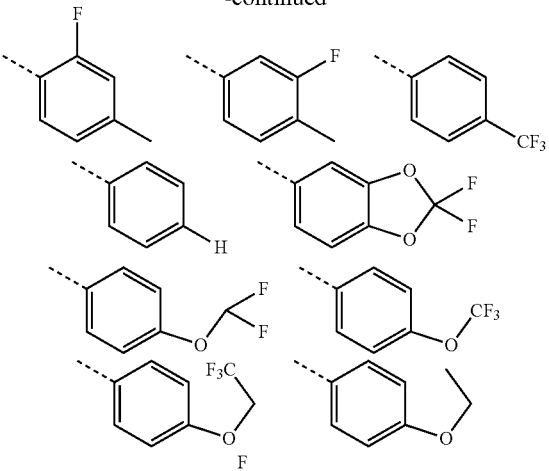

wherein the dashed bonds denotes the point of attachment of Y to the rest of the molecule. In embodiments, Y is selected from:

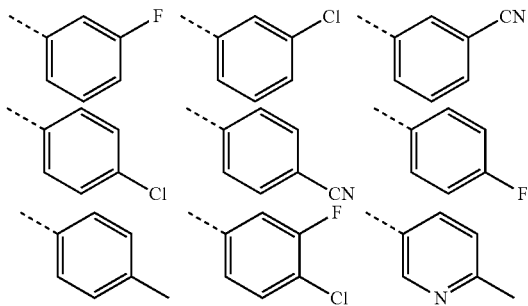

wherein the dashed bonds denotes the point of attachment of Y to the rest of the molecule.

In other embodiments, Y is selected from:

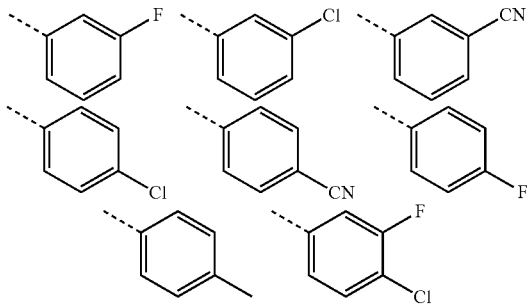

wherein the dashed bonds denotes the point of attachment of Y to the rest of the molecule.

In embodiments, Y is unsubstituted. In other embodiments, Y is substituted by 1 to 4 groups independently selected from $R^{14}$. In other embodiments, Y is substituted by 1 to 3 groups independently selected from $R^{14}$. In other embodiments, Y is substituted by 1 or 2 groups independently selected from $R^{14}$. In one embodiment, Y is substituted by 2 groups independently selected from $R^{14}$. In another embodiment, Y is substituted by 1 group independently selected from $R^{14}$.

In embodiments, $R^1$ is selected from $(G)_n$-$(C_{1-6}$-alkyl); $(G)_n$-$(C_{3-8}$-cycloalkyl); $(G)_n$-$(C_{5-8}$-cycloalkenyl); and $(G)_n$-$(C_{6-10}$-aryl), wherein G in each case is independently selected from C(O), S(O)$_2$, C(O)NR$^{10}$, and S(O)$_2$NR$^{10}$, wherein n in each case is 1, and wherein said alkyl, cycloalkyl, cycloalkenyl and aryl are optionally substituted by one or more groups independently selected from $R^{15}$.

In embodiments, $R^1$ is selected from $(G)_n$-$(C_{1-6}$-alkyl); $(G)_n$-$(C_{3-8}$-cycloalkyl); and $(G)_n$-$(C_{6-10}$-aryl), wherein G in each case is independently selected from C(O), and S(O)$_2$, and wherein n in each case is 1, and wherein said alkyl, cycloalkyl and aryl are optionally substituted by one or more groups independently selected from $R^{15}$.

In embodiments, $R^1$ is selected from $(G)_n$-$(C_{1-3}$-alkyl); $(G)_n$-$(C_{3-6}$-cycloalkyl); and $(G)_n$-phenyl, wherein G in each case is S(O)$_2$, and wherein n in each case is 1, and wherein said alkyl, cycloalkyl and phenyl are optionally substituted by one or more groups independently selected from $R^{15}$.

In embodiments, $R^1$ is selected from methylsulfonyl, cyclopropylsulfonyl, and phenylsulfonyl, each of which is optionally substituted by one or more groups independently selected from $R^{15}$.

In embodiments, $R^1$ is selected from: $(G)_n$-heterocycloalkyl, wherein said heterocycloalkyl is a 3- to 6-membered heterocycloalkyl comprising 1, 2 or 3 ring heteroatoms selected from N, S and O; $(G)_n$-heterocycloalkenyl, wherein said heterocycloalkenyl is a 5- to 6-membered heterocycloalkenyl comprising 1, 2 or 3 ring heteroatoms selected from N, S and O; and $(G)_n$-heteroaryl, wherein said heteroaryl is a 5- to 10-membered heteroaryl comprising 1, 2, 3 or 4 ring heteroatoms selected from N, S and O, wherein G in each case is independently selected from C(O), S(O)$_2$, C(O)NR$^{10}$, and S(O)$_2$NR$^{10}$; and wherein n in each case is 1, and wherein said heterocycloalkyl, heterocycloalkenyl and heteroaryl are optionally substituted by one or more groups independently selected from $R^{15}$.

In embodiments, $R^1$ is selected from: $(G)_n$-heterocycloalkyl, wherein said heterocycloalkyl is a 3- to 6-membered heterocycloalkyl comprising 1, 2 or 3 ring heteroatoms selected from N, S and O; $(G)_n$-heterocycloalkenyl, wherein said heterocycloalkenyl is a 5- to 6-membered heterocycloalkenyl comprising 1, 2 or 3 ring heteroatoms selected from N, S and O; and $(G)_n$-heteroaryl, wherein said heteroaryl is a 5- to 10-membered heteroaryl comprising 1, 2, 3 or 4 ring heteroatoms selected from N, S and O, wherein G in each case is independently selected from C(O), and C(O)NR$^{10}$; and wherein n in each case is 1, and wherein said heterocycloalkyl, heterocycloalkenyl and heteroaryl are optionally substituted by one or more groups independently selected from $R^{15}$.

In embodiments, $R^1$ is $(G)_n$-heteroaryl, wherein said heteroaryl is a 5- to 10-membered heteroaryl comprising 1, 2, 3 or 4 ring heteroatoms selected from N, S and O; wherein G is independently selected from C(O), and C(O)NR$^{10}$; and wherein n is 1, and wherein said heteroaryl is optionally substituted by one or more groups independently selected from $R^{15}$.

In embodiments, $R^1$ is selected from N-morpholinylcarbonyl, pyrazolylcarbonyl, pyridinylcarbonyl, pyrimidinylcarbonyl, pyrazinylcarbonyl, pyridazinylcarbonyl, quinolonylcarbonyl, and N-(pyridinyl)aminocarbonyl, each of which is optionally substituted by one or more groups independently selected from $R^{15}$. In embodiments, $R^1$ is selected from pyrazol-3-ylcarbonyl, pyridin-2-ylcarbonyl, pyridin-3-ylcarbonyl, pyrimidin-4-ylcarbonyl, pyrazin-2-ylcarbonyl, pyridazin-3-ylcarbonyl, quinolin-2-ylcarbonyl, and (N-methyl-N-(pyridin-2-yl)amino)carbonyl, each of which is optionally substituted by one or more groups independently selected from $R^5$.

In embodiments, $R^1$ is pyridin-2-ylcarbonyl which is unsubstituted. In other embodiments, $R^1$ is pyridin-2-ylcarbonyl which is substituted by one or more groups independently selected from $R^{15}$, wherein one $R^{15}$ substituent is at the 3-, 4- or 5-position. In embodiments, $R^1$ is pyridin-2-ylcarbonyl which is substituted by one or two groups independently selected from $R^{15}$, wherein one $R^{15}$ substituent is at the 3- or 5-position. In embodiments, $R^1$ is pyridin-2-ylcarbonyl which is substituted by one or two groups independently selected from $R^5$, wherein one $R^{15}$ substituent is at the 3-position. In embodiments, $R^1$ is pyridin-2-ylcarbonyl which is substituted by one or two groups independently selected from $R^{15}$, wherein one $R^{15}$, substituent is at the 5-position. In embodiments, $R^1$ is pyridin-2-ylcarbonyl which is substituted by two groups independently selected from $R^{15}$, wherein one $R^{15}$ substituent is at the 3-position and the other $R^{15}$ substituent is at the 4-position. In embodiments, $R^1$ is pyridin-2-ylcarbonyl which is substituted by two groups independently selected from $R^{15}$, wherein one $R^{15}$ substituent is at the 3-position and the other $R^{15}$ substituent is at the 5-position.

In embodiments, $R^1$ is pyridin-3-ylcarbonyl which is unsubstituted. In other embodiments, $R^1$ is pyridin-3-ylcarbonyl which is substituted by one or more groups independently selected from $R^{15}$, wherein one $R^{15}$ substituent is at the 2-, 4- or 5-position. In embodiments, $R^1$ is pyridin-3-ylcarbonyl which is substituted by one or more groups independently selected from $R^{15}$, wherein one $R^{15}$ substituent is at the 5-position.

In embodiments, $R^1$ is pyrazin-2-ylcarbonyl which is unsubstituted. In other embodiments, $R^1$ is pyrazin-2-ylcarbonyl which is substituted by one or more groups independently selected from $R^{15}$, wherein one $R^{15}$ substituent is at the 6-position.

In an embodiment, n is 1. In such an embodiment, G may be selected from C(O), S(O)$_2$, C(O)NR$^{10}$, and S(O)$_2$NR$^{10}$. In embodiments, G is selected from C(O), and S(O)$_2$. In other embodiments, G is selected from C(O)NR$^{10}$, and S(O)$_2$NR$^{10}$. In embodiments, G is selected from C(O), and C(O)NR$^{10}$. In other embodiments, G is selected from S(O)$_2$, and S(O)$_2$NR$^{10}$. In an embodiment, G is C(O). In an embodiment, G is C(O), a is 1, and X$^1$ is NH. In another embodiment, G is S(O)$_2$. In another embodiment, G is C(O)NR$^{10}$.

In another embodiment, n is 0.

In embodiments, $R^1$ is selected from $C_{3-8}$-cycloalkyl; 3- to 6-membered heterocycloalkyl comprising 1, 2 or 3 ring heteroatoms selected from N, S and O; $C_{5-8}$-cycloalkenyl; 5- to 6-membered heterocycloalkenyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said cycloalkyl, heterocycloalkyl, cycloalkenyl, heterocycloalkenyl, aryl and heteroaryl are optionally substituted by one or more groups independently selected from $R^{15}$.

In embodiments, $R^1$ is selected from 3- to 6-membered heterocycloalkyl comprising 1, 2 or 3 ring heteroatoms selected from N, S and O; 5- to 6-membered heterocycloalkenyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said heterocycloalkyl, cycloalkenyl, heterocycloalkenyl, aryl and heteroaryl are optionally substituted by one or more groups independently selected from $R^{15}$.

In other embodiments, $R^1$ is selected from 3- to 6-membered heterocycloalkyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said heterocycloalkyl, aryl and heteroaryl are optionally substituted by one or more groups independently selected from $R^{15}$.

In embodiments, $R^1$ is selected from phenyl; and 6- to 10-membered heteroaryl comprising 1 or 2 ring nitrogen atoms, wherein said phenyl and heteroaryl are optionally substituted by one or more groups independently selected from $R^{15}$.

In embodiments, $R^1$ is selected from phenyl, quinolinyl, pyridyl, cinnolinyl, quinazolinyl, and pyrimidinyl, each of which is optionally substituted by one or more groups independently selected from $R^{15}$.

In embodiments, $R^1$ is selected from quinolinyl, pyridyl, cinnolinyl, quinazolinyl, and pyrimidinyl, each of which is optionally substituted by one or more groups independently selected from $R^{15}$.

In embodiments, $R^1$ is selected from quinolinyl, cinnolinyl, and quinazolinyl, each of which is optionally substituted by one or more groups independently selected from $R^{15}$.

In embodiments, $R^1$ is selected from quinolinyl, and cinnolinyl, each of which is optionally substituted by one or more groups independently selected from $R^{15}$.

In embodiments, $R^1$ is quinolinyl which is optionally substituted by one or more groups independently selected from $R^{15}$. In one embodiment, $R^1$ is quinolin-4-yl which is optionally substituted by one or more groups independently selected from $R^{15}$. In one embodiment, $R^1$ is unsubstituted quinolin-4-yl. In another embodiment, $R^1$ is quinolin-4-yl which is substituted by one or more groups independently selected from $R^{15}$, wherein one $R^{15}$ substituent is at the 6- or 7-position. In another embodiment, $R^1$ is quinolin-4-yl which is substituted by one or more groups independently selected from $R^{15}$ as defined herein, wherein one $R^{15}$ substituent is at the 6-position.

In embodiments, $R^1$ is selected from pyridyl, and pyrimidinyl, each of which is optionally substituted by one or more groups independently selected from $R^{15}$.

In embodiments, $R^1$ is pyridyl, which is optionally substituted by one or more groups independently selected from $R^{15}$. In one embodiment, $R^1$ is pyrid-4-yl, which is optionally substituted by one or more groups independently selected from $R^{15}$. In one embodiment, $R^1$ is unsubstituted pyrid-4-yl. In another embodiment, $R^1$ is pyrid-4-yl which is substituted by one or more groups independently selected from $R^{15}$, wherein one $R^{15}$ substituent is at the 2-position. In one embodiment, $R^1$ is pyrid-3-yl, which is optionally substituted by one or more groups independently selected from $R^{15}$. In another embodiment, $R^1$ is pyrid-3-yl which is substituted by one or more groups independently selected from $R^{15}$, wherein one $R^{15}$ substituent is at the 5-position.

In embodiments, $R^1$ is quinazolinyl, which is optionally substituted by one or more groups independently selected from $R^{15}$. In one embodiment, $R^1$ is quinazolin-4-yl, which is optionally substituted by one or more groups independently selected from $R^{15}$. In another embodiment, $R^1$ is quinazolin-4-yl which is substituted by one or more groups independently selected from $R^{15}$, wherein one $R^{15}$ substituent is at the 6-position.

In embodiments, $R^1$ is cinnolinyl, which is optionally substituted by one or more groups independently selected from $R^{15}$. In one embodiment, $R^1$ is cinnoolin-4-yl, which is optionally substituted by one or more groups independently selected from $R^{15}$. In another embodiment, $R^1$ is cinnolin-4-yl which is substituted by one or more groups independently selected from $R^{15}$, wherein one $R^{15}$ substituent is at the 6-position.

In embodiments, $R^1$ is phenyl, which is optionally substituted by one or more groups independently selected from $R^{15}$. In another embodiment, $R^1$ is phenyl which is substituted by one or more groups independently selected from $R^{15}$, wherein one $R^{15}$ substituent is at the 2-position. In another embodiment, $R^1$ is phenyl which is substituted by one or more groups independently selected from $R^{15}$, wherein one $R^{15}$ substituent is at the 4-position. In another embodiment, $R^1$ is phenyl which is substituted by one or more groups independently selected from $R^{15}$, wherein one $R^{15}$ substituent is at the 5-position. In another embodiment, $R^1$ is phenyl which is substituted by one or more groups independently selected from $R^{15}$, wherein one $R^{15}$ substituent is at the 6-position. In another embodiment, $R^1$ is phenyl which is substituted by one or more groups independently selected from $R^{15}$, wherein one $R^{15}$ substituent is at the 2-position and one $R^{15}$ substituent is at the 4-position. In another embodiment, $R^1$ is phenyl which is substituted by one or more groups independently selected from $R^{15}$, wherein one $R^{15}$ substituent is at the 2-position and one $R^{15}$ substituent is at the 5-position. In another embodiment, $R^1$ is phenyl which is substituted by one or more groups independently selected from $R^{15}$, wherein one $R^{15}$ substituent is at the 2-position, one $R^{15}$ substituent is at the 4-position, and one $R^{15}$ substituent is at the 6-position. In embodiments, $R^1$ is selected from 5- to 10-membered heteroaryl comprising 1, 2 or 3 ring nitrogen atoms, wherein said heteroaryl is optionally substituted by one or more groups independently selected from $R^{15}$.

In embodiments, $R^1$ is selected from benzimidazolyl, pyrazolyl, triazolyl and imidazolyl, each of which is optionally substituted by one or more groups independently selected from $R^{15}$.

In embodiments, $R^1$ is selected from benzimidazolyl, triazolyl and imidazolyl, each of which is optionally substituted by one or more groups independently selected from $R^{15}$.

In one embodiment, $R^1$ is benzimidazol-1-yl, which is optionally substituted by one or more groups independently selected from $R^{15}$. In one embodiment, $R^1$ is benzimidazol-1-yl, which is substituted by one or more groups independently selected from $R^{15}$, wherein one group is at the 6-position. In one embodiment, $R^1$ is benzimidazol-1-yl, which is substituted by one or more groups independently selected from $R^{15}$, wherein one group is at the 5-position. In one embodiment, $R^1$ is benzimidazol-1-yl, which is substituted by one or more groups independently selected from $R^{15}$, wherein one group is at the 7-position. In one embodiment, $R^1$ is benzimidazol-1-yl, which is substituted by one or more groups independently selected from $R^{15}$, wherein one group is at the 2-position. In one embodiment, $R^1$ is benzimidazol-1-yl, which is substituted by two or more groups independently selected from $R^{15}$, wherein one group is at the 5-position and one group is at the 6-position. In one embodiment, $R^1$ is benzimidazol-1-yl, which is substituted by two or more groups independently selected from $R^{15}$, wherein one group is at the 5-position and one group is at the 7-position. In one embodiment, $R^1$ is benzimidazol-1-yl, which is substituted by two or more groups independently selected from $R^{15}$, wherein one group is at the 2-position and one group is at the 6-position. In one embodiment, $R^1$ is unsubstituted benzimidazol-1-yl.

In one embodiment, $R^1$ is 1,2,4-triazol-1-yl, which is optionally substituted by one or more groups independently selected from $R^{15}$. In one embodiment, $R^1$ is 1,2,4-triazol-1-yl, which is substituted by one or more groups independently selected from $R^{15}$, wherein one group is at the 3-position. In one embodiment, $R^1$ is 1,2,3-triazol-1-yl, which is optionally substituted by one or more groups independently selected from $R^{15}$. In one embodiment, $R^1$ is 1,2,3-triazol-1-yl, which is substituted by one or more groups independently selected from $R^{15}$, wherein one group is at the 4-position. In one embodiment, $R^1$ is 1,2,3-triazol-1-yl, which is substituted by two groups independently selected from $R^{15}$, wherein one group is at the 4-position and one group is at the 5-position. In embodiments, $R^1$ is unsubstituted 1,2,4-triazol-1-yl or 1,2,3-triazol-1-yl.

In one embodiment, $R^1$ is imidazol-1-yl, which is optionally substituted by one or more groups independently selected from $R^{15}$. In one embodiment, $R^1$ is imidazol-1-yl, which is substituted by one or more groups independently selected from $R^{15}$, wherein one group is at the 4-position.

In one embodiment, $R^1$ is pyrazolyl, which is optionally substituted by one or more groups independently selected from $R^{15}$. In one embodiment, $R^1$ is pyrazol-1-yl, which is optionally substituted by one or more groups independently selected from $R^{15}$. In another embodiment, $R^1$ is pyrazol-1-yl which is substituted by one or more groups independently selected from $R^{15}$, wherein one $R^{15}$ substituent is at the 3-position. In one embodiment, $R^1$ is pyrazol-1-yl which is substituted by one group selected from $R^{15}$ (e.g. $C_{3-8}$-cycloalkyl), wherein said $R^{15}$ substituent is at the 3-position. In another embodiment, $R^1$ is pyrazol-1-yl which is substituted by one or more groups independently selected from $R^{15}$, wherein one $R^{15}$ substituent is at the 4-position. In another embodiment, $R^1$ is pyrazol-1-yl which is substituted by one or more groups independently selected from $R^{15}$, wherein one $R^{15}$ substituent is at the 5-position. In another embodiment, $R^1$ is pyrazol-3-yl, which is optionally substituted by one or more groups independently selected from $R^{15}$. In another embodiment, $R^1$ is pyrazol-4-yl, which is optionally substituted by one or more groups independently selected from $R^{15}$. In embodiments, $R^1$ is selected from pyrazol-3-yl and pyrazol-4-yl, and is substituted by one or more groups independently selected from $R^{15}$, wherein one group is at the 1-position. In one embodiment, $R^1$ is unsubstituted pyrazol-1-yl.

In embodiments, a is 0; and $R^1$ is attached to the rest of the molecule via a carbon or nitrogen atom of the said $R^1$. In embodiments, a is 0; and $R^1$ is attached to the rest of the molecule via a nitrogen atom of the said $R^1$. In one embodiment, $R^1$ is $N_3$. It will be appreciated that when $R^1$ is $N_3$, $X^1$ is generally not $N(R^{10})$, O, or S.

In embodiments, $R^1$ is selected from:

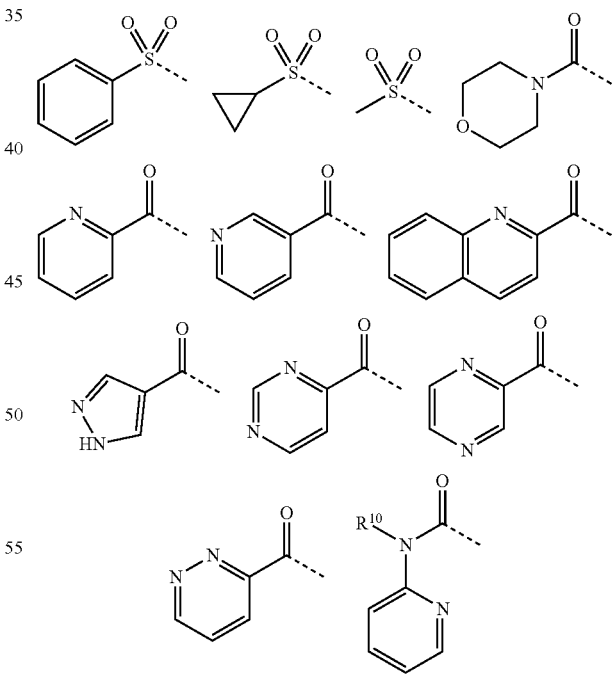

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

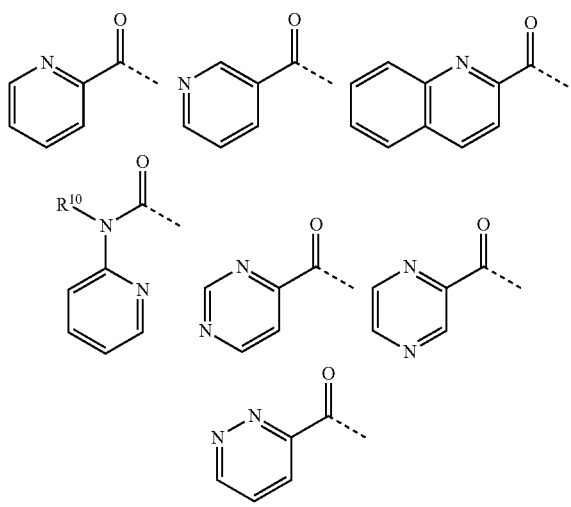

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

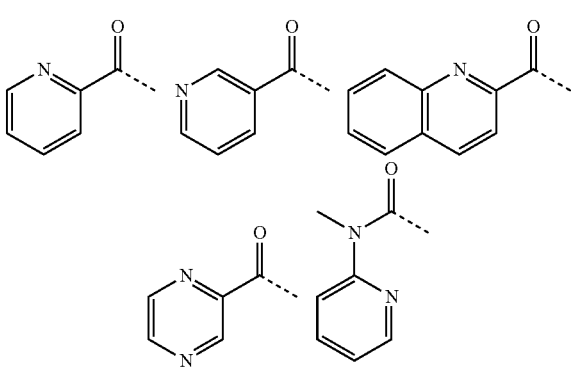

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

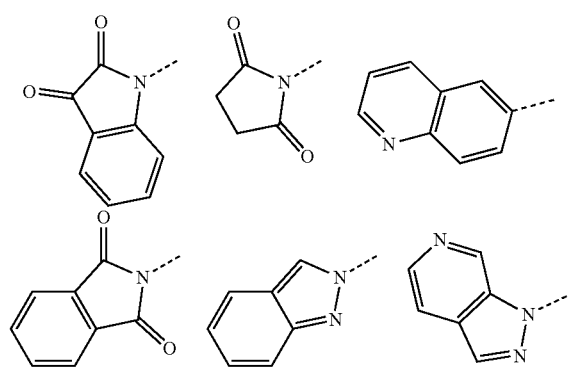

-continued

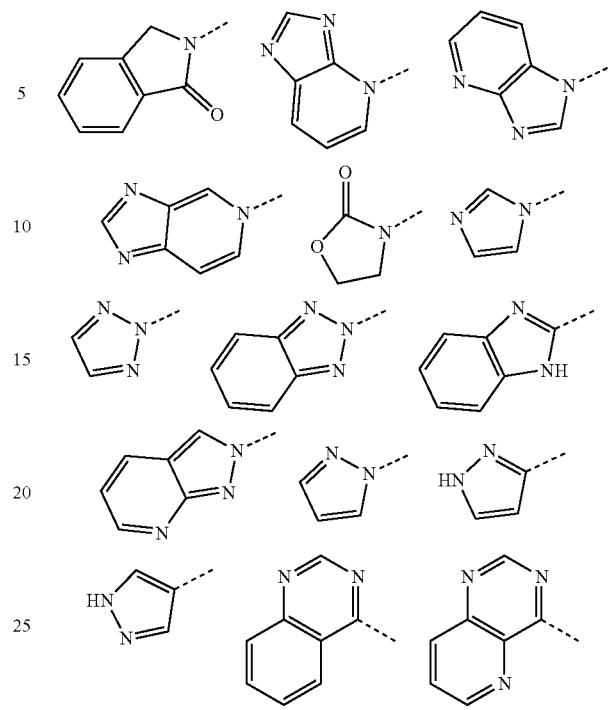

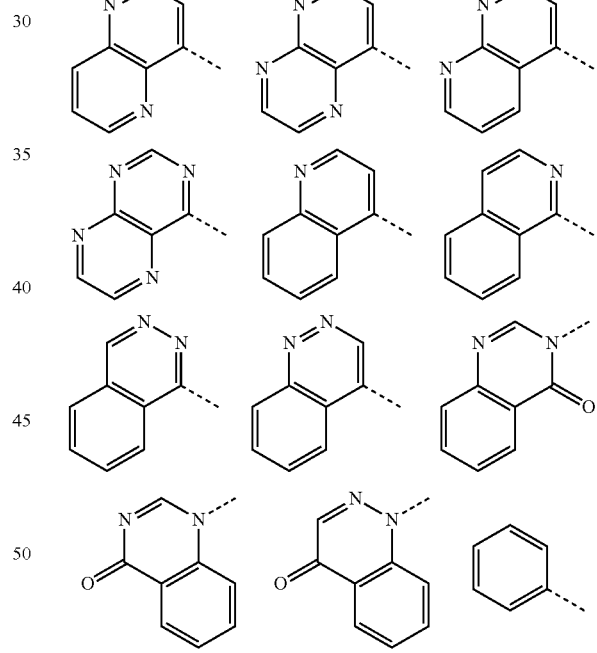

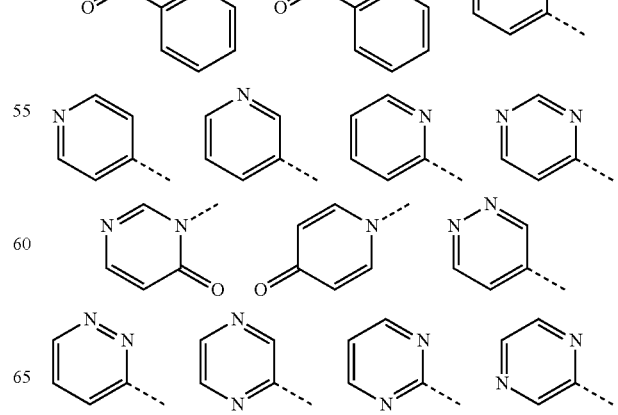

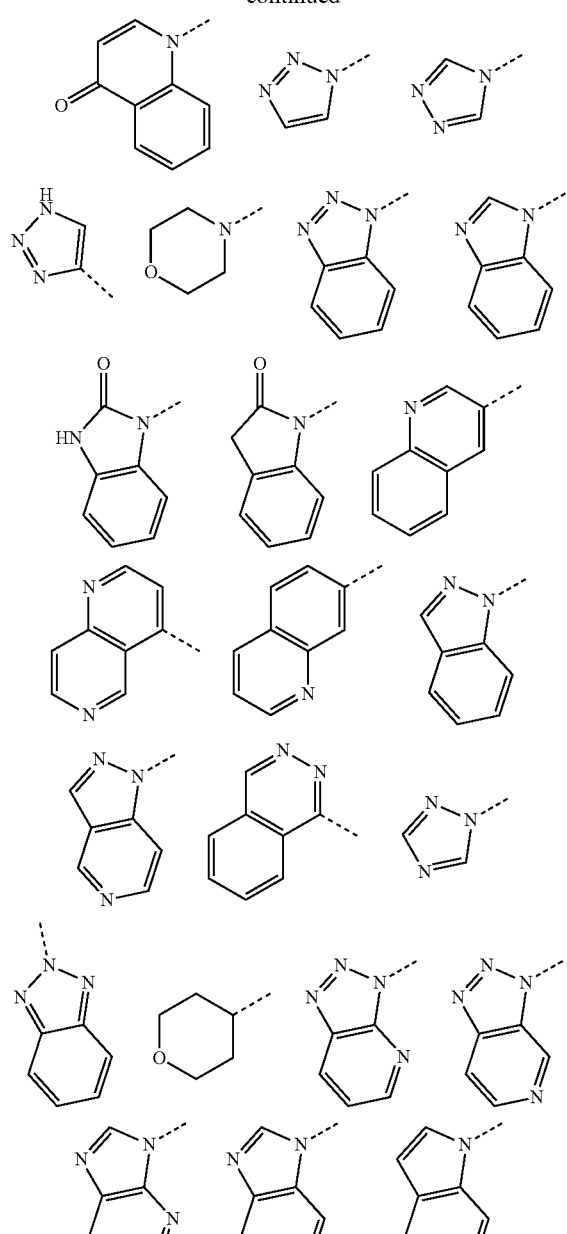
wherein the dashed bond denotes the point of attachment of $R^1$ to the rest of the molecule, and wherein said $R^1$ is optionally substituted with one or more substituents independently selected from $R^{15}$.
In embodiments, $R^1$ is selected from:
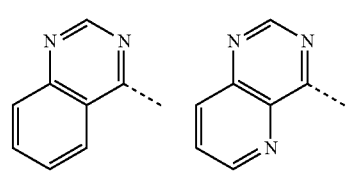
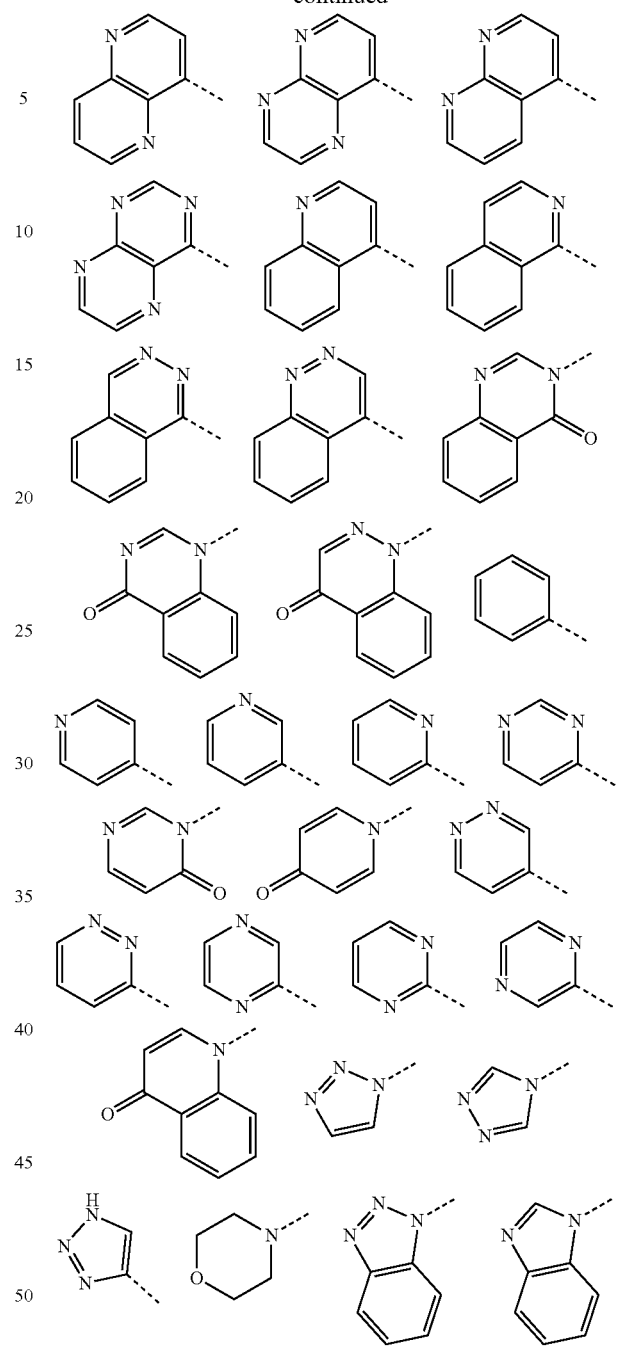
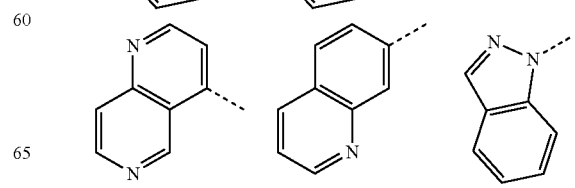

-continued

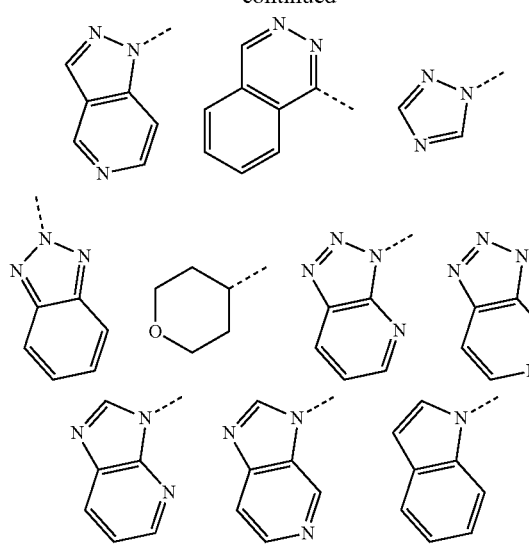

wherein the dashed bond denotes the point of attachment of R¹ to the rest of the molecule, and wherein said R¹ is optionally substituted with one or more substituents independently selected from $R^{15}$.

In embodiments, R¹ is selected from:

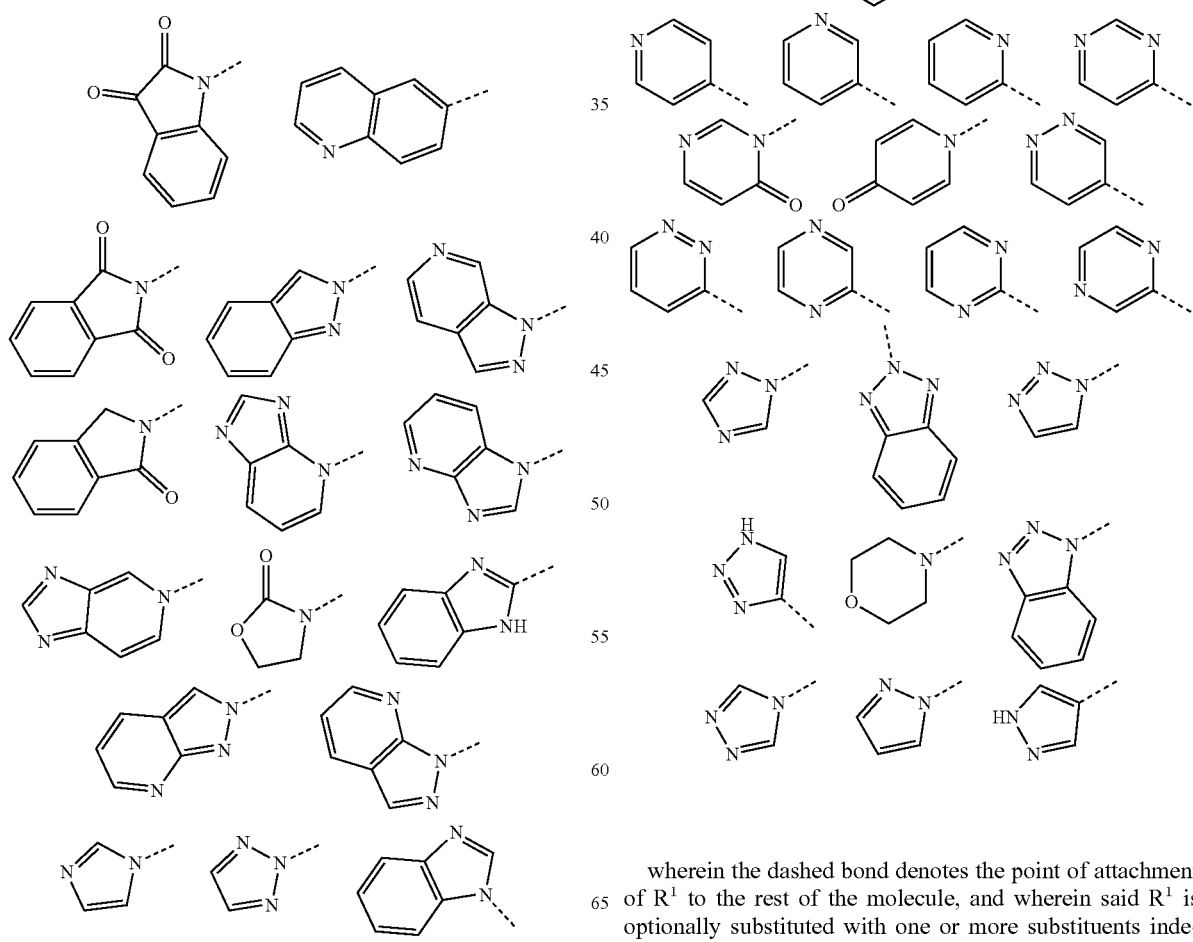

-continued

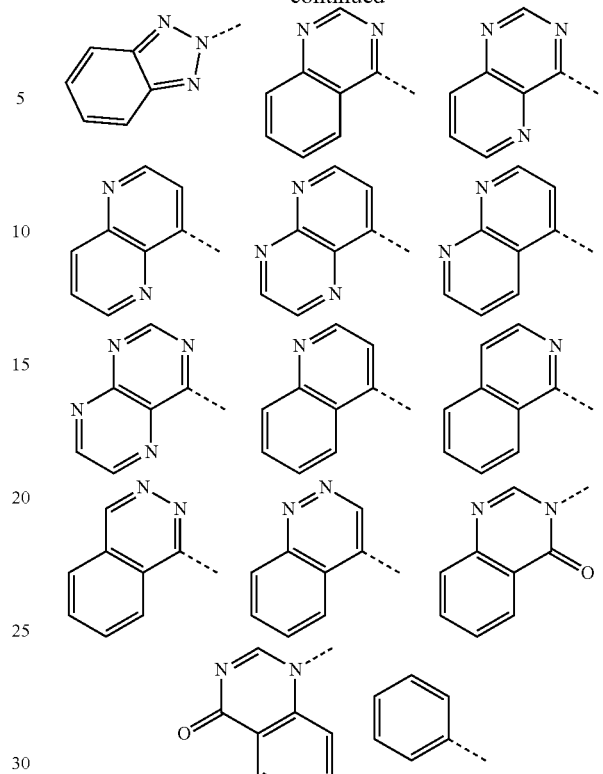

wherein the dashed bond denotes the point of attachment of R¹ to the rest of the molecule, and wherein said R¹ is optionally substituted with one or more substituents independently selected from $R^{15}$.

In embodiments, R¹ is selected from:
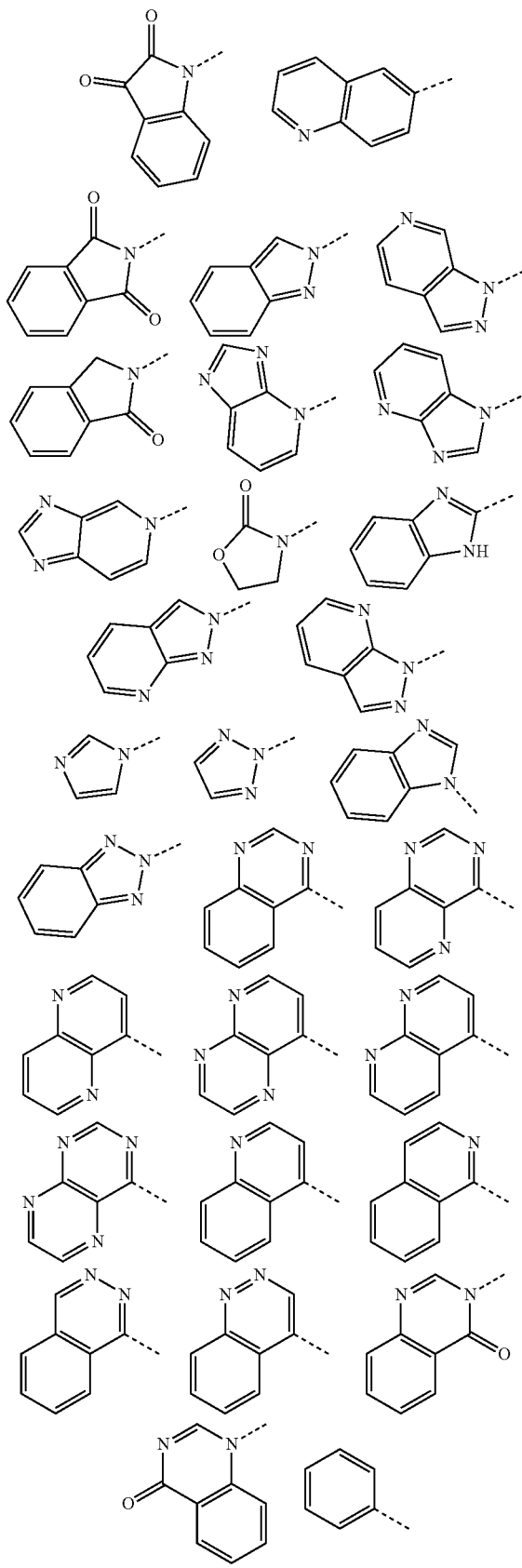
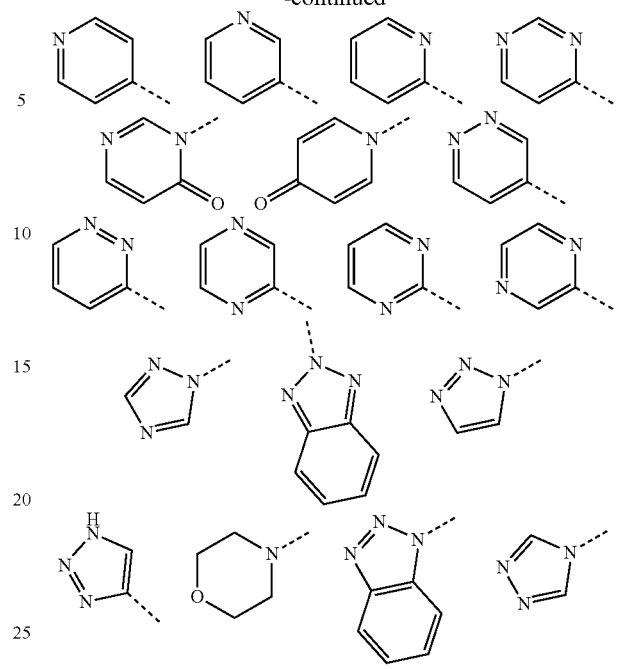
wherein the dashed bond denotes the point of attachment of R¹ to the rest of the molecule, and wherein said R¹ is optionally substituted with one or more substituents independently selected from R¹⁵.
In embodiments, R¹ is selected from:
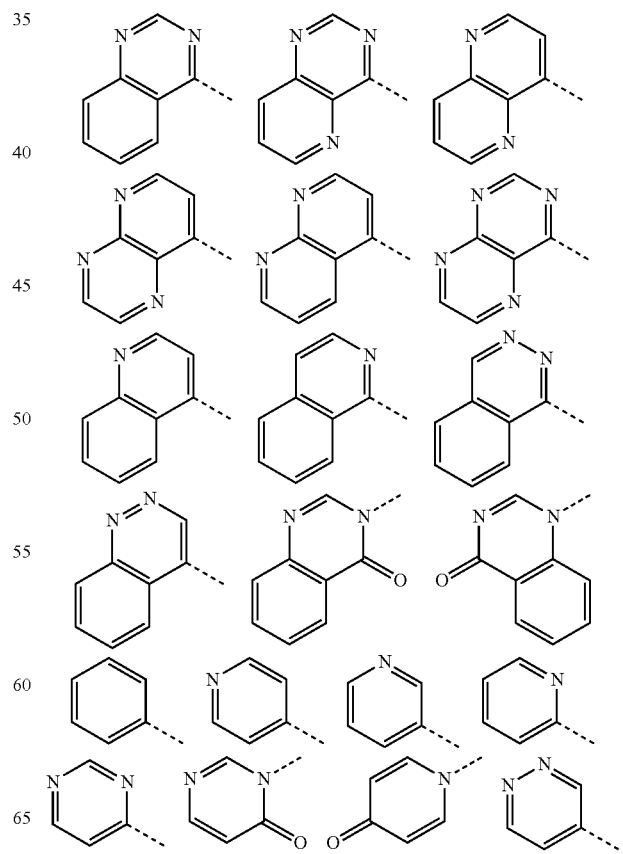

-continued

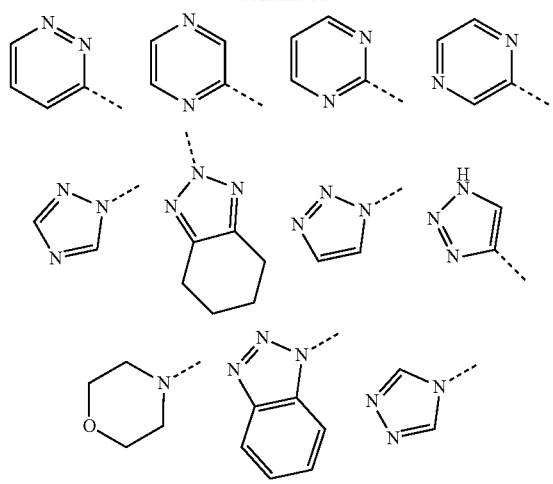

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

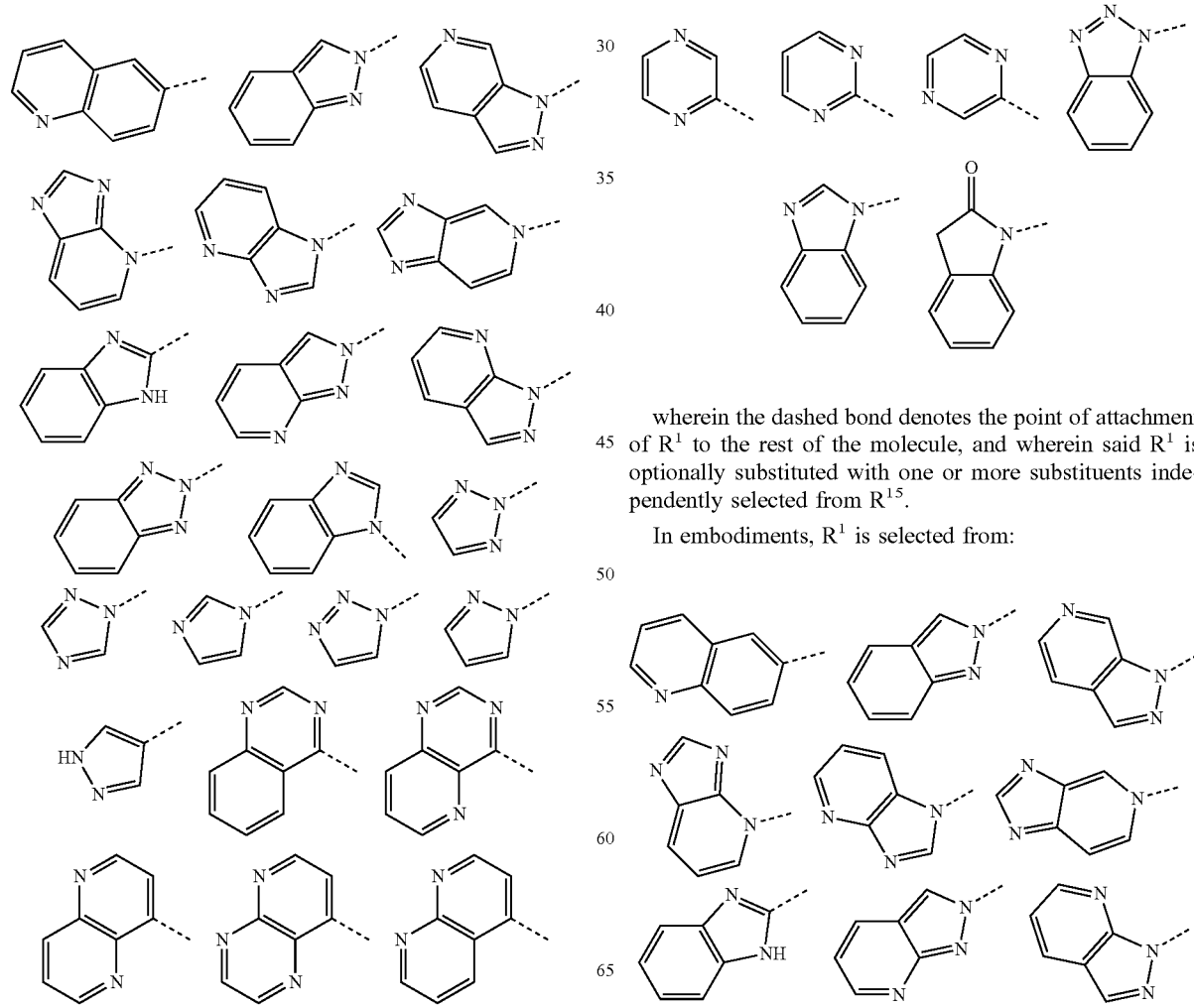

-continued

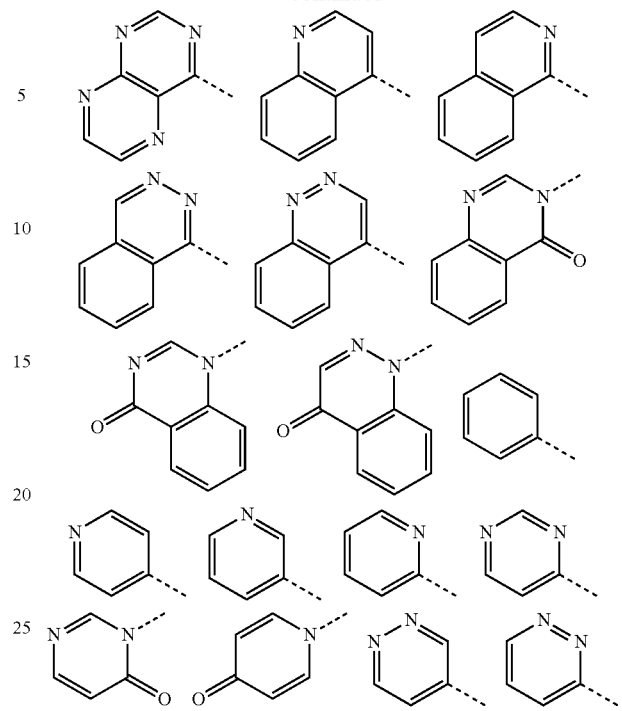

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

-continued

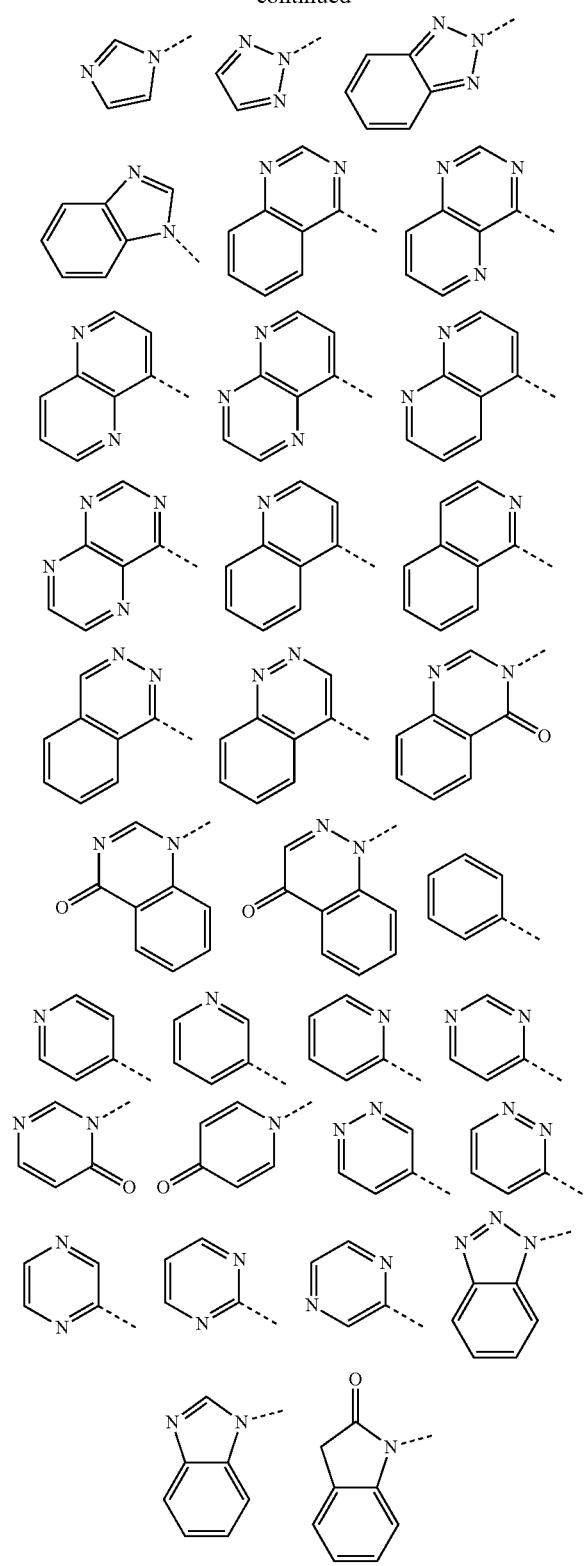

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

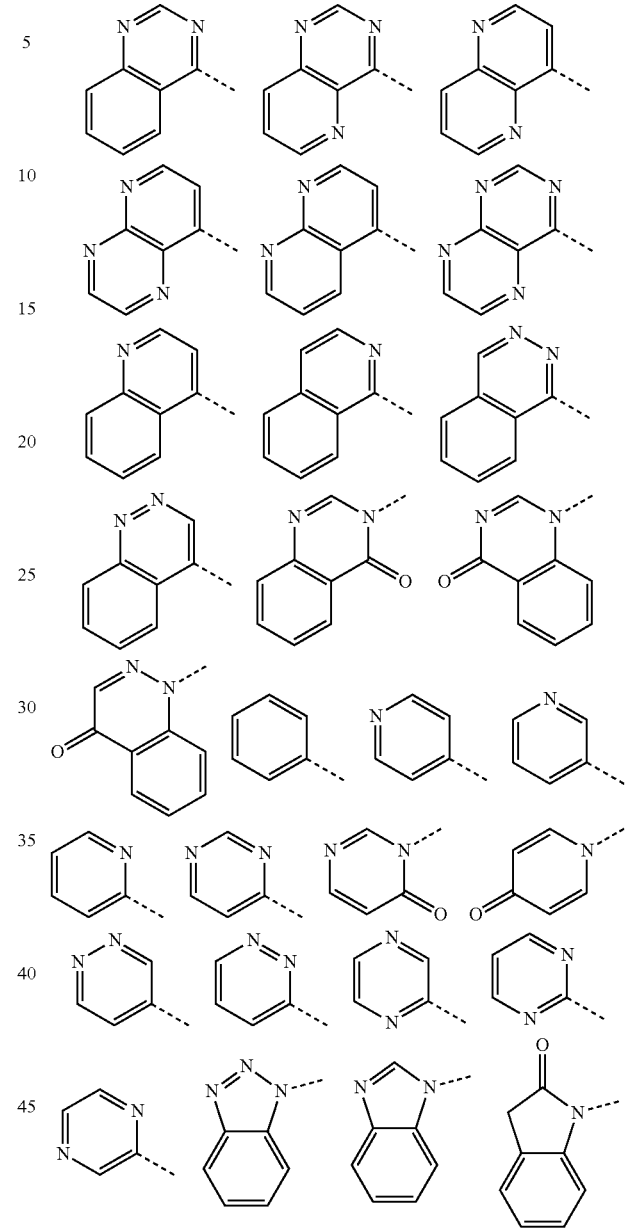

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

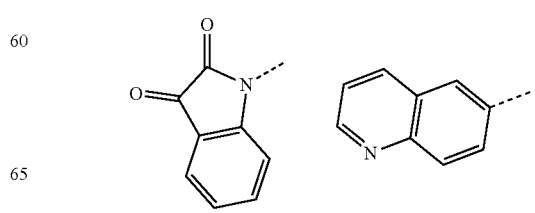

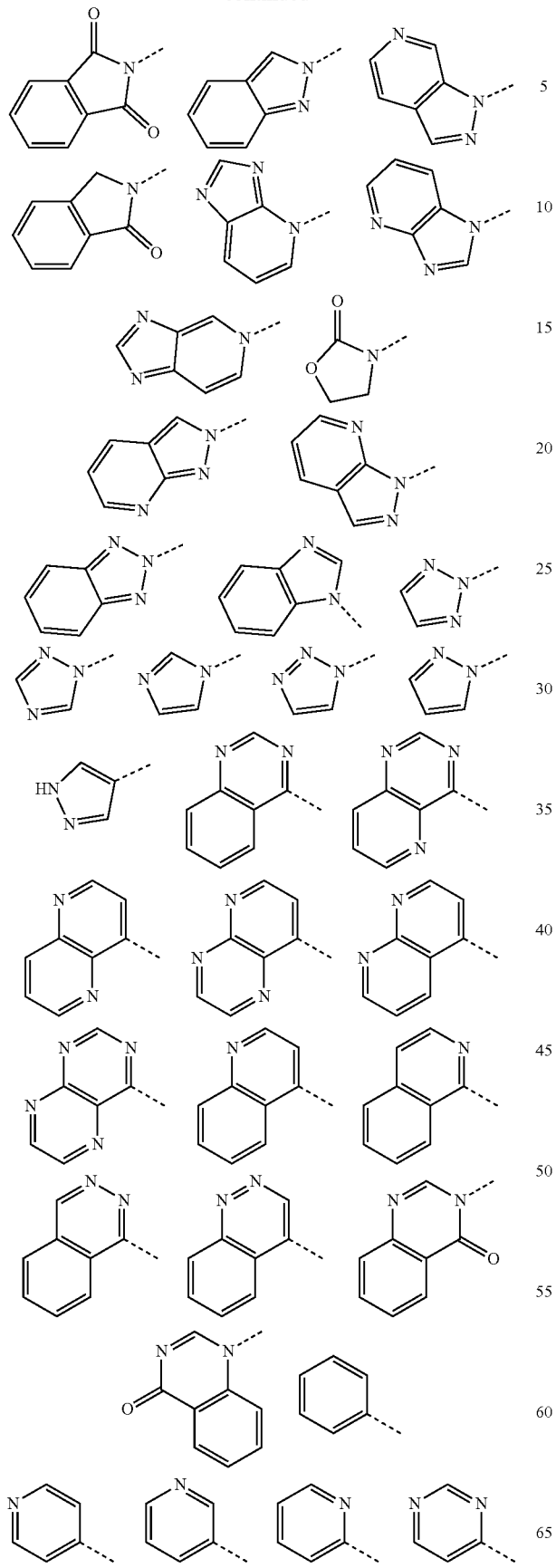
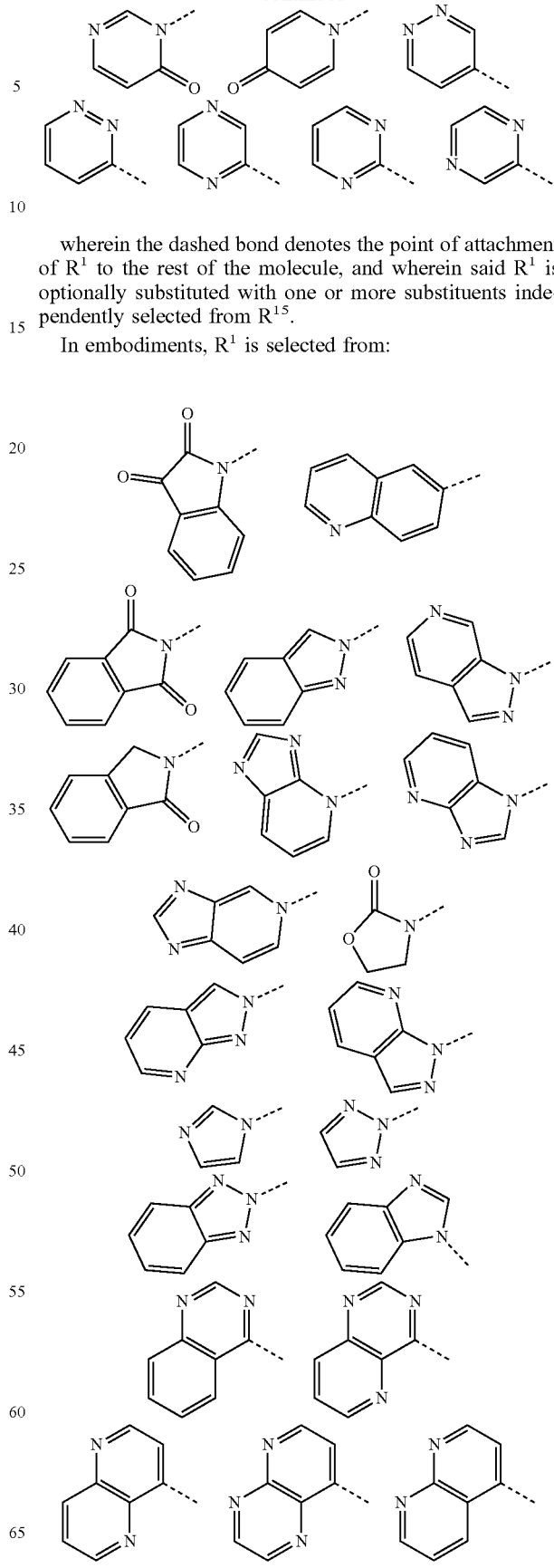
wherein the dashed bond denotes the point of attachment of $R^1$ to the rest of the molecule, and wherein said $R^1$ is optionally substituted with one or more substituents independently selected from $R^{15}$.
In embodiments, $R^1$ is selected from:

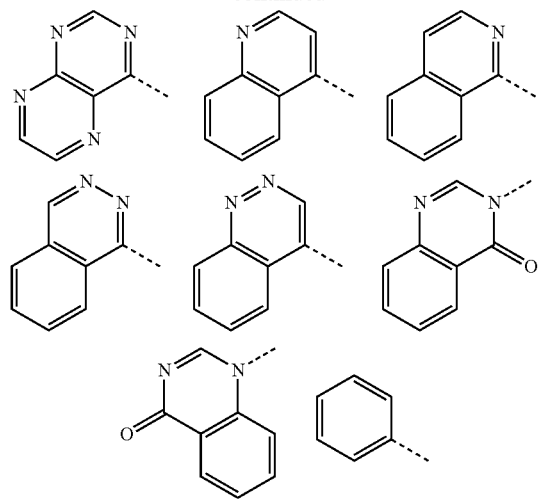

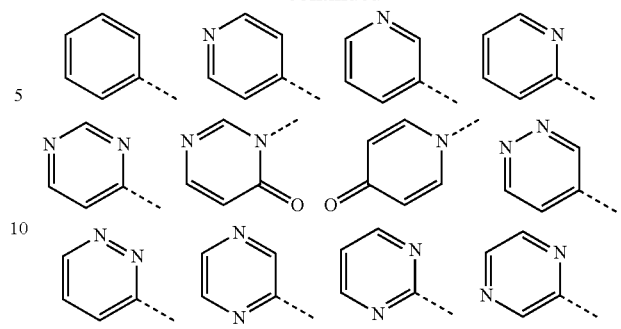

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

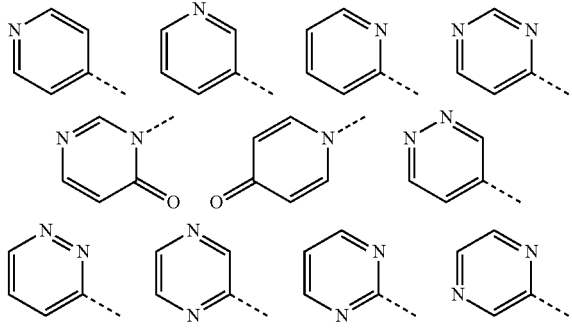

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

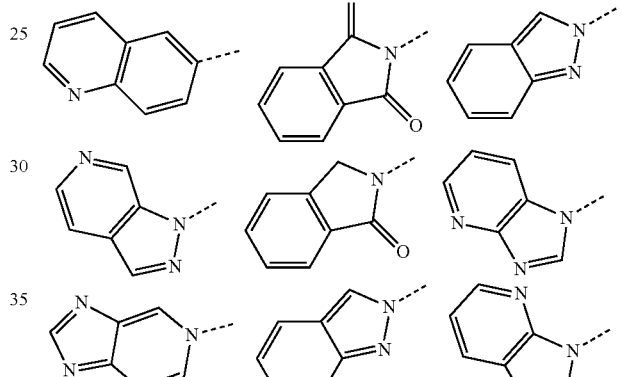

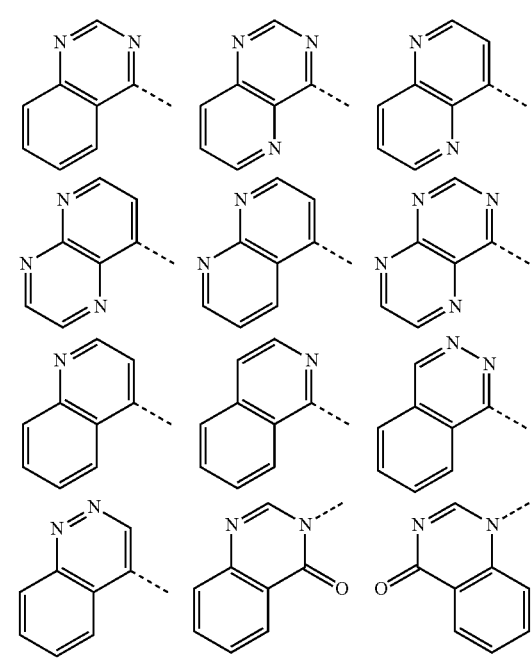

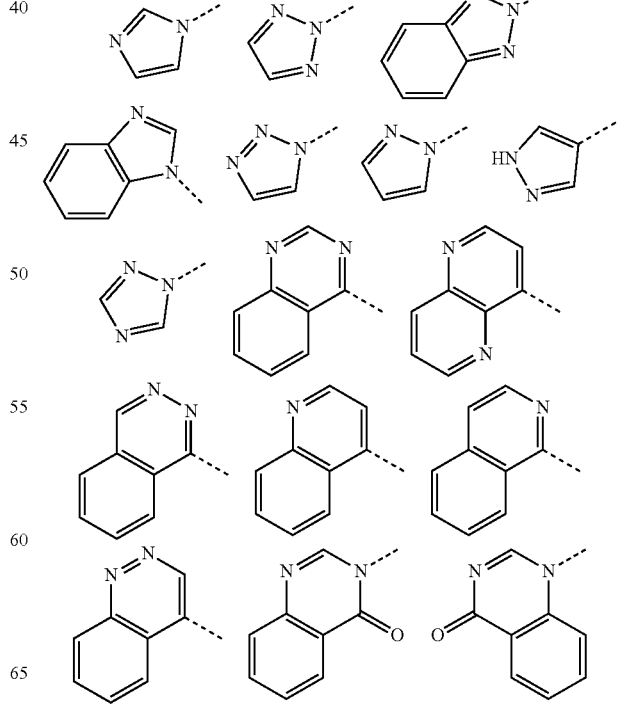

-continued

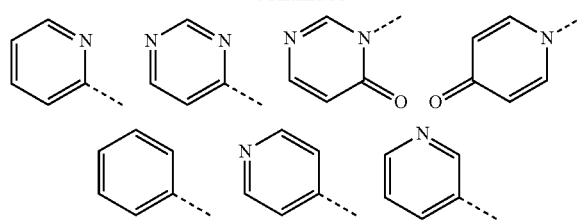

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

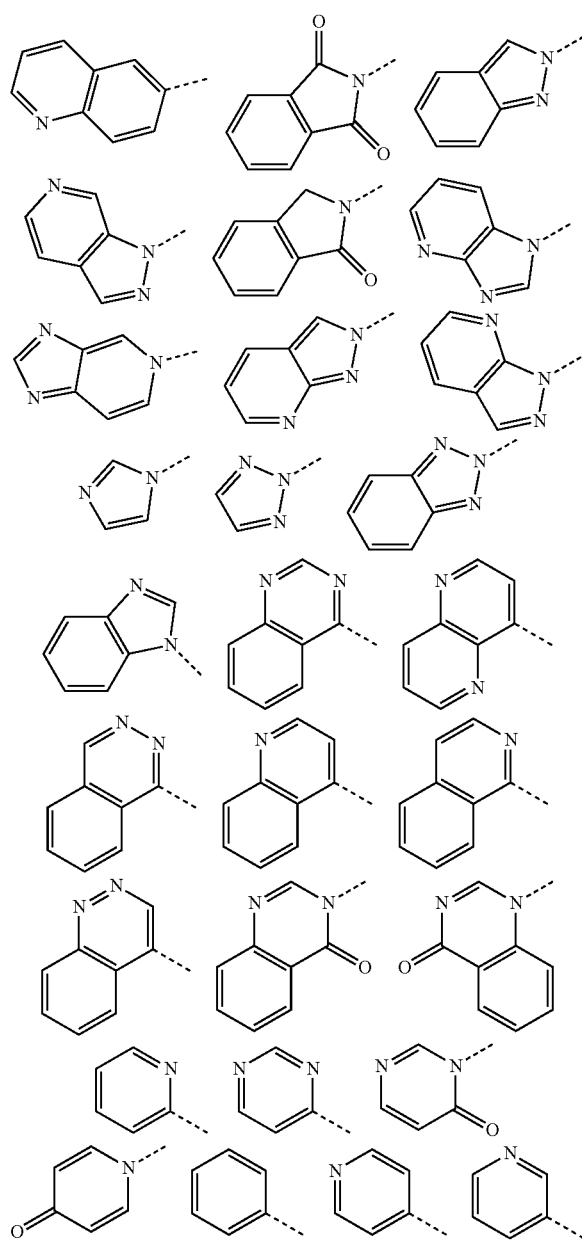

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

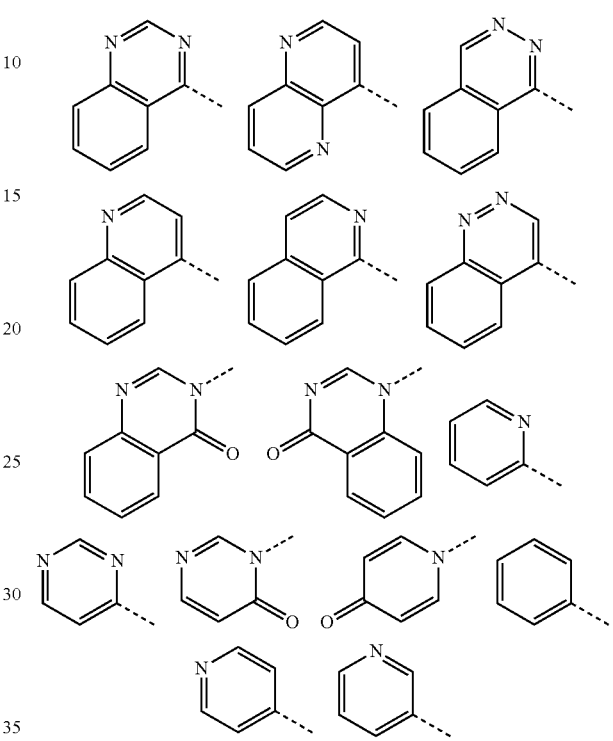

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

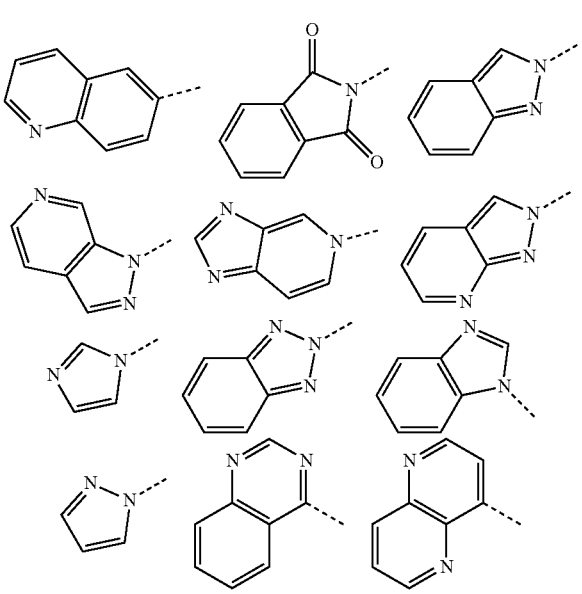

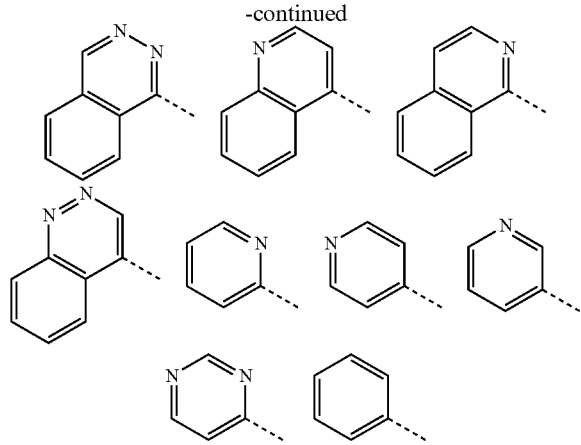

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

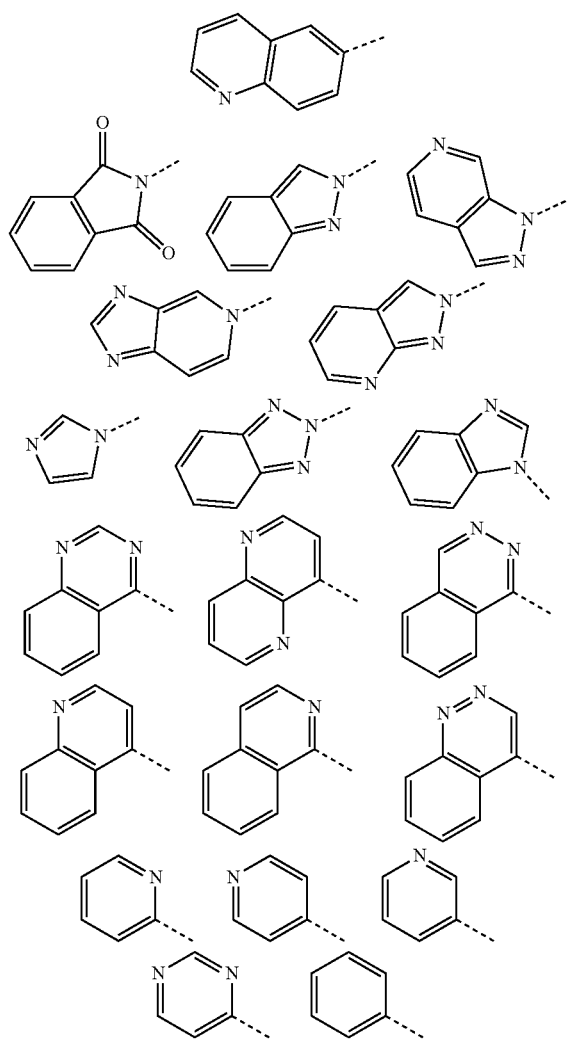

wherein the dashed bond denotes the point of attachment of $R^1$ to the rest of the molecule, and wherein said $R^1$ is optionally substituted with one or more substituents independently selected from $R^{15}$.

In embodiments, $R^1$ is selected from:

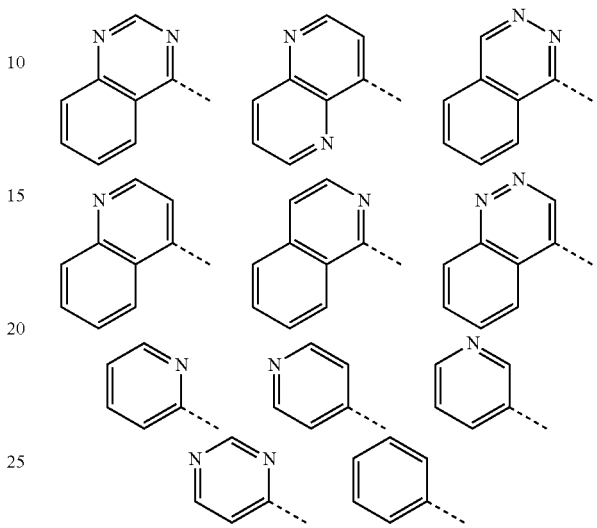

wherein the dashed bond denotes the point of attachment of $R^1$ to the rest of the molecule, and wherein said $R^1$ is optionally substituted with one or more substituents independently selected from $R^{15}$.

In embodiments, $R^1$ is substituted by 1 or 2 groups independently selected from $R^{15}$. In one embodiment, $R^1$ is substituted by 2 groups independently selected from $R^{15}$. In another embodiment, $R^1$ is substituted by 1 group selected from $R^{15}$. In embodiments, $R^1$ is not substituted by $R^{15}$.

In embodiments, $R^1$ is selected from:

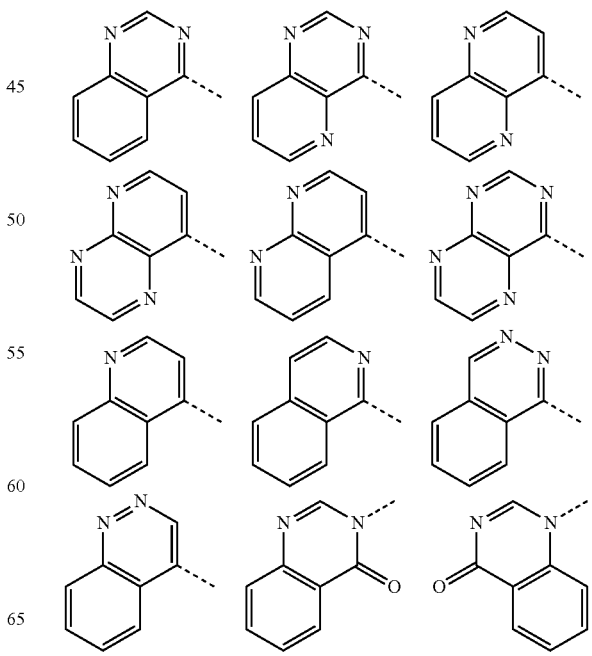

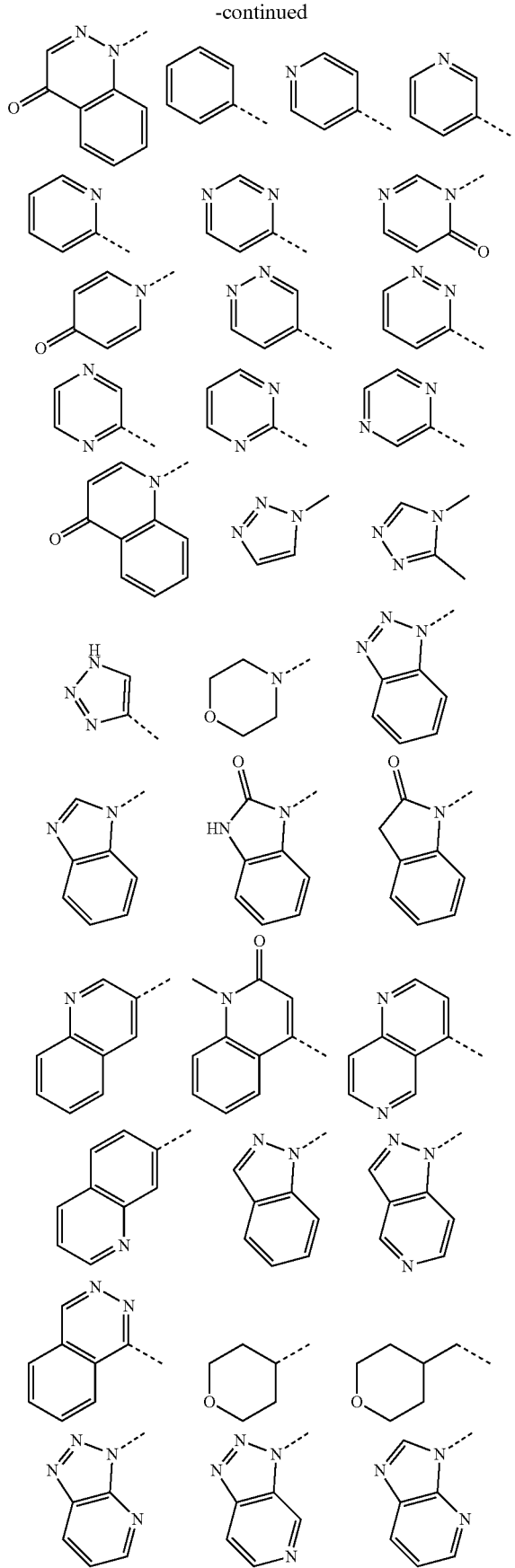
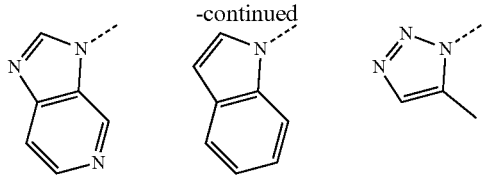

wherein the dashed bond denotes the point of attachment of $R^1$ to the rest of the molecule.

In embodiments, $R^2$ is selected from H, halogen, OH, $NH_2$, and $C_{1-4}$-alkyl. In embodiments, $R^2$ is selected from H, F, Cl, OH, and $NH_2$. In other embodiments, $R^2$ is selected from $C_{1-3}$-alkyl, e.g. ethyl or methyl. In embodiments, $R^2$ is selected from H, F, and methyl. In other embodiments, $R^2$ is selected from H, and F. In other embodiments, $R^2$ is selected from H, OH, $NH_2$, and $C_{1-3}$-alkyl. In other embodiments, $R^2$ is selected from H, OH, and $NH_2$. In one embodiment, $R^2$ is selected from H.

In embodiments, b is 1 or 2; and $R^3$ and $R^4$ are in each case independently selected from H, halogen, CN, OH, $C_{1-6}$-alkyl, and $C_{3-8}$-cycloalkyl; or one or both geminal $R^3$ and $R^4$ pairs, taken together with the carbon atom to which they are attached, independently forms a 3- to 6-membered cycloalkyl group or a 3- to 6-membered heterocycloalkyl group which comprises 1, 2 or 3 ring heteroatoms selected from N, S and O, wherein said alkyl, cycloalkyl and heterocycloalkyl are optionally substituted by one or more groups independently selected from $R^{16}$.

In embodiments, b is 1 or 2; $R^3$ is in each case independently selected from H, halogen, and $C_{1-6}$-alkyl; and $R^4$ is in each case independently selected from H, halogen, CN, and $C_{1-6}$-alkyl, wherein said alkyl is optionally substituted by one or more groups independently selected from $R^{16}$.

In embodiments, b is 1 or 2; and $R^3$ and $R^4$ are in each case independently selected from H, and $C_{3-8}$-cycloalkyl; or one or both geminal $R^3$ and $R^4$ pairs, taken together with the carbon atom to which they are attached, independently forms a 3- to 6-membered cycloalkyl group or a 3- to 6-membered heterocycloalkyl group which comprises 1, 2 or 3 ring heteroatoms selected from N, S and O, wherein said cycloalkyl and heterocycloalkyl are optionally substituted by one or more groups independently selected from $R^{16}$.

In embodiments, b is 1 or 2; and $R^3$ and $R^4$ are in each case independently selected from H, and $C_{3-8}$-cycloalkyl, or one or both geminal $R^3$ and $R^4$ pairs, taken together with the carbon atom to which they are attached, independently forms a 3- to 6-membered cycloalkyl group or a 3- to 6-membered heterocycloalkyl group which comprises 1 or 2 ring oxygen atoms, wherein said cycloalkyl and heterocycloalkyl are optionally substituted by one or more groups independently selected from $R^{16}$.

In embodiments, b is 1 or 2; $R^3$ is in each case independently selected from H and F; and $R^4$ is in each case independently selected from H, halogen, CN, and $C_{1-4}$-alkyl. In embodiments, b is 1 or 2; $R^3$ is in each case independently selected from H; and $R^4$ is in each case independently selected from H, methyl, and ethyl.

In other embodiments, b is 1 or 2; and $R^3$ and $R^4$ are in each case independently selected from $C_{1-6}$-alkyl, $(C_{1-4}$-alkyl$)$-$SO_2R^{17}$, $(C_{1-4}$-alkyl$)$-$N(R^{18})_2$, $(C_{1-4}$-alkyl$)$-NH-$COR^{19}$, $(C_{1-4}$-alkyl$)$-$NHSO_2R^{20}$, $(C_{1-4}$-alkyl$)$-$CON(R^{21})_2$, $(C_{1-4}$-alkyl$)$-$CO_2R^{22}$ and $(C_{1-4}$-alkyl$)$-$SO_2N(R^{23})_2$, wherein said alkyl are optionally substituted by one or more groups independently selected from $R^{16}$.

In embodiments, b is 1; and $R^3$ and $R^4$ are independently selected from H, halogen, CN, OH, $C_{1-6}$-alkyl, and $C_{3-8}$-cycloalkyl; or $R^3$ and $R^4$, taken together with the carbon atom to which they are attached, form a 3- to 6-membered cycloalkyl group or a 3- to 6-membered heterocycloalkyl group which comprises 1, 2 or 3 ring heteroatoms selected from N, S and O, wherein said alkyl, cycloalkyl and heterocycloalkyl are optionally substituted by one or more groups independently selected from $R^{16}$.

In embodiments, b is 1; $R^3$ is independently selected from H, halogen, and $C_{1-6}$-alkyl; and $R^4$ is independently selected from H, halogen, CN, and $C_{1-6}$-alkyl, wherein said alkyl is optionally substituted by one or more groups independently selected from $R^{16}$.

In embodiments, b is 1; and $R^3$ and $R^4$ are independently selected from H, and $C_{3-8}$-cycloalkyl; or $R^3$ and $R^4$, taken together with the carbon atom to which they are attached, form a 3- to 6-membered cycloalkyl group or a 3- to 6-membered heterocycloalkyl group which comprises 1, 2 or 3 ring heteroatoms selected from N, S and O, wherein said cycloalkyl and heterocycloalkyl are optionally substituted by one or more groups independently selected from $R^{16}$.

In embodiments, b is 1; and $R^3$ and $R^4$ are independently selected from H, and $C_{3-8}$-cycloalkyl, or $R^3$ and $R^4$, taken together with the carbon atom to which they are attached, form a 3- to 6-membered cycloalkyl group or a 3- to 6-membered heterocycloalkyl group which comprises 1 or 2 ring oxygen atoms, wherein said cycloalkyl and heterocycloalkyl are optionally substituted by one or more groups independently selected from $R^{16}$.

In embodiments, b is 1; $R^3$ is selected from H, methyl, and F; and $R^4$ is selected from H, halogen, CN, and $C_{1-4}$-alkyl. In embodiments, b is 1; $R^3$ is selected from H and methyl; and $R^4$ is selected from H, methyl, and ethyl. In embodiments, b is 1; $R^3$ is selected from H; and $R^4$ is selected from methyl and ethyl.

In embodiments, b is 1; $R^3$ is selected from H and F; and $R^4$ is selected from H, halogen, CN, and $C_{1-4}$-alkyl. In embodiments, b is 1; $R^3$ is selected from H; and $R^4$ is selected from H, methyl, and ethyl.

In embodiments, b is 1; and $R^3$ and $R^4$ taken together with the carbon atom to which they are attached form a 3- to 6-membered cycloalkyl group or a 3- to 6-membered heterocycloalkyl group which comprises 1, 2 or 3 ring heteroatoms selected from N, S and O, wherein said cycloalkyl and heterocycloalkyl are optionally substituted by one or more groups independently selected from $R^{16}$.

In embodiments, b is 1; and $R^3$ and $R^4$ taken together with the carbon atom to which they are attached form a 3- to 6-membered cycloalkyl group or a 3- to 6-membered heterocycloalkyl group which comprises 1 or 2 ring oxygen atoms, wherein said cycloalkyl and heterocycloalkyl are optionally substituted by one or more groups independently selected from $R^{16}$.

In embodiments, b is 2; $R^3$ and $R^4$ of one geminal $R^3$ and $R^4$ pair are independently selected from H, halogen, CN, OH, $C_{1-6}$-alkyl, and $C_{3-8}$-cycloalkyl; and the other geminal $R^3$ and $R^4$ pair, taken together with the carbon atom to which they are attached, forms a 3- to 6-membered cycloalkyl group or a 3- to 6-membered heterocycloalkyl group which comprises 1, 2 or 3 ring heteroatoms selected from N, S and O, wherein said alkyl, cycloalkyl and heterocycloalkyl are optionally substituted by one or more groups independently selected from $R^{16}$.

In embodiments, b is 2; $R^3$ and $R^4$ of one geminal $R^3$ and $R^4$ pair are independently selected from H, halogen, CN, OH, $C_{1-6}$-alkyl, and $C_{3-8}$-cycloalkyl; and the other geminal $R^3$ and $R^4$ pair, taken together with the carbon atom to which they are attached, forms a 3- to 6-membered cycloalkyl group or a 3- to 6-membered heterocycloalkyl group which comprises 1 or 2 ring oxygen atoms, wherein said alkyl, cycloalkyl and heterocycloalkyl are optionally substituted by one or more groups independently selected from $R^{16}$.

In embodiments, c is 1; and $R^5$ is selected from H; $C_{1-6}$-alkyl; $C_{3-8}$-cycloalkyl; 3- to 6-membered heterocycloalkyl comprising 1, 2 or 3 ring heteroatoms selected from N, S and O; $C_{5-8}$-cycloalkenyl; 5- to 6-membered heterocycloalkenyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said alkyl, cycloalkyl, heterocycloalkyl, cycloalkenyl, heterocycloalkenyl, aryl and heteroaryl are optionally substituted by one or more groups selected from $R^{24}$.

In embodiments, c is 1; and $R^5$ is selected from H; $C_{1-6}$-alkyl; $C_{3-8}$-cycloalkyl; 3- to 6-membered heterocycloalkyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said alkyl, cycloalkyl, heterocycloalkyl, aryl and heteroaryl are optionally substituted by one or more groups selected from $R^{24}$.

In embodiments, c is 1; and $R^5$ is selected from H, and $C_{1-6}$-alkyl optionally substituted by one or more groups selected from $R^{24}$. In embodiments, c is 1; and $R^5$ is selected from H, and $C_{1-6}$-alkyl. In one embodiment, c is 1; and $R^5$ is H.

In embodiments, e is 1; and $R^6$ and $R^7$ are independently selected from H, halogen, CN, OH, $C_{1-6}$-alkyl, and $C_{3-8}$-cycloalkyl, wherein said alkyl and cycloalkyl are optionally substituted by one or more groups independently selected from $R^{16}$.

In embodiments, e is 1; and $R^6$ and $R^7$ are independently selected from H, and $C_{3-8}$-cycloalkyl optionally substituted by one or more groups independently selected from $R^{16}$.

In embodiments, e is 1; $R^6$ is selected from H, halogen and $C_{1-4}$-alkyl; and $R^7$ is selected from H, halogen, CN, and $C_{1-6}$-alkyl, wherein said alkyl is optionally substituted by one or more groups independently selected from $R^{16}$.

In embodiments, e is 1; $R^6$ is selected from H, F and methyl; and $R^7$ is selected from H, halogen, CN, and $C_{1-6}$-alkyl, wherein said alkyl is optionally substituted by one or more groups independently selected from $R^{16}$.

In embodiments, e is 1; $R^6$ is selected from H, and F; and $R^7$ is selected from H, halogen, CN, and $C_{1-4}$-alkyl optionally substituted by one or more groups independently selected from halogen and OH. In embodiments, e is 1; $R^6$ is H; and $R^7$ is selected from H, halogen, CN, and $C_{1-4}$-alkyl optionally substituted by OH. In embodiments, e is 1; and $R^6$ and $R^7$ are independently selected from H.

In other embodiments, e is 1; and $R^6$ and $R^7$ are in each case independently selected from $C_{1-6}$-alkyl, $(C_{1-4}$-alkyl)-$SO_2R^{17}$, $(C_{1-4}$-alkyl)-$N(R^{18})_2$, $(C_{1-4}$-alkyl)-$NHCOR^{19}$, $(C_{1-4}$-alkyl)-$NHSO_2R^{20}$, $(C_{1-4}$-alkyl)-$CON(R^{21})_2$, $(C_{1-4}$-alkyl)-$CO_2R^{22}$ and $(C_{1-4}$-alkyl)-$SO_2N(R^{23})_2$, wherein said alkyl are optionally substituted by one or more groups independently selected from $R^{16}$.

In embodiments, $R^8$ and $R^9$ are independently selected from H, halogen, CN, OH, $C_{1-6}$-alkyl, and $C_{3-8}$-cycloalkyl, wherein said alkyl and cycloalkyl are optionally substituted by one or more groups independently selected from $R^{16}$.

In embodiments, $R^8$ and $R^9$ are independently selected from H, and $C_{3-8}$-cycloalkyl optionally substituted by one or more groups independently selected from $R^{16}$.

In embodiments, $R^8$ is selected from H, and F; and $R^9$ is selected from H, halogen, CN, and $C_{1-6}$-alkyl optionally substituted by one or more groups independently selected from $R^{16}$.

In embodiments, $R^8$ is selected from H, and F; and $R^9$ is selected from H, halogen, CN, and $C_{1-6}$-alkyl optionally substituted by one or more groups independently selected from halogen and OH.

In embodiments, $R^8$ is H; and $R^9$ is selected from H, halogen, CN, and $C_{1-4}$-alkyl optionally substituted by OH.

In embodiments $R^8$ and $R^9$ are independently selected from H.

In embodiments, $R^8$ and $R^9$ are independently selected from $C_{1-4}$-alkyl optionally substituted by one or more groups independently selected from $R^{16}$. In embodiments, $R^8$ and $R^9$ are independently selected from $(C_{0-4}$-alkyl)-$CO_2R^{22}$ wherein said $R^{22}$ is $C_{1-6}$-alkyl which is optionally substituted by one or more groups independently selected from halogen and OH.

In embodiments, $R^{10}$ is selected from H; $C_{1-6}$-alkyl; $C_{3-8}$-cycloalkyl; 3- to 6-membered heterocycloalkyl comprising 1, 2 or 3 ring heteroatoms selected from N, S and O; $C_{5-8}$-cycloalkenyl; 5- to 6-membered heterocycloalkenyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said alkyl, cycloalkyl, heterocycloalkyl, cycloalkenyl, heterocycloalkenyl, aryl and heteroaryl are optionally substituted by one or more groups independently selected from $R^{24}$.

In embodiments, $R^{10}$ is selected from H; $C_{1-6}$-alkyl; $C_{3-8}$-cycloalkyl; 3- to 6-membered heterocycloalkyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said alkyl, cycloalkyl, heterocycloalkyl, aryl and heteroaryl are optionally substituted by one or more groups independently selected from $R^{24}$.

In other embodiments $R^{10}$ is selected from H, and $C_{1-6}$-alkyl optionally substituted by one or more groups independently selected from $R^{24}$. In embodiments, $R^{10}$ is $C_{1-6}$-alkyl. In one embodiment $R^{10}$ is H.

In embodiments, $R^{11}$ and $R^{12}$ are independently selected from H, halogen, CN, OH, $C_{1-6}$-alkyl, and $C_{3-8}$-cycloalkyl, wherein said alkyl and cycloalkyl are optionally substituted by one or more groups independently selected from $R^{16}$.

In embodiments, $R^{11}$ and $R^{12}$ are independently selected from H, and $C_{3-8}$-cycloalkyl optionally substituted by one or more groups independently selected from $R^{16}$.

In embodiments, $R^{11}$ is selected from H, and F; and $R^{12}$ is selected from H, halogen, CN, and $C_{1-6}$-alkyl optionally substituted by one or more groups independently selected from $R^{16}$.

In embodiments, $R^{11}$ is selected from H, and F; and $R^{12}$ is selected from H, halogen, CN, and $C_{1-6}$-alkyl optionally substituted by one or more groups independently selected from halogen and OH.

In embodiments, $R^{11}$ is H; and $R^{12}$ is selected from H, halogen, CN, and $C_{1-4}$-alkyl optionally substituted by OH.

In embodiments $R^{11}$ and $R^{12}$ are independently selected from H.

In other embodiments, $R^{11}$ and $R^{12}$ are in each case independently selected from $C_{1-6}$-alkyl, $(C_{1-4}$-alkyl)-$SO_2R^{17}$, $(C_{1-4}$-alkyl)-$N(R^{18})_2$, $(C_{1-4}$-alkyl)-$NHCOR^{19}$, $(C_{1-4}$-alkyl)-$NHSO_2R^{20}$, $(C_{1-4}$-alkyl)-$CON(R^{21})_2$, $(C_{1-4}$-alkyl)-$CO_2R^{22}$ and $(C_{1-4}$-alkyl)-$SO_2N(R^{23})_2$, wherein said alkyl are optionally substituted by one or more groups independently selected from $R^{16}$.

In embodiments, $R^{13}$ is selected from H; $C_{1-6}$-alkyl; $C_{3-8}$-cycloalkyl; 3- to 6-membered heterocycloalkyl comprising 1, 2 or 3 ring heteroatoms selected from N, S and O; $C_{5-8}$-cycloalkenyl; 5- to 6-membered heterocycloalkenyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said alkyl, cycloalkyl, heterocycloalkyl, cycloalkenyl, heterocycloalkenyl, aryl and heteroaryl are optionally substituted by one or more groups independently selected from $R^{24}$.

In embodiments, $R^{13}$ is selected from H; $C_{1-6}$-alkyl; $C_{3-8}$-cycloalkyl; 3- to 6-membered heterocycloalkyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said alkyl, cycloalkyl, heterocycloalkyl, aryl and heteroaryl are optionally substituted by one or more groups independently selected from $R^{24}$.

In other embodiments $R^{13}$ is selected from H, and $C_{1-6}$-alkyl optionally substituted by one or more groups independently selected from $R^{24}$. In embodiments, $R^{13}$ is $C_{1-6}$-alkyl. In one embodiment $R^{13}$ is H.

In embodiments, one of $R^3$ and $R^5$, together with one of $R^{11}$ and $R^{13}$ and the atoms intervening between them, form a 5- or 6-membered cycloalkyl, cycloalkenyl or aryl group, or a 5- or 6-membered heterocycloalkyl, heterocycloalkenyl or heteroaryl group which comprises 1, 2, 3 or 4 ring heteroatoms selected from N, S and O, wherein said cycloalkyl, cycloalkenyl, aryl, heterocycloalkyl, heterocycloalkenyl and heteroaryl are optionally substituted by one or more groups independently selected from $R^{24}$.

In embodiments, $R^3$ together with $R^{11}$ and the atoms intervening between them, form a 5- or 6-membered cycloalkyl, cycloalkenyl or aryl group, or a 5- or 6-membered heterocycloalkyl, heterocycloalkenyl or heteroaryl group which comprises 1, 2, 3 or 4 ring heteroatoms selected from N, S and O, wherein said cycloalkyl, cycloalkenyl, aryl, heterocycloalkyl, heterocycloalkenyl and heteroaryl are optionally substituted by one or more groups independently selected from $R^{24}$.

In embodiments, $R^3$ together with $R^{11}$ and the atoms intervening between them, form a 5- or 6-membered heterocycloalkyl, heterocycloalkenyl or heteroaryl group which comprises 1, 2 or 3 ring heteroatoms selected from N and O, wherein said cycloalkyl, cycloalkenyl, aryl, heterocycloalkyl, heterocycloalkenyl and heteroaryl are optionally substituted by one or more groups independently selected from $R^{24}$.

In embodiments, A is O; and $R^3$ together with $R^{11}$ and the atoms intervening between them, form a 5- or 6-membered cycloalkyl, cycloalkenyl, or aryl group, or a 5- or 6-membered heterocycloalkyl, heterocycloalkenyl or heteroaryl group which comprises 1, 2, 3 or 4 ring heteroatoms selected from N, S and O.

In embodiments, A is O; and $R^3$ together with $R^{11}$ and the atoms intervening between them, form a 5- or 6-membered heterocycloalkyl, heterocycloalkenyl or heteroaryl group which comprises 1, 2 or 3 ring heteroatoms selected from N and O.

In other embodiments, A is O; and $R^3$ together with $R^{11}$ and the atoms intervening between them, form a 5- or 6-membered heteroaryl group which comprises 1, 2 or 3 ring heteroatoms selected from N, S and O.

In embodiments, A is O; and $R^3$ together with $R^{11}$ and the atoms intervening between them, form a 5-membered heteroaryl group which comprises 2 or 3 ring heteroatoms selected from N and O. In embodiments, A is O; and $R^3$ together with $R^{11}$ and the atoms intervening between them, form a 1,3,4-oxadiazole diradical.

In embodiments, $R^3$ together with $R^{13}$ and the atoms intervening between them, form a 5- or 6-membered heterocycloalkyl, heterocycloalkenyl or heteroaryl group which comprises 1, 2, 3 or 4 ring heteroatoms selected from N, S and O, wherein said heterocycloalkyl, heterocycloalkenyl and heteroaryl are optionally substituted by one or more groups independently selected from $R^{24}$.

In embodiments, $R^5$ together with $R^{11}$ and the atoms intervening between them, form a 5- or 6-membered heterocycloalkyl, heterocycloalkenyl or heteroaryl group which comprises 1, 2, 3 or 4 ring heteroatoms selected from N, S and O, wherein said heterocycloalkyl, heterocycloalkenyl and heteroaryl are optionally substituted by one or more groups independently selected from $R^{24}$.

In embodiments, $R^5$ together with $R^{13}$ and the atoms intervening between them, form a 5- or 6-membered heterocycloalkyl, heterocycloalkenyl or heteroaryl group which comprises 1, 2, 3 or 4 ring heteroatoms selected from N, S and O, wherein said heterocycloalkyl, heterocycloalkenyl and heteroaryl are optionally substituted by one or more groups independently selected from $R^{24}$.

In embodiments, any two $R^{14}$ substituents on adjacent ring atoms may, together with the ring atoms to which they are attached, independently form a 5- or 6-membered cyclic group optionally comprising 1, 2 or 3 ring heteroatoms selected from N, S and O, which cyclic group is optionally substituted by one or more groups independently selected from halogen, $C_{1-4}$-alkyl and $C_{1-4}$-haloalkyl, and any remaining $R^{14}$ is in each case independently selected from halogen; CN; OH; $C_{1-6}$-alkyl; O—($C_{1-6}$-alkyl); O—($C_{1-6}$-haloalkyl); and O—($C_{1-6}$-alkyl-$C_{3-6}$-cycloalkyl).

In embodiments, $R^{14}$ is in each case independently selected from halogen, CN, OH, $C_{1-6}$-alkyl, O—($C_{1-6}$-alkyl), O—($C_{1-6}$-haloalkyl), and O—($C_{1-6}$-alkyl-$C_{3-6}$-cycloalkyl).

In embodiments, $R^{14}$ is in each case independently selected from halogen, CN, OH, $C_{1-6}$-alkyl, O—($C_{1-6}$-alkyl), and O—($C_{1-6}$-haloalkyl).

In embodiments, $R^{14}$ is in each case independently selected from F, Cl, Br, CN, OH, $C_{1-6}$-alkyl, O—($C_{1-6}$-alkyl), and O—($C_{1-6}$-haloalkyl). In embodiments, $R^{14}$ is in each case independently selected from Cl, Br, CN, OH, methyl, ethyl, methoxy, isopropyloxy, and O—($C_{1-3}$-fluoroalkyl). In embodiments, $R^{14}$ is in each case independently selected from Cl, CN, OH, methyl, ethyl, methoxy, isopropyloxy, and O—($C_{1-3}$-fluoroalkyl).

In embodiments, two $R^{14}$ substituents on adjacent ring atoms, together with the ring atoms to which they are attached, form a 5- or 6-membered cyclic group optionally comprising 1, 2 or 3 ring heteroatoms selected from N, S and O, which cyclic group is optionally substituted by one or more groups independently selected from halogen, $C_{1-4}$-alkyl and $C_{1-4}$-haloalkyl.

In embodiments, $R^{15}$ is in each case independently selected from halogen, CN, OH, oxo, $NO_2$, $C_{1-6}$-alkyl, $C_{2-6}$-alkenyl, $C_{2-6}$-alkynyl, ($C_{0-4}$-alkyl)-O—($C_{1-6}$-alkyl), ($C_{0-4}$-alkyl)-$SO_2R^{17}$, ($C_{0-4}$-alkyl)-N($R^8$)$_2$, ($C_{0-4}$-alkyl)-NHCOR$^{19}$, ($C_{0-4}$-alkyl)-NHSO$_2R^{20}$, ($C_{0-4}$-alkyl)-CON($R^{21}$)$_2$, ($C_{0-4}$-alkyl)-CO$_2R^{22}$, ($C_{0-4}$-alkyl)-SO$_2$N($R^{23}$)$_2$, and ($C_{0-4}$-alkyl)-cycloalkyl, wherein said cycloalkyl is a 3- to 8-membered cycloalkyl, and wherein each said alkyl, alkenyl, alkynyl and cycloalkyl is optionally and independently substituted by one or more groups independently selected from halogen, OH, O($C_{1-4}$-alkyl), oxo, C(O)—($C_{1-4}$-alkyl), C(O)O—($C_{1-4}$-alkyl), and $NH_2$.

In embodiments, $R^{15}$ is in each case independently selected from halogen, CN, OH, oxo, $NO_2$, $C_{1-6}$-alkyl, $C_{2-6}$-alkenyl, ($C_{0-4}$-alkyl)-O—($C_{1-6}$-alkyl), ($C_{0-4}$-alkyl)-$SO_2R^{17}$, ($C_{0-4}$-alkyl)-N($R^{18}$)$_2$, ($C_{0-4}$-alkyl)-NHCOR$^{19}$, ($C_{0-4}$-alkyl)-NHSO$_2R^{20}$, ($C_{0-4}$-alkyl)-CON($R^{21}$)$_2$, ($C_{0-4}$-alkyl)-CO$_2R^{22}$, and ($C_{0-4}$-alkyl)-SO$_2$N($R^{23}$)$_2$, wherein each said alkyl and alkenyl is optionally and independently substituted by one or more groups independently selected from halogen, OH, O($C_{1-4}$-alkyl), oxo, C(O)—($C_{1-4}$-alkyl), C(O)O—($C_{1-4}$-alkyl), and $NH_2$.

In embodiments, $R^{15}$ is in each case independently selected from halogen, CN, oxo, OH, $C_{1-6}$-alkyl, O—($C_{1-6}$-alkyl), ($C_{0-4}$-alkyl)-$SO_2R^{17}$, ($C_{0-4}$-alkyl)-N($R^8$)$_2$, ($C_{0-4}$-alkyl)-NHCOR$^{19}$, ($C_{0-4}$-alkyl)-NHSO$_2R^{20}$, ($C_{0-4}$-alkyl)-CON($R^{21}$)$_2$, ($C_{0-4}$-alkyl)-CO$_2R^{22}$, and ($C_{0-4}$-alkyl)-SO$_2$N($R^{23}$)$_2$, wherein said alkyl are optionally substituted by one or more groups independently selected from halogen, OH and $NH_2$.

In embodiments, $R^{15}$ is in each case independently selected from halogen, CN, oxo, OH, $NO_2$, $C_{1-6}$-alkyl, $C_{2-6}$-alkenyl, ($C_{0-4}$-alkyl)-O—($C_{1-6}$-alkyl), ($C_{0-4}$-alkyl)-$SO_2R^{17}$, ($C_{0-4}$-alkyl)-N($R^{18}$)$_2$, ($C_{0-4}$-alkyl)-NHCOR$^{19}$, ($C_{0-4}$-alkyl)-NHSO$_2R^{20}$, ($C_{0-4}$-alkyl)-CON($R^{21}$)$_2$, ($C_{0-4}$-alkyl)-CO$_2R^{22}$, and ($C_{0-4}$-alkyl)-SO$_2$N($R^{23}$)$_2$.

In embodiments, $R^{15}$ is in each case independently selected from halogen, CN, oxo, OH, $C_{1-6}$-alkyl, O—($C_{1-6}$-alkyl), ($C_{0-4}$-alkyl)-$SO_2R^{17}$, ($C_{0-4}$-alkyl)-N($R^{18}$)$_2$, ($C_{0-4}$-alkyl)-NHCOR$^{19}$, ($C_{0-4}$-alkyl)-NHSO$_2R^{20}$, ($C_{0-4}$-alkyl)-CON($R^{21}$)$_2$, ($C_{0-4}$-alkyl)-CO$_2R^{22}$, and ($C_{0-4}$-alkyl)-SO$_2$N($R^{23}$)$_2$.

In other embodiments, $R^{15}$ is in each case independently selected from $C_{1-6}$-alkyl, ($C_{1-4}$-alkyl)-$SO_2R^{17}$, ($C_{1-4}$-alkyl)-N($R^{18}$)$_2$, ($C_{1-4}$-alkyl)-NHCOR$^{19}$, ($C_{1-4}$-alkyl)-NHSO$_2R^{20}$, ($C_{1-4}$-alkyl)-CON($R^{21}$)$_2$, ($C_{1-4}$-alkyl)-CO$_2R^{22}$ and ($C_{1-4}$-alkyl)-SO$_2$N($R^{23}$)$_2$.

In embodiments, $R^{15}$ is in each case independently selected from halogen, CN, oxo, OH, $NO_2$, $C_{1-6}$-alkyl, $C_{2-6}$-alkenyl, $C_{2-6}$-alkynyl, ($C_{0-4}$-alkyl)-O—($C_{1-6}$-alkyl), and ($C_{0-4}$-alkyl)-cycloalkyl, wherein said cycloalkyl is a 3- to 8-membered cycloalkyl, and wherein each said alkyl, alkenyl, alkynyl and cycloalkyl is optionally and independently substituted by one or more groups independently selected from halogen, OH, and $NH_2$. In embodiments, In embodiments, $R^{15}$ is in each case independently selected from halogen, CN, oxo, OH, $NO_2$, $C_{1-6}$-alkyl, $C_{2-6}$-alkenyl, $C_{2-6}$-alkynyl, ($C_{0-4}$-alkyl)-O—($C_{1-6}$-alkyl), and ($C_{0-4}$-alkyl)-cycloalkyl, wherein said cycloalkyl is a 3- to 8-membered cycloalkyl. In embodiments, $R^{15}$ is in each case independently selected from halogen, CN, oxo, OH, $NO_2$, $C_{1-6}$-alkyl, ($C_{0-4}$-alkyl)-O—($C_{1-6}$-alkyl), and ($C_{0-4}$-alkyl)-cycloalkyl, wherein said cycloalkyl is a 3- to 8-membered cycloalkyl. In embodiments, $R^{15}$ is in each case independently selected from halogen, CN, oxo, $C_{1-6}$-alkyl, O—($C_{1-6}$-alkyl), $C_{2-6}$-alkenyl, $C_{2-6}$-alkynyl, and 3- to 8-membered cycloalkyl. In embodiments, $R^{15}$ is in each case independently selected from halogen, CN, oxo, OH, $C_{1-6}$-alkyl, and O—($C_{1-6}$-alkyl). In embodiments, $R^{15}$ is in each case independently selected from halogen, CN, oxo, $C_{1-6}$-alkyl, $C_{2-6}$-alkenyl, $C_{2-6}$-alkynyl, and 3- to 8-membered cycloalkyl. In embodiments, $R^{15}$ is in each case independently selected from halogen, CN, methyl, ethyl, vinyl, propenyl, ethynyl and cyclopropyl. In embodiments, $R^{15}$ is in each case independently selected from halogen, CN, methyl, ethyl, ethynyl and cyclopropyl. In embodiments, $R^{15}$ is in each case independently selected from halogen, CN, OH, $C_{1-6}$-alkyl, and O—($C_{1-6}$-alkyl). In embodiments, $R^{15}$ is in each case independently selected from halogen, CN, OH, and $C_{1-6}$-alkyl. In embodiments, $R^{15}$ is in each case independently selected from halogen, CN, and $C_{1-6}$-alkyl. In embodiments, $R^{15}$ is in each case independently selected from halogen, and $C_{1-6}$-alkyl. In embodiments, $R^{15}$ is in each case independently selected from halogen, methyl, and ethyl. In embodiments, $R^{15}$ is in each case independently selected from Br, Cl, F, methyl, and ethyl. In embodiments, $R^{15}$ is in each case independently selected from Cl, F, CN, methyl, and ethyl. In embodiments, $R^{15}$ is in each case independently selected from Cl, F, methyl, and ethyl. In embodiments, $R^{15}$ is in each case independently selected from F, and methyl. In embodiments, $R^{15}$ is in each case independently selected from F, and ethynyl.

In embodiments, $R^{16}$ is in each case independently selected from halogen; CN; OH; $C_{1-6}$-alkyl; O—($C_{1-6}$-alkyl); ($C_{0-4}$-alkyl)-heteroaryl, wherein said heteroaryl is a 5- to 10-membered heteroaryl comprising 1, 2, 3 or 4 ring heteroatoms selected from N, S and O; ($C_{0-4}$-alkyl)-heterocycloalkenyl, wherein said heterocycloalkenyl is a 5- to 6-membered heterocycloalkenyl comprising 1 or 2 ring heteroatoms selected from N and O; ($C_{0-4}$-alkyl)-heterocycloalkyl, wherein said heterocycloalkyl is a 4- to 6-membered heterocycloalkyl comprising 1 or 2 ring heteroatoms selected from N and O; ($C_{0-4}$-alkyl)-aryl, wherein said aryl is a 6- to 10-membered aryl; ($C_{0-4}$-alkyl)-cycloalkenyl, wherein said cycloalkenyl is a 4- to 8-membered cycloalkenyl; and ($C_{0-4}$-alkyl)-cycloalkyl, wherein said cycloalkyl is a 3- to 8-membered cycloalkyl, wherein said alkyl, heteroaryl, heterocycloalkenyl, heterocycloalkyl, aryl, cycloalkenyl and cycloalkyl are optionally substituted by one or more groups independently selected from halogen, OH and $NH_2$.

In embodiments, $R^{16}$ is in each case independently selected from halogen; CN; OH; $C_{1-6}$-alkyl; O—($C_{1-6}$-alkyl); ($C_{0-4}$-alkyl)-heteroaryl, wherein said heteroaryl is a 5- to 10-membered heteroaryl comprising 1, 2, 3 or 4 ring heteroatoms selected from N, S and O; ($C_{0-4}$-alkyl)-heterocycloalkenyl, wherein said heterocycloalkenyl is a 5- to 6-membered heterocycloalkenyl comprising 1 or 2 ring heteroatoms selected from N and O; ($C_{0-4}$-alkyl)-heterocycloalkyl, wherein said heterocycloalkyl is a 4- to 6-membered heterocycloalkyl comprising 1 or 2 ring heteroatoms selected from N and O; ($C_{0-4}$-alkyl)-aryl, wherein said aryl is a 6- to 10-membered aryl; ($C_{0-4}$-alkyl)-cycloalkenyl, wherein said cycloalkenyl is a 4- to 8-membered cycloalkenyl; and ($C_{0-4}$-alkyl)-cycloalkyl, wherein said cycloalkyl is a 3- to 8-membered cycloalkyl.

In other embodiments, $R^{16}$ is in each case independently selected from halogen; CN; OH; $C_{1-6}$-alkyl; O—($C_{1-6}$-alkyl); ($C_{0-4}$-alkyl)-heteroaryl, wherein said heteroaryl is a 5- to 10-membered heteroaryl comprising 1, 2, 3 or 4 ring heteroatoms selected from N, S and O; ($C_{0-4}$-alkyl)-heterocycloalkyl, wherein said heterocycloalkyl is a 4- to 6-membered heterocycloalkyl comprising 1 or 2 ring heteroatoms selected from N and O; ($C_{0-4}$-alkyl)-aryl, wherein said aryl is a 6- to 10-membered aryl; and ($C_{0-4}$-alkyl)-cycloalkyl, wherein said cycloalkyl is a 3- to 8-membered cycloalkyl.

In other embodiments, $R^{16}$ is in each case independently selected from halogen; CN; OH; $C_{1-6}$-alkyl; O—($C_{1-6}$-alkyl); and ($C_{0-4}$-alkyl)-heterocycloalkyl, wherein said heterocycloalkyl is a 4- to 6-membered heterocycloalkyl comprising 1 or 2 ring heteroatoms selected from N and O. In other embodiments, $R^{16}$ is in each case independently selected from halogen, and OH. In other embodiments, $R^{16}$ is in each case independently selected from ($C_{0-4}$-alkyl)-heterocycloalkyl, wherein said heterocycloalkyl is a 4- to 6-membered heterocycloalkyl comprising 1 or 2 ring heteroatoms selected from N and O.

In embodiments, $R^{17}$ to $R^{23}$ are in each case independently selected from H; $C_{1-6}$-alkyl; $C_{3-8}$-cycloalkyl; 3- to 6-membered heterocycloalkyl comprising 1, 2 or 3 ring heteroatoms selected from N, S and O; $C_{6-10}$-aryl; and 5- to 10-membered heteroaryl comprising 1, 2, 3 or 4 ring heteroatoms selected from N, S and O, wherein said alkyl, cycloalkyl, heterocycloalkyl, aryl and heteroaryl are optionally substituted by one or more groups independently selected from halogen, OH, $C_{1-6}$-alkyl and $C_{1-6}$-haloalkyl.

In embodiments, $R^{17}$ to $R^{23}$ are in each case independently selected from H; $C_{1-6}$-alkyl; $C_{3-8}$-cycloalkyl; and $C_{6-10}$-aryl, wherein said alkyl, cycloalkyl and aryl are optionally substituted by one or more groups independently selected from halogen and OH.

In embodiments, $R^{17}$ to $R^{23}$ are in each case independently selected from H; $C_{1-6}$-alkyl; and $C_{6-10}$-aryl, wherein said alkyl, and aryl are optionally substituted by one or more groups selected from halogen and OH. In embodiments, $R^{17}$ to $R^{23}$ are in each case independently selected from H; $C_{1-6}$-alkyl; and $C_{6-10}$-aryl, wherein said alkyl, and aryl are optionally substituted by one or more groups selected from halogen. In embodiments, $R^{17}$ to $R^{23}$ are in each case independently selected from H, and $C_{1-6}$-alkyl optionally substituted by one or more groups selected from halogen. In embodiments, $R^{17}$ to $R^{23}$ are in each case independently selected from H.

In embodiments, for a pair of $R^{18}$ attached to a single nitrogen atom, at least one of said $R^{18}$ is H. In embodiments, for a pair of $R^{18}$ attached to a single nitrogen atom, each said $R^{18}$ is independently selected from H.

In embodiments, a pair of $R^{18}$ attached to the same nitrogen atom, taken together with the intervening nitrogen atom, forms a 3- to 10-membered heterocycloalkyl or heterocycloalkenyl group comprising 1, 2 or 3 ring heteroatoms selected from N, S and O, wherein said heterocycloalkyl or heterocycloalkenyl group is optionally substituted by one or more groups independently selected from halogen, OH, $C_{1-6}$-alkyl and $C_{1-6}$-haloalkyl. In embodiments, a pair of $R^{18}$ attached to the same nitrogen atom, taken together with the intervening nitrogen atom, forms a 3- to 8-membered heterocycloalkyl group comprising 1, 2 or 3 ring heteroatoms selected from N, S and O, wherein said heterocycloalkyl group is optionally substituted by one or more groups independently selected from halogen, OH, $C_{1-6}$-alkyl and $C_{1-6}$-haloalkyl. In embodiments, a pair of $R^{18}$ attached to the same nitrogen atom, taken together with the intervening nitrogen atom, forms a 4- to 6-membered heterocycloalkyl group comprising 1 or 2 ring heteroatoms selected from N, S and O, wherein said heterocycloalkyl group is optionally substituted by one or more groups independently selected from halogen, OH, $C_{1-6}$-alkyl and $C_{1-6}$-haloalkyl.

In embodiments, for a pair of $R^{21}$ attached to a single nitrogen atom, at least one of said $R^{21}$ is H. In embodiments, for a pair of $R^{21}$ attached to a single nitrogen atom, each said $R^{21}$ is independently selected from H.

In embodiments, a pair of $R^{21}$ attached to the same nitrogen atom, taken together with the intervening nitrogen atom, forms a 3- to 10-membered heterocycloalkyl or heterocycloalkenyl group comprising 1, 2 or 3 ring heteroatoms selected from N, S and O, wherein said heterocycloalkyl or heterocycloalkenyl group is optionally substituted by one or more groups independently selected from halogen, OH, $C_{1-6}$-alkyl and $C_{1-6}$-haloalkyl. In embodiments, a pair of $R^{21}$ attached to the same nitrogen atom, taken together with the intervening nitrogen atom, forms a 3- to 8-membered heterocycloalkyl group comprising 1, 2 or 3 ring heteroatoms selected from N, S and O, wherein said heterocycloalkyl group is optionally substituted by one or more groups independently selected from halogen, OH, $C_{1-6}$-alkyl and $C_{1-6}$-haloalkyl. In embodiments, a pair of $R^{21}$ attached to the same nitrogen atom, taken together with the intervening nitrogen atom, forms a 4- to 6-membered heterocycloalkyl group comprising 1 or 2 ring heteroatoms selected from N, S and O, wherein said heterocycloalkyl group is optionally substituted by one or more groups independently selected from halogen, OH, $C_{1-6}$-alkyl and $C_{1-6}$-haloalkyl.

In embodiments, for a pair of $R^{23}$ attached to a single nitrogen atom, at least one of said $R^{23}$ is H. In embodiments, for a pair of $R^{23}$ attached to a single nitrogen atom, each said $R^{23}$ is independently selected from H.

In embodiments, a pair of $R^{23}$ attached to the same nitrogen atom, taken together with the intervening nitrogen atom, forms a 3- to 10-membered heterocycloalkyl or heterocycloalkenyl group comprising 1, 2 or 3 ring heteroatoms selected from N, S and O, wherein said heterocycloalkyl or heterocycloalkenyl group is optionally substituted by one or more groups independently selected from halogen, OH, $C_{1-6}$-alkyl and $C_{1-6}$-haloalkyl. In embodiments, a pair of $R^{23}$ attached to the same nitrogen atom, taken together with the intervening nitrogen atom, forms a 3- to 8-membered heterocycloalkyl group comprising 1, 2 or 3 ring heteroatoms selected from N, S and O, wherein said heterocycloalkyl group is optionally substituted by one or more groups independently selected from halogen, OH, $C_{1-6}$-alkyl and $C_{1-6}$-haloalkyl. In embodiments, a pair of $R^{23}$ attached to the same nitrogen atom, taken together with the intervening nitrogen atom, forms a 4- to 6-membered heterocycloalkyl group comprising 1 or 2 ring heteroatoms selected from N, S and O, wherein said heterocycloalkyl group is optionally substituted by one or more groups independently selected from halogen, OH, $C_{1-6}$-alkyl and $C_{1-6}$-haloalkyl.

In embodiments, $R^{24}$ is in each case independently selected from halogen; CN; OH; $C_{1-6}$-alkyl; O—($C_{1-6}$-alkyl); ($C_{0-4}$-alkyl)-heteroaryl, wherein said heteroaryl is a 5- to 10-membered heteroaryl comprising 1, 2, 3 or 4 ring heteroatoms selected from N, S and O; ($C_{0-4}$-alkyl)-heterocycloalkenyl, wherein said heterocycloalkenyl is a 5- or 6-membered heterocycloalkenyl comprising 1 or 2 ring heteroatoms selected from N and O; ($C_{0-4}$-alkyl)-heterocycloalkyl, wherein said heterocycloalkyl is a 4- to 6-membered heterocycloalkyl comprising 1 or 2 ring heteroatoms selected from N and O; ($C_{0-4}$-alkyl)-aryl, wherein said aryl is a 6- to 10-membered aryl; ($C_{0-4}$-alkyl)-cycloalkenyl, wherein said cycloalkenyl is a 4- to 8-membered cycloalkenyl; and ($C_{0-4}$-alkyl)-cycloalkyl, wherein said cycloalkyl is a 3- to 8-membered cycloalkyl, wherein said alkyl, heteroaryl, heterocycloalkenyl, heterocycloalkyl, aryl, cycloalkenyl and cycloalkyl are optionally substituted by one or more groups independently selected from halogen, OH and $NH_2$.

In embodiments, $R^{24}$ is in each case independently selected from halogen; CN; OH; $C_{1-6}$-alkyl; O—($C_{1-6}$-alkyl); ($C_{0-4}$-alkyl)-heteroaryl, wherein said heteroaryl is a 5- to 10-membered heteroaryl comprising 1, 2, 3 or 4 ring heteroatoms selected from N, S and O; ($C_{0-4}$-alkyl)-heterocycloalkenyl, wherein said heterocycloalkenyl is a 5- or 6-membered heterocycloalkenyl comprising 1 or 2 ring heteroatoms selected from N and O; ($C_{0-4}$-alkyl)-heterocycloalkyl, wherein said heterocycloalkyl is a 4- to 6-membered heterocycloalkyl comprising 1 or 2 ring heteroatoms selected from N and O; ($C_{0-4}$-alkyl)-aryl, wherein said aryl is a 6- to 10-membered aryl; ($C_{0-4}$-alkyl)-cycloalkenyl, wherein said cycloalkenyl is a 4- to 8-membered cycloalkenyl; and ($C_{0-4}$-alkyl)-cycloalkyl, wherein said cycloalkyl is a 3- to 8-membered cycloalkyl.

In embodiments, $R^{24}$ is in each case independently selected from halogen; CN; OH; $C_{1-6}$-alkyl; O—($C_{1-6}$-alkyl); ($C_{0-4}$-alkyl)-heteroaryl, wherein said heteroaryl is a 5- to 10-membered heteroaryl comprising 1, 2, 3 or 4 ring heteroatoms selected from N, S and O; ($C_{0-4}$-alkyl)-heterocycloalkyl, wherein said heterocycloalkyl is a 4- to 6-membered heterocycloalkyl comprising 1 or 2 ring heteroatoms selected from N and O; ($C_{0-4}$-alkyl)-aryl, wherein said aryl is a 6- to 10-membered aryl; and ($C_{0-4}$-alkyl)-cycloalkyl, wherein said cycloalkyl is a 3- to 8-membered cycloalkyl.

In embodiments, $R^{24}$ is in each case independently selected from CN, OH, $C_{1-6}$-alkyl, O—($C_{1-6}$-alkyl), and ($C_{0-4}$-alkyl)-heterocycloalkyl, wherein said heterocycloalkyl is a 4- to 6-membered heterocycloalkyl comprising 1 or 2 ring heteroatoms selected from N and O. In embodiments, $R^{24}$ is in each case independently selected from OH, $C_{1-6}$-alkyl, and O—($C_{1-6}$-alkyl). In embodiments, $R^{24}$ is in each case OH.

In embodiments, $R^{24}$ is in each case independently selected from ($C_{0-4}$-alkyl)-heterocycloalkyl, wherein said heterocycloalkyl is a 4- to 6-membered heterocycloalkyl comprising 1 or 2 ring heteroatoms selected from N and O.

In embodiments, the compound has a defined stereochemistry at the carbon atom of the bicyclo[3.1.0]hexane to which the group $X^1$ (or $R^1$) is attached. Compounds disclosed herein having said defined stereochemistry are referred to using the suffix "a" or "b", respectively.

Accordingly, in embodiments, the compound is characterised by formula (Ia),

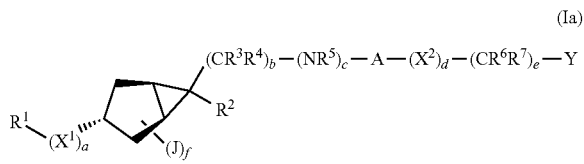

(Ia)

or a pharmaceutically acceptable salt or prodrug thereof, wherein a, b, c, d, e, f, A, J, $X^1$, $X^2$, Y, and $R^1$ to $R^7$ are as defined herein.

In other embodiments, the compound is characterised by formula (Ib),

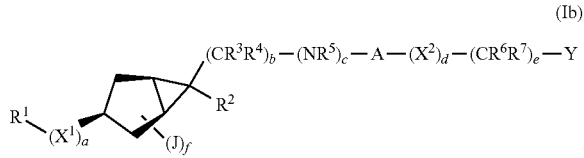

(Ib)

or a pharmaceutically acceptable salt or prodrug thereof, wherein a, b, c, d, e, f, A, J, $X^1$, $X^2$, Y, and $R^1$ to $R^7$ are as defined herein.

In embodiments, the compound has a defined stereochemistry at the carbon atom of the bicyclo[3.1.0]hexane to which the group $R^2$ is attached. Compounds disclosed herein having said defined stereochemistry are referred to using the suffix "c" or "d", respectively.

Accordingly, in embodiments, the compound is characterised by formula (Ic),

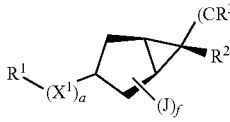
(Ic)

or a pharmaceutically acceptable salt or prodrug thereof, wherein a, b, c, d, e, f, A, J, $X^1$, $X^2$, Y, and $R^1$ to $R^7$ are as defined herein.

In other embodiments, the compound is characterised by formula (Id),

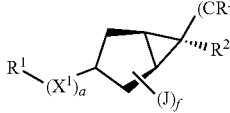
(Id)

or a pharmaceutically acceptable salt or prodrug thereof, wherein a, b, c, d, e, f, A, J, $X^1$, $X^2$, Y, and $R^1$ to $R^7$ are as defined herein.

In embodiments, the compound has a defined stereochemistry both at the carbon atom of the bicyclo[3.1.0]hexane to which the group $X^1$ (or $R^1$) is attached and also at the carbon atom of the bicyclo[3.1.0]hexane to which the group $R^2$ is attached. Compounds disclosed herein having said defined stereochemistry are referred to using the suffix "ac", "ad", "bc" or "bd", respectively.

Accordingly, in embodiments, the compound is characterised by formula (Iac),

(Iac)

or a pharmaceutically acceptable salt or prodrug thereof, wherein a, b, c, d, e, f, A, J, $X^1$, $X^2$, Y, and $R^1$ to $R^7$ are as defined herein.

In other embodiments, the compound is characterised by formula (Iad),

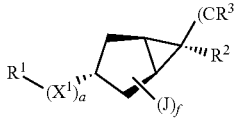
(Iad)

or a pharmaceutically acceptable salt or prodrug thereof, wherein a, b, c, d, e, f, A, J, $X^1$, $X^2$, Y, and $R^1$ to $R^7$ are as defined herein.

In other embodiments, the compound is characterised by formula (Ibc),

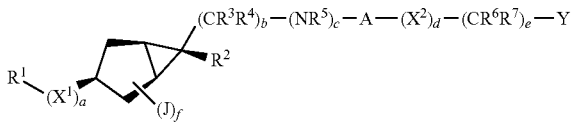
(Ibc)

or a pharmaceutically acceptable salt or prodrug thereof, wherein a, b, c, d, e, f, A, J, $X^1$, $X^2$, Y, and $R^1$ to $R^7$ are as defined herein.

In other embodiments, the compound is characterised by formula (Ibd),

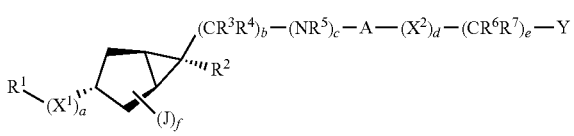
(Ibd)

or a pharmaceutically acceptable salt or prodrug thereof, wherein a, b, c, d, e, f, A, J, $X^1$, $X^2$, Y, and $R^1$ to $R^7$ are as defined herein.

In other aspects and embodiments, the invention provides a compound characterised by formula (II),

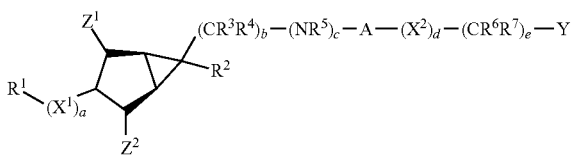
(II)

or a pharmaceutically acceptable salt or prodrug thereof, wherein:
$Z^1$ and $Z^2$ are each independently selected from H and J, and
a, b, c, d, e, A, J, $X^1$, $X^2$, Y, and $R^1$ to $R^7$ are as defined herein.

In embodiments, $Z^1$ is selected from H and J; and $Z^2$ is H.
In embodiments, $Z^1$ is H; and $Z^2$ is selected from H and J.
In embodiments, $Z^1$ and $Z^2$ are each independently selected from H.

In other aspects and embodiments, the invention provides a compound characterised by formula (III),

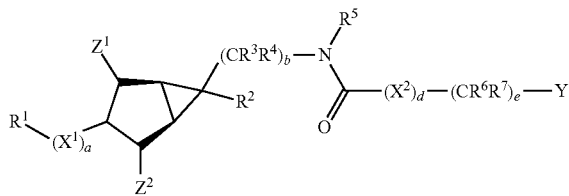
(III)

or a pharmaceutically acceptable salt or prodrug thereof, wherein:
b is 0 or 1, and
a, d, e, $X^1$, $X^2$, Y, $Z^1$, $Z^2$ and $R^1$ to $R^7$ are as defined herein.

In other aspects and embodiments, the invention provides a compound characterised by formula (IV),

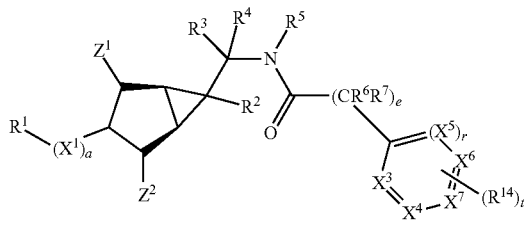

(IV)

or a pharmaceutically acceptable salt or prodrug thereof, wherein:
r is 0 or 1;
t is 0, 1, 2 or 3;
$X^3$ to $X^7$ are independently selected from CH, $CR^{14}$ and N, wherein no more than three of $X^3$ to $X^7$ may be N, and
a, e, $X^1$, $Z^1$, $Z^2$, $R^1$ to $R^7$, and $R^{14}$ are as defined herein.

In embodiments, r is 0. In embodiments, r is 1.
In embodiments, t is 0, 1 or 2. In embodiments, t is 0 or 1. In embodiments, t is 1, 2 or 3. In embodiments, t is 1 or 2. In embodiments, t is 2 or 3. In embodiments, t is 1. In embodiments, t is 2. In embodiments, t is 3.

In embodiments, two of $X^3$ to $X^7$ are nitrogen. In embodiments, one of $X^3$ to $X^7$ is nitrogen.

In embodiments, all of $X^3$ to $X^7$ are CH or $CR^{14}$. In embodiments, $X^7$ is CH or $CR^{14}$.

In embodiments, the compound is characterised by formula (IVa),

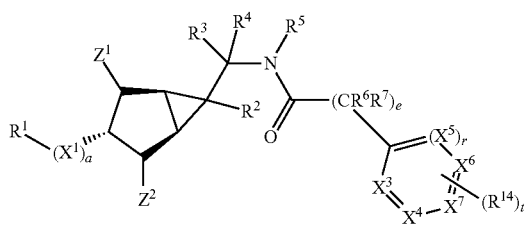

(IVa)

or a pharmaceutically acceptable salt or prodrug thereof, wherein a, e, r, t, $X^1$, $X^3$ to $X^7$, $Z^1$, $Z^2$, $R^1$ to $R^7$, and $R^{14}$ are as defined herein.

In embodiments, the compound is characterised by formula (IVac),

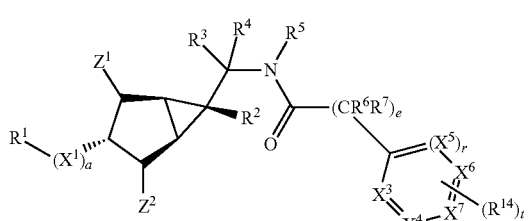

(IVac)

or a pharmaceutically acceptable salt or prodrug thereof, wherein a, e, r, t, $X^1$, $X^3$ to $X^7$, $Z^1$, $Z^2$, $R^1$ to $R^7$, and $R^{14}$ are as defined herein.

In embodiments, the compound is characterised by formula (IVbc),

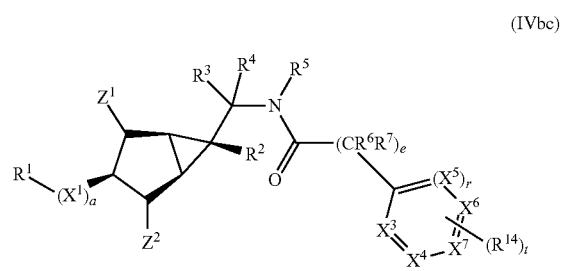

(IVbc)

or a pharmaceutically acceptable salt or prodrug thereof, wherein a, e, r, t, $X^1$, $X^3$ to $X^7$, $Z^1$, $Z^2$, $R^1$ to $R^7$, and $R^{14}$ are as defined herein.

In embodiments of formulae (IV), e is 0. In other embodiments of formulae (IV), e is 1; and $R^6$ and $R^7$ are independently selected from H. In other embodiments of formulae (IV), e is 0; and $R^3$ and $R^4$ are independently methyl.

In other aspects and embodiments, the invention provides a compound characterised by formula (V),

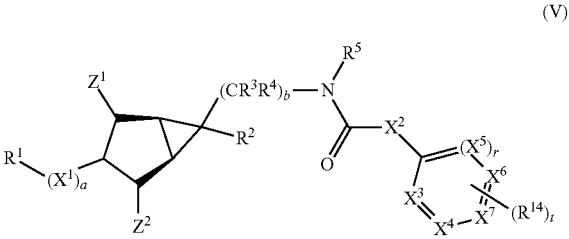

(V)

or a pharmaceutically acceptable salt or prodrug thereof, wherein a, b, r, t, $X^1$ to $X^7$, $Z^1$, $Z^2$, $R^1$ to $R^5$, and $R^{14}$ are as defined herein.

In embodiments, the compound is characterised by formula (Va),

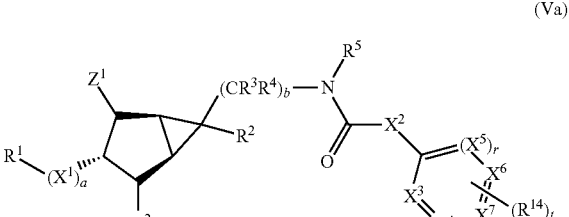

(Va)

or a pharmaceutically acceptable salt or prodrug thereof, wherein a, b, r, t, $X^1$ to $X^7$, $Z^1$, $Z^2$, $R^1$ to $R^5$, and $R^{14}$ are as defined herein.

In embodiments, the compound is characterised by formula (Vac),

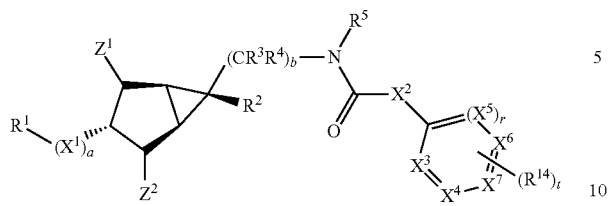

(Vac)

or a pharmaceutically acceptable salt or prodrug thereof, wherein a, b, r, t, $X^1$ to $X^7$, $Z^1$, $Z^2$, $R^1$ to $R^5$, and $R^{14}$ are as defined herein.

In embodiments, the compound is characterised by formula (Vbc),

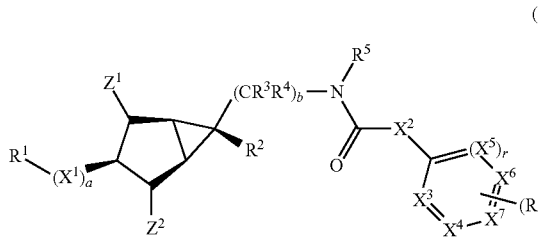

(Vbc)

or a pharmaceutically acceptable salt or prodrug thereof, wherein a, b, r, t, $X^1$ to $X^7$, $Z^1$, $Z^2$, $R^1$ to $R^5$, and $R^{14}$ are as defined herein.

In embodiments of formulae (V), b is 1; and $X^2$ is $NR^{13}$. In other embodiments of formulae (V), b is 0; and $X^2$ is $NR^{13}$.

In other aspects and embodiments, the invention provides a compound characterised by formula (XVI),

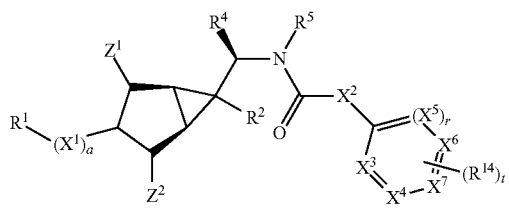

(XVI)

or a pharmaceutically acceptable salt or prodrug thereof, wherein a, r, t, $X^1$ to $X^7$, $Z^1$, $Z^2$, $R^1$, $R^2$, $R^4$, $R^5$, and $R^{14}$ are as defined herein.

In embodiments, the compound is characterised by formula (XVIac),

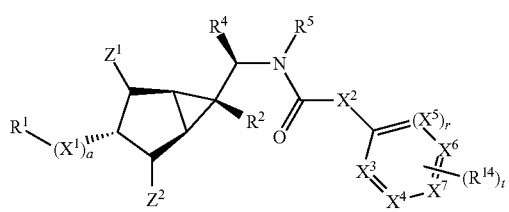

(XVIac)

or a pharmaceutically acceptable salt or prodrug thereof, wherein a, b, r, t, $X^1$ to $X^7$, $Z^1$, $Z^2$, $R^1$ to $R^5$, and $R^{14}$ are as defined herein.

In other aspects and embodiments, the invention provides a compound characterised by formula (VIII) or formula (IX),

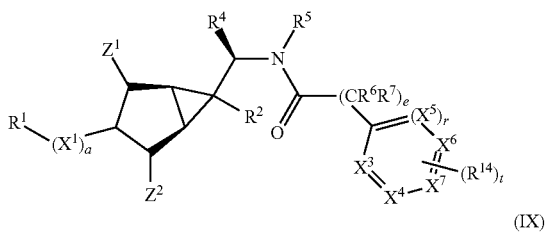

(VIII)

(IX)

or a pharmaceutically acceptable salt or prodrug thereof, wherein a, e, r, t, $X^1$, $X^3$ to $X^7$, $Z^1$, $Z^2$, $R^1$, $R^2$, $R^4$ to $R^7$, and $R^{14}$ are as defined herein.

In embodiments: e is 0; and $R^4$ is $C_{1-6}$-alkyl optionally substituted by one or more groups independently selected from $R^{16}$.

In embodiments, the compound is a compound of formula (VIII) or a pharmaceutically acceptable salt or prodrug thereof. In embodiments, the compound is characterised by formula (VIIIa),

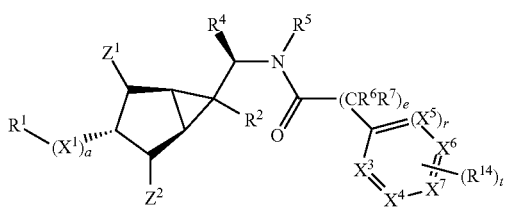

(VIIIa)

or a pharmaceutically acceptable salt or prodrug thereof, wherein a, e, r, t, $X^1$, $X^3$ to $X^7$, $Z^1$, $Z^2$, $R^1$, $R^2$, $R^4$ to $R^7$, and $R^{14}$ are as defined herein.

In embodiments, the compound is characterised by formula (VIIIac),

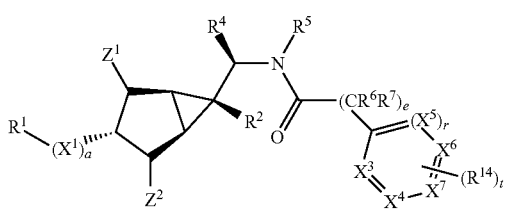

(VIIIac)

or a pharmaceutically acceptable salt or prodrug thereof, wherein a, e, r, t, $X^1$, $X^3$ to $X^7$, $Z^1$, $Z^2$, $R^1$, $R^2$, $R^4$ to $R^7$, and $R^{14}$ are as defined herein.

In embodiments, the compound is characterised by formula (VIIIbc),

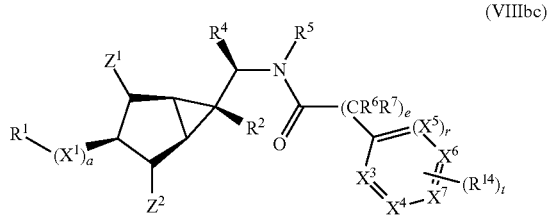

(VIIIbc)

or a pharmaceutically acceptable salt or prodrug thereof, wherein a, e, r, t, $X^1$, $X^3$ to $X^7$, $Z^1$, $Z^2$, $R^1$, $R^2$, $R^4$ to $R^7$, and $R^{14}$ are as defined herein.

In other aspects and embodiments, the invention provides a compound characterised by formula (XII),

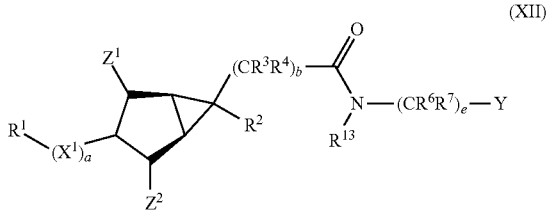

(XII)

or a pharmaceutically acceptable salt or prodrug thereof, wherein:

b is 1 or 2, and a, e, $X^1$, Y, $Z^1$, $Z^2$ and $R^1$ to $R^4$, $R^6$, $R^7$, and $R^{13}$ are as defined herein.

In other aspects and embodiments, the invention provides a compound characterised by formula (XIII),

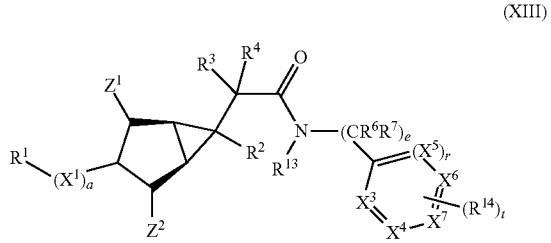

(XIII)

or a pharmaceutically acceptable salt or prodrug thereof, wherein a, e, r, t, $X^1$, $X^3$ to $X^7$, $Z^1$, $Z^2$, $R^1$ to $R^4$, $R^6$, $R^7$, $R^{13}$, and $R^{14}$ are as defined herein.

In embodiments, the invention provides a compound characterised by formula (XIIIa),

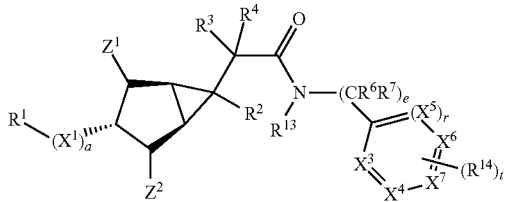

(XIIIa)

or a pharmaceutically acceptable salt or prodrug thereof, wherein a, e, r, t, $X^1$, $X^3$ to $X^7$, $Z^1$, $Z^2$, $R^1$ to $R^4$, $R^6$, $R^7$, $R^{13}$, and $R^{14}$ are as defined herein.

In embodiments, the invention provides a compound characterised by formula (XIIIac),

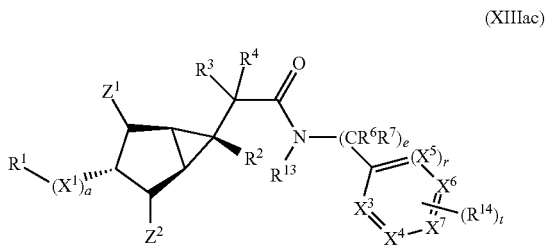

(XIIIac)

or a pharmaceutically acceptable salt or prodrug thereof, wherein a, e, r, t, $X^1$, $X^3$ to $X^7$, $Z^1$, $Z^2$, $R^1$ to $R^4$, $R^6$, $R^7$, $R^{13}$, and $R^{14}$ are as defined herein.

In other aspects and embodiments, the invention provides a compound characterised by formula (XIV) or formula (XV),

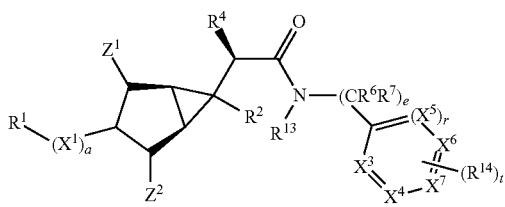

(XIV)

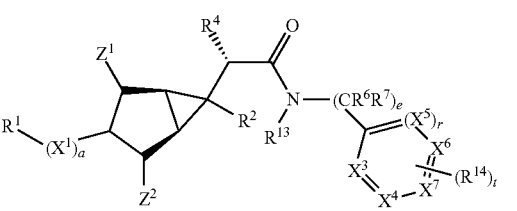

(XV)

or a pharmaceutically acceptable salt or prodrug thereof, wherein a, e, r, t, $X^1$, $X^3$ to $X^7$, $Z^1$, $Z^2$, $R^1$, $R^2$, $R^4$, $R^6$, $R^7$, $R^{13}$, and $R^{14}$ are as defined herein.

In embodiments, the invention provides a compound characterised by formula (XIVac),

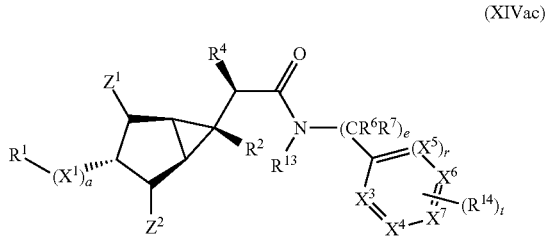

(XIVac)

or a pharmaceutically acceptable salt or prodrug thereof, wherein a, e, r, t, $X^1$, $X^3$ to $X^7$, $Z^1$, $Z^2$, $R^1$, $R^2$, $R^4$, $R^6$, $R^7$, $R^{13}$, and $R^{14}$ are as defined herein.

In embodiments, the invention provides a compound characterised by formula (XVac),

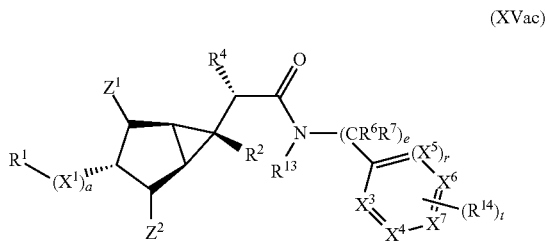

(XVac)

or a pharmaceutically acceptable salt or prodrug thereof, wherein a, e, r, t, $X^1$, $X^3$ to $X^7$, $Z^1$, $Z^2$, $R^1$, $R^2$, $R^4$, $R^6$, $R^7$, $R^{13}$, and $R^{14}$ are as defined herein.

In other aspects and embodiments, the invention provides a compound characterised by formula (X) or formula (XI),

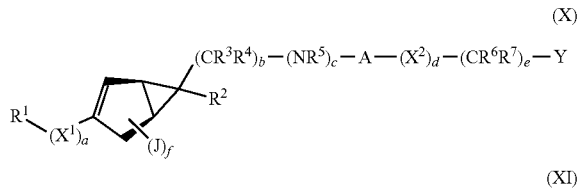

(X)

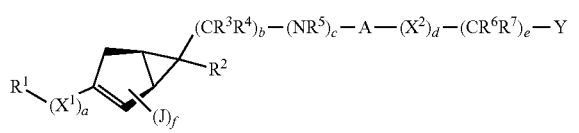

(XI)

or a pharmaceutically acceptable salt or prodrug thereof, wherein:
a, b, c, d, e, f, A, J, $X^1$, $X^2$, Y, and $R^1$ to $R^7$ are as defined herein.

In embodiments, a mixture of compounds characterised by formula (X) and formula (XI), or the pharmaceutically acceptable salts or prodrugs thereof, is provided.

In embodiments: a is 0; and $R^1$ is 5- to 10-membered heteroaryl comprising 1, 2, 3 or 4 ring heteroatoms selected from N, S and O, wherein said heteroaryl is optionally substituted by one or more groups independently selected from $R^{15}$.

The nomenclature used to denote stereochemical information in the compounds of formula (Ia), (Ib), (Ic), (Id), (Iac), (Iad), (Ibc) and (Ibd) applies analogously to other formulae described herein. Accordingly, in embodiments the compound is characterised by formula (IIa), (IIb), (IIc), (IId), (IIac), (IIad), (IIbc) or (IIbd), or a pharmaceutically acceptable salt or prodrug thereof. In other embodiments the compound is characterised by formula (IIIa), (IIIb), (IIIc), (IIId), (IIIac), (IIIad), (IIIbc) or (IIIbd), or a pharmaceutically acceptable salt or prodrug thereof. In other embodiments the compound is characterised by formula (IVa), (IVb), (IVc), (IVd), (IVac), (IVad), (IVbc) or (IVbd), or a pharmaceutically acceptable salt or prodrug thereof. In other embodiments the compound is characterised by formula (Va), (Vb), (Vc), (Vd), (Vac), (Vad), (Vbc) or (Vbd), or a pharmaceutically acceptable salt or prodrug thereof. In other embodiments the compound is characterised by formula (VIc) or (VId), or a pharmaceutically acceptable salt or prodrug thereof. In other embodiments the compound is characterised by formula (VIIc) or (VIId), or a pharmaceutically acceptable salt or prodrug thereof. In other embodiments the compound is characterised by formula (VIIIa), (VIIIb), (VIIIc), (VIIId), (VIIIac), (VIIIad), (VIIIbc) or (VIIIbd), or a pharmaceutically acceptable salt or prodrug thereof. In other embodiments, the compound is characterised by formula (IXa), (IXb), (IXc), (IXd), (IXac), (IXad), (IXbc) or (IXbd), or a pharmaceutically acceptable salt or prodrug thereof. In other embodiments, the compound is characterised by formula (Xc) or (Xd), or a pharmaceutically acceptable salt or prodrug thereof. In other embodiments, the compound is characterised by formula (XIc) or (XId), or a pharmaceutically acceptable salt or prodrug thereof. In other embodiments the compound is characterised by formula (XIIa), (XIIb), (XIIc), (XIId), (XIIac), (XIIad), (XIIbc) or (XIIbd), or a pharmaceutically acceptable salt or prodrug thereof. In other embodiments the compound is characterised by formula (XIIIa), (XIIIb), (XIIIc), (XIIId), (XIIIac), (XIIIad), (XIIIbc) or (XIIIbd), or a pharmaceutically acceptable salt or prodrug thereof. In other embodiments the compound is characterised by formula (XIVa), (XIVb), (XIVc), (XIVd), (XIVac), (XIVad), (XIVbc) or (XIVbd), or a pharmaceutically acceptable salt or prodrug thereof. In other embodiments the compound is characterised by formula (XVa), (XVb), (XVc), (XVd), (XVac), (XVad), (XVbc) or (XVbd), or a pharmaceutically acceptable salt or prodrug thereof. In other embodiments the compound is characterised by formula (XVIa), (XVIb), (XVIc), (XVId), (XVIac), (XVIad), (XVIbc) or (XVIbd), or a pharmaceutically acceptable salt or prodrug thereof.

In one aspect, the compound is selected from the group consisting of Compounds 1 to 363:

| | |
|---|---|
| Compound 1 | 4-chloro-N-(1-((1R,3r,5S,6r)-3-hydroxybicyclo[3.1.0]hexan-6-yl)propyl)benzamide |
| Compound 2 | 4-chloro-N-(1-((1R,3r,5S,6r)-3-(quinolin-4-yloxy)bicyclo[3.1.0]hexan-6-yl)propyl)benzamide |
| Compound 3 | 4-chloro-N-(1-((1R,3s,5S,6r)-3-hydroxybicyclo[3.1.0]hexan-6-yl)propyl)benzamide |
| Compound 4 | 4-chloro-N-(1-((1R,3s,5S,6r)-3-(quinolin-4-yloxy)bicyclo[3.1.0]hexan-6-yl)propyl)benzamide |
| Compound 5 | 4-chloro-N-(1-((1R,3s,5S,6r)-3-((6-fluoroquinazolin-4-yl)oxy)bicyclo[3.1.0]hexan-6-yl)propyl)benzamide |

-continued

| | |
|---|---|
| Compound 6 | 4-chloro-N-(1-((1R,3s,5S,6r)-3-(6-fluoro-4-oxoquinazolin-3(4H)-yl)bicyclo[3.1.0]hexan-6-yl)propyl)benzamide |
| Compound 7 | 2-(4-chlorophenyl)-N-((1R,3s,5S,6r)-3-((6-fluoroquinolin-4-yl)oxy)bicyclo[3.1.0]hexan-6-yl)acetamide |
| Compound 8 | (1R,5S)-N-(4-chlorophenyl)-3-(quinolin-4-yloxy)bicyclo[3.1.0]hexane-6-carboxamide |
| Compound 9 | 4-chloro-N-(((1R,3s,5S,6r)-3-((6-fluoroquinolin-4-yl)oxy)bicyclo[3.1.0]hexan-6-yl)methyl)benzamide |
| Compound 10 | 1-(4-chlorophenyl)-3-((1R,3s,5S,6r)-3-((6-fluoroquinolin-4-yl)oxy)bicyclo[3.1.0]hexan-6-yl)urea |
| Compound 11 | 2-(4-chlorophenyl)-5-(3-(quinolin-4-yloxy)bicyclo[3.1.0]hexan-6-yl)-1,3,4-oxadiazole |
| Compound 12 | 4-((6-(2-(4-chlorophenoxy)ethyl)bicyclo[3.1.0]hexan-3-yl)oxy)-6-fluoro-2-(trifluoromethyl)quinoline |
| Compound 13 | 4-chloro-N-(1-((1R,3s,5S,6r)-3-((6-fluoroquinazolin-4-yl)oxy)bicyclo[3.1.0]hexan-6-yl)ethyl)benzamide |
| Compound 14 | 4-chloro-N-(1-((1R,3s,5S,6r)-3-(4-fluorophenoxy)bicyclo[3.1.0]hexan-6-yl)propyl)benzamide |
| Compound 15 | 4-chloro-N-(1-((1R,3s,5S,6r)-3-((2-methylpyridin-4-yl)oxy)bicyclo[3.1.0]hexan-6-yl)propyl)benzamide |
| Compound 16 | (1R,5S)-N-(4-chlorobenzyl)-3-(quinolin-4-yloxy)bicyclo[3.1.0]hexane-6-carboxamide |
| Compound 17 | (1R,5S)-N-(4-chlorobenzyl)-3-((6-fluoro-2-(trifluoromethyl)quinolin-4-yl)oxy)bicyclo[3.1.0]hexane-6-carboxamide |
| Compound 18 | 4-chloro-N-(1-((1R,3s,5S,6r)-3-((6-fluoropyridin-3-yl)oxy)bicyclo[3.1.0]hexan-6-yl)propyl)benzamide |
| Compound 19 | 4-chloro-N-(1-((1R,3s,5S,6r)-3-((6-fluoroquinolin-4-yl)oxy)bicyclo[3.1.0]hexan-6-yl)propyl)benzamide |
| Compound 20 | 4-chloro-N-(1-((1R,3s,5S,6r)-3-((6-fluoro-2-methylquinolin-4-yl)oxy)bicyclo[3.1.0]hexan-6-yl)propyl)benzamide |
| Compound 21 | 4-chloro-N-(1-((1R,3s,5S,6r)-3-((7-chloroquinazolin-4-yl)oxy)bicyclo[3.1.0]hexan-6-yl)propyl)benzamide |
| Compound 22 | 4-chloro-N-(1-((1R,3s,5S,6r)-3-((6-fluoro-2-(trifluoromethyl)quinolin-4-yl)oxy)bicyclo[3.1.0]hexan-6-yl)propyl)benzamide |
| Compound 23 | 4-chloro-N-(((1R,3s,5S,6s)-3-((6-fluoroquinolin-4-yl)oxy)bicyclo[3.1.0]hexan-6-yl)methyl)benzamide |
| Compound 24 | 4-chloro-N-(((1R,3s,5S,6s)-3-((6-fluoro-2-(trifluoromethyl)quinolin-4-yl)oxy)bicyclo[3.1.0]hexan-6-yl)methyl)benzamide |
| Compound 25 | 4-chloro-N-(3-((6-fluoro-2-(trifluoromethyl)quinolin-4-yl)oxy)bicyclo[3.1.0]hexan-6-yl)benzamide |
| Compound 26 | 4-chloro-N-(3-(quinolin-4-yloxy)bicyclo[3.1.0]hexan-6-yl)benzamide |
| Compound 27 | 1-(4-bromophenyl)-N-(3-(quinolin-4-yloxy)bicyclo[3.1.0]hexan-6-yl)methanesulfonamide |
| Compound 28 | 4-chloro-N-(3-(quinolin-4-yloxy)bicyclo[3.1.0]hexan-6-yl)benzenesulfonamide |
| Compound 29 | 1-(4-chlorophenyl)-3-((1R,3r,5S,6r)-3-((6-fluoroquinolin-4-yl)oxy)bicyclo[3.1.0]hexan-6-yl)urea |
| Compound 30 | 2-(4-chlorophenyl)-N-((1R,5S)-3-(quinolin-4-yloxy)bicyclo[3.1.0]hexan-6-yl)acetamide |
| Compound 31 | 2-(4-chlorophenyl)-N-((1R,3r,5S)-3-((6-fluoroquinolin-4-yl)oxy)bicyclo[3.1.0]hexan-6-yl)acetamide |
| Compound 32 | 4-chloro-N-(((1R,3r,5S,6r)-3-((6-fluoroquinolin-4-yl)oxy)bicyclo[3.1.0]hexan-6-yl)methyl)benzamide |
| Compound 33 | 4-chloro-N-(((1R,3r,5S,6r)-3-((4-chloroquinolin-6-yl)oxy)bicyclo[3.1.0]hexan-6-yl)methyl)benzamide |
| Compound 34 | 4-chloro-N-(1-((1R,3s,5S,6r)-3-(7-fluoro-4-oxoquinazolin-3(4H)-yl)bicyclo[3.1.0]hexan-6-yl)propyl)benzamide |
| Compound 35 | 4-chloro-N-(1-((1R,3s,5S,6r)-3-((7-fluoroquinazolin-4-yl)oxy)bicyclo[3.1.0]hexan-6-yl)propyl)benzamide |
| Compound 36 | 4-chloro-N-(1-((1R,3s,5S,6r)-3-(5-fluoro-4-oxoquinazolin-3(4H)-yl)bicyclo[3.1.0]hexan-6-yl)propyl)benzamide |
| Compound 37 | 4-chloro-N-(1-((1R,3s,5S,6r)-3-((5-fluoroquinazolin-4-yl)oxy)bicyclo[3.1.0]hexan-6-yl)propyl)benzamide |
| Compound 38 | N-(1-((1R,3s,5S,6r)-3-((1,5-naphthyridin-4-yl)oxy)bicyclo[3.1.0]hexan-6-yl)propyl)-4-chlorobenzamide |

-continued

| | |
|---|---|
| Compound 39 | 4-chloro-N-(1-((1R,3s,5S,6r)-3-((3-fluoropyridin-2-yl)oxy)bicyclo[3.1.0]hexan-6-yl)propyl)benzamide |
| Compound 40 | 4-chloro-N-(1-((1R,3s,5S,6r)-3-((6-methylpyridin-2-yl)oxy)bicyclo[3.1.0]hexan-6-yl)propyl)benzamide |
| Compound 41 | 4-chloro-N-(1-((1R,3s,5S,6r)-3-((3-methylpyridin-2-yl)oxy)bicyclo[3.1.0]hexan-6-yl)propyl)benzamide |
| Compound 42 | 4-chloro-N-(1-((1R,3s,5S,6r)-3-(2,5-difluorophenoxy)bicyclo[3.1.0]hexan-6-yl)propyl)benzamide |
| Compound 43 | 4-chloro-N-(1-((1R,3s,5S,6r)-3-(quinolin-8-yloxy)bicyclo[3.1.0]hexan-6-yl)propyl)benzamide |
| Compound 44 | 4-chloro-N-(1-((1R,3s,5S,6r)-3-(2,6-difluorophenoxy)bicyclo[3.1.0]hexan-6-yl)propyl)benzamide |
| Compound 45 | N-(1-((1R,3s,5S,6r)-3-(2-(2-amino-2-oxoethyl)phenoxy)bicyclo[3.1.0]hexan-6-yl)propyl)-4-chlorobenzamide |
| Compound 46 | 4-chloro-N-(1-((1R,3s,5S,6r)-3-(cinnolin-4-yloxy)bicyclo[3.1.0]hexan-6-yl)propyl)benzamide |
| Compound 47 | 4-chloro-N-(1-((1R,3s,5S,6r)-3-(4-oxocinnolin-1(4H)-yl)bicyclo[3.1.0]hexan-6-yl)propyl)benzamide |
| Compound 48 | 4-chloro-N-(1-((1R,3s,5S,6r)-3-(2-((dimethylamino)methyl)phenoxy)bicyclo[3.1.0]hexan-6-yl)propyl)benzamide |
| Compound 49 | 4-chloro-N-(1-((1R,3s,5S,6r)-3-(quinolin-3-yloxy)bicyclo[3.1.0]hexan-6-yl)propyl)benzamide |
| Compound 50 | 4-chloro-N-(1-((1R,3s,5S,6r)-3-((1-methyl-2-oxo-1,2-dihydroquinolin-4-yl)oxy)bicyclo[3.1.0]hexan-6-yl)propyl)benzamide |
| Compound 51 | N-(1-((1R,3s,5S,6r)-3-(1H-pyrazolo[4,3-c]pyridin-1-yl)bicyclo[3.1.0]hexan-6-yl)propyl)-4-chlorobenzamide |
| Compound 52 | 4-chloro-N-(1-((1R,3s,5S,6r)-3-((5-fluoro-2-methylpyrimidin-4-yl)oxy)bicyclo[3.1.0]hexan-6-yl)propyl)benzamide |
| Compound 53 | 4-chloro-N-(1-((1R,3s,5S,6r)-3-(7-chloro-4-oxoquinazolin-3(4H)-yl)bicyclo[3.1.0]hexan-6-yl)propyl)benzamide |
| Compound 54 | 4-chloro-N-(1-((1R,3s,5S,6r)-3-((5-fluoropyrimidin-4-yl)oxy)bicyclo[3.1.0]hexan-6-yl)propyl)benzamide |
| Compound 55 | N-(1-((1R,3s,5S,6r)-3-((1,6-naphthyridin-4-yl)oxy)bicyclo[3.1.0]hexan-6-yl)propyl)-4-chlorobenzamide |
| Compound 56 | 4-chloro-N-(1-((1R,3s,5S,6r)-3-((7-fluoroquinolin-4-yl)oxy)bicyclo[3.1.0]hexan-6-yl)propyl)benzamide |
| Compound 57 | 4-chloro-N-(1-((1R,3s,5S,6r)-3-((4-chloroquinolin-7-yl)oxy)bicyclo[3.1.0]hexan-6-yl)propyl)benzamide |
| Compound 58 | 4-chloro-N-(1-((1R,3s,5S,6r)-3-((5-fluoropyridin-3-yl)oxy)bicyclo[3.1.0]hexan-6-yl)propyl)benzamide |
| Compound 59 | 4-chloro-N-(1-((1R,3s,5S,6r)-3-(quinazolin-4-yloxy)bicyclo[3.1.0]hexan-6-yl)propyl)benzamide |
| Compound 60 | 4-chloro-N-(1-((1R,3s,5S,6r)-3-((2-chloropyridin-3-yl)oxy)bicyclo[3.1.0]hexan-6-yl)propyl)benzamide |
| Compound 61 | 2-(4-chlorophenyl)-N-((1R,3s,5S,6r)-3-((6-fluoroquinazolin-4-yl)oxy)bicyclo[3.1.0]hexan-6-yl)acetamide |
| Compound 62 | 2-(4-chlorophenyl)-N-((1R,3s,5S,6r)-3-(6-fluoro-4-oxoquinazolin-3(4H)-yl)bicyclo[3.1.0]hexan-6-yl)acetamide |
| Compound 63 | 4-chloro-N-(1-((1R,3s,5S,6r)-3-(6-fluoro-4-oxoquinazolin-3(4H)-yl)bicyclo[3.1.0]hexan-6-yl)ethyl)benzamide |
| Compound 64 | 4-chloro-N-(1-((1R,3s,5S,6r)-3-((6-fluoroquinazolin-4-yl)oxy)bicyclo[3.1.0]hexan-6-yl)ethyl)benzamide |
| Compound 65 | 4-chloro-N-(((1R,3s,5S,6r)-3-(6-fluoro-4-oxoquinazolin-3(4H)-yl)bicyclo[3.1.0]hexan-6-yl)methyl)benzamide |
| Compound 66 | 4-cyano-N-(1-((1R,3s,5S,6r)-3-((6-fluoroquinazolin-4-yl)oxy)bicyclo[3.1.0]hexan-6-yl)propyl)benzamide |
| Compound 67 | 4-cyano-N-(1-((1R,3s,5S,6r)-3-(6-fluoro-4-oxoquinazolin-3(4H)-yl)bicyclo[3.1.0]hexan-6-yl)propyl)benzamide |
| Compound 68 | N-(1-((1R,3s,5S,6r)-3-((6-fluoroquinazolin-4-yl)oxy)bicyclo[3.1.0]hexan-6-yl)propyl)-2-methoxypyrimidine-5-carboxamide |
| Compound 69 | 2,2-difluoro-N-(1-((1R,3s,5S,6r)-3-((6-fluoroquinazolin-4-yl)oxy)bicyclo[3.1.0]hexan-6-yl)propyl)benzo[d][1,3]dioxole-5-carboxamide |
| Compound 70 | 4-chloro-N-(1-((1R,3s,5S,6r)-3-((7-fluoroquinazolin-4-yl)oxy)bicyclo[3.1.0]hexan-6-yl)ethyl)benzamide |

-continued

| | |
|---|---|
| Compound 71 | 4-chloro-N-(1-((1R,3s,5S,6r)-3-((3-methylpyridin-2-yl)oxy)bicyclo[3.1.0]hexan-6-yl)ethyl)benzamide |
| Compound 72 | 4-chloro-N-(1-((1R,3s,5S,6r)-3-(phthalazin-1-yloxy)bicyclo[3.1.0]hexan-6-yl)propyl)benzamide |
| Compound 73 | 4-chloro-N-(1-((1R,3s,5S,6r)-3-morpholinobicyclo[3.1.0]hexan-6-yl)propyl)benzamide |
| Compound 74 | N-(1-((1R,3s,5S,6r)-3-(6-fluoro-4-oxoquinazolin-3(4H)-yl)bicyclo[3.1.0]hexan-6-yl)propyl)-6-methoxynicotinamide |
| Compound 75 | 5-chloro-N-(1-((1R,3s,5S,6r)-3-(6-fluoro-4-oxoquinazolin-3(4H)-yl)bicyclo[3.1.0]hexan-6-yl)propyl)picolinamide |
| Compound 76 | 5-cyano-N-(1-((1R,3s,5S,6r)-3-(6-fluoro-4-oxoquinazolin-3(4H)-yl)bicyclo[3.1.0]hexan-6-yl)propyl)picolinamide |
| Compound 77 | 5-chloro-N-(1-((1R,5S)-3-(cinnolin-4-yloxy)bicyclo[3.1.0]hexan-6-yl)propyl)picolinamide |
| Compound 78 | N-(1-((1R,3s,5S,6r)-3-((6-fluoroquinazolin-4-yl)oxy)bicyclo[3.1.0]hexan-6-yl)propyl)-6-methoxynicotinamide |
| Compound 79 | 2-(4-chlorophenyl)-N-((1R,3s,5S,6r)-3-(cinnolin-4-yloxy)bicyclo[3.1.0]hexan-6-yl)acetamide |
| Compound 80 | N-(1-((1R,3s,5S,6r)-3-(cinnolin-4-yloxy)bicyclo[3.1.0]hexan-6-yl)propyl)-4-cyanobenzamide |
| Compound 81 | N-(1-((1R,3s,5S,6r)-3-(1H-1,2,4-triazol-1-yl)bicyclo[3.1.0]hexan-6-yl)propyl)-4-chlorobenzamide |
| Compound 82 | N-(1-((1R,3s,5S,6r)-3-(cinnolin-4-yloxy)bicyclo[3.1.0]hexan-6-yl)propyl)-5-cyanopicolinamide |
| Compound 83 | 5-cyano-N-(1-((1R,3s,5S,6r)-3-(4-oxocinnolin-1(4H)-yl)bicyclo[3.1.0]hexan-6-yl)propyl)picolinamide |
| Compound 84 | ethyl 3-(4-chlorobenzamido)-3-((1R,3s,5S,6r)-3-(cinnolin-4-yloxy)bicyclo[3.1.0]hexan-6-yl)propanoate |
| Compound 85 | 2-(4-chlorophenyl)-N-((1R,3s,5S,6r)-3-(4-oxocinnolin-1(4H)-yl)bicyclo[3.1.0]hexan-6-yl)acetamide |
| Compound 86 | 2-(4-chlorophenyl)-N-((1R,3s,5S,6r)-3-(cinnolin-4-yloxy)bicyclo[3.1.0]hexan-6-yl)-N-methylacetamide |
| Compound 87 | 4-cyano-N-(2-((1R,5S)-3-(4-oxocinnolin-1(4H)-yl)bicyclo[3.1.0]hexan-6-yl)propan-2-yl)benzamide |
| Compound 88 | N-(2-((1R,5S)-3-(cinnolin-4-yloxy)bicyclo[3.1.0]hexan-6-yl)propan-2-yl)-4-cyanobenzamide |
| Compound 89 | N-(1-((1R,3s,5S,6r)-3-(1H-benzo[d]imidazol-1-yl)bicyclo[3.1.0]hexan-6-yl)propyl)-4-chlorobenzamide |
| Compound 90 | N-(1-((1R,3s,5S,6r)-3-azidobicyclo[3.1.0]hexan-6-yl)propyl)-4-chlorobenzamide |
| Compound 91 | 4-chloro-N-(1-((1R,3s,5S,6r)-3-(4-cyclopropyl-1H-1,2,3-triazol-1-yl)bicyclo[3.1.0]hexan-6-yl)propyl)benzamide |
| Compound 92 | 4-chloro-N-(1-((1R,3s,5S,6r)-3-((4-chloro-2-methylpyridin-3-yl)oxy)bicyclo[3.1.0]hexan-6-yl)propyl)benzamide |
| Compound 93 | 4-chloro-N-(1-((1R,3s,5S,6r)-3-((3-fluoro-2-methylpyridin-4-yl)oxy)bicyclo[3.1.0]hexan-6-yl)propyl)benzamide |
| Compound 94 | 1-((1R,3s,5S,6r)-6-(1-(4-chlorobenzamido)propyl)bicyclo[3.1.0]hexan-3-yl)-1H-1,2,3-triazole-4-carboxylic acid |
| Compound 95 | 1-((1R,3s,5S,6r)-6-(1-(4-chlorobenzamido)propyl)bicyclo[3.1.0]hexan-3-yl)-1H-1,2,3-triazole-4-carboxamide |
| Compound 96 | 4-chloro-N-(1-((1R,3s,5S,6r)-3-((tetrahydro-2H-pyran-4-yl)methoxy)bicyclo[3.1.0]hexan-6-yl)propyl)benzamide |
| Compound 97 | 4-chloro-N-(1-((1R,3s,5S,6r)-3-(4-(2-hydroxypropan-2-yl)-1H-1,2,3-triazol-1-yl)bicyclo[3.1.0]hexan-6-yl)propyl)benzamide |
| Compound 98 | 4-chloro-N-(1-((1R,3s,5S,6r)-3-(4-(pyrrolidine-1-carbonyl)-1H-1,2,3-triazol-1-yl)bicyclo[3.1.0]hexan-6-yl)propyl)benzamide |
| Compound 99 | N-(1-((1R,3s,5S,6r)-3-(1H-benzo[d][1,2,3]triazol-1-yl)bicyclo[3.1.0]hexan-6-yl)propyl)-4-chlorobenzamide |
| Compound 100 | N-(1-((1R,3s,5S,6r)-3-(2H-benzo[d][1,2,3]triazol-2-yl)bicyclo[3.1.0]hexan-6-yl)propyl)-4-chlorobenzamide |
| Compound 101 | 4-chloro-N-(1-((1R,3s,5S,6r)-3-((tetrahydro-2H-pyran-4-yl)oxy)bicyclo[3.1.0]hexan-6-yl)propyl)benzamide |
| Compound 102 | 4-cyano-N-(1-((1R,3s,5S,6r)-3-((7-fluoroquinazolin-4-yl)oxy)bicyclo[3.1.0]hexan-6-yl)ethyl)benzamide |

-continued

| | |
|---|---|
| Compound 103 | 4-chloro-N-((S)-1-((1R,3R,5S,6r)-3-(cinnolin-4-yloxy)bicyclo[3.1.0]hexan-6-yl)propyl)benzamide |
| Compound 104 | 4-chloro-N-((R)-1-((1R,3S,5S,6r)-3-(cinnolin-4-yloxy)bicyclo[3.1.0]hexan-6-yl)propyl)benzamide |
| Compound 105 | 4-cyano-N-(1-((1R,3r,5S,6r)-3-hydroxybicyclo[3.1.0]hexan-6-yl)ethyl)benzamide |
| Compound 106 | 4-cyano-N-(1-((1R,3s,5S,6r)-3-hydroxybicyclo[3.1.0]hexan-6-yl)ethyl)benzamide |
| Compound 107 | 4-cyano-N-(1-((1R,3s,5S,6r)-3-((6-fluoroquinazolin-4-yl)oxy)bicyclo[3.1.0]hexan-6-yl)ethyl)benzamide |
| Compound 108 | 4-cyano-N-(1-((1R,3s,5S,6r)-3-(6-fluoro-4-oxoquinazolin-3(4H)-yl)bicyclo[3.1.0]hexan-6-yl)ethyl)benzamide |
| Compound 109 | 2-(4-Chlorophenyl)-N-(3-(6-fluoroquinolin-4-yl)-3-azabicyclo[3.1.0]hexan-6-yl)acetamide |
| Compound 110 | N-(3-(6-fluoroquinolin-4-yl)-3-azabicyclo[3.1.0]hexan-6-yl)-3-hydroxy-2-phenylpropanamide |
| Compound 111 | 2-(4-bromophenyl)-N-(3-(6-fluoroquinolin-4-yl)-3-azabicyclo[3.1.0]hexan-6-yl)-2-hydroxyacetamide |
| Compound 112 | 2-(5-chloro-3-fluoropyridin-2-yl)-N-(3-(6-fluoroquinolin-4-yl)-3-azabicyclo[3.1.0]hexan-6-yl)acetamide |
| Compound 113 | N-(1-((1R,5S,6R)-bicyclo[3.1.0]hex-2-en-6-yl)propyl)-4-chlorobenzamide |
| Compound 114 | 4-chloro-N-(1-((1R,3s,5S,6r)-3-(2,3-dioxoindolin-1-yl)bicyclo[3.1.0]hexan-6-yl)propyl)benzamide |
| Compound 115 | N-(1-((1R,3s,5S,6r)-3-((6-fluoroquinazolin-4-yl)oxy)bicyclo[3.1.0]hexan-6-yl)ethyl)-6-methoxynicotinamide |
| Compound 116 | 4-chloro-N-(1-((1R,3s,5S,6r)-3-(phenylsulfonamido)bicyclo[3.1.0]hexan-6-yl)propyl)benzamide |
| Compound 117 | N-((1R,3s,5S,6r)-6-(1-(4-chlorobenzamido)propyl)bicyclo[3.1.0]hexan-3-yl)picolinamide |
| Compound 118 | N-((1R,3s,5S,6r)-6-(1-(4-chlorobenzamido)propyl)bicyclo[3.1.0]hexan-3-yl)quinoline-2-carboxamide |
| Compound 119 | 4-chloro-N-(1-((1R,3s,5S,6r)-3-(3,3-difluoro-2-oxoindolin-1-yl)bicyclo[3.1.0]hexan-6-yl)propyl)benzamide |
| Compound 120 | 4-cyano-N-(1-((1R,3s,5S,6r)-3-(7-fluoro-4-oxoquinazolin-3(4H)-yl)bicyclo[3.1.0]hexan-6-yl)ethyl)benzamide |
| Compound 121 | 4-chloro-N-(1-((1R,3s,5S,6r)-3-(5-fluoro-2-oxoindolin-1-yl)bicyclo[3.1.0]hexan-6-yl)propyl)benzamide |
| Compound 122 | 4-chloro-N-(1-((1R,3s,5S,6r)-3-(3,3-dimethyl-2,5-dioxopyrrolidin-1-yl)bicyclo[3.1.0]hexan-6-yl)propyl)benzamide |
| Compound 123 | 4-chloro-N-(1-((1R,3s,5S,6r)-3-((6-fluoroquinazolin-4-yl)amino)bicyclo[3.1.0]hexan-6-yl)propyl)benzamide |
| Compound 124 | N-(1-((1R,3s,5S,6r)-3-((7-fluoroquinazolin-4-yl)oxy)bicyclo[3.1.0]hexan-6-yl)ethyl)-6-methoxynicotinamide |
| Compound 125 | 4-chloro-N-(1-((1R,3s,5S,6r)-3-(6-fluoro-1H-benzo[d]imidazol-1-yl)bicyclo[3.1.0]hexan-6-yl)propyl)benzamide |
| Compound 126 | 4-chloro-N-(1-((1R,3r,5S,6r)-3-((6-fluoroquinolin-4-yl)oxy)bicyclo[3.1.0]hexan-6-yl)propyl)benzamide |
| Compound 127 | 4-chloro-N-(1-((1R,3r,5S,6r)-3-((4-chloroquinolin-6-yl)oxy)bicyclo[3.1.0]hexan-6-yl)propyl)benzamide |
| Compound 128 | N-(1-((1R,3s,5S,6r)-3-hydroxybicyclo[3.1.0]hexan-6-yl)ethyl)-6-methoxynicotinamide |
| Compound 129 | 4-cyano-N-(1-((1R,3s,5S,6r)-3-(4-cyclopropyl-1H-1,2,3-triazol-1-yl)bicyclo[3.1.0]hexan-6-yl)ethyl)benzamide |
| Compound 130 | 4-cyano-N-((R)-1-((1R,3S,5S,6r)-3-((6-fluoroquinazolin-4-yl)oxy)bicyclo[3.1.0]hexan-6-yl)ethyl)benzamide |
| Compound 131 | 4-cyano-N-((S)-1-((1R,3R,5S,6r)-3-((6-fluoroquinazolin-4-yl)oxy)bicyclo[3.1.0]hexan-6-yl)ethyl)benzamide |
| Compound 132 | 4-cyano-N-((R)-1-((1R,3S,5S,6r)-3-((7-fluoroquinazolin-4-yl)oxy)bicyclo[3.1.0]hexan-6-yl)ethyl)benzamide |
| Compound 133 | 4-cyano-N-((S)-1-((1R,3R,5S,6r)-3-((7-fluoroquinazolin-4-yl)oxy)bicyclo[3.1.0]hexan-6-yl)ethyl)benzamide |

| | |
|---|---|
| Compound 134 | Ethyl 3-(4-chlorobenzamido)-3-((1R,3s,5S,6r)-3-((6-fluoroquinazolin-4-yl)oxy)bicyclo[3.1.0]hexan-6-yl)propanoate |
| Compound 135 | N-(1-((1R,3s,5S,6r)-3-(cinnolin-4-yloxy)bicyclo[3.1.0]hexan-6-yl)ethyl)-4-cyanobenzamide |
| Compound 136 | 4-cyano-N-(1-((1R,3s,5S,6r)-3-(4-oxocinnolin-1(4H)-yl)bicyclo[3.1.0]hexan-6-yl)ethyl)benzamide |
| Compound 137 | 4-chloro-N-(1-((1R,3s,5S,6r)-3-((6-fluoroquinazolin-4-yl)oxy)bicyclo[3.1.0]hexan-6-yl)-3-hydroxypropyl)benzamide |
| Compound 138 | 4-chloro-N-(1-((1R,3r,5S,6r)-3-(cinnolin-4-yloxy)bicyclo[3.1.0]hexan-6-yl)propyl)benzamide |
| Compound 139 | 4-chloro-N-(1-((1R,3s,5S,6r)-3-(cinnolin-4-yloxy)bicyclo[3.1.0]hexan-6-yl)-3-hydroxypropyl)benzamide |
| Compound 140 | 4-chloro-N-(3-hydroxy-1-((1R,3s,5S,6r)-3-(4-oxocinnolin-1(4H)-yl)bicyclo[3.1.0]hexan-6-yl)propyl)benzamide |
| Compound 141 | 4-chloro-N-((R)-1-((1R,3S,5S,6r)-3-(4-(2-hydroxypropan-2-yl)-1H-1,2,3-triazol-1-yl)bicyclo[3.1.0]hexan-6-yl)propyl)benzamide |
| Compound 142 | 4-chloro-N-((S)-1-((1R,3R,5S,6r)-3-(4-(2-hydroxypropan-2-yl)-1H-1,2,3-triazol-1-yl)bicyclo[3.1.0]hexan-6-yl)propyl)benzamide |
| Compound 143 | N-((1R,3s,5S,6r)-6-(1-(4-cyanobenzamido)ethyl)bicyclo[3.1.0]hexan-3-yl)picolinamide |
| Compound 144 | N-((1R,3s,5S,6r)-6-(1-(4-chlorobenzamido)propyl)bicyclo[3.1.0]hexan-3-yl)-5-fluoropicolinamide |
| Compound 145 | N-((1R,3s,5S,6r)-6-(1-(4-chlorobenzamido)propyl)bicyclo[3.1.0]hexan-3-yl)nicotinamide |
| Compound 146 | 4-chloro-N-(1-((1R,3s,5S,6r)-3-(4-(hydroxymethyl)-1H-1,2,3-triazol-1-yl)bicyclo[3.1.0]hexan-6-yl)propyl)benzamide |
| Compound 147 | 4-chloro-N-(1-((1R,3s,5S,6r)-3-(4-(prop-1-en-2-yl)-1H-1,2,3-triazol-1-yl)bicyclo[3.1.0]hexan-6-yl)propyl)benzamide |
| Compound 148 | 3-(4-chlorobenzamido)-3-((1R,3s,5S,6r)-3-((6-fluoroquinazolin-4-yl)oxy)bicyclo[3.1.0]hexan-6-yl)propanoic acid |
| Compound 149 | N-((1R,3s,5S,6r)-6-(1-(4-chlorobenzamido)propyl)bicyclo[3.1.0]hexan-3-yl)pyrimidine-4-carboxamide |
| Compound 150 | 6-chloro-N-((1R,3s,5S,6r)-6-(1-(4-chlorobenzamido)propyl)bicyclo[3.1.0]hexan-3-yl)pyrazine-2-carboxamide |
| Compound 151 | N-((1R,3s,5S,6r)-6-(1-(4-chlorobenzamido)propyl)bicyclo[3.1.0]hexan-3-yl)pyridazine-3-carboxamide |
| Compound 152 | N-((1R,3s,5S,6r)-6-(1-(4-chlorobenzamido)propyl)bicyclo[3.1.0]hexan-3-yl)pyrazine-2-carboxamide |
| Compound 153 | 4-chloro-N-(1-((1R,3s,5S,6r)-3-(5-cyclopropyl-1H-1,2,3-triazol-1-yl)bicyclo[3.1.0]hexan-6-yl)propyl)benzamide |
| Compound 154 | 4-chloro-N-(1-((1R,3s,5S,6r)-3-(5-(2-hydroxypropan-2-yl)-1H-1,2,3-triazol-1-yl)bicyclo[3.1.0]hexan-6-yl)propyl)benzamide |
| Compound 155 | 4-chloro-N-(1-((1R,3s,5S,6r)-3-(5-(hydroxymethyl)-1H-1,2,3-triazol-1-yl)bicyclo[3.1.0]hexan-6-yl)propyl)benzamide |
| Compound 156 | N-((1R,3s,5S,6r)-6-(1-(4-chlorobenzamido)propyl)bicyclo[3.1.0]hexan-3-yl)piperazine-1-carboxamide |
| Compound 157 | N-((1R,3s,5S,6r)-6-(1-(4-chlorobenzamido)propyl)bicyclo[3.1.0]hexan-3-yl)morpholine-4-carboxamide |
| Compound 158 | 3-chloro-N-((1R,3s,5S,6r)-6-(1-(4-chlorobenzamido)propyl)bicyclo[3.1.0]hexan-3-yl)-4-(trifluoromethyl)picolinamide |
| Compound 159 | 4-chloro-N-(1-((1R,3s,5S,6r)-3-(methylsulfonamido)bicyclo[3.1.0]hexan-6-yl)propyl)benzamide |

| | |
|---|---|
| Compound 160 | 4-chloro-N-(1-((1R,3s,5S,6r)-3-((1-methylcyclopropane)-1-sulfonamido)bicyclo[3.1.0]hexan-6-yl)propyl)benzamide |
| Compound 161 | 4-chloro-N-(1-((1R,3s,5S,6r)-3-(1,3-dioxoisoindolin-2-yl)bicyclo[3.1.0]hexan-6-yl)propyl)benzamide |
| Compound 162 | 4-chloro-N-(1-((1R,3s,5S,6r)-3-(6-fluoro-1H-indazol-1-yl)bicyclo[3.1.0]hexan-6-yl)propyl)benzamide |
| Compound 163 | 4-chloro-N-(1-((1R,3s,5S,6r)-3-(6-fluoro-2H-indazol-2-yl)bicyclo[3.1.0]hexan-6-yl)propyl)benzamide |
| Compound 164 | N-((1R,3s,5S,6r)-6-(1-(4-chlorobenzamido)propyl)bicyclo[3.1.0]hexan-3-yl)-5-methoxypicolinamide |
| Compound 165 | 4-chloro-N-(1-((1R,3s,5S,6r)-3-(5-ethyl-1H-1,2,3-triazol-1-yl)bicyclo[3.1.0]hexan-6-yl)propyl)benzamide |
| Compound 166 | 4-chloro-N-(1-((1R,3s,5S,6r)-3-(cyano(phenyl)methyl)bicyclo[3.1.0]hexan-6-yl)propyl)benzamide |
| Compound 167 | 4-chloro-N-(1-((1R,3s,5S,6r)-3-(4-ethyl-1H-1,2,3-triazol-1-yl)bicyclo[3.1.0]hexan-6-yl)propyl)benzamide |
| Compound 168 | 4-chloro-N-(1-((1R,3s,5S,6r)-3-(4-cyclopropyl-1H-1,2,3-triazol-1-yl)bicyclo[3.1.0]hexan-6-yl)-2-hydroxyethyl)benzamide |
| Compound 169 | Methyl 2-(4-chlorobenzamido)-2-((1R,3s,5S,6r)-3-(4-cyclopropyl-1H-1,2,3-triazol-1-yl)bicyclo[3.1.0]hexan-6-yl)acetate |
| Compound 170 | N-((1R,3s,5S,6r)-6-(1-(4-chlorobenzamido)propyl)bicyclo[3.1.0]hexan-3-yl)-5-fluoronicotinamide |
| Compound 171 | N-((1R,3s,5S,6r)-6-(1-(4-chlorobenzamido)propyl)bicyclo[3.1.0]hexan-3-yl)-3,5-difluoropicolinamide |
| Compound 172 | 4-chloro-N-(1-((1R,3s,5S,6r)-3-(3-cyclopropyl-4H-1,2,4-triazol-4-yl)bicyclo[3.1.0]hexan-6-yl)propyl)benzamide |
| Compound 173 | 4-chloro-N-(1-((1R,3s,5S,6r)-3-(4-cyclopropyl-1H-1,2,3-triazol-1-yl)bicyclo[3.1.0]hexan-6-yl)-2-methoxyethyl)benzamide |
| Compound 174 | N-(1-((1R,3s,5S,6r)-3-(1H-pyrazolo[3,4-c]pyridin-1-yl)bicyclo[3.1.0]hexan-6-yl)propyl)-4-chlorobenzamide |
| Compound 175 | 4-chloro-N-(1-((1R,3s,5S,6r)-3-(1-oxoisoindolin-2-yl)bicyclo[3.1.0]hexan-6-yl)propyl)benzamide |
| Compound 176 | 4-chloro-N-(1-((1R,3s,5S,6r)-3-(5,6-dichloro-1H-benzo[d]imidazol-1-yl)bicyclo[3.1.0]hexan-6-yl)propyl)benzamide |
| Compound 177 | N-((1R,3s,5S,6r)-6-(1-(4-chlorobenzamido)propyl)bicyclo[3.1.0]hexan-3-yl)-1H-pyrazole-4-carboxamide |
| Compound 178 | N-(1-((1R,3s,5S,6r)-3-(6-bromo-1H-benzo[d][1,2,3]triazol-1-yl)bicyclo[3.1.0]hexan-6-yl)propyl)-4-chlorobenzamide |
| Compound 179 | N-(1-((1R,3s,5S,6r)-3-(5-bromo-2H-benzo[d][1,2,3]triazol-2-yl)bicyclo[3.1.0]hexan-6-yl)propyl)-4-chlorobenzamide |
| Compound 180 | 4-chloro-N-(1-((1R,3s,5S,6r)-3-(2-oxo-2,3-dihydro-1H-benzo[d]imidazol-1-yl)bicyclo[3.1.0]hexan-6-yl)propyl)benzamide |
| Compound 181 | 4-chloro-N-(1-((1R,3s,5S,6r)-3-(3-methyl-2-oxo-2,3-dihydro-1H-benzo[d]imidazol-1-yl)bicyclo[3.1.0]hexan-6-yl)propyl)benzamide |
| Compound 182 | N-(1-((1R,3s,5S,6r)-3-(4H-imidazo[4,5-b]pyridin-4-yl)bicyclo[3.1.0]hexan-6-yl)propyl)-4-chlorobenzamide |
| Compound 183 | N-(1-((1R,3s,5S,6r)-3-(1H-imidazo[4,5-b]pyridin-1-yl)bicyclo[3.1.0]hexan-6-yl)propyl)-4-chlorobenzamide |
| Compound 184 | N-(1-((1R,3s,5S,6r)-3-(3H-imidazo[4,5-b]pyridin-3-yl)bicyclo[3.1.0]hexan-6-yl)propyl)-4-chlorobenzamide |
| Compound 185 | 4-chloro-N-(1-((1R,3s,5S,6r)-3-(2-oxooxazolidin-3-yl)bicyclo[3.1.0]hexan-6-yl)propyl)benzamide |
| Compound 186 | 4-chloro-N-(1-((1R,3r,5S,6r)-3-(4-cyclopropyl-1H-1,2,3-triazol-1-yl)bicyclo[3.1.0]hexan-6-yl)propyl)benzamide |
| Compound 187 | 4-chloro-N-(1-((1R,3r,5S,6r)-3-(4-(hydroxymethyl)-1H-1,2,3-triazol-1-yl)bicyclo[3.1.0]hexan-6-yl)propyl)benzamide |
| Compound 188 | N-((1R,3s,5S,6r)-6-(1-(4-chlorobenzamido)propyl)bicyclo[3.1.0]hexan-3-yl)-3-fluoropicolinamide |
| Compound 189 | 4-chloro-N-(1-((1R,3s,5S,6r)-3-(3-methyl-3-(pyridin-2-yl)ureido)bicyclo[3.1.0]hexan-6-yl)propyl)benzamide |

-continued

| | |
|---|---|
| Compound 190 | Ethyl 2-(((1R,3s,5S,6r)-6-(1-(4-chlorobenzamido)propyl)bicyclo[3.1.0]hexan-3-yl)amino)-2-phenylacetate |
| Compound 191 | 4-chloro-N-(1-((1R,3r,5S,6r)-3-(5-cyclopropyl-1H-1,2,3-triazol-1-yl)bicyclo[3.1.0]hexan-6-yl)propyl)benzamide |
| Compound 192 | 4-chloro-N-(1-((1R,3s,5S,6r)-3-(5-fluoro-2-oxo-2,3-dihydro-1H-benzo[d]imidazol-1-yl)bicyclo[3.1.0]hexan-6-yl)propyl)benzamide |
| Compound 193 | 4-chloro-N-(1-((1R,3s,5S,6r)-3-((6-fluoro-1H-benzo[d]imidazol-2-yl)oxy)bicyclo[3.1.0]hexan-6-yl)propyl)benzamide |
| Compound 194 | 4-chloro-N-(1-((1R,3s,5S,6r)-3-(4-fluoro-1H-benzo[d]imidazol-1-yl)bicyclo[3.1.0]hexan-6-yl)propyl)benzamide |
| Compound 195 | 4-chloro-N-(1-((1R,3s,5S,6r)-3-(7-fluoro-1H-benzo[d]imidazol-1-yl)bicyclo[3.1.0]hexan-6-yl)propyl)benzamide |
| Compound 196 | N-(1-((1R,3s,5S,6r)-3-(1H-imidazo[4,5-c]pyridin-1-yl)bicyclo[3.1.0]hexan-6-yl)propyl)-4-chlorobenzamide |
| Compound 197 | N-(1-((1R,3s,5S,6r)-3-(3H-imidazo[4,5-c]pyridin-3-yl)bicyclo[3.1.0]hexan-6-yl)propyl)-4-chlorobenzamide |
| Compound 198 | N-(1-((1R,3s,5S,6r)-3-(5H-imidazo[4,5-c]pyridin-5-yl)bicyclo[3.1.0]hexan-6-yl)propyl)-4-chlorobenzamide |
| Compound 199 | 4-chloro-N-(1-((1R,3s,5S,6r)-3-(5-fluoro-1H-benzo[d]imidazol-1-yl)bicyclo[3.1.0]hexan-6-yl)propyl)benzamide |
| Compound 200 | 4-chloro-N-(1-((1R,3s,5S,6r)-3-(4-phenyl-1H-imidazol-1-yl)bicyclo[3.1.0]hexan-6-yl)propyl)benzamide |
| Compound 201 | 4-chloro-N-(1-((1R,3s,5S,6r)-3-(2-methyl-1H-imidazol-1-yl)bicyclo[3.1.0]hexan-6-yl)propyl)benzamide |
| Compound 202 | methyl (S/R)-2-((1R,3S,5S,6S)-6-((R/S)-1-(4-chlorobenzamido)propyl)bicyclo [3.1.0]hexan-3-yl)-2-phenylacetate |
| Compound 203 | methyl (S/R)-2-((1R,3R,5S,6S)-6-((S/R)-1-(4-chlorobenzamido)propyl)bicyclo[3.1.0]hexan-3-yl)-2-phenylacetate |
| Compound 204 | 4-chloro-N-(1-((1R,3s,5S,6r)-3-(4-phenyl-2H-1,2,3-triazol-2-yl)bicyclo[3.1.0]hexan-6-yl)propyl)benzamide |
| Compound 205 | 4-chloro-N-(1-((1R,3s,5S,6r)-3-(7-fluoro-2H-indazol-2-yl)bicyclo[3.1.0]hexan-6-yl)propyl)benzamide |
| Compound 206 | 4-chloro-N-(1-((1R,3s,5S,6r)-3-(7-fluoro-1H-indazol-1-yl)bicyclo[3.1.0]hexan-6-yl)propyl)benzamide |
| Compound 207 | 4-chloro-N-(1-((1R,3s,5S,6r)-3-(5-fluoro-2H-indazol-2-yl)bicyclo[3.1.0]hexan-6-yl)propyl)benzamide |
| Compound 208 | 4-chloro-N-(1-((1R,3s,5S,6r)-3-(5-fluoro-1H-indazol-1-yl)bicyclo[3.1.0]hexan-6-yl)propyl)benzamide |
| Compound 209 | 4-chloro-N-(1-((1R,3s,5S,6r)-3-(4-fluoro-2H-indazol-2-yl)bicyclo[3.1.0]hexan-6-yl)propyl)benzamide |
| Compound 210 | 4-chloro-N-(1-((1R,3s,5S,6r)-3-(4-fluoro-1H-indazol-1-yl)bicyclo[3.1.0]hexan-6-yl)propyl)benzamide |
| Compound 211 | N-(1-((1R,3s,5S,6r)-3-(2H-pyrazolo[3,4-b]pyridin-2-yl)bicyclo[3.1.0]hexan-6-yl)propyl)-4-chlorobenzamide |
| Compound 212 | N-(1-((1R,3s,5S,6r)-3-(1H-pyrazolo[3,4-b]pyridin-1-yl)bicyclo[3.1.0]hexan-6-yl)propyl)-4-chlorobenzamide |
| Compound 213 | 4-chloro-N-(1-((1R,3s,5S,6r)-3-(4,6-difluoro-2H-benzo[d][1,2,3]triazol-2-yl)bicyclo[3.1.0]hexan-6-yl)propyl)benzamide |
| Compound 214 | 4-chloro-N-(1-((1R,3r,5S,6r)-3-(4-(methoxymethyl)-1H-1,2,3-triazol-1-yl)bicyclo[3.1.0]hexan-6-yl)propyl)benzamide |
| Compound 215 | 4-chloro-N-(1-((1R,3r,5S,6r)-3-(4-((2-methoxyethoxy)methyl)-1H-1,2,3-triazol-1-yl)bicyclo[3.1.0]hexan-6-yl)propyl)benzamide |
| Compound 216 | 4-chloro-N-(1-((1R,3r,5S,6r)-3-(4-(ethoxymethyl)-1H-1,2,3-triazol-1-yl)bicyclo[3.1.0]hexan-6-yl)propyl)benzamide |
| Compound 217 | 2-(((1R,3s,5S,6r)-6-(1-(4-chlorobenzamido)propyl)bicyclo[3.1.0]hexan-3-yl)amino)-2-phenylacetic acid |
| Compound 218 | 3-chloro-N-((1R,3s,5S,6r)-6-(1-(4-chlorobenzamido)propyl)bicyclo[3.1.0]hexan-3-yl)picolinamide |
| Compound 219 | N-((1R,3s,5S,6r)-6-(1-(4-chlorobenzamido)propyl)bicyclo[3.1.0]hexan-3-yl)-4-(trifluoromethyl)nicotinamide |
| Compound 220 | N-((1R,3r,5S,6r)-6-(1-(4-chlorobenzamido)propyl)bicyclo[3.1.0]hexan-3-yl)-3-fluoropicolinamide |

| | |
|---|---|
| Compound 221 | N-((1R,3r,5S,6r)-6-(1-(4-chlorobenzamido)propyl)bicyclo[3.1.0]hexan-3-yl)-5-fluoropicolinamide |
| Compound 222 | 3-chloro-N-((1R,3r,5S,6r)-6-(1-(4-chlorobenzamido)propyl)bicyclo[3.1.0]hexan-3-yl)-4-(trifluoromethyl)picolinamide |
| Compound 223 | N-((1R,3s,5S,6r)-6-(1-(4-chlorobenzamido)propyl)bicyclo[3.1.0]hexan-3-yl)-2-methylnicotinamide |
| Compound 224 | 4-chloro-N-(1-((1R,3s,5S,6r)-3-((2-(methylamino)-2-oxo-1-phenylethyl)amino)bicyclo[3.1.0]hexan-6-yl)propyl)benzamide |
| Compound 225 | N-((1R,3s,5S,6r)-6-(1-(4-chlorobenzamido)propyl)bicyclo[3.1.0]hexan-3-yl)-4-(trifluoromethyl)picolinamide |
| Compound 226 | 4-chloro-N-(1-((1R,3s,5S,6r)-3-(pyridin-2-ylamino)bicyclo[3.1.0]hexan-6-yl)propyl)benzamide |
| Compound 227 | 4-chloro-N-(1-((1R,3s,5S,6r)-3-((5-fluoropyridin-2-yl)amino)bicyclo[3.1.0]hexan-6-yl)propyl)benzamide |
| Compound 228 | 2-((1R,3s,5S,6r)-6-(1-(4-chlorobenzamido)propyl)bicyclo[3.1.0]hexan-3-yl)-2-phenylacetic acid |
| Compound 229 | 4-chloro-N-(1-((1R,3s,5S,6r)-3-(5-fluoro-1H-indol-1-yl)bicyclo[3.1.0]hexan-6-yl)propyl)benzamide |
| Compound 230 | 4-chloro-N-((R/S)-1-((1R,3S,5S,6S)-3-((S/R)-2-(methylamino)-2-oxo-1-phenylethyl)bicyclo[3.1.0]hexan-6-yl)propyl)benzamide |
| Compound 231 | 4-chloro-N-((R/S)-1-((1R,3S,5S,6S)-3-((R/S)-2-(methylamino)-2-oxo-1-phenylethyl)bicyclo[3.1.0]hexan-6-yl)propyl)benzamide |
| Compound 232 | 4-chloro-N-(1-((1R,3s,5S,6r)-3-(4-(1,3-dioxoisoindolin-2-yl)-1H-1,2,3-triazol-1-yl)bicyclo[3.1.0]hexan-6-yl)propyl)benzamide |
| Compound 233 | 3-(1-((1R,3s,5S,6r)-6-(1-(4-chlorobenzamido)propyl)bicyclo[3.1.0]hexan-3-yl)-1H-1,2,3-triazol-4-yl)azetidine-1-carboxylate |
| Compound 234 | 4-chloro-N-(1-((1R,3s,5S,6r)-3-(6-cyano-3H-imidazo[4,5-b]pyridin-3-yl)bicyclo[3.1.0]hexan-6-yl)propyl)benzamide |
| Compound 235 | 4-chloro-N-(1-((1R,3s,5S,6r)-3-(6-cyano-1H-imidazo[4,5-b]pyridin-1-yl)bicyclo[3.1.0]hexan-6-yl)propyl)benzamide |
| Compound 236 | 4-chloro-N-(1-((1R,3s,5S,6r)-3-((5-fluoro-3-nitropyridin-2-yl)amino)bicyclo[3.1.0]hexan-6-yl)propyl)benzamide |
| Compound 237 | N-(1-((1R,3s,5S,6r)-3-(4-(azetidin-3-yl)-1H-1,2,3-triazol-1-yl)bicyclo[3.1.0]hexan-6-yl)propyl)-4-chlorobenzamide |
| Compound 238 | 4-chloro-N-(1-((1R,3s,5S,6r)-3-(4-(dimethylamino)-1H-1,2,3-triazol-1-yl)bicyclo[3.1.0]hexan-6-yl)propyl)benzamide |
| Compound 239 | N-(1-((1R,3s,5S,6r)-3-(4-amino-1H-1,2,3-triazol-1-yl)bicyclo[3.1.0]hexan-6-yl)propyl)-4-chlorobenzamide |
| Compound 240 | 4-chloro-N-(1-((1R,3s,5S,6r)-3-(6-fluoro-3H-imidazo[4,5-b]pyridin-3-yl)bicyclo[3.1.0]hexan-6-yl)propyl)benzamide |
| Compound 241 | 4-chloro-N-(1-((1R,3s,5S,6r)-3-(5,6-difluoro-1H-benzo[d]imidazol-1-yl)bicyclo[3.1.0]hexan-6-yl)propyl)benzamide |
| Compound 242 | 4-cyano-N-(1-((1R,3s,5S,6r)-3-(4-(methoxymethyl)-1H-1,2,3-triazol-1-yl)bicyclo[3.1.0]hexan-6-yl)ethyl)benzamide |
| Compound 243 | 4-chloro-N-(1-((1R,3s,5S,6r)-3-((3,5-difluoro-2-nitrophenyl)amino)bicyclo[3.1.0]hexan-6-yl)propyl)benzamide |
| Compound 244 | 4-chloro-N-(1-((1R,3s,5S,6r)-3-((2,3-difluoro-6-nitrophenyl)amino)bicyclo[3.1.0]hexan-6-yl)propyl)benzamide |
| Compound 245 | 4-chloro-N-(1-((1R,3s,5S,6r)-3-(6,7-difluoro-1H-benzo[d]imidazol-1-yl)bicyclo[3.1.0]hexan-6-yl)propyl)benzamide |
| Compound 246 | 4-chloro-N-(1-((1R,3s,5S,6r)-3-(4,6-difluoro-1H-benzo[d]imidazol-1-yl)bicyclo[3.1.0]hexan-6-yl)propyl)benzamide |
| Compound 247 | 4-chloro-N-((R)-1-((1R,3S,5S,6r)-3-(6-fluoro-1H-benzo[d]imidazol-1-yl)bicyclo[3.1.0]hexan-6-yl)propyl)benzamide |

-continued

| | |
|---|---|
| Compound 248 | 4-chloro-N-((S)-1-((1R,3S,5S,6r)-3-(6-fluoro-1H-benzo[d]imidazol-1-yl)bicyclo[3.1.0]hexan-6-yl)propyl)benzamide |
| Compound 249 | (1R,5S,6s)-N-(4-chlorobenzyl)-3-(6-fluoroquinazolin-4-yl)-3-azabicyclo[3.1.0]hexane-6-carboxamide |
| Compound 250 | (1R,5S,6s)-N-(4-chlorophenyl)-3-(6-fluoroquinazolin-4-yl)-3-azabicyclo[3.1.0]hexane-6-carboxamide |
| Compound 251 | (1R,5S,6r)-N-(4-chlorobenzyl)-3-(6-fluoroquinazolin-4-yl)-3-azabicyclo[3.1.0]hexane-6-carboxamide |
| Compound 252 | (1R,5S,6r)-N-(4-chlorophenyl)-3-(6-fluoroquinazolin-4-yl)-3-azabicyclo[3.1.0]hexane-6-carboxamide |
| Compound 253 | 4-chloro-N-(1-((1R,3s,5S,6r)-3-((7-chloroquinazolin-4-yl)oxy)bicyclo[3.1.0]hexan-6-yl)propyl)benzamide |
| Compound 254 | 4-chloro-N-(1-((1R,5R,6S)-3-(5-(trifluoromethyl)pyridin-3-yl)bicyclo[3.1.0]hex-2-en-6-yl)propyl)benzamide |
| Compound 255 | 4-chloro-N-(1-((1R,5R,6S)-3-(7-fluoroquinazolin-4-yl)bicyclo[3.1.0]hex-2-en-6-yl)propyl)benzamide |
| Compound 256 | N-(1-((1R,3s,5S,6r)-3-(4-acetamido-1H-1,2,3-triazol-1-yl)bicyclo[3.1.0]hexan-6-yl)propyl)-4-chlorobenzamide |
| Compound 257 | N-(1-((1R,3s,5S,6r)-3-(4-(1-acetylazetidin-3-yl)-1H-1,2,3-triazol-1-yl)bicyclo[3.1.0]hexan-6-yl)propyl)-4-chlorobenzamide |
| Compound 258 | 4-chloro-N-(1-((1R,3s,5S,6r)-3-(5-cyclopropyl-1H-1,2,4-triazol-1-yl)bicyclo[3.1.0]hexan-6-yl)propyl)benzamide |
| Compound 259 | 4-chloro-N-(1-((1R,3s,5S,6r)-3-(3-cyclopropyl-1H-1,2,4-triazol-1-yl)bicyclo[3.1.0]hexan-6-yl)propyl)benzamide |
| Compound 260 | 4-chloro-N-((R)-1-((1R,3S,5S,6r)-3-(5,6-difluoro-1H-benzo[d]imidazol-1-yl)bicyclo[3.1.0]hexan-6-yl)propyl)benzamide |
| Compound 261 | 4-chloro-N-(1-((1R,3s,5S,6r)-3-(4-cyclopropyl-1H-imidazol-1-yl)bicyclo[3.1.0]hexan-6-yl)propyl)benzamide |
| Compound 262 | 4-chloro-N-(1-((1R,3S,5S,6r)-3-(4-(propen-2-yl)-1H-1,2,3-triazol-1-yl)bicyclo[3.1.0]hexan-6-yl)propyl)benzamide |
| Compound 263 | 4-chloro-N-(1-((1R,3s,5S,6r)-3-(pyrazol-1-yl)bicyclo[3.1.0]hexan-6-yl)ethyl)benzamide |
| Compound 264 | 4-chloro-N-(1-((1R,3s,5S,6r)-3-((2,4-difluoro-6-nitrophenyl)amino)bicyclo[3.1.0]hexan-6-yl)propyl)benzamide |
| Compound 265 | 4-chloro-N-((R)-1-((1R,3S,5S,6r)-3-(5,6-difluoro-1H-benzo[d]imidazol-1-yl)bicyclo[3.1.0]hexan-6-yl)ethyl)benzamide |
| Compound 266 | 4-chloro-N-((R)-1-((1R,3S,5S,6r)-3-(6-fluoroquinolin-4-yl)bicyclo[3.1.0]hexan-6-yl)propyl)benzamide |
| Compound 267 | 4-chloro-N-(1-((1R,3s,5S,6r)-3-(5,7-difluoro-1H-benzo[d]imidazol-1-yl)bicyclo[3.1.0]hexan-6-yl)propyl)benzamide |
| Compound 268 | 4-cyano-N-((R)-1-((1R,3S,5S,6r)-3-(5,6-difluoro-1H-benzo[d]imidazol-1-yl)bicyclo[3.1.0]hexan-6-yl)propyl)benzamide |
| Compound 269 | 4-chloro-N-(1-((1R,3s,5S,6r)-3-((4-cyano-2-nitrophenyl)amino)bicyclo[3.1.0]hexan-6-yl)propyl)benzamide |
| Compound 270 | 4-chloro-N-(1-((1R,3s,5S,6r)-3-((4-chloro-2-nitrophenyl)amino)bicyclo[3.1.0]hexan-6-yl)propyl)benzamide |
| Compound 271 | 4-chloro-N-(1-((1R,3s,5S,6r)-3-(5-cyano-1H-benzo[d]imidazol-1-yl)bicyclo[3.1.0]hexan-6-yl)propyl)benzamide |
| Compound 272 | 4-chloro-N-(1-((1R,3s,5S,6r)-3-(5-chloro-1H-benzo[d]imidazol-1-yl)bicyclo[3.1.0]hexan-6-yl)propyl)benzamide |
| Compound 273 | 4-chloro-N-((R)-1-((1R,3S,5S,6r)-3-(6-chloro-1H-benzo[d]imidazol-1-yl)bicyclo[3.1.0]hexan-6-yl)propyl)benzamide |
| Compound 274 | 4-cyano-N-((R)-1-((1R,3S,5S,6r)-3-(5,6-difluoro-1H-benzo[d]imidazol-1-yl)bicyclo[3.1.0]hexan-6-yl)ethyl)benzamide |
| Compound 275 | 4-chloro-N-((R)-1-((1R,3S,5S,6r)-3-(6-fluoro-2-methyl-1H-benzo[d]imidazol-1-yl)bicyclo[3.1.0]hexan-6-yl)propyl)benzamide |
| Compound 276 | 4-chloro-N-((R)-1-((1R,3S,5S,6r)-3-(6-fluoro-2-(trifluoromethyl)-1H-benzo[d]imidazol-1-yl)bicyclo[3.1.0]hexan-6-yl)propyl)benzamide |

-continued

| | |
|---|---|
| Compound 277 | 4-cyano-N-((R)-1-((1R,3S,5S,6r)-3-(6-fluoroquinolin-4-yl)bicyclo[3.1.0]hexan-6-yl)propyl)benzamide |
| Compound 278 | 4-cyano-N-((R)-1-((1R,3S,5S,6r)-3-(6-fluoroquinolin-4-yl)bicyclo[3.1.0]hexan-6-yl)ethyl)benzamide |
| Compound 279 | 4-chloro-N-((R)-1-((1R,3S,5S,6r)-3-(6-fluoroquinazolin-4-yl)bicyclo[3.1.0]hexan-6-yl)propyl)benzamide |
| Compound 280 | 4-chloro-N-(((1R,5S,6s)-3-(6-fluoroquinazolin-4-yl)-3-azabicyclo[3.1.0]hexan-6-yl)methyl)benzamide |
| Compound 281 | N-(4-chlorophenyl)-2-((1R,3s,5S,6r)-3-(5,6-difluoro-1H-benzo[d]imidazol-1-yl)bicyclo[3.1.0]hexan-6-yl)propanamide |
| Compound 282 | 4-chloro-N-((R)-1-((1R,3S,5S,6r)-3-(6-cyano-1H-benzo[d]imidazol-1-yl)bicyclo[3.1.0]hexan-6-yl)propyl)benzamide |
| Compound 283 | N-((1R)-1-((1R,5S,6r)-3-azidobicyclo[3.1.0]hexan-6-yl)propyl)-4-cyanobenzamide |
| Compound 284 | 4-chloro-N-((R)-1-((1R,3S,5S,6r)-3-((5-chloro-2-nitrophenyl)amino)bicyclo[3.1.0]hexan-6-yl)propyl)benzamide |
| Compound 285 | 4-chloro-N-((R)-1-((1R,3S,5S,6r)-3-(6-fluoroquinolin-4-yl)bicyclo[3.1.0]hexan-6-yl)ethyl)benzamide |
| Compound 286 | 4-chloro-N-((R)-1-((1R,3R,5S,6r)-3-(6-fluoroquinolin-4-yl)bicyclo[3.1.0]hexan-6-yl)propyl)benzamide |
| Compound 287 | 4-chloro-N-(2-((1R,3s,5S,6r)-3-(5,6-difluoro-1H-benzo[d]imidazol-1-yl)bicyclo[3.1.0]hexan-6-yl)propan-2-yl)benzamide |
| Compound 288 | 4-cyano-N-((R)-1-((1R,3S,5S,6r)-3-(6-cyano-1H-benzo[d]imidazol-1-yl)bicyclo[3.1.0]hexan-6-yl)propyl)benzamide |
| Compound 289 | N-((R)-1-((1R,3S,5S,6r)-3-(6-chloro-1H-benzo[d]imidazol-1-yl)bicyclo[3.1.0]hexan-6-yl)propyl)-4-cyanobenzamide |
| Compound 290 | diethyl 2-((1R,3S,5S,6r)-6-((R)-1-(4-chlorobenzamido)propyl)bicyclo[3.1.0]hexan-3-yl)malonate |
| Compound 291 | 4-chloro-N-((R)-1-((1R,3S,5S,6r)-3-(1,3-dihydroxypropan-2-yl)bicyclo[3.1.0]hexan-6-yl)propyl)benzamide |
| Compound 292 | 4-chloro-N-((R)-1-((1R,3S,5S,6r)-3-(1-cyclopropyl-1H-pyrazol-4-yl)bicyclo[3.1.0]hexan-6-yl)propyl)benzamide |
| Compound 293 | 4-cyano-N-((R)-1-((1R,3S,5S,6r)-3-(6-cyano-2-methyl-1H-benzo[d]imidazol-1-yl)bicyclo[3.1.0]hexan-6-yl)propyl)benzamide |
| Compound 294 | N-((R)-1-((1R,3S,5S,6r)-3-(6-chloro-2-methyl-1H-benzo[d]imidazol-1-yl)bicyclo[3.1.0]hexan-6-yl)propyl)-4-cyanobenzamide |
| Compound 295 | 4-cyano-N-((1R)-1-((1R,3S,5S,6r)-3-(4-(tetrahydrofuran-3-yl)-1H-1,2,3-triazol-1-yl)bicyclo[3.1.0]hexan-6-yl)propyl)benzamide |
| Compound 296 | 4-cyano-N-((R)-1-((1R,3R,5S,6r)-3-hydroxybicyclo[3.1.0]hexan-6-yl)ethyl)benzamide |
| Compound 297 | 4-cyano-N-((R)-1-((1R,3S,5S,6r)-3-hydroxybicyclo[3.1.0]hexan-6-yl)ethyl)benzamide |
| Compound 298 | (R)-N-(4-chlorophenyl)-2-((1R,3S,5S,6r)-3-(5,6-difluoro-1H-benzo[d]imidazol-1-yl)bicyclo[3.1.0]hexan-6-yl)propanamide |
| Compound 299 | (S)-N-(4-chlorophenyl)-2-((1R,3R,5S,6r)-3-(5,6-difluoro-1H-benzo[d]imidazol-1-yl)bicyclo[3.1.0]hexan-6-yl)propanamide |
| Compound 300 | dimethyl 1-((1R,3S,5S,6r)-6-((R)-1-(4-cyanobenzamido)propyl)bicyclo[3.1.0]hexan-3-yl)-1H-1,2,3-triazole-4,5-dicarboxylate |
| Compound 301 | 4-chloro-N-(((1R,3s,5S,6r)-3-(5,6-difluoro-1H-benzo[d]imidazol-1-yl)bicyclo[3.1.0]hexan-6-yl)methyl)benzamide |
| Compound 302 | 4-cyano-N-(((1R,3s,5S,6r)-3-(5,6-difluoro-1H-benzo[d]imidazol-1-yl)bicyclo[3.1.0]hexan-6-yl)methyl)benzamide |
| Compound 303 | 4-chloro-N-((R)-1-((1R,3R,5S,6r)-3-(5-cyclopropylpyridin-3-yl)bicyclo[3.1.0]hexan-6-yl)propyl)benzamide |
| Compound 304 | 4-chloro-N-((R)-1-((1R,3S,5S,6r)-3-(4-iodo-1H-pyrazol-1-yl)bicyclo[3.1.0]hexan-6-yl)propyl)benzamide |
| Compound 305 | 4-chloro-N-((R)-1-((1R,3S,5S,6r)-3-(4-vinyl-1H-pyrazol-1-yl)bicyclo[3.1.0]hexan-6-yl)propyl)benzamide |

-continued

| | |
|---|---|
| Compound 306 | N-((R)-1-((1R,3S,5S,6r)-3-(5,6-difluoro-1H-benzo[d]imidazol-1-yl)bicyclo[3.1.0]hexan-6-yl)propyl)-4-fluorobenzamide |
| Compound 307 | 4-chloro-N-((R)-1-((1R,3S,5S,6r)-3-(5,6-difluoro-1H-benzo[d]imidazol-1-yl)bicyclo[3.1.0]hexan-6-yl)propyl)-3-fluorobenzamide |
| Compound 308 | N-((R)-1-((1R,3S,5S,6r)-3-(5,6-difluoro-1H-benzo[d]imidazol-1-yl)bicyclo[3.1.0]hexan-6-yl)propyl)-2-methylisonicotinamide |
| Compound 309 | N-((R)-1-((1R,3S,5S,6r)-3-(5,6-difluoro-1H-benzo[d]imidazol-1-yl)bicyclo[3.1.0]hexan-6-yl)propyl)-2-methylthiazole-4-carboxamide |
| Compound 310 | 3-chloro-N-(R)-1-((1R,3S,5S,6r)-3-(5,6-difluoro-1H-benzo[d]imidazol-1-yl)bicyclo[3.1.0]hexan-6-yl)propyl)benzamide |
| Compound 311 | N-((R)-1-((1R,3S,5S,6r)-3-(5,6-difluoro-1H-benzo[d]imidazol-1-yl)bicyclo[3.1.0]hexan-6-yl)propyl)-6-methylnicotinamide |
| Compound 312 | N-((R)-1-((1R,3S,5S,6r)-3-(5,6-difluoro-1H-benzo[d]imidazol-1-yl)bicyclo[3.1.0]hexan-6-yl)propyl)-3-fluorobenzamide |
| Compound 313 | 3-cyano-N-((R)-1-((1R,3S,5S,6r)-3-(5,6-difluoro-1H-benzo[d]imidazol-1-yl)bicyclo[3.1.0]hexan-6-yl)propyl)benzamide |
| Compound 314 | N-(((1R,3s,5S,6r)-3-(5,6-difluoro-1H-benzo[d]imidazol-1-yl)bicyclo[3.1.0]hexan-6-yl)methyl)-4-fluorobenzamide |
| Compound 315 | 4-chloro-N-(((1R,3s,5S,6r)-3-(5,6-difluoro-1H-benzo[d]imidazol-1-yl)bicyclo[3.1.0]hexan-6-yl)methyl)-3-fluorobenzamide |
| Compound 316 | 3-chloro-N-(((1R,3s,5S,6r)-3-(5,6-difluoro-1H-benzo[d]imidazol-1-yl)bicyclo[3.1.0]hexan-6-yl)methyl)benzamide |
| Compound 317 | N-(((1R,3s,5S,6r)-3-(5,6-difluoro-1H-benzo[d]imidazol-1-yl)bicyclo[3.1.0]hexan-6-yl)methyl)-6-methylnicotinamide |
| Compound 318 | N-(((1R,3s,5S,6r)-3-(5,6-difluoro-1H-benzo[d]imidazol-1-yl)bicyclo[3.1.0]hexan-6-yl)methyl)-6-methoxynicotinamide |
| Compound 319 | N-(((1R,3s,5S,6r)-3-(5,6-difluoro-1H-benzo[d]imidazol-1-yl)bicyclo[3.1.0]hexan-6-yl)methyl)-1-methyl-1H-pyrazole-4-carboxamide |
| Compound 320 | N-(((1R,3s,5S,6r)-3-(5,6-difluoro-1H-benzo[d]imidazol-1-yl)bicyclo[3.1.0]hexan-6-yl)methyl)-3-fluorobenzamide |
| Compound 321 | 3-cyano-N-(((1R,3s,5S,6r)-3-(5,6-difluoro-1H-benzo[d]imidazol-1-yl)bicyclo[3.1.0]hexan-6-yl)methyl)benzamide |
| Compound 322 | N-(((1R,3s,5S,6r)-3-(5,6-difluoro-1H-benzo[d]imidazol-1-yl)bicyclo[3.1.0]hexan-6-yl)methyl)-4-methylbenzamide |
| Compound 323 | N-(((1R,3s,5S,6r)-3-(5,6-difluoro-1H-benzo[d]imidazol-1-yl)bicyclo[3.1.0]hexan-6-yl)methyl)-3-methylbenzamide |
| Compound 324 | N-((R)-1-((1R,3S,5S,6r)-3-(1H-pyrazol-1-yl)bicyclo[3.1.0]hexan-6-yl)propyl)-4-chlorobenzamide |
| Compound 325 | 4-chloro-N-((R)-1-((1R,3S,5S,6r)-3-(4-cyano-1H-pyrazol-1-yl)bicyclo[3.1.0]hexan-6-yl)propyl)benzamide |
| Compound 326 | methyl 1-((1R,3S,5S,6r)-6-((R)-1-(4-chlorobenzamido)propyl)bicyclo[3.1.0]hexan-3-yl)-1H-pyrazole-4-carboxylate |
| Compound 327 | N-((1R,3S,5S,6r)-6-((R)-1-(4-chlorobenzamido)propyl)bicyclo[3.1.0]hexan-3-yl)-3-fluoropicolinamide |
| Compound 328 | 1-((1R,3S,5S,6r)-6-((R)-1-(4-chlorobenzamido)propyl)bicyclo[3.1.0]hexan-3-yl)-1H-pyrazole-4-carboxylic acid |
| Compound 329 | N-((R)-1-((1R,3S,5S,6r)-3-(4-bromo-1H-pyrazol-1-yl)bicyclo[3.1.0]hexan-6-yl)propyl)-4-chlorobenzamide |
| Compound 330 | 4-chloro-N-((R)-1-((1R,3S,5S,6r)-3-(4-methyl-1H-pyrazol-1-yl)bicyclo[3.1.0]hexan-6-yl)propyl)benzamide |
| Compound 331 | 4-chloro-N-((R)-1-((1R,3S,5S,6r)-3-((2-cyanophenyl)amino)bicyclo[3.1.0]hexan-6-yl)propyl)benzamide |
| Compound 332 | 4-chloro-N-((R)-1-((1R,3S,5S,6r)-3-(4-(trifluoromethyl)-1H-pyrazol-1-yl)bicyclo[3.1.0]hexan-6-yl)propyl)benzamide |

| | |
|---|---|
| Compound 333 | N-((1R,3S,5S,6r)-6-((R)-1-(4-chlorobenzamido)propyl)bicyclo[3.1.0]hexan-3-yl)picolinamide |
| Compound 334 | N-((1R,3S,5S,6r)-6-((R)-1-(4-chlorobenzamido)propyl)bicyclo[3.1.0]hexan-3-yl)-5-fluoronicotinamide |
| Compound 335 | N-((1R,3S,5S,6r)-6-((R)-1-(4-chlorobenzamido)propyl)bicyclo[3.1.0]hexan-3-yl)nicotinamide |
| Compound 336 | 4-chloro-N-((R)-1-((1R,3S,5S,6r)-3-((6-fluoroquinazolin-4-yl)amino)bicyclo[3.1.0]hexan-6-yl)propyl)benzamide |
| Compound 337 | 4-chloro-N-((R)-1-((1R,3S,5S,6r)-3-((6-ethynylquinazolin-4-yl)amino)bicyclo[3.1.0]hexan-6-yl)propyl)benzamide |
| Compound 338 | 4-chloro-N-((R)-1-((1R,3S,5S,6r)-3-((6-methylquinazolin-4-yl)amino)bicyclo[3.1.0]hexan-6-yl)propyl)benzamide |
| Compound 339 | N-(4-chlorophenyl)-2-((1R,3s,5S,6r)-3-((6-fluoroquinazolin-4-yl)oxy)bicyclo[3.1.0]hexan-6-yl)propanamide |
| Compound 340 | N-(4-chlorophenyl)-2-((1R,3s,5S,6r)-3-((6-fluorocinnolin-4-yl)oxy)bicyclo[3.1.0]hexan-6-yl)propanamide |
| Compound 341 | 4-chloro-2-(((1R,3S,5S,6r)-6-((R)-1-(4-chlorobenzamido)ethyl)bicyclo[3.1.0]hexan-3-yl)oxy)benzoic acid |
| Compound 342 | 4-chloro-N-((R)-1-((1R,3S,5S,6r)-3-(5-cyclopropyl-1H-pyrazol-1-yl)bicyclo[3.1.0]hexan-6-yl)propyl)benzamide |
| Compound 343 | 4-chloro-N-((R)-1-((1R,3S,5S,6r)-3-(3-cyclopropyl-1H-pyrazol-1-yl)bicyclo[3.1.0]hexan-6-yl)propyl)benzamide |
| Compound 344 | 1-(4-chlorophenyl)-3-((R)-1-((1R,3S,5S,6r)-3-(5,6-difluoro-1H-benzo[d]imidazol-1-yl)bicyclo[3.1.0]hexan-6-yl)propyl)urea |
| Compound 345 | N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide |
| Compound 346 | 2-(((1R,3S,5S,6r)-6-((R)-1-(4-chlorobenzamido)propyl)bicyclo[3.1.0]hexan-3-yl)amino)benzoic acid |
| Compound 347 | N-(4-chlorophenyl)-2-((1R,3s,5S,6r)-3-((6-fluoroquinolin-4-yl)oxy)bicyclo[3.1.0]hexan-6-yl)propanamide |
| Compound 348 | 4-chloro-N-((R)-1-((1R,3S,5S,6r)-3-(4-cyclopropyl-1H-pyrazol-1-yl)bicyclo[3.1.0]hexan-6-yl)propyl)benzamide |
| Compound 349 | 1-(4-chloro-3-fluorophenyl)-3-((R)-1-((1R,3S,5S,6r)-3-(5,6-difluoro-1H-benzo[d]imidazol-1-yl)bicyclo[3.1.0]hexan-6-yl)propyl)urea |
| Compound 350 | (R)-N-(4-chlorophenyl)-2-((1R,3S,5S,6r)-3-((6-fluoroquinazolin-4-yl)oxy)bicyclo[3.1.0]hexan-6-yl)propanamide |
| Compound 351 | (S)-N-(4-chlorophenyl)-2-((1R,3R,5S,6r)-3-((6-fluoroquinazolin-4-yl)oxy)bicyclo[3.1.0]hexan-6-yl)propanamide |
| Compound 352 | N-((R)-1-((1R,3S,5S,6r)-3-(5,6-difluoro-1H-benzo[d]imidazol-1-yl)bicyclo[3.1.0]hexan-6-yl)propyl)-1-(trifluoromethyl)cyclopropane-1-carboxamide |
| Compound 353 | 1-((R)-1-((1R,3S,5S,6r)-3-(5,6-difluoro-1H-benzo[d]imidazol-1-yl)bicyclo[3.1.0]hexan-6-yl)propyl)-3-(oxetan-3-yl)urea |
| Compound 354 | N-((R)-1-((1R,3S,5S,6r)-3-(5,6-difluoro-1H-benzo[d]imidazol-1-yl)bicyclo[3.1.0]hexan-6-yl)propyl)-3,3-difluoroazetidine-1-carboxamide |
| Compound 355 | N-((R)-1-((1R,3S,5S,6r)-3-(5,6-difluoro-1H-benzo[d]imidazol-1-yl)bicyclo[3.1.0]hexan-6-yl)propyl)-4,4-difluoropiperidine-1-carboxamide |
| Compound 356 | N-((R)-1-((1R,3S,5S,6r)-3-(5,6-difluoro-1H-benzo[d]imidazol-1-yl)bicyclo[3.1.0]hexan-6-yl)propyl)morpholine-4-carboxamide |
| Compound 357 | 1-cyclopropyl-3-((R)-1-((1R,3S,5S,6r)-3-(5,6-difluoro-1H-benzo[d]imidazol-1-yl)bicyclo[3.1.0]hexan-6-yl)propyl)urea |
| Compound 358 | (R)-N-(4-chlorophenyl)-2-((1R,3s,5S,6r)-3-((6-fluorocinnolin-4-yl)oxy)bicyclo[3.1.0]hexan-6-yl)propanamide |

| | |
|---|---|
| Compound 359 | (S)-N-(4-chlorophenyl)-2-((1R,3s,5S,6r)-3-((6-fluorocinnolin-4-yl)oxy)bicyclo[3.1.0]hexan-6-yl)propanamide |
| Compound 360 | (R)-N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide |
| Compound 361 | (S)-N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide |
| Compound 362 | (R)-N-(4-chlorophenyl)-2-((1R,3s,5S,6r)-3-((6-fluoroquinolin-4-yl)oxy)bicyclo[3.1.0]hexan-6-yl)propanamide |
| Compound 363 | (S)-N-(4-chlorophenyl)-2-((1R,3s,5S,6r)-3-((6-fluoroquinolin-4-yl)oxy)bicyclo[3.1.0]hexan-6-yl)propanamide | and the pharmaceutically acceptable salts and prodrugs thereof.

In an embodiment, the compound is selected from the group consisting of Compounds 1 to 262, and the pharmaceutically acceptable salts and prodrugs thereof.

In an embodiment, the compound is selected from the group consisting of: Compounds 2, 4, 5, 6, 7, 9, 10, 13, 14, 15, 18, 19, 20, 21, 22, 23, 30, 34, 35, 36, 37, 38, 39, 40, 42, 46, 47, 49, 50, 52, 54, 55, 56, 58, 59, 61, 63, 64, 66, 69, 70, 78, 84, 87, 88, 89, 91, 92, 93, 97, 99, 100, 102, 103, 104, 107, 115, 117, 118, 119, 123, 124, 125, 126, 127, 130, 131, 132, 134, 138, 144, 145, 147, 150, 153, 158, 161, 162, 163, 165, 167, 170, 171, 174, 176, 178, 181, 184, 186, 188, 189, 194, 195, 196, 198, 199, 200, 205, 207, 208, 209, 211, 213, 214, 218, 219, 220, 221, 225, 227, 229, 238, 240, 241, 245, 246, 247, 248, 253, 265, 266, 267, 268, 272, 273, 274, 275, 277, 278, 279, 281, 282, 285, 286, 287, 288, 298, 299, 301, 303, 304, 305, 306, 307, 315, 324, 325, 326, 327, 329, 330, 331, 332, 333, 334, 335, 336, 337, 338, 339, 340, 342, 343, 344, 345, 347, 348 and 349; and the pharmaceutically acceptable salts and prodrugs thereof. In another embodiment, the compound is selected from the group consisting of: Compounds 2, 4, 5, 6, 7, 9, 13, 14, 15, 19, 20, 23, 34, 35, 36, 37, 38, 40, 42, 46, 50, 56, 58, 59, 61, 63, 64, 66, 69, 70, 78, 87, 88, 89, 93, 99, 100, 102, 104, 107, 115, 117, 119, 123, 125, 126, 127, 130, 131, 132, 138, 144, 145, 147, 162, 163, 165, 167, 170, 176, 178, 186, 188, 194, 195, 199, 205, 207, 209, 211, 218, 219, 229, 241, 245, 246, 247, 248, 253, 265, 266, 267, 268, 272, 273, 275, 277, 278, 281, 282, 285, 286, 287, 298, 299, 301, 304, 305, 306, 307, 324, 327, 330, 331, 333, 334, 335, 336, 337, 338, 339, 340, 343, 344, 345, 347, 348 and 349; and the pharmaceutically acceptable salts and prodrugs thereof. In another embodiment, the compound is selected from the group consisting of: Compounds 2, 4, 5, 7, 9, 13, 15, 19, 20, 35, 36, 37, 56, 59, 61, 64, 66, 78, 87, 89, 93, 99, 102, 107, 115, 119, 123, 125, 126, 127, 130, 132, 147, 162, 163, 170, 176, 186, 194, 195, 199, 205, 207, 209, 211, 229, 241, 245, 246, 247, 248, 265, 266, 267, 268, 272, 273, 275, 277, 281, 282, 286, 287, 298, 305, 306, 307, 327, 331, 333, 334, 336, 337, 338, 339, 340, 343, 344, 345, 347, 348 and 349; and the pharmaceutically acceptable salts and prodrugs thereof. In another embodiment, the compound is selected from the group consisting of: Compounds 2, 4, 5, 7, 9, 13, 15, 19, 20, 35, 36, 37, 56, 59, 61, 64, 66, 78, 87, 89, 93, 99, 102, 107, 115, 119, 123, 125, 126, 127, 130, 132, 147, 162, 163, 170, 176, 186, 194, 195, 199, 205, 207, 209, 211, 229, 241, 245, 246, 247, 248, 265, 266, 267, 268, 272, 273, 275, 277, 281, 282, 286, 287, 299, 305, 306, 307, 327, 331, 333, 334, 336, 337, 338, 339, 340, 343, 344, 345, 347, 348 and 349; and the pharmaceutically acceptable salts and prodrugs thereof. In another embodiment, the compound is selected from the group consisting of: Compounds 4, 5, 7, 9, 13, 19, 56, 59, 64, 66, 87, 107, 123, 125, 127, 130, 132, 147, 199, 205, 207, 209, 229, 245, 247, 266, 268, 273, 277, 281, 286, 298, 307, 336, 337, 338, 339, 340, 343, 344, 345, 347 and 349; and the pharmaceutically acceptable salts and prodrugs thereof. In another embodiment, the compound is selected from the group consisting of: Compounds 4, 5, 7, 9, 13, 19, 56, 59, 64, 66, 87, 107, 123, 125, 127, 130, 132, 147, 199, 205, 207, 209, 229, 245, 247, 266, 268, 273, 277, 281, 286, 299, 307, 336, 337, 338, 339, 340, 343, 344, 345, 347 and 349; and the pharmaceutically acceptable salts and prodrugs thereof.

In an embodiment, the compound is selected from the group consisting of: Compounds 2, 4, 5, 6, 7, 9, 10, 13, 14, 15, 18, 19, 20, 21, 22, 23, 30, 34, 35, 36, 37, 38, 39, 40, 42, 46, 47, 49, 50, 52, 54, 55, 56, 58, 59, 61, 63, 64, 66, 69, 70, 78, 84, 87, 88, 89, 91, 92, 93, 99, 100, 102, 103, 104, 107, 115, 117, 118, 119, 123, 124, 125, 126, 127, 130, 131, 132, 134, 138, 144, 145, 147, 150, 153, 158, 161, 162, 163, 165, 167, 170, 171, 174, 176, 178, 181, 184, 186, 188, 189, 194, 195, 196, 198, 199, 200, 205, 207, 208, 209, 211, 213, 214, 218, 219, 220, 221, 225, 227, 229, 238, 240, 241, 245, 246, 247, 248, 253, 260, and 262; and the pharmaceutically acceptable salts and prodrugs thereof. In another embodiment, the compound is selected from the group consisting of: Compounds 2, 4, 5, 6, 7, 9, 13, 14, 15, 19, 20, 23, 34, 35, 36, 37, 38, 40, 42, 46, 50, 56, 58, 59, 61, 63, 64, 66, 69, 70, 78, 87, 88, 89, 93, 99, 100, 102, 104, 107, 115, 117, 119, 123, 125, 126, 127, 130, 131, 132, 138, 144, 145, 147, 162, 163, 165, 167, 170, 176, 178, 186, 188, 194, 195, 199, 205, 207, 209, 211, 218, 219, 229, 241, 245, 246, 247, 248, 253, and 260; and the pharmaceutically acceptable salts and prodrugs thereof. In another embodiment, the compound is selected from the group consisting of: Compounds 2, 4, 5, 7, 9, 13, 15, 19, 20, 35, 36, 37, 56, 59, 61, 64, 66, 78, 87, 89, 93, 99, 102, 107, 115, 119, 123, 125, 126, 127, 130, 132, 147, 162, 163, 170, 176, 186, 194, 195, 199, 205, 207, 209, 211, 229, 241, 245, 246, 247, 248, and 260; and the pharmaceutically acceptable salts and prodrugs thereof. In another embodiment, the compound is selected from the group consisting of: Compounds 4, 5, 7, 9, 13, 19, 56, 59, 64, 66, 87, 107, 123, 125, 127, 130, 132, 147, 199, 205, 207, 209, 229, 245, 247, and 260; and the pharmaceutically acceptable salts and prodrugs thereof.

In an embodiment, the compound is selected from the group consisting of: Compounds 2, 4, 5, 6, 7, 9, 10, 13, 14, 15, 18, 19, 20, 21, 22, 23, 26, 29, 30, 31, 32, 33, 34, 35, 36, 37, 38, 39, 40, 41, 42, 43, 44, 45, 46, 47, 49, 50, 51, 52, 53, 54, 55, 56, 57, 58, 59, and 60; and the pharmaceutically acceptable salts and prodrugs thereof. In another embodiment, the compound is selected from the group consisting of: Compounds 2, 4, 5, 6, 7, 9, 10, 13, 14, 15, 18, 19, 20, 21, 22, 23, 30, 34, 35, 36, 37, 38, 39, 40, 41, 42, 43, 45, 46, 47, 49, 50, 51, 52, 53, 54, 55, 56, 58, 59, and 60; and the pharmaceutically acceptable salts and prodrugs thereof. In another embodiment, the compound is selected from the group consisting of: Compounds 2, 4, 5, 6, 7, 9, 13, 14, 15, 19, 20, 23, 34, 35, 36, 37, 38, 40, 42, 46, 50, 56, 58, and 59; and the pharmaceutically acceptable salts and prodrugs thereof. In another embodiment, the compound is selected from the group consisting of: Compounds 4, 5, 7, 9, 13, 19, 56, and 59; and the pharmaceutically acceptable salts and prodrugs thereof.

In embodiments, Compound 1 is 4-chloro-N—((S)-1-((1R,3S,5S,6r)-3-hydroxybicyclo[3.1.0]hexan-6-yl)propyl)benzamide; Compound 2 is 4-chloro-N—((S)-1-((1R,3S,5S,6r)-3-(quinolin-4-yloxy)bicyclo[3.1.0]hexan-6-yl)propyl)benzamide; Compound 3 is 4-chloro-N—((S)-1-((1R,3R,5S,6r)-3-hydroxybicyclo[3.1.0]hexan-6-yl)propyl)benzamide; Compound 4 is 4-chloro-N—((S)-1-((1R,3R,5S,6r)-3-(quinolin-4-yloxy)bicyclo[3.1.0]hexan-6-yl)propyl)benzamide; Compound 5 is 4-chloro-N—((S)-1-((1R,3R,5S,6r)-3-((6-fluoroquinazolin-4-yl)oxy)bicyclo[3.1.0]hexan-6-yl)propyl)benzamide; Compound 6 is 4-chloro-N—((S)-1-((1R,3R,5S,6r)-3-(6-fluoro-4-oxoquinazolin-3 (4H)-yl)bicyclo[3.1.0]hexan-6-yl)propyl)benzamide; Compound 7 is 2-(4-chlorophenyl)-N-((1R,3s,5S)-3-((6-fluoroquinolin-4-yl)oxy)bicyclo[3.1.0]hexan-6-yl)acetamide; Compound 8 is (1R,5S)—N-(4-chlorophenyl)-3-(quinolin-4-yloxy)bicyclo[3.1.0]hexane-6-carboxamide; Compound 9 is 4-chloro-N-(((1R,3s,5 S,6r)-3-((6-fluoroquinolin-4-yl)oxy)bicyclo[3.1.0]hexan-6-yl)methyl)benzamide; Compound 10 is 1-(4-chlorophenyl)-3-((1R,3s,5S,6r)-3-((6-fluoroquinolin-4-yl)oxy)bicyclo[3.1.0]hexan-6-yl)urea; Compound 11 is 2-(4-chlorophenyl)-5-(3-(quinolin-4-yloxy)bicyclo[3.1.0]hexan-6-yl)-1,3,4-oxadiazole; Compound 12 is 4-(((1R,5 S)-6-(2-(4-chlorophenoxy)ethyl)bicyclo[3.1.0]hexan-3-yl)oxy)-6-fluoro-2-(trifluoromethyl)quinolone; Compound 13 is 4-chloro-N—((R)-1-((1R,3S,5S,6r)-3-((6-fluoroquinazolin-4-yl)oxy)bicyclo[3.1.0]hexan-6-yl)ethyl)benzamide; Compound 14 is 4-chloro-N—((S)-1-((1R,3R,5S,6r)-3-(4-fluorophenoxy)bicyclo[3.1.0]hexan-6-yl)propyl)benzamide; Compound 15 is 4-chloro-N—((S)-1-((1R,3R,5 S,6r)-3-((2-methylpyridin-4-yl)oxy)bicyclo[3.1.0]hexan-6-yl)propyl)benzamide; Compound 16 is (1R,5S)—N-(4-chlorobenzyl)-3-(quinolin-4-yloxy)bicyclo[3.1.0]hexane-6-carboxamide; Compound 17 is (1R,5S)—N-(4-chlorobenzyl)-3-((6-fluoro-2-(trifluoromethyl)quinolin-4-yl)oxy)bicyclo[3.1.0]hexane-6-carboxamide; Compound 18 is 4-chloro-N—((S)-1-((1R,3R,5 S,6r)-3-((6-fluoropyridin-3-yl)oxy)bicyclo[3.1.0]hexan-6-yl)propyl)benzamide; Compound 19 is 4-chloro-N—((S)-1-((1R,3R,5S,6r)-3-((6-fluoroquinolin-4-yl)oxy)bicyclo[3.1.0]hexan-6-yl)propyl)benzamide; Compound 20 is 4-chloro-N—((S)-1-((1R,3R,5S,6r)-3-((6-fluoro-2-methylquinolin-4-yl)oxy)bicyclo[3.1.0]hexan-6-yl)propyl)benzamide; Compound 21 is 4-chloro-N—((S)-1-((1R,3R,5S,6r)-3-((7-chloroquinazolin-4-yl)oxy)bicyclo[3.1.0]hexan-6-yl)propyl)benzamide; Compound 22 is 4-chloro-N—((S)-1-((1R,3R,5 S,6r)-3-((6-fluoro-2-(trifluoromethyl)quinolin-4-yl)oxy)bicyclo[3.1.0]hexan-6-yl)propyl)benzamide; Compound 23 is 4-chloro-N-(((1R,3s,5S,6s)-3-((6-fluoroquinolin-4-yl)oxy)bicyclo[3.1.0]hexan-6-yl)methyl)benzamide; Compound 24 is 4-chloro-N-(((1R,3s,5 S,6s)-3-((6-fluoro-2-(trifluoromethyl)quinolin-4-yl)oxy)bicyclo[3.1.0]hexan-6-yl)methyl)benzamide; Compound 25 is 4-chloro-N-(3-(((6-fluoro-2-(trifluoromethyl)quinolin-4-yl)oxy)bicyclo[3.1.0]hexan-6-yl)benzamide; Compound 26 is 4-chloro-N-(3-(quinolin-4-yloxy)bicyclo[3.1.0]hexan-6-yl)benzamide; Compound 27 is 1-(4-bromophenyl)-N-(3-(quinolin-4-yloxy)bicyclo[3.1.0]hexan-6-yl)methanesulfonamide; Compound 28 is 4-chloro-N-(3-(quinolin-4-yloxy)bicyclo[3.1.0]hexan-6-yl)benzenesulfonamide; Compound 29 is 1-(4-chlorophenyl)-3-((1R,5 S,6r)-3-((6-fluoroquinolin-4-yl)oxy)bicyclo[3.1.0]hexan-6-yl)urea; Compound 30 is 2-(4-chlorophenyl)-N-((1R,5S)-3-(quinolin-4-yloxy)bicyclo[3.1.0]hexan-6-yl)acetamide; Compound 31 is 2-(4-chlorophenyl)-N-((1R,3r,5S)-3-((6-fluoroquinolin-4-yl)oxy)bicyclo[3.1.0]hexan-6-yl)acetamide; Compound 32 is 4-chloro-N-(((1R,3r,5S,6r)-3-((6-fluoroquinolin-4-yl)oxy)bicyclo[3.1.0]hexan-6-yl)methyl)benzamide; Compound 33 is 4-chloro-N-(((1R,3r,5S,6r)-3-((4-chloroquinolin-6-yl)oxy)bicyclo[3.1.0]hexan-6-yl)methyl)benzamide; Compound 34 is 4-chloro-N—((S)-1-((1R,3R,5S,6r)-3-(7-fluoro-4-oxoquinazolin-3(4H)-yl)bicyclo[3.1.0]hexan-6-yl)propyl)benzamide; Compound 35 is 4-chloro-N—((S)-1-((1R,3R,5 S,6r)-3-((7-fluoroquinazolin-4-yl)oxy)bicyclo[3.1.0]hexan-6-yl)propyl)benzamide; Compound 36 is 4-chloro-N—((S)-1-((1R,3R,5S,6r)-3-(5-fluoro-4-oxoquinazolin-3(4H)-yl)bicyclo[3.1.0]hexan-6-yl)propyl)benzamide; Compound 37 is 4-chloro-N—((S)-1-((1R,3R,5 S,6r)-3-((5-fluoroquinazolin-4-yl)oxy)bicyclo[3.1.0]hexan-6-yl)propyl)benzamide; Compound 38 is N—((S)-1-((1R,3R,5S,6r)-3-((1,5-naphthyridin-4-yl)oxy)bicyclo[3.1.0]hexan-6-yl)propyl)-4-chlorobenzamide; Compound 39 is 4-chloro-N—((S)-1-((1R,3R,5S,6r)-3-((3-fluoropyridin-2-yl)oxy)bicyclo[3.1.0]hexan-6-yl)propyl)benzamide; Compound 40 is 4-chloro-N—((S)-1-((1R,3R,5S,6r)-3-((6-methylpyridin-2-yl)oxy)bicyclo[3.1.0]hexan-6-yl)propyl)benzamide; Compound 41 is 4-chloro-N—((S)-1-((1R,3R,5S,6r)-3-((3-methylpyridin-2-yl)oxy)bicyclo[3.1.0]hexan-6-yl)propyl)benzamide; Compound 42 is 4-chloro-N—((S)-1-((1R,3R,5S,6r)-3-(2,5-difluorophenoxy)bicyclo[3.1.0]hexan-6-yl)propyl)benzamide; Compound 43 is 4-chloro-N—((S)-1-((1R,3R,5S,6r)-3-(quinolin-8-yloxy)bicyclo[3.1.0]hexan-6-yl)propyl)benzamide; Compound 44 is 4-chloro-N—((S)-1-((1R,3R,5 S,6r)-3-(2,6-difluorophenoxy)bicyclo[3.1.0]hexan-6-yl)propyl)benzamide; Compound 45 is N—((S)-1-((1R,3R,5S,6r)-3-(2-(2-amino-2-oxoethyl)phenoxy)bicyclo[3.1.0]hexan-6-yl)propyl)-4-chlorobenzamide; Compound 46 is 4-chloro-N—((S)-1-((1R,3R,5S,6r)-3-(cinnolin-4-yloxy)bicyclo[3.1.0]hexan-6-yl)propyl)benzamide; Compound 47 is 4-chloro-N—((S)-1-((1R,3R,5S,6r)-3-(4-oxocinnolin-1(4H)-yl)bicyclo[3.1.0]hexan-6-yl)propyl)benzamide; Compound 48 is 4-chloro-N—((S)-1-((1R,3R,5S,6r)-3-(2-((dimethylamino)methyl)phenoxy)bicyclo[3.1.0]hexan-6-yl)propyl)benzamide; Compound 49 is 4-chloro-N—((S)-1-((1R,3R,5S,6r)-3-(quinolin-3-yloxy)bicyclo[3.1.0]hexan-6-yl)propyl)benzamide; Compound 50 is 4-chloro-N—((S)-1-((1R,3R,5S,6r)-3-((1-methyl-2-oxo-1,2-dihydroquinolin-4-yl)oxy)bicyclo[3.1.0]hexan-6-yl)propyl)benzamide; Compound 51 is N—((S)-1-((1R,3R,5S,6r)-3-(1H-pyrazolo[4,3-c]pyridin-1-yl)bicyclo[3.1.0]hexan-6-yl)propyl)-4-chlorobenzamide; Compound 52 is 4-chloro-N—((S)-1-((1R,3R,5S,6r)-3-((5-fluoro-2-methylpyrimidin-4-yl)oxy)bicyclo[3.1.0]hexan-6-yl)propyl)benzamide; Compound 53 is 4-chloro-N—((S)-1-((1R,3R,5 S,6r)-3-(7-chloro-4-oxoquinazolin-3(4H)-yl)bicyclo[3.1.0]hexan-6-yl)propyl)benzamide; Compound 54 is 4-chloro-N—((S)-1-((1R,3R,5S,6r)-3-((5-fluoropyrimidin-4-yl)oxy)bicyclo[3.1.0]hexan-6-yl)propyl)benzamide; Compound 55 is N—((S)-1-((1R,3R,5S,6r)-3-((1,6-naphthyridin-4-yl)oxy)bicyclo[3.1.0]hexan-6-yl)propyl)-4-chlorobenzamide; Compound 56 is 4-chloro- N—((S)-1-((1R,3R,5S,6r)-3-((7-fluoroquinolin-4-yl)oxy) bicyclo[3.1.0]hexan-6-yl)propyl)benzamide; Compound 57 is 4-chloro-N—((S)-1-((1R,3R,5 S,6r)-3-((4-chloroquinolin-7-yl)oxy)bicyclo[3.1.0]hexan-6-yl)propyl)benzamide; Compound 58 is 4-chloro-N—((S)-1-((1R,3R,5S,6r)-3-((5-fluoropyridin-3-yl)oxy)bicyclo[3.1.0]hexan-6-yl)propyl) benzamide; Compound 59 is 4-chloro-N—((S)-1-((1R,3R,5S,6r)-3-(quinazolin-4-yloxy)bicyclo[3.1.0]hexan-6-yl) propyl)benzamide; Compound 60 is 4-chloro-N—((S)-1-((1R,3R,5S,6r)-3-((2-chloropyridin-3-yl)oxy)bicyclo[3.1.0] hexan-6-yl)propyl)benzamide; Compound 61 is 2-(4-chlorophenyl)-N-((1R,3s,5S,6r)-3-((6-fluoroquinazolin-4-yl)oxy)bicyclo[3.1.0]hexan-6-yl)acetamide; Compound 62 is 2-(4-chlorophenyl)-N-((1R,3s,5 S,6r)-3-(6-fluoro-4-oxoquinazolin-3 (4H)-yl)bicyclo[3.1.0]hexan-6-yl)acetamide; Compound 63 is 4-chloro-N—((R)-1-((1R,3 S,5 S,6r)-3-(6-fluoro-4-oxoquinazolin-3(4H)-yl)bicyclo[3.1.0]hexan-6-yl) ethyl)benzamide; Compound 64 4-chloro-N—((R)-1-((1R,3 S,5 S,6r)-3-((6-fluoroquinazolin-4-yl)oxy)bicyclo[3.1.0] hexan-6-yl)ethyl)benzamide; Compound 65 is 4-chloro-N-(((1R,3s,5 S,6r)-3-(6-fluoro-4-oxoquinazolin-3(4H)-yl)bicyclo[3.1.0]hexan-6-yl)methyl)benzamide; Compound 66 is 4-cyano-N—((S)-1-((1R,3R,5 S,6r)-3-((6-fluoroquinazolin-4-yl)oxy)bicyclo[3.1.0]hexan-6-yl)propyl)benzamide; Compound 67 is 4-cyano-N—((S)-1-((1R,3R,5S,6r)-3-(6-fluoro-4-oxoquinazolin-3(4H)-yl)bicyclo[3.1.0]hexan-6-yl) propyl)benzamide; Compound 68 is N—((S)-1-((1R,3R,5 S,6r)-3-((6-fluoroquinazolin-4-yl)oxy)bicyclo[3.1.0]hexan-6-yl)propyl)-2-methoxypyrimidine-5-carboxamide; Compound 69 is 2,2-difluoro-N—((R)-1-((1R,3S,5S,6s)-3-((6-fluoroquinazolin-4-yl)oxy)bicyclo[3.1.0]hexan-6-yl)propyl) benzo[d][1,3]dioxole-5-carboxamide; Compound 70 is 4-chloro-N—((R)-1-((1R,3S,5S,6r)-3-((7-fluoroquinazolin-4-yl)oxy)bicyclo[3.1.0]hexan-6-yl)ethyl)benzamide; Compound 71 is 4-chloro-N—((R)-1-((1R,3S,5S,6r)-3-((3-methylpyridin-2-yl)oxy)bicyclo[3.1.0]hexan-6-yl)ethyl) benzamide; Compound 72 is 4-chloro-N—((S)-1-((1R,3R,5S,6r)-3-(phthalazin-1-yloxy)bicyclo[3.1.0]hexan-6-yl) propyl)benzamide; Compound 73 is 4-chloro-N—((S)-1-((1R,3R,5S,6r)-3-morpholinobicyclo[3.1.0]hexan-6-yl) propyl)benzamide; Compound 74 is N—((S)-1-((1R,3R,5 S,6r)-3-(6-fluoro-4-oxoquinazolin-3(4H)-yl)bicyclo[3.1.0] hexan-6-yl)propyl)-6-methoxynicotinamide; Compound 75 is 5-chloro-N—((R)-1-((1R,3S,5S,6s)-3-(6-fluoro-4-oxoquinazolin-3(4H)-yl)bicyclo[3.1.0]hexan-6-yl)propyl)picolinamide; Compound 76 is 5-cyano-N—((R)-1-((1R,3 S,5 S,6s)-3-(6-fluoro-4-oxoquinazolin-3 (4H)-yl)bicyclo[3.1.0] hexan-6-yl)propyl)picolinamide; Compound 77 is 5-chloro-N-(1-((1R,5 S)-3-(cinnolin-4-yloxy)bicyclo[3.1.0]hexan-6-yl)propyl)picolinamide; Compound 78 is N—((R)-1-((1R,3 S,5 S,6s)-3-((6-fluoroquinazolin-4-yl)oxy)bicyclo[3.1.0] hexan-6-yl)propyl)-6-methoxynicotinamide; Compound 79 is 2-(4-chlorophenyl)-N-((1R,3s,5S,6r)-3-(cinnolin-4-yloxy)bicyclo[3.1.0]hexan-6-yl)acetamide; Compound 80 is N—((S)-1-((1R,3R,5S,6r)-3-(cinnolin-4-yloxy)bicyclo [3.1.0]hexan-6-yl)propyl)-4-cyanobenzamide; Compound 81 is N—((R)-1-((1R,3S,5S,6r)-3-(1H-1,2,4-triazol-1-yl)bicyclo[3.1.0]hexan-6-yl)propyl)-4-chlorobenzamide; Compound 82 is N—((S)-1-((1R,3R,5S,6r)-3-(cinnolin-4-yloxy) bicyclo[3.1.0]hexan-6-yl)propyl)-5-cyanopicolinamide; Compound 83 is 5-cyano-N—((S)-1-((1R,3R,5 S,6r)-3-(4-oxocinnolin-1 (4H)-yl)bicyclo[3.1.0]hexan-6-yl)propyl)picolinamide; Compound 84 is ethyl (S)-3-(4-chlorobenzamido)-3-((1R,3S,5S,6r)-3-(cinnolin-4-yloxy)bicyclo [3.1.0]hexan-6-yl)propanoate; Compound 85 is 2-(4-chlorophenyl)-N-((1R,3s,5 S,6r)-3-(4-oxocinnolin-1 (4H)-yl)bicyclo[3.1.0]hexan-6-yl)acetamide; Compound 86 is 2-(4-chlorophenyl)-N-((1R,3s,5S,6r)-3-(cinnolin-4-yloxy) bicyclo[3.1.0]hexan-6-yl)-N-methylacetamide; Compound 87 is 4-cyano-N-(2-((1R,3s,5 S,6r)-3-(4-oxocinnolin-1 (4H)-yl)bicyclo[3.1.0]hexan-6-yl)propan-2-yl)benzamide; Compound 88 is N-(2-((1R,3s,5S,6r)-3-(cinnolin-4-yloxy) bicyclo[3.1.0]hexan-6-yl)propan-2-yl)-4-cyanobenzamide; Compound 89 is N—((R)-1-((1R,3S,5S,6r)-3-(1H-benzo[d] imidazol-1-yl)bicyclo[3.1.0]hexan-6-yl)propyl)-4-chlorobenzamide; Compound 90 is N—((R)-1-((1R,3S,5S,6r)-3-azidobicyclo[3.1.0]hexan-6-yl)propyl)-4-chlorobenzamide; Compound 91 is 4-chloro-N—((R)-1-((1R,3S,5S,6r)-3-(4-cyclopropyl-1H-1,2,3-triazol-1-yl) bicyclo[3.1.0]hexan-6-yl)propyl)benzamide; Compound 92 is 4-chloro-N—((S)-1-((1R,3R,5S,6r)-3-((4-chloro-2-methylpyridin-3-yl)oxy)bicyclo[3.1.0]hexan-6-yl)propyl)benzamide; Compound 93 is 4-chloro-N—((S)-1-((1R,3R,5S,6r)-3-((3-fluoro-2-methylpyridin-4-yl)oxy)bicyclo[3.1.0] hexan-6-yl)propyl)benzamide; Compound 94 is 1-((1R,3S,5S,6r)-6-((R)-1-(4-chlorobenzamido)propyl)bicyclo[3.1.0] hexan-3-yl)-1H-1,2,3-triazole-4-carboxylic acid; Compound 95 is 1-((1R,3S,5S,6r)-6-((R)-1-(4-chlorobenzamido)propyl)bicyclo[3.1.0]hexan-3-yl)-1H-1,2,3-triazole-4-carboxamide; Compound 96 is 4-chloro-N—((R)-1-((1R,3S,5S,6r)-3-((tetrahydro-2H-pyran-4-yl)methoxy) bicyclo[3.1.0]hexan-6-yl)propyl)benzamide; Compound 97 is 4-chloro-N—((R)-1-((1R,3S,5S,6r)-3-(4-(2-hydroxypropan-2-yl)-1H-1,2,3-triazol-1-yl)bicyclo[3.1.0]hexan-6-yl) propyl)benzamide; Compound 98 is 4-chloro-N—((R)-1-((1R,3S,5S,6r)-3-(4-(pyrrolidine-1-carbonyl)-1H-1,2,3-triazol-1-yl)bicyclo[3.1.0]hexan-6-yl)propyl)benzamide; Compound 99 is N—((R)-1-((1R,3S,5S,6r)-3-(1H-benzo[d] [1,2,3]triazol-1-yl)bicyclo[3.1.0]hexan-6-yl)propyl)-4-chlorobenzamide; Compound 100 is N—((R)-1-((1R,3S,5S,6r)-3-(2H-benzo[d][1,2,3]triazol-2-yl)bicyclo[3.1.0]hexan-6-yl)propyl)-4-chlorobenzamide; Compound 101 is 4-chloro-N—((S)-1-((1R,3R,5S,6r)-3-((tetrahydro-2H-pyran-4-yl) oxy)bicyclo[3.1.0]hexan-6-yl)propyl)benzamide; Compound 102 is 4-cyano-N—((S)-1-((1R,3R,5S,6r)-3-((7-fluoroquinazolin-4-yl)oxy)bicyclo[3.1.0]hexan-6-yl)ethyl) benzamide; Compound 103 is 4-chloro-N—((S)-1-((1R,3R,5S,6r)-3-(cinnolin-4-yloxy)bicyclo[3.1.0]hexan-6-yl) propyl)benzamide; Compound 104 is 4-chloro-N—((R)-1-((1R,3S,5S,6r)-3-(cinnolin-4-yloxy)bicyclo[3.1.0]hexan-6-yl)propyl)benzamide; Compound 105 is 4-cyano-N—((R)-1-((1R,3R,5S,6r)-3-hydroxybicyclo[3.1.0]hexan-6-yl)ethyl) benzamide; Compound 106 is 4-cyano-N—((R)-1-((1R,3S,5S,6r)-3-hydroxybicyclo[3.1.0]hexan-6-yl)ethyl)benzamide; Compound 107 is 4-cyano-N—((R)-1-((1R,3S,5S,6r)-3-((6-fluoroquinazolin-4-yl)oxy)bicyclo[3.1.0]hexan-6-yl)ethyl)benzamide; and/or Compound 108 is 4-cyano-N—((S)-1-((1R,3R,5 S,6r)-3-(6-fluoro-4-oxoquinazolin-3(4H)-yl)bicyclo[3.1.0]hexan-6-yl)ethyl)benzamide.

The compounds of the invention are useful as inhibitors of IDO1, IDO2 and/or TDO. In particular, compounds of the invention are useful as inhibitors of IDO1. Assays for determining the inhibitory activity of compounds against IDO1 (e.g. against mouse or human IDO1, or a fragment thereof having catalytic activity) are known in the art and are also set out in the following Examples. The activity values listed below may, for example, be determined according to an assay as set out in the following Examples, e.g. as set out in Example 17 and/or Example 18.

In embodiments, compounds of the invention have an $IC_{50}$ value (e.g. an inhibitory activity against IDO1 in a cell-based assay) of less than 10 µM, less than 5 µM, less than 2 µM, less than 1 µM, less than 500 nM, less than 200 nM, less than 100 nM, less than 75 nM, less than 50 nM, less than 40 nM, less than 30 nM, less than 25 nM, less than 20 nM, less than 15 nM, less than 10 nM, less than 8 nM, less than 6 nM, less than 5 nM, less than 4 nM, less than 3 nM, less than 2.5 nM, or less than 2 nM.

The compounds of the invention may be selective for IDO1 and/or IDO2 over TDO. In particular, the compounds of the invention may be selective for IDO1 over TDO. Assays for determining the selectivity of a compound for IDO1 (or IDO2) over TDO are known in the art and are illustrated in the following Examples.

In embodiments, the compounds of the invention are selective for IDO1 over TDO by a value of at least 100 times, at least 200 times, at least 500 times, at least 1000 times, at least 2000 times, at least 5000 times or at least 10000 times. By "selective" is meant that the concentration of compound which results in 50% maximal inhibition ($IC_{50}$) of TDO is at least the stated factor more than the concentration of compound which results in 50% maximal inhibition of IDO1. Thus, a compound having an $IC_{50}$ value of 10 nM against IDO1, and having an $IC_{50}$ value of 20 μM against TDO, is selective for IDO1 over TDO by a value of 2000 times.

Salts

Presently disclosed compounds that are basic in nature are generally capable of forming a wide variety of different salts with various inorganic and/or organic acids. Although such salts are generally pharmaceutically acceptable for administration to animals and humans, it is often desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g. by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained. Presently disclosed compounds that are positively charged, e.g. containing a quaternary ammonium, may also form salts with the anionic component of various inorganic and/or organic acids.

Acids which can be used to prepare pharmaceutically acceptable salts of compounds are those which can form non-toxic acid addition salts, e.g. salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, malate, maleate, fumarate, gluconate, saccharate, benzoate, methanesulfonate and pamoate [i.e. 1,1'-methylene-bis-(2-hydroxy-3-naphthoate)] salts.

Presently disclosed compounds that are acidic in nature, e.g. compounds containing a carboxylic acid or tetrazole moiety, are generally capable of forming a wide variety of different salts with various inorganic and/or organic bases. Although such salts are generally pharmaceutically acceptable for administration to animals and humans, it is often desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g. by treating the corresponding acidic compounds with an aqueous solution containing the desired pharmacologically acceptable cations, and then evaporating the resulting solution to dryness, e.g. under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents may be employed in order to ensure completeness of reaction and maximum product yields of the desired solid salt.

Bases which can be used to prepare the pharmaceutically acceptable base addition salts of compounds are those which can form non-toxic base addition salts, e.g. salts containing pharmacologically acceptable cations, such as, alkali metal cations (e.g. potassium and sodium), alkaline earth metal cations (e.g. calcium and magnesium), ammonium or other water-soluble amine addition salts such as N-methylglucamine (meglumine), lower alkanolammonium, and other such bases of organic amines.

Prodrugs

Pharmaceutically acceptable prodrugs for use according to the present disclosure are derivatives of IDO1 inhibitors, e.g. compounds characterized by formula (I), which can be converted in vivo into the compounds described herein. The prodrugs, which may themselves have some activity, become fully pharmaceutically active in vivo when they undergo, for example, solvolysis under physiological conditions or through enzymatic degradation. Methods for preparing prodrugs of compounds as described herein would be apparent to one of skill in the art based on the present disclosure.

Stereochemistry

Stereoisomers (e.g. cis and trans isomers) and all optical isomers of a presently disclosed compound (e.g. R- and S-enantiomers), as well as racemic, diastereomeric and other mixtures of such isomers are within the scope of the present disclosure.

For example, where the group $CR^3R^4$ contains one or more chiral carbon atoms, the compounds of the invention may exist predominantly as a single enantiomer (or diastereomer), or as a mixture of isomers (e.g. enantiomers or diastereomers).

In embodiments, the compounds of the invention are present as a racemic mixture, e.g. said R- and S-isomers (or all enantiomers or diastereomers) are present in approximately equal amounts. In other embodiments the compounds of the invention are present as a mixture of isomers in which one enantiomer (or diastereomer) is present in an enantiomeric excess of at least about 5%, 10%, 25%, 40%, 70%, 80%, 90%, 95%, 97%, 98% or 99%, e.g. about 100%.

Methods for preparing enantioenriched and/or enantiopure compounds would be apparent to the person of skill in the art based on the present disclosure. Examples of such methods include chemical resolution (e.g. crystallization) and chiral chromatography.

The compounds presently disclosed may exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, all tautomers are within the scope of the present disclosure.

Where compounds are characterized by structural formulae that indicate stereochemical information, the invention extends to mixtures of one or more of said compounds characterized by the said structural formulae. Thus, in embodiments, the invention provides a mixture of compounds characterized by formulae (Ia) and (Ib), or pharmaceutically acceptable salts or prodrugs of one or more thereof. In other embodiments, the invention provides a mixture of compounds characterized by formulae (Iac) and (Ibd), or pharmaceutically acceptable salts or prodrugs of one or more thereof.

Other Forms

Pharmaceutically acceptable hydrates, solvates, polymorphs, etc., of the compounds described herein are also within the scope of the present disclosure. Compounds as described herein may be in an amorphous form and/or in one or more crystalline forms.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Within the ambit of isotopically-labelled compounds, deuterated compounds, e.g. compounds of the invention which have one or more hydrogen atoms replaced by deuterium, are preferred.

Pharmaceutical Compositions

The present disclosure provides pharmaceutical compositions comprising at least one compound of the invention, e.g. a compound characterized by formula (I), and at least one pharmaceutically acceptable excipient, e.g. for use according to the methods disclosed herein.

The pharmaceutically acceptable excipient can be any such excipient known in the art including those described in, for example, Remington's Pharmaceutical Sciences, Mack Publishing Co. (A. R. Gennaro edit. 1985). Pharmaceutical compositions of the compounds presently disclosed may be prepared by conventional means known in the art including, for example, mixing at least one presently disclosed compound with a pharmaceutically acceptable excipient.

A pharmaceutical composition or dosage form of the invention can include an agent and another carrier, e.g. compound or composition, inert or active, such as a detectable agent, label, adjuvant, diluent, binder, stabilizer, buffers, salts, lipophilic solvents, preservative, adjuvant or the like. Carriers also include pharmaceutical excipients and additives, for example, proteins, peptides, amino acids, lipids, and carbohydrates (e.g. sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1 to 99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

Carriers which may be used include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g. cyclodextrins, such as 2-hydroxypropyl-β-cyclodextrin), polyethylene glycols, flavoring agents, antimicrobial agents, sweeteners, antioxidants, antistatic agents, surfactants (e.g. polysorbates such as "TWEEN 20" and "TWEEN 80"), lipids (e.g. phospholipids, fatty acids), steroids (e.g. cholesterol), and chelating agents (e.g. EDTA).

The present disclosure also provides pharmaceutical compositions, and kits comprising said compositions, which contain at least one compound as described herein, e.g. a compound characterized by formula (I), and at least one further pharmaceutically-active agent. These pharmaceutical compositions and kits may be adapted to allow simultaneous, subsequent and/or separate administration of the compound and the further active agent. For example, the compound and the further active agent may be formulated in separate dosage forms, e.g. in separate tablets, capsules, lyophilisates or liquids, or they may be formulated in the same dosage form, e.g. in the same tablet, capsule, lyophilisate or liquid. Where the compound and the further active agent are formulated in the same dosage form, the compound and the further active agent may be present substantially in admixture, e.g. within the core of a tablet, or they may be present substantially in discrete regions of the dosage form, e.g. in separate layers of the same tablet.

A further aspect of the present invention provides a pharmaceutical composition comprising: (i) a compound as described herein, e.g. a compound characterized by formula (I); (ii) a further active agent; and (iii) a pharmaceutically acceptable excipient.

Another aspect of the present invention provides a kit comprising (i) a compound as described herein, e.g. a compound characterized by formula (I); (ii) instructions for the use of the compound in therapy, e.g. in a method as described herein; and (iii) optionally a further active agent.

In one embodiment, said further active agent is a chemotherapeutic agent or an immunotherapeutic agent. Examples of such further active agents are provided below.

The pharmaceutical compositions can be formulated so as to provide slow, extended, or controlled release of the active ingredient therein using, for example, hydroxypropylmethyl cellulose in varying proportions to provide the desired release profile, other polymer matrices, liposomes and/or microspheres. The pharmaceutical compositions can also optionally contain opacifying agents and may be of a composition that releases the active ingredient(s) only, or preferentially, in a certain portion of the gastrointestinal tract, optionally, in a delayed manner, e.g. by using an enteric coating. Examples of embedding compositions include polymeric substances and waxes. The active ingredient can also be in micro-encapsulated form, if appropriate, with one or more pharmaceutically acceptable carriers, excipients, or diluents well known in the art (see, e.g., Remington's). The compounds presently disclosed may be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

Chemical Synthesis

An illustrative synthetic method (Schemes I and II) is shown below for the preparation of compounds characterised by formula (I) in which $X^1$ is a heteroatom (O, S or NH) and the linker between the bicyclo[3.1.0]hexane and group Y contains an amide (e.g. —NH—C(O)—) or a sulfonamide (e.g. —NH—S(O)$_2$—):

EtMgBr. In step (iv), D is converted to the protected precursor compound E by reaction with the Y-containing fragment as an activated sulfonic or carboxylic acid. For example, D may be treated with an acid (e.g. TFA) and then coupled with the Y-containing fragment using conventional means (e.g. using EDC and HOBt). In step (v), the protected precursor compound E is deprotected (e.g. using TBAF, where PG is a silane protecting group) to yield the general precursor compound F.

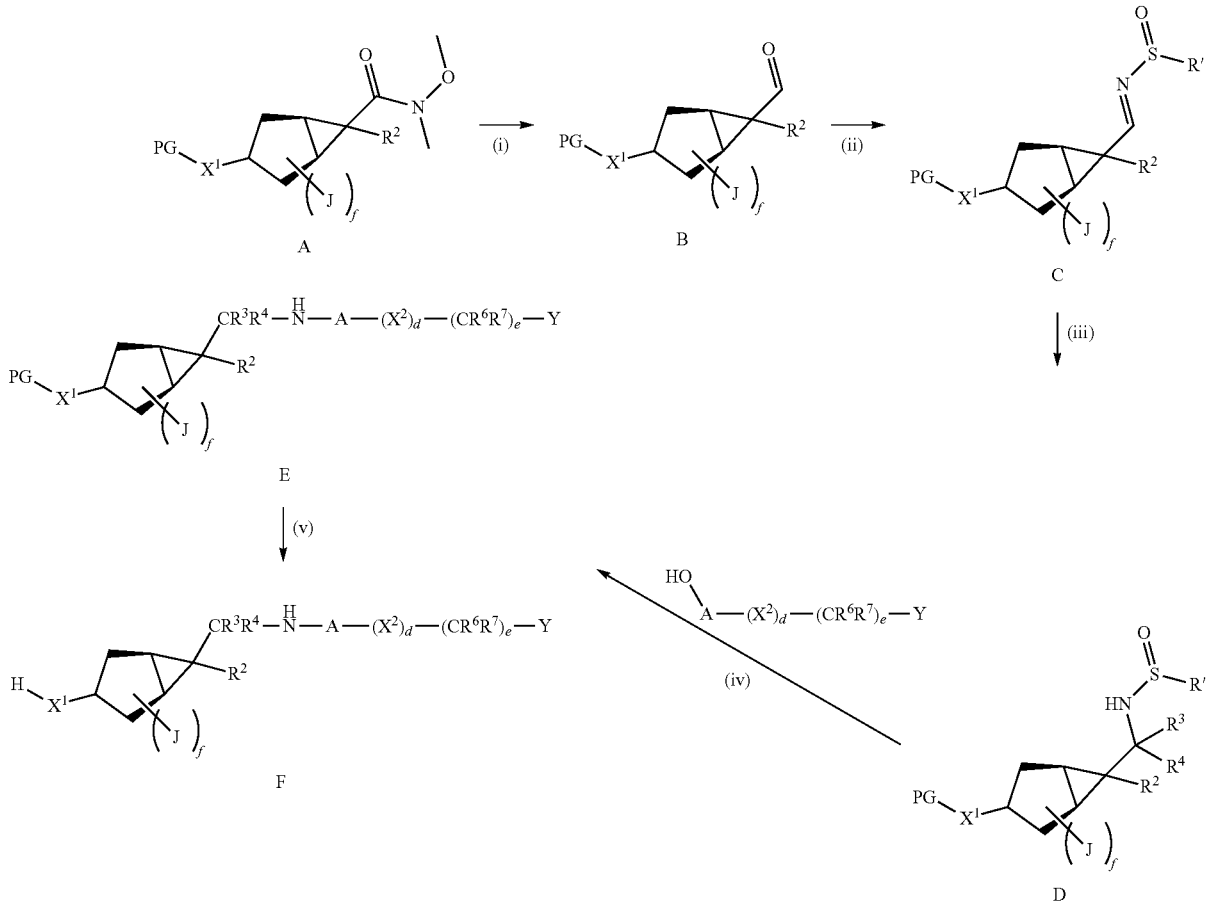

Scheme I

In step (i) of Scheme I, compound A (which may be commercially available, or prepared according to general synthetic methodology known to the person of skill in the art) is reduced (e.g. using DIBAL-H) to yield the corresponding aldehyde, B. The group "PG" is a protecting group for $X^1$, which may be for example a silane (e.g. TBDMS) in the case where $X^1$ is O. In step (ii), the aldehyde is reacted with a sulfinamide (e.g. Ellman sulfinamide) to yield the sulfinylimine C, e.g. in the presence of a lewis acid such as trimethylaluminium. The use of a chiral sulfinamide (e.g. Andersen reagent) may allow diastereomeric resolution of compounds C or D to be separated. In step (iii), C is converted to a corresponding sulfinylamine D, either by reduction of the imine (e.g. to provide a compound in which $R^3$ and $R^4$ are hydrogen) or by treatment with a nucleophilic reagent for the introduction of $R^3$ (and/or $R^4$ with reoxidation, if necessary). For example, where $R^3$ is alkyl, this may be introduced by reacting C with a Grignard reagent, e.g.

If required, compound F can be further reacted to attach a group $R^1$, as indicated in Scheme II below:

Scheme II

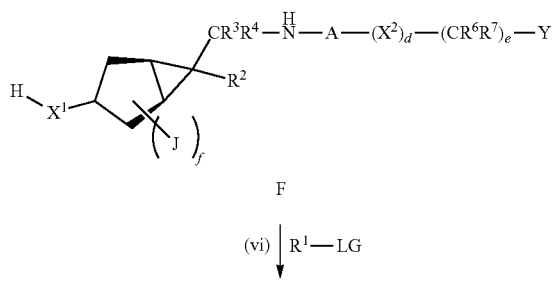

-continued

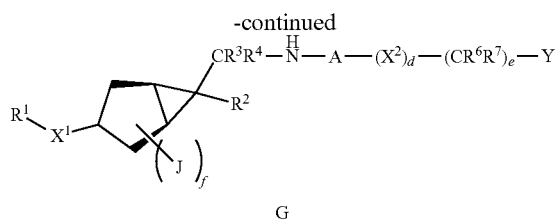

G

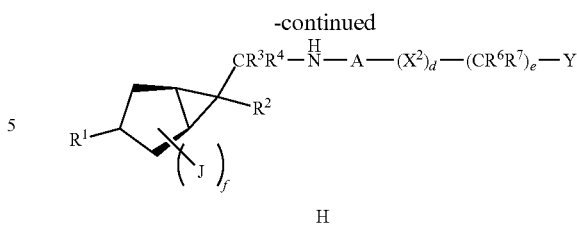

H

In step (vi) the precursor compound F is activated (e.g. using NaH) and reacted with $R^1$-LG in which LG denotes a leaving group (e.g. chlorine). This is particularly useful, for example, where $R^1$ is an aryl or heteroaryl group, in which case step (vi) is a nucleophilic aromatic substitution ($S_NAr$).

Alternatively, in compounds where $X^1$ is absent (i.e. where a is 0), precursor compound F can be further reacted to attach the group $R^1$ directly to the bicyclo[3.1.0]hexane, as indicated in Scheme III below:

Scheme III

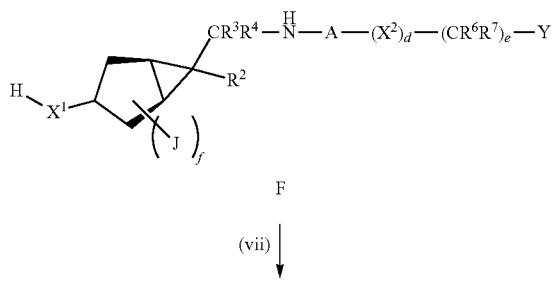

In step (vii) the H—$X^1$ group of F is first converted into a suitable leaving group. For example, where H—$X^1$ is HO— it may be reacted with $MeSO_2Cl$ in triethylamine. The thus-modified compound is then reacted with a nucleophilic functionality on $R^1$. For example, where $R^1$ is 4-quinazolinonyl, 4-quinazolinone may be treated with a base (e.g. LiH in DMF) and then reacted with the modified compound F to yield the corresponding compound H. The $R^1$ used may be substituted with one or more groups $R^{15}$ as defined herein. The $R^{15}$ groups may then be further functionalised (e.g. via palladium coupling or hydrolysis).

Alternatively, compounds in which $X^1$ is absent (i.e. where a is 0) can be synthetised as indicated in Scheme III' below:

Scheme III'

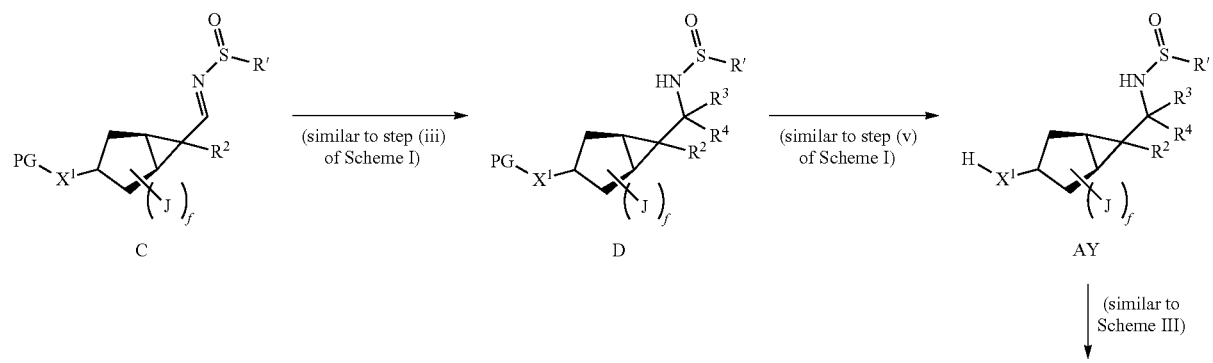

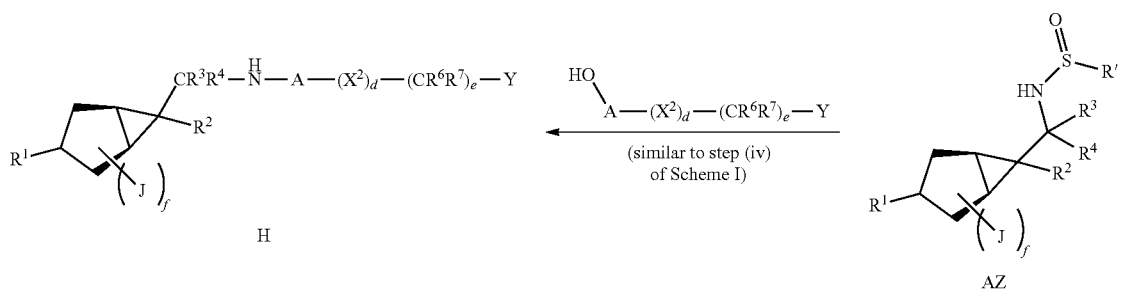

In the first step of Scheme III', compound C is converted to a corresponding sulfinylamine D by similar procedures as described in step (iii) of Scheme I. The H—$X^1$ group of compound D (which may be e.g. an alcohol) is then deprotected to yield compound AY by similar procedures as described in step (v) of Scheme I. Compound AY is then converted into compound AZ by similar procedures as described in Scheme III. Finally, compound AZ is reacted with a Y-containing fragment to yield compound H by similar procedures as described in step (iv) of Scheme I.

In a further alternative, the general precursor compound F can be reacted via a Mitsunobu reaction, as indicated in Scheme IV below:

Scheme IV

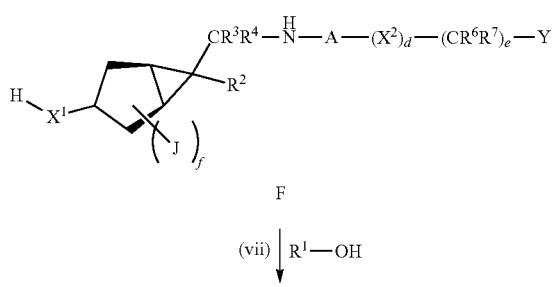

F (vii) | $R^1$—OH

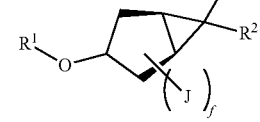

J

In step (viii), compound F is reacted with the alcohol $R^1$—OH, a phosphine (e.g. $Ph_3P$) and an azodicarboxylate (e.g. DEAD, DIAD or ADDP) to yield the product J. This method is useful, for example, for preparing aryl or heteroaryl ether compounds of the present disclosure.

It is noted that the Mitsunobu reaction illustrated in Scheme IV may provide more than one product. Such multiple products may be separated (e.g. using preparative HPLC), which may provide a quick route to preparing multiple compounds of the present disclosure. For example, where the reagent $R^1$—OH is 4-quinazolinone, the product J may contain a group $R^1$ which is coupled to the bicyclo [3.1.0]hexane via an oxygen atom (attached to C4 of the quinazoline) or which is coupled directly to the bicyclo [3.1.0]hexane (e.g. via a nitrogen atom at N1 or at N3 of the quinazoline).

An illustrative synthetic method (Scheme V) is shown below for the preparation of compounds characterised by formula (I) in which the linker between the bicyclo[3.1.0] hexane and group Y contains an amide or a sulfonamide in the opposite orientation to the products of Scheme I (e.g. which contain —C(O)—NH— or —S(O)$_2$—NH—):

Scheme V

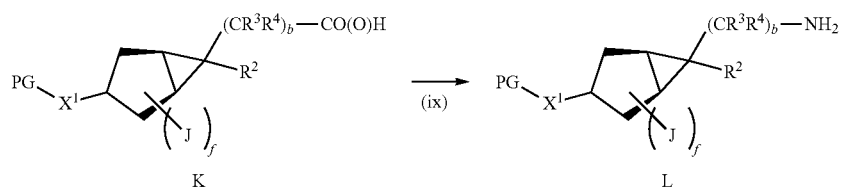

K          L

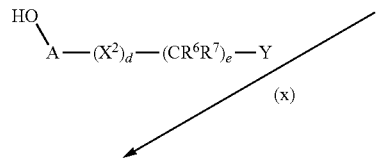

(x)

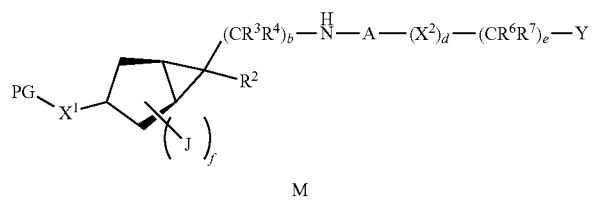

M

| (xi)

-continued

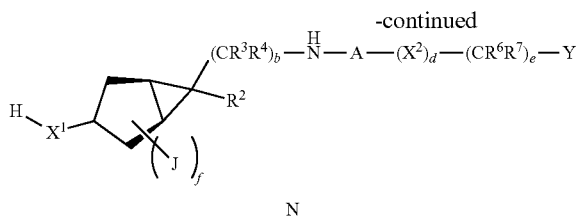

N

In step (ix) of Scheme V, carboxylic acid compound K (which may be commercially available, or prepared according to general synthetic methodology known to the person of skill in the art) is converted into the corresponding amine L, e.g. via a Curtius rearrangement. The group "PG" is a protecting group for $X^1$, which may be for example a silane (e.g. TBDMS) in the case where $X^1$ is O. L is then reacted with the activated Y-containing carboxylic acid or sulfonic acid fragment in a step (x), which is analogous to step (iv) of Scheme 1, to yield protected precursor M. For example, L may be coupled with the Y-containing fragment using conventional means (e.g. using EDC and HOBt). In step (xi), the protected precursor compound M is deprotected (e.g. using TBAF, where PG is a silane protecting group) to yield the general precursor compound N.

An illustrative synthetic method (Scheme VI) is shown below for the preparation of compound O, which may be further used for the preparation of compounds Q and R:

Scheme VI

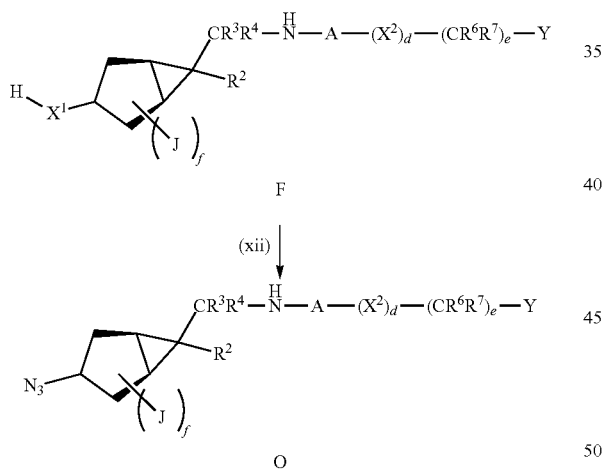

In step (xii) the H—$X^1$ group of compound F (which may be prepared according to the synthetic method of Scheme I) is first converted into a suitable leaving group. For example, where H—$X^1$ is H—O it may be reacted with $MeSO_2Cl$ in the presence of triethylamine. The converted compound is then reacted with sodium azide to yield the corresponding compound O.

An illustrative synthetic method (Scheme VII) is shown below for the preparation of compounds characterized by formula (I) in which $X^1$ is NH, and $R^1$ is selected from $(G)_n$-($C_{1-6}$-alkyl), $(G)_n$-($C_{3-8}$-cycloalkyl), $(G)_n$-heterocycloalkyl, $(G)_n$-($C_{5-8}$-cycloalkenyl), $(G)_n$-heterocycloalkenyl, $(G)_n$-($C_{6-10}$-aryl), and $(G)_n$-heteroaryl, wherein n in each case is 1 and G is selected from C(O), $S(O)_2$, C(O)$NR^{10}$, and $S(O)_2NR^{10}$:

Scheme VII

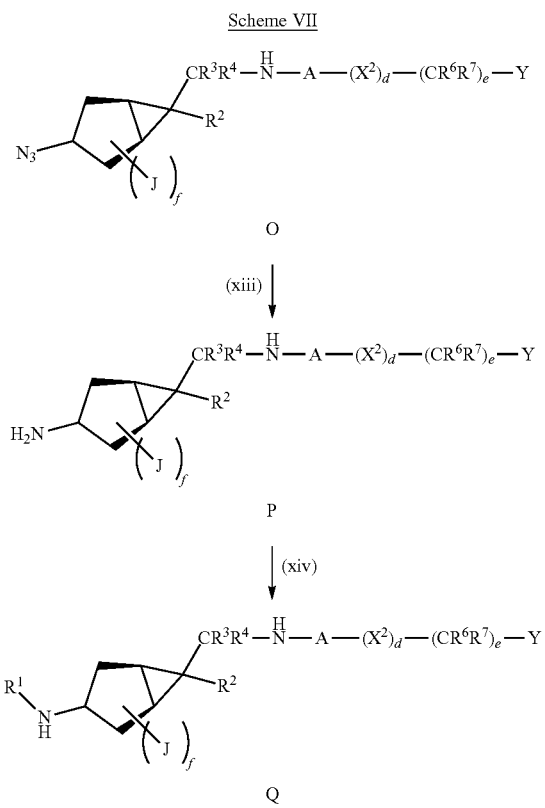

In step (xiii) of Scheme VII, azide compound O (which may be prepared according to the synthetic method of Scheme VI) is reduced into the corresponding amine P, e.g. via a Staudinger reaction using triphenylphosphine. P is then reacted, in step (xiv), with the acidic moiety of HO—$R^1$ (e.g. the carboxylic acid or sulfonic acid) via an amide coupling reaction (e.g. using HOBt and EDC) to yield compound Q. Alternatively, P is reacted with the acid halide moiety of X—$R^1$ (e.g. acyl chloride or sulfonyl chloride) in the presence of a base (e.g. triethylamine) to yield compound Q.

For compounds characterized by formula (I) in which $X^1$ is NH, n is 0, and $R^1$ is selected from $C_{6-10}$-aryl and 5- to 10-membered heteroaryl, compound P may be reacted, in step (xiv) of Scheme VII, with $R^1$-LG in which LG denotes a leaving group (e.g. using palladium coupling, in particular via Buchwald-Hartwig cross coupling), to yield compound Q.

An illustrative synthetic method (Scheme VIII) is shown below for the preparation of compounds characterized by formula (I) in which n is 0, and $R^1$ is a 1,2,3-triazole:

Scheme VIII

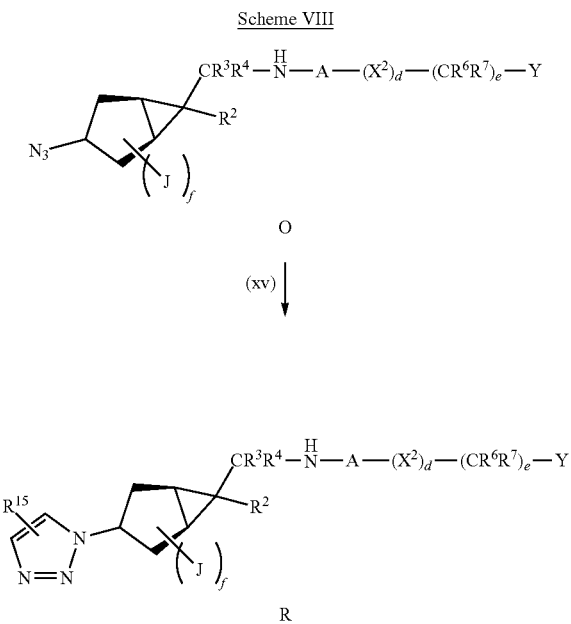

Scheme IX

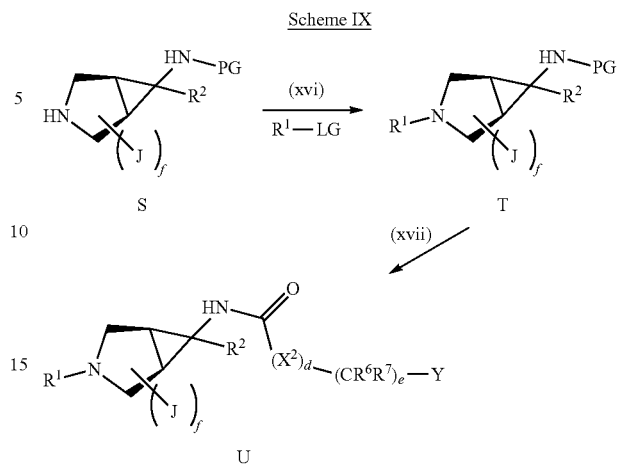

In step (xv) of Scheme VIII, azide compound O (which may be prepared according to the synthetic method of Scheme VI) is reacted with an alkyne (e.g. via an azide-alkyne cycloaddition using a Click catalyst such as copper (II) sulfate with sodium ascorbate) to yield the corresponding 1,2,3-triazole compound R. The alkyne used in the cycloaddition may be substituted with one or two groups $R^{15}$ as defined herein.

An illustrative synthetic method (Scheme IX) is shown below for the preparation of compounds characterised by formula (VI) in which W is N:

In step (xvi) of Scheme IX, cycloamine S (which may be commercially available, or prepared according to general synthetic methodology known to the person of skill in the art) is reacted with $R^1$-LG in which LG denotes a leaving group (e.g. chlorine) in the presence of a base (e.g. DIEA) to give compound T. This is particularly useful, for example, where $R^1$ is an aryl or heteroaryl group, in which case step (xvi) is a nucleophilic aromatic substitution ($S_NAr$). The group "PG" is a protecting group for the primary amine, which may be for example a Boc group. In step (xvii), the primary amine is deprotected (e.g. using hydrochloric acid where PG is Boc) and is then reacted with the acidic moiety of HO—$R^1$ (e.g. the carboxylic acid or sulfonic acid) via an amide coupling reaction (e.g. using DIEA and HATU) to yield compound U. Alternatively, the deprotected amine intermediate is reacted with the acid halide moiety of X—$R^1$ group (e.g. acyl chloride or sulfonyl chloride) in the presence of a base (e.g. triethylamine) to yield compound U.

An illustrative synthetic method (Scheme X) is shown below for the preparation of compounds characterised by formula (X) or formula (XI):

Scheme X

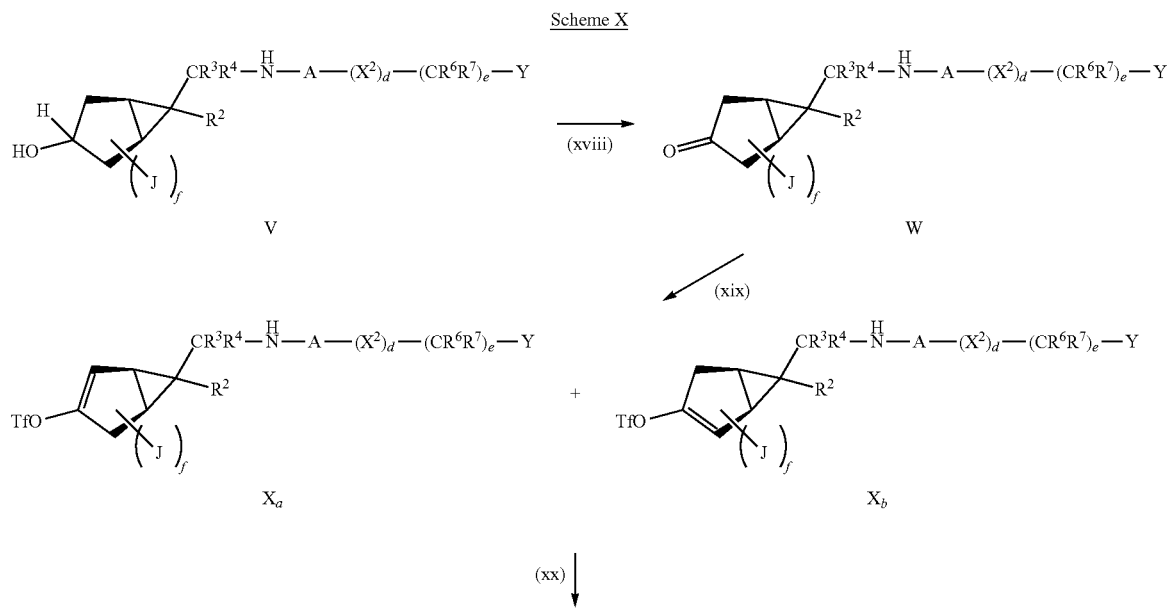

-continued

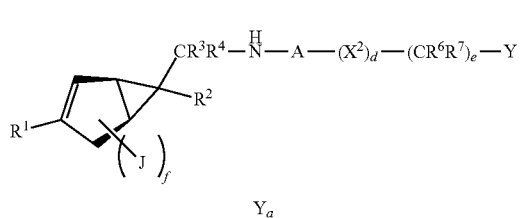

Y$_a$

+

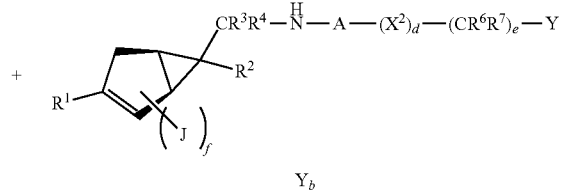

Y$_b$ (xxi) ↓

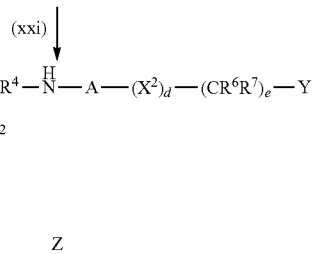

Z

In step (xviii), alcohol compound V (which may be prepared according to the synthetic method of Scheme I) is oxidised (e.g. using DMP) to give the ketone compound W. In step (xix), enolates of compound W are prepared (e.g. using a base such as LiHMDS) and stabilised as one or both of the enol ether compounds X$_a$ and X$_b$ (shown as the triflate, which may be prepared e.g. by reaction of the enolate with 1,1,1-trifluoro-N-phenyl-N-((trifluoromethyl) sulfonyl)methanesulfonamide). In step (xx), compound(s) X is/are transformed into the corresponding boronate ester(s) (e.g. the pinacol boronate esters, using palladium coupling), which is further reacted with R$^1$-LG in which LG denotes a leaving group (e.g. using palladium coupling), to yield one or more of compounds Y$_a$ and Y$_b$. Where a mixture of compounds Y$_a$ and Y$_b$ is obtained, this may be resolved using techniques known in the art. Compounds Y$_a$ and Y$_b$ (resolved or as mixtures) can be further derivatized into the corresponding alkane by a reductive method (step xxi, e.g. via catalytic hydrogenation, triethyl silane mediated reduction, or other condition known to those skilled in the art) to yield compounds Z.

One such alternative synthetic method is illustrated in Scheme XI below for preparation of compounds Z:

Scheme XI

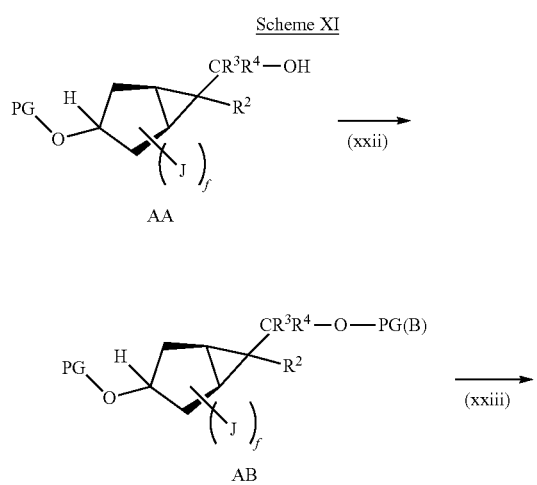

-continued

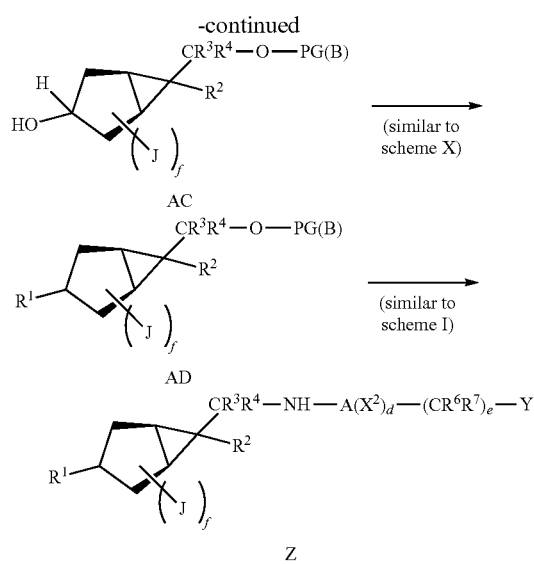

In step (xxii) of Scheme XI, the alcohol compound AA (which may be commercially available, or prepared according to general synthetic methodology known to the person of skill in the art) is protected (e.g. using DHP) to yield the bis-ether AB, with orthogonally protected alcohols, denoted as OPG and OPG(B). The group "PG" may be for example a silane (e.g. TBDMSi) in the case where X$^1$ is O and can be selectively cleaved as described in Scheme I. In step (xxiii), the protected precursor compound AB is deprotected (e.g. using TBAF, where PG is a silane protecting group) to yield the general precursor compound AC. Compound AC can be transformed by similar procedures as described in Scheme X to yield compounds of the type AD wherein the same descriptors of R$^{1-4}$ etc. are applied as described previously. Compound AD can be transformed into compounds of structure Z as shown in Scheme X using similar methods to those described in Scheme I.

A further alternative synthetic method is illustrated in Scheme XII below for preparation of compounds Z:

Scheme XII

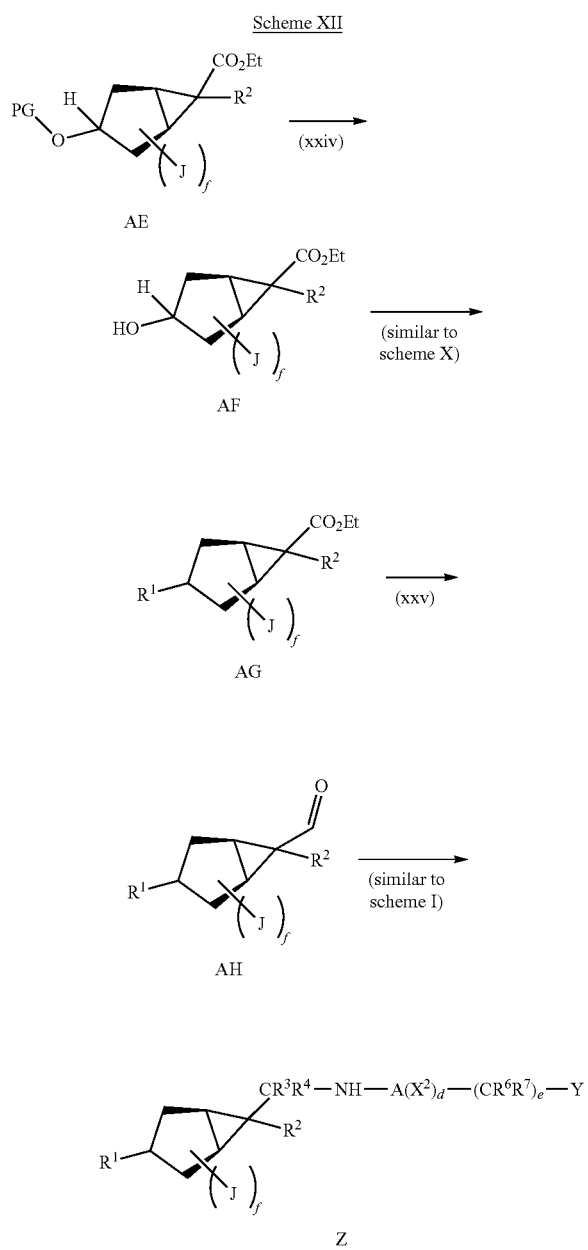

Scheme XIII

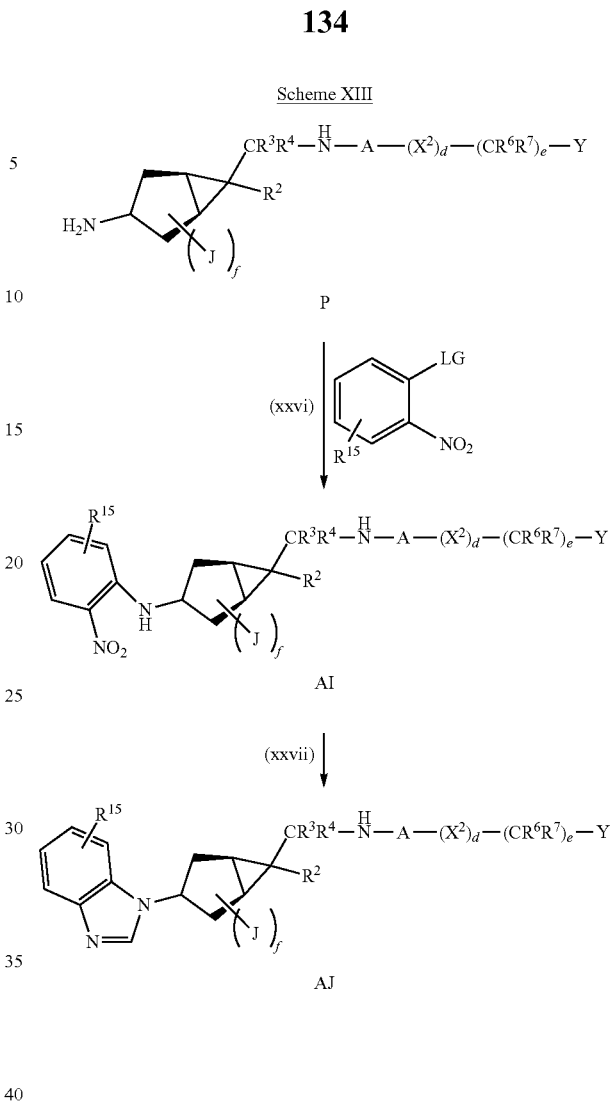

In step (xxiv) of Scheme XII, the protected alcohol compound AE (which may be commercially available, or prepared according to general synthetic methodology known to the person of skill in the art) is deprotected (e.g. using TBAF, where PG is a silane protecting group) to yield the general precursor compound AF. Compound AF can then be transformed by similar procedures as described in Scheme X to yield compounds of the type AG. In step (xxv), compound AG is reduced to the corresponding alcohol (e.g. using DIBAL-H), and oxidised to the corresponding aldehyde AH (e.g. using DMP). Compound AH can be further transformed into compounds of structure Z using similar methods to those described in steps (ii) to (iv) of Scheme I.

An illustrative synthetic method (Scheme XIII) is shown below for the preparation of compounds characterized by formula (I) in which $R^1$ is a benzimidazol-1-yl:

In step (xxvi) of Scheme XIII, amine compound P (which may be prepared according to the synthetic method of Scheme VII) is reacted with a nitrobenzene compound which carries a leaving group "LG" (e.g. a halogen) at the alpha position (and which is optionally further substituted by one or more $R^{15}$ groups e.g. halogens), under basic conditions (e.g. $K_2CO_3$) to yield compound AI. In step (xxvii), compound AI is cyclized to form the corresponding benzimidazole AJ (e.g. using formic acid, ammonium chloride and iron). Alternative acids may be used in step (xxvii) to form corresponding 2-substituted benzimidazole compounds (e.g. using acetic acid or trifluoroactetic acid). An illustrative synthetic method (Scheme XIV) is shown below for the preparation of compounds characterized by formula (I) in which a is 0, b is 1, c is 0, d is 1 and $X^2$ is $NR^{13}$:

Scheme XIV

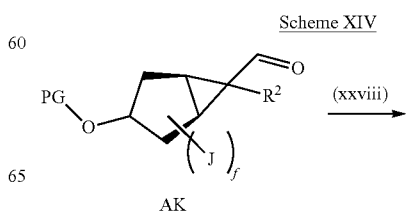

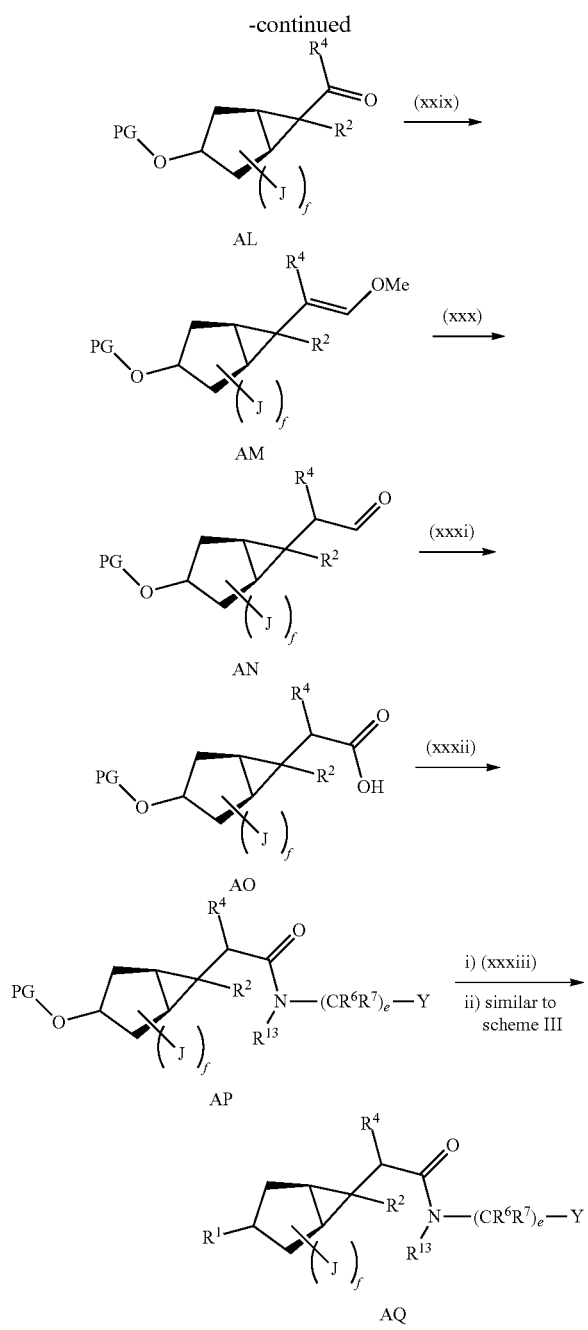

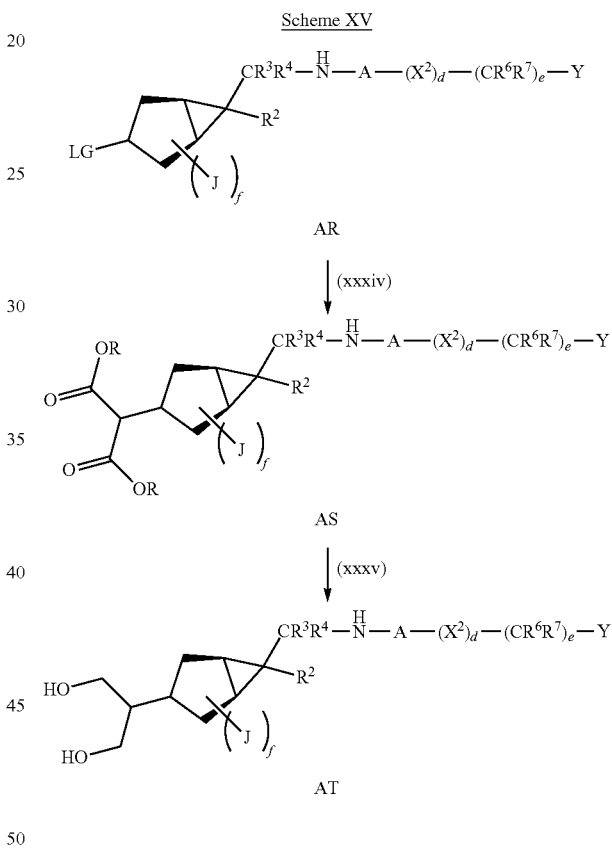

compound AP. In step (xxxiii), the alcohol moiety of AP is deprotected (e.g. using TBAF, where PG is a silane protecting group) to yield the corresponding alcohol, which is then transformed into compound AQ using similar methods to those described in Scheme I.

Scheme XIV can readily be modified to produce e.g. compounds characterized by formula (I) in which $X^1$ is O, n is 0, and $R^1$ is selected from $C_{6-10}$-aryl and 5- to 10-membered heteroaryl. For example, the alcohol protecting group of compound AP may be removed and the alcohol activated (e.g. using NaH) and then reacted with $R^1$-LG, as described under Scheme II above.

An illustrative synthetic method (Scheme XV) is shown below for the preparation of compounds characterized by formula (I) in which $R^1$ is H, a is 1, and $X^1$ is $C(R^8)(R^9)$:

In step (xxviii) of Scheme XIV, aldehyde compound AK (which may be prepared according to the synthetic method of Scheme I) is converted to a corresponding ketone AL, e.g. by treatment with a nucleophilic reagent for the introduction of $R^4$ (or $R^3$) followed by oxidation of the resulting alcohol. For example, where $R^4$ is alkyl, this may be introduced by reacting AK with a Grignard reagent, e.g. MeMgBr, and then oxidizing the secondary alcohol which results, e.g. using DMP. In step (xxix), compound AL is converted into compound AM by a Wittig reaction (e.g. using (methoxymethyl)triphenylphosphonium chloride and LHDMS). In step (xxx), AM is deprotected to yield AN (e.g. using PPTS). In step (xxxi), AN is oxidized to yield the corresponding carboxylic acid AO (e.g. via a Pinnick oxidation reaction). In step (xxxii) AO is reacted with an amine (e.g. $NH_2R^{13}$) via an amide coupling reaction (e.g. using DIEA and HATU) to yield In step (xxxiv) of Scheme XV, compound AR (which may be prepared according to the synthetic method of Scheme III) is reacted with a 1,3-diester (e.g. diethyl malonate) in basic conditions (e.g. NaH) to yield the corresponding AS compound wherein R is an alkyl moiety. The group "LG" is a leaving group, which may be for example mesylate. In step (xxxv), compound AS is reduced to yield its corresponding alcohol AT (e.g. using LAH).

An illustrative synthetic method (Scheme XVI) is shown below for the preparation of compounds characterized by formula (I) in which a is 0 and $R^1$ is pyrazol-4-yl optionally substituted by $R^{15}$ at the 1-position:

Scheme XVI

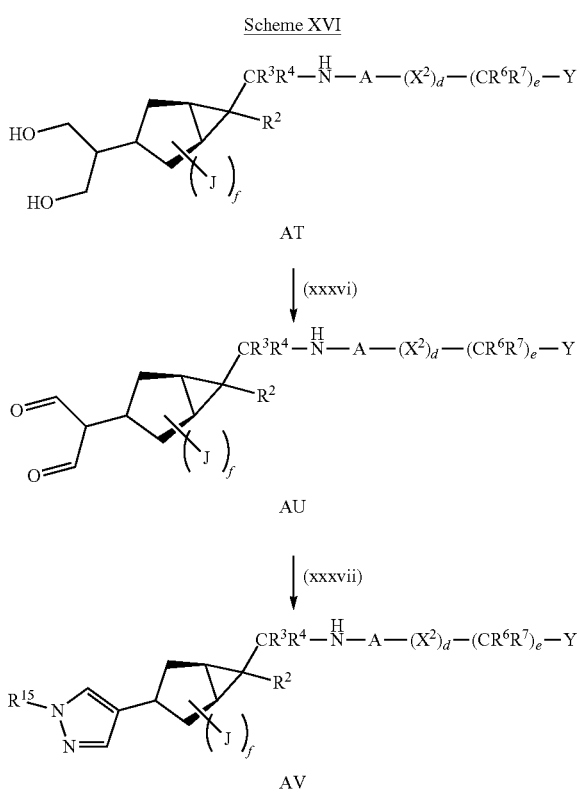

In step (xxxvi) of Scheme XVI, compound AT is oxidised to its corresponding aldehyde AU (e.g. using TEMPO and iodobenzene diacetate). In step (xxxvii), compound AU is then reacted with a hydrazine (e.g. cyclopropylhydrazine hydrochloride) to yield the corresponding pyrazol-4-yl compound AV.

An illustrative synthetic method (Scheme XVII) is shown below for the preparation of compounds characterized by formula (I) in which c is 1, A is C(O), d is 1, and $X^2$ is NH:

Scheme XVII

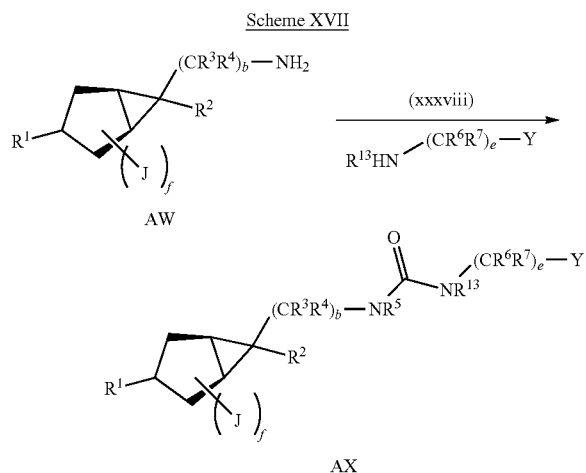

In step (xxxviii) of Scheme XVII, the amine moiety of compound AW is reacted with carbonyldiimidazole to form the corresponding intermediate carbonylimidazolide. The latter is then further reacted with an amine compound of formula $NH(R^{13})$—$(CR^6R^7)_e$—Y to yield compound AX.

Alternative methods for the synthesis of compounds of the present disclosure would be apparent to the skilled person on the basis of their common general knowledge and the teaching of the present application.

Medical Indications

The compounds described herein, and pharmaceutical compositions thereof, are useful in therapy, in particular in the therapeutic treatment of IDO1, IDO2 and/or TDO mediated conditions in a subject, and especially in the therapeutic treatment of IDO1 mediated conditions in a subject. Subjects to be treated according to the methods described herein include vertebrates, such as mammals. In preferred embodiments the mammal is a human patient.

The present invention provides a method for treating an IDO1, IDO2 and/or TDO mediated condition (e.g. an IDO1 mediated condition) in a subject, the method comprising administering to the subject an effective amount of a compound as defined herein, e.g. a compound characterised by formula (I). Also provided is a compound as defined herein, e.g. a compound characterised by formula (I), for use in a method of treating an IDO1, IDO2 and/or TDO mediated condition (e.g. an IDO1 mediated condition) in a subject. Further provided is the use of a compound as defined herein, e.g. a compound characterised by formula (I), in the manufacture of a medicament for use in a method of treating an IDO1, IDO2 and/or TDO mediated condition (e.g. an IDO1 mediated condition) in a subject.

The KYN pathway has been implicated in a number of conditions, including: cancers; neurological and neuropsychological diseases and disorders; autoimmune diseases and disorders; infections; and cataracts.

In embodiments, the IDO1, IDO2 and/or TDO mediated condition (e.g. the IDO1 mediated condition) is selected from a cancer; a neurological or neuropsychological disease or disorder; an autoimmune disease or disorder; an infection; a cataract; and a vascular disease.

In embodiments, the IDO1, IDO2 and/or TDO mediated condition (e.g. the IDO1 mediated condition) is characterised by the overexpression of IDO1, IDO2 and/or TDO, respectively (e.g. by the overexpression of IDO1).

In embodiments, the treatment of the IDO1, IDO2 and/or TDO mediated condition (e.g. the IDO1 mediated condition) comprises administering a compound of the invention in combination with another therapeutic intervention for said condition. The other therapeutic intervention may be performed before, during and/or after administering the compound of the invention.

Cancers

Overexpression of IDO1, IDO2 and/or TDO occurs in a significant number of cancer types, including breast cancer, prostate cancer, colon cancer, colorectal carcinoma, head and neck carcinoma, glioblastoma, astrocytoma, lung carcinoma, bladder carcinoma, hepatocarcinoma, lymphocytic leukaemia, melanoma, mesothelioma, neuroblastoma, and brain tumour. For example, the deregulation of IDO1 in tumour cells has been shown to be linked to the cancer suppressive gene bridging integrator 1 (Bin1), which is a down-regulator of IDO1. Clinical observations suggest that high expression levels of IDO1 and loss or attenuation of Bin1 are frequent in a number of cancers including advanced breast cancer, prostate cancer, melanoma, astrocytoma, neuroblastoma, lymphocytic leukaemia and colon cancer.

Furthermore, metabolites of KYN such as QUIN affect the biosynthesis of $NAD^+$, which may be involved in cancer cell proliferation. For example, in glioblastoma multiforme, genotoxic anticancer drugs such as temozolomide (TMZ), hydroxyurea, procarbazine, cisplatin, and nitrosamines, such as carmustine, lomustine, and nimustine, in combination with radiation are used to kill tumour cells which remain following surgery. However, the effectiveness of these drugs can be weakened by the tolerance of the tumour cells to DNA repair/damage. It is thought that modulation of the KYN pathway can enhance genotoxic treatment by diminishing the ability of the cancer cells to repair damaged DNA and/or to bypass the cytotoxic effects of DNA damage. Thus, treatment with a compound as defined herein in combination with immunotherapy, radiation therapy and/or chemotherapy is expected to enhance the efficacy of said therapy.

Accordingly, in one embodiment the IDO1, IDO2 and/or TDO mediated condition (e.g. the IDO1 mediated condition) is a cancer. In embodiments, the cancer is associated with low levels of L-TRP. In embodiments, the tumour microenvironment is depleted in L-TRP (e.g. below normal levels). In embodiments, the cancer is associated with high levels of L-TRP metabolites, e.g. KYN and/or QUIN. In embodiments, the concentration of said L-TRP metabolites in cells of the tumour are above normal levels for cells of that tissue type. In embodiments, the cancer is associated with overexpression of IDO1, IDO2 and/or TDO, e.g. overexpression of IDO1.

In embodiments the cancer is selected from head and neck cancer, breast cancer (e.g. metastatic breast cancer), prostate cancer (e.g. metastatic prostate cancer), ovarian cancer, endometrial cancer, colon cancer, lung cancer (e.g. non small cell lung cancer), bladder cancer, pancreatic cancer (e.g. metastatic pancreatic cancer), brain tumour (e.g. primary malignant brain tumour), gynecological cancer, peritoneal cancer, skin cancer, thyroid cancer, oesophageal cancer, cervical cancer, gastric cancer, liver cancer, stomach cancer, renal cell cancer, biliary tract cancer, hematologic cancer, and blood cancer. In embodiments, the cancer is selected from colorectal carcinoma, large intestinal colon carcinoma, head and neck carcinoma, lung carcinoma, lung adenocarcinoma, bladder carcinoma, Barret's adenocarcinoma, renal carcinoma, and hepatocarcinoma. In embodiments, the cancer is selected from glioblastoma, astrocytoma, melanoma (e.g. metastatic melanoma), mesothelioma, neuroblastoma, histiocytic lymphoma, and lymphocytic leukaemia. In embodiments, the cancer is a solid tumour (e.g. a malignant solid tumour) which may be an advanced-stage solid tumour.

In embodiments, the treatment of said IDO1, IDO2 and/or TDO mediated condition (e.g. said IDO1 mediated condition) as disclosed herein comprises administering a compound of the invention in combination with another therapeutic intervention for said condition. The other therapeutic intervention may be performed before, during and/or after administering the compound of the invention. Thus, in embodiments the subject is receiving (or has received, or will receive) said another therapeutic intervention for said IDO1, IDO2 and/or TDO mediated condition.

In embodiments, said another therapeutic intervention is immunotherapy, radiation therapy and/or chemotherapy. In embodiments, said another therapeutic intervention is immunotherapy. In embodiments, said another therapeutic intervention is radiation therapy. In embodiments, said another therapeutic intervention is chemotherapy. In embodiments, said another therapeutic intervention comprises radiation therapy and further comprises treatment with immunotherapy and/or with chemotherapy.

In embodiments, said radiotherapy comprises treatment with gamma radiation.

In embodiments, said immunotherapy comprises treatment with an immunotherapeutic agent selected from therapeutic antibodies. In embodiments, the therapeutic antibody is a humanised monoclonal antibody. In embodiments, said immunotherapy comprises treatment with an immunotherapeutic agent selected from vaccines. In embodiments, the vaccine is a gene therapy vaccine.

In embodiments, said chemotherapy comprises treatment with a chemotherapeutic agent selected from alkylating agents, alkyl sulfonates, aziridines, ethylenimines and methylamelamines, nitrogen mustards, nitrosureas, bisphosphonates, purine analogs, pyrimidine analogs, taxoids, platinum analogs, anti-hormonal agents, aromatase inhibitors, antiandrogens, protein kinase inhibitors, lipid kinase inhibitors, antisense oligonucleotides, ribozymes, anti-retroviral protease inhibitors, anti-angiogenic agents, and topoisomerase 1 inhibitors.

In embodiments, said cancer is partially or totally resistant to treatment with at least one chemotherapeutic and/or immunotherapeutic agent (e.g. as defined herein).

In embodiments, administration of the compounds as disclosed herein can treat subjects diagnosed as having said cancer or being at risk of developing said cancer. In embodiments, administration of compounds as disclosed herein improves prognosis, reduces angiogenesis, reduces the catabolism of L-TRP, decreases growth of malignant cells, and/or prevents or reduces tumour progression.

Neurological and Neuropsychological Diseases and Disorders

IDO1 is present in numerous cell types within the body, in particular in microglia, the macrophage-like cells located in the central nervous system. Expression of IDO1 is induced by proinflammatory cytokines and molecules, in particular by interferon gamma (IFN-γ) and, to a lesser extent, by IFN-α, IFN-β, interleukines, and tumor necrosis factors (TNF). TDO is present in small amount in the brain, where its expression is induced by corticosteroids and glucagon.

Increased levels of KYN, and its metabolites, have been observed in a number of neurological and neuropsychological diseases and disorders including Alzheimer's disease, amyotrophic lateral sclerosis, Huntington's disease, multiple sclerosis, and Parkinson's disease (Bostian, 2016; Lovelace, 2017). Decreasing the production of neurotoxic metabolites of KYN, which include QUIN and 3-hydroxykynurenine, may reduce neuronal loss and atrophy in various neurological disorders and diseases. Furthermore, the interaction between immune activation and the metabolism of L-TRP (which is a precursor of serotonin) via the KYN pathway is implicated in neuropsychological diseases and disorders such as schizophrenia, anorexia, and depression, including depressive and anxiety symptoms in the early puerperium (Lovelace, 2017).

Accordingly, in one embodiment, the IDO1, IDO2 and/or TDO mediated condition (e.g. the IDO1 mediated condition) is a neurological or neuropsychological disease or disorder. In embodiments, said condition is a neurological disease or disorder. In other embodiments, said condition is a neuropsychological disease or disorder.

In embodiments, the neurological or neuropsychological disease or disorder is associated with low levels of L-TRP. In embodiments, the cerebrospinal fluid and/or the serum of the subject is depleted in L-TRP (e.g. below normal levels). In embodiments, the neurological or neuropsychological disease or disorder is associated with high levels of L-TRP metabolites, e.g. KYN, QUIN and/or 3-hydroxykynurenine. In embodiments, the concentration of said L-TRP metabolites in microglia of the subject are above normal levels. In embodiments, the neurological or neuropsychological disease or disorder is associated with overexpression of IDO1, IDO2 and/or TDO, e.g. overexpression of IDO1.

In embodiments, the neurological disease or disorder is selected from Alzheimer's disease, amyotrophic lateral sclerosis, Huntington's disease, multiple sclerosis, Parkinson's disease, and HAND. In embodiments, the neuropsychological disease or disorder is selected from schizophrenia, anorexia, depression, and anxiety (e.g. depressive and anxiety symptoms in the early puerperium).

Autoimmune Diseases and Disorders

Catabolism of L-TRP may prevent normal proliferation in various cell types, and may increase the susceptibility of cells to apoptosis. In particular, antigen-specific T-cells have been shown to be susceptible to L-TRP deprivation. In addition, L-TRP catabolism leads to the formation of metabolites which have been shown to increase apoptosis of helper T-cells and natural killer T-cells. Further, KYN induces the formation of regulatory T-cells which may suppress immune cells. Furthermore, L-TRP levels in rheumatoid arthritis patients have been shown to be lower than in healthy patients, this may be due to overexpression of IDO1. Accordingly, in one embodiment, the IDO1, IDO2 and/or TDO mediated condition (e.g. the IDO1 mediated condition) is an autoimmune disease or disorder.

In embodiments, the autoimmune disease or disorder is associated with low levels of L-TRP. In embodiments, the serum of the subject is depleted in L-TRP (e.g. below normal levels). In embodiments, the autoimmune disease or disorder is associated with high levels of L-TRP metabolites, e.g. KYN, QUIN and/or 3-hydroxykynurenine. In embodiments, the autoimmune disease or disorder is associated with overexpression of IDO1, IDO2 and/or TDO, e.g. overexpression of IDO1.

In embodiments, the autoimmune disease or disorder is selected from arthritis, rheumatoid arthritis, and multiple sclerosis.

Infections

Antigen-specific T-cells have been shown to be susceptible to L-TRP deprivation. In addition, L-TRP catabolism leads to the formation of metabolites which have been shown to increase apoptosis of helper T-cells and natural killer T-cells. Further, KYN induces the formation of regulatory T-cells which may suppress immune cells. Thus, IDO1, IDO2 and/or TDO may influence the progression of infectious diseases in which the immune system is compromised.

In particular, HIV infections may be caused by CD4$^+$ T-cell depletion, combined with chronic immune activation and inflammation responses. Elevated levels of KYN metabolites and IFN-γ are commonly found in HIV patients, and catabolism of L-TRP may be a factor in HIV disease progression, through immune suppression and/or the generation of neurotoxic KYN metabolites. Elevated levels of KYN neurotoxic metabolites such as QUIN in HIV infected patients have also been linked to the progression of HAND. Those KYN metabolites may be produced in the central nervous system, possibly by microglia, in response to peripheral immune and inflammatory signals.

IDO1 activity is elevated in sepsis and has been associated with disease severity. Further, IDO1 activity has been shown to correlate with hypotension in cases of human septic shock. In this regard, KYN is thought to be a vasodilator which may contribute to the hypotension observed in septic shock.

Accordingly, in embodiments the infection is selected from influenza virus infection, peritonitis, sepsis, Chlamydia trachomatis infection, and HIV.

In embodiments, the infection is associated with low levels of L-TRP. In embodiments, the plasma of the subject is depleted in L-TRP (e.g. below normal levels). In embodiments, the infection is associated with high levels of L-TRP metabolites, e.g. KYN, QUIN and/or 3-hydroxykynurenine. In embodiments, the plasma of the subject has a ratio of KYN to L-TRP above normal levels. In embodiments, the infection is associated with overexpression of IDO1, IDO2 and/or TDO, e.g. overexpression of IDO1.

In embodiments, the treatment of said infection comprises administering a compound of the invention in combination with another therapeutic intervention for said infection. Said another therapeutic intervention may be performed before, during and/or after administering the compound of the invention. Thus, in embodiments the subject is receiving (or has received, or will receive) said another therapeutic intervention for said infection.

In embodiments, the infection is a viral infection and said another therapeutic intervention is treatment with an antiviral agent. In embodiments, the infection is HIV infection and said another therapeutic intervention is treatment with an antiretroviral agent. In embodiments, the infection is a bacterial infection and said another therapeutic intervention is treatment with an antibacterial agent.

Other Conditions

The KYN pathway has also been implicated in other conditions. For example, elevated lenticular levels of IDO1 and KYN metabolites have been observed in association with cataracts. IDO1 activity has also been shown to correlate with carotid artery intima/media thickness, which is an early marker of atherosclerosis (a leading cause of cardiovascular diseases). Elevated levels of KYN have also been associated with the risk of acute myocardial infarction.

Accordingly, in one embodiment, the IDO1, IDO2 and/or TDO mediated condition (e.g. the IDO1 mediated condition) is a cataract. In embodiments, the cataract is age related, or is associated with diabetes in the subject.

In another embodiment, the IDO1, IDO2 and/or TDO mediated condition (e.g. the IDO1 mediated condition) is a vascular disease. In embodiments, the vascular disease is a cardiovascular disease. In embodiments, the IDO1, IDO2 and/or TDO mediated condition (e.g. the IDO1 mediated condition) is atherosclerosis. In embodiments, the IDO1, IDO2 and/or TDO mediated condition (e.g. the IDO1 mediated condition) is myocardial infarction, in particular acute myocardial infarction.

Administration and Dosages

A presently disclosed compound can be formulated as a pharmaceutical composition for oral, buccal, parenteral (e.g. intravenous, intraperitoneal, intramuscular or subcutaneous), topical, rectal or intranasal administration or in a form suitable for administration by inhalation or insufflation. In one embodiment, the compound or pharmaceutical composition is formulated for systemic administration, e.g. via a non-parenteral route. In another embodiment, the compound or pharmaceutical composition is formulated for oral administration, e.g. in solid form. Such modes of administration and the methods for preparing appropriate pharmaceutical compositions are described, for example, in Gibaldi's Drug Delivery Systems in Pharmaceutical Care (1st ed., American Society of 15 Health-System Pharmacists 2007).

In solid dosage forms for oral administration (e.g. capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, microcrystalline cellulose, calcium phosphate and/or silicic acid; (2) binders, such as, for example, carboxymethylcellulose, alginates, gelatine, pregelatinized maize starch, polyvinyl pyrrolidone, hydroxypropyl methylcellulose, sucrose and/or acacia; (3) humectants, such as glycerol; (4) disintegrating agents, such as agar-agar, calcium carbonate, sodium starch glycolate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, sodium lauryl sulphate, acetyl alcohol and glycerol monostearate; (8) absorbents, such as kaolin and bentonite clay; (9) lubricants, such as talc, silica, calcium stearate, magnesium stearate, solid polyethylene glycols, sodium lauryl sulfate, and mixtures thereof; and (10) colouring agents. In the case of capsules, tablets, and pills, the pharmaceutical compositions can also comprise buffering agents. Solid compositions of a similar type can also be prepared using fillers in soft and hard-filled gelatine capsules, and excipients such as lactose or milk sugars, as well as high molecular weight polyethylene glycols and the like.

A tablet can be made by compression or moulding, optionally with one or more accessory ingredients. Compressed tablets can be prepared using binders (for example, gelatine or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent. The tablets and other solid dosage forms, such as dragees, capsules, pills, and granules, can optionally be scored or prepared with coatings and shells, such as enteric coatings and other coatings well known in the art.

In embodiments, the pharmaceutical compositions are administered orally in a liquid form. Liquid dosage forms for oral administration of an active ingredient include pharmaceutically acceptable emulsions, microemulsions, solutions, suspensions, syrups and elixirs. Liquid preparations for oral administration may be presented as a dry product for constitution with water or other suitable vehicle before use. In addition to the active ingredient, the liquid dosage forms can contain inert diluents commonly used in the art, such as, for example, water or other solvents, solubilising agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g. cottonseed, groundnut, corn, germ, olive, castor and sesame oils), glycerol, tetrahydrofuryl alcohol, polyethylene glycols and fatty acid esters of sorbitan, and mixtures thereof. In addition to inert diluents, the liquid pharmaceutical compositions can include adjuvants such as wetting agents, emulsifying and suspending agents, sweetening, flavouring, colouring, perfuming and preservative agents, and the like. Suspensions, in addition to the active ingredient(s) can contain suspending agents such as, but not limited to, ethoxylated isostearyl alcohols, polyoxyethylene sorbitol and sorbitan esters, microcrystalline cellulose, aluminium metahydroxide, bentonite, agar-agar and tragacanth, and mixtures thereof. Suitable liquid preparations may be prepared by conventional means with a pharmaceutically acceptable additive(s) such as a suspending agent (e.g. sorbitol syrup, methyl cellulose or hydrogenated edible fats); emulsifying agent (e.g. lecithin or acacia); nonaqueous vehicle (e.g. almond oil, oily esters or ethyl alcohol); and/or preservative (e.g. methyl or propyl p-hydroxybenzoates or sorbic acid). The active ingredient(s) can also be administered as a bolus, electuary, or paste.

For buccal administration, the composition may take the form of tablets or lozenges formulated in a conventional manner.

In embodiments, the pharmaceutical compositions are administered by non-oral means such as by topical application, transdermal application, injection, and the like. In related embodiments, the pharmaceutical compositions are administered parenterally by injection, infusion, or implantation (e.g. intravenous, intramuscular, intra-arterial, subcutaneous, and the like).

Presently disclosed compounds may be formulated for parenteral administration by injection, including using conventional catheterisation techniques or infusion. Formulations for injection may be presented in unit dosage form, e.g. in ampules or in multi-dose containers, with an added preservative. The compositions may take such forms as suspensions, solutions or emulsions in oily or aqueous vehicles, and may contain a formulating agent such as a suspending, stabilising and/or dispersing agent recognised by those of skill in the art. Alternatively, the active ingredient may be in powder form for reconstitution with a suitable vehicle, e.g. sterile pyrogen-free water, before use.

The pharmaceutical compositions can be in the form of sterile injections. The pharmaceutical compositions can be sterilised by, for example, filtration through a bacteria-retaining filter, or by incorporating sterilising agents in the form of sterile solid compositions which can be dissolved in sterile water, or some other sterile injectable medium immediately before use. To prepare such a composition, the active ingredient is dissolved or suspended in a parenterally acceptable liquid vehicle. Exemplary vehicles and solvents include, but are not limited to, water, water adjusted to a suitable pH by addition of an appropriate amount of hydrochloric acid, sodium hydroxide or a suitable buffer, 1,3-butanediol, Ringer's solution and isotonic sodium chloride solution. The pharmaceutical composition can also contain one or more preservatives, for example, methyl, ethyl or n-propyl p-hydroxybenzoate. To improve solubility, a dissolution enhancing or solubilising agent can be added or the solvent can contain 10-60% w/w of propylene glycol or the like.

The pharmaceutical compositions can contain one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

Examples of suitable aqueous and nonaqueous carriers, which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminium monostearate and gelatine.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices. Materials for use in the preparation of microspheres and/or microcapsules include, but are not limited to, biodegradable/bioerodible polymers such as polyglactin, poly-(isobutyl cyanoacrylate), poly(2-hydroxyethyl-L-glutamine) and poly(lactic acid). Biocompatible carriers which can be used when formulating a controlled release parenteral formulation include carbohydrates such as dextrans, proteins such as albumin, lipoproteins or antibodies. Materials for use in implants can be non-biodegradable, e.g. polydimethylsiloxane, or biodegradable such as, e.g., poly(caprolactone), poly(lactic acid), poly(glycolic acid) or poly(ortho esters).

For topical administration, a presently disclosed compound may be formulated as an ointment or cream. Presently disclosed compounds may also be formulated in rectal compositions such as suppositories or retention enemas, e.g. containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurised container or a nebulizer, with the use of a suitable propellant, e.g. dichlorodifluoromethane, trichlorofluoromethane, dichlorotetrafluoroethane, carbon dioxide or other suitable gas. In the case of a pressurised aerosol, the dosage unit may be determined by providing a valve to deliver a metered amount. The pressurised container or nebulizer may contain a solution or suspension of the presently disclosed compound. Capsules and cartridges (made, for example, from gelatine) for use in an inhaler or insufflator may be formulated containing a powder mix of a presently disclosed compound and a suitable powder base such as lactose or starch.

Generally, the agents and compositions described herein are administered in an effective amount or quantity sufficient to inhibit IDO1, IDO2 and/or TDO in the subject receiving the agent or composition. Typically, the dose can be adjusted based on, e.g., age, physical condition, body weight, sex, diet, time of administration, and other clinical factors. The effective amount may also vary depending on the mode of administration, e.g. intravenous versus oral, as well as on the nature of the composition, e.g. rapidly disintegrating versus slow release compositions. Determination of an effective amount is within the capability of those skilled in the art. Generally, an effective amount for administration to a subject is in the range of about 0.1 to 1000 mg/kg.

In other aspects, the invention provides a dosage form or pharmaceutical composition as described herein for use in therapy, e.g. for use in a method as defined herein.

Having been generally described herein, the follow non-limiting examples are provided to further illustrate this invention.

EXAMPLES

Example 1: 4-Chloro-N-(1-((1R,3r,5S,6r)-3-hydroxybicyclo[3.1.0]hexan-6-yl)propyl) benzamide (Compound 1)

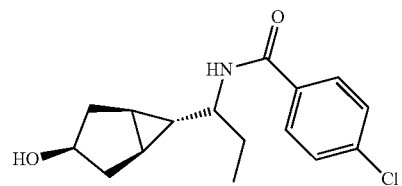 [SMILES: CCC(NC(=O)c1ccc(Cl)cc1)[C@H]1[C@@H]2C[C@H](O)C[C@@H]21]

Step 1:

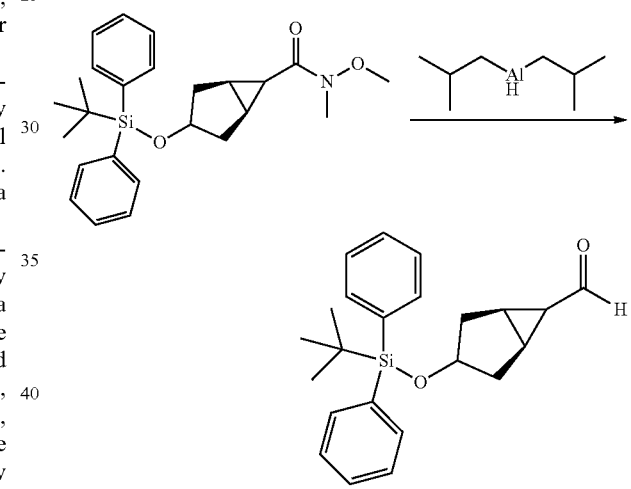

To a solution of (1R,5S)-3-((tert-butyldiphenylsilyl)oxy)-N-methoxy-N-methylbicyclo[3.1.0]hexane-6-carboxamide (22.4 g, 52.9 mmol) in dry toluene (264 mL) at −78° C. was added DIBAL-H (1 M in toluene, 58.2 mL, 58.2 mmol) dropwise over 17 min, and the resulting colorless solution was stirred at −78° C. for 3.5 hr. To the reaction at −78° C. was added EtOAc (135 mL) and allowed to warm in an ice bath for 15 min. To the reaction was added water (2.4 mL) and stirred for 5 min, 15% aqueous NaOH (2.6 mL) and stirred for 5 min, then water (6 mL) and the reaction allowed to warm to room temperature for 30 min. To the stirring reaction was added $MgSO_4$ and allowed stir at room temperature overnight. The reaction was filtered and the filtrate was washed with (150 mL/each) saturated $NH_4Cl$, water and saturated NaCl, dried over $MgSO_4$, filtered, and concentrated. The residue was purified via flash chromatography (0-30% EtOAc in hexanes, 330 g RediSep column, 200 mL/min, 20 min) to give (1R,5S)-3-((tert-butyldiphenylsilyl)oxy)bicyclo[3.1.0]hexane-6-carbaldehyde (17.64 g, 48.4 mmol, 92% yield). MS (ES$^+$) $C_{23}H_{28}O_2Si$ requires: 364, found: 387 [M+Na]$^+$.

Step 2:

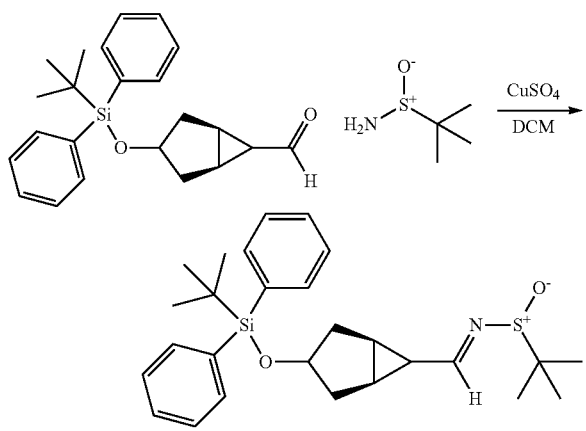

To a solution of (1R,5S)-3-((tert-butyldiphenylsilyl)oxy)bicyclo[3.1.0]hexane-6-carbaldehyde (3.22 g, 8.83 mmol) in DCM (17.67 mL) were added 2-methylpropane-2-sulfinamide (2.141 g, 17.67 mmol) and anhydrous copper(II) sulfate (1.410 g, 8.83 mmol) and the resulting mixture was stirred at RT overnight. The reaction was filtered through celite, concentrated and purified via flash chromatography (0-15% EtOAc in hexanes, 80 g Redisep, 100 mL/min) to give N-((E)-((1R,5 S)-3-((tert-butyldiphenylsilyl)oxy) bicyclo[3.1.0]hexan-6-yl)methylene)-2-methylpropane-2-sulfinamide (3.61 g, 7.72 mmol, 87% yield). MS (ES+) $C_{27}H_{37}NO_2SSi$ requires: 467, found: 468 [M+H]+.

Step 3:

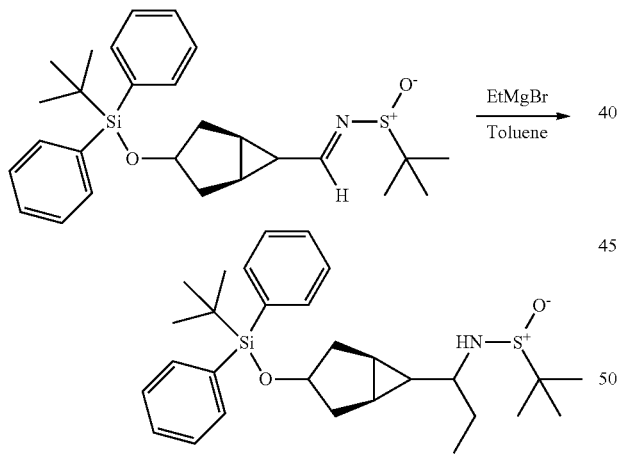

To a cooled −78° C. solution of N-((E)-((1R,5S)-3-((tert-butyldiphenylsilyl)oxy) bicyclo[3.1.0]hexan-6-yl)methylene)-2-methylpropane-2-sulfinamide (3 g, 6.41 mmol) in THF (64 mL) was added EtMgBr (8.55 mL of 3M solution in diethylether, 25.7 mmol). The resulting mixture was stirred at −78° C. for ~5 min, removed from the cooling bath, and allowed to warm to RT overnight. The reaction was cooled in ice and quenched with saturated NH4Cl (150 mL) and stirred for 1 hr. The mixture was diluted with DCM (200 mL) and the organic layer separated. The aqueous layer was extracted with DCM. The organic layers were combined, washed with saturated NaCl, dried over MgSO4, filtered, and concentrated to give N-(1-((1R,5S)-3-((tert-butyldiphenylsilyl)oxy)bicyclo[3.1.0]hexan-6-yl)propyl)-2-methylpropane-2-sulfinamide (3.33 g, 6.69 mmol) which was used directly in the next step. MS (ES+) $C_{29}H_{43}NO_2SSi$ requires: 497, found: 498[M+H]+.

Step 4:

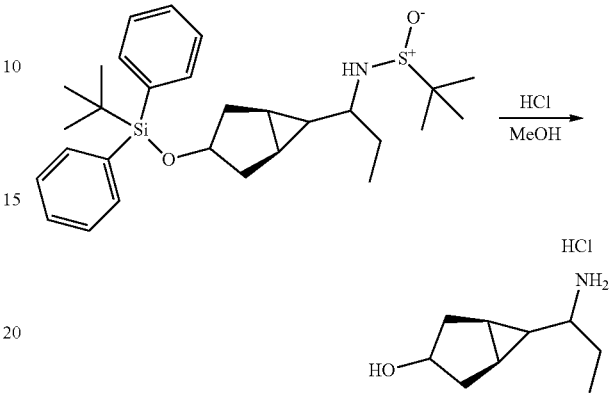

To a solution of N-(1-((1R,5S)-3-((tert-butyldiphenylsilyl)oxy)bicyclo[3.1.0]hexan-6-yl) propyl)-2-methylpropane-2-sulfinamide (3.33 g, 6.69 mmol) in MeOH (50 mL) was added a methanolic solution of HCl previously prepared by the slow addition of acetyl chloride (19.03 mL, 268 mmol), with stirring, to MeOH (25 mL), cooled in an ice bath, which was then stirred for 5 min, and then used as above. The reaction was stirred at room temperature overnight. The reaction was concentrated to remove the excess acidic methanol at reduced pressure and the residue was azeotroped with DCM/Toluene (3×) to give (1R,3r,5S)-6-(1-aminopropyl)bicyclo[3.1.0]hexan-3-ol hydrochloride as an off white solid, used directly in the next step. MS (ES+) $C_9H_{17}NO$ requires: 155, found: 156 [M+H]+.

Step 5:

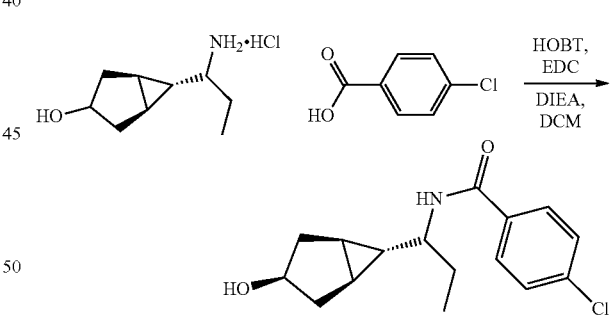

To a suspension of (1R,5S,6r)-6-((S)-1-aminopropyl)bicyclo[3.1.0]hexan-3-ol hydrochloride (the product of step 4) in DCM (60 mL) were added 4-chlorobenzoic acid (1.152 g, 7.36 mmol) DIEA (3.50 mL, 20.07 mmol) and HOBT (1.332 g, 8.70 mmol) and the resulting mixture was stirred at RT for 10 min. To this solution was added EDC (1.411 g, 7.36 mmol) and the mixture stirred at RT overnight. The reaction was diluted with DCM (60 mL) and washed with aqueous HCl (0.25 M), NaOH (0.25M), water, and saturated NaCl (100 mL/each). Each of the aqueous phases was extracted with DCM (30 mL). The final combined DCM layer was dried over MgSO4, filtered and purified by flash chromatography on silica gel (0-50% [20% 2-propanol in EtOAc]/Hexanes) to give 4-chloro-N-(1-((1R,3r,5S,6r)-3-hydroxybicyclo[3.1.0]hexan-6-yl)propyl)benzamide (0.4 g, 1.362 mmol, 20% yield) (isomer to elute first) as a white solid. MS (ES$^+$) C$_{16}$H$_{20}$ClNO$_2$ requires: 293, found: 294 [M+H]$^+$.

Example 2: 4-Chloro-N-(1-((1R,3r,5S,6r)-3-(quinolin-4-yloxy)bicyclo[3.1.0]hexan-6-yl)propyl)benzamide (Compound 2)

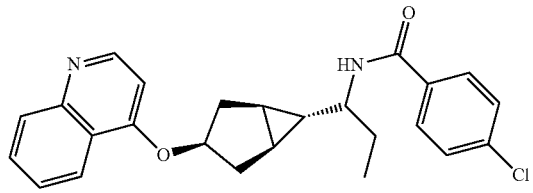 [SMILES: CCC(NC(=O)c1ccc(Cl)cc1)[C@H]1[C@@H]2C[C@H](Oc3ccnc4ccccc34)C[C@@H]21]

Step 1:

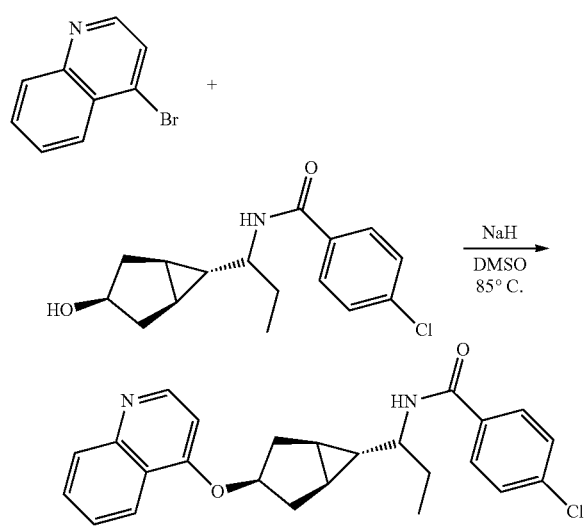

To a solution of 4-chloro-N-(1-((1R,3r,5S,6r)-3-hydroxybicyclo[3.1.0]hexan-6-yl)propyl)benzamide (49.3 mg, 0.168 mmol) in DMSO (0.34 mL) under nitrogen was added sodium hydride (60% in mineral oil, 15.0 mg, 0.375 mmol) and the mixture was stirred at RT for 30 min until gas evolution ceased. To the resulting yellow mixture was added 4-bromoquinoline (43.1 mg, 0.207 mmol), and the reaction was stirred at 80° C. overnight. To the mixture was added 2 drops of a sat. aq. ammonium chloride solution. The mixture was filtered into a tube through a 0.2 µM Whatman filter, rinsing with 3×0.3 mL of DMSO, and the filtrate was directly used for final purification by mass-triggered preparative HPLC (Mobile phase: A=0.1% TFA/H$_2$O, B=0.1% TFA/MeCN; Gradient: B=20-50%; 12 min; Column: C18) to give the title compound as a glassy yellow solid (55.3 mg, 62%). MS (ES$^+$) C$_{25}$H$_{25}$ClN$_2$O$_2$ requires: 420, found: 421 [M+H]$^+$. $^1$H NMR (600 MHz, CD3OD) δ ppm 0.97 (t, J=7.36 Hz, 3H), 1.27 (dt, J=9.06, 3.21 Hz, 1H), 1.55 (td, J=5.85, 3.40 Hz, 1H), 1.58-1.63 (m, 1H), 1.65-1.73 (m, 1H), 1.73-1.82 (m, 1H), 2.21-2.31 (m, 2H), 2.48-2.60 (m, 2H), 3.37-3.45 (m, 1H), 5.49 (t, J=6.61 Hz, 1H), 7.40 (d, J=6.80 Hz, 1H), 7.43-7.48 (m, 2H), 7.75-7.80 (m, 2H), 7.92 (ddd, J=8.40, 7.08, 1.13 Hz, 1H), 8.05-8.10 (m, 1H), 8.11-8.16 (m, 1H), 8.41 (d, J=8.69 Hz, 1H), 8.48 (d, J=7.93 Hz, 1H), 8.95 (d, J=6.42 Hz, 1H).

Example 3: 4-Chloro-N-(1-((1R,3s,5S,6r)-3-hydroxybicyclo[3.1.0]hexan-6-yl)propyl) benzamide (Compound 3)

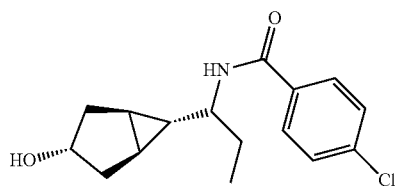 [SMILES: CCC(NC(=O)c1ccc(Cl)cc1)[C@H]1[C@@H]2C[C@@H](O)C[C@@H]21]

Step 1:

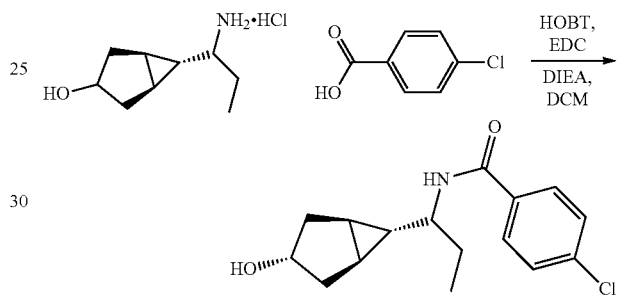

The flash chromatography purification of the above reaction of Step 5 of Example 1 produced a second eluting isomer as 4-chloro-N-(1-((1R,3s,5S,6r)-3-hydroxybicyclo[3.1.0]hexan-6-yl)propyl)benzamide (0.2 g, 0.681 mmol, 10% yield) as a white solid. MS (ES$^+$) C$_{16}$H$_{20}$ClNO$_2$ requires: 293, found: 294 [M+H]$^+$.

Example 4: 4-Chloro-N-(1-((1R,3s,5S,6r)-3-(quinolin-4-yloxy)bicyclo[3.1.0]hexan-6-yl) propyl)benzamide (Compound 4)

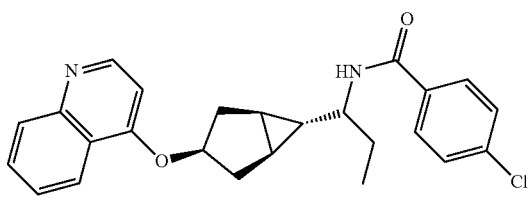 [SMILES: CCC(NC(=O)c1ccc(Cl)cc1)[C@H]1[C@@H]2C[C@H](Oc3ccnc4ccccc34)C[C@@H]21]

Step 1 (General S$_N$Ar Procedure):

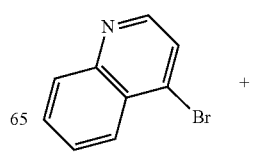

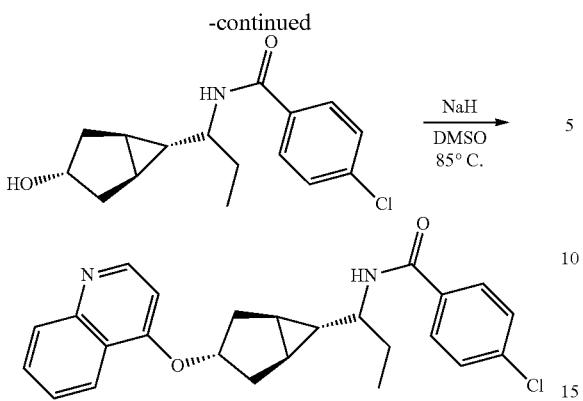

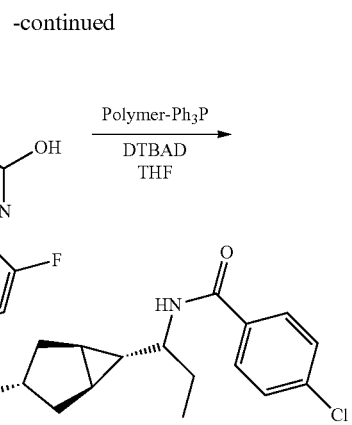

To a solution of 4-chloro-N-(1-((1R,3s,5S,6r)-3-hydroxybicyclo[3.1.0]hexan-6-yl)propyl)benzamide (24.7 mg, 0.084 mmol) in DMSO (0.17 mL) under nitrogen was added sodium hydride (60% in mineral oil, 8.1 mg, 0.203 mmol) and the mixture was stirred at RT for 30 min. To the resulting yellow mixture was added 4-bromoquinoline (24.6 mg, 0.118 mmol), and the resulting mixture was stirred at 80° C. overnight. To the mixture was added 2 drops of a sat. aq. ammonium chloride solution. The mixture was filtered into a tube through a 0.2 µM Whatman filter, rinsing with 3×0.3 mL of DMSO, and the filtrate was directly used for final purification by mass-triggered preparative HPLC (Mobile phase: A=0.1% TFA/H$_2$O, B=0.1% TFA/MeCN; Gradient: B=20-50%; 12 min; Column: C18) to give the title compound (32.9 mg, 73%). MS (ES$^+$) C$_{25}$H$_{25}$ClN$_2$O$_2$ requires: 420, found: 421 [M+H]$^+$. $^1$H NMR (600 MHz, CD$_3$OD) δ ppm 0.90 (dt, J=8.69, 3.40 Hz, 1H), 1.00 (t, J=7.37 Hz, 3H), 1.56 (td, J=6.04, 3.40 Hz, 1H), 1.64 (td, J=6.04, 3.40 Hz, 1H), 1.67-1.75 (m, 1H), 1.75-1.83 (m, 1H), 2.18-2.28 (m, 2H), 2.56 (dd, J=13.41, 6.99 Hz, 1H), 2.61-2.65 (m, 1H), 3.41 (qd, J=8.62, 5.85 Hz, 1H), 5.17 (quin, J=6.89 Hz, 1H), 7.46 (d, J=6.80 Hz, 1H), 7.47-7.50 (m, 2H), 7.79-7.84 (m, 2H), 7.88 (ddd, J=8.21, 6.89, 1.13 Hz, 1H), 8.04-8.08 (m, 1H), 8.09-8.14 (m, 1H), 8.34 (d, J=8.69 Hz, 1H), 8.45 (d, J=7.93 Hz, 1H), 8.94 (d, J=6.80 Hz, 1H).

Example 5: 4-Chloro-N-(1-((1R,3s,5S,6r)-3-((6-fluoroquinazolin-4-yl)oxy)bicyclo[3.1.0]hexan-6-yl)propyl)benzamide (Compound 5)

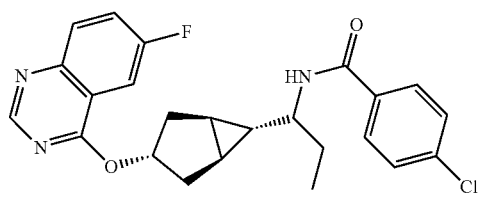 [SMILES: CCC(NC(=O)c1ccc(Cl)cc1)[C@H]1[C@@H]2C[C@@H](Oc3ncnc4ccc(F)cc34)C[C@@H]21]

Step 1 (Mitsunobu Procedure):

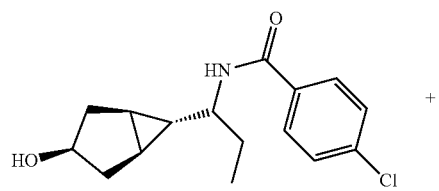

To a vial containing 4-chloro-N—((S)-1-((1R,3S,5S,6r)-3-hydroxybicyclo[3.1.0]hexan-6-yl)propyl)benzamide (10 mg, 0.034 mmol) dissolved in THF (0.5 mL) was added 6-fluoroquinazolin-4-ol (10.06 mg, 0.061 mmol) and polymer-bound PPh$_3$, 3 mmol/g (22.67 mg, 0.068 mmol). The mixture was stirred for 10 min and then DTBAD (15.68 mg, 0.068 mmol) was added and the reaction was stirred at RT overnight. The reaction was diluted with DCM and the mixture filtered through a celite pad, which was then rinsed with DCM. The filtrate was concentrated, resuspended in DCM (100 µL) and TFA (200 µL) and stirred at RT for 1.5 hours. The reaction was diluted with MeCN/EtOH (1:1, 2 mL), concentrated, dissolved in MeOH/DMSO, filtered, the filter rinsed with MeOH and the filtrate purified by mass-triggered preparative HPLC (Mobile phase: A=0.1% TFA/H$_2$O, B=0.1% TFA/MeCN; Gradient of B into A varied for 12 or 20 min; Column: C18) to give the title compound (3.9 mg, 8.87 µmol, 17% yield) as a white solid. MS (ES$^+$) C$_{24}$H$_{23}$ClFN$_3$O$_2$ requires: 439, found: 440[M+H]$^+$. $^1$H NMR (500 MHz, METHANOL-d4) δ ppm 1.00 (t, J=7.32 Hz, 3H) 1.08 (m, 1H) 1.50-1.62 (m, 2H) 1.65-1.84 (m, 2H) 2.18-2.25 (m, 2H) 2.25-2.33 (m, 2H) 3.35-3.45 (m, 1H), 4.9-5.00 (m, 1H), 7.48 (d, J=8.55 Hz, 2H) 7.60 (m, 1H) 7.73 (dd, J=9.00, 4.73 Hz, 1H) 7.79-7.89 (m, 3H) 8.36 (s, 1H) 8.42 (d, J=8.55 Hz, 1H).

Example 6: 4-Chloro-N-(1-((1R,3s,5 S,6r)-3-(6-fluoro-4-oxoquinazolin-3(4H)-yl) bicyclo[3.1.0]hexan-6-yl)propyl)benzamide (Compound 6)

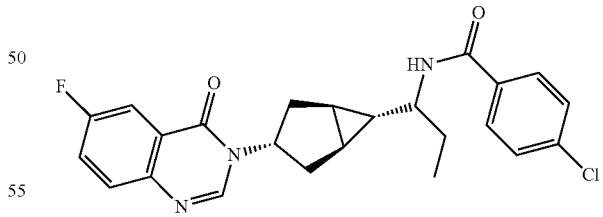

Step 1: (Mitsunobu, alternative product)

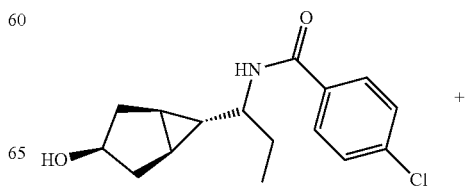

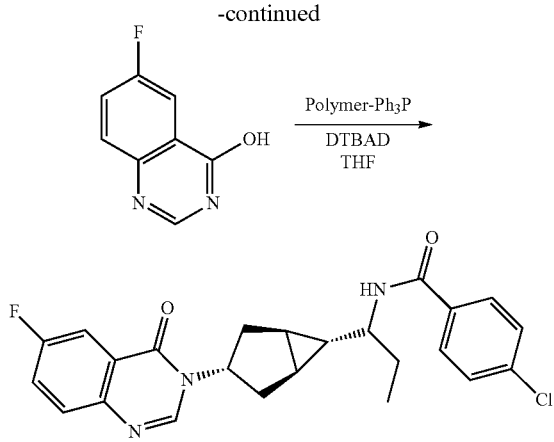

The HPLC method of Example 5 also yielded as a product 4-Chloro-N-(1-((1R,3s,5S,6r)-3-(6-fluoro-4-oxoquinazolin-3(4H)-yl)bicyclo[3.1.0]hexan-6-yl)propyl) benzamide (6.4 mg, 15 μmol, 29% yield) as a white solid. MS (ES+) $C_{24}H_{23}ClFN_3O_2$ requires: 439, found: 440[M+H]+.

Example 7: 2-(4-Chlorophenyl)-N-((1R,3s,5 S,6r)-3-((6-fluoroquinolin-4-yl)oxy)bicyclo[3.1.0]hexan-6-yl)acetamide (Compound 7)

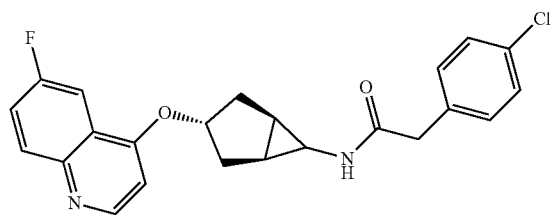 [SMILES: O=C(Cc1ccc(Cl)cc1)NC1[C@H]2C[C@H](Oc3ccnc4ccc(F)cc34)C[C@@H]12]

Step 1:

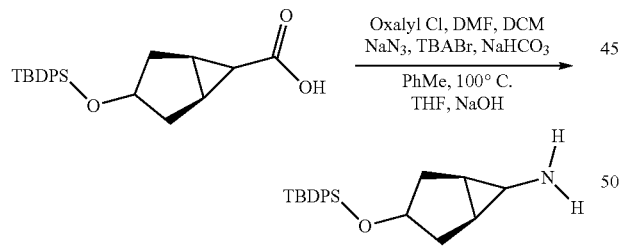

To a stirred suspension of (1R,5S,6r)-3-((tert-butyldiphenylsilyl)oxy)bicyclo[3.1.0]hexane-6-carboxylic acid (350 mg, 0.920 mmol) and DMF (2.1 μL, 0.028 mmol) in DCM (5 mL) was added oxalyl chloride (0.322 mL, 3.68 mmol) dropwise. The mixture was stirred at RT for 1 h, then concentrated under reduced pressure, treated with toluene (1 mL) and again concentrated under reduced pressure. The residue was redissolved in toluene (3 mL), cooled to 0° C., and a solution of sodium bicarbonate (0.098 g, 0.92 mmol), sodium azide (0.179 g, 2.76 mmol), and tetrabutylammonium bromide (0.059 g, 0.18 mmol) in water (0.3 mL) was added dropwise. The mixture was stirred at 0° C. for 3 h. The layers were separated and the organic layer was sequentially washed with cold water (3 mL) then a cold 20% aq. NaCl solution (3 mL), dried over $Na_2SO_4$ and filtered, using 3 mL of toluene in rinsing. The toluene solution was heated to 100° C. and stirred for 4 h, then concentrated under reduced pressure. The residue was treated with THF (3 mL) and an aqueous NaOH solution (0.5 M, 2.76 mL, 1.38 mmol), and the mixture was stirred at RT for 10 min. The mixture was then diluted with EtOAc, washed with a sat. aq. $NaHCO_3$ solution, and concentrated under reduced pressure. The residue was purified via $SiO_2$ gel chromatography (0% to 15% MeOH in DCM) to give (1R,5S,6r)-3-((Tert-butyldiphenylsilyl)oxy)bicyclo[3.1.0]hexan-6-amine as a colorless liquid (125 mg, 39% yield). MS (ES+) $C_{22}H_{29}NOSi$ requires: 351, found: 352 [M+H]+.

Step 2:

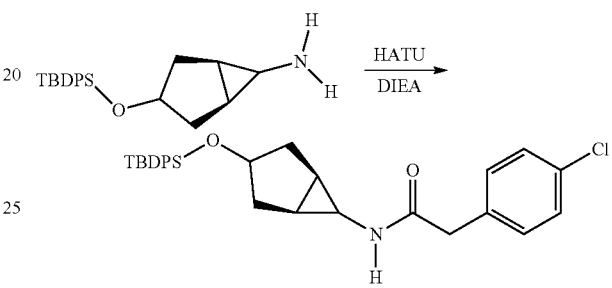

To a solution of (1R,5S)-3-((tert-butyldiphenylsilyl)oxy)bicyclo[3.1.0]hexan-6-amine (200 mg, 0.569 mmol) in DMF (1000 μL) were added 2-(4-chlorophenyl)acetic acid (146 mg, 0.853 mmol), HATU (324 mg, 0.853 mmol) and DIEA (199 μL, 1.138 mmol) and the resulting mixture was stirred at RT for 20 h. The resaction was adsorbed onto silica gel and purified via flash chromatography (0-100% EtOAc in hexanes to give N-((1R,5S)-3-((tert-butyldiphenylsilyl)oxy)bicyclo[3.1.0]hexan-6-yl)-2-(4-chlorophenyl)acetamide (224.6 mg, 0.446 mmol, 78% yield). MS (ES+) $C_{30}H_{34}ClNO_2Si$ requires: 504.135, found: 505.5 [M+H]+.

Step 3:

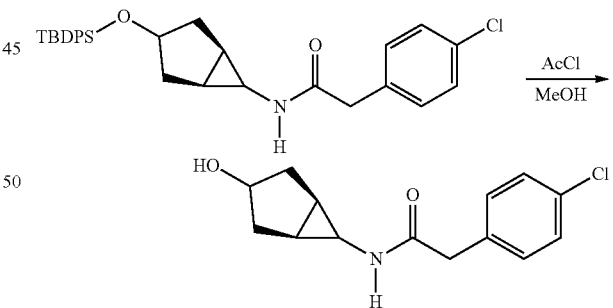

To MeOH (4455 μL), cooled at 0° C. was added acetyl chloride (1115 μL, 15.68 mmol) dropwise with stirring and the resulting mixture was stirred at RT for 10 min. Then to a cooled 0° C. solution of N-((1R,5S)-3-((tert-butyldiphenylsilyl)oxy)bicyclo[3.1.0]hexan-6-yl)-2-(4-chlorophenyl)acetamide (224.6 mg, 0.446 mmol) in MeOH (4455 μL) was added the above-prepared methanolic HCl solution. The resulting mixture was stirred at RT for 3 days. The reaction was adsorbed onto Celite and purified via flash chromatography (0-10% MeOH in DCM to give 2-(4-chlorophenyl)-N-((1R,5S)-3-hydroxybicyclo[3.1.0]hexan-6-yl)acetamide (82.5 mg, 0.310 mmol, 70% yield) as a tan amorphous material. MS(ES+) $C_{14}H_{16}ClNO_2$ requires: 265.735, found: 266.2 [M+H]+.

Step 4:

2-(4-Chlorophenyl)-N-((1R,3s,5S,6r)-3-((6-fluoroquinolin-4-yl)oxy)bicyclo[3.1.0]hexan-6-yl)acetamide

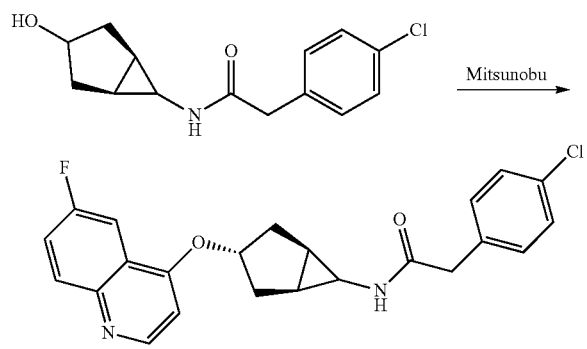

By the method of Mitsunobu procedure set out in Example 5, and using 2-(4-chlorophenyl)-N-((1R,5S)-3-hydroxybicyclo[3.1.0]hexan-6-yl)acetamide (20 mg, 0.075 mmol) and 6-fluoroquinolin-4-ol (14.73 mg, 0.090 mmol) and purification by mass-triggered preparative HPLC (Mobile phase: A=0.1% TFA/H₂O, B=0.1% TFA/MeCN; Gradient: B=20-60%; 20 min; Column: C18), 2-(4-chlorophenyl)-N-((1R,3s,5S)-3-((6-fluoroquinolin-4-yl)oxy)bicyclo[3.1.0]hexan-6-yl)acetamide (6.20 mg, 0.015 mmol, 20.05% yield) was obtained as a white solid. NMR showed presence of DTBAD so the product was diluted in 0.6 mL DCM, 0.3 mL of TFA was added and allowed to stir at RT for 3 h. The residue was purified by mass-triggered preparative HPLC (Mobile phase: A=0.1% TFA/H₂O, B=0.1% TFA/MeCN; Gradient: B=20-60%; 12 min; Column: C18) to give 2-(4-chlorophenyl)-N-((1R,3s,5S,6r)-3-((6-fluoroquinolin-4-yl)oxy)bicyclo[3.1.0]hexan-6-yl)acetamide (6.20 mg, 0.015 mmol, 20% yield) as a white solid. MS(ES+) $C_{23}H_{20}ClFN_2O_2$ requires: 410.869, found: 411.1 [M+H]+.

Example 8: (1R,5S)—N-(4-chlorophenyl)-3-(quinolin-4-yloxy)bicyclo[3.1.0]hexane-6-carboxamide (Compound 8)

Step 1:

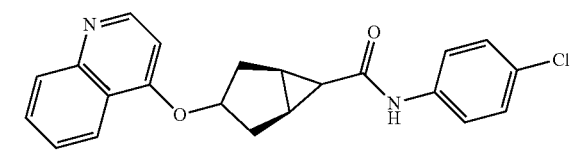

(1R,5S)-3-((tert-butyldiphenylsilyl)oxy)-N-(4-chlorophenyl)bicyclo[3.1.0]hexane-6-carboxamide was synthesized by standard HATU amide coupling (cf. Example 7, step 2), using 4-chloroaniline and DIEA in DMF, followed by flash chromatography to give (1R,5S)-3-((tert-butyldiphenylsilyl)oxy)-N-(4-chlorophenyl)bicyclo[3.1.0]hexane-6-carboxamide as a white solid. MS(ES+) $C_{29}H_{32}ClFNO_2Si$ requires: 490, found: 491 [M+H]+.

Step 2:

The product of step 1 was deprotected by a similar procedure to that described in Example 1, step 4, to give (1R,5S)—N-(4-chlorophenyl)-3-hydroxybicyclo[3.1.0]hexane-6-carboxamide (24 mg, 0.097 mmol, 17%) as an off-white solid. MS (ES+) $C_{13}H_{14}ClNO_2$ requires: 251.709, found: 252.2 [M+H]+.

Step 3:

(1R,5S)—N-(4-Chlorophenyl)-3-(quinolin-4-yloxy)bicyclo[3.1.0]hexane-6-carboxamide was synthesized by the S$_N$Ar procedure set out in Example 2, with 4-bromoquinoline and (1R,5S)—N-(4-chlorophenyl)-3-hydroxybicyclo[3.1.0]hexane-6-carboxamide being reacted to give (1R,5S)—N-(4-chlorophenyl)-3-(quinolin-4-yloxy)bicyclo[3.1.0]hexane-6-carboxamide (9.14 mg, 0.024 mmol, 25% yield) as a white powder.

Example 9: 4-Chloro-N-((((1R,3s,5S,6r)-3-((6-fluoroquinolin-4-yl)oxy)bicyclo[3.1.0]hexan-6-yl)methyl)benzamide (Compound 9)

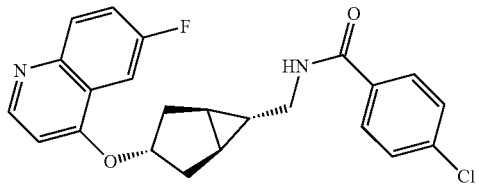 [SMILES: O=C(NC[C@@H]1[C@H]2C[C@H](Oc3ccnc4ccc(F)cc34)C[C@@H]12)c1ccc(Cl)cc1]

Step 1:

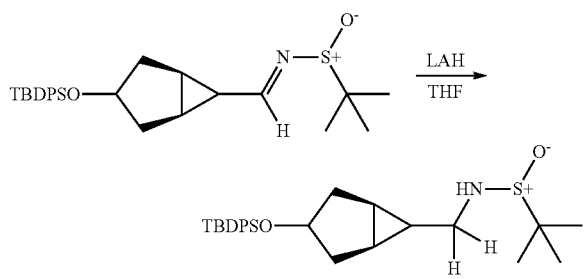

To a solution of (E)-N-(((1R,5S)-3-((tert-butyldiphenylsilyl)oxy)bicyclo[3.1.0]hexan-6-yl)methylene)-2-methylpropane-2-sulfinamide (93 mg, 0.199 mmol) in THF (1 mL) cooled in an acetone dry ice bath was added LAH (0.119 mL, 0.239 mmol) and the resulting mixture was allowed to warm to RT overnight. The reaction was cooled in ice and quenched with MeOH. The reaction was then diluted with saturated NH$_4$Cl and extracted with EtOAc (8 mL×6). The organic layers were washed with brine, dried over MgSO$_4$, filtered and concentrated to give N-(((1R,5S)-3-((tert-butyldiphenylsilyl)oxy)bicyclo[3.1.0]hexan-6-yl)methyl)-2-methylpropane-2-sulfinamide (91 mg, 0.194 mmol, 97% yield) as a clear semisolid. MS (ES$^+$) C$_{27}$H$_{39}$NO$_2$SSi requires: 469, found: 470 [M+H]$^+$.

Step 2:

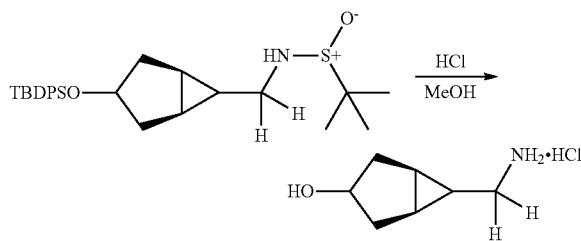

The product of step 1 was dissolved in MeOH, cooled in an acetone dry ice bath and HCl (0.5 mL of 4N solution in Dioxan, 2.0 mmol) was added and the reaction was removed from the bath (white ppt formed) and reaction was allowed to warm to RT (~5 min clear solution) and stirred at RT for 6 hr. Reaction was concentrated, and excess acidic methanol was azeotroped with addition of mixtures of DCM/toluene and DCM/Hexanes to give (1R,5S)-6-(aminomethyl)bicyclo[3.1.0]hexan-3-ol hydrochloride (25 mg, 0.197 mmol, 99% yield) as a white solid, used directly in step 3 as is. MS (ES$^+$) C$_7$H$_{13}$NO requires: 127, found: 128 [M+H]$^+$.

Step 3:

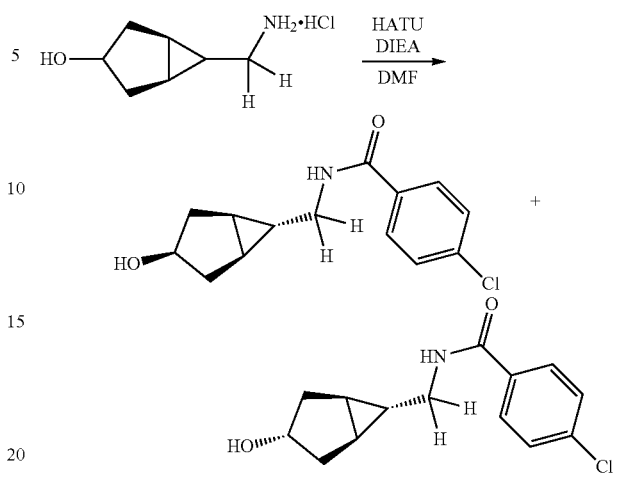

To a solution of (1R,5S)-6-(aminomethyl)bicyclo[3.1.0]hexan-3-ol hydrochloride (25 mg, 0.197 mmol) in DMF (2.00 mL) were added DIEA (0.174 mL, 0.994 mmol), 4-chlorobenzoic acid (34.2 mg, 0.219 mmol) and HATU (91 mg, 0.239 mmol) and the resulting mixture was stirred at RT 18 h. The mixture was concentrated and the residue was purified via flash chromatography on silica gel, eluent (0-90% EtOAc in hexanes) to give 4-chloro-N-(((1R,3r,5S,6r)-3-hydroxybicyclo[3.1.0]hexan-6-yl)methyl)benzamide (32.2 mg, 0.121 mmol, 61% yield) as a white solid. MS (ES$^+$) C$_{14}$H$_{16}$ClNO$_2$ requires: 265, found: 266 [M+H]$^+$.

A second isomer was also collected from the column, 4-chloro-N-(((1R,3s,5S,6r)-3-hydroxybicyclo[3.1.0]hexan-6-yl)methyl)benzamide (6.6 mg, 0.025 mmol, 12% yield) as a white solid. MS (ES$^+$) C$_{14}$H$_{16}$ClNO$_2$ requires: 265, found: 266 [M+H]$^+$.

Step 4:

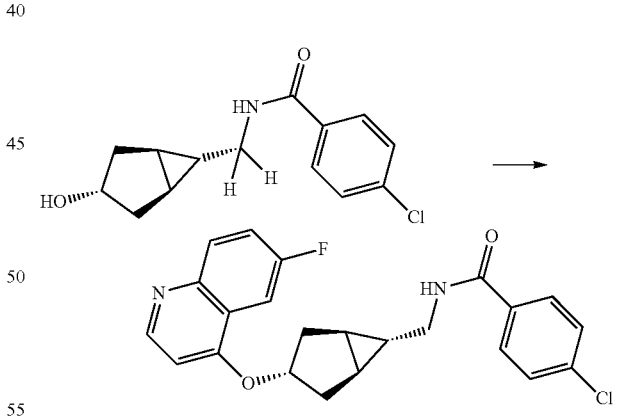

4-Chloro-N-(((1R,3s,5S,6r)-3-((6-fluoroquinolin-4-yl)oxy)bicyclo[3.1.0]hexan-6-yl)methyl)benzamide was synthesized by the method of the S$_N$Ar procedure set out in Example 2, using 4-chloro-N-(((1R,3s,5S,6r)-3-hydroxybicyclo[3.1.0]hexan-6-yl)methyl) benzamide (6.6 mg, 0.025 mmol), 4-chloro-6-fluoroquinoline (5.41 mg, 0.030 mmol), and KOtBu (5.57 mg, 0.050 mmol) in THF to give 4-chloro-N-(((1R,3s,5S,6r)-3-((6-fluoroquinolin-4-yl)oxy)bicyclo[3.1.0]hexan-6-yl)methyl)benzamide (4.8 mg, 0.012 mmol, 47% yield) as a white solid. MS (ES$^+$) C$_{23}$H$_{20}$ClFN$_2$O$_2$ requires: 410, found: 411 [M+H]$^+$.

Example 10: 1-(4-Chlorophenyl)-3-((1R,3s,5S,6r)-3-((6-fluoroquinolin-4-yl)oxy)bicyclo[3.1.0]hexan-6-yl)urea (Compound 10)

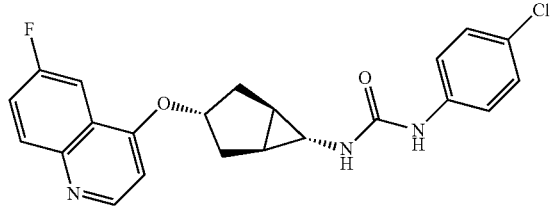 [SMILES: O=C(Nc1ccc(Cl)cc1)N[C@H]1[C@@H]2C[C@@H](Oc3ccnc4ccc(F)cc34)C[C@@H]21]

Step 1:

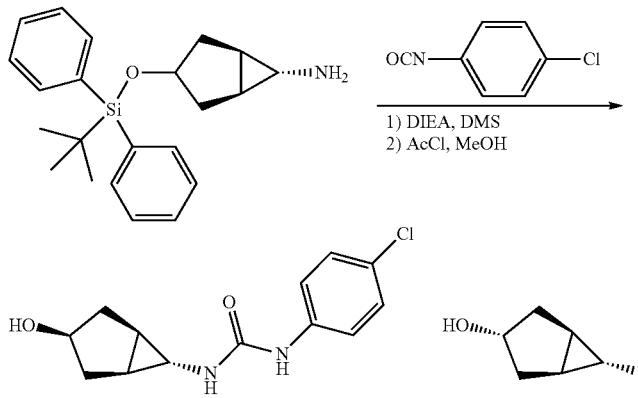

To a solution of (1R,5S,6r)-3-((tert-butyldiphenylsilyl)oxy)bicyclo[3.1.0]hexan-6-amine (100 mg, 0.284 mmol) in DMF (2 mL) were added DIEA (0.099 mL, 0.569 mmol) and 1-chloro-4-isocyanatobenzene (52.4 mg, 0.341 mmol) and the resulting mixture was stirred at room temperature overnight. The reaction was diluted with EtOAc, washed with water and saturated NaCl, dried over MgSO$_4$, filtered, and concentrated. The resulting crude material was dissolved in MeOH (2 mL) and HCl in MeOH (prepared from Acetyl Chloride (0.35 mL) added to MeOH (1 mL)) was added and the reaction was stirred at room temperature overnight. The reaction was concentrated, azeotroped with DCM, DCM/MeOH, DCM/hexanes. The residue was adsorbed onto Celite and purified via flash chromatography (0-100% EtOAc in hexanes to give 1-(4-chlorophenyl)-3-((1R,3r,5S,6r)-3-hydroxybicyclo[3.1.0]hexan-6-yl)urea (34.8 mg, 0.130 mmol, 46% yield). A second broad peak eluting after the first, was observed with the same mass and was isolated to give 1-(4-chlorophenyl)-3-((1R,3s,5S,6r)-3-hydroxybicyclo[3.1.0]hexan-6-yl)urea (3.2 mg, 0.012 mmol, 4% yield).

Step 2:

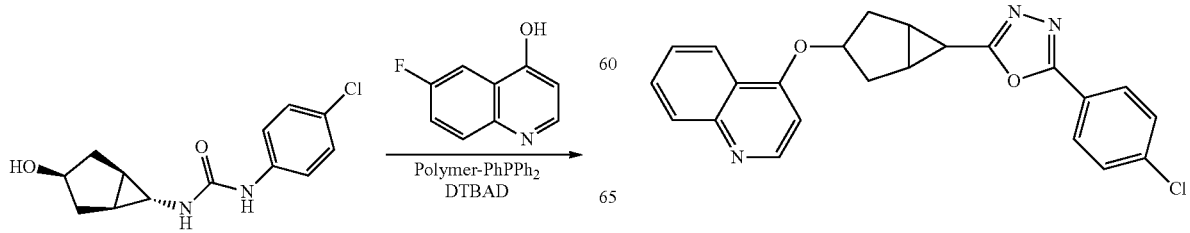

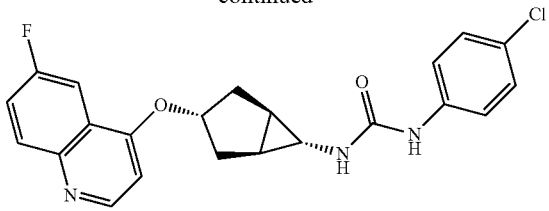

1-(4-Chlorophenyl)-3-((1R,3s,5S,6r)-3-((6-fluoroquinolin-4-yl)oxy)bicyclo[3.1.0]hexan-6-yl)urea was synthesized according to the general Mitsunobu procedure set out in Example 5, using 1-(4-chlorophenyl)-3-((1R,3r,5S,6r)-3-hydroxybicyclo[3.1.0]hexan-6-yl)urea (17 mg, 0.064 mmol) and 6-fluoroquinolin-4-ol (12.48 mg, 0.076 mmol) to give 1-(4-chlorophenyl)-3-((1R,3s,5S,6r)-3-((6-fluoroquinolin-4-yl)oxy)bicyclo[3.1.0]hexan-6-yl)urea (7.8 mg, 0.019 mmol, 30% yield) as a white solid. MS (ES$^+$) C$_{22}$H$_{19}$ClFN$_3$O$_2$ requires: 411, found: 412 [M+H]$^+$. $^1$H NMR (600 MHz, CHLOROFORM-d) δ ppm 1.74 (br. s., 2H) 2.17-2.26 (m, 2H) 2.35 (s, 1H) 2.57 (dd, J=13.79, 6.99 Hz, 1H) 4.66-4.74 (m, 1H) 5.27 (br. s., 1H) 6.71 (d, J=5.29 Hz, 1H) 6.98 (br. s., 1H) 7.25 (d, J=8.69 Hz, 1H) 7.33 (d, J=8.69 Hz, 1H) 7.42-7.54 (m, 1H) 7.76 (dd, J=9.44, 2.64 Hz, 1H) 8.08 (dd, J=9.06, 5.29 Hz, 1H) 8.72 (d, J=5.29 Hz, 1H).

Example 11: 2-(4-chlorophenyl)-5-(3-(quinolin-4-yloxy)bicyclo[3.1.0]hexan-6-yl)-1,3,4-oxadiazole (Compound 11)

Step 1:

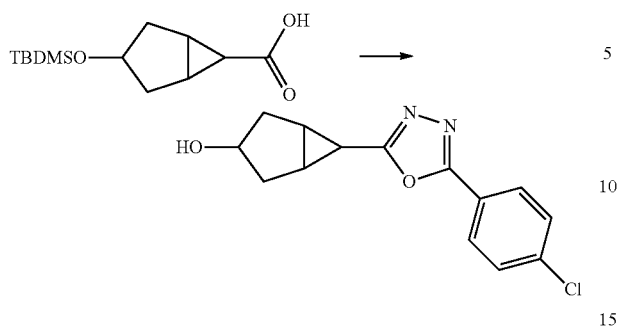

To a solution of 3-((tert-butyldiphenylsilyl)oxy)bicyclo[3.1.0]hexane-6-carboxylic acid (50 mg, 0.131 mmol) were added 4-chlorobenzohydrazide (26.9 mg, 0.158 mmol) and POCl$_3$ (245 µL, 2.63 mmol) and the resulting mixture was stirred at 80° C. for 20 min, then stopped and basified and extracted with EtOAc. The organic phase was concentrated and purified twice via silica gel chromatography (0-80% EtOAc in hexanes) and then purified by mass-triggered preparative HPLC (Mobile phase: A=0.1% TFA/H$_2$O, B=0.1% TFA/MeCN; Gradient: B=30-70%; 12 min; Column: C18) to give 6-(5-(4-chlorophenyl)-1,3,4-oxadiazol-2-yl)bicyclo[3.1.0]hexan-3-ol (2.5 mg, 9.03 µmol, 7% yield) as a yellow solid.

Step 2:

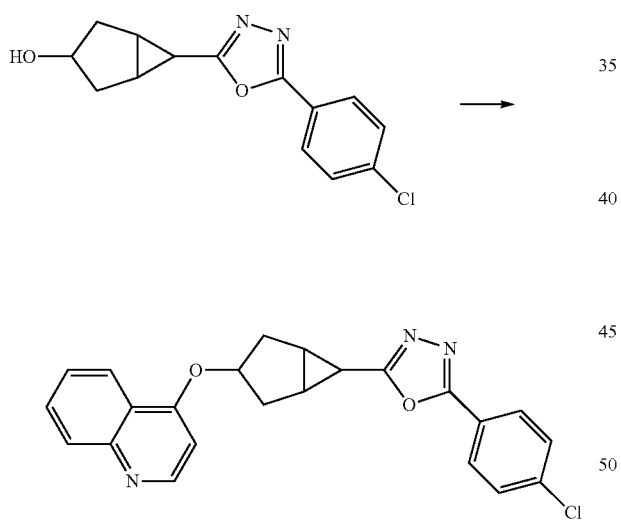

To a solution of 6-(5-(4-chlorophenyl)-1,3,4-oxadiazol-2-yl)bicyclo[3.1.0]hexan-3-ol (2.5 mg, 9.03 µmol) in DMSO (0.4 mL) were added sodium hydride (1.4 mg, 0.036 mmol) and the mixture was left 5 min and then 4-bromoquinoline (4.7 mg, 0.023 mmol) was added and the resulting mixture was stirred at 80° C. for 2 h. The mixture was directly purified by reverse phase preparative HPLC (Mobile phase: A=0.1% TFA/H$_2$O, B=0.1% TFA/MeCN; Gradient: B=20-60%; 20 min; Column: C18) to give 2-(4-chlorophenyl)-5-(3-(quinolin-4-yloxy)bicyclo[3.1.0]hexan-6-yl)-1,3,4-oxadiazole (1 mg, 1.931 µmol, 21% yield) as a white solid TFA salt. MS (ES$^+$) C$_{23}$H$_{18}$ClN$_3$O$_2$ requires: 403, found: 404 [M+H]$^+$.

Example 12: 4-((6-(2-(4-chlorophenoxy)ethyl)bicyclo[3.1.0]hexan-3-yl)oxy)-6-fluoro-2-(trifluoromethyl)quinolone (Compound 12)

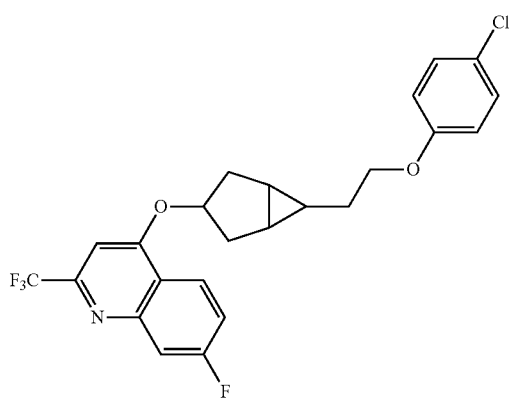 [SMILES: Fc1ccc2c(OC3CC4C(CCOc5ccc(Cl)cc5)C4C3)cc(C(F)(F)F)nc2c1]

Step 1:

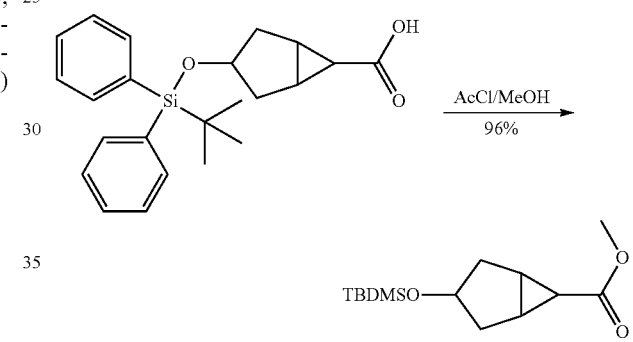

To MeOH (13 mL) was added acetyl chloride (0.224 mL, 3.15 mmol) dropwise and 3-((tert-butyldiphenylsilyl)oxy)bicyclo[3.1.0]hexane-6-carboxylic acid (1000 mg, 2.63 mmol) and the resulting mixture was stirred overnight at RT. The mixture was evaporated and methyl 3-((tert-butyldiphenylsilyl)oxy)bicyclo[3.1.0]hexane-6-carboxylate was recovered as a yellow oil that was used as such in the next step.

Step 2:

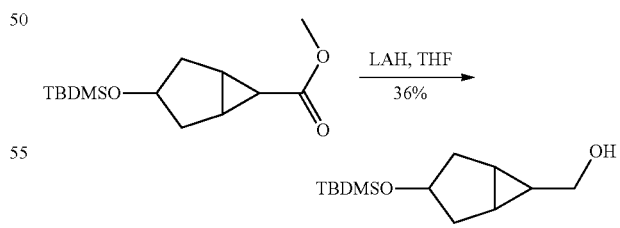

To a solution of methyl 3-((tert-butyldiphenylsilyl)oxy)bicyclo[3.1.0]hexane-6-carboxylate (1037 mg, 2.63 mmol) in THF (10 mL) was added LiAlH$_4$ (2.89 mL, 2.89 mmol) 1 M in THF and the resulting mixture was stirred at RT for 5 h, then additional 0.5 mL of LiAlH$_4$ 1 M in THF was added and the mixture was left overnight. The mixture was cooled at 0° C. and then acidified with 1N HCl dropwise and diluted with water, extracted with EtOAc, washed with brine and dried over Na$_2$SO$_4$. The solution was concentrated and the residue was purified via silica gel chromatography (0-20% EtOAc in hexanes) to give (3-((tert-butyldiphenylsilyl)oxy)bicyclo[3.1.0]hexan-6-yl)methanol (350 mg, 0.955 mmol, 36% yield) as a colorless liquid.

Step 3:

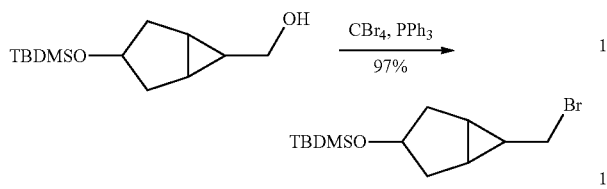

To a solution of (3-((tert-butyldiphenylsilyl)oxy)bicyclo[3.1.0]hexan-6-yl)methanol (300 mg, 0.818 mmol) in DCM (5 mL) was added triphenylphosphine (236 mg, 0.900 mmol) and tetrabromomethane (299 mg, 0.900 mmol) and the resulting mixture was stirred at RT for 6 h, 70% of conversion. Additional 0.4 equivalents of both reagents were added and the mixture was left 30 min and then concentrated and the residue was purified via silica gel chromatography (0-20% EtOAc in hexanes) to give ((6-(bromomethyl)bicyclo[3.1.0]hexan-3-yl)oxy)(tert-butyl)diphenylsilane (340 mg, 0.792 mmol, 97% yield) as a colorless amorphous material.

Step 4:

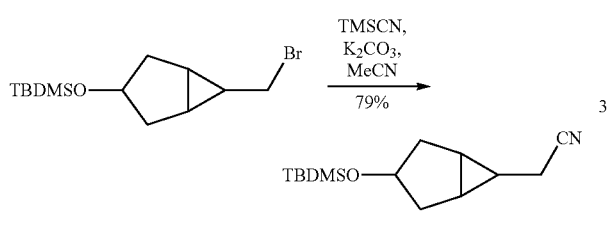

To a solution of ((6-(bromomethyl)bicyclo[3.1.0]hexan-3-yl)oxy)(tert-butyl)diphenylsilane (260 mg, 0.605 mmol) in acetonitrile (5 mL) was added potassium carbonate (92 mg, 0.666 mmol) and TMS-CN (0.089 mL, 0.666 mmol) and the resulting mixture was stirred at 80° C. overnight, filtered and concentrated and the residue was purified via silica gel chromatography (0-20% EtOAc in hexanes) to give 2-(3-((tert-butyldiphenylsilyl)oxy) bicyclo[3.1.0]hexan-6-yl)acetonitrile (180 mg, 0.479 mmol, 79% yield) as a colorless amorphous material.

Step 5:

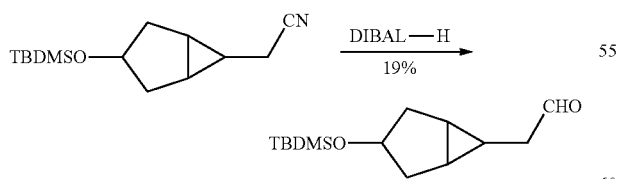

To a solution of 2-(3-((tert-butyldiphenylsilyl)oxy)bicyclo[3.1.0]hexan-6-yl)acetonitrile (180 mg, 0.479 mmol) in THF (4 mL) was added DIBAL-H (1 M in toluene) (0.527 mL, 0.527 mmol) at 0° C. and then heated at 50° C. for 48 h. The mixture was quenched with water taken up in EtOAc and washed with 1N HCl and then brine and dried over Na$_2$SO$_4$. The mixture was then filtered and the residue was purified via silica gel chromatography (0-20% EtOAc in hexanes) to give 2-(3-((tert-butyldiphenylsilyl)oxy)bicyclo[3.1.0]hexan-6-yl)acetaldehyde (35 mg, 0.092 mmol, 19% yield) as a colorless amorphous material.

Step 6:

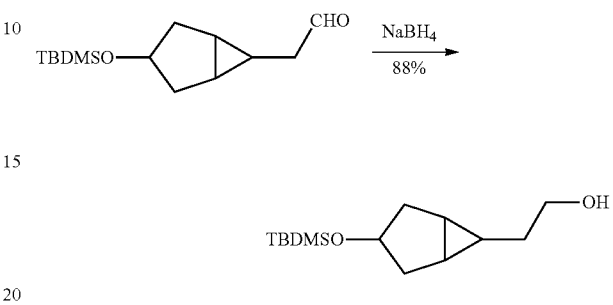

To a solution of 2-(3-((tert-butyldiphenylsilyl)oxy)bicyclo[3.1.0]hexan-6-yl)acetaldehyde (35 mg, 0.092 mmol) in MeOH (1 mL) were added sodium borohydride (3.85 mg, 0.102 mmol) and the resulting mixture was stirred at RT for 1 h, then evaporated and the residue was purified via silica gel chromatography (0-50% EtOAc in hexanes) to give 2-(3-((tert-butyldiphenylsilyl)oxy)bicyclo[3.1.0]hexan-6-yl)ethanol (31 mg, 0.081 mmol, 88% yield) as a colorless amorphous material.

Step 7:

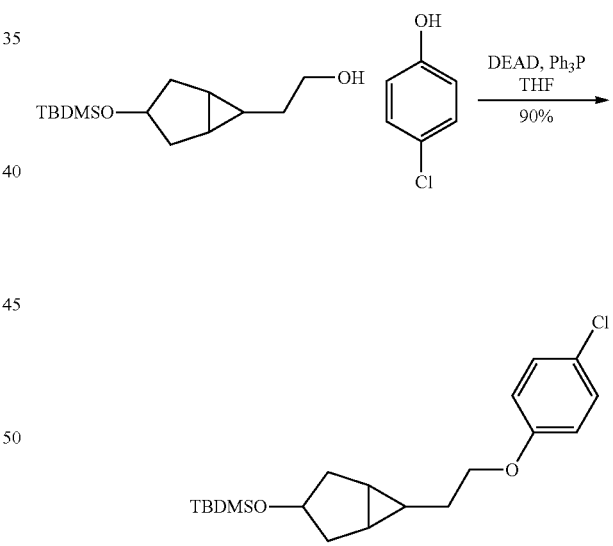

To a solution of 2-(3-((tert-butyldiphenylsilyl)oxy)bicyclo[3.1.0]hexan-6-yl)ethanol (31 mg, 0.081 mmol) in THF (1 mL) was added triphenylphosphine (32.0 mg, 0.122 mmol) and 4-chlorophenol (13.61 mg, 0.106 mmol) and DEAD (40% in toluene) (0.048 mL, 0.122 mmol) and the resulting mixture was stirred at RT for 1 h, then evaporated and the residue was purified via silica gel chromatography (0-20% EtOAc in hexanes) to give tert-butyl((6-(2-(4-chlorophenoxy)ethyl)bicyclo[3.1.0]hexan-3-yl)oxy)diphenylsilane (36 mg, 0.073 mmol, 90% yield) as a colorless amorphous material.

Step 8:

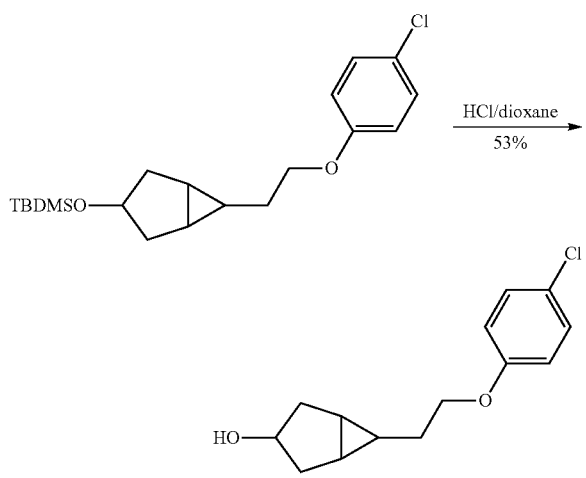

To a solution of tert-butyl((6-(2-(4-chlorophenoxy)ethyl)bicyclo[3.1.0]hexan-3-yl)oxy)diphenylsilane (36 mg, 0.073 mmol) in MeOH (1 mL) were added HCl (4N in dioxane) (0.183 mL, 0.733 mmol) and the resulting mixture was stirred at RT overnight, then evaporated and the residue was purified via silica gel chromatography (0-100% EtOAc in hexanes) to give 6-(2-(4-chlorophenoxy)ethyl)bicyclo[3.1.0]hexan-3-ol (10 mg, 0.040 mmol, 54% yield) as a colorless amorphous material.

Step 9:

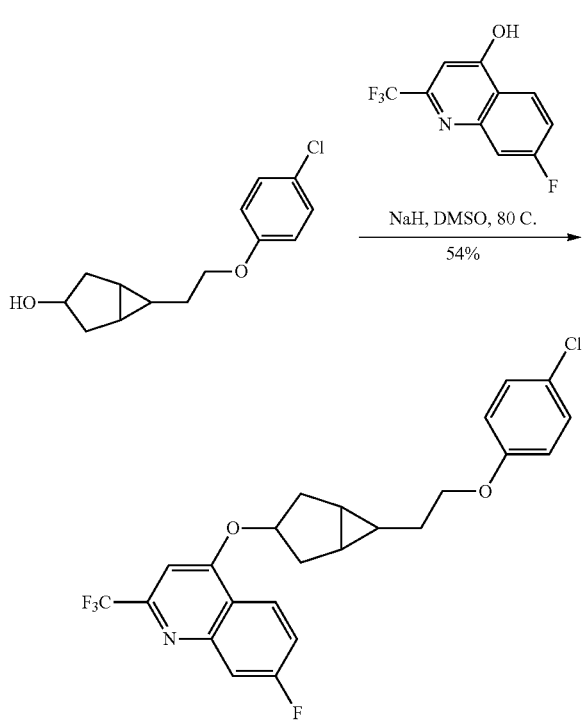

To a solution of 6-(2-(4-chlorophenoxy)ethyl)bicyclo[3.1.0]hexan-3-ol (10 mg, 0.040 mmol) in DMSO (0.400 mL) was added sodium hydride (6.33 mg, 0.158 mmol) and the mixture was left for 5 min and then 4-bromo-6-fluoro-2-(trifluoromethyl)quinoline (12.80 mg, 0.044 mmol) was added and the resulting mixture was stirred at 80° C. for 30 min. The mixture was quenched with 1N HCl and taken up in DCM and the organic phase was purified via silica gel chromatography (0-20% EtOAc in hexanes) to give 4-((6-(2-(4-chlorophenoxy)ethyl) bicyclo[3.1.0]hexan-3-yl)oxy)-6-fluoro-2-(trifluoromethyl)quinoline (10 mg, 0.021 mmol, 54% yield) as a white solid. MS (ES$^+$) $C_{24}H_{20}ClF_4NO_2$ requires: 465, found: 466 [M+H]$^+$.

Example 13: 4-Chloro-N-(1-(((1R,3s,5S,6r)-3-((6-fluoroquinazolin-4-yl)oxy)bicyclo[3.1.0]hexan-6-yl)ethyl)benzamide (Compound 13)

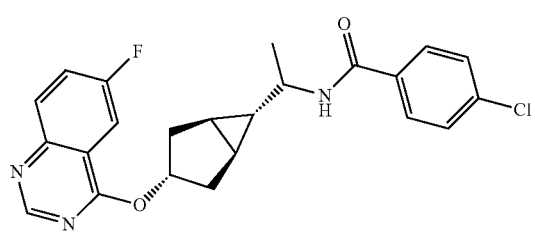 [SMILES: CC(NC(=O)c1ccc(Cl)cc1)[C@H]1[C@@H]2C[C@@H](Oc3ncnc4ccc(F)cc34)C[C@@H]21]

Step 1:

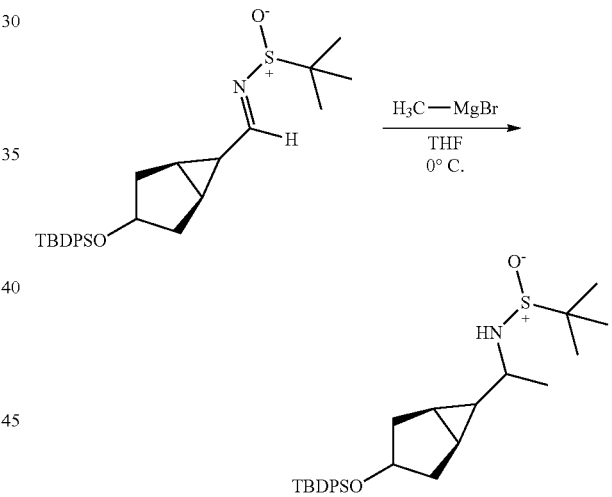

To (E)-N-(((1R,5S)-3-((tert-butyldiphenylsilyl)oxy)bicyclo[3.1.0]hexan-6-yl)methylene)-2-methylpropane-2-sulfinamide (424 mg, 0.908 mmol) in THF (1.5 mL) at 0° C. was added methylmagnesium bromide (1.8 mL, 1.8 mmol) dropwise under an argon atmosphere. The reaction mixture was stirred for 8 h. The reaction mixture was diluted with EtOAc (50 mL), 1 M HCl (50 mL) was added, and the layers were separated. The aqueous phase was extracted with EtOAc (3×50 mL), the combined organic layers were washed with sat NaCl, dried over Na$_2$SO$_4$, filtered and concentrated under reduced pressure. The residue was adsorbed onto silica gel and purified via flash chromatography (0-100% EtOAc in hexanes) to give N-(1-((1R,5S)-3-((tert-butyldiphenylsilyl)oxy)bicyclo[3.1.0]hexan-6-yl)ethyl)-2-methylpropane-2-sulfinamide (189.5 mg, 0.392 mmol, 43% yield) as a colorless oil. MS(ES$^+$) $C_{28}H_{41}NO_2SSi$ requires: 483.781, found: 484.2 [M+H]$^+$.

Step 2:

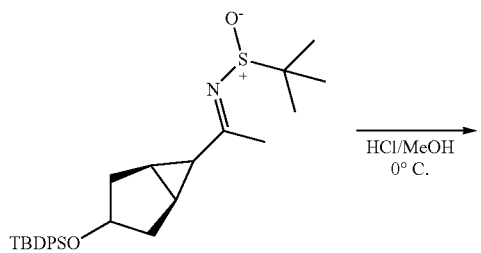

A procedure analogous to the general deprotection described in step 4 of Example 1 step 4 was used to synthesize (1R,5S)-6-(1-aminoethyl)bicyclo[3.1.0]hexan-3-ol hydrochloride MS(ES$^+$) C$_8$H$_{15}$NO requires: 141.211, found: 142.0 [M+H]$^+$.

Step 3:

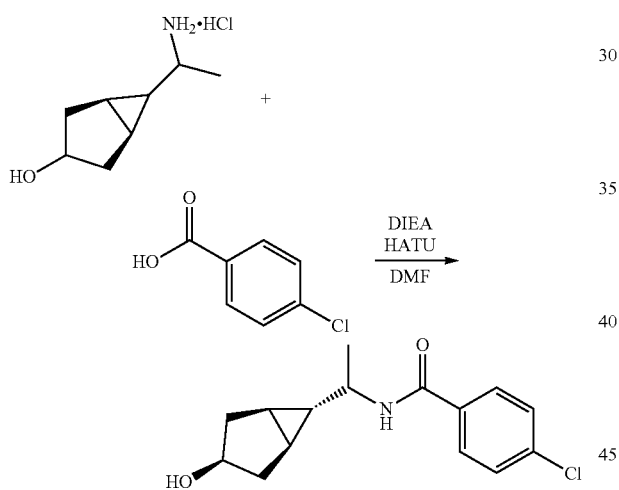

To a solution of (1R,5S)-6-(1-aminoethyl)bicyclo[3.1.0]hexan-3-ol hydrochloride (149 mg, 1.055 mmol) in DMF (5276 µl) was added 4-chlorobenzoic acid (330 mg, 2.110 mmol), HATU (602 mg, 1.583 mmol) and DIEA (921 µl, 5.28 mmol) and the resulting mixture was stirred at RT for 21 h. The residue was adsorbed onto silica gel and purified via flash chromatography (0-100% EtOAc). The product, containing residual HOAt was diluted with EtOAc (2 mL) and washed with saturated NaHCO$_3$ (2 mL). The layers were separated, and the organic layer was washed with saturated NaCl (2 mL), dried over Na$_2$SO$_4$, filtered and concentrated under reduced pressure to give 4-chloro-N-(1-((1R,3r,5S,6r)-3-hydroxybicyclo[3.1.0]hexan-6-yl)ethyl)benzamide (64 mg, 0.229 mmol, 22% yield) as a white solid. MS(ES$^+$) C$_{15}$H$_{18}$ClNO$_2$ requires: 279.762, found: 280.1 [M+H]$^+$.

Step 4:

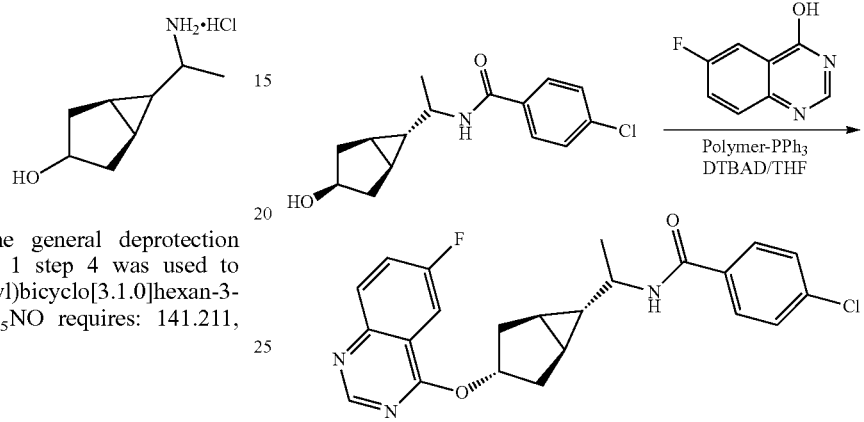

A procedure analogous to the general Mitsunobu procedure of Example 5 was used to couple 4-chloro-N-(1-((1R,3r,5 S,6r)-3-hydroxybicyclo[3.1.0]hexan-6-yl)ethyl)benzamide with 6-fluoroquinazolin-4-ol to synthesize 4-chloro-N-(1-((1R,3s,5S,6r)-3-(6-fluoro-4-oxoquinazolin-3(4H)-yl) bicyclo[3.1.0]hexan-6-yl)ethyl)benzamide, which was isolated from the purification (5.7 mg, 0.013 mmol, 6% yield) as a white solid. MS (ES$^+$) C$_{23}$H$_{21}$ClFN$_3$O$_2$ requires: 425.883, found: 426.1 [M+H]$^+$. $^1$H NMR (METHANOL-d$_4$) δ: 8.71 (s, 1H), 7.94 (m, 1H), 7.78-7.83 (m, 3H), 7.74 (m, 1H), 7.48 (d, J=8.3 Hz, 2H), 5.42 (t, J=7.4 Hz, 1H), 3.46-3.54 (m, 1H), 2.50-2.62 (m, 2H), 2.00-2.11 (m, 2H), 1.52-1.47 (m, 2H), 1.32 (d, J=6.8 Hz, 3H), 0.87-0.93 (m, 1H).

Example 14: Synthesis of Compounds 14 to 108

The following compounds in Table 1 were prepared according to the synthetic procedures described above in Examples 1-13. For each compound, the table indicates the chemical name, the calculated and measured mass, and the example which describes the method by which the compound was prepared. For example, Compound 14 was prepared analogously to Compound 5 in Example 5 (Mitsunobu reaction).

TABLE 1

| Compound | Name | Calc. Mass | Mass [M + H]$^+$ | Synthesis as per |
|---|---|---|---|---|
| 14 | 4-chloro-N-(1-((1R,3s,5S,6r)-3-(4-fluorophenoxy)bicyclo[3.1.0]hexan-6-yl)propyl)benzamide | 387 | 388 | Example 5 Mitsunobu |
| 15 | 4-chloro-N-(1-((1R,3s,5S,6r)-3-((2-methylpyridin-4-yl)oxy)bicyclo[3.1.0]hexan-6-yl)propyl)benzamide | 384 | 385 | Example 4 SNAr |

TABLE 1-continued

| Compound | Name | Calc. Mass | Mass [M + H]+ | Synthesis as per |
|---|---|---|---|---|
| 16 | (1R,5S)-N-(4-chlorobenzyl)-3-(quinolin-4-yloxy)bicyclo[3.1.0]hexane-6-carboxamide | 392 | 393 | Example 9, Example 4 SNAr |
| 17 | (1R,5S)-N-(4-chlorobenzyl)-3-((6-fluoro-2-(trifluoromethyl)quinolin-4-yl)oxy)bicyclo[3.1.0]hexane-6-carboxamide | 478 | 479 | Example 9, Example 4 SNAr |
| 18 | 4-chloro-N-(1-((1R,3s,5S,6r)-3-((6-fluoropyridin-3-yl)oxy)bicyclo[3.1.0]hexan-6-yl)propyl)benzamide | 388 | 389 | Example 5 Mitsunobu |
| 19 | 4-chloro-N-(1-((1R,3s,5S,6r)-3-((6-fluoroquinolin-4-yl)oxy)bicyclo[3.1.0]hexan-6-yl)propyl)benzamide | 438 | 439 | Example 5 Mitsunobu |
| 20 | 4-chloro-N-(1-((1R,3s,5S,6r)-3-((6-fluoro-2-methylquinolin-4-yl)oxy)bicyclo[3.1.0]hexan-6-yl)propyl)benzamide | 452 | 453 | Example 5 Mitsunobu |
| 21 | 4-chloro-N-(1-((1R,3s,5S,6r)-3-((7-chloroquinazolin-4-yl)oxy)bicyclo[3.1.0]hexan-6-yl)propyl)benzamide | 455 | 456 | Example 5 Mitsunobu |
| 22 | 4-chloro-N-(1-((1R,3s,5S,6r)-3-((6-fluoro-2-(trifluoromethyl)quinolin-4-yl)oxy)bicyclo[3.1.0]hexan-6-yl)propyl)benzamide | 506 | 507 | Example 4 SNAR |
| 23 | 4-chloro-N-(((1R,3s,5S,6s)-3-((6-fluoroquinolin-4-yl)oxy)bicyclo[3.1.0]hexan-6-yl)methyl)benzamide | 410 | 411 | Example 9, Example 4 SNAR |
| 24 | 4-chloro-N-(((1R,3s,5S,6s)-3-((6-fluoro-2-(trifluoromethyl)quinolin-4-yl)oxy)bicyclo[3.1.0]hexan-6-yl)methyl)benzamide | 478 | 479 | Example 9, Example 4 SNAR |
| 25 | 4-chloro-N-(3-((6-fluoro-2-(trifluoromethyl)quinolin-4-yl)oxy)bicyclo[3.1.0]hexan-6-yl)benzamide | 464 | 465 | Example 8 Example 4 SNAr |
| 26 | 4-chloro-N-(3-(quinolin-4-yloxy)bicyclo[3.1.0]hexan-6-yl)benzamide | 378 | 379 | Example 7, Example 4 SNAr |
| 27 | 1-(4-bromophenyl)-N-(3-(quinolin-4-yloxy)bicyclo[3.1.0]hexan-6-yl)methanesulfonamide | 472 | 474 | Example 7, Example 4 SNAr |
| 28 | 4-chloro-N-(3-(quinolin-4-yloxy)bicyclo[3.1.0]hexan-6-yl)benzenesulfonamide | 414 | 415 | Example 7, Example 4 SNAr |
| 29 | 1-(4-chlorophenyl)-3-((1R,3r,5S,6r)-3-((6-fluoroquinolin-4-yl)oxy)bicyclo[3.1.0]hexan-6-yl)urea | 411 | 412 | Example 7, Example 4 SNAr |
| 30 | 2-(4-chlorophenyl)-N-((1R,5S)-3-(quinolin-4-yloxy)bicyclo[3.1.0]hexan-6-yl)acetamide | 392 | 393 | Example 7, Example 4 SNAr |
| 31 | 2-(4-chlorophenyl)-N-((1R,3r,5S)-3-((6-fluoroquinolin-4-yl)oxy)bicyclo[3.1.0]hexan-6-yl)acetamide | 410 | 411 | Example 7, Example 4 SNAr |
| 32 | 4-chloro-N-(((1R,3r,5S,6r)-3-((6-fluoroquinolin-4-yl)oxy)bicyclo[3.1.0]hexan-6-yl)methyl)benzamide | 410 | 411 | Example 9, Example 4 SNAr |
| 33 | 4-chloro-N-(((1R,3r,5S,6r)-3-((4-chloroquinolin-6-yl)oxy)bicyclo[3.1.0]hexan-6-yl)methyl)benzamide | 426 | 427 | Example 9, Example 4 SNAr |
| 34 | 4-chloro-N-(1-((1R,3s,5S,6r)-3-(7-fluoro-4-oxoquinazolin-3(4H)-yl)bicyclo[3.1.0]hexan-6-yl)propyl)benzamide | 439 | 440 | Example 5 Mitsunobu |
| 35 | 4-chloro-N-(1-((1R,3s,5S,6r)-3-((7-fluoroquinazolin-4-yl)oxy)bicyclo[3.1.0]hexan-6-yl)propyl)benzamide | 439 | 440 | Example 5 Mitsunobu |

TABLE 1-continued

| Compound | Name | Calc. Mass | Mass [M + H]+ | Synthesis as per |
|---|---|---|---|---|
| 36 | 4-chloro-N-(1-((1R,3s,5S,6r)-3-(5-fluoro-4-oxoquinazolin-3(4H)-yl)bicyclo[3.1.0]hexan-6-yl)propyl)benzamide | 439 | 440 | Example 5 Mitsunobu |
| 37 | 4-chloro-N-(1-((1R,3s,5S,6r)-3-((5-fluoroquinazolin-4-yl)oxy)bicyclo[3.1.0]hexan-6-yl)propyl)benzamide | 439 | 440 | Example 5 Mitsunobu |
| 38 | N-(1-((1R,3s,5S,6r)-3-((1,5-naphthyridin-4-yl)oxy)bicyclo[3.1.0]hexan-6-yl)propyl)-4-chlorobenzamide | 421 | 422 | Example 4 SNAr |
| 39 | 4-chloro-N-(1-((1R,3s,5S,6r)-3-((3-fluoropyridin-2-yl)oxy)bicyclo[3.1.0]hexan-6-yl)propyl)benzamide | 388 | 389 | Example 4 SNAr |
| 40 | 4-chloro-N-(1-((1R,3s,5S,6r)-3-((6-methylpyridin-2-yl)oxy)bicyclo[3.1.0]hexan-6-yl)propyl)benzamide | 384 | 385 | Example 4 SNAr |
| 41 | 4-chloro-N-(1-((1R,3s,5S,6r)-3-((3-methylpyridin-2-yl)oxy)bicyclo[3.1.0]hexan-6-yl)propyl)benzamide | 384 | 385 | Example 4 SNAr |
| 42 | 4-chloro-N-(1-((1R,3s,5S,6r)-3-(2,5-difluorophenoxy)bicyclo[3.1.0]hexan-6-yl)propyl)benzamide | 405 | 406 | Example 5 Mitsunobu |
| 43 | 4-chloro-N-(1-((1R,3s,5S,6r)-3-(quinolin-8-yloxy)bicyclo[3.1.0]hexan-6-yl)propyl)benzamide | 420 | 421 | Example 5 Mitsunobu |
| 44 | 4-chloro-N-(1-((1R,3s,5S,6r)-3-(2,6-difluorophenoxy)bicyclo[3.1.0]hexan-6-yl)propyl)benzamide | 405 | 406 | Example 5, Mitsunobu |
| 45 | N-(1-((1R,3s,5S,6r)-3-(2-(2-amino-2-oxoethyl)phenoxy)bicyclo[3.1.0]hexan-6-yl)propyl)-4-chlorobenzamide | 426 | 427 | Example 5, Mitsunobu |
| 46 | 4-chloro-N-(1-((1R,3s,5S,6r)-3-(cinnolin-4-yloxy)bicyclo[3.1.0]hexan-6-yl)propyl)benzamide | 421 | 422 | Example 5 Mitsunobu |
| 47 | 4-chloro-N-(1-((1R,3s,5S,6r)-3-(4-oxocinnolin-1(4H)-yl)bicyclo[3.1.0]hexan-6-yl)propyl)benzamide | 421 | 422 | Example 5 Mitsunobu |
| 48 | 4-chloro-N-(1-((1R,3s,5S,6r)-3-(2-((dimethylamino)methyl)phenoxy)bicyclo[3.1.0]hexan-6-yl)propyl)benzamide | 426 | 427 | Example 5 Mitsunobu |
| 49 | 4-chloro-N-(1-((1R,3s,5S,6r)-3-(quinolin-3-yloxy)bicyclo[3.1.0]hexan-6-yl)propyl)benzamide | 420 | 421 | Example 5 Mitsunobu |
| 50 | 4-chloro-N-(1-((1R,3s,5S,6r)-3-((1-methyl-2-oxo-1,2-dihydroquinolin-4-yl)oxy)bicyclo[3.1.0]hexan-6-yl)propyl)benzamide | 450 | 451 | Example 5 Mitsunobu |
| 51 | N-(1-((1R,3s,5S,6r)-3-(1H-pyrazolo[4,3-c]pyridin-1-yl)bicyclo[3.1.0]hexan-6-yl)propyl)-4-chlorobenzamide | 394 | 395 | Example 5 Mitsunobu |
| 52 | 4-chloro-N-(1-((1R,3s,5S,6r)-3-((5-fluoro-2-methylpyrimidin-4-yl)oxy)bicyclo[3.1.0]hexan-6-yl)propyl)benzamide | 403 | 404 | Example 4 SNAR |
| 53 | 4-chloro-N-(1-((1R,3s,5S,6r)-3-(7-chloro-4-oxoquinazolin-3(4H)-yl)bicyclo[3.1.0]hexan-6-yl)propyl)benzamide | 455 | 456 | Example 5 Mitsunobu |
| 54 | 4-chloro-N-(1-((1R,3s,5S,6r)-3-((5-fluoropyrimidin-4-yl)oxy)bicyclo[3.1.0]hexan-6-yl)propyl)benzamide | 389 | 390 | Example 4 SNAr |
| 55 | N-(1-((1R,3s,5S,6r)-3-((1,6-naphthyridin-4-yl)oxy)bicyclo[3.1.0]hexan-6-yl)propyl)-4-chlorobenzamide | 421 | 422 | Example 4 SNAR |

TABLE 1-continued

| Compound | Name | Calc. Mass | Mass [M + H]⁺ | Synthesis as per |
|---|---|---|---|---|
| 56 | 4-chloro-N-(1-((1R,3s,5S,6r)-3-((7-fluoroquinolin-4-yl)oxy)bicyclo[3.1.0]hexan-6-yl)propyl)benzamide | 438 | 439 | Example 4 SNAr |
| 57 | 4-chloro-N-(1-((1R,3s,5S,6r)-3-((4-chloroquinolin-7-yl)oxy)bicyclo[3.1.0]hexan-6-yl)propyl)benzamide | 454 | 455 | Example 4 SNAr |
| 58 | 4-chloro-N-(1-((1R,3s,5S,6r)-3-((5-fluoropyridin-3-yl)oxy)bicyclo[3.1.0]hexan-6-yl)propyl)benzamide | 388 | 389 | Example 5 Mitsunobu |
| 59 | 4-chloro-N-(1-((1R,3s,5S,6r)-3-(quinazolin-4-yloxy)bicyclo[3.1.0]hexan-6-yl)propyl)benzamide | 421 | 422 | Example 4 SNAr |
| 60 | 4-chloro-N-(1-((1R,3s,5S,6r)-3-((2-chloropyridin-3-yl)oxy)bicyclo[3.1.0]hexan-6-yl)propyl)benzamide | 404 | 405 | Example 4 SNAr |
| 61 | 2-(4-chlorophenyl)-N-((1R,3s,5S,6r)-3-((6-fluoroquinazolin-4-yl)oxy)bicyclo[3.1.0]hexan-6-yl)acetamide | 411 | 412 | Example 7, Example 5 Mitsunobu |
| 62 | 2-(4-chlorophenyl)-N-((1R,3s,5S,6r)-3-(6-fluoro-4-oxoquinazolin-3(4H)-yl)bicyclo[3.1.0]hexan-6-yl)acetamide | 411 | 412 | Example 7, Example 5 Mitsunobu |
| 63 | 4-chloro-N-(1-((1R,3s,5S,6r)-3-(6-fluoro-4-oxoquinazolin-3(4H)-yl)bicyclo[3.1.0]hexan-6-yl)ethyl)benzamide | 425 | 426 | Example 5 Mitsunobu |
| 64 | 4-chloro-N-(1-((1R,3s,5S,6r)-3-((6-fluoroquinazolin-4-yl)oxy)bicyclo[3.1.0]hexan-6-yl)ethyl)benzamide | 425 | 426 | Example 5 Mitsunobu |
| 65 | 4-chloro-N-(((1R,3s,5S,6r)-3-(6-fluoro-4-oxoquinazolin-3(4H)-yl)bicyclo[3.1.0]hexan-6-yl)methyl)benzamide | 411 | 412 | Example 9, Example 5 Mitsunobu |
| 66 | 4-cyano-N-(1-((1R,3s,5S,6r)-3-((6-fluoroquinazolin-4-yl)oxy)bicyclo[3.1.0]hexan-6-yl)propyl)benzamide | 430 | 431 | Example 4 SNAr |
| 67 | 4-cyano-N-(1-((1R,3s,5S,6r)-3-(6-fluoro-4-oxoquinazolin-3(4H)-yl)bicyclo[3.1.0]hexan-6-yl)propyl)benzamide | 430 | 431 | Example 5 Mitsunobu |
| 68 | N-(1-((1R,3s,5S,6r)-3-((6-fluoroquinazolin-4-yl)oxy)bicyclo[3.1.0]hexan-6-yl)propyl)-2-methoxypyrimidine-5-carboxamide | 437 | 438 | Example 4 SNAr |
| 69 | 2,2-difluoro-N-(1-((1R,3s,5S,6r)-3-((6-fluoroquinazolin-4-yl)oxy)bicyclo[3.1.0]hexan-6-yl)propyl)benzo[d][1,3]dioxole-5-carboxamide | 485 | 486 | Example 5 Mitsunobu |
| 70 | 4-chloro-N-(1-((1R,3s,5S,6r)-3-((7-fluoroquinazolin-4-yl)oxy)bicyclo[3.1.0]hexan-6-yl)ethyl)benzamide | 425 | 426 | Example 4 SNAr |
| 71 | 4-chloro-N-(1-((1R,3s,5S,6r)-3-((3-methylpyridin-2-yl)oxy)bicyclo[3.1.0]hexan-6-yl)ethyl)benzamide | 370 | 371 | Example 4 SNAr |
| 72 | 4-chloro-N-(1-((1R,3s,5S,6r)-3-(phthalazin-1-yloxy)bicyclo[3.1.0]hexan-6-yl)propyl)benzamide | 421 | 422 | Example 5 Mitsunobu |
| 73 | 4-chloro-N-(1-((1R,3s,5S,6r)-3-morpholinobicyclo[3.1.0]hexan-6-yl)propyl)benzamide | 362 | 363 | MS displacement |
| 74 | N-(1-((1R,3s,5S,6r)-3-(6-fluoro-4-oxoquinazolin-3(4H)-yl)bicyclo[3.1.0]hexan-6-yl)propyl)-6-methoxynicotinamide | 436 | 437 | Example 5 Mitsunobu |

TABLE 1-continued

| Compound | Name | Calc. Mass | Mass [M + H]+ | Synthesis as per |
|---|---|---|---|---|
| 75 | 5-chloro-N-(1-((1R,3s,5S,6r)-3-(6-fluoro-4-oxoquinazolin-3(4H)-yl)bicyclo[3.1.0]hexan-6-yl)propyl)picolinamide | 440 | 441 | Example 5 Mitsunobu |
| 76 | 5-cyano-N-(1-((1R,3s,5S,6r)-3-(6-fluoro-4-oxoquinazolin-3(4H)-yl)bicyclo[3.1.0]hexan-6-yl)propyl)picolinamide | 431 | 432 | Example 5 Mitsunobu |
| 77 | 5-chloro-N-(1-((1R,5S)-3-(cinnolin-4-yloxy)bicyclo[3.1.0]hexan-6-yl)propyl)picolinamide | 422 | 423 | Example 5 Mitsunobu |
| 78 | N-(1-((1R,3s,5S,6r)-3-((6-fluoroquinazolin-4-yl)oxy)bicyclo[3.1.0]hexan-6-yl)propyl)-6-methoxynicotinamide | 436 | 437 | Example 5 Mitsunobu |
| 79 | 2-(4-chlorophenyl)-N-((1R,3s,5S,6r)-3-(cinnolin-4-yloxy)bicyclo[3.1.0]hexan-6-yl)acetamide | 393 | 394 | Example 7, Example 5 Mitsunobu |
| 80 | N-(1-((1R,3s,5S,6r)-3-(cinnolin-4-yloxy)bicyclo[3.1.0]hexan-6-yl)propyl)-4-cyanobenzamide | 412 | 413 | Example 1, Example 3, Example 4 |
| 81 | N-(1-((1R,3s,5S,6r)-3-(1H-1,2,4-triazol-1-yl)bicyclo[3.1.0]hexan-6-yl)propyl)-4-chlorobenzamide | 344 | 345 | Example 4 SNAr |
| 82 | N-(1-((1R,3s,5S,6r)-3-(cinnolin-4-yloxy)bicyclo[3.1.0]hexan-6-yl)propyl)-5-cyanopicolinamide | 413 | 414 | Example 5 Mitsunobu |
| 83 | 5-cyano-N-(1-((1R,3s,5S,6r)-3-(4-oxocinnolin-1(4H)-yl)bicyclo[3.1.0]hexan-6-yl)propyl)picolinamide | 413 | 414 | Example 5 Mitsunobu |
| 84 | ethyl 3-(4-chlorobenzamido)-3-((1R,3s,5S,6r)-3-(cinnolin-4-yloxy)bicyclo[3.1.0]hexan-6-yl)propanoate | 479 | 480 | Example 5 Mitsunobu |
| 85 | 2-(4-chlorophenyl)-N-((1R,3s,5S,6r)-3-(4-oxocinnolin-1(4H)-yl)bicyclo[3.1.0]hexan-6-yl)acetamide | 393 | 394 | Example 7, Example 5 Mitsunobu |
| 86 | 2-(4-chlorophenyl)-N-((1R,3s,5S,6r)-3-(cinnolin-4-yloxy)bicyclo[3.1.0]hexan-6-yl)-N-methylacetamide | 407 | 408 | Methylation with dimethyl sulfate |
| 87 | 4-cyano-N-(2-((1R,5S)-3-(4-oxocinnolin-1(4H)-yl)bicyclo[3.1.0]hexan-6-yl)propan-2-yl)benzamide | 412 | 413 | Exemplified |
| 88 | N-(2-((1R,5S)-3-(cinnolin-4-yloxy)bicyclo[3.1.0]hexan-6-yl)propan-2-yl)-4-cyanobenzamide | 412 | 413 | Exemplified |
| 89 | N-(1-((1R,3s,5S,6r)-3-(1H-benzo[d]imidazol-1-yl)bicyclo[3.1.0]hexan-6-yl)propyl)-4-chlorobenzamide | 393 | 394 | MS displacement |
| 90 | N-(1-((1R,3s,5S,6r)-3-azidobicyclo[3.1.0]hexan-6-yl)propyl)-4-chlorobenzamide | 318 | 319 | MS displacement |
| 91 | 4-chloro-N-(1-((1R,3s,5S,6r)-3-(4-cyclopropyl-1H-1,2,3-triazol-1-yl)bicyclo[3.1.0]hexan-6-yl)propyl)benzamide | 384 | 385 | Exemplified Click |
| 92 | 4-chloro-N-(1-((1R,3s,5S,6r)-3-((4-chloro-2-methylpyridin-3-yl)oxy)bicyclo[3.1.0]hexan-6-yl)propyl)benzamide | 418 | 419 | Example 4 SNAr |
| 93 | 4-chloro-N-(1-((1R,3s,5S,6r)-3-((3-fluoro-2-methylpyridin-4-yl)oxy)bicyclo[3.1.0]hexan-6-yl)propyl)benzamide | 402 | 403 | Example 4 SNAr |
| 94 | 1-((1R,3s,5S,6r)-6-(1-(4-chlorobenzamido)propyl)bicyclo[3.1.0]hexan-3-yl)-1H-1,2,3-triazole-4-carboxylic acid | 388 | 389 | Exemplified |
| 95 | 1-((1R,3s,5S,6r)-6-(1-(4-chlorobenzamido)propyl)bicyclo[3.1.0]hexan-3-yl)-1H-1,2,3-triazole-4-carboxamide | 387 | 388 | Exemplified |

TABLE 1-continued

| Compound | Name | Calc. Mass | Mass [M + H]+ | Synthesis as per |
|---|---|---|---|---|
| 96 | 4-chloro-N-(1-((1R,3s,5S,6r)-3-((tetrahydro-2H-pyran-4-yl)methoxy)bicyclo[3.1.0]hexan-6-yl)propyl)benzamide | 391 | 392 | MS displacement |
| 97 | 4-chloro-N-(1-((1R,3s,5S,6r)-3-(4-(2-hydroxypropan-2-yl)-1H-1,2,3-triazol-1-yl)bicyclo[3.1.0]hexan-6-yl)propyl)benzamide | 402 | 403 | Click |
| 98 | 4-chloro-N-(1-((1R,3s,5S,6r)-3-(4-(pyrrolidine-1-carbonyl)-1H-1,2,3-triazol-1-yl)bicyclo[3.1.0]hexan-6-yl)propyl)benzamide | 441 | 442 | HATU |
| 99 | N-(1-((1R,3s,5S,6r)-3-(1H-benzo[d][1,2,3]triazol-1-yl)bicyclo[3.1.0]hexan-6-yl)propyl)-4-chlorobenzamide | 394 | 395 | MS displacement |
| 100 | N-(1-((1R,3s,5S,6r)-3-(2H-benzo[d][1,2,3]triazol-2-yl)bicyclo[3.1.0]hexan-6-yl)propyl)-4-chlorobenzamide | 394 | 395 | MS displacement |
| 101 | 4-chloro-N-(1-((1R,3s,5S,6r)-3-((tetrahydro-2H-pyran-4-yl)oxy)bicyclo[3.1.0]hexan-6-yl)propyl)benzamide | 377 | 378 | MS displacement |
| 102 | 4-cyano-N-(1-((1R,3s,5S,6r)-3-((7-fluoroquinazolin-4-yl)oxy)bicyclo[3.1.0]hexan-6-yl)ethyl)benzamide | 416 | 417 | SNAr |
| 103 | 4-chloro-N-((S)-1-((1R,3R,5S,6r)-3-(cinnolin-4-yloxy)bicyclo[3.1.0]hexan-6-yl)propyl)benzamide | 421 | 422 | SNAr, Chiral SFC Separation |
| 104 | 4-chloro-N-((R)-1-((1R,3S,5S,6r)-3-(cinnolin-4-yloxy)bicyclo[3.1.0]hexan-6-yl)propyl)benzamide | 421 | 422 | SNAr, Chiral SFC Separation |
| 105 | 4-cyano-N-(1-((1R,3r,5S,6r)-3-hydroxybicyclo[3.1.0]hexan-6-yl)ethyl)benzamide | 270 | 271 | Example 1 |
| 106 | 4-cyano-N-(1-((1R,3s,5S,6r)-3-hydroxybicyclo[3.1.0]hexan-6-yl)ethyl)benzamide | 270 | 274 | Example 3 |
| 107 | 4-cyano-N-(1-((1R,3s,5S,6r)-3-((6-fluoroquinazolin-4-yl)oxy)bicyclo[3.1.0]hexan-6-yl)ethyl)benzamide | 416 | 417 | SNAr |
| 108 | 4-cyano-N-(1-((1R,3s,5S,6r)-3-(6-fluoro-4-oxoquinazolin-3(4H)-yl)bicyclo[3.1.0]hexan-6-yl)ethyl)benzamide | 416 | 417 | Example 5 Mitsunobu |

In more detail, the following synthetic schemes were used:

Synthesis of ethyl 3-(4-chlorobenzamido)-3-((1R,3s,5S, 6r)-3-(cinnolin-4-yloxy)bicyclo[3.1.0]hexan-6-yl)propanoate (Compound 84)

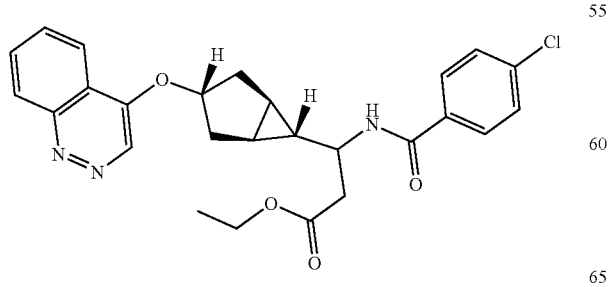

Step 1:

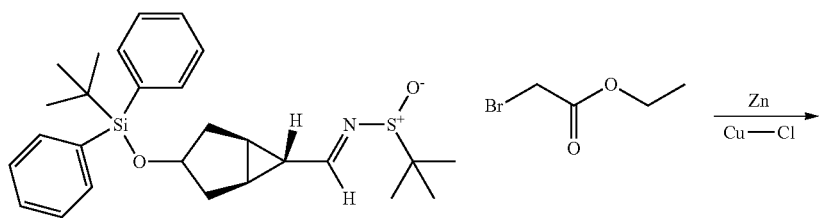

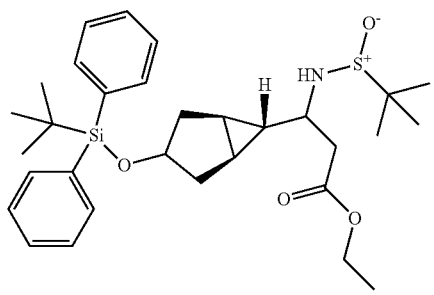

To a vial containing freshly activated zinc (327 mg, 5.00 mmol) was added CuCl (63.5 mg, 0.641 mmol), heated for 1 min, cooled, diluted with THF (1 mL), and heated in a dry block at 85° C. for 30 min. The mixture was cooled to room temperature, ethyl 2-bromoacetate (0.356 mL, 3.21 mmol, in THF, 1 mL) was added and the reaction was stirred at RT for 10 min, then at 50° C. for 30 min. The reaction was cooled to 0° C., N-((E)-((1R,5S,6r)-3-((tert-butyldiphenylsilyl)oxy) bicyclo[3.1.0]hexan-6-yl)methylene)-2-methylpropane-2-sulfinamide (320 mg, 0.684 mmol) in THF (2 mL) was added dropwise, and the reaction allowed to warm to room temperature overnight. The reaction was diluted with EtOAc, filtered through celite and washed with EtOAc. The filtrate was washed with sat'd NH$_4$Cl, sat'd NaCl, dried over MgSO4, filtered, concentrated (405.9 mg), and purified by flash chromatography to give ethyl 3-((1R,5S,6r)-3-((tert-butyldiphenylsilyl)oxy)bicyclo[3.1.0]hexan-6-yl)-3-((tert-butylsulfinyl)amino)propanoate (205 mg, 0.369 mmol, 53.9% yield) as a white solid. MS (ES$^+$) C$_{31}$H$_{45}$NO$_4$SSi requires: 555, found: 556 [M+H]$^+$.

Step 2:

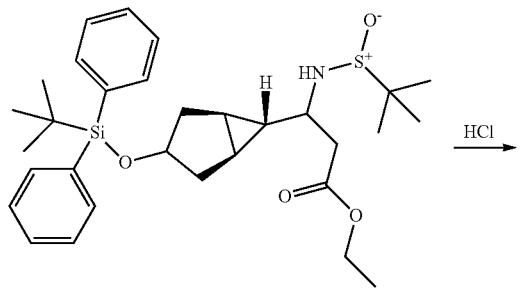

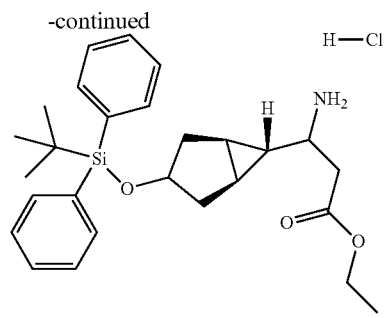

To a 0° C. solution of ethyl 3-((1R,5S,6r)-3-((tert-butyldiphenylsilyl)oxy)bicyclo[3.1.0]hexan-6-yl)-3-((tert-butylsulfinyl)amino)propanoate (205 mg, 0.369 mmol) in MeOH (3.6 mL) was added 4M HCl in Dioxane (460 μL, 1.84 mmol) The resulting mixture was stirred at 0° C. and warmed to RT over 1.5 hr. The reaction was concentrated and dried, to give ethyl 3-amino-3-((1R,5S,6r)-3-((tert-butyldiphenylsilyl)oxy)bicyclo[3.1.0]hexan-6-yl)propanoate hydrochloride (180 mg, 0.369 mmol, 100% yield, assumed) as an off white gum. MS (ES+) C$_{27}$H$_{37}$NO$_3$Si requires: 451, found: 452 [M+H]$^+$.

Step 3:

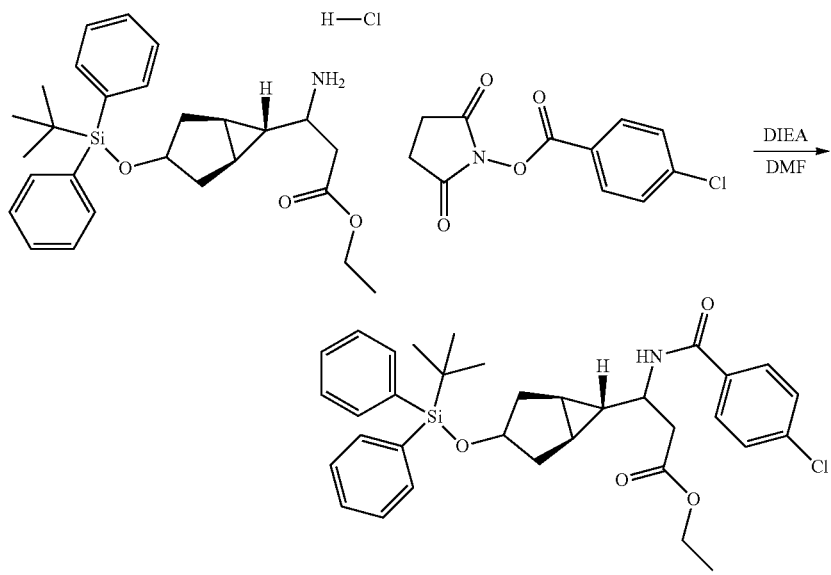

To a solution of ethyl 3-amino-3-((1R,5S,6r)-3-((tert-butyldiphenylsilyl)oxy)bicyclo[3.1.0]hexan-6-yl)propanoate hydrochloride (180 mg, 0.369 mmol) in DMF (1800 μL) was added DIEA (322 μl, 1.845 mmol) and the resulting mixture was stirred at room temperature for 10 min. To the solution was added 2,5-dioxopyrrolidin-1-yl 4-chlorobenzoate (103 mg, 0.406 mmol) and the reaction stirred at room temperature overnight. The reaction was concentrated, diluted with EtOAc and washed with sat'd NaHCO$_3$, water, and sat'd NaCl. The aqueous layers were extract with EtOAc (10 mL). The organic layers were combined, dried over MgSO$_4$, filtered, and concentrated to give ethyl 3-((1R,5S, 6r)-3-((tert-butyldiphenylsilyl)oxy)bicyclo[3.1.0]hexan-6-yl)-3-(4-chlorobenzamido)propanoate (227 mg, 0.346 mmol, 94% yield) as an off white solid. MS (ES+) C$_{34}$H$_{40}$ClNO$_4$Si requires: 589, found: 590 [M+H]+.

Step 4:

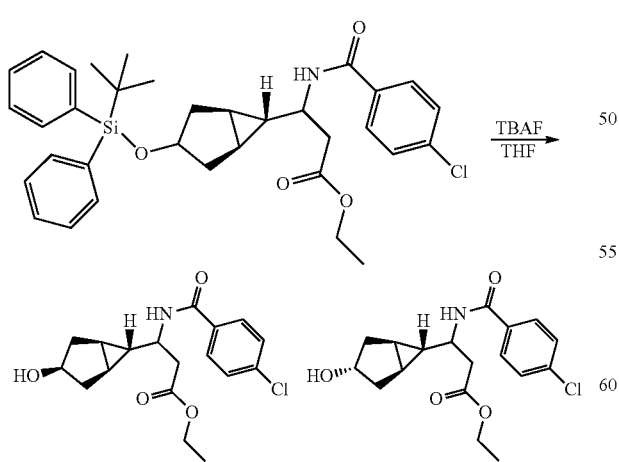

To a solution of ethyl 3-((1R,5S,6r)-3-((tert-butyldiphenylsilyl)oxy)bicyclo[3.1.0]hexan-6-yl)-3-(4-chlorobenzamido)propanoate (227 mg, 0.385 mmol) in THF (1900 μL) was added TBAF (1150 μL, 1.154 mmol) and the resulting solution was stirred at room temperature overnight. To the reaction was added more TBAF (1150 μL, 1.154 mmol) and stirred overnight. The reaction was concentrated, diluted with EtOAc, washed with water and sat'd NaCl. The aqueous layers were extracted with EtOAc. The organic layers were combined, dried over MgSO$_4$, filtered, concentrated, and purified by flash chromatography (0-50% of 8:2(EtOAc:IPA) in hexanes) to give ethyl 3-(4-chlorobenzamido)-3-((1R,3r,5S,6r)-3-hydroxybicyclo[3.1.0]hexan-6-yl)propanoate (86 mg, 0.244 mmol, 64% yield) as an off-white solid and ethyl 3-(4-chlorobenzamido)-3-((1R,3s,5S, 6r)-3-hydroxybicyclo[3.1.0]hexan-6-yl)propanoate (16 mg, 0.045 mmol, 12% yield) as a white solid. MS (ES$^+$) C$_{18}$H$_{22}$ClNO$_4$ requires: 351, found: 352 [M+H]$^+$.

Step 5:

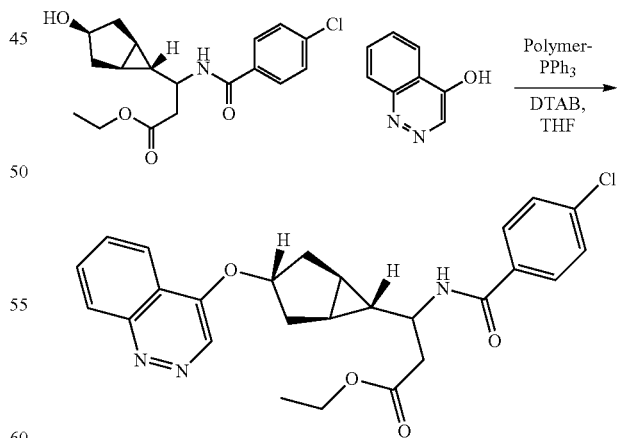

Ethyl 3-(4-chlorobenzamido)-3-((1R,3s,5 S,6r)-3-(cinnolin-4-yloxy)bicyclo[3.1.0]hexan-6-yl) propanoate was synthesized similar to the General Mitsunobu procedure from ethyl 3-(4-chlorobenzamido)-3-((1R,3r,5S,6r)-3-hydroxybicyclo[3.1.0]hexan-6-yl)propanoate (38.6 mg, 0.264 mmol) to give ethyl 3-(4-chlorobenzamido)-3-((1R,3s,5S,6r)-3-

(cinnolin-4-yloxy)bicyclo[3.1.0]hexan-6-yl)propanoate (44 mg, 0.092 mmol, 38.2% yield) white solid. MS (ES+) $C_{26}H_{26}ClN_3O_4$ requires: 479, found: 480 [M+H]+. 1H NMR (600 MHz, METHANOL-$d_4$) δ ppm 1.16 (d, J=9.44 Hz, 1H) 1.23 (t, J=7.18 Hz, 3H) 1.58-1.76 (m, 2H) 2.43-2.55 (m, 2H) 2.59-2.68 (m, 2H) 2.76 (d, J=6.80 Hz, 2H) 3.84-3.92 (m, 1H) 4.13 (q, J=6.55 Hz, 2H) 4.76-4.83 (m, 1H) 7.48 (d, J=8.31 Hz, 2H) 7.61-7.68 (m, 1H) 7.80 (d, J=8.69 Hz, 2H) 7.82-7.87 (m, 1H) 7.97 (d, J=8.69 Hz, 1H) 8.21-8.26 (m, 2H)

Synthesis of 2-(4-chlorophenyl)-N-((1R,3s, 5S 6r)-3-(cinnolin-4-yloxy)bicyclo[3.1.0]hexan-6-yl)-N-methylacetamide (Compound 86)

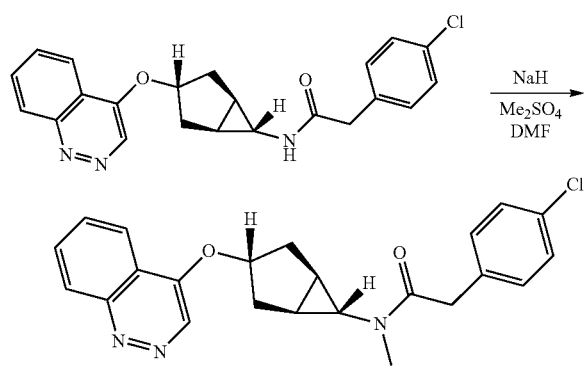

To a solution of 2-(4-chlorophenyl)-N-((1R,3 s,5 S,6r)-3-(cinnolin-4-yloxy)bicyclo[3.1.0]hexan-6-yl)acetamide (5.5 mg, 0.014 mmol) in DMF (0.3 mL) were added NaH (1.7 mg, 0.042 mmol) and dimethyl sulfate (2 µl, 0.02 mmol) and the resulting mixture was stirred at room temperature. After 1 h, additional dimethylsulfate was added. After several hours the mixture was quenched with 2 drops of conc. HCl, diluted with MeOH and purified by mass-triggered preparative HPLC (Mobile phase: A=0.1% TFA/$H_2O$, B=0.1% TFA/MeCN; Gradient: B=20-60%; 20 min; Column: C18) to give 2-(4-chlorophenyl)-N-((1R,3s,5S,6r)-3-(cinnolin-4-yloxy)bicyclo[3.1.0]hexan-6-yl)-N-methylacetamide (1.5 mg, 3.68 µmol, 26% yield) as an off-white amorphous material. MS(ES+) $C_{23}H_{22}ClN_3O_2$ requires: 407, found: 408 [M+H]+. 1H NMR (METHANOL-$d_4$) δ: 8.29-8.36 (m, 1H), 8.26 (d, J=8.3 Hz, 1H), 8.01 (d, J=8.7 Hz, 1H), 7.86-7.92 (m, 1H), 7.66-7.74 (m, 1H), 7.30-7.36 (m, 2H), 7.20-7.29 (m, 2H), 4.86-4.91 (m, 1H), 3.69-3.97 (m, 2H), 2.91-3.09 (m, 3H), 2.55-2.81 (m, 5H), 1.79-2.11 (m, 2H).

Synthesis of 4-cyano-N-(2-((1R,5S)-3-(4-oxocinnolin-1(4H)-yl)bicyclo[3.1.0]hexan-6-yl)propan-2-yl)benzamide (Compound 87)

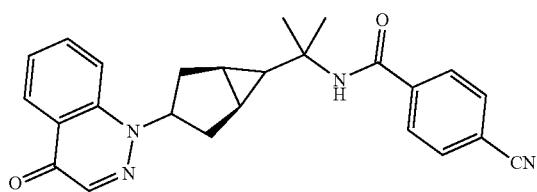

Step 1:

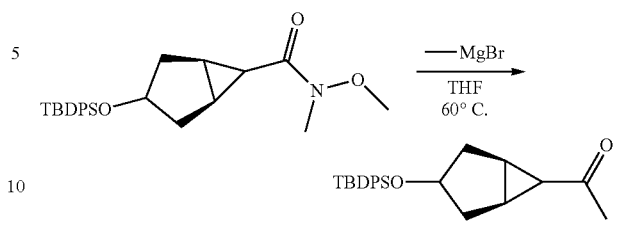

To a cooled 0° C. solution of (1R,5S)-3-((tert-butyldiphenylsilyl)oxy)-N-methoxy-N-methylbicyclo[3.1.0]hexane-6-carboxamide (2.74 g, 6.47 mmol) in THF (11 mL) was added methylmagnesium bromide (1M in THF) (12.94 mL, 12.94 mmol) and the resulting mixture was stirred at 0° C. for 10 min and then at 60° C. overnight. The reaction was allowed to cool to room temperature, diluted with EtOAc (100 mL), and washed with 1M HCl (100 mL) and sat'd NaCl (100 mL), dried over $Na_2SO_4$, filtered, and concentrated to give 1-((1R,5S)-3-((tert-butyldiphenylsilyl)oxy)bicyclo[3.1.0]hexan-6-yl)ethanone (1.88 g, 4.97 mmol, 77% yield) as a clear oil. Product was taken on without further purification. MS(ES+) $C_{24}H_{30}O_2Si$ requires: 378, found: 401 [M+Na]+.

Step 2:

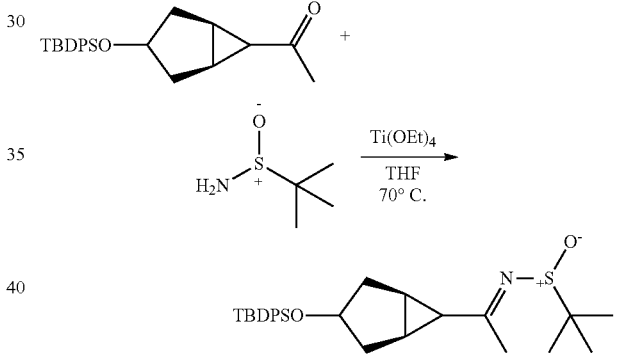

To a solution of 1-((1R,5 S)-3-((tert-butyldiphenylsilyl)oxy)bicyclo[3.1.0]hexan-6-yl)ethanone (1.88 g, 4.97 mmol) in THF (4 mL) were added 2-methylpropane-2-sulfinamide (0.722 g, 5.96 mmol) and tetraethoxytitanium (2.67 g, 9.93 mmol) and the resulting mixture was stirred at 70° C. for 44 h. The residue was adsorbed onto silica gel and purified via flash chromatography (0-100% EtOAc in hexanes) to give (E)-N-(1-((1R,5S)-3-((tert-butyldiphenylsilyl)oxy)bicyclo[3.1.0]hexan-6-yl)ethylidene)-2-methylpropane-2-sulfinamide (1.85 g, 3.84 mmol, 77% yield) as a clear oil. MS(ES+) $C_{28}H_{39}NO_2SSi$ requires: 481, found: 482 [M+H]+.

Step 3:

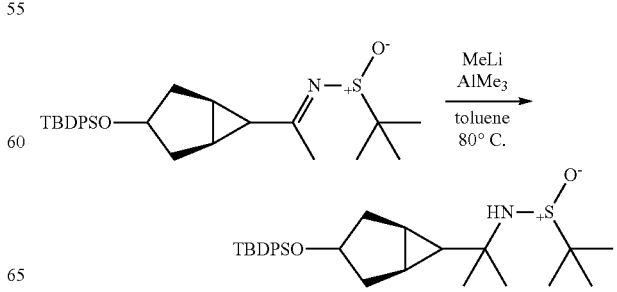

To a stirred solution of (E)-N-(1-((1R,5S)-3-((tert-butyldiphenylsilyl)oxy)bicyclo[3.1.0]hexan-6-yl)ethylidene)-2-methylpropane-2-sulfinamide (1.85 g, 3.84 mmol) in toluene (38.4 mL) at 80° C. was added trimethylaluminum (2 M in toluene) (2.112 mL, 4.22 mmol) under nitrogen atmosphere. After 20 minutes, methyllithium (5.28 mL, 8.45 mmol) was added dropwise and the mixture stirred at 80° C. for 4 hours. The reaction was quenched with 2 mL of water. The residue was adsorbed onto silica gel and purified via flash chromatography (0-80% EtOAc in hexanes to give N-(2-((1R,5S)-3-((tert-butyldiphenylsilyl)oxy)bicyclo[3.1.0]hexan-6-yl)propan-2-yl)-2-methylpropane-2-sulfinamide (394 mg, 0.791 mmol, 20.61% yield) as a yellow oil. MS(ES$^+$) $C_{29}H_{43}NO_2SSi$ requires: 497, found: 498 [M+H]$^+$.

Step 4:

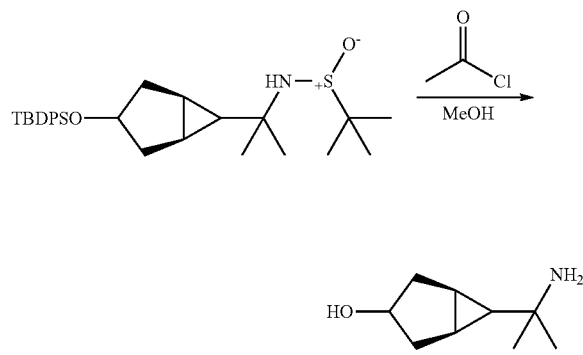

(1R,5S)-6-(2-aminopropan-2-yl)bicyclo[3.1.0]hexan-3-ol was synthesized similar to example 1 step 4 to give (1R,5S)-6-(2-aminopropan-2-yl)bicyclo[3.1.0]hexan-3-ol as an oily black suspension the was used immediately in the next step. MS(ES+) $C_9H_{17}NO$ requires: 155, found: 156 [M+H]$^+$.

Step 5:

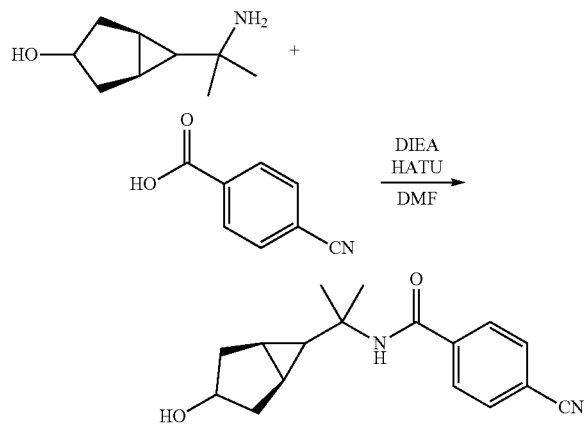

4-cyano-N-(2-((1R,5S)-3-hydroxybicyclo[3.1.0]hexan-6-yl)propan-2-yl)benzamide was synthesized similar Example 1 step 5 amide coupling procedure using HATU, DIEA, and DMF to give 4-cyano-N-(2-((1R,5S)-3-hydroxybicyclo[3.1.0]hexan-6-yl)propan-2-yl)benzamide as a yellow solid (80 mg, 0.28 mmol, 71% yield). MS (ES$^+$) $C_{17}H_{20}N_2O_2$ requires: 284, found: 285 [M+H]$^+$.

Step 6:

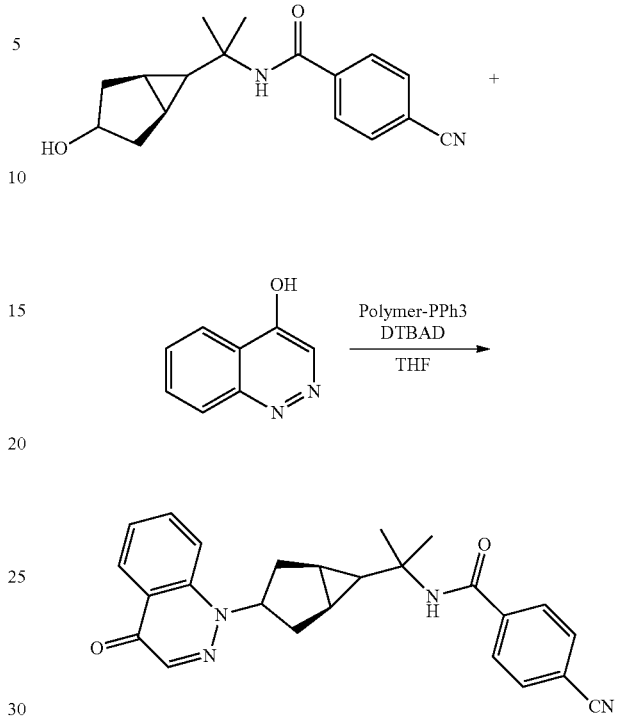

4-cyano-N-(2-((1R,5S)-3-(4-oxocinnolin-1(4H)-yl)bicyclo[3.1.0]hexan-6-yl)propan-2-yl)benzamide was synthesized using the General Mitsunobu Procedure to give a white powder (1 mg, 2 μmol, 1% yield). MS(ES$^+$) $C_{25}H_{24}N_4O_2$ requires: 412, found: 413 [M+H]$^+$. $^1$H NMR (METHANOL-d$_4$) δ: 9.07 (s, 1H), 8.32 (d, J=8.7 Hz, 1H), 8.23 (d, J=8.7 Hz, 1H), 7.88-7.96 (m, 3H), 7.76-7.86 (m, 3H), 5.07-5.13 (m, 1H), 2.56-2.63 (m, 2H), 2.12-2.19 (m, 2H), 1.67 (m, 2H), 1.38 (s, 6H), 1.35 (m, 1H).

Synthesis of N-(2-((R, 5S)-3-(cinnolin-4-yloxy)bicyclo[3.1.0]hexan-6-yl)propan-2-yl)-4-cyanobenzamide (Compound 88)

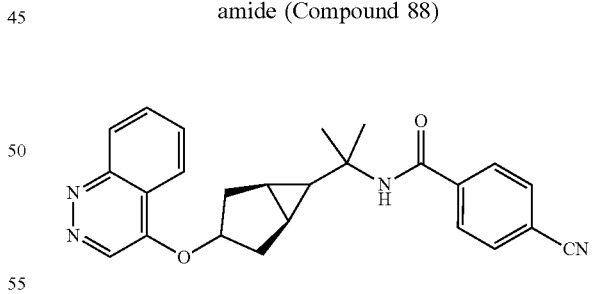

N-(2-((1R,5S)-3-(cinnolin-4-yloxy)bicyclo[3.1.0]hexan-6-yl)propan-2-yl)-4-cyanobenzamide was isolated from the purification of 4-cyano-N-(2-((1R,5S)-3-(4-oxocinnolin-1(4H)-yl)bicyclo[3.1.0]hexan-6-yl)propan-2-yl)benzamide (supra) with further elution to give a white solid (11 mg, 0.027 mmol, 18% yield). MS(ES$^+$) $C_{25}H_{24}N_4O_2$ requires: 412, found: 413 [M+H]$^+$. $^1$H NMR (METHANOL-d$_4$) δ: 8.26 (s, 1H), 8.24 (d, J=7.9 Hz, 1H), 7.97 (d, J=8.7 Hz, 1H), 7.89 (d, J=8.3 Hz, 2H), 7.80-7.86 (m, 3H), 7.62-7.67 (m, 1H), 4.86-4.92 (m, 1H), 2.61-2.70 (m, 2H), 2.47-2.54 (m, 2H), 1.73 (m, 2H), 1.50 (m, 1H), 1.40 (s, 6H).

Synthesis of N-(1-((1R,3s, 5S, 6r)-3-(1H-benzo[d]imidazol-1-yl)bicyclo[3.1.0]hexan-6-yl)propyl)-4-chlorobenzamide (Compound 89)

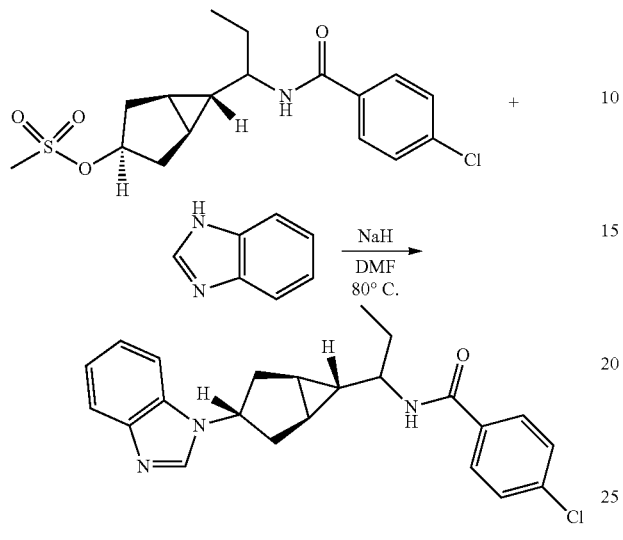

N-(1-((1R,3s,5S,6r)-3-(1H-benzo[d]imidazol-1-yl)bicyclo[3.1.0]hexan-6-yl)propyl)-4-chlorobenzamide was synthesized using the General Mesylate displacement procedure from (1R,3r,5S,6r)-6-(1-(4-chlorobenzamido)propyl)bicyclo[3.1.0]hexan-3-yl methanesulfonate and 1H-benzo[d]imidazole to give a white powder. MS(ES$^+$) C$_{23}$H$_{24}$ClN$_3$O requires: 393, found: 394 [M+H]$^+$. $^1$H NMR (METHANOL-d$_4$) δ: 9.50 (s, 1H), 8.45-8.50 (d, J=8.5 Hz, 1H), 7.97 (m, 1H), 7.75-7.87 (m, 3H), 7.62-7.71 (m, 2H), 7.49 (d, J=8.5 Hz, 2H), 4.83-4.90 (m, 1H), 3.40-3.51 (m, 1H), 2.52-2.68 (m, 2H), 2.34-2.47 (m, 2H), 1.71-1.85 (m, 2H), 1.59-1.71 (m, 2H), 1.14-1.20 (m, 1H), 1.01 (t, J=7.3 Hz, 3H).

Synthesis of N-(1-((R, 3s, 5S, 6r)-3-azidobicyclo[3.1.0]hexan-6-yl)propyl)-4-chlorobenzamide (Compound 90)

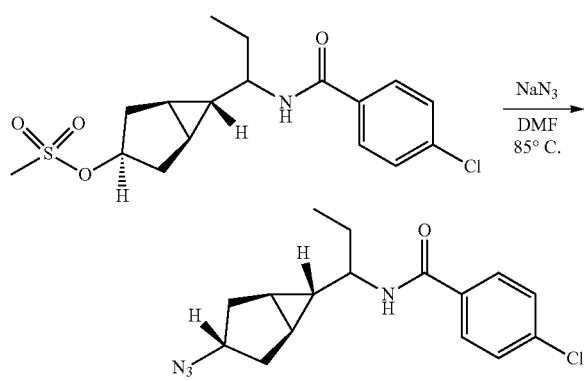

To a solution of (1R,3r,5S,6r)-6-(1-(4-chlorobenzamido)propyl)bicyclo[3.1.0]hexan-3-yl methanesulfonate (100 mg, 0.269 mmol) in DMF (672 µl) was added sodium azide (69.9 mg, 1.076 mmol) and the resulting mixture was stirred at 85° C. for 1 h. The reaction mixture was diluted with EtOAc (50 mL) and washed with H$_2$O (50 mL) and sat'd NaCl (50 mL), dried over Na$_2$SO$_4$, filtered, and concentrated to give N-(1-((1R,3s,5S,6r)-3-azidobicyclo[3.1.0]hexan-6-yl)propyl)-4-chlorobenzamide that was used without further purification. MS(ES$^+$) C$_{16}$H$_{19}$ClN$_4$O requires: 318, found: 319 [M+H]$^+$.

Synthesis of 4-chloro-N-(1-((1R,3s, 5S, 6r)-3-(4-cyclopropyl-1H-1,2,3-triazol-1-yl)bicyclo[3.1.0]hexan-6-yl)propyl)benzamide (Compound 91)

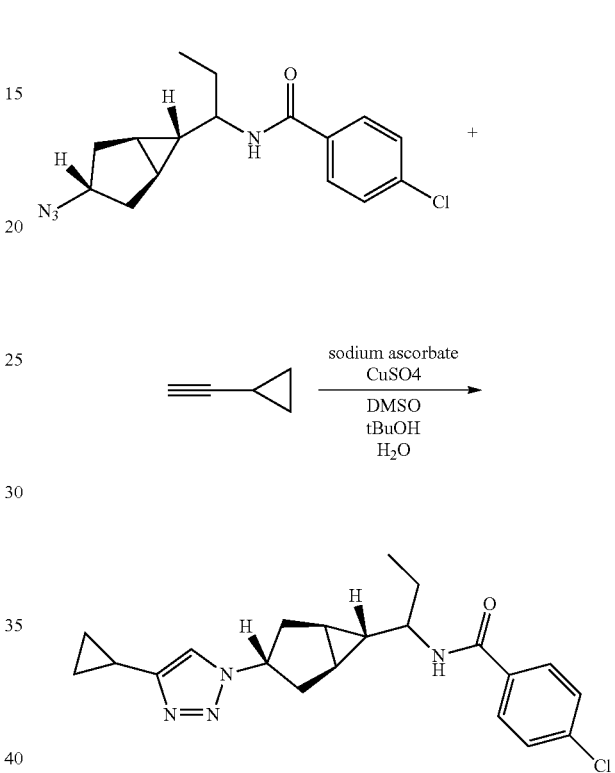

Step 1: (General "Click" Procedure for 1,4 Substituted Triazoles)

To a solution of N-(1-((1R,3s,5S,6r)-3-azidobicyclo[3.1.0]hexan-6-yl)propyl)-4-chlorobenzamide (10 mg, 0.031 mmol) in DMSO (35 µl) were added ethynylcyclopropane (2.5 mg, 0.038 mmol), sodium ascorbate (6 mg, 0.031 mmol) dissolved in 40 µL of water, copper(II) sulfate (0.5 mg, 3 µmol) dissolved in 10 µL of water, and tBuOH (160 µl) and the resulting mixture was stirred at room temperature for 72 h. The residue was acidified with TFA and purified by mass-triggered preparative HPLC (Mobile phase: A=0.1% TFA/H$_2$O, B=0.1% TFA/MeCN; Gradient: B=30-70%; 20 min; Column: C18) to give 4-chloro-N—((R)-1-((1R,3S,5S,6r)-3-(4-cyclopropyl-1H-1,2,3-triazol-1-yl)bicyclo[3.1.0]hexan-6-yl)propyl)benzamide (4 mg, 10 µmol, 33% yield) as a white solid. MS(ES$^+$) C$_{21}$H$_{25}$ClN$_4$O requires: 384, found: 385 [M+H]$^+$. $^1$H NMR (METHANOL-d$_4$) δ: 8.44 (d, J=8.5 Hz, 1H), 7.81 (d, J=8.5 Hz, 2H), 7.72 (s, 1H), 7.48 (d, J=8.5 Hz, 2H), 4.55-4.70 (m, 1H), 3.30-3.9 (m, 1H), 2.32-2.49 (m, 2H), 2.18-2.31 (m, 2H), 1.87-1.97 (m, 1H), 1.62-1.81 (m, 2H), 1.43-1.58 (m, 2H), 0.89-1.04 (m, 6H), 0.70-0.77 (n, 2H).

Synthesis of 1-((1R,3s, 5S, 6r)-6-(1-(4-chlorobenzamido)propyl)bicyclo[3.1.0]hexan-3-yl)-1H-1,2,3-triazole-4-carboxylic acid (Compound 94)

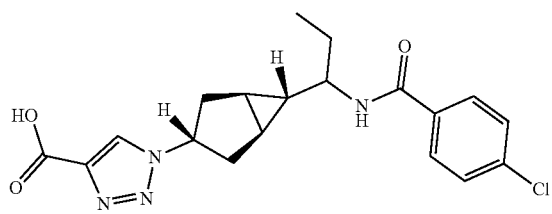 [SMILES: CCC(NC(=O)c1ccc(Cl)cc1)[C@H]1[C@@H]2C[C@@H](n3cc(C(=O)O)nn3)C[C@@H]21]

Step 1:

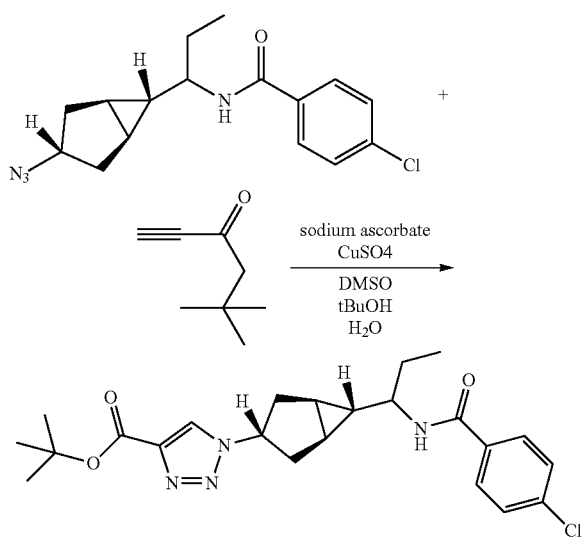

Tert-butyl 1-((1R,3s,5S,6r)-6-(1-(4-chlorobenzamido) propyl)bicyclo[3.1.0]hexan-3-yl)-1H-1,2,3-triazole-4-carboxylate was synthesized using the General Click Procedure for 1,4 Triazoles from N-(1-((1R,3s,5 S,6r)-3-azidobicyclo [3.1.0]hexan-6-yl)propyl)-4-chlorobenzamide and tert-butyl propiolate to give a pale pink solid. MS(ES$^+$) $C_{23}H_{29}ClN_4O_3$ requires: 444, found: 445 [M+H]$^+$.

Step 2:

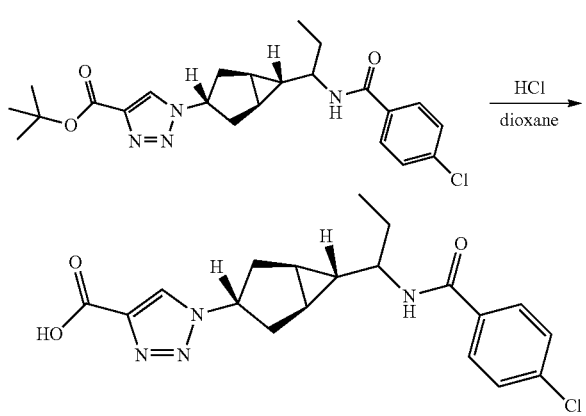

HCl (4 M in dioxane) (1058 µl, 4.23 mmol) was slowly added to tert-butyl 1-((1R,3s,5S,6r)-6-(1-(4-chlorobenzamido)propyl)bicyclo[3.1.0]hexan-3-yl)-1H-1,2,3-triazole-4-carboxylate (53 mg, 0.12 mmol) and the reaction mixture was allowed to stir at RT for 6 h. The volatiles were removed under reduced pressure to give 1-((1R,3s,5S,6r)-6-(1-(4-chlorobenzamido)propyl)bicyclo[3.1.0]hexan-3-yl)-1H-1,2,3-triazole-4-carboxylic acid (48 mg, 0.123 mmol, 102% yield) as a white crystalline solid. A small aliquot of product was purified by mass-triggered preparative HPLC (Mobile phase: A=0.1% TFA/H$_2$O, B=0.1% TFA/MeCN; Gradient: B=40-60%; 20 min; Column: C18). The rest of the product was taken on without further purification. MS(ES$^+$) $C_{19}H_{21}ClN_4O_3$ requires: 388, found: 389 [M+H]$^+$. $^1$H NMR (DMSO-d$_6$) δ: 13.04 (br. s., 1H), 8.71 (s, 1H), 8.33 (d, J=8.5 Hz, 1H), 7.88 (d, J=8.5 Hz, 2H), 7.54 (d, J=8.5 Hz, 2H), 4.63-4.83 (m, 1H), 3.35-3.42 (m, 1H), 2.27-2.43 (m, 2H), 2.15-2.26 (m, 2H), 1.55-1.71 (m, 2H), 1.37-1.51 (m, 2H), 0.96-1.03 (m, 1H), 0.85-0.95 (m, 3H).

Synthesis of 1-((R, 3s, 5S, 6r)-6-(1-(4-chlorobenzamido)propyl)bicyclo[3.1.0]hexan-3-yl)-1H-1,2,3-triazole-4-carboxamide (Compound 95)

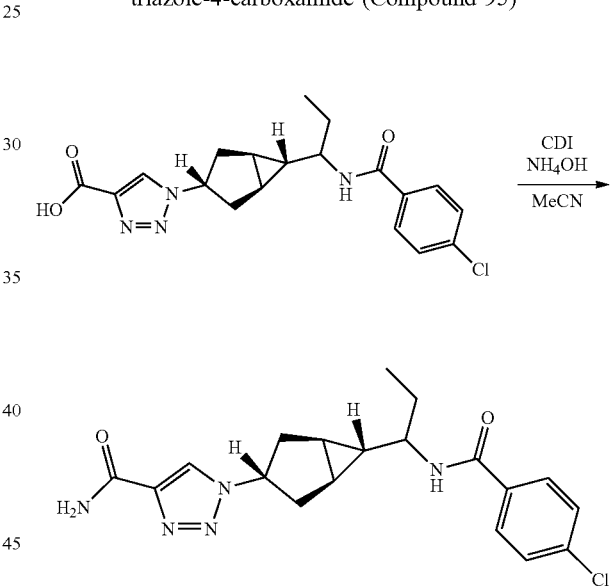

To a solution of 1-((1R,3s,5S,6r)-6-(1-(4-chlorobenzamido)propyl)bicyclo[3.1.0]hexan-3-yl)-1H-1,2,3-triazole-4-carboxylic acid (20 mg, 0.051 mmol) in acetonitrile (257 µl) was added CDI (8.34 mg, 0.051 mmol) and the resulting mixture was stirred at room temperature for 30 min. Ammonium hydroxide (40 µl, 1.0 mmol) was added and the reaction mixture was stirred at room temperature for 2 h. The residue was acidified with TFA and purified by reverse phase preparative HPLC (Mobile phase: A=0.1% TFA/H$_2$O, B=0.1% TFA/MeCN; Gradient: B=40-60%; 20 min; Column: C18) to give 1-((1R,3s,5S,6r)-6-(1-(4-chlorobenzamido)propyl)bicyclo[3.1.0]hexan-3-yl)-1H-1,2,3-triazole-4-carboxamide (1 mg, 2 µmol, 5% yield) as a white solid. MS(ES$^+$) $C_{19}H_{22}ClN_5O_2$ requires: 387, found: 388 [M+H]$^+$.

Synthesis of 4-chloro-N-(1-((1R,3s, 5S, 6r)-3-(4-(pyrrolidine-1-carbonyl)-1H-1,2,3-triazol-1-yl)bicyclo[3.1.0]hexan-6-yl)propyl)benzamide (Compound 98)

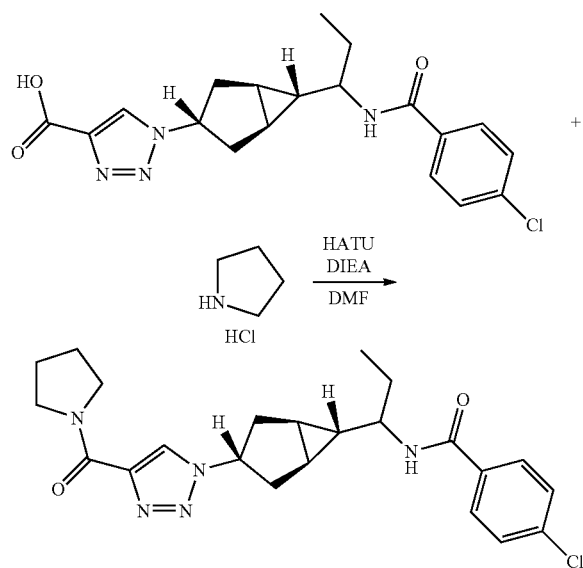

Step 1: (Standard HATU Amide Coupling)

To a solution of 1-((1R,3s,5S,6r)-6-(1-(4-chlorobenzamido)propyl)bicyclo[3.1.0]hexan-3-yl)-1H-1,2,3-triazole-4-carboxylic acid (10 mg, 0.026 mmol) in DMF (129 µl) were added pyrrolidine-HCl (2.74 mg, 0.039 mmol), HATU (14.67 mg, 0.039 mmol) and DIEA (13.47 µl, 0.077 mmol) and the resulting mixture was stirred at room temperature for 1 h. The residue was acidified with TFA, concentrated, and purified by mass-triggered preparative HPLC (Mobile phase: A=0.1% TFA/H$_2$O, B=0.1% TFA/MeCN; Gradient: B=30-70%; 20 min; Column: C18) to give 4-chloro-N-(1-((1R,3s,5S,6r)-3-(4-(pyrrolidine-1-carbonyl)-1H-1,2,3-triazol-1-yl)bicyclo[3.1.0]hexan-6-yl)propyl)benzamide (5.27 mg, 0.012 mmol, 46.4% yield) as a white powder. MS(ES$^+$) C$_{23}$H$_{28}$ClN$_5$O$_2$ requires: 441, found: 442 [M+H]$^+$. $^1$H NMR (METHANOL-d$_4$) δ: 8.37 (s, 1H), 7.81 (d, J=8.5 Hz, 2H), 7.47 (d, J=8.5 Hz, 2H), 4.69-4.80 (m, 1H), 3.96 (t, J=6.7 Hz, 2H), 3.60 (t, J=6.9 Hz, 2H), 3.35-3.43 (m, 1H), 2.38-2.54 (m, 2H), 2.25-2.37 (m, 2H), 1.90-2.05 (m, 4H), 1.64-1.82 (m, 2H), 1.49-1.61 (m, 2H), 1.00-1.07 (m, 1H), 0.99 (t, J=7.5 Hz, 3H).

Synthesis of 4-chloro-N-(1-((1R,3s, 5S, 6r)-3-((tetrahydro-2H-pyran-4-yl)oxy)bicyclo[3.1.0]hexan-6-yl)propyl)benzamide (Compound 101)

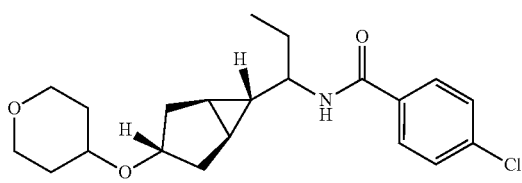 [SMILES: CCC(NC(=O)c1ccc(Cl)cc1)[C@H]1[C@@H]2C[C@@H](OC3CCOCC3)C[C@@H]21]

Step 1:

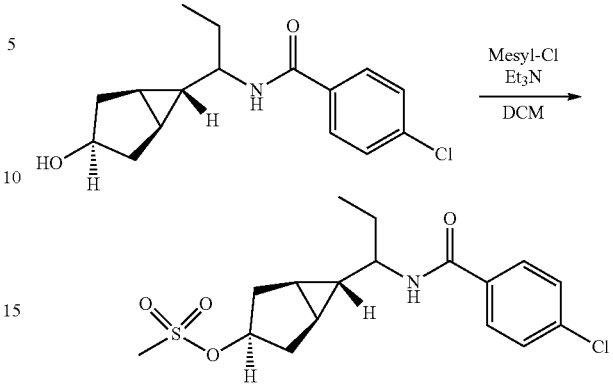

To a solution of 4-chloro-N-(1-((1R,3r,5S,6r)-3-hydroxybicyclo[3.1.0]hexan-6-yl)propyl)benzamide (264 mg, 0.674 mmol) in DCM (6 mL) were added triethylamine (188 µl, 1.35 mmol) and methanesulfonyl chloride (58 µl, 0.74 mmol) and the resulting mixture was stirred at room temperature for 1 h. The reaction mixture was diluted with DCM (50 mL) and washed with 1M HCl (50 mL). The layers were separated, and the organic layer was washed with sat'd NaCl (50 mL), dried over Na$_2$SO$_4$, filtered, concentrated, and purified via silica gel chromatography (0-80% EtOAc in hexanes) to give (1R,3r,5S,6r)-6-(1-(4-chlorobenzamido)propyl)bicyclo[3.1.0]hexan-3-yl methanesulfonate (208.7 mg, 0.561 mmol, 83% yield) as a pale yellow powder. MS(ES$^+$) C$_{17}$H$_{22}$ClNO$_4$S requires: 371, found: 372 [M+H]$^+$.

Step 2: (General Mesylate Displacement (S$_N$2) Procedure, "MS")

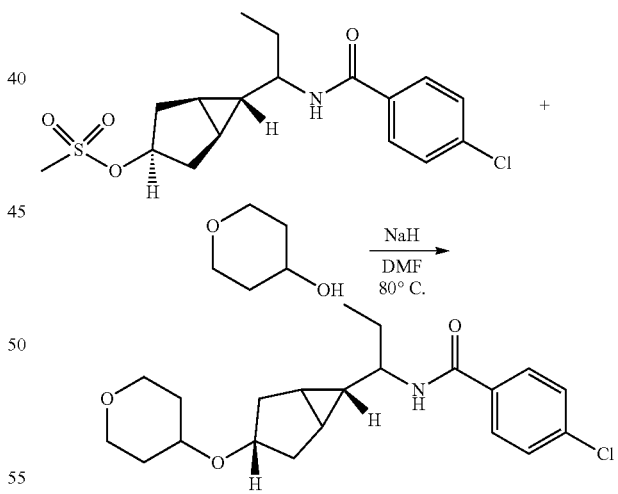

To a solution of tetrahydro-2H-pyran-4-ol (68 mg, 0.67 mmol) in DMF (336 µl) cooled in an ice bath was added sodium hydride (5.4 mg, 0.13 mmol) and the resulting mixture was stirred at RT for 5 min. (1R,3r,5S,6r)-6-(1-(4-chlorobenzamido)propyl)bicyclo[3.1.0]hexan-3-yl methanesulfonate (25 mg, 0.067 mmol) was added and the reaction mixture was heated to 80° C. and stirred for 5 h. The reaction was purified by mass-triggered preparative HPLC (Mobile phase: A=0.1% TFA/H$_2$O, B=0.1% TFA/MeCN; Gradient: B=40-80%; 20 min; Column: C18) to give 4-chloro-N-(1-((1R,3s,5 S,6r)-3-((tetrahydro-2H-pyran-4- yl)oxy)bicyclo[3.1.0]hexan-6-yl)propyl)benzamide (1 mg, 2.6 μmol, 4% yield) as a clear oil. MS(ES+) $C_{21}H_{28}ClNO_3$ requires: 377, found: 378 [M+H]+. 1H NMR (METHANOL-d4) δ: 7.78 (d, J=8.5 Hz, 2H), 7.46 (d, J=8.5 Hz, 2H), 3.77-3.92 (m, 3H), 3.36-3.53 (m, 3H), 3.19-3.27 (m, 1H), 2.06-2.22 (m, 2H), 1.78-1.89 (m, 2H), 1.56-1.74 (m, 4H), 1.37-1.51 (m, 2H), 1.22-1.35 (m, 2H), 0.90-1.00 (m, 3H), 0.65-0.72 (m, 1H)

Example 15: Synthesis of Compounds 109 to 263

The following compounds in Table 2 were prepared according to the synthetic procedures described herein. For each compound, the table indicates the chemical structure, the calculated and measured mass, and details of the method by which the compound was prepared. The terms "SNAr", "Amide coupling", "Mitsunobu", "1,4 Triazole", "Click", "MS", "1,5 Triazole" and "Bzl" are as described herein.

TABLE 2

| Compound | Structure | Calc. Mass | Mass [M + H]+ | Synthesis as per |
|---|---|---|---|---|
| 109 | 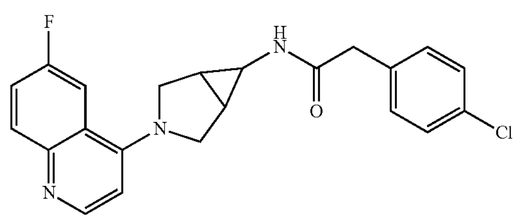 [SMILES: O=C(Cc1ccc(Cl)cc1)NC1C2CN(c3ccnc4ccc(F)cc34)CC21] | 395 | 396 | Exemplified |
| 110 | 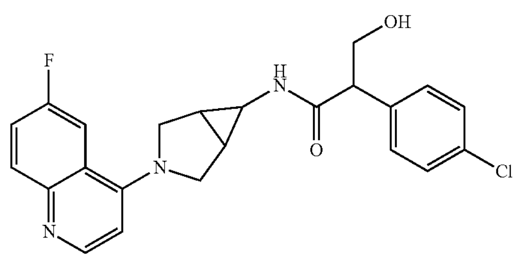 [SMILES: O=C(NC1C2CN(c3ccnc4ccc(F)cc34)CC21)C(CO)c1ccc(Cl)cc1] | 391 | 392 | Compound 109 |
| 111 | 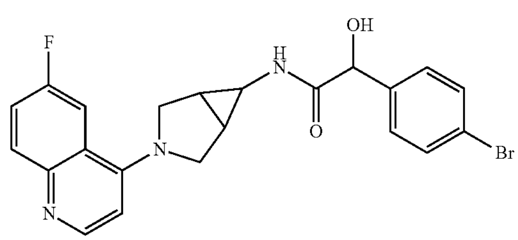 [SMILES: O=C(NC1C2CN(c3ccnc4ccc(F)cc34)CC21)C(O)c1ccc(Br)cc1] | 456 | 457 | Compound 109 |
| 112 | 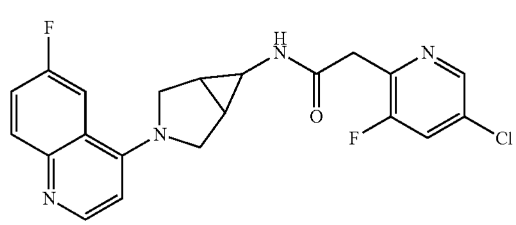 [SMILES: O=C(Cc1ncc(Cl)cc1F)NC1C2CN(c3ccnc4ccc(F)cc34)CC21] | 414 | 415 | Compound 109 |
| 113 | 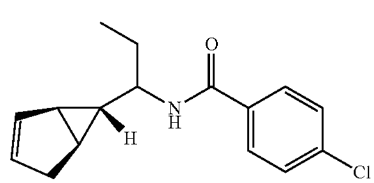 [SMILES: CCC(NC(=O)c1ccc(Cl)cc1)[C@H]1[C@@H]2C=CC[C@@H]21] | 275 | 276 | Exemplified |

TABLE 2-continued

| Compound | Structure | Calc. Mass | Mass [M + H]+ | Synthesis as per |
|---|---|---|---|---|
| 114 | 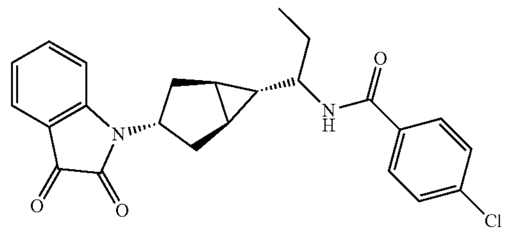 [SMILES: CCC(NC(=O)c1ccc(Cl)cc1)[C@H]1[C@@H]2C[C@@H](N3C(=O)C(=O)c4ccccc43)C[C@@H]21] | 422 | 423 | Exemplified |
| 115 | 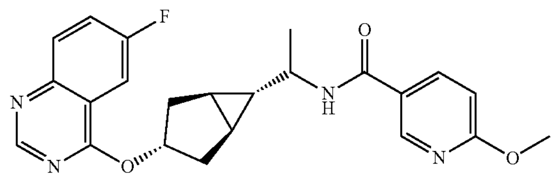 [SMILES: COc1ccc(C(=O)NC(C)[C@H]2[C@@H]3C[C@@H](Oc4ncnc5ccc(F)cc45)C[C@@H]32)cn1] | 422 | 423 | SNAr |
| 116 | 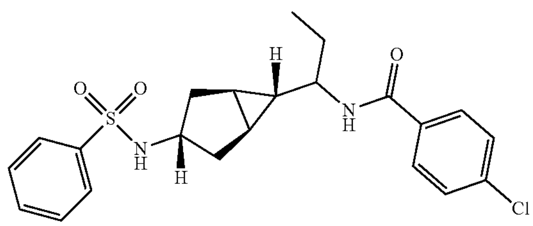 [SMILES: CCC(NC(=O)c1ccc(Cl)cc1)[C@H]1[C@@H]2C[C@@H](NS(=O)(=O)c3ccccc3)C[C@@H]21] | 432 | 433 | Exemplified |
| 117 | 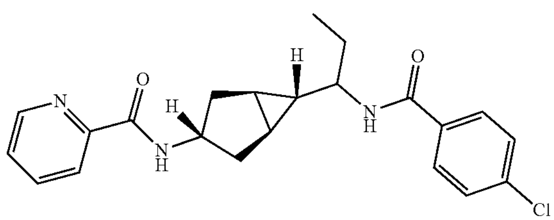 [SMILES: CCC(NC(=O)c1ccc(Cl)cc1)[C@H]1[C@@H]2C[C@@H](NC(=O)c3ccccn3)C[C@@H]21] | 397 | 398 | Exemplified |
| 118 | 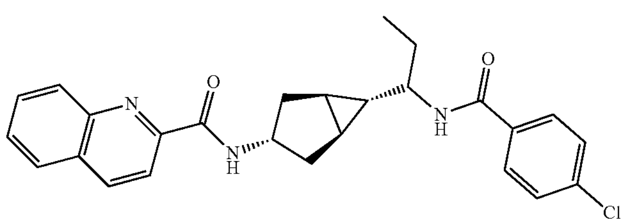 [SMILES: CCC(NC(=O)c1ccc(Cl)cc1)[C@H]1[C@@H]2C[C@@H](NC(=O)c3ccc4ccccc4n3)C[C@@H]21] | 447 | 448 | Amide coupling |
| 119 | 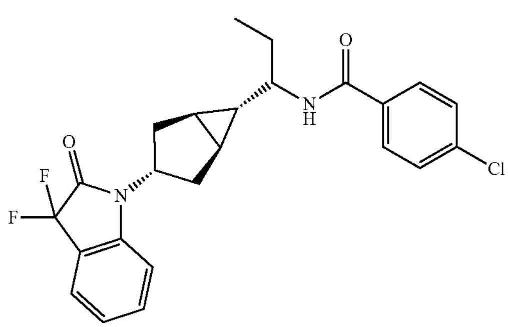 [SMILES: CCC(NC(=O)c1ccc(Cl)cc1)[C@H]1[C@@H]2C[C@@H](N3C(=O)C(F)(F)c4ccccc43)C[C@@H]21] | 444 | 445 | Exemplified |

TABLE 2-continued

| Compound | Structure | Calc. Mass | Mass [M + H]⁺ | Synthesis as per |
|---|---|---|---|---|
| 120 | 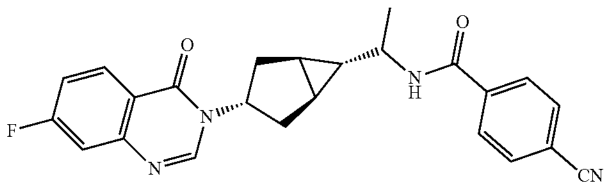 [SMILES: CC(NC(=O)c1ccc(C#N)cc1)[C@H]1[C@@H]2C[C@@H](n3cnc4cc(F)ccc4c3=O)C[C@@H]21] | 416 | 417 | Mitsunobu |
| 121 | 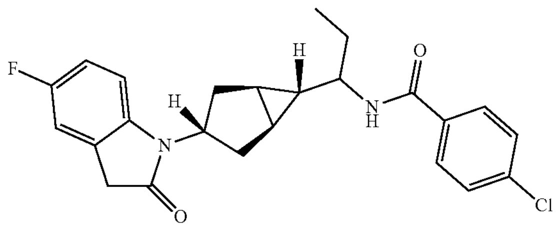 [SMILES: CCC(NC(=O)c1ccc(Cl)cc1)[C@H]1[C@@H]2C[C@@H](N3C(=O)Cc4cc(F)ccc43)C[C@@H]21] | 426 | 427 | Exemplified |
| 122 | 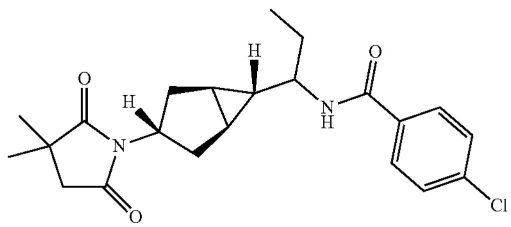 [SMILES: CCC(NC(=O)c1ccc(Cl)cc1)[C@H]1[C@@H]2C[C@@H](N3C(=O)CC(C)(C)C3=O)C[C@@H]21] | 402 | 403 | Exemplified |
| 123 | 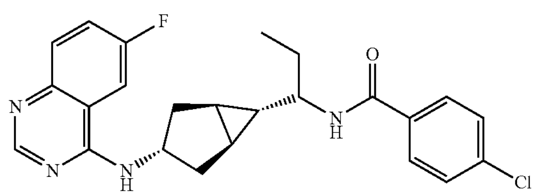 [SMILES: CCC(NC(=O)c1ccc(Cl)cc1)[C@H]1[C@@H]2C[C@@H](Nc3ncnc4ccc(F)cc34)C[C@@H]21] | 438 | 439 | SNAr |
| 124 | 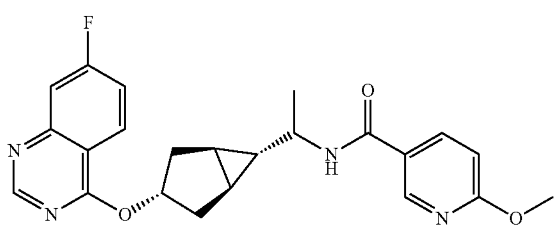 [SMILES: COc1ccc(C(=O)NC(C)[C@H]2[C@@H]3C[C@@H](Oc4ncnc5cc(F)ccc45)C[C@@H]32)cn1] | 422 | 423 | SNAr |
| 125 | 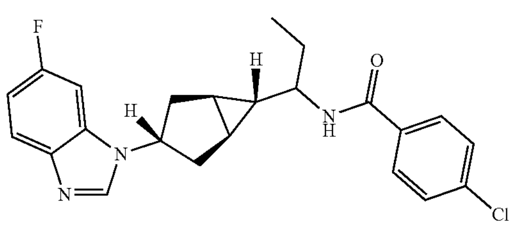 [SMILES: CCC(NC(=O)c1ccc(Cl)cc1)[C@H]1[C@@H]2C[C@@H](n3cnc4ccc(F)cc43)C[C@@H]21] | 411 | 412 | Exemplified |
| 126 | 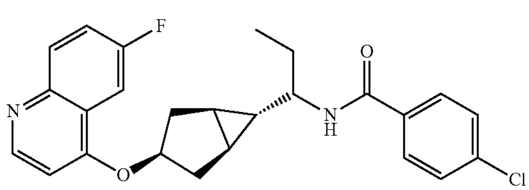 [SMILES: CCC(NC(=O)c1ccc(Cl)cc1)[C@H]1[C@@H]2C[C@H](Oc3ccnc4ccc(F)cc34)C[C@@H]21] | 438 | 439 | SNAr |

TABLE 2-continued

| Compound | Structure | Calc. Mass | Mass [M + H]+ | Synthesis as per |
|---|---|---|---|---|
| 127 | 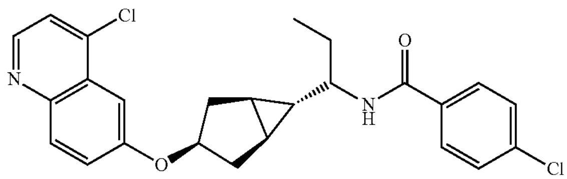 [SMILES: CCC(NC(=O)c1ccc(Cl)cc1)[C@H]1[C@@H]2C[C@H](Oc3ccc4nccc(Cl)c4c3)C[C@@H]21] | 454 | 455 | SNAr |
| 128 | 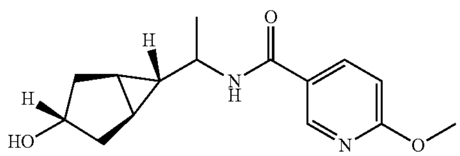 [SMILES: COc1ccc(C(=O)NC(C)[C@H]2[C@@H]3C[C@@H](O)C[C@@H]32)cn1] | 276 | 277 | Exemplified |
| 129 | 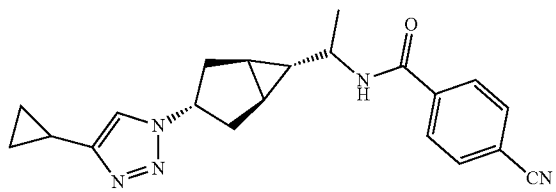 [SMILES: CC(NC(=O)c1ccc(C#N)cc1)[C@H]1[C@@H]2C[C@@H](n3cc(C4CC4)nn3)C[C@@H]21] | 361 | 362 | 1,4 Triazole, Click |
| 130 | 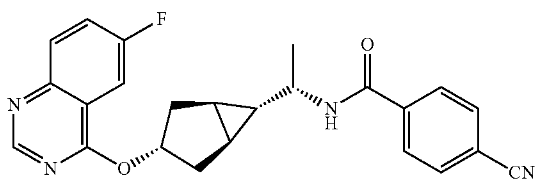 [SMILES: C[C@H](NC(=O)c1ccc(C#N)cc1)[C@H]1[C@@H]2C[C@@H](Oc3ncnc4ccc(F)cc34)C[C@@H]21] | 416 | 417 | SNAr |
| 131 | 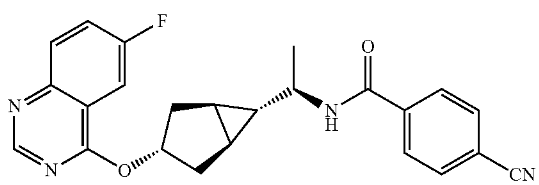 [SMILES: C[C@@H](NC(=O)c1ccc(C#N)cc1)[C@H]1[C@@H]2C[C@@H](Oc3ncnc4ccc(F)cc34)C[C@@H]21] | 416 | 417 | SNAr; compound 1 |
| 132 | 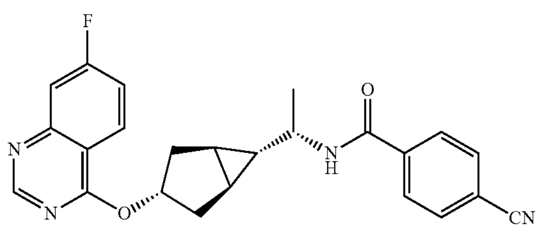 [SMILES: C[C@H](NC(=O)c1ccc(C#N)cc1)[C@H]1[C@@H]2C[C@@H](Oc3ncnc4cc(F)ccc34)C[C@@H]21] | 416 | 417 | SNAr |
| 133 | 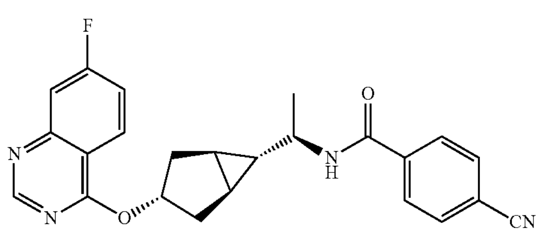 [SMILES: C[C@@H](NC(=O)c1ccc(C#N)cc1)[C@H]1[C@@H]2C[C@@H](Oc3ncnc4cc(F)ccc34)C[C@@H]21] | 416 | 417 | SNAr |

TABLE 2-continued

| Compound | Structure | Calc. Mass | Mass [M + H]+ | Synthesis as per |
|---|---|---|---|---|
| 134 | 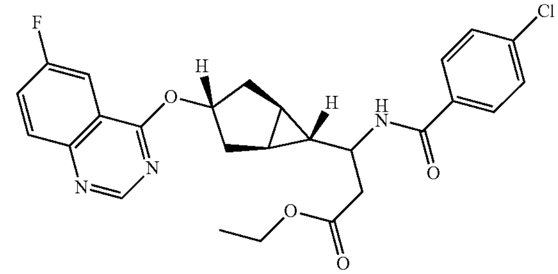 [SMILES: CCOC(=O)CC(NC(=O)c1ccc(Cl)cc1)[C@H]1[C@@H]2C[C@@H](Oc3ncnc4ccc(F)cc34)C[C@@H]21] | 497 | 498 | Exemplified |
| 135 | 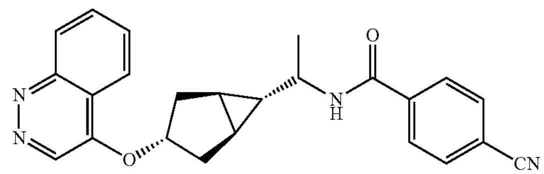 [SMILES: CC(NC(=O)c1ccc(C#N)cc1)[C@H]1[C@@H]2C[C@@H](Oc3cnnc4ccccc34)C[C@@H]21] | 398 | 399 | MS |
| 136 | 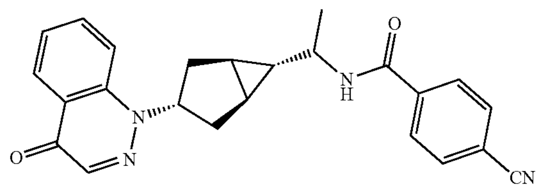 [SMILES: CC(NC(=O)c1ccc(C#N)cc1)[C@H]1[C@@H]2C[C@@H](n3ncc(=O)c4ccccc43)C[C@@H]21] | 398 | 399 | MS |
| 137 | 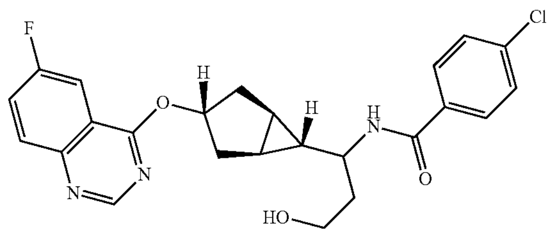 [SMILES: O=C(NC(CCO)[C@H]1[C@@H]2C[C@@H](Oc3ncnc4ccc(F)cc34)C[C@@H]21)c1ccc(Cl)cc1] | 455 | 456 | Exemplified |
| 138 | 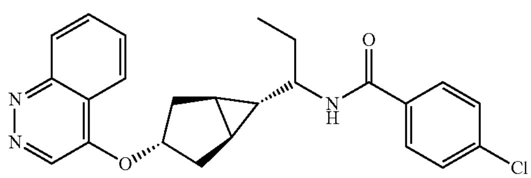 [SMILES: CCC(NC(=O)c1ccc(Cl)cc1)[C@H]1[C@@H]2C[C@@H](Oc3cnnc4ccccc34)C[C@@H]21] | 421 | 422 | SNAr |
| 139 | 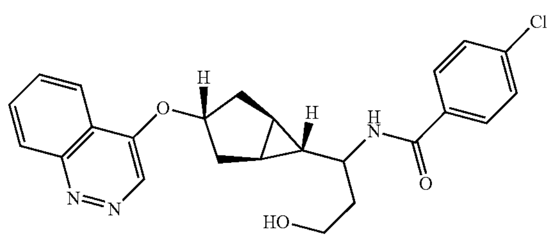 [SMILES: O=C(NC(CCO)[C@H]1[C@@H]2C[C@@H](Oc3cnnc4ccccc34)C[C@@H]21)c1ccc(Cl)cc1] | 437 | 438 | Exemplified |
| 140 | 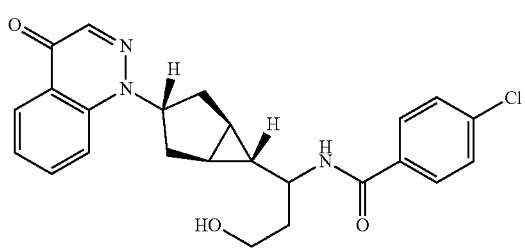 [SMILES: O=C(NC(CCO)[C@H]1[C@@H]2C[C@@H](n3ncc(=O)c4ccccc43)C[C@@H]21)c1ccc(Cl)cc1] | 437 | 438 | Exemplified |

TABLE 2-continued

| Compound | Structure | Calc. Mass | Mass [M + H]+ | Synthesis as per |
|---|---|---|---|---|
| 141 | 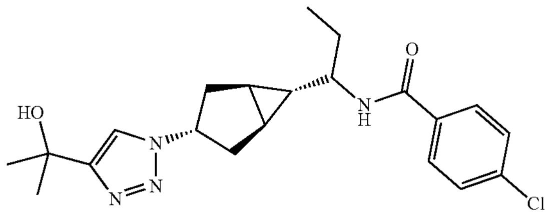 [SMILES: CCC(NC(=O)c1ccc(Cl)cc1)[C@H]1[C@@H]2C[C@@H](n3cc(C(C)(C)O)nn3)C[C@@H]21] | 402 | 403 | 1,4 Triazole, Click |
| 142 | 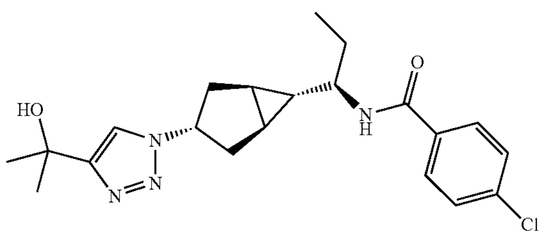 [SMILES: CC[C@@H](NC(=O)c1ccc(Cl)cc1)[C@H]1[C@@H]2C[C@@H](n3cc(C(C)(C)O)nn3)C[C@@H]21] | 402 | 403 | 1,4 Triazole, Click |
| 143 | 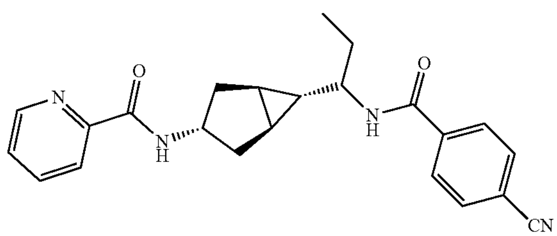 [SMILES: CCC(NC(=O)c1ccc(C#N)cc1)[C@H]1[C@@H]2C[C@@H](NC(=O)c3ccccn3)C[C@@H]21] | 374 | 375 | Amide coupling |
| 144 | 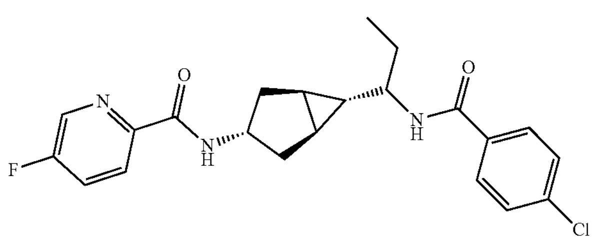 [SMILES: CCC(NC(=O)c1ccc(Cl)cc1)[C@H]1[C@@H]2C[C@@H](NC(=O)c3ccc(F)cn3)C[C@@H]21] | 415 | 416 | Amide coupling |
| 145 | 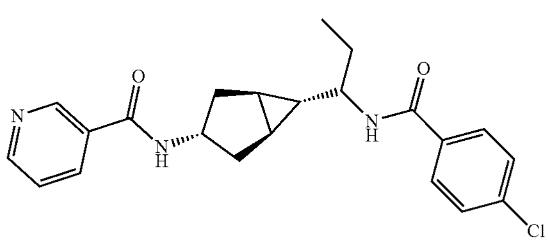 [SMILES: CCC(NC(=O)c1ccc(Cl)cc1)[C@H]1[C@@H]2C[C@@H](NC(=O)c3cccnc3)C[C@@H]21] | 397 | 398 | Amide coupling |
| 146 | 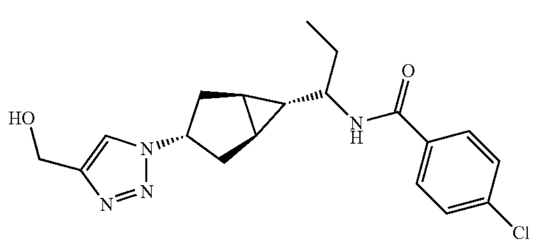 [SMILES: CCC(NC(=O)c1ccc(Cl)cc1)[C@H]1[C@@H]2C[C@@H](n3cc(CO)nn3)C[C@@H]21] | 374 | 375 | 1,4 Triazole, Click |

TABLE 2-continued

| Compound | Structure | Calc. Mass | Mass [M + H]+ | Synthesis as per |
|---|---|---|---|---|
| 147 | 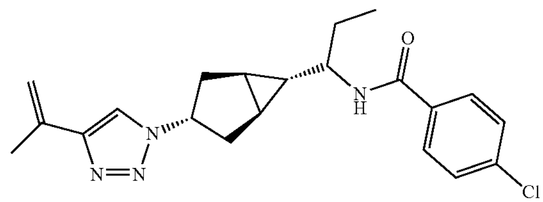 [SMILES: C=C(C)c1cn([C@@H]2C[C@@H]3[C@H](C2)[C@H]3C(CC)NC(=O)c2ccc(Cl)cc2)nn1] | 384 | 385 | 1,4 Triazole, Dehydrated with Burgess reagent |
| 148 | 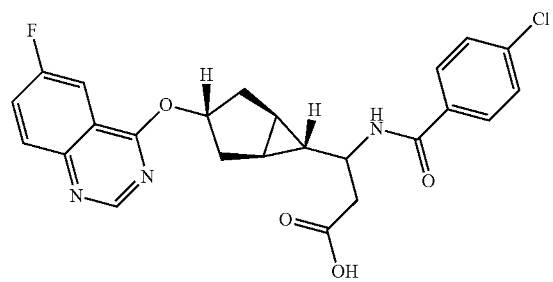 [SMILES: O=C(O)CC(NC(=O)c1ccc(Cl)cc1)[C@H]1[C@@H]2C[C@@H](Oc3ncnc4ccc(F)cc34)C[C@@H]21] | 469 | 470 | Exemplified |
| 149 | 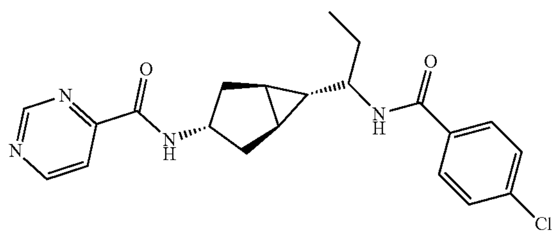 [SMILES: CCC(NC(=O)c1ccc(Cl)cc1)[C@H]1[C@@H]2C[C@@H](NC(=O)c3ccncn3)C[C@@H]21] | 398 | 399 | Amide coupling |
| 150 | 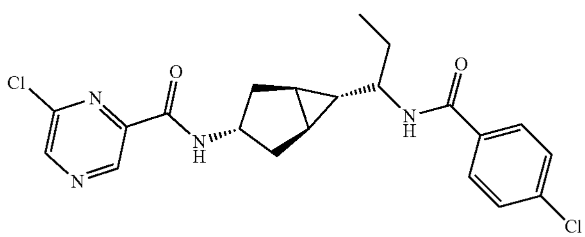 [SMILES: CCC(NC(=O)c1ccc(Cl)cc1)[C@H]1[C@@H]2C[C@@H](NC(=O)c3cncc(Cl)n3)C[C@@H]21] | 432 | 433 | Amide coupling |
| 151 | 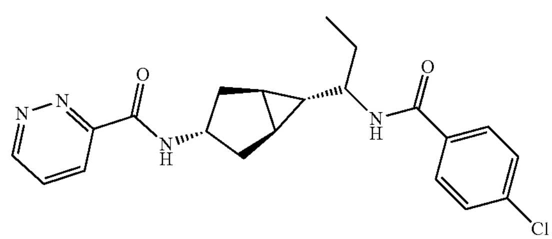 [SMILES: CCC(NC(=O)c1ccc(Cl)cc1)[C@H]1[C@@H]2C[C@@H](NC(=O)c3cccnn3)C[C@@H]21] | 398 | 399 | Amide coupling |
| 152 | 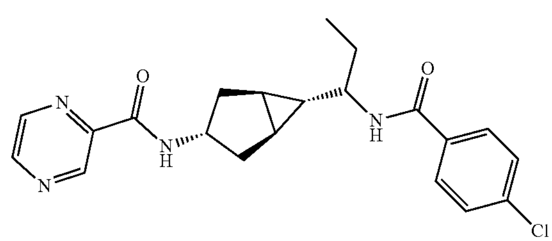 [SMILES: CCC(NC(=O)c1ccc(Cl)cc1)[C@H]1[C@@H]2C[C@@H](NC(=O)c3cnccn3)C[C@@H]21] | 398 | 399 | Amide coupling |

TABLE 2-continued

| Compound | Structure | Calc. Mass | Mass [M + H]+ | Synthesis as per |
|---|---|---|---|---|
| 153 | 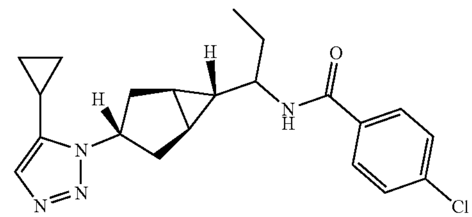 [SMILES: CCC(NC(=O)c1ccc(Cl)cc1)[C@H]1[C@@H]2C[C@@H](n3nncc3C3CC3)C[C@@H]21] | 384 | 385 | Exemplified |
| 154 | 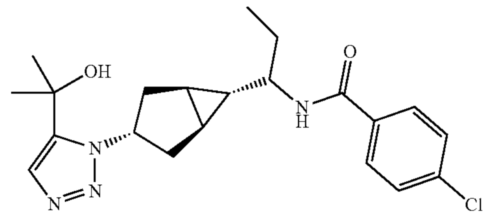 [SMILES: CCC(NC(=O)c1ccc(Cl)cc1)[C@H]1[C@@H]2C[C@@H](n3nncc3C(C)(C)O)C[C@@H]21] | 402 | 403 | 1,5 Triazole |
| 155 | 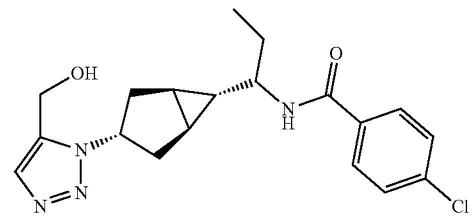 [SMILES: CCC(NC(=O)c1ccc(Cl)cc1)[C@H]1[C@@H]2C[C@@H](n3nncc3CO)C[C@@H]21] | 374 | 375 | 1,5 Triazole |
| 156 | 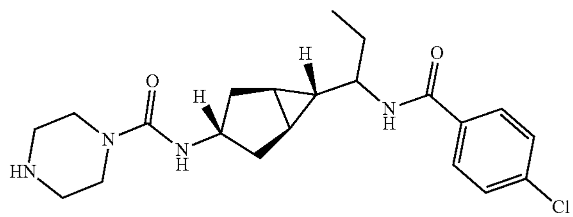 [SMILES: CCC(NC(=O)c1ccc(Cl)cc1)[C@H]1[C@@H]2C[C@@H](NC(=O)N3CCNCC3)C[C@@H]21] | 404 | 405 | Exemplified |
| 157 | 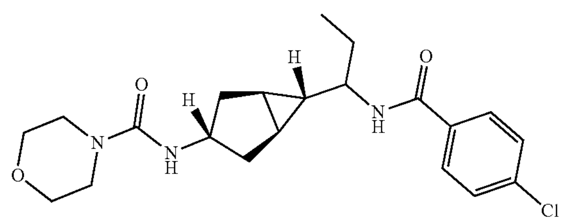 [SMILES: CCC(NC(=O)c1ccc(Cl)cc1)[C@H]1[C@@H]2C[C@@H](NC(=O)N3CCOCC3)C[C@@H]21] | 405 | 406 | Exemplified |
| 158 | 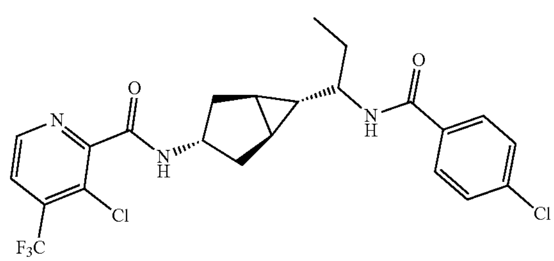 [SMILES: CCC(NC(=O)c1ccc(Cl)cc1)[C@H]1[C@@H]2C[C@@H](NC(=O)c3nccc(C(F)(F)F)c3Cl)C[C@@H]21] | 499 | 500 | Amide coupling |
| 159 | 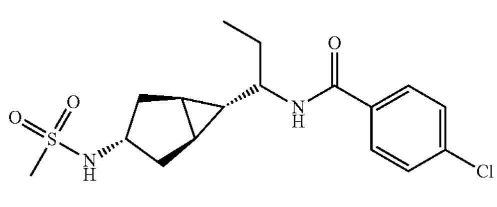 [SMILES: CCC(NC(=O)c1ccc(Cl)cc1)[C@H]1[C@@H]2C[C@@H](NS(C)(=O)=O)C[C@@H]21] | 370 | 371 | Compound 116 |

TABLE 2-continued

| Compound | Structure | Calc. Mass | Mass [M + H]+ | Synthesis as per |
|---|---|---|---|---|
| 160 | 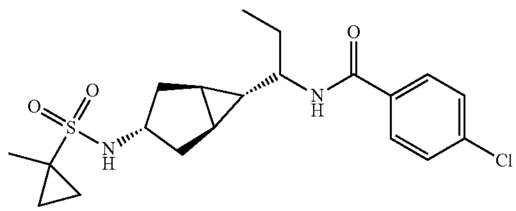 [SMILES: CCC(NC(=O)c1ccc(Cl)cc1)[C@H]1[C@@H]2C[C@@H](NS(=O)(=O)C3(C)CC3)C[C@@H]21] | 410 | 411 | Compound 116 |
| 161 | 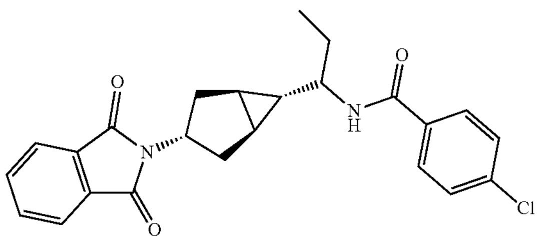 [SMILES: CCC(NC(=O)c1ccc(Cl)cc1)[C@H]1[C@@H]2C[C@@H](N3C(=O)c4ccccc4C3=O)C[C@@H]21] | 422 | 423 | Exemplified |
| 162 | 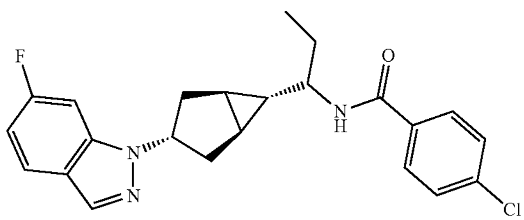 [SMILES: CCC(NC(=O)c1ccc(Cl)cc1)[C@H]1[C@@H]2C[C@@H](n3ncc4ccc(F)cc43)C[C@@H]21] | 411 | 412 | MS |
| 163 | 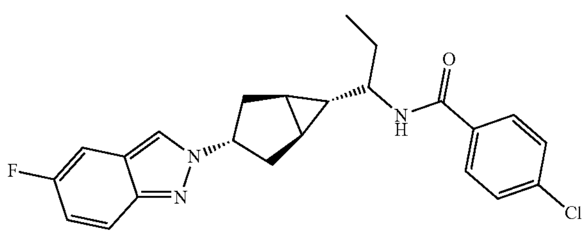 [SMILES: CCC(NC(=O)c1ccc(Cl)cc1)[C@H]1[C@@H]2C[C@@H](n3cc4cc(F)ccc4n3)C[C@@H]21] | 411 | 412 | MS |
| 164 | 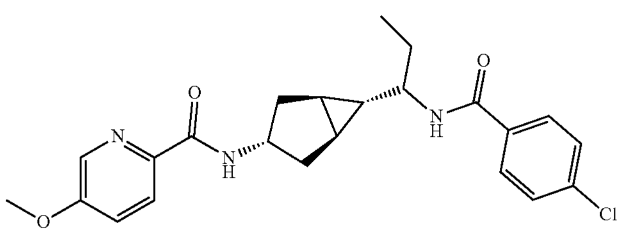 [SMILES: CCC(NC(=O)c1ccc(Cl)cc1)[C@H]1[C@@H]2C[C@@H](NC(=O)c3ccc(OC)cn3)C[C@@H]21] | 427 | 428 | Amide coupling |
| 165 | 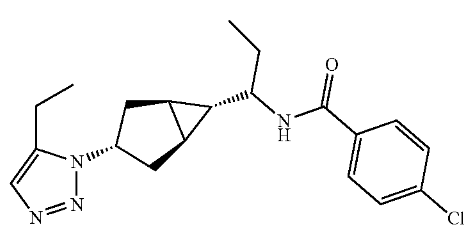 [SMILES: CCc1cnnn1[C@@H]1C[C@@H]2[C@H](C1)[C@H]2C(CC)NC(=O)c1ccc(Cl)cc1] | 372 | 373 | 1,5 Triazole |

TABLE 2-continued

| Compound | Structure | Calc. Mass | Mass [M + H]+ | Synthesis as per |
|---|---|---|---|---|
| 166 | 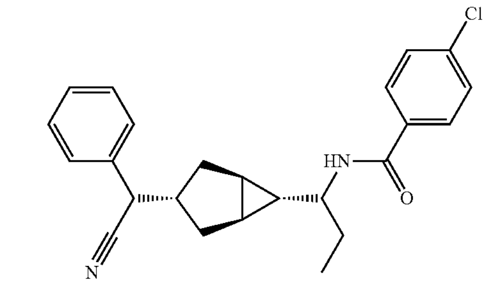 [SMILES: CCC(NC(=O)c1ccc(Cl)cc1)[C@H]1[C@@H]2C[C@@H](C(C#N)c3ccccc3)C[C@@H]21] | 392 | 393 | Exemplified |
| 167 | 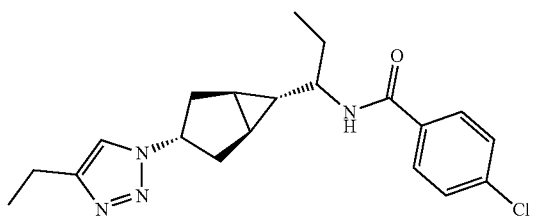 [SMILES: CCc1cn([C@@H]2C[C@@H]3[C@H](C2)[C@H]3C(CC)NC(=O)c2ccc(Cl)cc2)nn1] | 372 | 373 | 1,4 Triazole, Click |
| 168 | 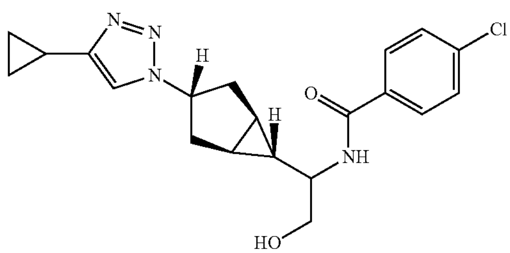 [SMILES: O=C(NC(CO)[C@H]1[C@@H]2C[C@@H](n3cc(C4CC4)nn3)C[C@@H]21)c1ccc(Cl)cc1] | 386 | 837 | Exemplified |
| 169 | 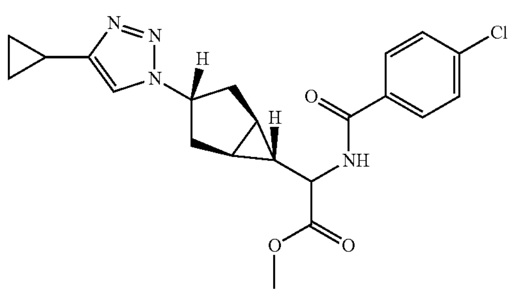 [SMILES: COC(=O)C(NC(=O)c1ccc(Cl)cc1)[C@H]1[C@@H]2C[C@@H](n3cc(C4CC4)nn3)C[C@@H]21] | 401 | 402 | Exemplified |
| 170 | 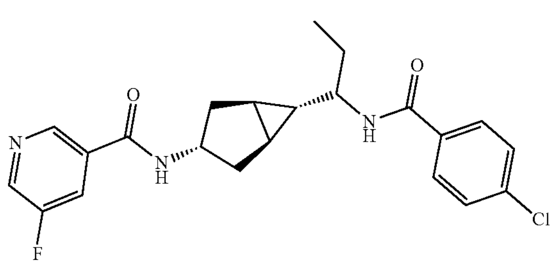 [SMILES: CCC(NC(=O)c1ccc(Cl)cc1)[C@H]1[C@@H]2C[C@@H](NC(=O)c3cncc(F)c3)C[C@@H]21] | 415 | 416 | Amide coupling |
| 171 | 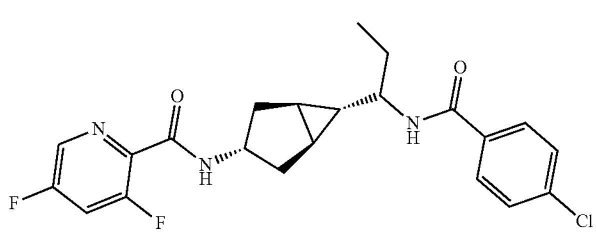 [SMILES: CCC(NC(=O)c1ccc(Cl)cc1)[C@H]1[C@@H]2C[C@@H](NC(=O)c3ncc(F)cc3F)C[C@@H]21] | 433 | 434 | Amide coupling |

TABLE 2-continued

| Compound | Structure | Calc. Mass | Mass [M + H]+ | Synthesis as per |
|---|---|---|---|---|
| 172 | 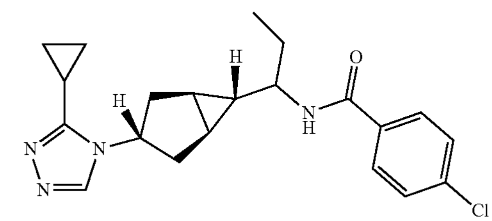 [SMILES: CCC(NC(=O)c1ccc(Cl)cc1)[C@H]1[C@@H]2C[C@@H](n3cnnc3C3CC3)C[C@@H]21] | 384 | 385 | Exemplified |
| 173 | 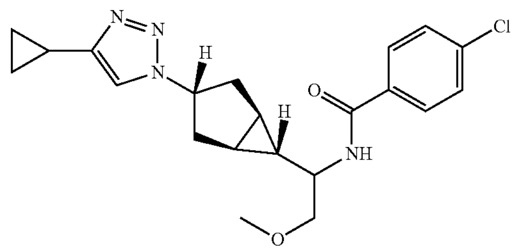 [SMILES: COCC(NC(=O)c1ccc(Cl)cc1)[C@H]1[C@@H]2C[C@@H](n3cc(C4CC4)nn3)C[C@@H]21] | 400 | 401 | Exemplified |
| 174 | 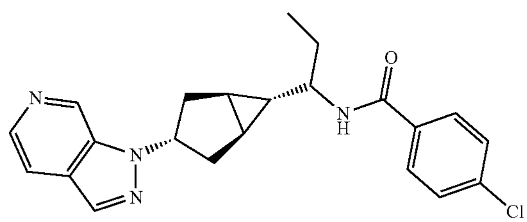 [SMILES: CCC(NC(=O)c1ccc(Cl)cc1)[C@H]1[C@@H]2C[C@@H](n3ncc4ccncc43)C[C@@H]21] | 394 | 395 | MS |
| 175 | 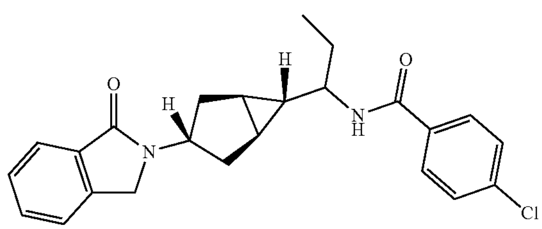 [SMILES: CCC(NC(=O)c1ccc(Cl)cc1)[C@H]1[C@@H]2C[C@@H](N3Cc4ccccc4C3=O)C[C@@H]21] | 408 | 409 | Exemplified |
| 176 | 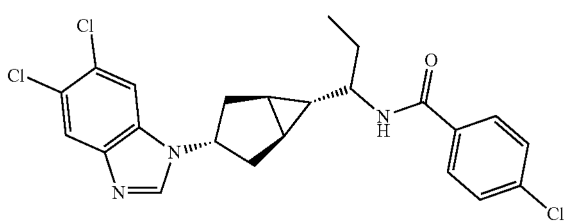 [SMILES: CCC(NC(=O)c1ccc(Cl)cc1)[C@H]1[C@@H]2C[C@@H](n3cnc4cc(Cl)c(Cl)cc43)C[C@@H]21] | 461 | 462 | MS |
| 177 | 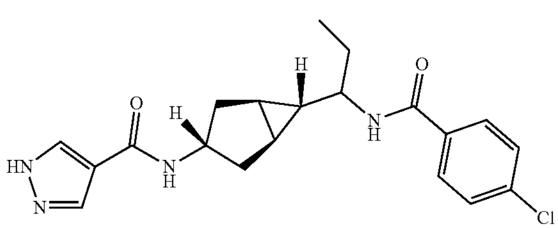 [SMILES: CCC(NC(=O)c1ccc(Cl)cc1)[C@H]1[C@@H]2C[C@@H](NC(=O)c3cn[nH]c3)C[C@@H]21] | 386 | 387 | Exemplified |

TABLE 2-continued

| Compound | Structure | Calc. Mass | Mass [M + H]+ | Synthesis as per |
|---|---|---|---|---|
| 178 | 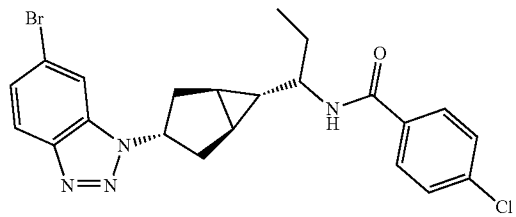 [SMILES: CCC(NC(=O)c1ccc(Cl)cc1)[C@H]1[C@@H]2C[C@@H](n3nnc4ccc(Br)cc43)C[C@@H]21] | 472 | 473 | MS |
| 179 | 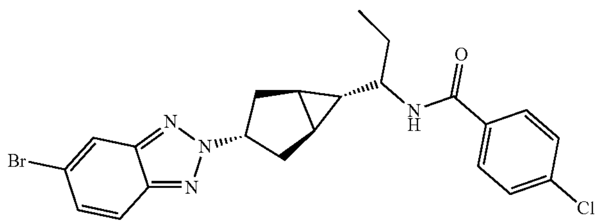 [SMILES: CCC(NC(=O)c1ccc(Cl)cc1)[C@H]1[C@@H]2C[C@@H](n3nc4ccc(Br)cc4n3)C[C@@H]21] | 472 | 473 | MS |
| 180 | 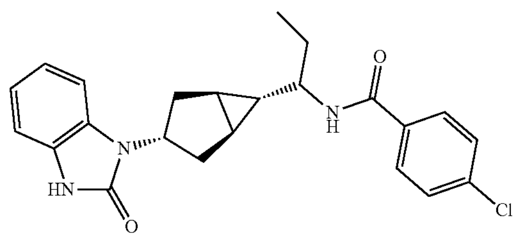 [SMILES: CCC(NC(=O)c1ccc(Cl)cc1)[C@H]1[C@@H]2C[C@@H](n3c(=O)[nH]c4ccccc43)C[C@@H]21] | 409 | 410 | MS |
| 181 | 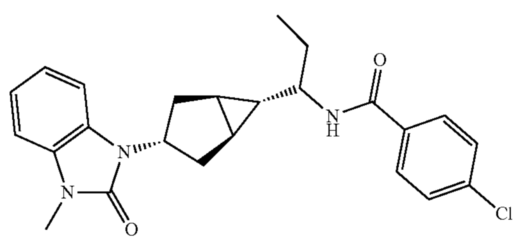 [SMILES: CCC(NC(=O)c1ccc(Cl)cc1)[C@H]1[C@@H]2C[C@@H](n3c(=O)n(C)c4ccccc43)C[C@@H]21] | 423 | 424 | MS |
| 182 | 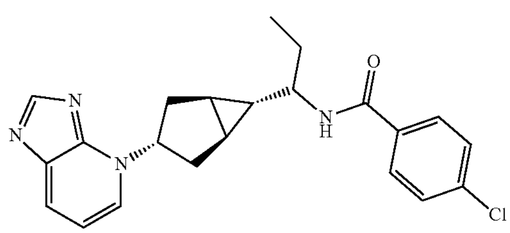 [SMILES: CCC(NC(=O)c1ccc(Cl)cc1)[C@H]1[C@@H]2C[C@@H](n3cccc4ncnc3-4)C[C@@H]21] | 394 | 395 | MS |
| 183 | 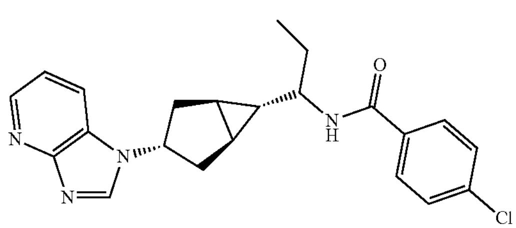 [SMILES: CCC(NC(=O)c1ccc(Cl)cc1)[C@H]1[C@@H]2C[C@@H](n3cnc4ncccc43)C[C@@H]21] | 394 | 395 | MS |

TABLE 2-continued

| Compound | Structure | Calc. Mass | Mass [M + H]+ | Synthesis as per |
|---|---|---|---|---|
| 184 | 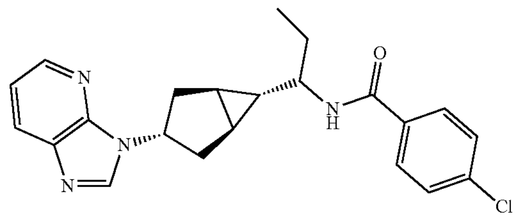 [SMILES: CCC(NC(=O)c1ccc(Cl)cc1)[C@H]1[C@@H]2C[C@@H](n3cnc4cccnc43)C[C@@H]21] | 394 | 395 | MS |
| 185 | 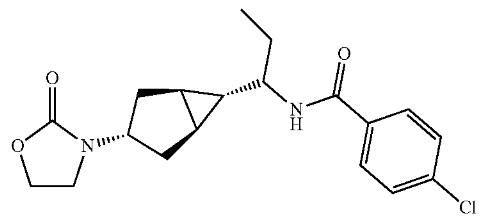 [SMILES: CCC(NC(=O)c1ccc(Cl)cc1)[C@H]1[C@@H]2C[C@@H](N3CCOC3=O)C[C@@H]21] | 362 | 363 | MS |
| 186 | 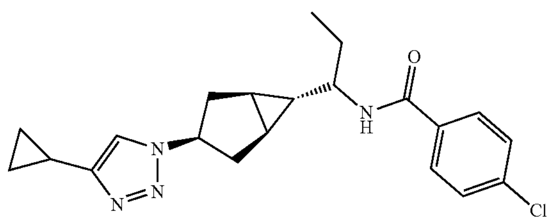 [SMILES: CCC(NC(=O)c1ccc(Cl)cc1)[C@H]1[C@@H]2C[C@H](n3cc(C4CC4)nn3)C[C@@H]21] | 384 | 385 | 1,4 Triazole, Click |
| 187 | 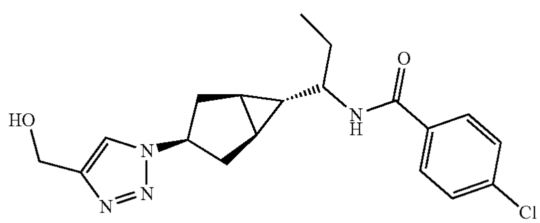 [SMILES: CCC(NC(=O)c1ccc(Cl)cc1)[C@H]1[C@@H]2C[C@H](n3cc(CO)nn3)C[C@@H]21] | 374 | 375 | 1,4 Triazole, Click |
| 188 | 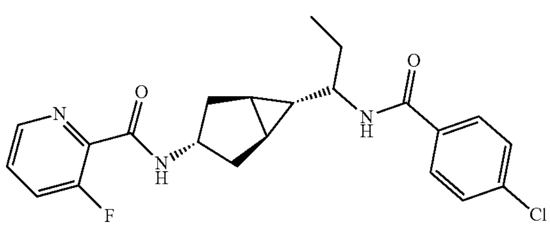 | 415 | 416 | Amide coupling |
| 189 | 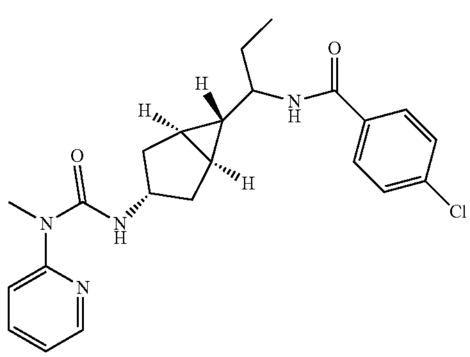 [SMILES: CCC(NC(=O)c1ccc(Cl)cc1)[C@H]1[C@@H]2C[C@@H](NC(=O)N(C)c3ccccn3)C[C@@H]21] | 426 | 427 | Exemplified |

TABLE 2-continued

| Compound | Structure | Calc. Mass | Mass [M + H]+ | Synthesis as per |
|---|---|---|---|---|
| 190 | 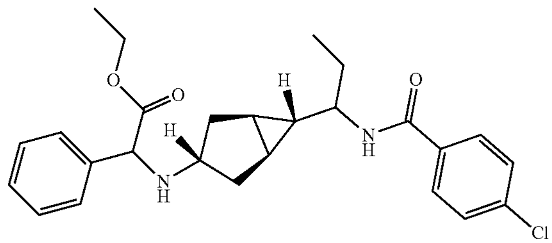 [SMILES: CCOC(=O)C(N[C@@H]1C[C@@H]2[C@H](C1)[C@H]2C(CC)NC(=O)c1ccc(Cl)cc1)c1ccccc1] | 454 | 455 | Exemplified |
| 191 | 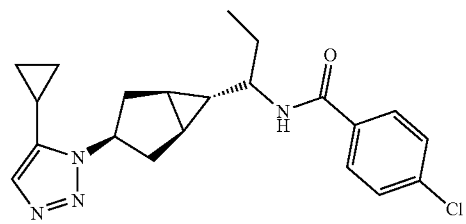 [SMILES: CCC(NC(=O)c1ccc(Cl)cc1)[C@H]1[C@@H]2C[C@H](n3nncc3C3CC3)C[C@@H]21] | 384 | 385 | 1,5 Triazole |
| 192 | 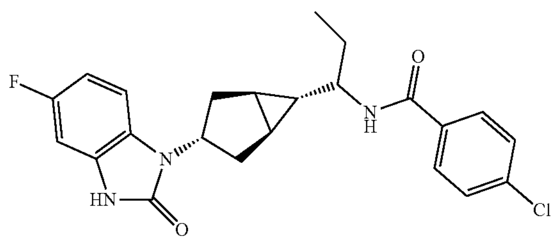 [SMILES: CCC(NC(=O)c1ccc(Cl)cc1)[C@H]1[C@@H]2C[C@@H](n3c(=O)[nH]c4cc(F)ccc43)C[C@@H]21] | 427 | 428 | MS |
| 193 | 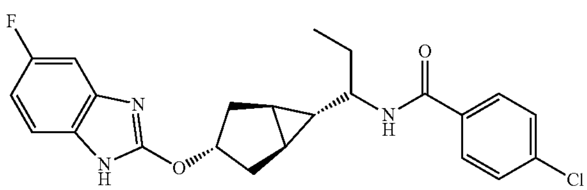 [SMILES: CCC(NC(=O)c1ccc(Cl)cc1)[C@H]1[C@@H]2C[C@@H](Oc3nc4cc(F)ccc4[nH]3)C[C@@H]21] | 427 | 428 | MS |
| 194 | 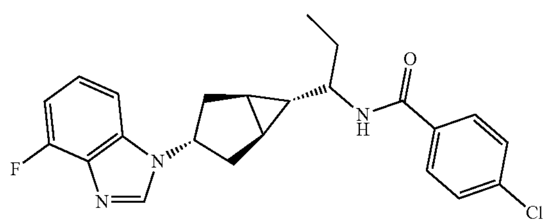 [SMILES: CCC(NC(=O)c1ccc(Cl)cc1)[C@H]1[C@@H]2C[C@@H](n3cnc4c(F)cccc43)C[C@@H]21] | 411 | 412 | MS |
| 195 | 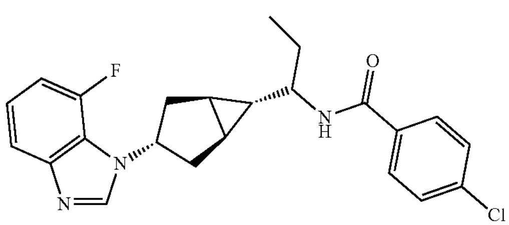 [SMILES: CCC(NC(=O)c1ccc(Cl)cc1)[C@H]1[C@@H]2C[C@@H](n3cnc4cccc(F)c43)C[C@@H]21] | 411 | 412 | MS |
| 196 | 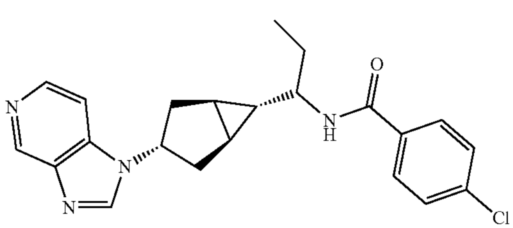 [SMILES: CCC(NC(=O)c1ccc(Cl)cc1)[C@H]1[C@@H]2C[C@@H](n3cnc4cnccc43)C[C@@H]21] | 394 | 395 | MS |

TABLE 2-continued

| Compound | Structure | Calc. Mass | Mass [M + H]+ | Synthesis as per |
|---|---|---|---|---|
| 197 | 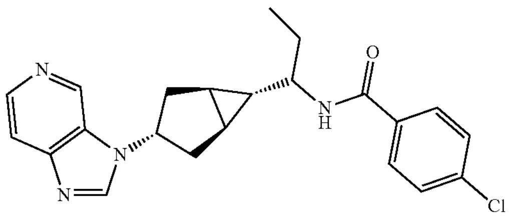 [SMILES: CCC(NC(=O)c1ccc(Cl)cc1)[C@H]1[C@@H]2C[C@@H](n3cnc4ccncc43)C[C@@H]21] | 394 | 395 | MS |
| 198 | 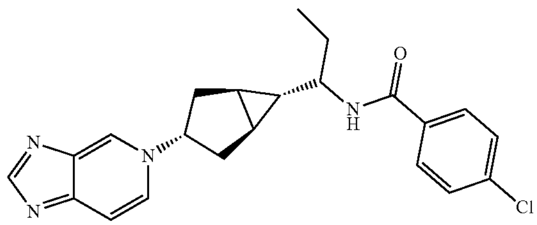 [SMILES: CCC(NC(=O)c1ccc(Cl)cc1)[C@H]1[C@@H]2C[C@@H](n3ccc4ncnc-4c3)C[C@@H]21] | 394 | 395 | MS |
| 199 | 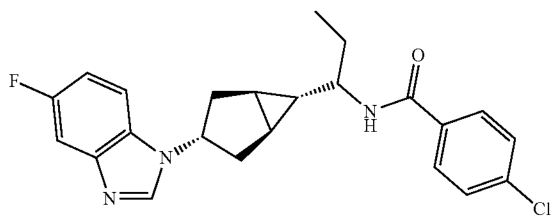 [SMILES: CCC(NC(=O)c1ccc(Cl)cc1)[C@H]1[C@@H]2C[C@@H](n3cnc4cc(F)ccc43)C[C@@H]21] | 411 | 412 | MS |
| 200 | 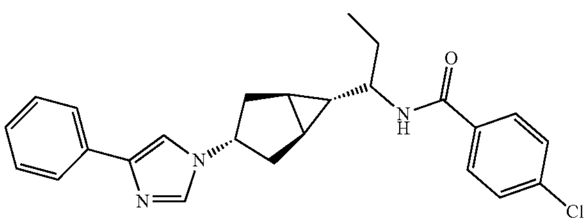 [SMILES: CCC(NC(=O)c1ccc(Cl)cc1)[C@H]1[C@@H]2C[C@@H](n3cnc(-c4ccccc4)c3)C[C@@H]21] | 419 | 420 | MS |
| 201 | 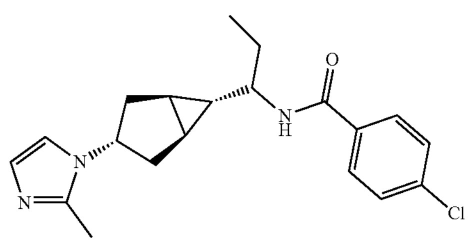 [SMILES: CCC(NC(=O)c1ccc(Cl)cc1)[C@H]1[C@@H]2C[C@@H](n3ccnc3C)C[C@@H]21] | 357 | 358 | MS |
| 202 | 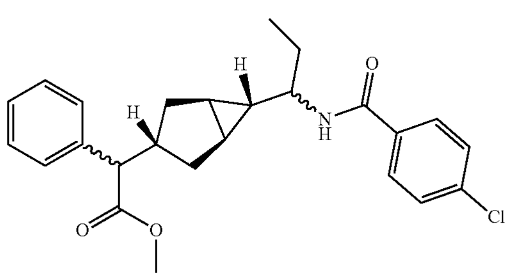 [SMILES: CCC(NC(=O)c1ccc(Cl)cc1)[C@H]1[C@@H]2C[C@@H](C(C(=O)OC)c3ccccc3)C[C@@H]21] | 425 | 426 | Exemplified |

TABLE 2-continued

| Compound | Structure | Calc. Mass | Mass [M + H]+ | Synthesis as per |
|---|---|---|---|---|
| 203 | 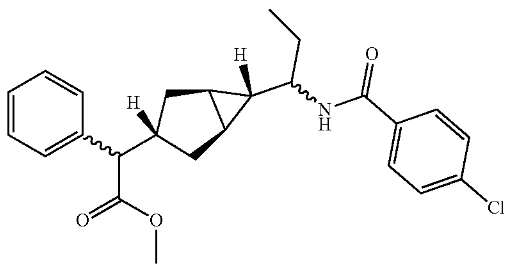 [SMILES: CCC(NC(=O)c1ccc(Cl)cc1)[C@H]1[C@@H]2C[C@@H](C(C(=O)OC)c3ccccc3)C[C@@H]21] | 425 | 426 | Exemplified |
| 204 | 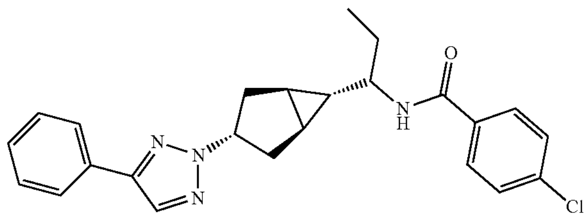 [SMILES: CCC(NC(=O)c1ccc(Cl)cc1)[C@H]1[C@@H]2C[C@@H](n3ncc(-c4ccccc4)n3)C[C@@H]21] | 420 | 421 | MS |
| 205 | 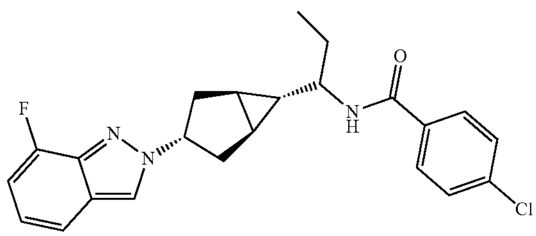 [SMILES: CCC(NC(=O)c1ccc(Cl)cc1)[C@H]1[C@@H]2C[C@@H](n3cc4cccc(F)c4n3)C[C@@H]21] | 411 | 412 | MS |
| 206 | 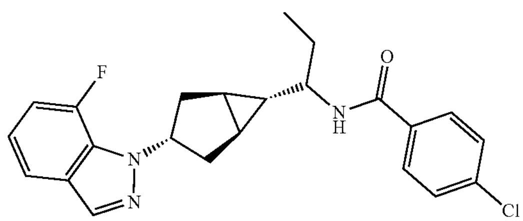 [SMILES: CCC(NC(=O)c1ccc(Cl)cc1)[C@H]1[C@@H]2C[C@@H](n3ncc4cccc(F)c43)C[C@@H]21] | 411 | 412 | MS |
| 207 | 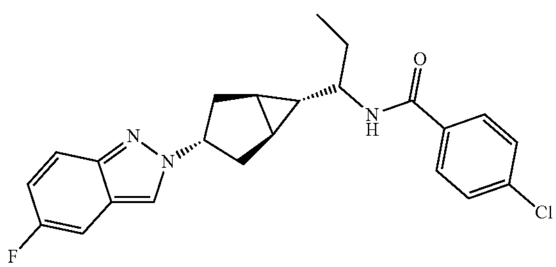 [SMILES: CCC(NC(=O)c1ccc(Cl)cc1)[C@H]1[C@@H]2C[C@@H](n3cc4cc(F)ccc4n3)C[C@@H]21] | 411 | 412 | MS |
| 208 | 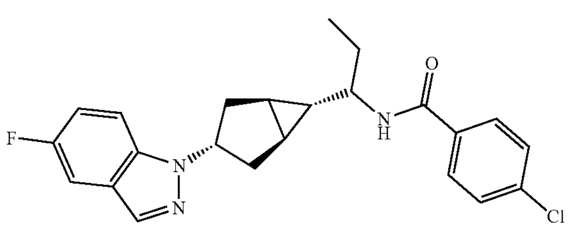 [SMILES: CCC(NC(=O)c1ccc(Cl)cc1)[C@H]1[C@@H]2C[C@@H](n3ncc4cc(F)ccc43)C[C@@H]21] | 411 | 412 | MS |

TABLE 2-continued

| Compound | Structure | Calc. Mass | Mass [M + H]+ | Synthesis as per |
|---|---|---|---|---|
| 209 | 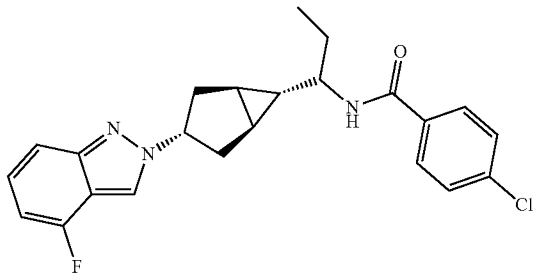 [SMILES: CCC(NC(=O)c1ccc(Cl)cc1)[C@H]1[C@@H]2C[C@@H](n3cc4c(F)cccc4n3)C[C@@H]21] | 411 | 412 | MS |
| 210 | 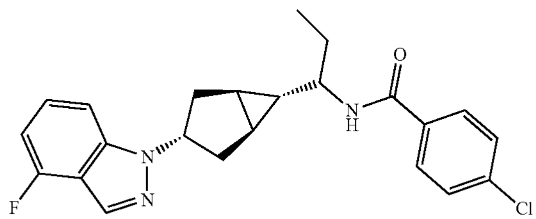 [SMILES: CCC(NC(=O)c1ccc(Cl)cc1)[C@H]1[C@@H]2C[C@@H](n3ncc4c(F)cccc43)C[C@@H]21] | 411 | 412 | MS |
| 211 | 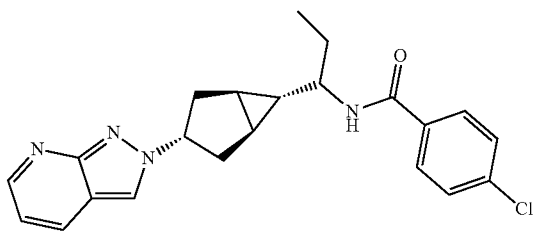 [SMILES: CCC(NC(=O)c1ccc(Cl)cc1)[C@H]1[C@@H]2C[C@@H](n3cc4cccnc4n3)C[C@@H]21] | 394 | 395 | MS |
| 212 | 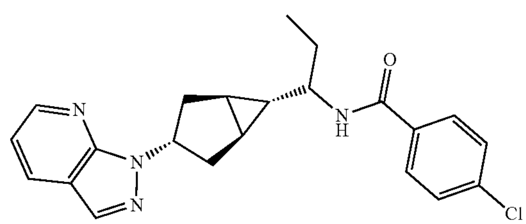 [SMILES: CCC(NC(=O)c1ccc(Cl)cc1)[C@H]1[C@@H]2C[C@@H](n3ncc4cccnc43)C[C@@H]21] | 394 | 395 | MS |
| 213 | 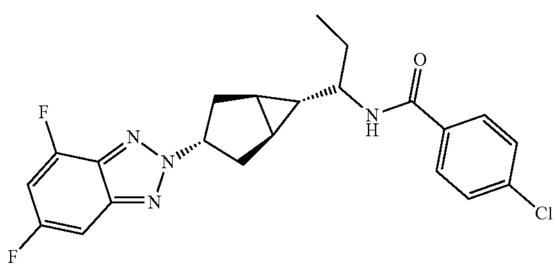 [SMILES: CCC(NC(=O)c1ccc(Cl)cc1)[C@H]1[C@@H]2C[C@@H](n3nc4cc(F)cc(F)c4n3)C[C@@H]21] | 430 | 431 | MS |
| 214 | 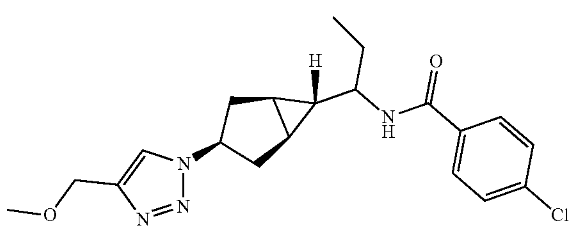 [SMILES: CCC(NC(=O)c1ccc(Cl)cc1)[C@H]1[C@@H]2C[C@H](n3cc(COC)nn3)C[C@@H]21] | 388 | 389 | Exemplified |

TABLE 2-continued

| Compound | Structure | Calc. Mass | Mass [M + H]+ | Synthesis as per |
|---|---|---|---|---|
| 215 | 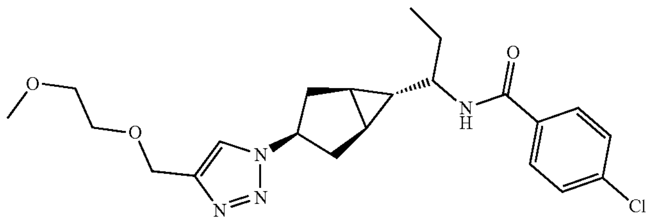 [SMILES: CCC(NC(=O)c1ccc(Cl)cc1)[C@H]1[C@@H]2C[C@H](n3cc(COCCOC)nn3)C[C@@H]21] | 432 | 433 | 1,4 Triazole, Click |
| 216 | 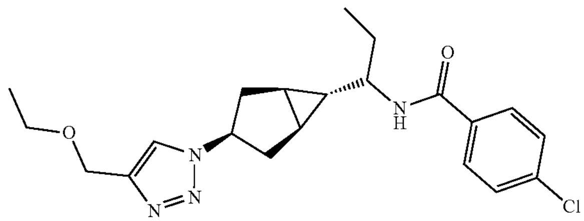 [SMILES: CCOCc1cn([C@H]2C[C@@H]3[C@H](C2)[C@H]3C(CC)NC(=O)c2ccc(Cl)cc2)nn1] | 402 | 403 | 1,4 Triazole, Click (Alkylation with iodoethane) |
| 217 | 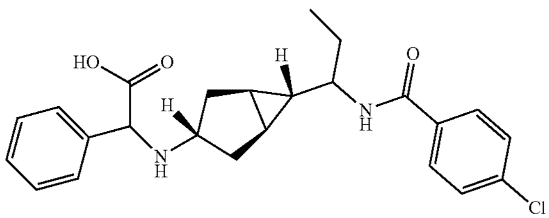 [SMILES: CCC(NC(=O)c1ccc(Cl)cc1)[C@H]1[C@@H]2C[C@@H](NC(C(=O)O)c3ccccc3)C[C@@H]21] | 426 | 427 | Exemplified |
| 218 | 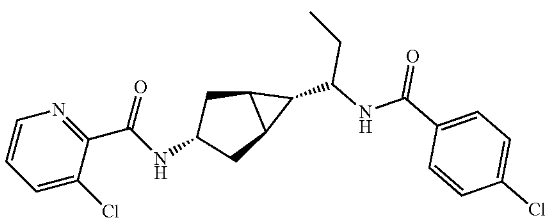 [SMILES: CCC(NC(=O)c1ccc(Cl)cc1)[C@H]1[C@@H]2C[C@@H](NC(=O)c3ncccc3Cl)C[C@@H]21] | 431 | 432 | Amide coupling |
| 219 | 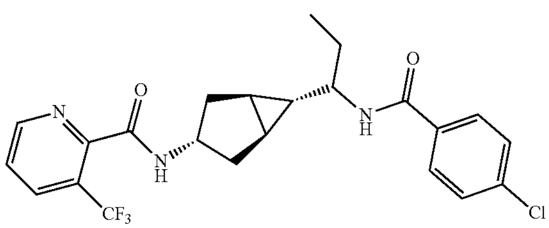 [SMILES: CCC(NC(=O)c1ccc(Cl)cc1)[C@H]1[C@@H]2C[C@@H](NC(=O)c3ncccc3C(F)(F)F)C[C@@H]21] | 465 | 466 | Amide coupling |
| 220 | 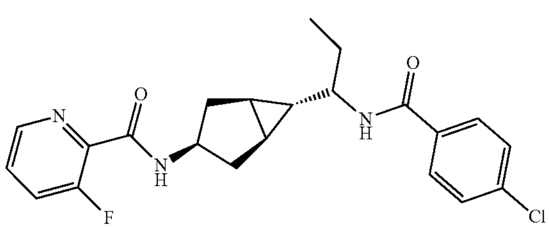 [SMILES: CCC(NC(=O)c1ccc(Cl)cc1)[C@H]1[C@@H]2C[C@H](NC(=O)c3ncccc3F)C[C@@H]21] | 415 | 416 | Amide coupling |
| 221 | 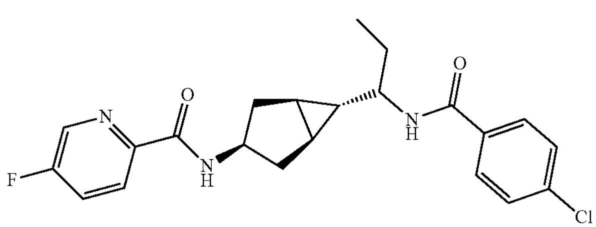 [SMILES: CCC(NC(=O)c1ccc(Cl)cc1)[C@H]1[C@@H]2C[C@H](NC(=O)c3ccc(F)cn3)C[C@@H]21] | 415 | 416 | Amide coupling |

TABLE 2-continued

| Compound | Structure | Calc. Mass | Mass [M + H]+ | Synthesis as per |
|---|---|---|---|---|
| 222 | 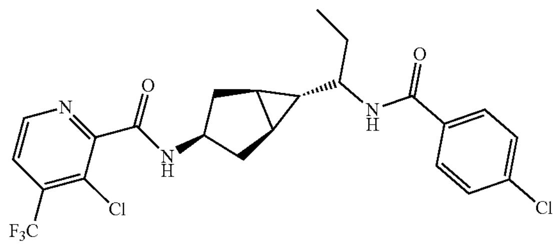 [SMILES: CCC(NC(=O)c1ccc(Cl)cc1)[C@H]1[C@@H]2C[C@H](NC(=O)c3nccc(C(F)(F)F)c3Cl)C[C@@H]21] | 499 | 500 | Amide coupling |
| 223 | 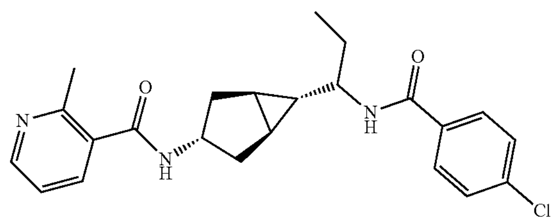 [SMILES: CCC(NC(=O)c1ccc(Cl)cc1)[C@H]1[C@@H]2C[C@@H](NC(=O)c3cccnc3C)C[C@@H]21] | 411 | 412 | Amide coupling |
| 224 | 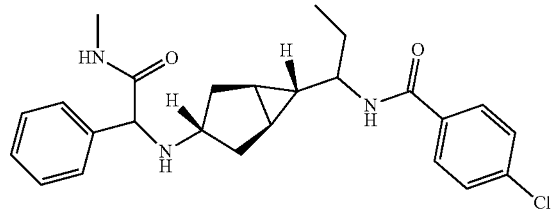 [SMILES: CCC(NC(=O)c1ccc(Cl)cc1)[C@H]1[C@@H]2C[C@@H](NC(C(=O)NC)c3ccccc3)C[C@@H]21] | 439 | 440 | Exemplified |
| 225 | 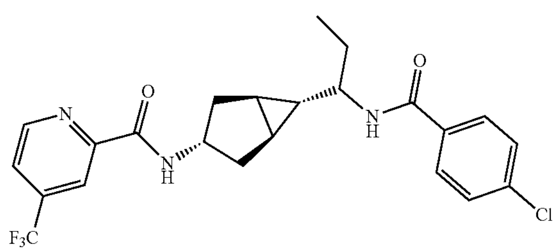 [SMILES: CCC(NC(=O)c1ccc(Cl)cc1)[C@H]1[C@@H]2C[C@@H](NC(=O)c3cc(C(F)(F)F)ccn3)C[C@@H]21] | 465 | 466 | Amide coupling |
| 226 | 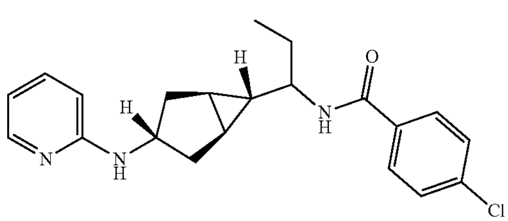 [SMILES: CCC(NC(=O)c1ccc(Cl)cc1)[C@H]1[C@@H]2C[C@@H](Nc3ccccn3)C[C@@H]21] | 369 | 370 | Exemplified |
| 227 | 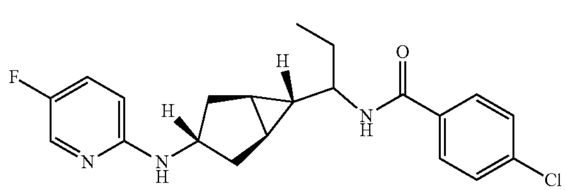 [SMILES: CCC(NC(=O)c1ccc(Cl)cc1)[C@H]1[C@@H]2C[C@@H](Nc3ccc(F)cn3)C[C@@H]21] | 387 | 388 | Exemplified |

TABLE 2-continued

| Compound | Structure | Calc. Mass | Mass [M + H]+ | Synthesis as per |
|---|---|---|---|---|
| 228 | 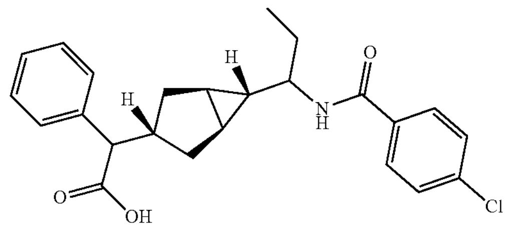 [SMILES: CCC(NC(=O)c1ccc(Cl)cc1)[C@H]1[C@@H]2C[C@@H](C(C(=O)O)c3ccccc3)C[C@@H]21] | 411 | 412 | Exemplified |
| 229 | 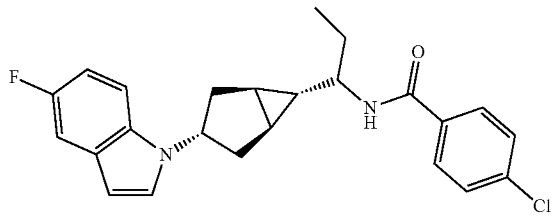 [SMILES: CCC(NC(=O)c1ccc(Cl)cc1)[C@H]1[C@@H]2C[C@@H](n3ccc4cc(F)ccc43)C[C@@H]21] | 410 | 411 | MS |
| 230 | 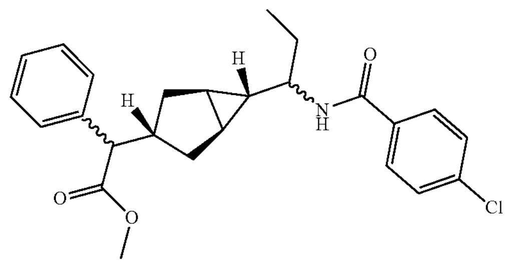 [SMILES: CCC(NC(=O)c1ccc(Cl)cc1)[C@H]1[C@@H]2C[C@@H](C(C(=O)OC)c3ccccc3)C[C@@H]21] | 424 | 425 | Exemplified |
| 231 | 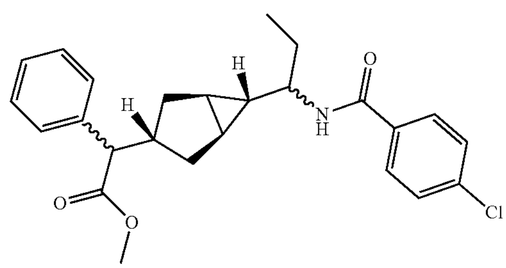 [SMILES: CCC(NC(=O)c1ccc(Cl)cc1)[C@H]1[C@@H]2C[C@@H](C(C(=O)OC)c3ccccc3)C[C@@H]21] | 424 | 425 | Exemplified |
| 232 | 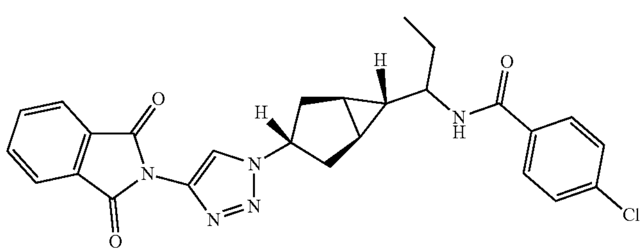 [SMILES: CCC(NC(=O)c1ccc(Cl)cc1)[C@H]1[C@@H]2C[C@@H](n3cc(N4C(=O)c5ccccc5C4=O)nn3)C[C@@H]21] | 489 | 490 | Exemplified |
| 233 | 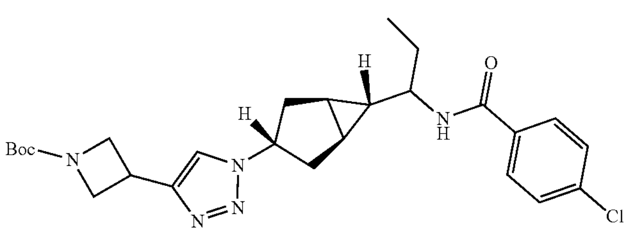 [SMILES: CCC(NC(=O)c1ccc(Cl)cc1)[C@H]1[C@@H]2C[C@@H](n3cc(C4CN(C(=O)OC(C)(C)C)C4)nn3)C[C@@H]21] | 499 | 500 | Exemplified |

TABLE 2-continued

| Compound | Structure | Calc. Mass | Mass [M + H]+ | Synthesis as per |
|---|---|---|---|---|
| 234 | 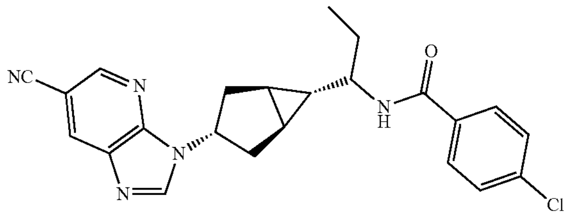 [SMILES: CCC(NC(=O)c1ccc(Cl)cc1)[C@H]1[C@@H]2C[C@@H](n3cnc4cc(C#N)cnc43)C[C@@H]21] | 419 | 420 | MS |
| 235 | 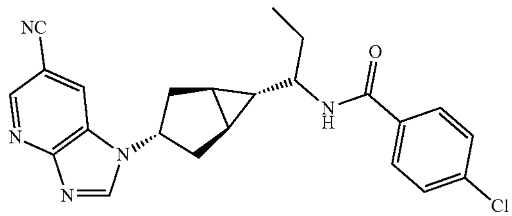 [SMILES: CCC(NC(=O)c1ccc(Cl)cc1)[C@H]1[C@@H]2C[C@@H](n3cnc4ncc(C#N)cc43)C[C@@H]21] | 419 | 420 | MS |
| 236 | 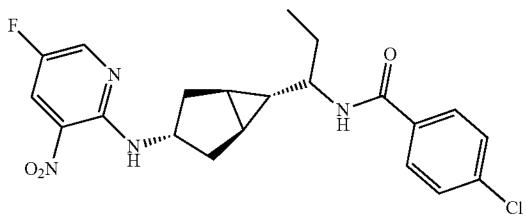 [SMILES: CCC(NC(=O)c1ccc(Cl)cc1)[C@H]1[C@@H]2C[C@@H](Nc3ncc(F)cc3[N+](=O)[O-])C[C@@H]21] | 432 | 433 | SNAr (DIEA/DMSO) |
| 237 | 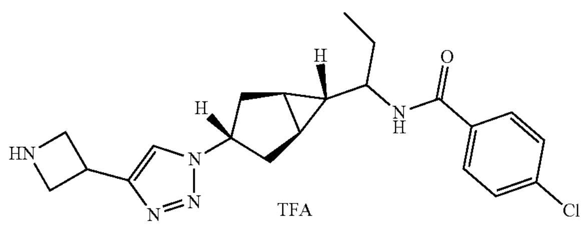 [SMILES: CCC(NC(=O)c1ccc(Cl)cc1)[C@H]1[C@@H]2C[C@@H](n3cc(C4CNC4)nn3)C[C@@H]21] | 399 | 400 | Exemplified |
| 238 | 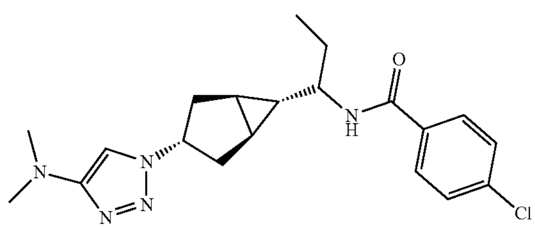 [SMILES: CCC(NC(=O)c1ccc(Cl)cc1)[C@H]1[C@@H]2C[C@@H](n3cc(N(C)C)nn3)C[C@@H]21] | 387 | 388 | 1,4 Triazole, Click (Reductive Amination with paraformaldehyde/ NaBH₃CN/AcOH) |
| 239 | 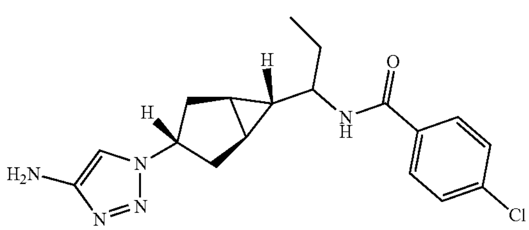 [SMILES: CCC(NC(=O)c1ccc(Cl)cc1)[C@H]1[C@@H]2C[C@@H](n3cc(N)nn3)C[C@@H]21] | 359 | 360 | Exemplified |
| 240 | 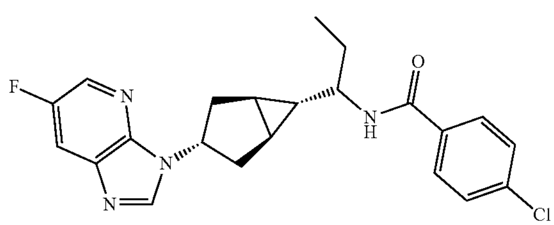 [SMILES: CCC(NC(=O)c1ccc(Cl)cc1)[C@H]1[C@@H]2C[C@@H](n3cnc4cc(F)cnc43)C[C@@H]21] | 412 | 412 | BzI |

TABLE 2-continued

| Compound | Structure | Calc. Mass | Mass [M + H]+ | Synthesis as per |
|---|---|---|---|---|
| 241 | 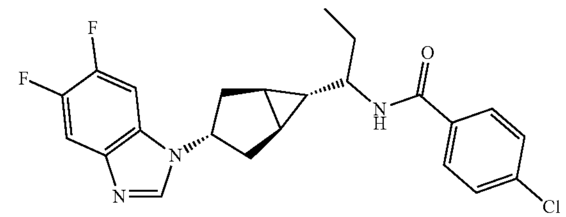 [SMILES: CCC(NC(=O)c1ccc(Cl)cc1)[C@H]1[C@@H]2C[C@@H](n3cnc4cc(F)c(F)cc43)C[C@@H]21] | 429 | 430 | MS |
| 242 | 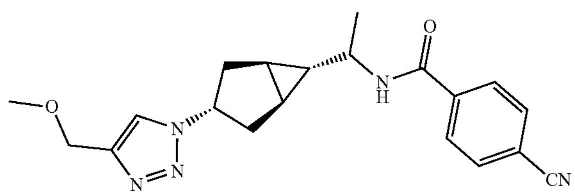 [SMILES: COCc1cn([C@@H]2C[C@@H]3[C@H](C2)[C@H]3C(C)NC(=O)c2ccc(C#N)cc2)nn1] | 365 | 366 | 1,4 Triazole, Click (Alkylation with dimethyl sulfate) |
| 243 | 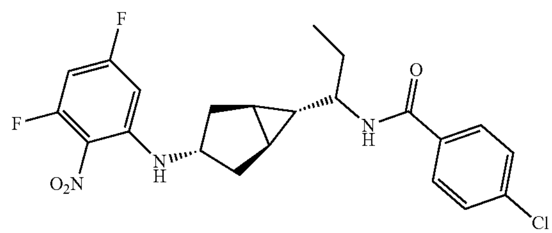 [SMILES: CCC(NC(=O)c1ccc(Cl)cc1)[C@H]1[C@@H]2C[C@@H](Nc3cc(F)cc(F)c3[N+](=O)[O-])C[C@@H]21] | 449 | 450 | SNAr (K$_2$CO$_3$/THF) |
| 244 | 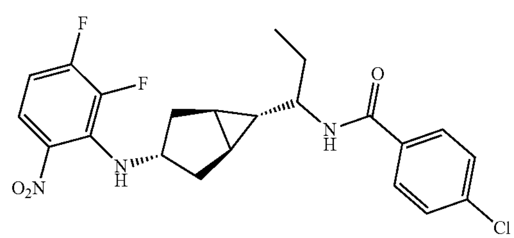 [SMILES: CCC(NC(=O)c1ccc(Cl)cc1)[C@H]1[C@@H]2C[C@@H](Nc3c([N+](=O)[O-])ccc(F)c3F)C[C@@H]21] | 449 | 450 | SNAr (K$_2$CO$_3$/THF) |
| 245 | 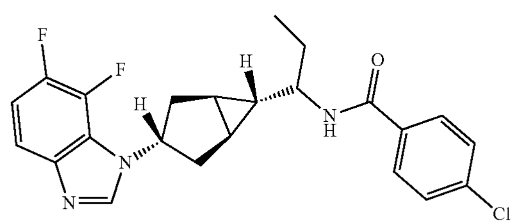 [SMILES: CCC(NC(=O)c1ccc(Cl)cc1)[C@H]1[C@@H]2C[C@@H](n3cnc4ccc(F)c(F)c43)C[C@@H]21] | 429 | 430 | Exemplified |
| 246 | 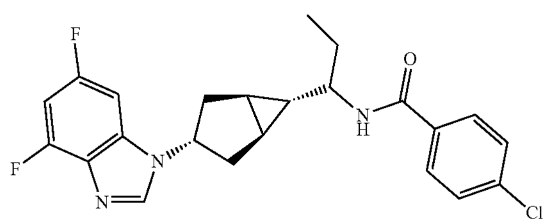 [SMILES: CCC(NC(=O)c1ccc(Cl)cc1)[C@H]1[C@@H]2C[C@@H](n3cnc4c(F)cc(F)cc43)C[C@@H]21] | 429 | 432 | BzI |
| 247 | 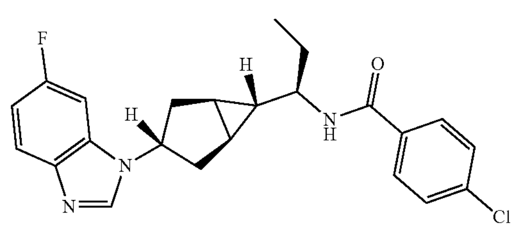 [SMILES: CC[C@@H](NC(=O)c1ccc(Cl)cc1)[C@H]1[C@@H]2C[C@@H](n3cnc4ccc(F)cc43)C[C@@H]21] | 411 | 412 | Exemplified |

TABLE 2-continued

| Compound | Structure | Calc. Mass | Mass [M + H]+ | Synthesis as per |
|---|---|---|---|---|
| 248 | 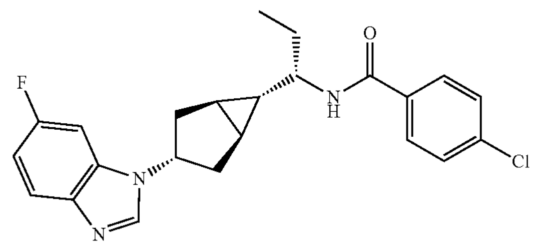 [SMILES: CC[C@H](NC(=O)c1ccc(Cl)cc1)[C@H]1[C@@H]2C[C@@H](n3cnc4ccc(F)cc43)C[C@@H]21] | 411 | 412 | Exemplified |
| 249 | 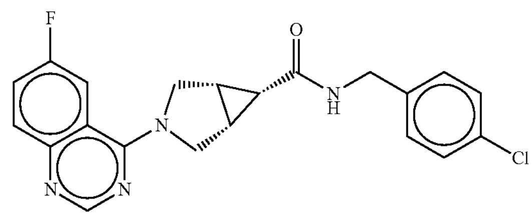 | 396 | 397 | Compound 109 |
| 250 | 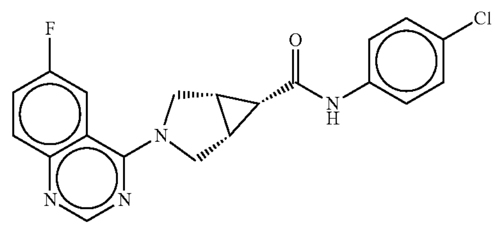 | 382 | 383 | Compound 109 |
| 251 | 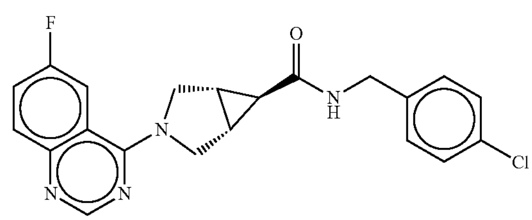 | 396 | 397 | Compound 109 |
| 252 | 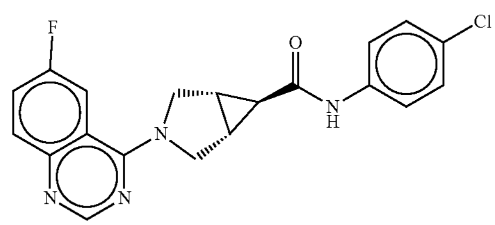 | 382 | 383 | Compound 109 |
| 253 | 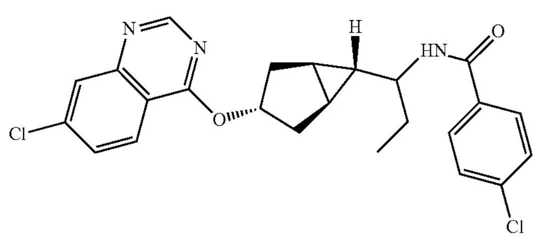 [SMILES: CCC(NC(=O)c1ccc(Cl)cc1)[C@H]1[C@@H]2C[C@@H](Oc3ncnc4cc(Cl)ccc34)C[C@@H]21] | 455 | 456 | Compound 21 |

TABLE 2-continued

| Compound | Structure | Calc. Mass | Mass [M + H]+ | Synthesis as per |
|---|---|---|---|---|
| 254 | 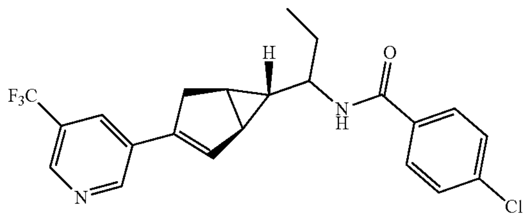 [SMILES: CCC(NC(=O)c1ccc(Cl)cc1)[C@@H]1[C@H]2C=C(c3cncc(C(F)(F)F)c3)C[C@H]21] | 420 | 421 | Exemplified |
| 255 | 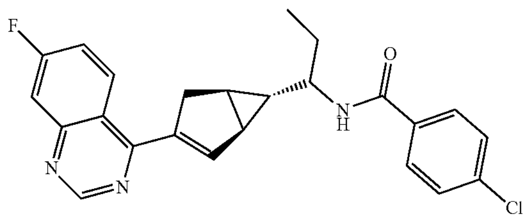 [SMILES: CCC(NC(=O)c1ccc(Cl)cc1)[C@@H]1[C@H]2C=C(c3ncnc4cc(F)ccc34)C[C@H]21] | 421 | 422 | Exemplified |
| 256 | 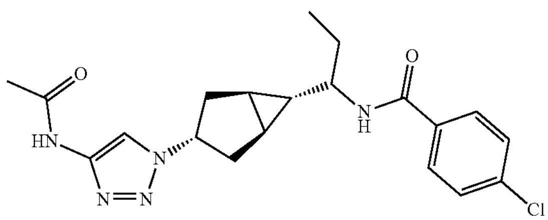 [SMILES: CCC(NC(=O)c1ccc(Cl)cc1)[C@H]1[C@@H]2C[C@@H](n3cc(NC(C)=O)nn3)C[C@@H]21] | 401 | 402 | 1,4 Triazole (Acylation with AcCl, K$_2$CO$_3$/MeOH) |
| 257 | 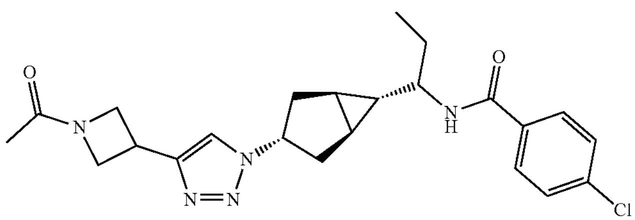 [SMILES: CCC(NC(=O)c1ccc(Cl)cc1)[C@H]1[C@@H]2C[C@@H](n3cc(C4CN(C(C)=O)C4)nn3)C[C@@H]21] | 441 | 442 | 1,4 Triazole (Acylation with AcCl) |
| 258 | 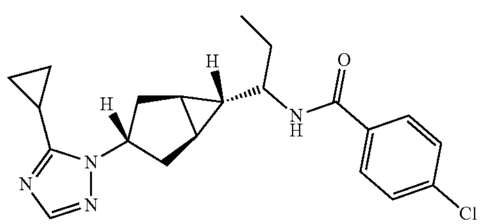 [SMILES: CCC(NC(=O)c1ccc(Cl)cc1)[C@H]1[C@@H]2C[C@@H](n3ncnc3C3CC3)C[C@@H]21] | 384 | 385 | MS |
| 259 | 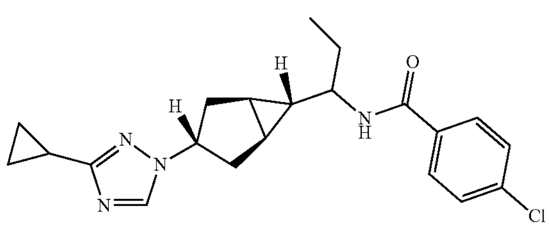 [SMILES: CCC(NC(=O)c1ccc(Cl)cc1)[C@H]1[C@@H]2C[C@@H](n3cnc(C4CC4)n3)C[C@@H]21] | 384 | 385 | MS |
| 260 | 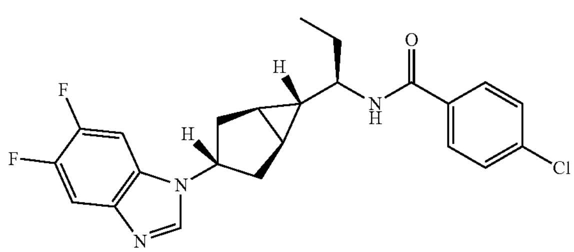 [SMILES: CC[C@@H](NC(=O)c1ccc(Cl)cc1)[C@H]1[C@@H]2C[C@@H](n3cnc4cc(F)c(F)cc43)C[C@@H]21] | 429 | 430 | Exemplified |

TABLE 2-continued

| Compound | Structure | Calc. Mass | Mass [M + H]+ | Synthesis as per |
|---|---|---|---|---|
| 261 | 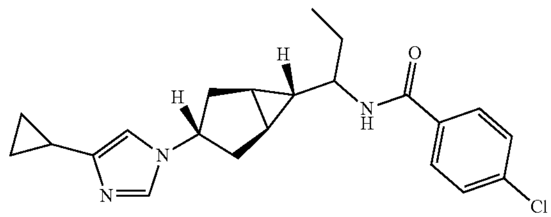 [SMILES: CCC(NC(=O)c1ccc(Cl)cc1)[C@H]1[C@@H]2C[C@@H](n3cnc(C4CC4)c3)C[C@@H]21] | 383 | 384 | Exemplified |
| 262 | | 384 | nd | Similar to compound 97 (dehydration under acidic conditions, in DMSO) | nd = not determined

In more detail, the following synthetic schemes were used:

Synthesis of 2-(4-Chlorophenyl)-N-(3-(6-fluoroquinolin-4-yl)-3-azabicyclo[3.1.0]hexan-6-yl) acetamide (Compound 109)

Step 1:

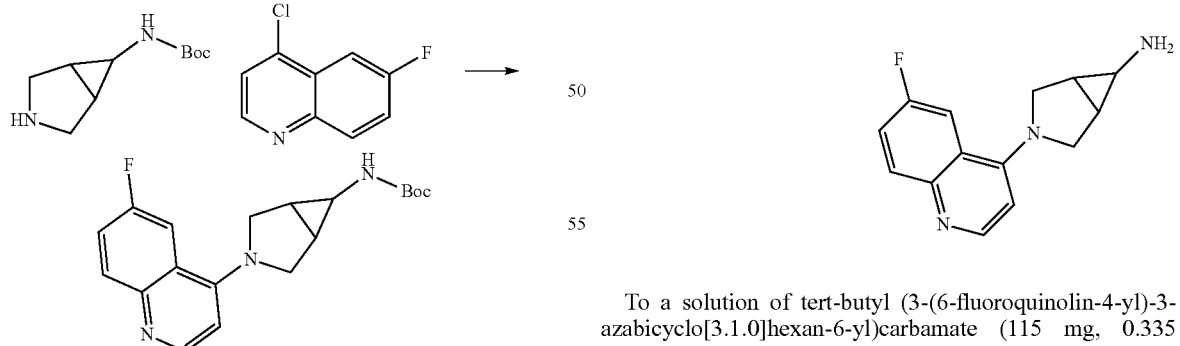

To a solution of tert-butyl 3-azabicyclo[3.1.0]hexan-6-ylcarbamate (300 mg, 1.51 mmol) in DMF (7.566 mL) were added DIEA (529 µl, 3.03 mmol) and 4-chloro-6-fluoroquinoline (330 mg, 1.82 mmol) and the resulting mixture was stirred at RT for 3 days. Then the reaction mixture was heated to 60° C. and stirred for 18 h. The reaction mixture was diluted with EtOAc (50 mL) and washed with H$_2$O (50 mL). The layers were separated, and the organic layer was washed with sat. NaCl (50 mL), dried over Na$_2$SO4, filtered, and concentrated and purified via silica gel chromatography (0-10% MeOH in DCM) to give tert-butyl (3-(6-fluoroquinolin-4-yl)-3-azabicyclo[3.1.0]hexan-6-yl)carbamate (115 mg, 0.35 mmol, 22% yield) as a yellow solid. MS(ES$^+$) C$_{19}$H$_{22}$FN$_3$O$_2$ requires: 343, found: 344 [M+H]$^+$.

Step 2:

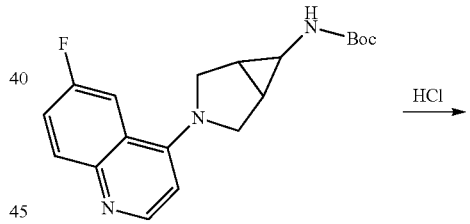

To a solution of tert-butyl (3-(6-fluoroquinolin-4-yl)-3-azabicyclo[3.1.0]hexan-6-yl)carbamate (115 mg, 0.335 mmol) in THF (1340 µl) and methanol at room temperature was added HCl (1 mL, 2.00 mmol, 4 M in dioxane) over 6 h. The volatiles were removed under reduced pressure to give 3-(6-fluoroquinolin-4-yl)-3-azabicyclo[3.1.0]hexan-6-amine (96.8 mg, 0.398 mmol, 119% yield) as a tan solid and HCl salt. The crude product was taken on without purification. MS(ES$^+$) C$_{14}$H$_{14}$FN$_3$ requires: 243, found: 244 [M+H]$^+$.

Step 3:

To a solution of 3-(6-fluoroquinolin-4-yl)-3-azabicyclo[3.1.0]hexan-6-amine (15 mg, 0.062 mmol) in DMF (308 µl) were added 2-(4-chlorophenyl)acetic acid (12.62 mg, 0.074 mmol), HATU (35.2 mg, 0.092 mmol) and DIEA (53.8 µl, 0.308 mmol) and the resulting mixture was stirred at room temperature until consumption of starting material was observed. The residue was adsorbed onto silica gel and purified via flash chromatography (0-10% MeOH/1% NH$_4$OH in DCM) to give the desired product. The product was dissolved in DCM (2 mL), washed with sat'd NaHCO$_3$ (2 mL) and sat'd NaCl (2 mL), dried over Na$_2$SO4, filtered, and concentrated to give 2-(4-chlorophenyl)-N-(3-(6-fluoroquinolin-4-yl)-3-azabicyclo[3.1.0]hexan-6-yl)acetamide (7.2 mg, 0.018 mmol, 29.5% yield) as a white powder. MS(ES$^+$) C$_{22}$H$_{19}$ClFN$_3$O requires: 395, found: 396 [M+H]$^+$. $^1$H NMR (METHANOL-d$_4$) δ: 8.40 (d, J=5.3 Hz, 1H), 7.96-7.98 (m, 1H), 7.88-7.92 (m, 1H), 7.44-7.51 (m, 1H), 7.30-7.34 (m, 2H), 7.24-7.29 (m, 2H), 6.75 (d, J=5.7 Hz, 1H), 4.06 (d, J=9.8 Hz, 2H), 3.62 (d, J=9.8 Hz, 2H), 3.48 (s, 2H), 2.72 (br. s., 1H), 1.90 (br. s., 2H).

Synthesis of N-(1-((1R,5S,6R)-bicyclo[3.1.0]hex-2-en-6-yl)propyl)-4-chlorobenzamide (Compound 113)

The title compound (5.7 mg, 0.013 mmol, 5% yield) was isolated from the purification of 4-chloro-N-(1-((1R,3s,5S,6r)-3-((tetrahydro-2H-pyran-4-yl)oxy)bicyclo[3.1.0]hexan-6-yl) propyl)benzamide (Compound 101, above) as a white solid. MS(ES$^+$) C$_{16}$H$_{18}$ClNO requires: 275, found: 276 [M+H]$^+$. $^1$H NMR (METHANOL-d$_4$) δ: 7.80 (d, J=7.9 Hz, 2H), 7.47 (d, J=7.9 Hz, 2H), 5.80-5.96 (m, 1H), 5.32-5.46 (m, 1H), 3.36-3.45 (m, 1H), 2.49-2.63 (m, 1H), 2.25-2.40 (m, 1H), 1.83-1.91 (m, 1H), 1.64-1.81 (m, 2H), 1.54-1.63 (m, 1H), 0.97 (t, J=7.0 Hz, 3H), 0.38-0.45 (m, 1H).

Synthesis of 4-chloro-N-(1-((1R,3s, 5S, 6r)-3-(2,3-dioxoindolin-1-yl)bicyclo[3.1.0]hexan-6-yl)propyl)benzamide (Compound 114)

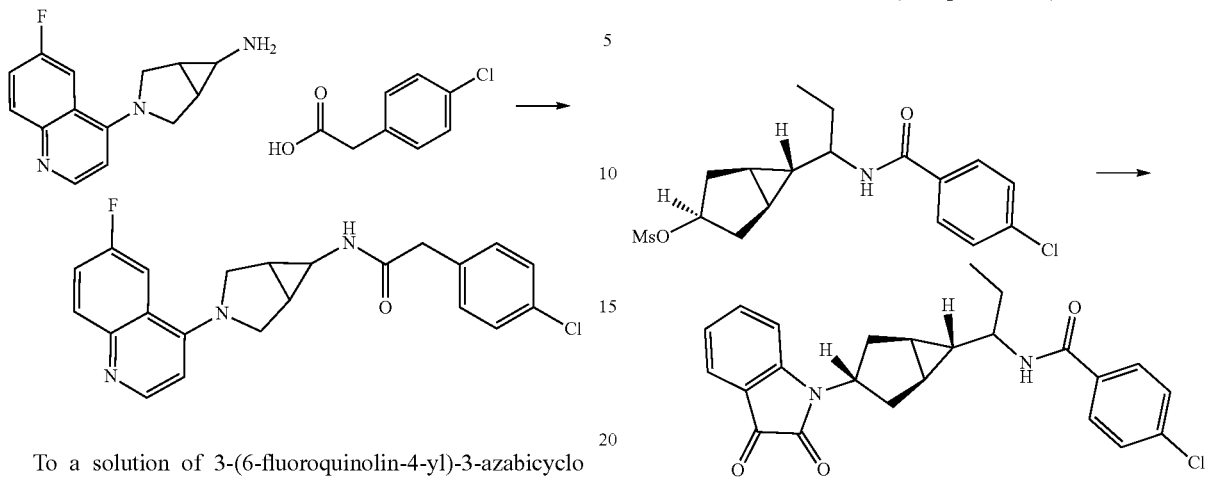

To a solution of (1R,3r,5S,6r)-6-(1-(4-chlorobenzamido)propyl)bicyclo[3.1.0]hexan-3-yl methanesulfonate ("MS" procedure, above) (33.2 mg, 0.089 mmol) in DMF (893 µl) was added K$_2$CO$_3$ (37 mg, 0.266 mmol) and indoline-2,3-dione (14.45 mg, 0.098 mmol). The solution was stirred overnight at 80° C. Water was added to the solution then it was extracted with EtOAc. The organics were collected, dried with Na$_2$SO$_4$, filtered, and concentrated. The residue was purified by mass-triggered preparative HPLC (Mobile phase: A=0.1% TFA/H$_2$O, B=0.1% TFA/MeCN; Gradient: B=[40]-[90]%; 12 min; Column: C18) to yield 4-chloro-N-(1-((1R,3s,5S,6r)-3-(2,3-dioxoindolin-1-yl)bicyclo[3.1.0]hexan-6-yl)propyl) benzamide (7.4 mg, 0.017 mmol, 19% yield). MS (ES$^+$) C$_{24}$H$_{23}$ClN$_2$O$_3$ requires 422, found 423 [M+H]$^+$.

Synthesis of 4-chloro-N-(1-((R, 3s,5S,6r)-3-(phenylsulfonamido)bicyclo[3.1.0]hexan-6-yl)propyl)benzamide (Compound 116)

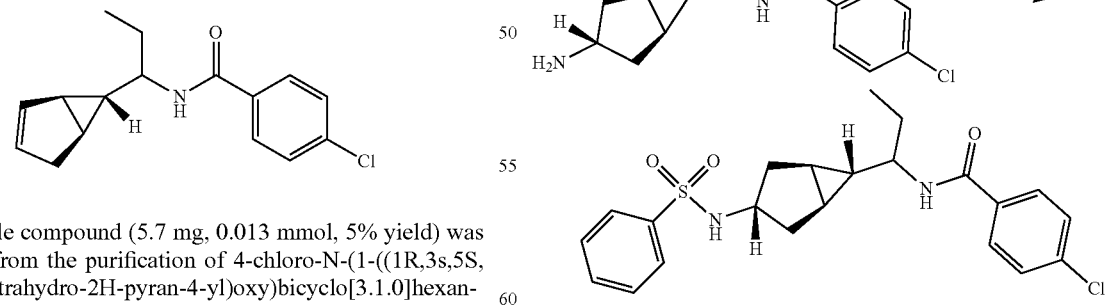

To a solution of N-(1-((1R,3s,5 S,6r)-3-aminobicyclo[3.1.0]hexan-6-yl)propyl)-4-chlorobenzamide (25 mg, 0.085 mmol) in DCM (854 µl) was added triethylamine (23.8 µl, 0.171 mmol) and benzenesulfonyl chloride (16.6 mg, 0.094 mmol). The solution was stirred at room temperature for 2 hours then concentrated. The residue was purified by mass-triggered preparative HPLC (Mobile phase: A=0.1% TFA/H₂O, B=0.1% TFA/MeCN; Gradient: B=[50]-[90]%; 12 min; Column: C18) to yield 4-chloro-N-(1-((1R,3s,5S,6r)-3-(phenylsulfonamido)bicyclo[3.1.0]hexan-6-yl)propyl)benzamide (25 mg, 0.058 mmol, 67.6% yield). MS (ES⁺) C$_{22}$H$_{25}$ClN$_2$O$_3$S requires 432, found 433 [M+H)]⁺.

Synthesis of N-((1R,3s, 5S, 6r)-6-(1-(4-chlorobenzamido)propyl)bicyclo[3.1.0]hexan-3-yl)picolinamide (Compound 117)

Step 1:

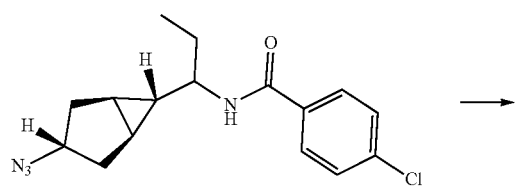

To a solution of N-(1-((1R,3s,5S,6r)-3-azidobicyclo[3.1.0]hexan-6-yl)propyl)-4-chlorobenzamide (1 g, 3.14 mol) in THF (9.51 mL) and water (0.951 mL) was added triphenylphosphine (2.468 g, 9.41 mmol). The solution was heated to 55° C. for 1.5 h. The solution was concentrated under reduced pressure and the residue was purified by column chromatography (isocratic 20% MeOH/1% triethylamine/79% DCM) to yield N-(1-((1R,3s,5S,6r)-3-aminobicyclo[3.1.0]hexan-6-yl)propyl)-4-chlorobenzamide (893 mg, 3.05 mmol, 97% yield). MS (ES⁺) C$_{16}$H$_{21}$ClN$_2$O requires 292, found 293 [M+H]⁺.

Step 2: (General "Amide coupling")

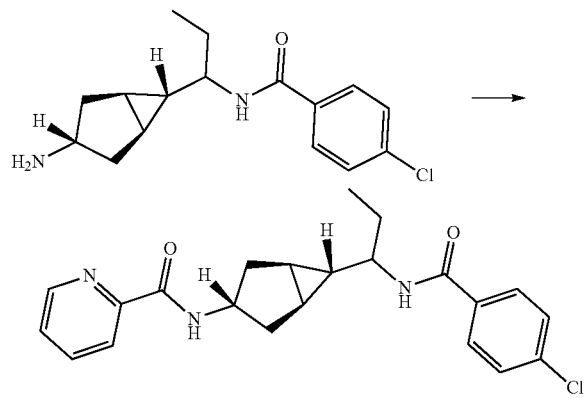

To a solution of N-(1-((1R,3s,5 S,6r)-3-aminobicyclo[3.1.0]hexan-6-yl)propyl)-4-chlorobenzamide (25 mg, 0.085 mmol) in DMF (854 µl) was added triethylamine (35.7 µl, 0.256 mmol), picolinic acid (11.56 mg, 0.094 mmol) and 2,4,6-tripropyl-1,3,5,2,4,6-trioxatriphosphinane 2,4,6-trioxide (75 µl, 0.128 mmol). The solution was heated to 65° C. and stirred for 2 hours. The reaction was quenched with water and extracted with EtOAc. The organics were collected and concentrated under reduced pressure. The residue was purified by mass-triggered preparative HPLC (Mobile phase: A=0.1% TFA/H₂O, B=0.1% TFA/MeCN; Gradient: B=[50]-[90]%; 12 min; Column: C18) to yield N-((1R,3s,5S,6r)-6-(1-(4-chlorobenzamido)propyl)bicyclo[3.1.0]hexan-3-yl)picolinamide (15.3 mg, 0.038 mmol, 45% yield). MS (ES⁺) C$_{22}$H$_{24}$ClN$_3$O$_2$ requires 397, found 398 [M+H]⁺. ¹H NMR (CHLOROFORM-d) δ: 8.53 (d, J=4.3 Hz, 1H), 8.14 (d, J=7.9 Hz, 1H), 7.93 (d, J=8.5 Hz, 1H), 7.80-7.87 (m, 1H), 7.74 (d, J=8.5 Hz, 2H), 7.36-7.47 (m, 3H), 6.36 (d, J=8.5 Hz, 1H), 4.07-4.23 (m, 1H), 3.34-3.44 (m, 1H), 2.23-2.40 (m, 2H), 1.59-1.80 (m, 4H), 1.36-1.51 (m, 2H), 0.98 (t, J=7.5 Hz, 3H), 0.84-0.86 (m, 1H).

Synthesis of 4-chloro-N-(1-((1R,3s, 5S, 6r)-3-(3,3-difluoro-2-oxoindolin-1-yl)bicyclo[3.1.0]hexan-6-yl)propyl)benzamide (Compound 119)

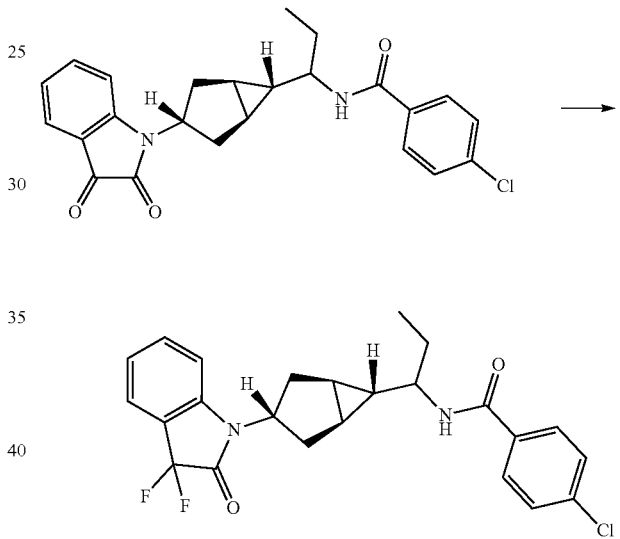

To a solution of 4-chloro-N-(1-((1R,3s,5S,6r)-3-(2,3-dioxoindolin-1-yl)bicyclo[3.1.0]hexan-6-yl)propyl)benzamide (3.7 mg, 8.75 µmol) in DCM (175 µl) was added (diethylamino)sulfur trifluoride (3.47 µl, 0.026 mmol). The solution was stirred at room temperature for 6 hours. The solution was concentrated and purified by mass-triggered preparative HPLC (Mobile phase: A=0.1% TFA/H₂O, B=0.1% TFA/MeCN; Gradient: B=[30]-[70]%; 12 min; Column: C18) to yield 4-chloro-N-(1-((1R,3s,5S,6r)-3-(3,3-difluoro-2-oxoindolin-1-yl)bicyclo[3.1.0]hexan-6-yl)propyl)benzamide (0.6 mg, 1.35 µm, 15% yield). MS (ES⁺) C$_{24}$H$_{23}$ClF$_2$N$_2$O$_2$ requires 444, found 445 [M+H]⁺. ¹H NMR (METHANOL-d$_4$) δ: 8.38 (br. d., J=8.2 Hz, 1H), 7.81 (d, J=8.2 Hz, 2H), 7.53-7.63 (m, 2H), 7.47 (d, J=8.2 Hz, 2H), 7.18-7.25 (m, 1H), 7.14 (d, J=7.9 Hz, 1H), 4.48-4.58 (m, 1H), 3.33-3.46 (m, 1H), 2.32-2.54 (m, 2H), 1.92-2.11 (m, 2H), 1.63-1.85 (m, 2H), 1.47-1.61 (m, 2H), 0.91-1.07 (m, 4H).

Synthesis of 4-chloro-N-(1-((1R,3s, 5S, 6r)-3-(5-fluoro-2-oxoindolin-1-yl)bicyclo[3.1.0]hexan-6-yl)propyl)benzamide (Compound 121)

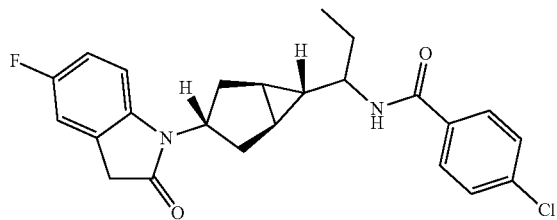 [SMILES: CCC(NC(=O)c1ccc(Cl)cc1)[C@H]1[C@@H]2C[C@@H](N3C(=O)Cc4cc(F)ccc43)C[C@@H]21]

Step 1:

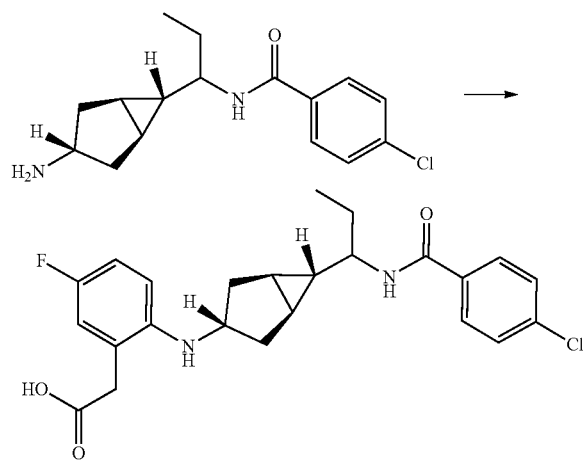

Synthesis similar to 4-chloro-N-(1-((1R,3s,5S,6r)-3-(pyridin-2-ylamino)bicyclo[3.1.0]hexan-6-yl)propyl)benzamide (Compound 226) was used to give the intermediate, 2-(2-(((1R,3s,5S,6r)-6-(1-(4-chlorobenzamido)propyl)bicyclo[3.1.0]hexan-3-yl)amino)-5-fluorophenyl)acetic acid, MS (ES⁺) $C_{24}H_{26}ClFN_3O_3$ requires 444, found 445 [M+H]⁺.

Step 2:

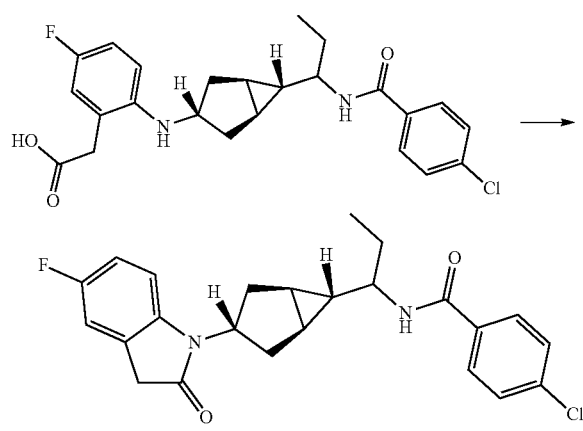

2-(2-(((1R,3s,5S,6r)-6-(1-(4-chlorobenzamido)propyl)bicyclo[3.1.0]hexan-3-yl)amino)-5-fluorophenyl)acetic acid was ring closed using dicyclohexylcarbodiimide (DCC, 1.5 eq) in DCM/EtOAc (1/1, 0.1M) and purified by mass directed HPLC to give 4-chloro-N-(1-((1R,3s,5S,6r)-3-(5-fluoro-2-oxoindolin-1-yl)bicyclo[3.1.0]hexan-6-yl)propyl)benzamide. MS (ES⁺) $C_{24}H_{24}ClFN_2O_2$ requires 426, found 427 [M+H]⁺.

Synthesis of 4-chloro-N-(1-((1R,3s, 5S, 6r)-3-(3,3-dimethyl-2,5-dioxopyrrolidin-1-yl)bicyclo[3.1.0]hexan-6-yl)propyl)benzamide (Compound 122)

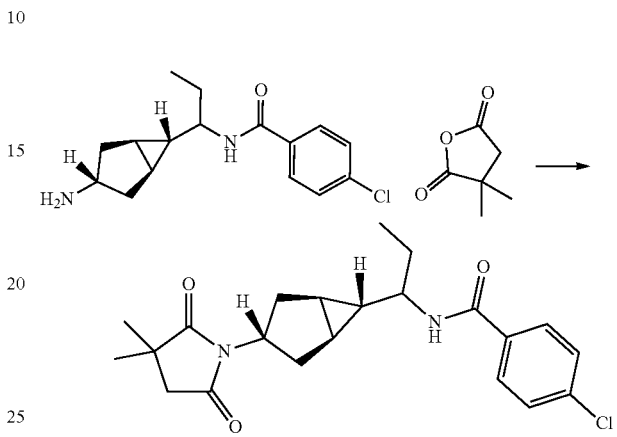

N-(1-((1R,3s,5S,6r)-3-aminobicyclo[3.1.0]hexan-6-yl)propyl)-4-chlorobenzamide (25 mg, 0.085 mmol) was dissolved in Dioxane (854 µl) and 3,3-dimethyldihydrofuran-2,5-dione (10.60 µl, 0.094 mmol) was added. The solution was heated to 80° C. and stirred for 2 hours. To the reaction was added PTSA (1.624 mg, 8.54 µmol) and the reaction was stirred at 80° C. until complete. The mixture was concentrated and purified by mass-triggered preparative HPLC (Mobile phase: A=0.1% TFA/H₂O, B=0.1% TFA/MeCN; Gradient: B=[30]-[70]%; 12 min; Column: C18) to give 4-chloro-N-(1-((1R,3s,5S,6r)-3-(3,3-dimethyl-2,5-dioxopyrrolidin-1-yl)bicyclo[3.1.0]hexan-6-yl)propyl)benzamide. MS ES+$C_{22}H_{27}ClN_2O_3$ requires 402, found 403 [M+H]⁺.

Synthesis of 4-chloro-N-(1-((R, 3s, 5S, 6r)-3-(6-fluoro-1H-benzo[d]imidazol-1-yl)bicyclo[3.1.0]hexan-6-yl)propyl)benzamide (Compound 125)

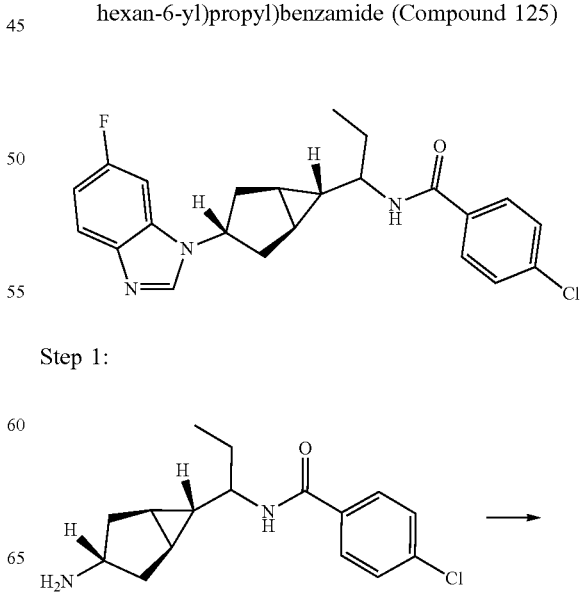

Step 1:

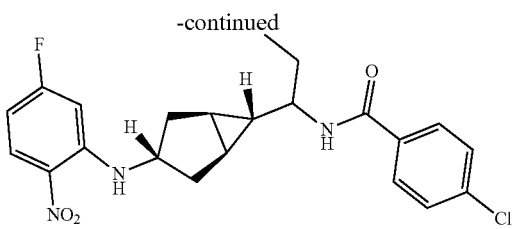

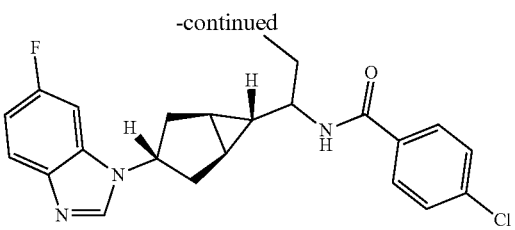

To a suspension of 2-bromo-4-fluoro-1-nitrobenzene (24.79 mg, 0.113 mmol) in dioxane (1025 µl) was added RuPhos pre-catalyst fourth generation (17.43 mg, 0.020 mmol), 2-dicyclohexylphosphino-2',6'-diisopropoxybiphenyl (9.56 mg, 0.020 mmol), sodium tert-butoxide (49.2 mg, 0.512 mmol), and N-(1-((1R,3s,5S,6r)-3-aminobicyclo[3.1.0]hexan-6-yl)propyl)-4-chlorobenzamide (30 mg, 0.102 mmol). The solution was degassed with $N_2$ for 2 minutes then stirred at 65° C. for 2 hours. The solution was concentrated and purified by mass-triggered preparative HPLC (Mobile phase: A=0.1% TFA/$H_2O$, B=0.1% TFA/MeCN; Gradient: B=[40]-[80]%; 12 min; Column: C18) to yield 4-chloro-N-(1-((1R,3s,5S,6r)-3-((5-fluoro-2-nitrophenyl)amino)bicyclo[3.1.0]hexan-6-yl)propyl)benzamide (9.2 mg, 0.021 mmol, 20% yield). MS (ES$^+$) $C_{22}H_{23}ClFN_3O_3$ requires 431, found 432 [M+H]$^+$.

Step 2:

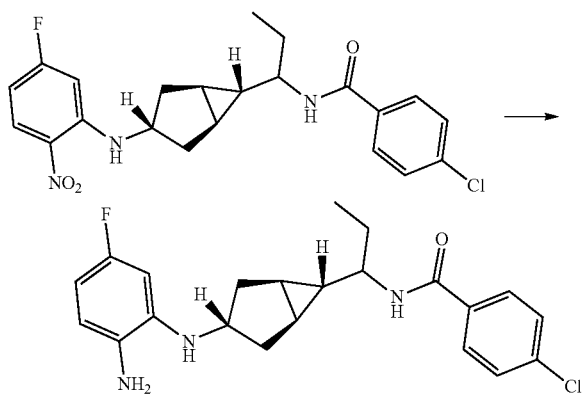

To a solution of 4-chloro-N-(1-((1R,3s,5S,6r)-3-((5-fluoro-2-nitrophenyl)amino)bicyclo[3.1.0]hexan-6-yl)propyl)benzamide (9.2 mg, 0.021 mmol) in Ethanol (160 µl) and water (53 µl) was added iron (7.14 mg, (0.128 mmol) and ammonium chloride (1.14 mg, 0.021 mmol).

The mixture was heated at reflux for 2 hours, then cooled to room temperature and filtered through celite. The filtrate was concentrated to yield N-(1-((1R,3s,5S,6r)-3-((2-amino-5-fluorophenyl)amino)bicyclo[3.1.0]hexan-6-yl)propyl)-4-chlorobenzamide (8.1 mg, 0.020 mol, 95% yield). MS (ES$^+$) $C_{22}H_{25}ClFN_3O$ requires 401, found 402 [M+H]$^+$.

Step 3:

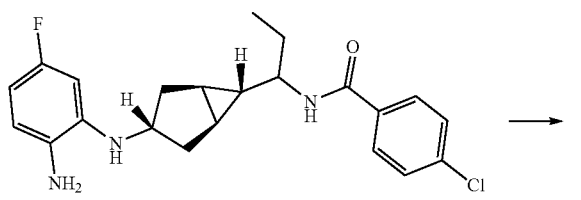

To a solution of N-(1-((1R,3s,5S,6r)-3-((2-amino-5-fluorophenyl)amino)bicyclo[3.1.0]hexan-6-yl)propyl)-4-chlorobenzamide (8.1 mg, 0.020 mol) in toluene (202 µl) was added trimethylorthoformate (2.4 µl, 0.022 mmol) and p-toluenesulfonic acid monohydrate (0.4 mg, 2.015 µmol). The solution was stirred at reflux for 2 h. The solution was cooled to room temperature, concentrated, and purified by mass-triggered preparative HPLC (Mobile phase: A=0.1% TFA/$H_2O$, B=0.1% TFA/MeCN; Gradient: B=[30]-[70]%; 12 min; Column: C18) to yield 4-chloro-N-(1-((1R,3s,5S,6r)-3-(6-fluoro-1H-benzo[d]imidazol-1-yl)bicyclo[3.1.0]hexan-6-yl)propyl)benzamide (1.2 mg, 2.91 µmol, 14.46% yield). MS (ES) $C_{23}H_{23}ClFN_3O$ requires 411, found 412. $^1$H NMR (DMSO-d$_6$) δ: 8.30-8.40 (m, 2H), 7.90 (d, J=8.3 Hz, 2H), 7.63 (dd, J=8.7, 4.9 Hz, 1H), 7.50-7.58 (m, 3H), 7.01-7.07 (m, 1H), 4.56-4.650 (m, 1H), 3.38-3.46 (m, 1H), 2.13-2.38 (m, 4H), 1.61-7.72 (m, 2H), 1.37-1.52 (m, 2H), 1.11-1.18 (m, 1H), 0.93 (t, J=7.4 Hz, 3H).

Synthesis of N-(1-((1R,3s, 5S, 6r)-3-hydroxybicyclo[3.1.0]hexan-6-yl)ethyl)-6-methoxynicotinamide (Compound 128)

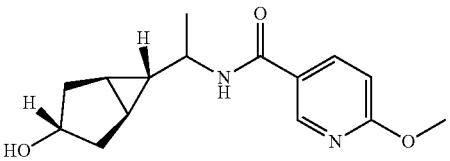 [SMILES: COc1ccc(C(=O)NC(C)[C@H]2[C@@H]3C[C@@H](O)C[C@@H]32)cn1]

Step 1:

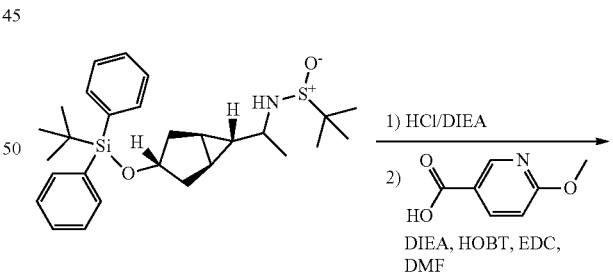

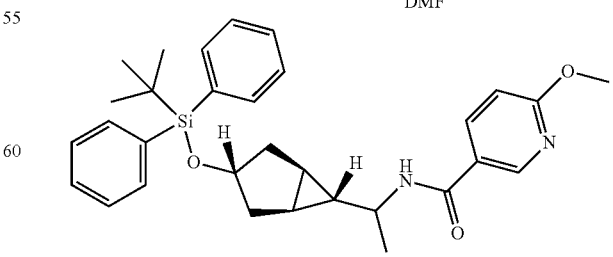

To a solution of N-(1-((1R,3s,5S,6r)-3-((tert-butyldiphenylsilyl)oxy)bicyclo[3.1.0]hexan-6-yl)ethyl)-2-methylpropane-2-sulfinamide (27.5 g, 56.8 mmol) in anhydrous EtOH (500 mL) cooled in an ice bath was added 4M HCl in Dioxane (21.3 mL, 85 mmol) and the resulting mixture was stirred and allowed to warm to room temperature over 1.5 hr. The reaction was neutralized with DIEA (29.8 mL, 171 mmol) and concentrated to give the deprotected amine as an off white gum. The intermediate was dissolved in DMF (100 mL), DIEA (29.8 mL, 171 mmol), HOBT (9.58 g, 62.5 mmol), and EDC (13.08 g, 68.2 mmol) were added and the resulting mixture was stirred at room temperature overnight. The reaction was diluted with water, acidified with 0.2M HCl, and extracted with EtOAc (2×). The organic layers were washed with 0.2M NaOH, water, sat'd NaCl, combined, dried over MgSO$_4$, filtered, concentrated, and purified by flash chromatography to give N-(1-((1R,3s,5S,6r)-3-((tert-butyldiphenylsilyl)oxy)bicyclo[3.1.0]hexan-6-yl)ethyl)-6-methoxynicotinamide (27.5 g, 53.4 mmol, 94% yield). MS (ES$^+$) C$_{31}$H$_{38}$N$_2$O$_3$Si requires: 514, found: 515 [M+H]$^+$.

Step 2:

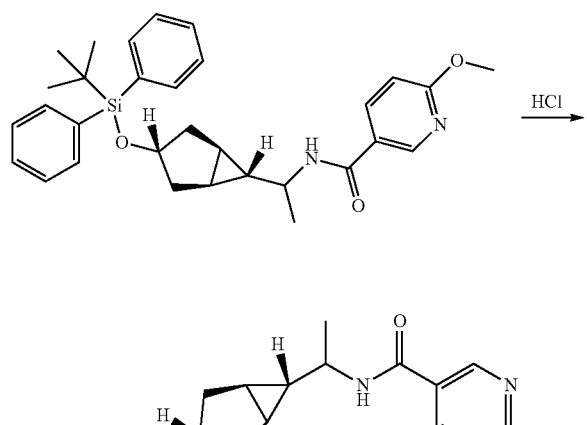

To a solution of N-(1-((1R,3s,5S,6r)-3-((tert-butyldiphenylsilyl)oxy)bicyclo[3.1.0]hexan-6-yl)ethyl)-6-methoxynicotinamide (27.5 g, 53.4 mmol) in ethanol (107 mL) cooled in an ice bath was added 4 M HCl (in dioxane, 134 mL, 534 mmol) dropwise and the reaction was stirred and allowed to warm to room temperature overnight. The reaction was concentrated and refluxed in a mixture of EtOH (100 mL) and water (10 mL) for 5 min. The resulting mixture was concentrated and triturated with warm toluene/EtOAc and warm IPA/EtOAc. The resulting solid was filtered, rinsed with EtOAc and Hexanes, and dried to give the crude product as a white solid. The solid was partitioned between DCM (150 mL) and 0.5 M NaOH (400 mL) and the layers separated. The aqueous layer was extracted with DCM (3×150 mL). The organic layers were combined, washed with water and sat'd NaCl, dried over NaSO$_4$, filtered, and concentrated to give the desired product N-(1-((1R,3s,5S,6r)-3-hydroxybicyclo[3.1.0]hexan-6-yl)ethyl)-6-methoxynicotinamide (2.3 g, 8.32 mmol, 15.6% yield) as a white solid. MS (ES$^+$) C$_{15}$H$_{20}$N$_2$O$_3$ requires: 276, found: 277 [M+H]$^+$.

Synthesis of Ethyl 3-(4-chlorobenzamido)-3-((1R, 3s, 5S, 6r)-3-((6-fluoroquinazolin-4-yl)oxy) bicyclo [3.1.0]hexan-6-yl)propanoate (Compound 134)

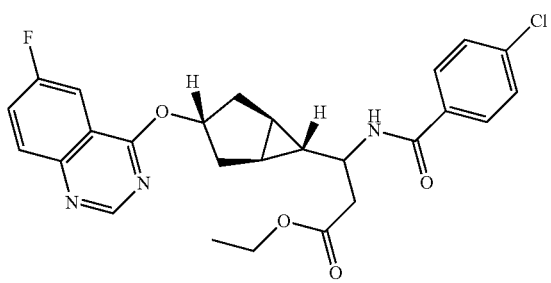 [SMILES: CCOC(=O)CC(NC(=O)c1ccc(Cl)cc1)[C@H]1[C@@H]2C[C@@H](Oc3ncnc4ccc(F)cc34)C[C@@H]21]

The title compound was synthesized similar to ethyl (S)-3-(4-chlorobenzamido)-3-((1R,3R,5S,6r)-3-(cinnolin-4-yloxy)bicyclo[3.1.0]hexan-6-yl)propanoate (Compound 84) using the general SNAr procedure from ethyl 3-(4-chlorobenzamido)-3-((1R,3r,5S,6r)-3-hydroxybicyclo[3.1.0]hexan-6-yl)propanoate (0.623 g, 3.41 mmol) to give ethyl 3-(4-chlorobenzamido)-3-((1R,3s,5S,6r)-3-((6-fluoroquinazolin-4-yl)oxy)bicyclo[3.1.0]hexan-6-yl)propanoate (453 mg, 0.910 mmol, 32.0% yield). MS (ES$^+$) C$_{26}$H$_{25}$ClFN$_3$O$_4$ requires: 497, found: 498 [M+H]$^+$.

Synthesis of 4-chloro-N-(1-((1R,3s, 5S, 6r)-3-((6-fluoroquinazolin-4-yl)oxy)bicyclo[3.1.0]hexan-6-yl)-3-hydroxypropyl)benzamide (Compound 137)

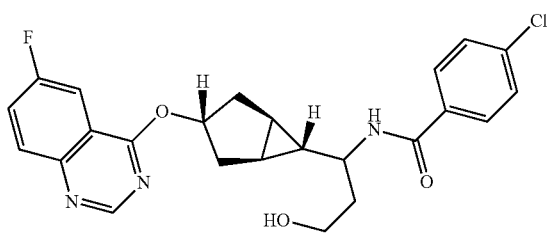 [SMILES: O=C(NC(CCO)[C@H]1[C@@H]2C[C@@H](Oc3ncnc4ccc(F)cc34)C[C@@H]21)c1ccc(Cl)cc1]

To a 0° C. solution of LAH (100 µl, 0.100 mmol) was added ethyl 3-(4-chlorobenzamido)-3-((1R,3s,5S,6r)-3-((6-fluoroquinazolin-4-yl)oxy)bicyclo[3.1.0]hexan-6-yl)propanoate (50 mg, 0.100 mmol) in THF (1004 µl). The resulting mixture was stirred at 25° C. for 30 min. The reaction mixture was cooled to 0° C., Na$_2$SO$_4$·10H$_2$O, was added and the mixture was allowed to stir for 30 min. The reaction mixture was filtered through Celite, and the filtrate was concentrated, and purified by mass-triggered preparative HPLC (Mobile phase: A=0.1% TFA/H2O, B=0.1% TFA/MeCN; Gradient: B=20-50%; 12 min; Column: C18) to give 4-chloro-N-(1-((1R,3s,5S,6r)-3-((6-fluoroquinazolin-4-yl)oxy)bicyclo[3.1.]hexan-6-yl)-3-hydroxypropyl)benzamide (9 mg, 0.020 mmol, 19.66% yield) as a pale yellow liquid. MS (ES$^+$) C$_{24}$H$_{23}$ClFN$_3$O$_3$ requires: 455, found: 456 [M+H]$^+$.

Synthesis of 4-chloro-N-(1-((1R,3s, 5S, 6r)-3-(cinnolin-4-yloxy)bicyclo[3.1.0]hexan-6-yl)-3-hydroxypropyl)benzamide (Compound 139) and 4-chloro-N-(3-hydroxy-1-((1R,3s, 5S, 6r)-3-(4-oxocinnolin-1(4H)-yl)bicyclo[3.1.0]hexan-6-yl)propyl)benzamide (Compound 140)

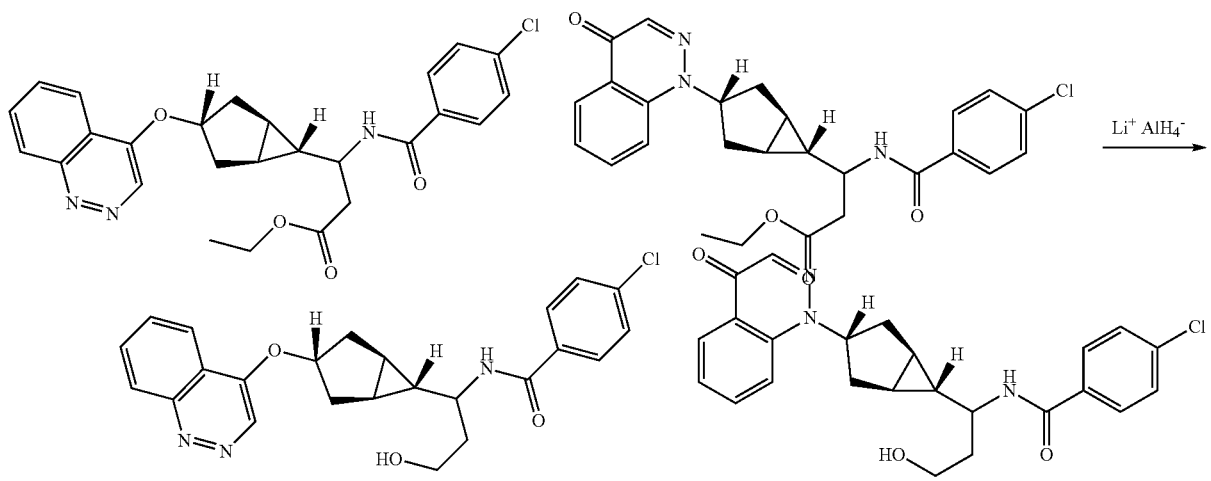

To a 0° C. solution of a mixture of ethyl 3-(4-chlorobenzamido)-3-((1R,3s,5S,6r)-3-(cinnolin-4-yloxy)bicyclo[3.1.0]hexan-6-yl)propanoate and ethyl 3-(4-chlorobenzamido)-3-((1R,3s,5S,6r)-3-(4-oxocinnolin-1(4H)-yl)bicyclo[3.1.0]hexan-6-yl)propanoate (10 mg, 0.021 mmol) in THF (208 μl) was added dropwise a solution of LAH in THF (20.84 μl, 0.021 mmol) and the resulting mixture was stirred at 0° C. for 2 h. To the reaction was added water (1.5 μl), stirred for 15 min, and warmed to room temperature. The reaction was filtered through celite, diluted with water and extracted with EtOAc. The crude was purified twice by flash chromatography on silica gel (0-20% of 8:2:1 DCM:MeOH: NH₄OH in DCM) to give 4-chloro-N-(1-((1R,3s,5S,6r)-3-(cinnolin-4-yloxy)bicyclo[3.1.0]hexan-6-yl)-3-hydroxypropyl)benzamide (0.83 mg, 1.895 μmol, 9.10% yield) and 4-chloro-N—((S)-3-hydroxy-1-((1R,3R,5 S,6r)-3-(4-oxocinnolin-1(4H)-yl)bicyclo[3.1.0]hexan-6-yl)propyl)benzamide (0.5 mg, 1.142 μmol, 5.48% yield) and 4-chloro-N-(3-hydroxy-1-((1R,3s,5S,6r)-3-(4-oxocinnolin-1 (4H)-yl)bicyclo[3.1.0]hexan-6-yl)propyl)benzamide (0.5 mg, 1.142 μmol, 5.48% yield). MS (ES⁺) C₂₄H₂₄ClN₃O₃ requires: 437, found: 438 [M+H]⁺.

Synthesis of 3-(4-chlorobenzamido)-3-((1R,3s, 5S, 6r)-3-((6-fluoroquinazolin-4-yl)oxy)bicyclo[3.1.0] hexan-6-yl)propanoic acid (Compound 148)

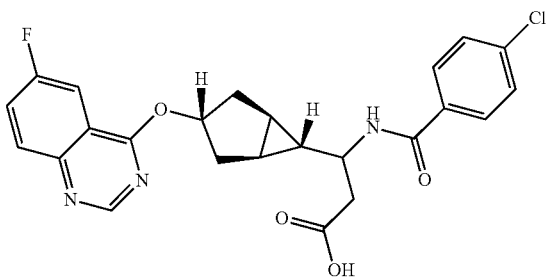

To a solution of ethyl 3-(4-chlorobenzamido)-3-((1R,3s, 5S,6r)-3-((6-fluoroquinazolin-4-yl)oxy)bicyclo[3.1.0] hexan-6-yl)propanoate (45 mg, 0.090 mmol) in THF (753 μl)/MeOH (75 μl)/Water (75 μl) was added LiOH (21.64 mg, 0.904 mmol) and the resulting mixture was stirred at 25° C. for 10 h. The reaction was concentrated and purified via silica gel chromatography (0-10% MeOH in DCM) to give 3-(4-chlorobenzamido)-3-((1R,3s,5S,6r)-3-((6-fluoroquinazolin-4-yl)oxy)bicyclo[3.1.0]hexan-6-yl)propanoic acid (42 mg, 0.089 mmol, 99% yield) as an off-white solid. MS (ES⁺) C₂₄H₂₁ClFN₃O₄ requires: 469, found: 470 [M+H]⁺.

Synthesis of 4-chloro-N-(1-((1R,3s, 5S, 6r)-3-(5-cyclopropyl-1H-1,2,3-triazol-1-yl)bicyclo[3.1.0] hexan-6-yl)propyl)benzamide (Compound 153)

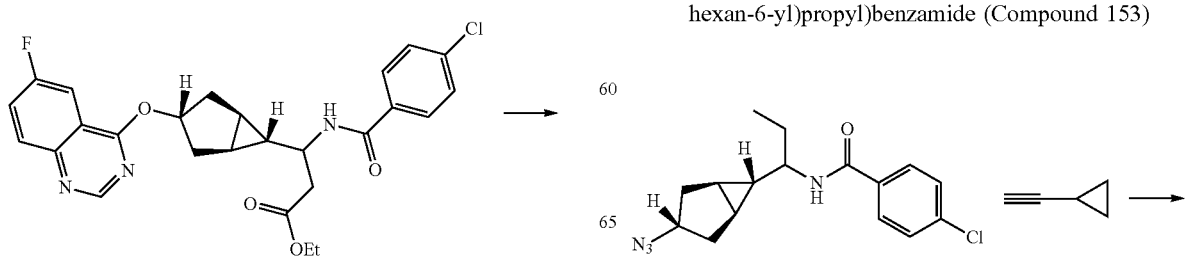

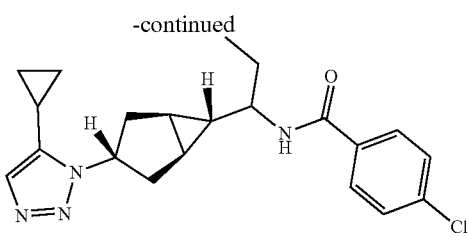

Step 1: (General "1,5 Triazole" Procedure for 1,5-Substituted Triazoles)

To a solution of N-(1-((1R,3s,5S,6r)-3-azidobicyclo[3.1.0]hexan-6-yl)propyl)-4-chlorobenzamide (50 mg, 0.157 mmol) in dioxane (1 mL) were added ethynylcyclopropane (14 µl, 0.17 mmol) and pentamethylcyclopentadienylbis(triphenylphosphine)ruthenium(II) chloride (2.5 mg, 3.1 µmol) and the resulting mixture was stirred at 60° C. for 24 h. The reaction mixture was allowed to cool to room temperature, filtered through glass fiber paper, and the filtrate was concentrated under reduced pressure. The residue was purified by mass-triggered preparative HPLC (Mobile phase: A=0.1% TFA/H$_2$O, B=0.1% TFA/MeCN; Gradient: B=40-80%; 12 min; Column: C18) to give 4-chloro-N-(1-((1R,3s,5S,6r)-3-(5-cyclopropyl-1H-1,2,3-triazol-1-yl)bicyclo[3.1.0]hexan-6-yl)propyl)benzamide TFA salt (8 mg, 0.016 mmol, 10% yield) as a pale yellow liquid. MS (ES$^+$) C$_{21}$H$_{25}$ClN$_4$O requires: 384, found: 385 [M+H]$^+$. $^1$H NMR (METHANOL-d$_4$) δ: 8.38 (d, J=8.3 Hz, 1H), 7.82 (d, J=8.3 Hz, 2H), 7.48 (d, J=8.7 Hz, 2H), 7.34 (s, 1H), 4.71-4.81 (m, 1H), 3.35-3.47 (m, 1H), 2.33-2.54 (m, 4H), 1.65-1.90 (m, 3H), 1.50-1.62 (m, 2H), 1.03-1.10 (m, 3H), 1.00 (t, J=7.6 Hz, 3H), 0.66-0.77 (m, 2H).

Synthesis of N-((1R,3s, 5S, 6r)-6-(1-(4-chlorobenzamido)propyl)bicyclo[3.1.0]hexan-3-yl)piperazine-1-carboxamide (Compound 156)

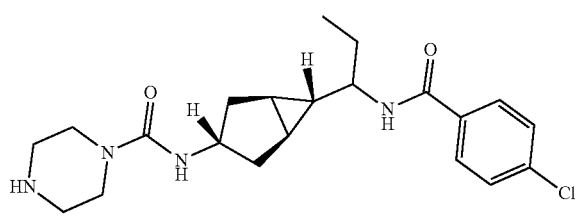 [SMILES: CCC(NC(=O)c1ccc(Cl)cc1)[C@H]1[C@@H]2C[C@@H](NC(=O)N3CCNCC3)C[C@@H]21]

Step 1:

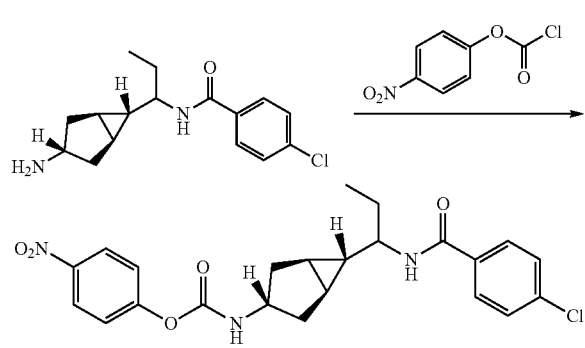

To a cooled 0° C. solution of N-(1-((1R,3s,5S,6r)-3-aminobicyclo[3.1.0]hexan-6-yl)propyl)-4-chlorobenzamide (50 mg, 0.17 mmol) in DCM (1.7 mL) were added TEA (26 µl, 0.18 mmol) and 4-nitrophenyl carbonochloridate (38 mg, 0.19 mmol). The resulting mixture was stirred at 0° C. for 1 h. The reaction mixture was partitioned between DCM (5 mL) and H2O (5 mL) and the layers were separated. The aqueous phase was extracted with DCM (5 mL), the combined organic layers were washed with sat'd NaCl, dried over Na$_2$SO$_4$, filtered and concentrated under reduced pressure. The product was used in next step without further purification. MS (ES$^+$) C$_{23}$H$_{24}$ClN$_3$O$_5$ requires: 457, found: 458 [M+H]$^+$.

Step 2:

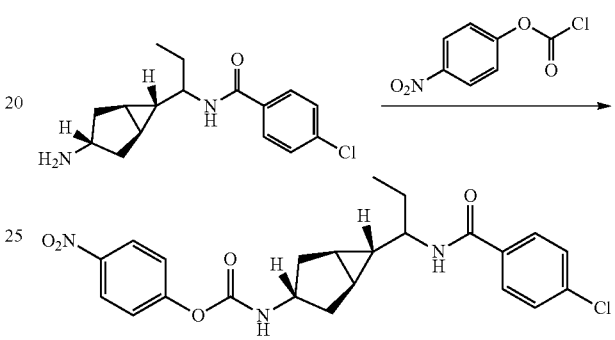

To a suspension of 4-nitrophenyl ((1R,3s,5S,6r)-6-(1-(4-chlorobenzamido)propyl)bicyclo[3.1.0]hexan-3-yl)carbamate (78 mg, 0.17 mmol) in ethanol (1.7 mL) was added piperazine (16 mg, 0.19 mmol) and the resulting mixture was stirred at 25° C. for 1 h. The mixture was neutralized with HCl (6 N) then extracted with DCM (3×10 mL). The combined organics were washed with brine (20 mL), dried over Na$_2$SO$_4$, filtered and concentrated. The residue was purified by mass-triggered preparative HPLC (Mobile phase: A=0.1% TFA/H$_2$O, B=0.1% TFA/MeCN; Gradient: B=10-40%; 12 min; Column: C18) to give N-((1R,3s,5S,6r)-6-(1-(4-chlorobenzamido)propyl)bicyclo[3.1.0]hexan-3-yl)piperazine-1-carboxamide TFA salt (16 mg, 0.031 mmol, 18% yield) as a white powder. MS (ES$^+$) C$_{21}$H$_{29}$ClN$_4$O$_2$ requires: 404, found: 405 [M+H]$^+$.

Synthesis of N-((1R,3s, 5S, 6r)-6-(1-(4-chlorobenzamido)propyl)bicyclo[3.1.0]hexan-3-yl)morpholine-4-carboxamide (Compound 157)

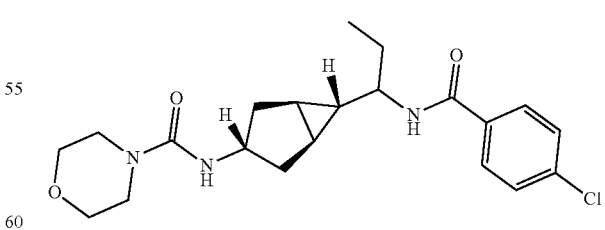

The title compound was synthesized similar to N-((1R,3s,5S,6r)-6-(1-(4-chlorobenzamido)propyl)bicyclo[3.1.0]hexan-3-yl)piperazine-1-carboxamide (Compound 156) to give N-((1R,3s,5S,6r)-6-(1-(4-chlorobenzamido)propyl)bicyclo[3.1.0]hexan-3-yl)morpholine-4-carboxamide TFA salt (25 mg, 0.048 mmol, 28% yield) as a white powder. MS (ES⁺) $C_{21}H_{24}ClN_3O_3$ requires: 405, found: 406 [M+H]⁺. ¹H NMR (DMSO-d₆) δ: 8.31 (d, J=8.7 Hz, 1H), 7.87 (d, J=8.7 Hz, 2H), 7.54 (d, J=8.7 Hz, 2H), 6.22 (d, J=7.9 Hz, 1H), 3.66-3.77 (m, 1H), 3.45-3.56 (m, 4H), 3.15-3.26 (m, 5H), 1.84-2.01 (m, 2H), 1.48-1.67 (m, 4H), 1.18 (m, 2H), 0.86 (t, J=7.4 Hz, 3H), 0.78-0.83 (m, 1H).

Synthesis of 4-chloro-N-(1-((1R,3s, 5S, 6r)-3-(1,3-dioxoisoindolin-2-yl)bicyclo[3.1.0]hexan-6-yl)propyl)benzamide (Compound 161)

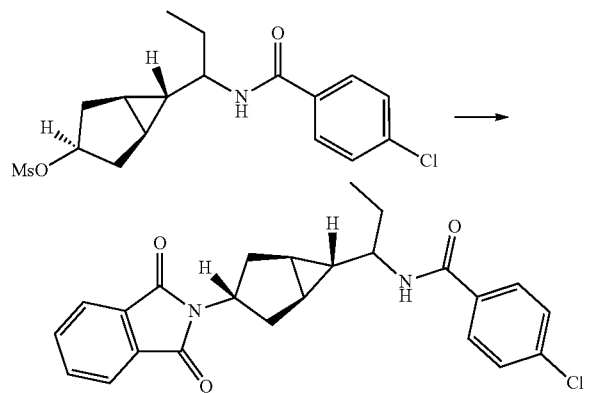

The title compound was synthesized via the general mesylate (MS) procedure with the following modifications. To a solution of (1R,3r,5S,6r)-6-(1-(4-chlorobenzamido)propyl) bicyclo[3.1.0]hexan-3-yl methanesulfonate (20 mg, 0.054 mmol) in DMF (538 μl) was added potassium phthalimide (14.94 mg, 0.081 mmol). The solution was stirred for 2 days at 55° C. The solution was cooled to room temperature, concentrated, and purified by silica gel chromatography (0-60% EtOAc/Hexanes) to yield 4-chloro-N-(1-((1R,3s,5S,6r)-3-(1,3-dioxoisoindolin-2-yl)bicyclo[3.1.0]hexan-6-yl)propyl)benzamide (11.2 mg, 0.026 mmol, 49.2% yield). MS (ES⁺) $C_{24}H_{23}ClN_2O_3$ requires 422, found 423 [M+H]⁺.

Synthesis of 4-chloro-N-(1-((R, 3s, 5S, 6r)-3-(cyano(phenyl)methyl)bicyclo[3.1.0]hexan-6-yl)propyl)benzamide (Compound 166)

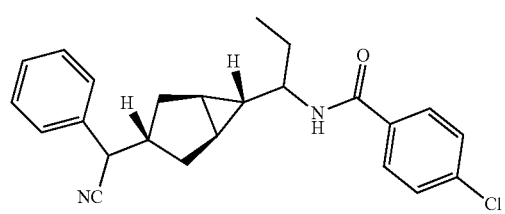 [SMILES: CCC(NC(=O)c1ccc(Cl)cc1)[C@H]1[C@@H]2C[C@@H](C(C#N)c3ccccc3)C[C@@H]21]

The title compound was synthesized similar to methyl (S)-2-((1R,3S,5S,6S)-6-((R)-1-(4-chlorobenzamido)propyl)bicyclo[3.1.0]hexan-3-yl)-2-phenylacetate (Compound 202, below) from (1R,3S,5S,6r)-6-((S)-1-(4-chlorobenzamido)propyl)bicyclo[3.1.0]hexan-3-yl methanesulfonate (50 mg, 0.134 mmol) and 2-phenylacetonitrile (17.33 mg, 0.148 mmol) to give 4-chloro-N-(1-((1R,3s,5 S,6r)-3-(cyano(phenyl)methyl)bicyclo[3.1.0]hexan-6-yl)propyl) benzamide (11 mg, 0.028 mmol, 21% yield) as an off-white solid. MS (ES⁺) $C_{24}H_{25}ClN_2O$ requires: 392, found: 393 [M+H]⁺.

Synthesis of 4-chloro-N-(1-((1R,3s, 5S, 6r)-3-(4-cyclopropyl-1H-1,2,3-triazol-1-yl)bicyclo[3.1.0]hexan-6-yl)-2-hydroxyethyl)benzamide (Compound 168)

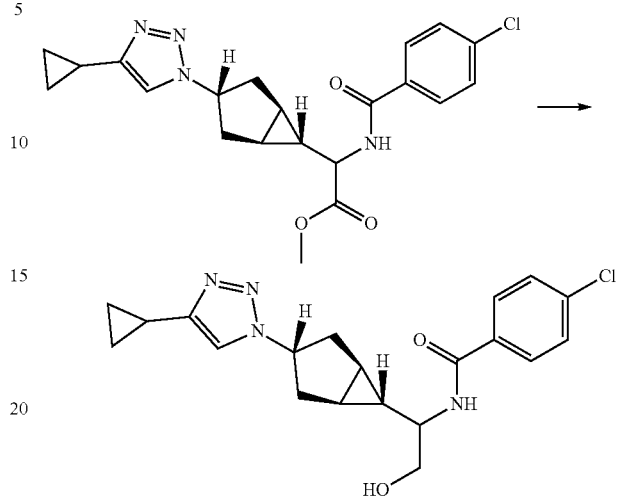

The title compound was synthesized similar to Compound 139 (above) from methyl 2-(4-chlorobenzamido)-2-((1R,3s,5S,6r)-3-(4-cyclopropyl-1H-1,2,3-triazol-1-yl)bicyclo[3.1.0]hexan-6-yl)acetate (20.2 mg, 0.049 mmol) and LAH in THF (48.7 μl, 0.049 mmol) to give 4-chloro-N-(1-((1R, 3s,5S,6r)-3-(4-cyclopropyl-1H-1,2,3-triazol-1-yl)bicyclo[3.1.0]hexan-6-yl)-2-hydroxyethyl)benzamide (15.1 mg, 0.039 mmol, 80% yield) as a white solid. MS (ES⁺) $C_{20}H_{23}ClN_4O_2$ requires: 386, found: 387 [M+H]⁺.

Synthesis of Methyl 2-(4-chlorobenzamido)-2-((1R, 3s, 5S, 6r)-3-(4-cyclopropyl-1H-1,2,3-triazol-1-yl)bicyclo[3.1.0]hexan-6-yl)acetate (Compound 169)

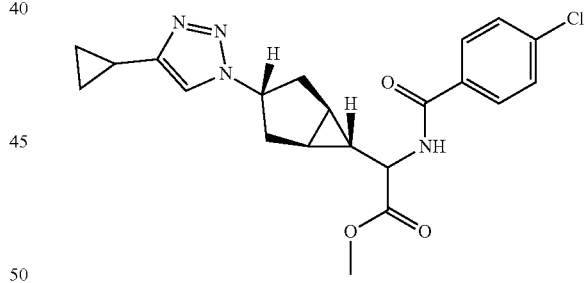

Step 1:

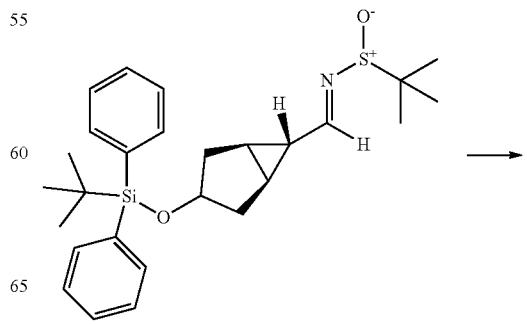

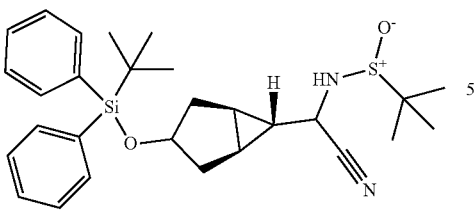

To a solution of N-((E)-((1R,5S,6r)-3-((tert-butyldiphenylsilyl)oxy)bicyclo[3.1.0]hexan-6-yl)methylene)-2-methylpropane-2-sulfinamide (1.97 g, 4.21 mmol) in DCM (42.1 mL) were added TMS-CN (5.6 mL, 42 mmol) and Ti(iOPr)$_4$ (3 eq) and heated at refluxed for 2.5 days. The reaction was diluted with DCM, cooled in an icebath, quenched with sat'd NaHCO$_3$, filtered through celite, and rinsed with DCM and H$_2$O. The filtrate was washed with sat'd NaCl, dried over Na$_2$SO$_4$, filtered, concentrated, supported on celite, and purified by flash chromatography (0-80%, EtOAc in hexanes) to give N-(((1R,5S,6r)-3-((tert-butyldiphenylsilyl)oxy)bicyclo[3.1.0]hexan-6-yl)(cyano)methyl)-2-methylpropane-2-sulfinamide (1.12 g, 2.264 mmol, 53.7% yield). MS (ES) C$_{28}$H$_{38}$N$_2$O$_2$SSi requires: 494, found: 495 [M+H]$^+$.

Step 2:

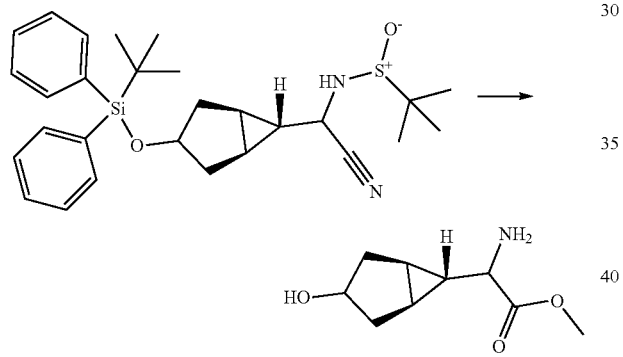

To a solution of N-(((1R,5S,6r)-3-((tert-butyldiphenylsilyl)oxy)bicyclo[3.1.0]hexan-6-yl)(cyano)methyl)-2-methylpropane-2-sulfinamide (0.56 g, 1.132 mmol) in MeOH (3 mL) was added H$_2$SO$_4$ (concentrated 98%, 0.603 mL, 11.32 mmol) and the resulting mixture was stirred and heated at reflux for 15 h. The reaction was cooled to 0° C., neutralized with DIEA, concentrated, and dried to give methyl 2-amino-2-((1R,5S)-3-hydroxybicyclo[3.1.0]hexan-6-yl)acetate (210 mg, 1.134 mmol, 100% yield) as a brown/yellow viscous semi/solid (assumed 100% yield). MS (ES$^+$) C$_9$H$_{15}$NO$_3$ requires: 185, found: 186 [M+H]$^+$.

Step 3:

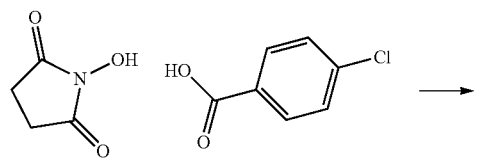

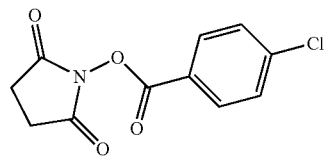

To 4-chlorobenzoic acid (20 g, 128 mmol) was added bis(2,5-dioxopyrrolidin-1-yl) carbonate (40 g, 156 mmol), DMAP (0.4 g, 3.27 mmol), and then DMF (125 mL). The mixture was warmed (heat gun) slightly, and then stirred at room temperature overnight. The reaction mixture was poured into ice water (500 mL water, 200 mL of ice) and the resulting mixture was stirred for 1 h. The resulting white solid was filtered off and washed with water, 0.25 M HCl (100 mL), 0.25 M NaOH (100 mL), water, hexanes, ethyl ether, hexanes, and dried to give 2,5-dioxopyrrolidin-1-yl 4-chlorobenzoate (31.5 g, 124 mmol, 97% yield) as a white solid. MS (ES$^+$) C$_{11}$H$_8$ClNO$_4$ requires: 253, found: 139 [M−NHS]$^+$}

Step 4:

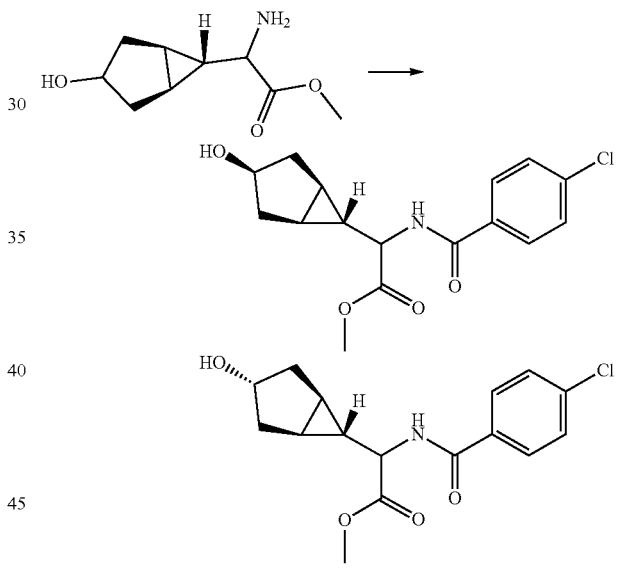

To a solution of methyl 2-amino-2-((1R,5S,6r)-3-hydroxybicyclo[3.1.0]hexan-6-yl)acetate (210 mg, 1.134 mmol) in DMF (5669 μl) were added DIEA (594 μl, 3.40 mmol) and 2,5-dioxopyrrolidin-1-yl 4-chlorobenzoate (316 mg, 1.247 mmol). The reaction was stirred at room temperature overnight, diluted with 0.25 M HCl, and extracted with EtOAc (2×50 mL w/10% hexanes). The organic layers were washed with 0.25 M NaOH and sat'd NaCl, combined, dried over Na$_2$SO$_4$, filtered, concentrated and purified by flash chromatography on silica gel (0-100% EtOAc in hexanes) to give methyl 2-(4-chlorobenzamido)-2-((1R,3r,5S,6r)-3-hydroxybicyclo[3.1.0]hexan-6-yl)acetate (102 mg, 0.315 mmol, 28% yield) and methyl 2-(4-chlorobenzamido)-2-((1R,3s,5S,6r)-3-hydroxybicyclo[3.1.0]hexan-6-yl)acetate (43 mg, 0.133 mmol, 12% yield) as white solids. MS (ES$^+$) C$_{16}$H$_{18}$ClNO$_4$ requires: 323, found: 324 [M+H]$^+$.

Step 5:

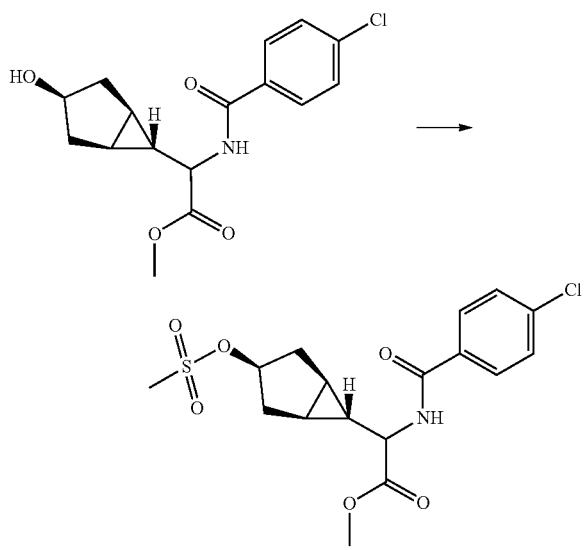

Synthesis similar to Compound 90 (above) was employed, using methyl 2-(4-chlorobenzamido)-2-((1R,3r,5S,6r)-3-hydroxybicyclo[3.1.0]hexan-6-yl)acetate (102 mg, 0.315 mmol) and Ms-Cl (29.5 μl, 0.378 mmol) to give methyl 2-(4-chlorobenzamido)-2-((1R,3r,5S,6r)-3-((methylsulfonyl)oxy)bicyclo[3.1.0]hexan-6-yl)acetate (119 mg, 0.296 mmol, 94% yield) as a clear liquid. MS (ES+) $C_{17}H_{20}ClNO_6S$ requires: 401, found: 402 [M+H]+.

Step 6:

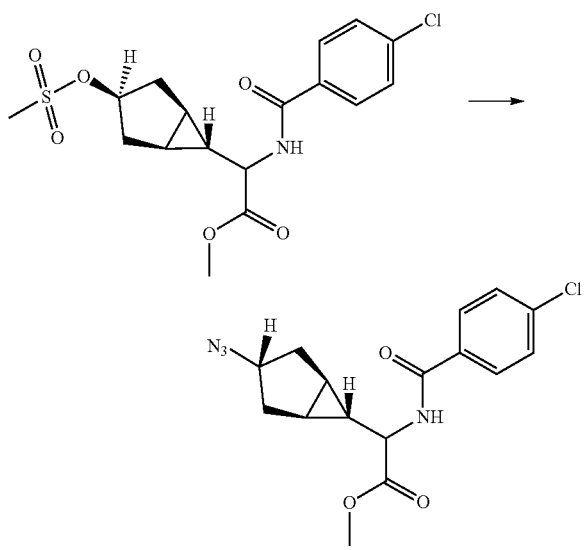

Synthesis similar to Compound 90 (above) was employed, using methyl 2-(4-chlorobenzamido)-2-((1R,3r,5S,6r)-3-((methylsulfonyl)oxy)bicyclo[3.1.0]hexan-6-yl)acetate (117 mg, 0.291 mmol) and sodium azide (76 mg, 1.165 mmol) to give methyl 2-((1R,3s,5S,6r)-3-azidobicyclo[3.1.0]hexan-6-yl)-2-(4-chlorobenzamido)acetate (83.2 mg, 0.239 mmol, 82% yield) as a clear liquid. MS (ES+) $C_{16}H_{17}ClN_4O_3$ requires: 348, found: 349 [M+H]+.

Step 7:

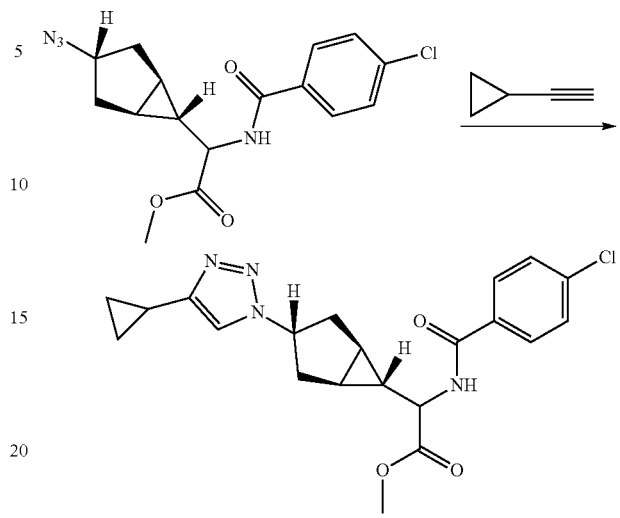

Synthesis similar to Compound 91 (above—general 1,4 triazole procedure) was employed, using methyl 2-((1R,3s,5S,6r)-3-azidobicyclo[3.1.0]hexan-6-yl)-2-(4-chlorobenzamido) acetate (81.5 mg, 0.234 mmol) and ethynylcyclopropane (18.53 mg, 0.280 mmol) to give methyl 2-(4-chlorobenzamido)-2-((1R,3s,5 S,6r)-3-(4-cyclopropyl-1H-1,2,3-triazol-1-yl) bicyclo[3.1.0]hexan-6-yl)acetate (73.4 mg, 0.177 mmol, 76% yield) as a white solid. MS (ES+) $C_{21}H_{23}ClN_4O_3$ requires: 414, found: 415[M+H]+.

Synthesis of 4-chloro-N-(1-((1R,3s, 5S, 6r)-3-(3-cyclopropyl-4H-1,2,4-triazol-4-yl)bicyclo[3.1.0] hexan-6-yl)propyl)benzamide (Compound 172)

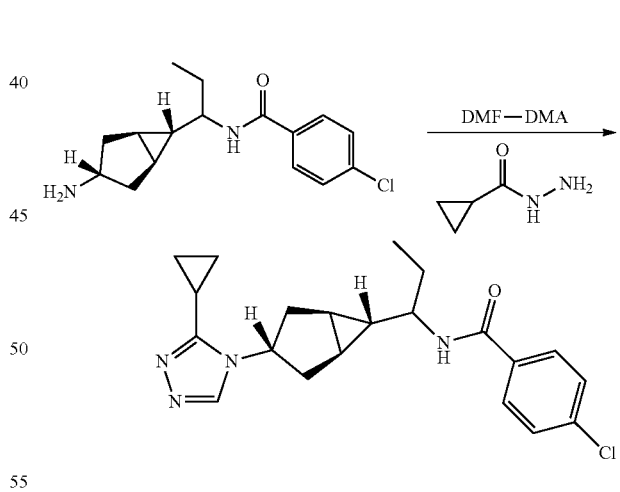

To a solution of cyclopropanecarbohydrazide (38 mg, 0.38 mmol) in DCM (228 μl) was added DMF-DMA (50 μl, 0.38 mmol) and the resulting mixture was stirred at 40° C. for 1 h. The volatiles were removed under reduced pressure to give a yellow solid. To this solid was added N-(1-((1R, 3s,5S,6r)-3-aminobicyclo[3.1.0]hexan-6-yl)propyl)-4-chlorobenzamide (100 mg, 0.342 mmol) and AcOH (228 μl) and the resulting solution was capped and heated in a microwave reactor at 150° C. for 5 min. The reaction mixture was allowed to cool to room temperature and the volatiles were removed under reduced pressure. The residue was purified by mass-triggered preparative HPLC (Mobile phase:

A=0.1% TFA/H$_2$O, B=0.1% TFA/MeCN; Gradient: B=30-70%; 12 min; Column: C18) to give 4-chloro-N-(1-((1R,3s,5 S,6r)-3-(3-cyclopropyl-4H-1,2,4-triazol-4-yl)bicyclo[3.1.0]hexan-6-yl)propyl)benzamide TFA salt (45 mg, 0.090 mmol, 26% yield) as a white powder. MS (ES) C$_{21}$H$_{25}$ClN$_4$O requires: 384, found: 385 [M+H]$^+$. $^1$H NMR (DMSO-d$_6$) δ: 9.20 (br. s., 1H), 8.32 (d, J=8.7 Hz, 1H), 7.89 (d, J=8.3 Hz, 2H), 7.54 (d, J=8.3 Hz, 2H), 4.46-4.60 (m, 1H), 3.33-3.45 (m, 1H), 2.28-2.44 (m, 2H), 2.06-2.27 (m, 3H), 1.57-1.71 (m, 2H), 1.38-1.51 (m, 2H), 1.09-1.17 (m, 2H), 1.04-1.08 (m, 2H), 0.96-1.02 (m, 1H), 0.90 (t, J=7.4 Hz, 3H).

Synthesis of 4-chloro-N-(1-((1R,3s, 5S, 6r)-3-(4-cyclopropyl-1H-1,2,3-triazol-1-yl)bicyclo[3.1.0]hexan-6-yl)-2-methoxyethyl)benzamide (Compound 173)

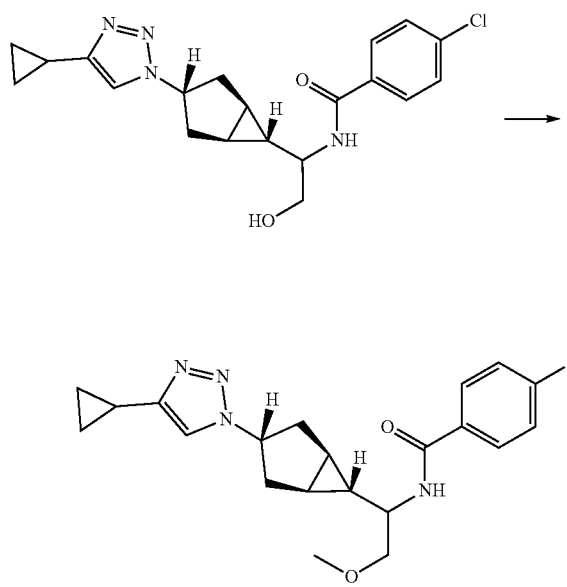

To a 0° C. solution of 4-chloro-N-(1-((1R,3s,5S,6r)-3-(4-cyclopropyl-1H-1,2,3-triazol-1-yl)bicyclo[3.1.0]hexan-6-yl)-2-hydroxyethyl)benzamide (12 mg, 0.031 mmol) in THF (200 L) was added NaH (1.365 mg, 0.034 mmol). The reaction was stirred at room temperature for 30 min, dimethyl sulfate (3.26 μL, 0.034 mmol) added, and continued stirring for 2 h. The reaction was diluted with sat'd NH$_4$Cl (2 mL) and extracted with EtOAc (2×2 mL). The organic layers were combined, washed with sat'd NaCl, dried over MgSO$_4$, filtered, concentrated, and purified by flash chromatography on silica gel (0-100% of 8:2 EtOAc:IPA in hexanes) to give 4-chloro-N-(1-((1R,3s,5S,6r)-3-(4-cyclopropyl-1H-1,2,3-triazol-1-yl)bicyclo[3.1.0]hexan-6-yl)-2-methoxyethyl)benzamide (2 mg, 4.99 μmol, 16.08% yield) as a white solid. MS (ES$^+$) C$_{21}$H$_{25}$ClN$_4$O$_2$ requires: 400, found: 401 [M+H]$^+$.

Synthesis of 4-chloro-N-(1-((1R,3s, 5S, 6r)-3-(1-oxoisoindolin-2-yl)bicyclo[3.1.0]hexan-6-yl)propyl)benzamide (Compound 175)

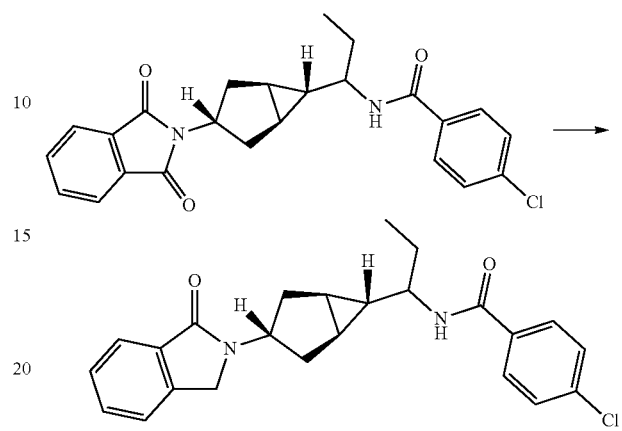

To a solution of 4-chloro-N-(1-((1R,3s,5 S,6r)-3-(1,3-dioxoisoindolin-2-yl)bicyclo[3.1.0]hexan-6-yl)propyl)benzamide (11.2 mg, 0.026 mmol) in acetic acid (530 μl) was added zinc (3.98 mg, 0.061 mmol). The mixture was heated to 115° C. and stirred for 12 hours then cooled to room temperature, and filtered through celite. The filtrate was concentrated and purified by mass-triggered preparative HPLC (Mobile phase: A=0.1% TFA/H$_2$O, B=0.1% TFA/MeCN; Gradient: B=[30]-[70]%; 12 min; Column: C18) to yield 4-chloro-N-(1-((1R,3s,5S,6r)-3-(1-oxoisoindolin-2-yl)bicyclo[3.1.0]hexan-6-yl)propyl)benzamide (1.6 mg, 3.91 μmol, 14.77% yield). MS (ES$^+$) C$_{24}$H$_{25}$ClN$_2$O$_2$ requires 408, found 409 [M+H]$^+$. $^1$H NMR (DMSO-d$_6$) δ: 8.34 (d, J=8.5 Hz, 1H), 7.89 (d, J=8.5 Hz, 2H), 7.65 (d, J=7.6 Hz, 1H), 7.52-7.59 (m, 4H), 7.44-7.50 (m, 1H), 4.44 (s, 2H), 4.27-4.40 (m, 1H), 3.25-3.31 (m, 1H), 1.83-2.04 (m, 4H), 1.50-1.70 (m, 2H), 1.29-1.37 (m, 2H), 0.97-1.04 (m, 1H), 0.90 (t, J=7.3 Hz, 3H).

Synthesis of N-((1R,3s, 5S, 6r)-6-(1-(4-chlorobenzamido)propyl)bicyclo[3.1.0]hexan-3-yl)-1H-pyrazole-4-carboxamide (Compound 177)

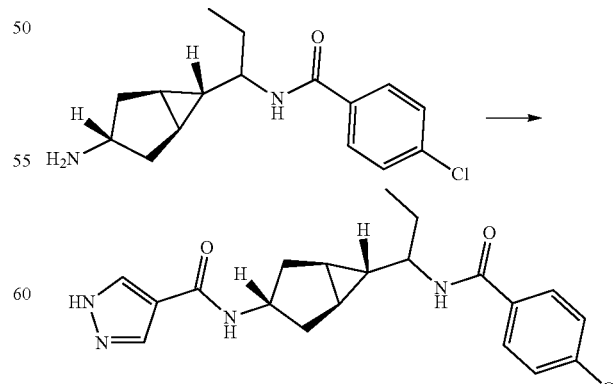

The title compound was synthesized similar to the general Amide coupling procedure with the following modifications.

To a solution of N-(1-((1R,3s,5S,6r)-3-aminobicyclo[3.1.0]hexan-6-yl)propyl)-4-chlorobenzamide (20 mg, 0.068 mmol) in DMF (683 μl) was added DIEA (35.8 μl, 0.205 mmol), HOBT (13.6 mg, 0.089 mmol), and EDC (14.4 mg, 0.075 mmol). The solution was stirred at room temperature for 18 hours. The solution was concentrated and the residue was purified by mass-triggered preparative HPLC (Mobile phase: A=0.1% TFA/H₂O, B=0.1% TFA/MeCN; Gradient: B=[30]-[70]%; 12 min; Column: C18) to yield N-((1R,3s,5S,6r)-6-(1-(4-chlorobenzamido)propyl)bicyclo[3.1.0]hexan-3-yl)-1H-pyrazole-4-carboxamide (3.3 mg, 8.53 μmol, 12% yield). MS ES⁺ C₂₀H₂₃ClN₄O₂ requires 386, found 387 [M+H]⁺.

Synthesis of 4-chloro-N-(1-((1R,3s, 5S, 6r)-3-(3-methyl-3-(pyridin-2-yl) ureido)bicyclo[3.1.0]hexan-6-yl)propyl)benzamide (Compound 189)

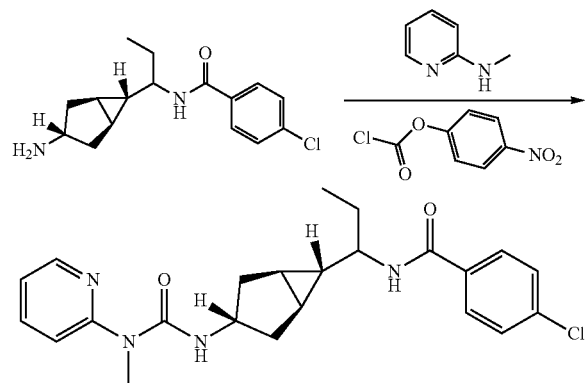

To a solution of N-methylpyridin-2-amine (18 μl, 0.18 mmol) in DMF (0.9 mL) were added diisopropylethylamine (60 μl, 0.34 mmol) and 4-nitrophenyl carbonochloridate (33 mg, 0.16 mmol), and the resulting solution was stirred at room temperature for 1 h. To the solution was added N-(1-((1R,3s,5S,6r)-3-aminobicyclo[3.1.0]hexan-6-yl)propyl)-4-chlorobenzamide (27 mg, 0.092 mmol) and the solution was stirred at room temperature for 12 h, then at 60° C. for 24 h. The solution was allowed to cool, concentrated, and purified by flash chromatography (50-80% EtOAc in hexanes) to give 9.6 mg of a white solid. The solid was dissolved in THF (0.5 mL), and the resulting solution was treated with 4.0 M HCl in dioxane (0.1 mL). The solution was concentrated to an off-white solid and triturated (3×) with a mixture of diethyl ether/THF (1/0.2 mL), redissolved in methanol and concentrated to give 4-chloro-N-(1-((1R,3s,5S,6r)-3-(3-methyl-3-(pyridin-2-yl)ureido)bicyclo[3.1.0]hexan-6-yl)propyl) benzamide hydrochloride (1.6 mg, 3.45 μmol, 4% yield) as an off-white solid. MS (ES⁺) C₂₃H₂₇ClN₄O₂ requires: 426, found: 427 [M+H]⁺.

Synthesis of ethyl 2-(((R,3s,5S,6r)-6-(1-(4-chlorobenzamido)propyl)bicyclo[3.1.0]hexan-3-yl)amino)-2-phenylacetate (Compound 190)

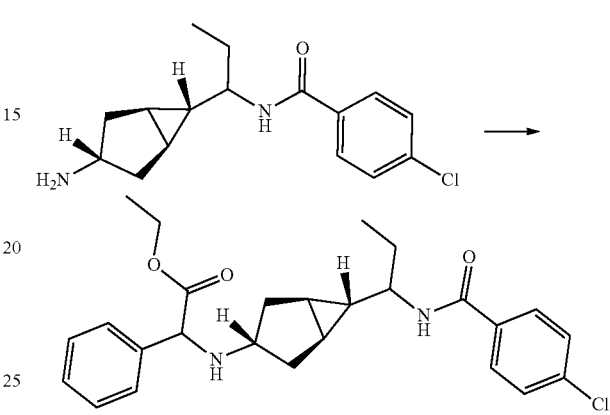

To a solution of N-(1-((1R,3s,5 S,6r)-3-aminobicyclo[3.1.0]hexan-6-yl)propyl)-4-chlorobenzamide (100 mg, 0.342 mmol) in ACN (876 μl) was added DIEA (74.6 μl) and ethyl-2-bromo-2-phenylacetate (69.2 mg, 0.285 mmol). The solution was heated to 100° C. and stirred for 60 minutes under microwave irradiation. The solution was cooled to room temperature and purified by silica gel chromatography (0-50% EtOAc/Hexanes) to yield ethyl 2-(((1R,3s,5 S,6r)-6-(1-(4-chlorobenzamido)propyl)bicyclo[3.1.0]hexan-3-yl)amino)-2-phenylacetate (125.3 mg, 0.275 mmol, 97% yield). MS (ES⁺) C₂₆H₃₁ClN₂O₃ requires 454, found 455 [M+H]⁺.

Synthesis of methyl (S)-2-((1R,3S,5S, 6S)-6-((R)-1-(4-chlorobenzamido)propyl)bicyclo[3.1.0]hexan-3-yl)-2-phenylacetate and methyl (R)-2-((R, 3S, 5S, 6S)-6-((S)-1-(4-chlorobenzamido)propyl)bicyclo[3.1.0]hexan-3-yl)-2-phenylacetate (Compound 202); and methyl (S)-2-((R, 3R, 5S,6S)-6-((S)-1-(4-chlorobenzamido)propyl)bicyclo[3.1.0]hexan-3-yl)-2-phenylacetate and methyl (R)-2-((1R,3R,5S, 6S)-6-((R)-1-(4-chlorobenzamido)propyl) bicyclo[3.1.0]hexan-3-yl)-2-phenylacetate (Compound 203)

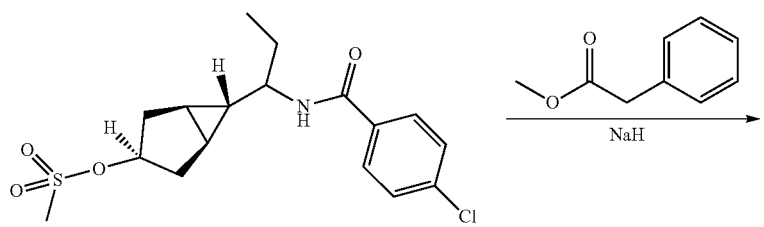

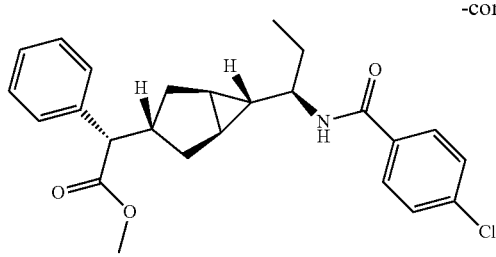
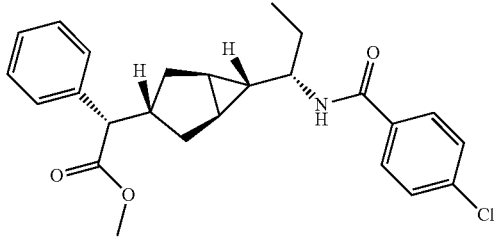
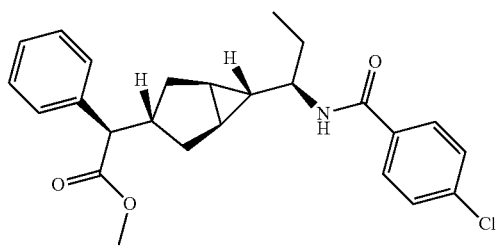
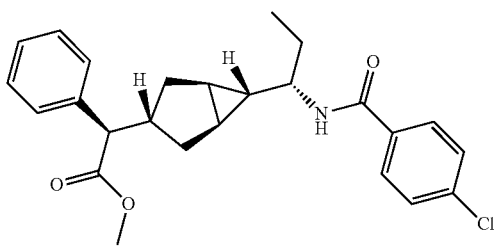

To a 0° C. suspension of NaH (43.0 mg, 1.076 mmol) in DMF (1 mL) was added methyl 2-phenylacetate (97 mg, 0.645 mmol) dissolved in DMF (2 mL) and the solution was stirred at 0° C. for 5 min then at room temperature for 20 min. To the mixture was added (1R,3r,5S,6r)-6-(1-(4-chlorobenzamido)propyl)bicyclo[3.1.0]hexan-3-yl methanesulfonate (200 mg, 0.538 mmol) and the reaction was stirred overnight at room temperature then heated to 85° C. for 5 h. The reaction was quenched with saturated NH$_4$Cl/water and extracted with EtOAc (2×50 mL). The organics were collected, washed with saturated NaCl, dried over MgSO$_4$, concentrated, and purified by flash chromatography (0-30% EtOAc in hexanes) to give two separate fractions of a mix of stereoisomers (14.6 mg, 0.034 mmol, 7% yield) and (4.1 mg, 9.63 μmol, 2% yield). MS (ES$^+$) C$_{25}$H$_{28}$ClNO$_3$ requires: 425, found: 426 [M+H]$^+$.

Synthesis of 4-chloro-N-(1-((1R,3r, 5S, 6r)-3-(4-(methoxymethyl)-1H-1,2,3-triazol-1-yl)bicyclo[3.1.0]hexan-6-yl)propyl)benzamide (Compound 214)

clo[3.1.0]hexan-6-yl)propyl)benzamide (40 mg, 0.107 mmol) dissolved in THF (1 mL). The reaction was stirred in the icebath for 5 min and then at room temperature for 15 min. To the reaction cooled in an icebath was added dimethyl sulfate (0.011 mL, 0.117 mmol) and the reaction stirred in the icebath for 5 min and then at room temperature for 4 hr. The reaction was neutralized with NH$_4$Cl (24 mg), diluted with DCM, concentrated, and purified by flash chromatography (0-70% 8:2 EtOAc:IPA in hexanes) to give 4-chloro-N-(1-((1R,3r,5S,6r)-3-(4-(methoxymethyl)-1H-1,2,3-triazol-1-yl)bicyclo[3.1.0]hexan-6-yl)propyl)benzamide (17 mg, 0.044 mmol, 41.0% yield) as a white solid. MS (ES$^+$) C$_{20}$H$_{25}$ClN$_4$O$_2$ requires: 388, found: 389 [M+H]$^+$. $^1$H NMR (DMSO-d$_6$) δ: 8.31 (d, J=8.3 Hz, 1H), 8.09 (s, 1H), 7.83-7.88 (m, 2H), 7.50-7.55 (m, 2H), 5.08-5.12 (m, 1H), 4.42 (s, 2H), 3.32-3.37 (m, 1H), 3.25 (s, 3H), 2.51-2.58 (m, 2H), 2.04-2.27 (m, 2H), 1.48-1.69 (m, 2H), 1.32-1.45 (m, 2H), 0.81-0.92 (m, 4H).

Synthesis of 2-(((1R,3s, 5S, 6r)-6-(1-(4-chlorobenzamido)propyl)bicyclo[3.1.0]hexan-3-yl)amino)-2-phenylacetic acid (Compound 217)

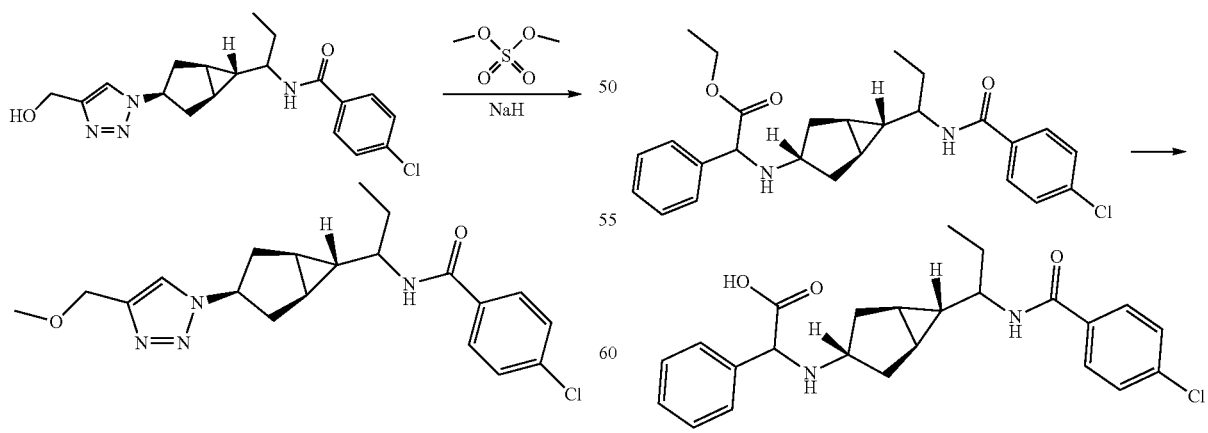

To a vial containing NaH (8.54 mg, 0.213 mmol) was added THF (0.2 mL) and the resulting mixture was cooled in an icebath. To the reaction was added 4-chloro-N-(1-((1R,3r,5S,6r)-3-(4-(hydroxymethyl)-1H-1,2,3-triazol-1-yl)bicy- To a solution of ethyl 2-(((1R,3s,5S,6r)-6-(1-(4-chlorobenzamido)propyl)bicyclo[3.1.0]hexan-3-yl)amino)-2-phenylacetate (120 mg, 0.264 mmol) in THF (2.2 mL)/

MeOH (220 µl)/Water (220 µl) was added LiOH (63.2 mg, 2.64 mmol). The solution was stirred at room temperature for 18 hours. The solution was neutralized with 6N HCl then extracted with DCM (3×5 mL). The organics were collected, washed with brine, dried over Na$_2$SO$_4$, filtered, concentrated, and purified by silica gel chromatography (0-30% MeOH/DCM) to yield 2-(((1R,3s,5S,6r)-6-(1-(4-chlorobenzamido)propyl)bicyclo[3.1.0]hexan-3-yl)amino)-2-phenylacetic acid (42.4 mg, 0.099 mmol, 37.7% yield). MS (ES$^+$) C$_{24}$H$_{27}$ClN$_2$O$_3$ requires 426, found 427 [M+H]$^+$.

Synthesis of 4-chloro-N-(1-((1R,3s, 5S, 6r)-3-((2-(methylamino)-2-oxo-1-phenylethyl)amino) bicyclo[3.1.0]hexan-6-yl)propyl)benzamide (Compound 224)

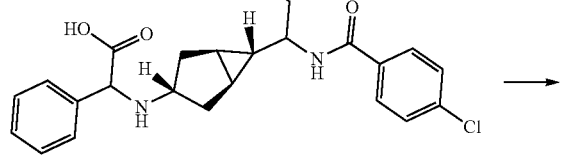

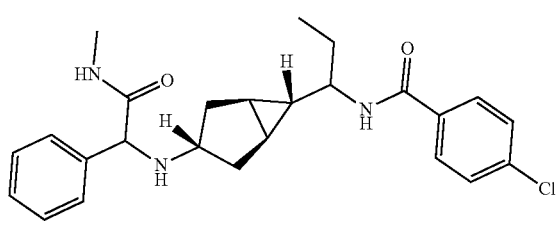

To a solution of 2-(((1R,3s,5S,6r)-6-(1-(4-chlorobenzamido)propyl)bicyclo[3.1.0]hexan-3-yl)amino)-2-phenylacetic acid (42.4 mg, 0.099 mmol) in DMF (993 µl) was added methylamine hydrochloride (7.38 mg, 0.109 mmol), DIEA (69.4 µl, 0.397 mmol), and HOBT (19.77 mg, 0.129 mmol). The mixture was stirred for 10 minutes at room temperature then EDC (20.94 mg, 0.109 mmol) was added and the mixture was stirred for 18 hours at 50° C. The mixture was cooled to room temperature, concentrated, and purified by mass-triggered preparative HPLC (Mobile phase: A=0.1% TFA/H$_2$O, B=0.1% TFA/MeCN; Gradient: B=[30]-[70]%; 12 min; Column: C18) to 4-chloro-N-(1-((1R,3s,5S,6r)-3-((2-(methylamino)-2-oxo-1-phenylethyl)amino)bicyclo[3.1.0]hexan-6-yl)propyl)benzamide (12.3 mg, 0.028 mmol, 28.1% yield) as a TFA salt. MS (ES$^+$) C$_{25}$H$_{30}$ClN$_3$O$_2$ requires: 439, found 440 [M+H]$^+$. $^1$H NMR (DMSO-d$_6$) δ: 9.39-9.72 (m, 2H), 8.53-8.74 (m, 1H), 8.21-8.27 (m, 1H), 7.81-7.91 (m, 2H), 7.51-7.62 (m, 4H), 7.43-7.50 (m, 3H), 4.78-4.87 (m, 1H), 3.17-3.29 (m, 1H), 2.80-2.93 (m, 1H), 2.58-2.66 (m, 3H), 1.95-2.19 (m, 2H), 1.72-1.93 (m, 2H), 1.47-1.62 (m, 2H), 1.23-1.37 (m, 2H), 0.77-0.88 (m, 3H), 0.57-0.66 (m, 1H).

Synthesis of 4-chloro-N-(1-((R, 3s, 5S, 6r)-3-(pyridin-2-ylamino)bicyclo[3.1.0]hexan-6-yl) propyl) benzamide (Compound 226)

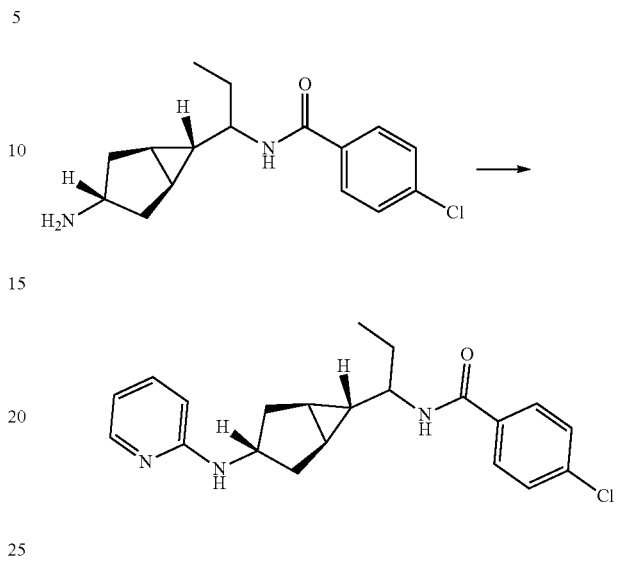

To a suspension of 2-chloropyridine (10.66 mg, 0.094 mmol) in dioxane (854 µl) was added RuPhos pre-catalyst fourth generation (14.52 mg, 0.017 mmol), RuPhos (7.97 mg, 0.017 mmol), sodium tert-butoxide (41 mg, 0.427 mmol), and N-(1-((1R,3s,5S,6r)-3-aminobicyclo[3.1.0]hexan-6-yl)propyl)-4-chlorobenzamide (25 mg, 0.085 mmol). The reaction was degassed with N$_2$ for 2 minutes then stirred at 65° C. for 2 hours. The solution was concentrated, and purified by mass-triggered preparative HPLC (Mobile phase: A=0.1% TFA/H$_2$O, B=0.1% TFA/MeCN; Gradient: B=[40]-[80]%; 12 min; Column: C18) to yield 4-chloro-N-(1-((1R,3s,5S,6r)-3-(pyridin-2-ylamino)bicyclo[3.1.0]hexan-6-yl)propyl) benzamide (9.5 mg, 0.026 mmol, 30% yield). MS (ES$^+$) C$_{21}$H$_{24}$ClN$_3$O requires 369, found 370 [M+H]$^+$. $^1$H NMR (DMSO-d$_6$) δ: 8.65-8.87 (m, 1H), 8.31 (d, J=8.3 Hz, 1H), 7.78-7.96 (m, 4H), 7.54 (d, J=8.7 Hz, 2H), 6.98 (d, J=7.9 Hz, 1H), 6.78-6.85 (m, 1H), 3.74-3.84 (m, 1H), 3.28-3.38 (m, 1H), 2.12-2.37 (m, 2H), 1.56-1.74 (m, 4H), 1.27-1.43 (m, 2H), 0.84-0.96 (m, 4H).

Synthesis of 4-chloro-N-(1-((R, 3s, 5S, 6r)-3-((5-fluoropyridin-2-yl)amino)bicyclo[3.1.0]hexan-6-yl) propyl)benzamide (Compound 227)

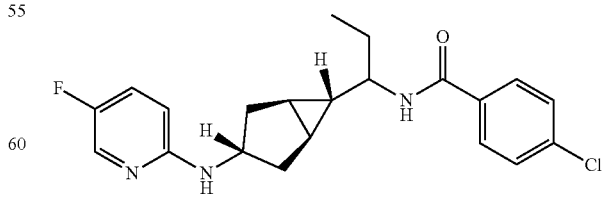

The title compound was synthesized similar to 4-chloro-N-(1-((1R,3s,5S,6r)-3-(pyridin-2-ylamino)bicyclo[3.1.0] hexan-6-yl)propyl)benzamide (Compound 226 above). MS (ES) C$_{21}$H$_{23}$ClFN$_3$O requires 387, found 388 [M+H]$^+$.

Synthesis of 2-((1R,3s, 5S, 6r)-6-(1-(4-chlorobenzamido)propyl)bicyclo[3.1.0]hexan-3-yl)-2-phenylacetic acid (Compound 228)

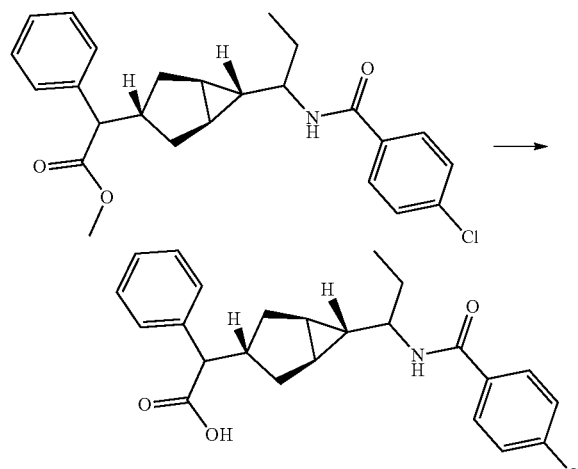

To a solution of methyl 2-((1R,3s,5S,6r)-6-(1-(4-chlorobenzamido)propyl)bicyclo[3.1.0]hexan-3-yl)-2-phenylacetate (30 mg, 0.070 mmol) in MeOH (4 mL) containing methyl amine was added LiOH (1 M, 2 mL, 2 mmol) and stirred at room temperature overnight. To the reaction was added THF (2 mL) and heated at 40° C. overnight. The reaction was diluted with water, acidified with concentrated HCl, and extracted with EtOAc (3×). The organic layers were washed with sat'd NaCl, combined, dried over MgSO$_4$, filtered and concentrated to give 2-((1R,3s,5 S,6r)-6-(1-(4-chlorobenzamido)propyl)bicyclo[3.1.0]hexan-3-yl)-2-phenylacetic acid (25.9 mg, 0.063 mmol, 89% yield) as a white solid. MS (ES$^+$) C$_{24}$H$_{26}$ClNO$_3$ requires: 411, found: 412 [M+H]$^+$.

Synthesis of 4-chloro-N—((R)-1-((R, 3S, 5S, 6S)-3-((S)-2-(methylamino)-2-oxo-1-phenylethyl) bicyclo[3.1.0]hexan-6-yl)propyl)benzamide and 4-chloro-N—((S)-1-((1R,3S,5S, 6S)-3-((R)-2-(methylamino)-2-oxo-1-phenylethyl) bicyclo[3.1.0]hexan-6-yl)propyl)benzamide (Compound 230); and 4-chloro-N—((R)-1-((R, 3S, 5S, 6S)-3-((R)-2-(methylamino)-2-oxo-1-phenylethyl) bicyclo[3.1.0]hexan-6-yl) propyl)benzamide and 4-chloro-N—((S)-1-((1R,3S,5S,6S)-3-((S)-2-(methylamino)-2-oxo-1-phenylethyl) bicyclo[3.1.0]hexan-6-yl) propyl)benzamide (Compound 231)

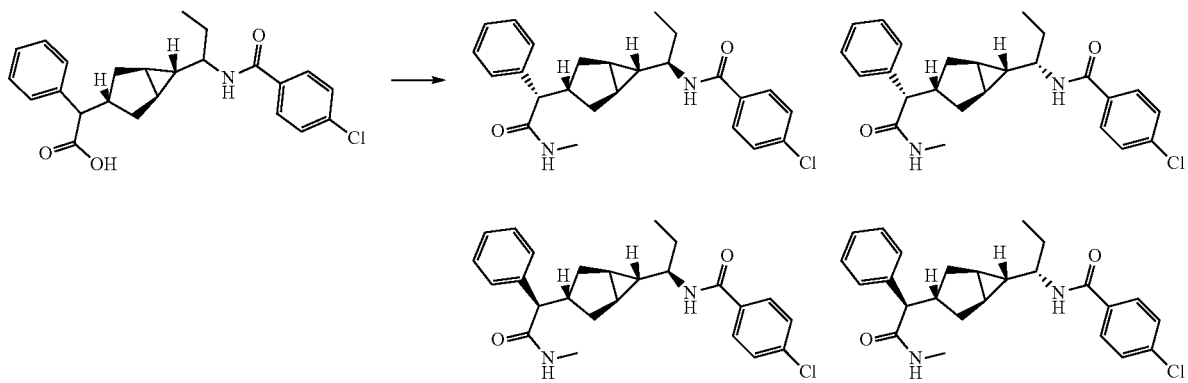 [SMILES: CCC(NC(=O)c1ccc(Cl)cc1)[C@H]1[C@@H]2C[C@@H](C(C(=O)O)c3ccccc3)C[C@@H]21 ; CC[C@@H](NC(=O)c1ccc(Cl)cc1)[C@H]1[C@@H]2C[C@@H]([C@H](C(=O)NC)c3ccccc3)C[C@@H]21 ; CC[C@H](NC(=O)c1ccc(Cl)cc1)[C@H]1[C@@H]2C[C@@H]([C@H](C(=O)NC)c3ccccc3)C[C@@H]21 ; CC[C@@H](NC(=O)c1ccc(Cl)cc1)[C@H]1[C@@H]2C[C@@H]([C@@H](C(=O)NC)c3ccccc3)C[C@@H]21 ; CC[C@H](NC(=O)c1ccc(Cl)cc1)[C@H]1[C@@H]2C[C@@H]([C@@H](C(=O)NC)c3ccccc3)C[C@@H]21]

The title compounds were synthesized via the Amide coupling procedure using compound 217, HATU, DIEA, and methyl amine HCl and were purified by mass-triggered preparative HPLC (Mobile phase: A=0.1% TFA/H2O, B=0.1% TFA/MeCN; Gradient: B=30-70%; 20 min; Column: C18) to give two separate fractions of a mix of stereoisomers (1.9 mg, 4.5 μmol, 7% yield) and (5.8 mg, 14 μmol, 21% yield), as white solids. MS (ES$^+$) C$_{25}$H$_{29}$ClN$_2$O$_2$ requires: 424, found: 425 [M+H]$^+$.

Synthesis of 4-chloro-N-(1-((R, 3s, 5S, 6r)-3-(4-(1,3-dioxoisoindolin-2-yl)-1H-1,2,3-triazol-1-yl)bicyclo[3.1.0]hexan-6-yl)propyl)benzamide (Compound 232)

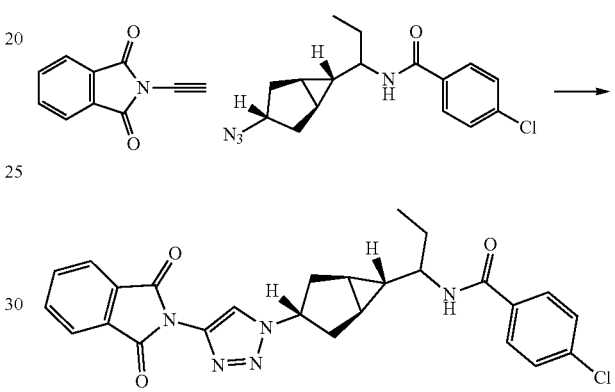

The title compound was synthesized similar to N-(1-((1R, 3s,5S,6r)-3-azidobicyclo[3.1.0]hexan-6-yl)propyl)-4-chlorobenzamide (Compound 90) from the alkyne 2-ethynylisoindoline-1,3-dione (see e.g. Ronnenbaum et al., Tetrahedron (2016) 72(40):6136-6141) with the following modifications. The reaction was concentrated, diluted with minimal MeOH and precipitated by addition of a solution comprising water (8 mL) and conc. NH$_4$OH (0.25 mL). The resulting solid was filtered, washed with water and hexanes, and dried to give 4-chloro-N-(1-((1R,3s,5S,6r)-3-(4-(1,3-dioxoisoindolin-2-yl)-1H-1,2,3-triazol-1-yl)bicyclo[3.1.0]hexan-6-yl)propyl)benzamide (80 mg, 0.131 mmol, 69% yield) as a light grey solid. MS (ES$^+$) C$_{26}$H$_{24}$ClN$_5$O$_3$ requires: 489, found: 490 [M+H]$^+$.

273

Synthesis of tert-butyl 3-(1-((1R,3s, 5S,6r)-6-(1-(4-chlorobenzamido)propyl)bicyclo[3.1.0]hexan-3-yl)-1H-1,2,3-triazol-4-yl)azetidine-1-carboxylate (Compound 233)

274

Synthesis of N-(1-((1R,3s, 5S, 6r)-3-(4-(azetidin-3-yl)-1H-1,2,3-triazol-1-yl)bicyclo[3.1.0]hexan-6-yl)propyl)-4-chlorobenzamide (Compound 237)

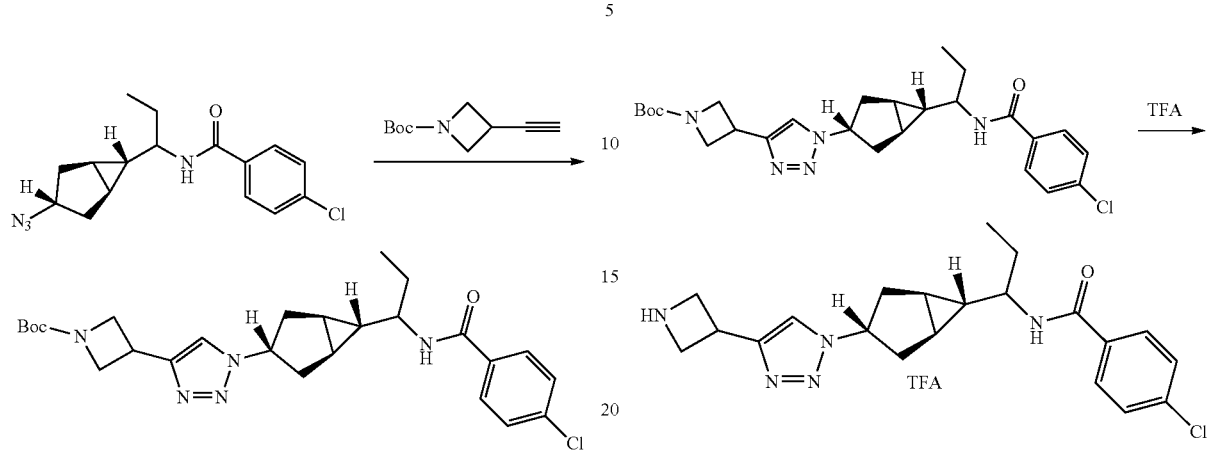

To a vial containing N-(1-((1R,3s,5S,6r)-3-azidobicyclo[3.1.0]hexan-6-yl)propyl)-4-chlorobenzamide (20 mg, 0.063 mmol) were added tert-butyl 3-ethynylazetidine-1-carboxylate (13.64 mg, 0.075 mmol) and DCM (314 μl) solution containing AcOH (0.4 μl, 6.27 μmol) and DIEA (1 μl, 6.27 μmol). To this solution was added CuI (0.836 mg, 4.39 μmol) and the resulting mixture was stirred at RT for 2 days. The reaction was purified by flash chromatography (0 to 70% EtOAc in hexanes) to give tert-butyl 3-(1-((1R,3s,5S,6r)-6-(1-(4-chlorobenzamido)propyl)bicyclo[3.1.0]hexan-3-yl)-1H-1,2,3-triazol-4-yl)azetidine-1-carboxylate (36 mg, 0.062 mmol, 99% yield) as a white solid. MS (ES$^+$) $C_{26}H_{34}ClN_5O_3$ requires: 499, found: 500 [M+H]$^+$.

To a suspension of tert-butyl 3-(1-((1R,3s,5S,6r)-6-(1-(4-chlorobenzamido)propyl)bicyclo[3.1.0]hexan-3-yl)-1H-1,2,3-triazol-4-yl)azetidine-1-carboxylate (31 mg, 0.062 mmol) in DCM (0.3 mL) was added TFA (100 μl, 1.298 mmol) and the resulting mixture was stirred at room temperature for 2 h. The reaction was concentrated and residual TFA was azeotroped with ACN, EtOH, and toluene to give the TFA salt of N-(1-((1R,3s,5S,6r)-3-(4-(azetidin-3-yl)-1H-1,2,3-triazol-1-yl)bicyclo[3.1.0]hexan-6-yl)propyl)-4-chlorobenzamide (30 mg, 0.060 mmol, 97% yield) as a light brown semisolid and used without further purification. MS (ES) $C_{21}H_{26}ClN_5O$ requires: 399, found: 400 [M+H]$^+$.

Synthesis of N-(1-((1R,3s, 5S, 6r)-3-(4-amino-1H-1,2,3-triazol-1-yl)bicyclo[3.1.0]hexan-6-yl)propyl)-4-chlorobenzamide (Compound 239)

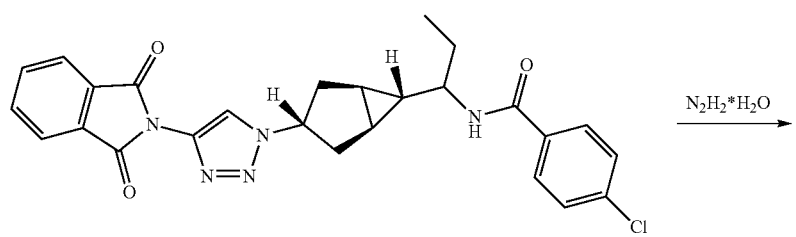

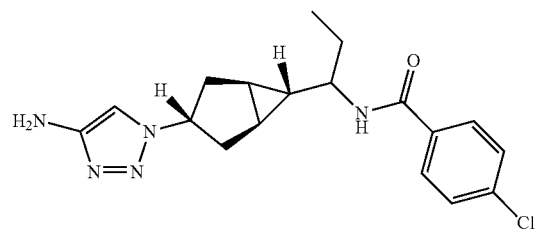

To a solution of 4-chloro-N-(1-((1R,3s,5S,6r)-3-(4-(1,3-dioxoisoindolin-2-yl)-1H-1,2,3-triazol-1-yl)bicyclo[3.1.0]hexan-6-yl)propyl)benzamide (76 mg, 0.155 mmol) in MeOH (1551 µl) was added hydrazine hydrate (19 µl, 0.310 mmol) and the resulting mixture was stirred at 80° C. for 2 h. The reaction was partitioned between 0.1 M NaOH and EtOAc. The resulting precipitate was filtered from the mixture and washed with water and EtOAc to give the desired product. The organic layer of the filtrate was separated from the aqueous layer, washed with sat'd NaCl, dried over MgSO$_4$, filtered, concentrated, and combined with the previous precipitate to give N-(1-((1R,3s,5S,6r)-3-(4-amino-1H-1,2,3-triazol-1-yl)bicyclo[3.1.0]hexan-6-yl)propyl)-4-chlorobenzamide (50.8 mg, 0.141 mmol, 91% yield). MS (ES$^+$) C$_{18}$H$_{22}$ClN$_5$O requires: 359, found: 360 [M+H]$^+$.

Synthesis of 4-chloro-N-(1-((1R,3s, 5S, 6r)-3-(6,7-difluoro-1H-benzo[d]imidazol-1-yl)bicyclo[3.1.0]hexan-6-yl)propyl)benzamide (Compound 245)

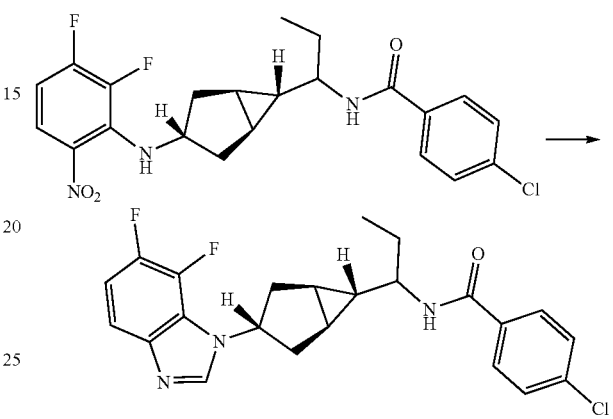

Step 1:

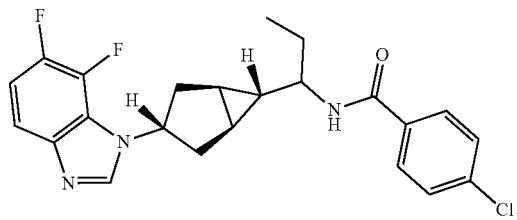 [SMILES: CCC(NC(=O)c1ccc(Cl)cc1)[C@H]1[C@@H]2C[C@@H](n3cnc4ccc(F)c(F)c43)C[C@@H]21]

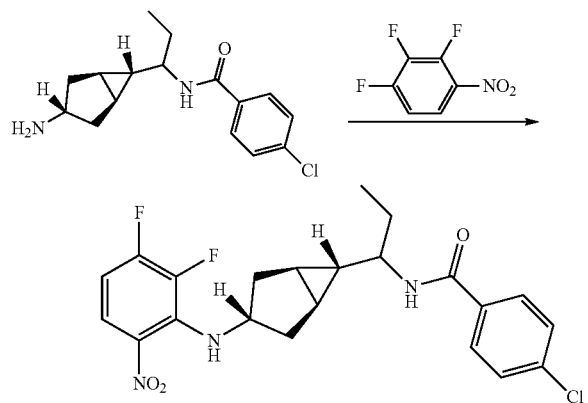

To a solution of N-(1-((1R,3s,5 S,6r)-3-aminobicyclo[3.1.0]hexan-6-yl)propyl)-4-chlorobenzamide (30 mg, 0.102 mmol) in THF (205 µl) were added K$_2$CO$_3$ (28.3 mg, 0.205 mmol) and 1,2,3-trifluoro-4-nitrobenzene (19.05 mg, 0.108 mmol). The reaction was stirred at room temperature for 1 hr, THF (200 µl) added, and stirring continued overnight. The reaction was diluted with water, extracted with ethyl acetate (2×), the organic layers washed with brine, combined, dried over MgSO$_4$, filtered, concentrated, and purified by flash chromatography on silica gel (0-100% EtOAc in hexanes) to give 4-chloro-N-(1-((1R,3s,5 S,6r)-3-((2,3-difluoro-6-nitrophenyl)amino)bicyclo[3.1.0]hexan-6-yl)propyl) benzamide (33 mg, 0.073 mmol, 71.6% yield) as a yellow solid. MS (ES$^+$) C$_{22}$H$_{22}$ClF$_2$N$_3$O$_3$ requires: 449, found: 450 [M+H]$^+$.

Step 2: (General one step synthesis of benzimidazoles "BzI")

To a suspension of 4-chloro-N-(1-((1R,3s,5S,6r)-3-((2,3-difluoro-6-nitrophenyl)amino) bicyclo[3.1.0]hexan-6-yl)propyl)benzamide (28 mg, 0.062 mmol) in 2-Propanol (311 µl) and Formic Acid (311 µl) were added NH$_4$Cl (33.3 mg, 0.622 mmol) and iron (34.8 mg, 0.622 mmol) and the resulting mixture was stirred at 80° C. for 6 h. The reaction was diluted with DCM and some MeOH, filtered through celite, and the filtrate concentrated. The crude was diluted with DCM and washed with 0.2M NaOH and sat'd NaCl. The aqueous layers were extracted with DCM (3×10 mL). The organic layers were combined, dried over Na$_2$SO$_4$, filtered, concentrated, and purified by flash chromatography on silica gel (0-20% of 8:2:1 DCM:MeOH:NH$_4$OH in DCM) to give 4-chloro-N-(1-((1R,3s,5S,6r)-3-(6,7-difluoro-1H-benzo[d]imidazol-1-yl)bicyclo[3.1.0]hexan-6-yl)propyl)benzamide (6 mg, 0.014 mmol, 22.42% yield) as an off white solid. MS (ES$^+$) C$_{23}$H$_{22}$ClF$_2$N$_3$O requires: 429, found: 430 [M+H]$^+$.

Synthesis of 4-chloro-N—((R)-1-((1R,3S,5S, 6r)-3-(6-fluoro-1H-benzo[d]imidazol-1-yl)bicyclo[3.1.0]hexan-6-yl)propyl)benzamide (Compound 247) and 4-chloro-N—((S)-1-((1R,3S,5S, 6r)-3-(6-fluoro-1H-benzo[d]imidazol-1-yl) bicyclo[3.1.0]hexan-6-yl) propyl)benzamide (Compound 248)

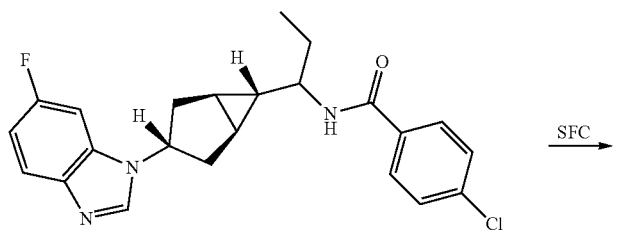

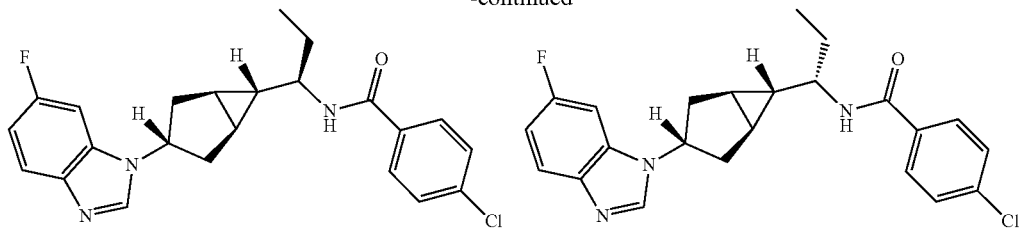

Enantiomers of the title compound (Compound 125) were separated by preparative SFC using the following conditions: column: 2.1×25.0 cm Chiralcel OX-H from Chiral Technologies (West Chester, Pa.); CO$_2$ co-solvent (Solvent B): Ethanol with 0.25% Isopropylamine; isocratic method 35% co-solvent at 80 g/min; system pressure 120 bar; column temperature 25° C.; sample diluent Methanol; to give 4-chloro-N—((R)-1-((1R,3S,5 S,6r)-3-(6-fluoro-1H-benzo[d]imidazol-1-yl)bicyclo[3.1.0]hexan-6-yl)propyl) benzamide as a white solid. MS (ES$^+$) C$_{23}$H$_{23}$ClFN$_3$O requires 411, found 412. Compound 247 was also synthesized using the general BzI procedure from the enantiomerically pure Compound 1 (confirmed as the R enantiomer by Mosher analysis) that was synthesized similar to Example 1 from the chiral auxiliary, (S)-2-methylpropane-2-sulfinamide.

Also obtained from the above procedure was 4-chloro-N—((S)-1-((1R,3S,5S,6r)-3-(6-fluoro-1H-benzo[d]imidazol-1-yl)bicyclo[3.1.0]hexan-6-yl)propyl)benzamide (Compound 248) as a white solid. MS (ES$^+$) C$_{23}$H$_{23}$ClFN$_3$O requires 411, found 412.

Synthesis of 4-chloro-N-(1-((1R,5R,6S)-3-(5-(trifluoromethyl)pyridin-3-yl)bicyclo[3.1.0]hex-2-en-6-yl)propyl)benzamide (Compound 254)

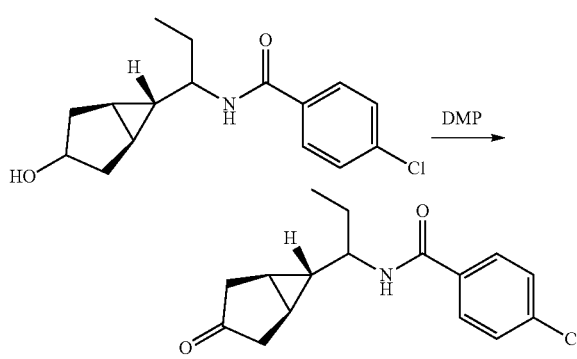

Step 1:

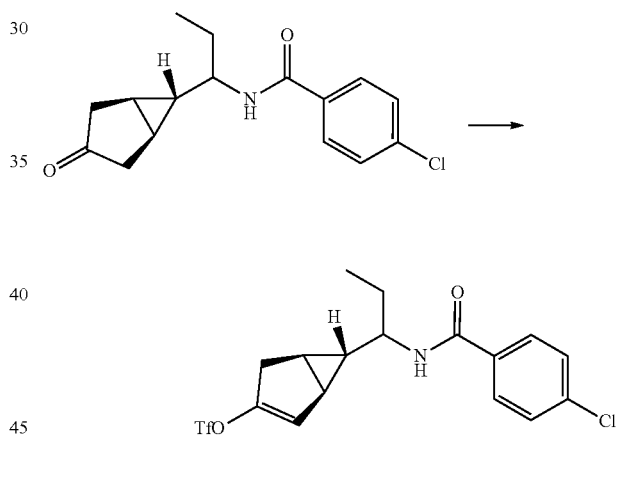

To a solution of 4-chloro-N-(1-((1R,5S,6r)-3-hydroxybicyclo[3.1.0]hexan-6-yl)propyl)benzamide (1 g, 3.40 mmol) in DCM (34.0 mL) was added Dess-Martin Periodinane (1.73 g, 4.08 mmol) and the resulting mixture was stirred at 25° C. for 1 h. Sat NaHCO$_3$ (20 mL) was added, and the layers were separated. The aqueous phase was extracted with DCM (3×15 mL), the combined organic layers were washed with H$_2$O, brine, dried over Na$_2$SO$_4$, filtered and concentrated, and purified via silica gel chromatography (0-80% EtOAc in hexanes) to give 4-chloro-N-(1-((1R,5S,6r)-3-oxobicyclo[3.1.0]hexan-6-yl)propyl)benzamide as a pale yellow liquid. MS (ES) C$_{16}$H$_{18}$ClNO$_2$ requires: 291, found: 292 [M+H]$^+$.

Step 2:

To a cooled −50° C. solution of 4-chloro-N-(1-((1R,5S,6r)-3-oxobicyclo[3.1.0]hexan-6-yl)propyl)benzamide (100 mg, 0.343 mmol) in THF (2285 μl) was added LiHMDS (1M THF, 754 μl, 0.754 mmol). The resulting mixture was stirred at −30° C. for 1 h. A solution of 1,1,1-trifluoro-N-phenyl-N-((trifluoromethyl)sulfonyl)methanesulfonamide (135 mg, 0.377 mmol) in THF (1142 μl) was added dropwise to the −30° C. solution and the resulting mixture was stirred at 25° C. for 18 hr. Sat NH$_4$Cl (20 mL) was added, and the layers were separated. The aqueous phase was extracted with EtOAc (3×20 mL), the combined organic layers dried over Na$_2$SO$_4$, filtered and concentrated, and purified via silica gel chromatography (0-65% EtOAc in hexanes) to give (1S,5R, 6S)-6-(1-(4-chlorobenzamido)propyl)bicyclo[3.1.0]hex-2-en-3-yl trifluoromethanesulfonate as a colorless liquid. MS (ES$^+$) C$_{17}$H$_{17}$ClF$_3$NO$_4$S requires: 423, found: 424 [M+H]$^+$.

Step 3:

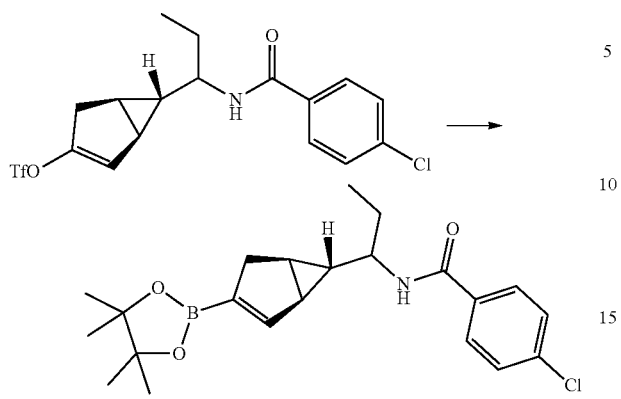

A solution of (1S,5R,6S)-6-(1-(4-chlorobenzamido)propyl)bicyclo[3.1.0]hex-2-en-3-yl trifluoromethanesulfonate (65 mg, 0.153 mmol), 4,4,4',4',5,5,5',5'-octamethyl-2,2'-bi(1,3,2-dioxaborolane) (46.3 mg, 0.183 mmol) and potassium acetate (45.2 mg, 0.460 mmol) in Dioxane (511 μl) was degassed in the sonicator for 2 min. and then purged with $N_2$ for 2 minutes. $PdCl_2$(dppf) (11.22 mg, 0.015 mmol) was added and the mixture was degassed with $N_2$ for an additional 1 minute. The reaction mixture was heated to 105° C. and stirred for 18 h. The reaction mixture was allowed to cool to room temperature, $H_2O$ (50 mL) was added, and the layers were separated. The aqueous phase was extracted with EtOAc (3×50 mL), the combined organic layers were washed with sat NaCl, dried over $Na_2SO_4$, filtered and concentrated, and purified via silica gel chromatography (0-20% EtOAc in hexanes) to give 4-chloro-N-(1-((1R,5R,6S)-3-(4,4,5,5-tetramethyl-1,3,2-dioxaborolan-2-yl)bicyclo[3.1.0]hex-2-en-6-yl)propyl)benzamide as a yellow liquid. MS (ES$^+$) $C_{22}H_{29}BClNO_3$ requires: 401, found: 402 [M+H]$^+$.

Step 4:

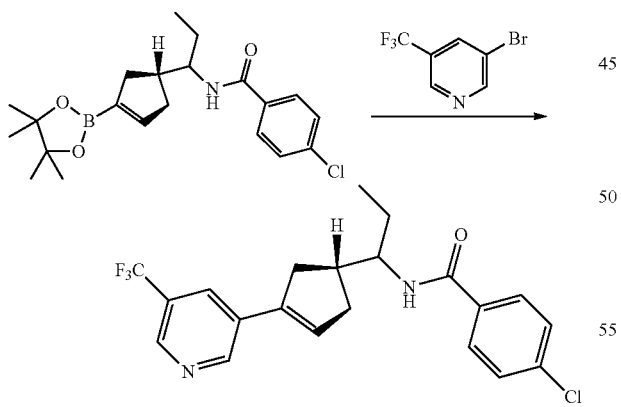

A solution of 4-chloro-N-(1-((1R,5R,6S)-3-(4,4,5,5-tetramethyl-1,3,2-dioxaborolan-2-yl)bicyclo[3.1.0]hex-2-en-6-yl)propyl)benzamide (58 mg, 0.14 mmol), 3-bromo-5-(trifluoromethyl)pyridine (36 mg, 0.16 mmol) and $K_2CO_3$ (62 mg, 0.45 mmol) in Dioxane (875 μl)/Water (87 μl) was degassed with $N_2$ for 2 minutes. $PdCl_2$(dppf)-$CH_2Cl_2$ adduct (26 mg, 0.03 mmol) was added and the mixture was degassed with $N_2$ for an additional 1 minute. The reaction mixture was heated to 100° C. and stirred for 5 h. The reaction mixture was allowed to cool to room temperature and filtered through Celite, and the filtrate was concentrated, and purified via silica gel chromatography (0-80% EtOAc in hexanes) to give 4-chloro-N-(1-((1R,5R,6S)-3-(5-(trifluoromethyl)pyridin-3-yl)bicyclo[3.1.0]hex-2-en-6-yl) propyl) benzamide (32 mg, 0.076 mmol, 52% yield) as a colorless liquid. MS (ES$^+$)$C_{24}H_{21}ClFN_3O$ requires: 420, found: 421 [M+H]$^+$.

Synthesis of 4-chloro-N-(1-((1R,5R,6S)-3-(7-fluoroquinazolin-4-yl)bicyclo[3.1.0]hex-2-en-6-yl)propyl) benzamide (Compound 255)

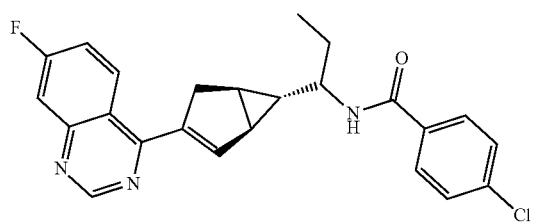 [SMILES: CCC(NC(=O)c1ccc(Cl)cc1)[C@@H]1[C@H]2C=C(c3ncnc4cc(F)ccc34)C[C@H]21]

The title compound was synthesized similar to 4-chloro-N-(1-((1R,5R,6S)-3-(5-(trifluoromethyl)pyridin-3-yl)bicyclo[3.1.0]hex-2-en-6-yl)propyl)benzamide (Compound 254, above) from 4-chloro-N-(1-((1R,5R,6S)-3-(4,4,5,5-tetramethyl-1,3,2-dioxaborolan-2-yl)bicyclo[3.1.0]hex-2-en-6-yl)propyl)benzamide and 4-chloro-7-fluoroquinazoline to give 4-chloro-N-(1-((1R,5R,6S)-3-(7-fluoroquinazolin-4-yl)bicyclo[3.1.0]hex-2-en-6-yl)propyl) benzamide (21 mg, 0.050 mmol, 34.5% yield) as a colorless liquid. MS (ES$^+$) $C_{24}H_{21}ClFN_3O$ requires: 421, found: 422 [M+H]$^+$.

Synthesis of 4-chloro-N—((R)-1-((R, 3S, 5S, 6r)-3-(5,6-difluoro-1H-benzo[d]imidazol-1-yl)bicyclo[3.1.0]hexan-6-yl)propyl)benzamide (Compound 260)

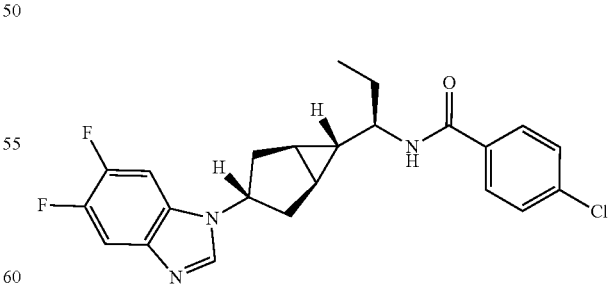

The title compound was synthesized similar to the general MS displacement procedure from the enantiomerically pure Compound 1 (confirmed as the R enantiomer by Mosher analysis) that was synthesized similar to Example 1 from the chiral auxiliary, (S)-2-methylpropane-2-sulfinamide.

Synthesis of 4-chloro-N-(1-((1R,3s, 5S, 6r)-3-(4-cyclopropyl-1H-imidazol-1-yl)bicyclo[3.1.0]hexan-6-yl)propyl)benzamide (Compound 261)

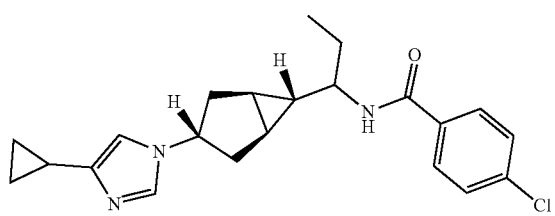 [SMILES: CCC(NC(=O)c1ccc(Cl)cc1)[C@H]1[C@@H]2C[C@@H](n3cnc(C4CC4)c3)C[C@@H]21]

Step 1:

To a vial containing N-(1-((1R,3s,5S,6r)-3-aminobicyclo[3.1.0]hexan-6-yl)propyl)-4-chlorobenzamide (100 mg, 0.342 mmol) dissolved in EtOH (1708 μl) was added N-methyl morpholine (75 μl, 0.683 mmol) and 2-bromo-1-cyclopropylethanone (61.2 mg, 0.376 mmol) and the solution was stirred at 55° C. overnight. The reaction was concentrated and purified via flash chromatography (0-100% 80:20:1 DCM:MeOH:NH4OH in DCM) to give 4-chloro-N-(1-((1R,3 s,5 S,6r)-3-((2-cyclopropyl-2-oxoethyl)amino)bicyclo[3.1.0]hexan-6-yl) propyl)benzamide (2.1 mg, 5.6 μmol, 1% yield) as a yellow solid. MS (ES+) $C_{21}H_{27}ClN_2O_2$ requires: 374, found: 375[M+H]$^+$.

Step 2:

To a solution of 4-chloro-N-(1-((1R,3s,5S,6r)-3-((2-cyclopropyl-2-oxoethyl)amino)bicyclo[3.1.0]hexan-6-yl)propyl)benzamide (2.1 mg, 5.60 μmol) in AcOH (150 μl) was added potassium thiocyanate (4.5 mg, 0.046 mmol) and the resulting mixture was stirred at room temperature overnight and at 80° C. for 5 h. The reaction was diluted with MeOH and purified by mass-triggered preparative HPLC (Mobile phase: A=0.1% TFA/H2O, B=0.1% TFA/MeCN; Gradient: B=20-60%; 20 min; Column: C18) to give 4-chloro-N-(1-((1R,3s,5 S,6r)-3-(4-cyclopropyl-1H-imidazol-1-yl)bicyclo[3.1.0]hexan-6-yl)propyl) benzamide (0.9 mg, 1.9 μmol, 33% yield) as an off-white TFA salt solid. MS (ES+) $C_{22}H_{26}ClN_3O$ requires: 383, found: 384 [M+H]$^+$.

Synthesis of Pyrazole-Substituted Compounds

Analogues of Compound 63 in which the oxoquinazolinyl group is replaced by a pyrazole may be prepared e.g. by methods as described herein. For example, compounds in which the group "R$^1$—(X$^1$)$_a$—" represent pyrazol-1-yl may be prepared e.g. according to the process used to prepare Compound 89. Compounds in which the group "R$^1$—(X$^1$)$_a$—" represent pyrazol-3-yl or pyrazol-4-yl may be prepared e.g. according to the process used to prepare Compound 254 (e.g. using a corresponding 3-bromopyrazole or 4-bromopyrazole). 4-chloro-N-(1-((1R,3s,5S,6r)-3-(pyrazol-1-yl)bicyclo[3.1.0]hexan-6-yl)ethyl)benzamide (Compound 263) is synthesised, as described above, from the corresponding starting materials:

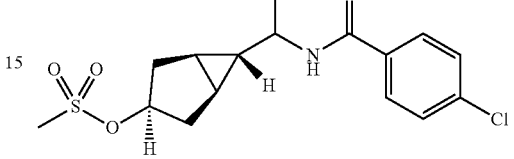

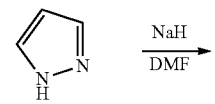

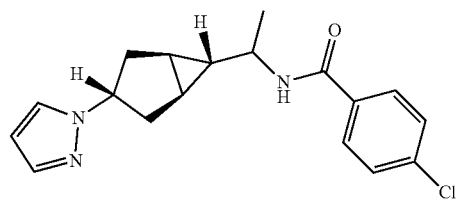

Example 16: Synthesis of Compounds 264 to 363

The following compounds in Table 3 were prepared according to the synthetic procedures described herein. For each compound, the table indicates the chemical structure, the calculated and measured mass, and details of the method by which the compound was prepared. The terms "SNAr", "Amide coupling", "1,4 Triazole", "MS", "BzI" and "General Urea" are as described herein.

TABLE 3

| Compound | Structure | Calc. Mass | Mass [M + H]$^+$ | Synthesis as per |
|---|---|---|---|---|
| 264 | 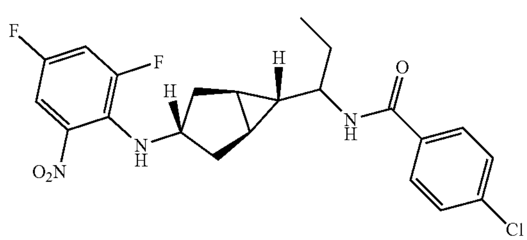 [SMILES: CCC(NC(=O)c1ccc(Cl)cc1)[C@H]1[C@@H]2C[C@@H](Nc3c(F)cc(F)cc3[N+](=O)[O-])C[C@@H]21] | 449 | 450 | SNAr |

TABLE 3-continued

| Compound | Structure | Calc. Mass | Mass [M + H]+ | Synthesis as per |
|---|---|---|---|---|
| 265 | 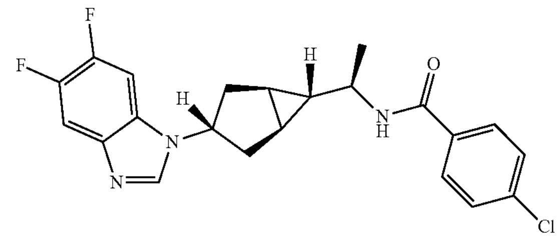 [SMILES: C[C@@H](NC(=O)c1ccc(Cl)cc1)[C@H]1[C@@H]2C[C@@H](n3cnc4cc(F)c(F)cc43)C[C@@H]21] | 415 | 416 | Compound 260 |
| 266 | 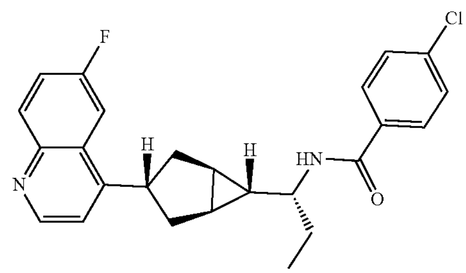 [SMILES: CC[C@@H](NC(=O)c1ccc(Cl)cc1)[C@H]1[C@@H]2C[C@@H](c3ccnc4ccc(F)cc34)C[C@@H]21] | 422 | 423 | Exemplified |
| 267 | 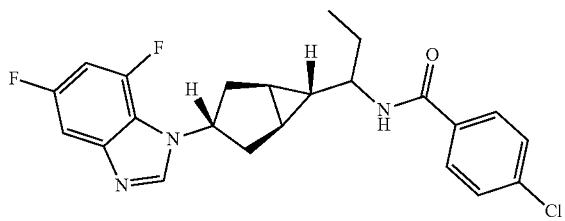 [SMILES: CCC(NC(=O)c1ccc(Cl)cc1)[C@H]1[C@@H]2C[C@@H](n3cnc4cc(F)cc(F)c43)C[C@@H]21] | 429 | 430 | Bzl |
| 268 | 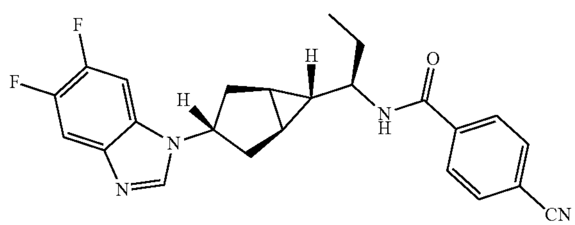 [SMILES: CC[C@@H](NC(=O)c1ccc(C#N)cc1)[C@H]1[C@@H]2C[C@@H](n3cnc4cc(F)c(F)cc43)C[C@@H]21] | 420 | 421 | Compound 260 |
| 269 | 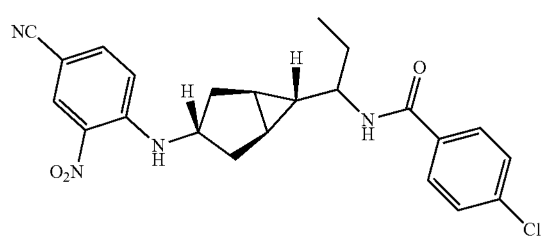 [SMILES: CCC(NC(=O)c1ccc(Cl)cc1)[C@H]1[C@@H]2C[C@@H](Nc3ccc(C#N)cc3[N+](=O)[O-])C[C@@H]21] | 438 | 439 | SNAr |
| 270 | 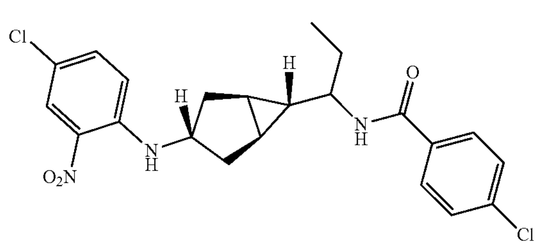 [SMILES: CCC(NC(=O)c1ccc(Cl)cc1)[C@H]1[C@@H]2C[C@@H](Nc3ccc(Cl)cc3[N+](=O)[O-])C[C@@H]21] | 447 | 448 | SNAr |

TABLE 3-continued

| Compound | Structure | Calc. Mass | Mass [M + H]+ | Synthesis as per |
|---|---|---|---|---|
| 271 | 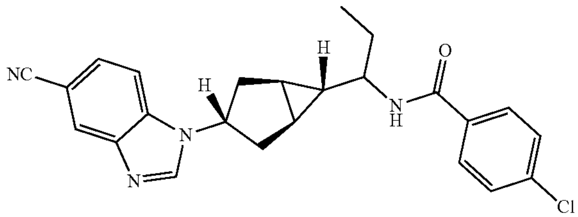 [SMILES: CCC(NC(=O)c1ccc(Cl)cc1)[C@H]1[C@@H]2C[C@@H](n3cnc4cc(C#N)ccc43)C[C@@H]21] | 418 | 419 | Bzl |
| 272 | 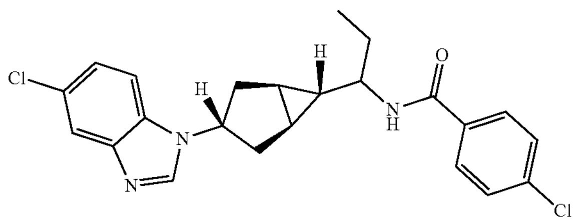 [SMILES: CCC(NC(=O)c1ccc(Cl)cc1)[C@H]1[C@@H]2C[C@@H](n3cnc4cc(Cl)ccc43)C[C@@H]21] | 427 | 428 | Bzl |
| 273 | 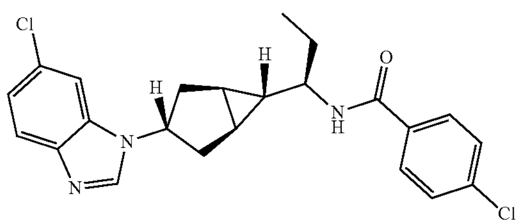 [SMILES: CC[C@@H](NC(=O)c1ccc(Cl)cc1)[C@H]1[C@@H]2C[C@@H](n3cnc4ccc(Cl)cc43)C[C@@H]21] | 427 | 428 | Bzl |
| 274 | 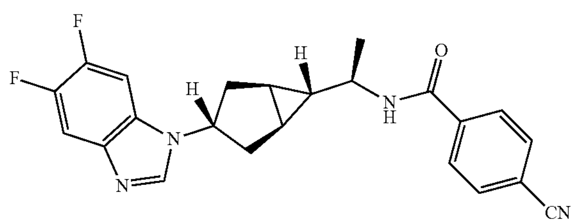 [SMILES: C[C@@H](NC(=O)c1ccc(C#N)cc1)[C@H]1[C@@H]2C[C@@H](n3cnc4cc(F)c(F)cc43)C[C@@H]21] | 406 | 407 | MS |
| 275 | 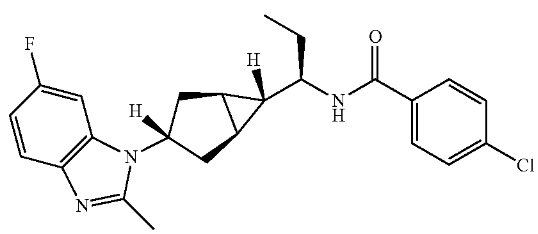 [SMILES: CC[C@@H](NC(=O)c1ccc(Cl)cc1)[C@H]1[C@@H]2C[C@@H](n3c(C)nc4ccc(F)cc43)C[C@@H]21] | 425 | 426 | Bzl (using acetic acid) |
| 276 | 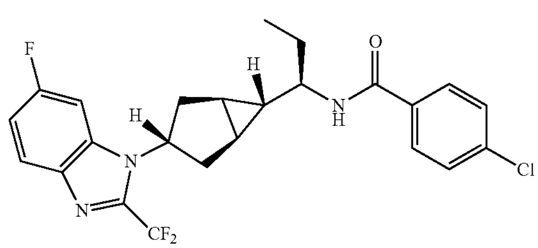 | 479 | 480 | Bzl (using TFA) |

TABLE 3-continued

| Compound | Structure | Calc. Mass | Mass [M + H]+ | Synthesis as per |
|---|---|---|---|---|
| 277 | 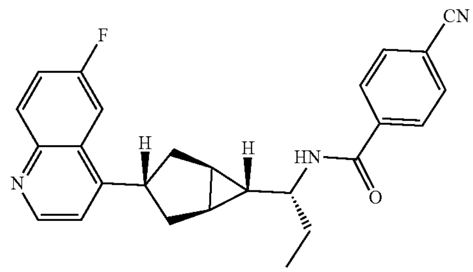 [SMILES: CC[C@@H](NC(=O)c1ccc(C#N)cc1)[C@H]1[C@@H]2C[C@@H](c3ccnc4ccc(F)cc34)C[C@@H]21] | 413 | 414 | Compound 266 |
| 278 | 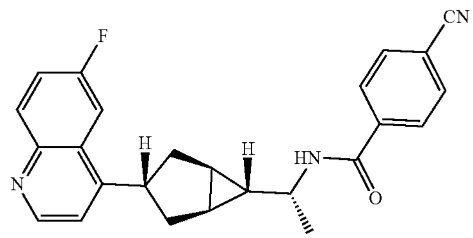 [SMILES: C[C@@H](NC(=O)c1ccc(C#N)cc1)[C@H]1[C@@H]2C[C@@H](c3ccnc4ccc(F)cc34)C[C@@H]21] | 399 | 400 | Compound 266 |
| 279 | 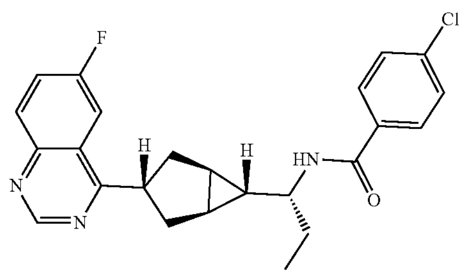 [SMILES: CC[C@@H](NC(=O)c1ccc(Cl)cc1)[C@H]1[C@@H]2C[C@@H](c3ncnc4ccc(F)cc34)C[C@@H]21] | 423 | 424 | Compound 266 |
| 280 | 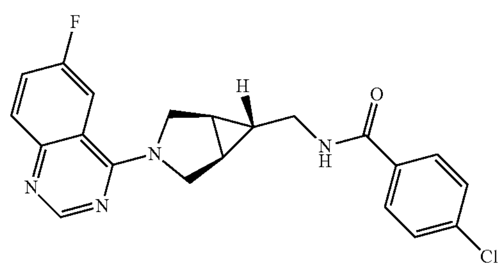 [SMILES: O=C(NC[C@@H]1[C@H]2CN(c3ncnc4ccc(F)cc34)C[C@@H]12)c1ccc(Cl)cc1] | 396 | 397 | Compound 8 and Compound 109 |
| 281 | 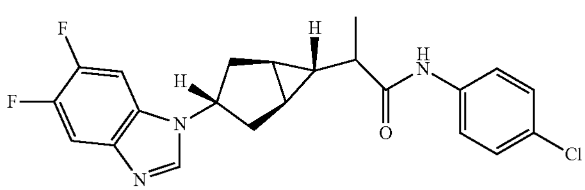 [SMILES: CC(C(=O)Nc1ccc(Cl)cc1)[C@H]1[C@@H]2C[C@@H](n3cnc4cc(F)c(F)cc43)C[C@@H]21] | 415 | 416 | Exemplified |
| 282 | 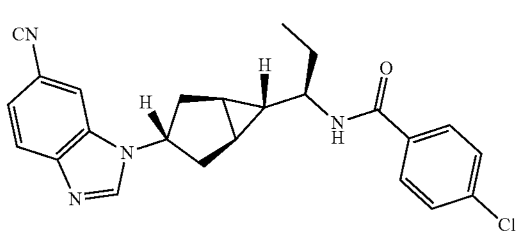 | 418 | 419 | Bzl |

TABLE 3-continued

| Compound | Structure | Calc. Mass | Mass [M + H]+ | Synthesis as per |
|---|---|---|---|---|
| 283 | 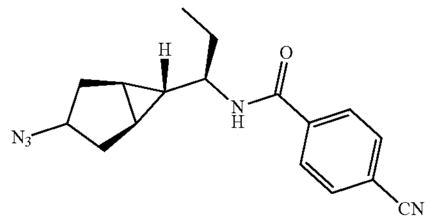 | 309 | 310 | MS |
| 284 | 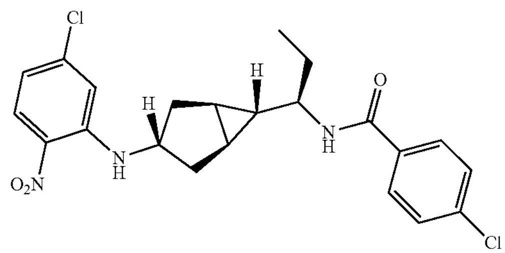 [SMILES: CC[C@@H](NC(=O)c1ccc(Cl)cc1)[C@H]1[C@@H]2C[C@@H](Nc3cc(Cl)ccc3[N+](=O)[O-])C[C@@H]21] | 447 | 448 | SNAr |
| 285 | 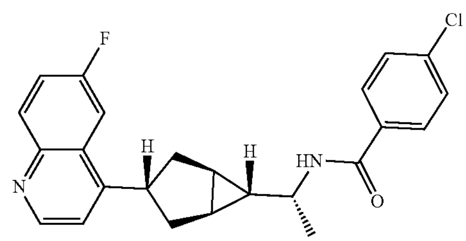 [SMILES: C[C@@H](NC(=O)c1ccc(Cl)cc1)[C@H]1[C@@H]2C[C@@H](c3ccnc4ccc(F)cc34)C[C@@H]21] | 408 | 409 | Compound 266 |
| 286 | 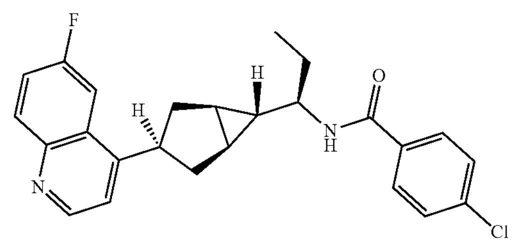 [SMILES: CC[C@@H](NC(=O)c1ccc(Cl)cc1)[C@H]1[C@@H]2C[C@H](c3ccnc4ccc(F)cc34)C[C@@H]21] | 422 | 423 | Compound 266 |
| 287 | 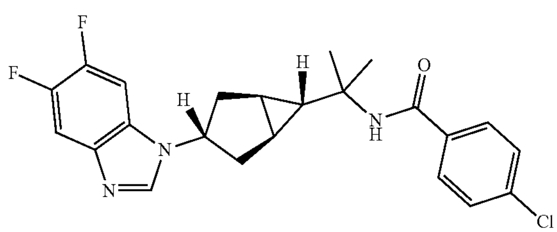 [SMILES: CC(C)(NC(=O)c1ccc(Cl)cc1)[C@H]1[C@@H]2C[C@@H](n3cnc4cc(F)c(F)cc43)C[C@@H]21] | 429 | 430 | Compound 87 (with final step of mesylation/mesyl displacement) |
| 288 | 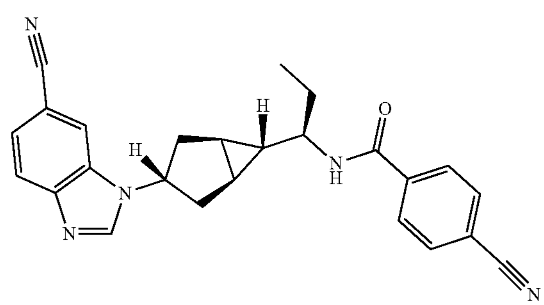 [SMILES: CC[C@@H](NC(=O)c1ccc(C#N)cc1)[C@H]1[C@@H]2C[C@@H](n3cnc4ccc(C#N)cc43)C[C@@H]21] | 409 | 410 | Bzl |

TABLE 3-continued

| Compound | Structure | Calc. Mass | Mass [M + H]+ | Synthesis as per |
|---|---|---|---|---|
| 289 | 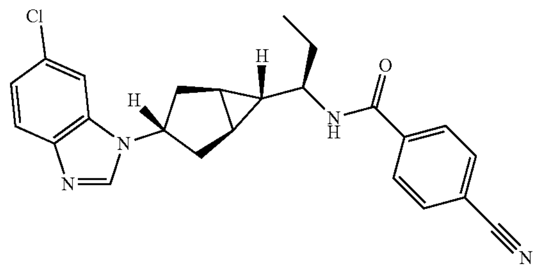 [SMILES: CC[C@@H](NC(=O)c1ccc(C#N)cc1)[C@H]1[C@@H]2C[C@@H](n3cnc4ccc(Cl)cc43)C[C@@H]21] | 418 | 419 | Bzl |
| 290 | 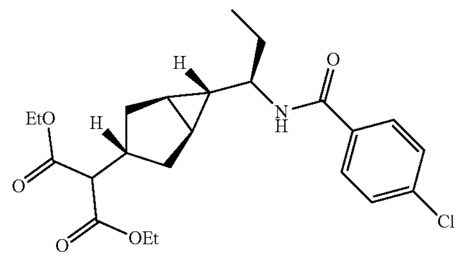 [SMILES: CCOC(=O)C(C(=O)OCC)[C@@H]1C[C@@H]2[C@H](C1)[C@H]2[C@@H](CC)NC(=O)c1ccc(Cl)cc1] | 435 | 436 | Exemplified |
| 291 | 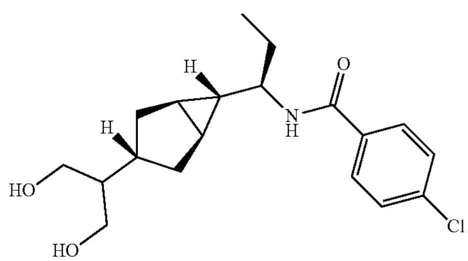 [SMILES: CC[C@@H](NC(=O)c1ccc(Cl)cc1)[C@H]1[C@@H]2C[C@@H](C(CO)CO)C[C@@H]21] | 351 | 352 | Exemplified |
| 292 | 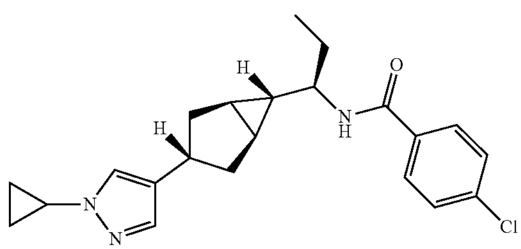 [SMILES: CC[C@@H](NC(=O)c1ccc(Cl)cc1)[C@H]1[C@@H]2C[C@@H](c3cnn(C4CC4)c3)C[C@@H]21] | 383 | 384 | Exemplified |
| 293 | 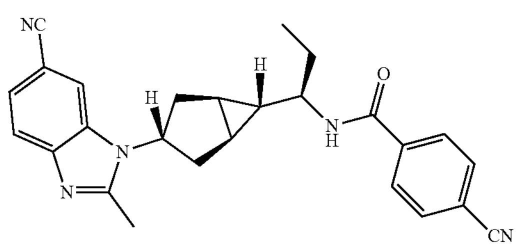 [SMILES: CC[C@@H](NC(=O)c1ccc(C#N)cc1)[C@H]1[C@@H]2C[C@@H](n3c(C)nc4ccc(C#N)cc43)C[C@@H]21] | 423 | 424 | Bzl (using acetic acid) |
| 294 | 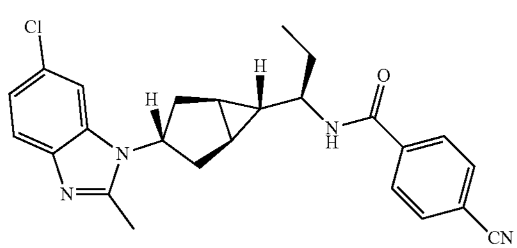 | 432 | 433 | Bzl (using acetic acid) |

TABLE 3-continued

| Compound | Structure | Calc. Mass | Mass [M + H]+ | Synthesis as per |
|---|---|---|---|---|
| 295 | 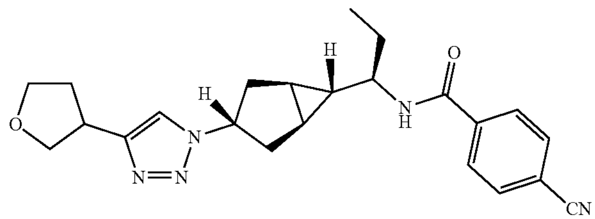 [SMILES: CC[C@@H](NC(=O)c1ccc(C#N)cc1)[C@H]1[C@@H]2C[C@@H](n3cc(C4CCOC4)nn3)C[C@@H]21] | 405 | 406 | 1,4 Triazole |
| 296 | 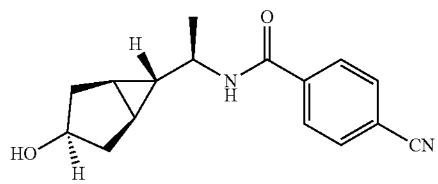 [SMILES: C[C@@H](NC(=O)c1ccc(C#N)cc1)[C@H]1[C@@H]2C[C@H](O)C[C@@H]21] | 270 | 271 | Compounds 1 and 3 (using (S)-2-methylpropane-2-sulfinamide) |
| 297 | 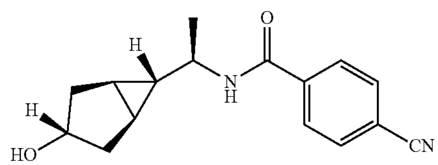 [SMILES: C[C@@H](NC(=O)c1ccc(C#N)cc1)[C@H]1[C@@H]2C[C@@H](O)C[C@@H]21] | 270 | 271 | Compounds 1 and 3 (using (S)-2-methylpropane-2-sulfinamide) |
| 298 | 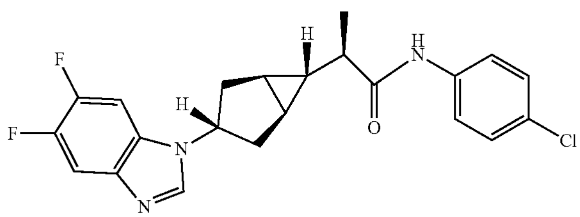 [SMILES: C[C@@H](C(=O)Nc1ccc(Cl)cc1)[C@H]1[C@@H]2C[C@@H](n3cnc4cc(F)c(F)cc43)C[C@@H]21] | 415 | 416 | Compound 281 (with SFC purification) |
| 299 | 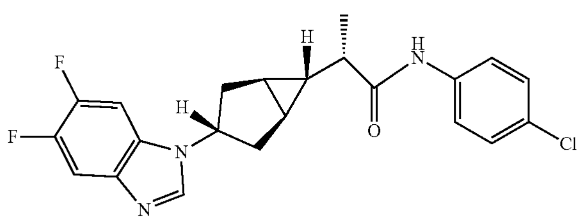 [SMILES: C[C@H](C(=O)Nc1ccc(Cl)cc1)[C@H]1[C@@H]2C[C@@H](n3cnc4cc(F)c(F)cc43)C[C@@H]21] | 415 | 416 | Compound 281 (with SFC purification) |
| 300 | 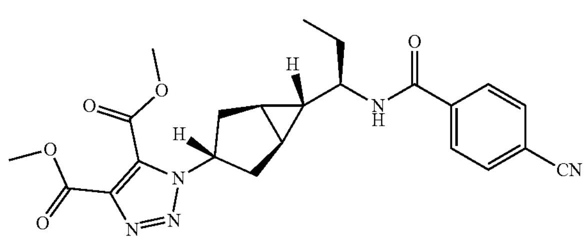 [SMILES: CC[C@@H](NC(=O)c1ccc(C#N)cc1)[C@H]1[C@@H]2C[C@@H](n3nnc(C(=O)OC)c3C(=O)OC)C[C@@H]21] | 451 | 452 | 1,4 Triazole (followed by alkyne addition (10 eq) and microwave heating at 150° C. for 30 min) |
| 301 | 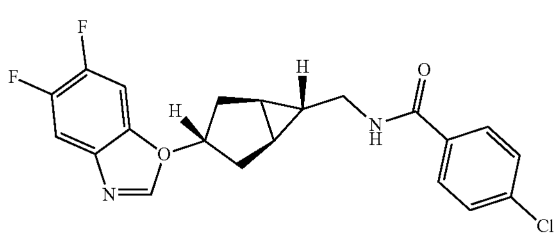 | 401 | 402 | Exemplified |

TABLE 3-continued

| Compound | Structure | Calc. Mass | Mass [M + H]+ | Synthesis as per |
|---|---|---|---|---|
| 302 | 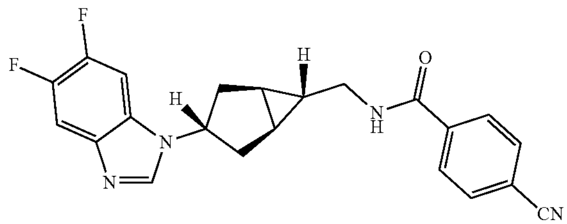 [SMILES: N#Cc1ccc(C(=O)NC[C@@H]2[C@H]3C[C@H](n4cnc5cc(F)c(F)cc54)C[C@@H]23)cc1] | 392 | 393 | Compound 301 |
| 303 | 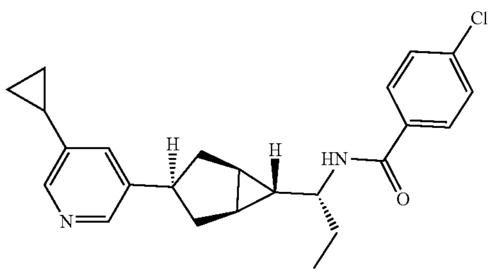 [SMILES: CC[C@@H](NC(=O)c1ccc(Cl)cc1)[C@H]1[C@@H]2C[C@H](c3cncc(C4CC4)c3)C[C@@H]21] | 394 | 395 | Compound 266 |
| 304 | 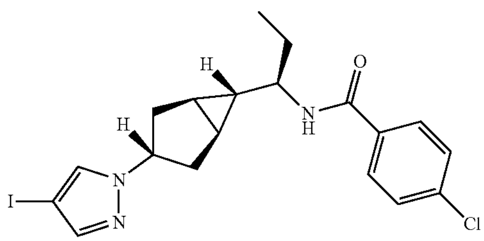 [SMILES: CC[C@@H](NC(=O)c1ccc(Cl)cc1)[C@H]1[C@@H]2C[C@@H](n3cc(I)cn3)C[C@@H]21] | 469 | 470 | MS |
| 305 | 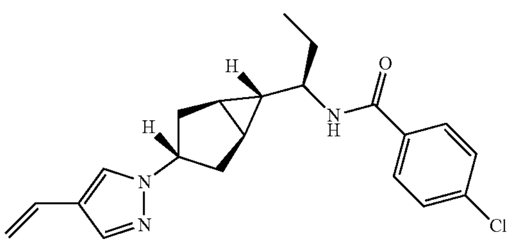 [SMILES: C=Cc1cnn([C@@H]2C[C@@H]3[C@H](C2)[C@H]3[C@@H](CC)NC(=O)c2ccc(Cl)cc2)c1] | 369 | 370 | MS (followed by Suzuki coupling) |
| 306 | 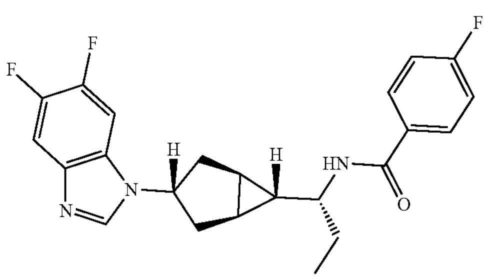 [SMILES: CC[C@@H](NC(=O)c1ccc(F)cc1)[C@H]1[C@@H]2C[C@@H](n3cnc4cc(F)c(F)cc43)C[C@@H]21] | 413 | 414 | Exemplified |
| 307 | 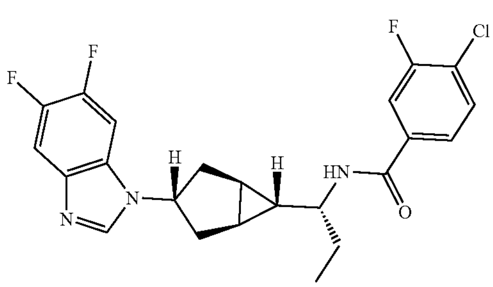 [SMILES: CC[C@@H](NC(=O)c1ccc(Cl)c(F)c1)[C@H]1[C@@H]2C[C@@H](n3cnc4cc(F)c(F)cc43)C[C@@H]21] | 447 | 448 | Compound 306 |

TABLE 3-continued

| Compound | Structure | Calc. Mass | Mass [M + H]+ | Synthesis as per |
|---|---|---|---|---|
| 308 | 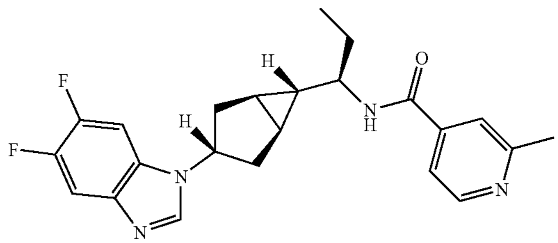 [SMILES: CC[C@@H](NC(=O)c1ccnc(C)c1)[C@H]1[C@@H]2C[C@@H](n3cnc4cc(F)c(F)cc43)C[C@@H]21] | 410 | 411 | Compound 306 |
| 309 | 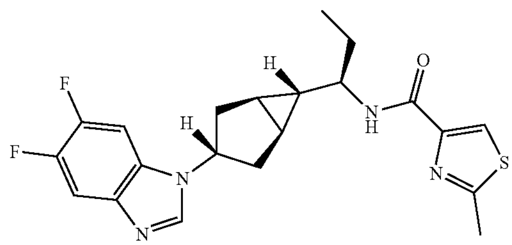 [SMILES: CC[C@@H](NC(=O)c1csc(C)n1)[C@H]1[C@@H]2C[C@@H](n3cnc4cc(F)c(F)cc43)C[C@@H]21] | 416 | 417 | Compound 306 |
| 310 | 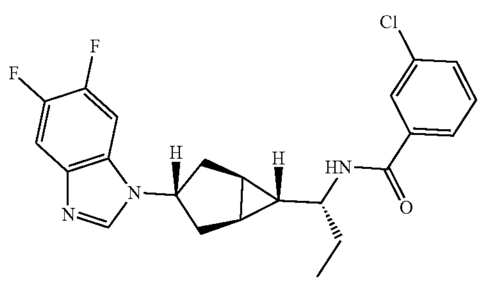 [SMILES: CC[C@@H](NC(=O)c1cccc(Cl)c1)[C@H]1[C@@H]2C[C@@H](n3cnc4cc(F)c(F)cc43)C[C@@H]21] | 429 | 430 | Compound 306 |
| 311 | 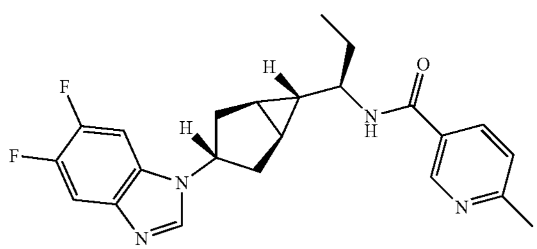 [SMILES: CC[C@@H](NC(=O)c1ccc(C)nc1)[C@H]1[C@@H]2C[C@@H](n3cnc4cc(F)c(F)cc43)C[C@@H]21] | 410 | 411 | Compound 306 |
| 312 | 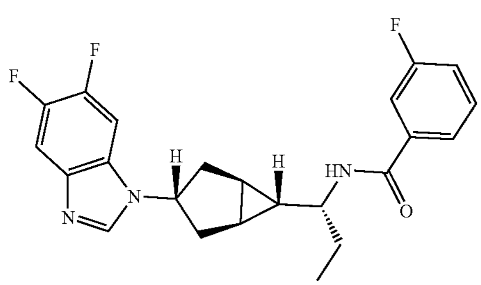 [SMILES: CC[C@@H](NC(=O)c1cccc(F)c1)[C@H]1[C@@H]2C[C@@H](n3cnc4cc(F)c(F)cc43)C[C@@H]21] | 413 | 414 | Compound 306 |
| 313 | 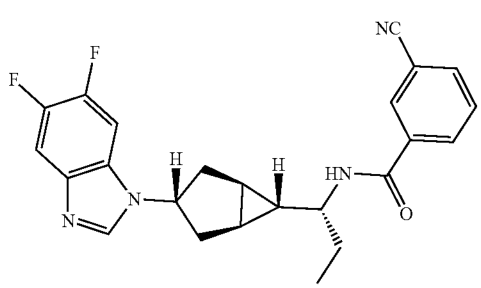 [SMILES: CC[C@@H](NC(=O)c1cccc(C#N)c1)[C@H]1[C@@H]2C[C@@H](n3cnc4cc(F)c(F)cc43)C[C@@H]21] | 420 | 421 | Compound 306 |

TABLE 3-continued

| Compound | Structure | Calc. Mass | Mass [M + H]+ | Synthesis as per |
|---|---|---|---|---|
| 314 | 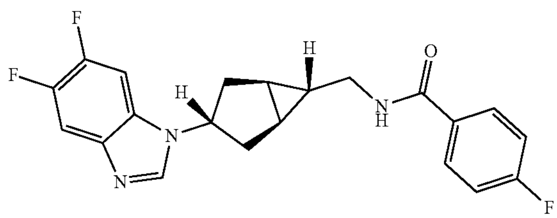 [SMILES: O=C(NC[C@@H]1[C@H]2C[C@H](n3cnc4cc(F)c(F)cc43)C[C@@H]12)c1ccc(F)cc1] | 385 | 386 | Compound 301 |
| 315 | 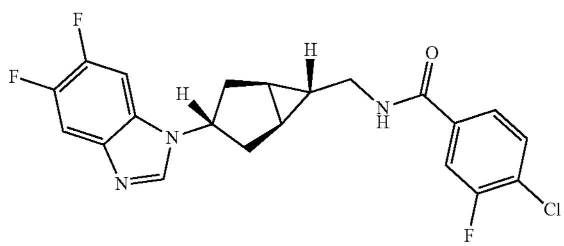 [SMILES: O=C(NC[C@@H]1[C@H]2C[C@H](n3cnc4cc(F)c(F)cc43)C[C@@H]12)c1ccc(Cl)c(F)c1] | 419 | 420 | Compound 301 |
| 316 | 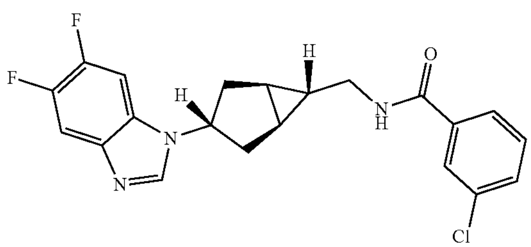 [SMILES: O=C(NC[C@@H]1[C@H]2C[C@H](n3cnc4cc(F)c(F)cc43)C[C@@H]12)c1cccc(Cl)c1] | 401 | 402 | Compound 301 |
| 317 | 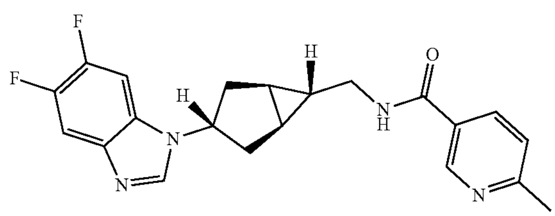 [SMILES: Cc1ccc(C(=O)NC[C@@H]2[C@H]3C[C@H](n4cnc5cc(F)c(F)cc54)C[C@@H]23)cn1] | 382 | 383 | Compound 301 |
| 318 | 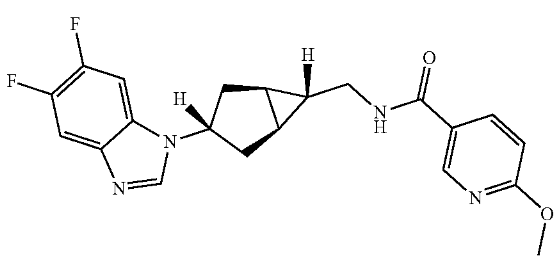 [SMILES: COc1ccc(C(=O)NC[C@@H]2[C@H]3C[C@H](n4cnc5cc(F)c(F)cc54)C[C@@H]23)cn1] | 398 | 399 | Compound 301 |
| 319 | 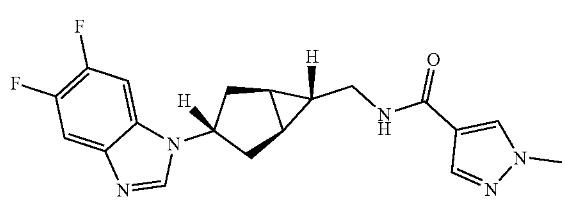 [SMILES: Cn1cc(C(=O)NC[C@@H]2[C@H]3C[C@H](n4cnc5cc(F)c(F)cc54)C[C@@H]23)cn1] | 371 | 372 | Compound 301 |

TABLE 3-continued

| Compound | Structure | Calc. Mass | Mass [M + H]+ | Synthesis as per |
|---|---|---|---|---|
| 320 | 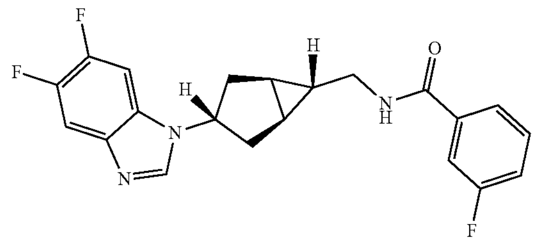 [SMILES: O=C(NC[C@@H]1[C@H]2C[C@H](n3cnc4cc(F)c(F)cc43)C[C@@H]12)c1cccc(F)c1] | 385 | 386 | Compound 301 |
| 321 | 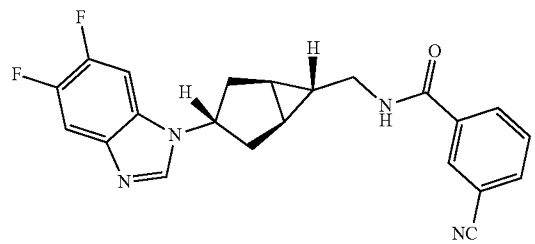 [SMILES: N#Cc1cccc(C(=O)NC[C@@H]2[C@H]3C[C@H](n4cnc5cc(F)c(F)cc54)C[C@@H]23)c1] | 392 | 393 | Compound 301 |
| 322 | 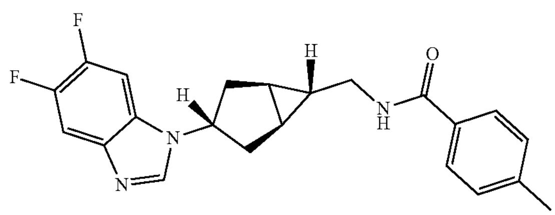 [SMILES: Cc1ccc(C(=O)NC[C@@H]2[C@H]3C[C@H](n4cnc5cc(F)c(F)cc54)C[C@@H]23)cc1] | 381 | 382 | Compound 301 |
| 323 | 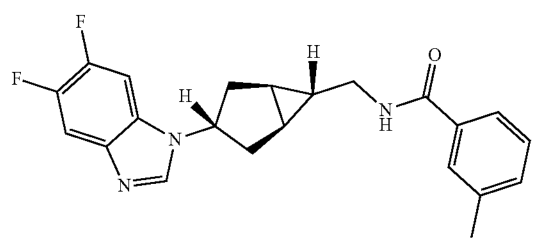 [SMILES: Cc1cccc(C(=O)NC[C@@H]2[C@H]3C[C@H](n4cnc5cc(F)c(F)cc54)C[C@@H]23)c1] | 381 | 382 | Compound 301 |
| 324 | 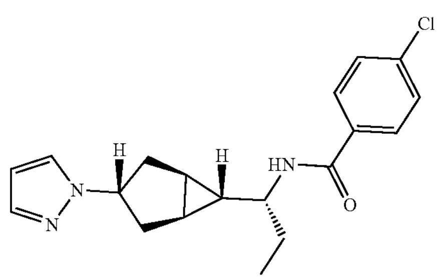 [SMILES: CC[C@@H](NC(=O)c1ccc(Cl)cc1)[C@H]1[C@@H]2C[C@@H](n3cccn3)C[C@@H]21] | 343 | 344 | MS |
| 325 | 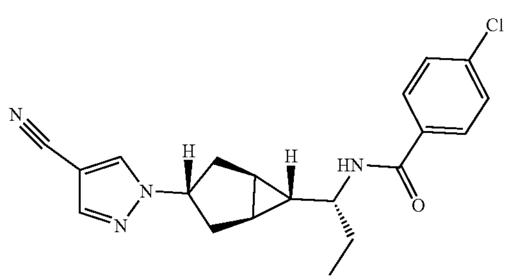 [SMILES: CC[C@@H](NC(=O)c1ccc(Cl)cc1)[C@H]1[C@@H]2C[C@@H](n3cc(C#N)cn3)C[C@@H]21] | 368 | 369 | MS |

TABLE 3-continued

| Compound | Structure | Calc. Mass | Mass [M + H]⁺ | Synthesis as per |
|---|---|---|---|---|
| 326 | 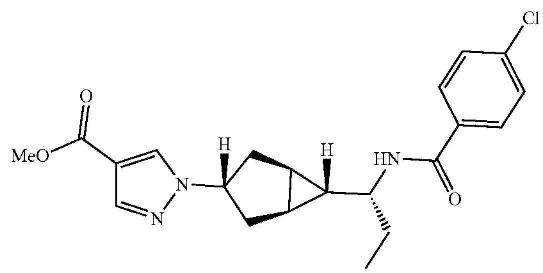 [SMILES: CC[C@@H](NC(=O)c1ccc(Cl)cc1)[C@H]1[C@@H]2C[C@@H](n3cc(C(=O)OC)cn3)C[C@@H]21] | 401 | 402 | MS |
| 327 | 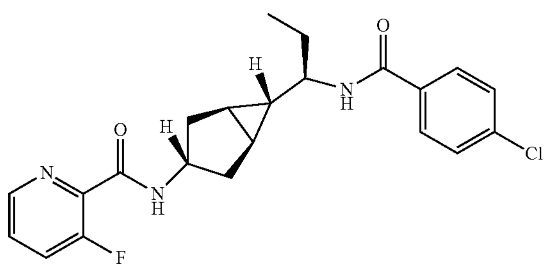 [SMILES: CC[C@@H](NC(=O)c1ccc(Cl)cc1)[C@H]1[C@@H]2C[C@@H](NC(=O)c3ncccc3F)C[C@@H]21] | 415 | 416 | Amide coupling |
| 328 | 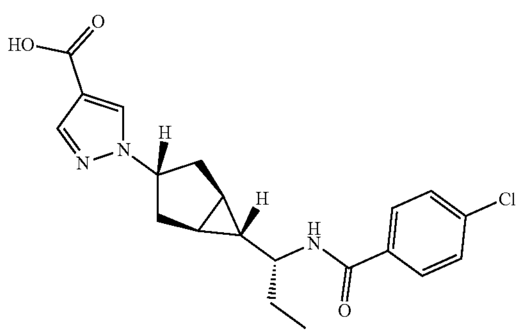 [SMILES: CC[C@@H](NC(=O)c1ccc(Cl)cc1)[C@H]1[C@@H]2C[C@@H](n3cc(C(=O)O)cn3)C[C@@H]21] | 387 | 388 | MS (followed by hydrolysis) |
| 329 | 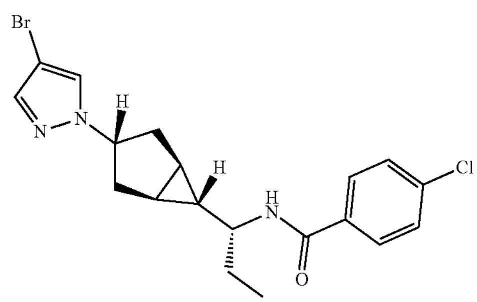 [SMILES: CC[C@@H](NC(=O)c1ccc(Cl)cc1)[C@H]1[C@@H]2C[C@@H](n3cc(Br)cn3)C[C@@H]21] | 421 | 422 | MS |
| 330 | 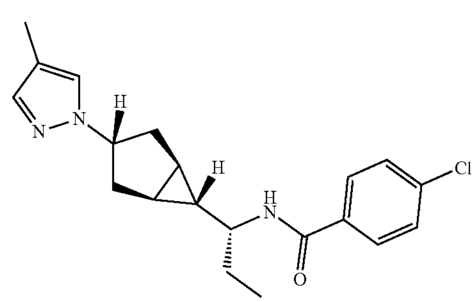 [SMILES: CC[C@@H](NC(=O)c1ccc(Cl)cc1)[C@H]1[C@@H]2C[C@@H](n3cc(C)cn3)C[C@@H]21] | 357 | 358 | MS |

TABLE 3-continued

| Compound | Structure | Calc. Mass | Mass [M + H]+ | Synthesis as per |
|---|---|---|---|---|
| 331 | 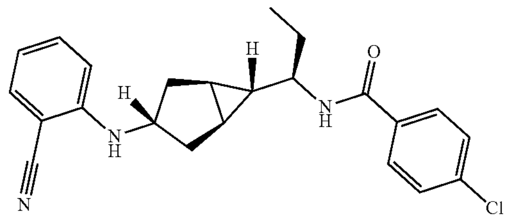 [SMILES: CC[C@@H](NC(=O)c1ccc(Cl)cc1)[C@H]1[C@@H]2C[C@@H](Nc3ccccc3C#N)C[C@@H]21] | 393 | 394 | Exemplified |
| 332 | 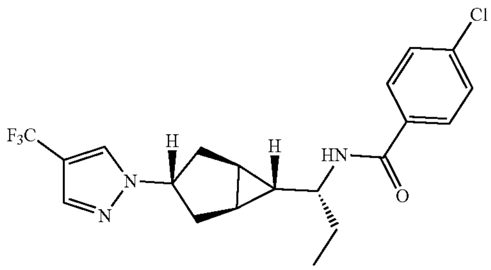 [SMILES: CC[C@@H](NC(=O)c1ccc(Cl)cc1)[C@H]1[C@@H]2C[C@@H](n3cc(C(F)(F)F)cn3)C[C@@H]21] | 411 | 412 | MS |
| 333 | 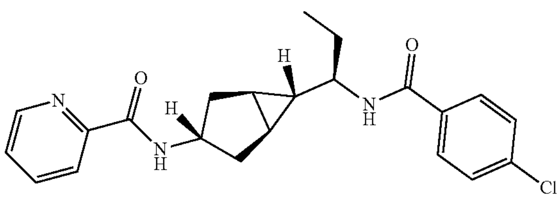 [SMILES: CC[C@@H](NC(=O)c1ccc(Cl)cc1)[C@H]1[C@@H]2C[C@@H](NC(=O)c3ccccn3)C[C@@H]21] | 397 | 398 | Amide coupling |
| 334 | 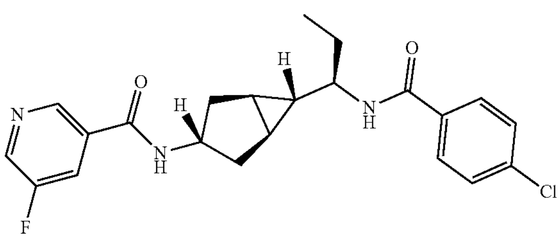 [SMILES: CC[C@@H](NC(=O)c1ccc(Cl)cc1)[C@H]1[C@@H]2C[C@@H](NC(=O)c3cncc(F)c3)C[C@@H]21] | 415 | 416 | Amide coupling |
| 335 | 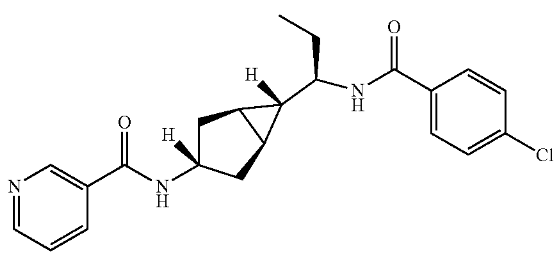 [SMILES: CC[C@@H](NC(=O)c1ccc(Cl)cc1)[C@H]1[C@@H]2C[C@@H](NC(=O)c3cccnc3)C[C@@H]21] | 397 | 398 | Amide coupling |
| 336 | 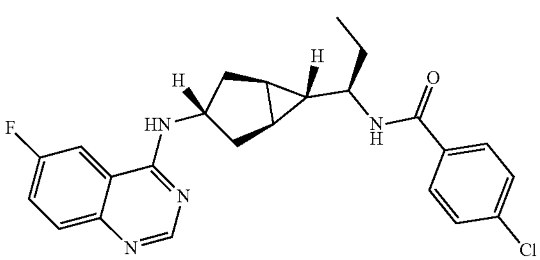 [SMILES: CC[C@@H](NC(=O)c1ccc(Cl)cc1)[C@H]1[C@@H]2C[C@@H](Nc3ncnc4ccc(F)cc34)C[C@@H]21] | 438 | 439 | SNAr |

TABLE 3-continued
| Compound | Structure | Calc. Mass | Mass [M + H]+ | Synthesis as per |
|---|---|---|---|---|
| 337 | 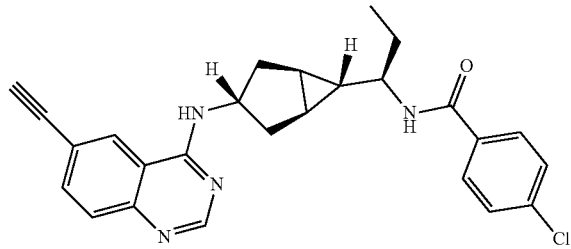 [SMILES: C#Cc1ccc2ncnc(N[C@@H]3C[C@@H]4[C@H](C3)[C@H]4[C@@H](CC)NC(=O)c3ccc(Cl)cc3)c2c1] | 444 | 445 | SNAr |
| 338 | 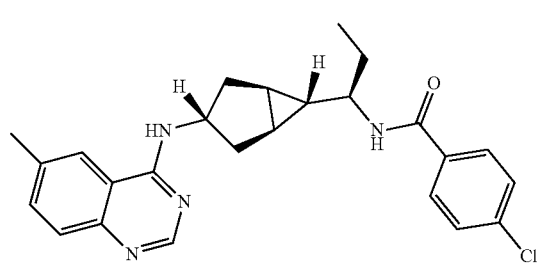 [SMILES: CC[C@@H](NC(=O)c1ccc(Cl)cc1)[C@H]1[C@@H]2C[C@@H](Nc3ncnc4ccc(C)cc34)C[C@@H]21] | 434 | 435 | SNAr |
| 339 | 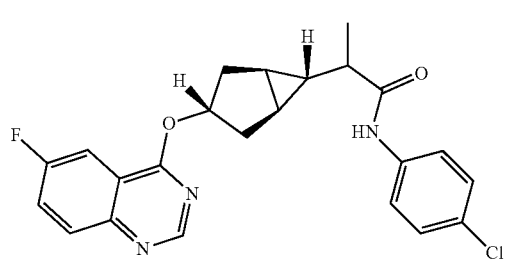 [SMILES: CC(C(=O)Nc1ccc(Cl)cc1)[C@H]1[C@@H]2C[C@@H](Oc3ncnc4ccc(F)cc34)C[C@@H]21] | 425 | 426 | Intermediate per Compound 281 followed by SNAr |
| 340 | 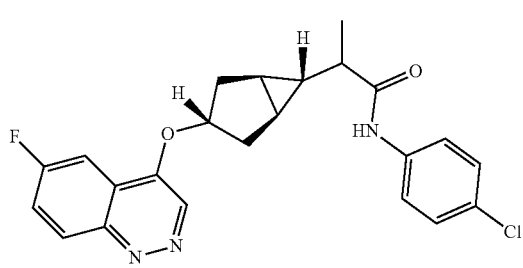 [SMILES: CC(C(=O)Nc1ccc(Cl)cc1)[C@H]1[C@@H]2C[C@@H](Oc3cnnc4ccc(F)cc34)C[C@@H]21] | 425 | 426 | Intermediate per Compound 281 followed by SNAr |
| 341 | 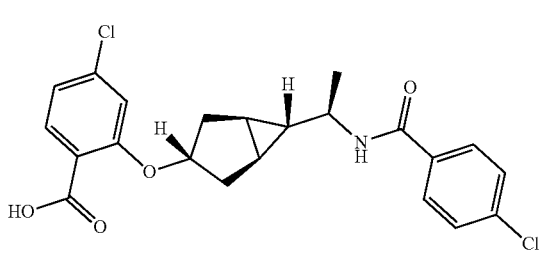 [SMILES: C[C@@H](NC(=O)c1ccc(Cl)cc1)[C@H]1[C@@H]2C[C@@H](Oc3cc(Cl)ccc3C(=O)O)C[C@@H]21] | 433 | 434 | SNAr |
| 342 | 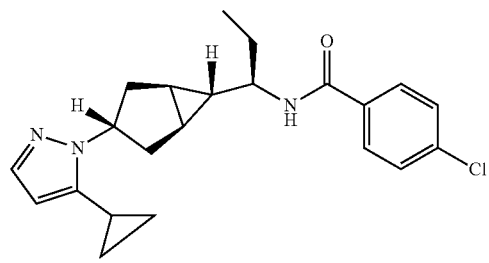 [SMILES: CC[C@@H](NC(=O)c1ccc(Cl)cc1)[C@H]1[C@@H]2C[C@@H](n3nccc3C3CC3)C[C@@H]21] | 383 | 384 | MS |

TABLE 3-continued

| Compound | Structure | Calc. Mass | Mass [M + H]+ | Synthesis as per |
|---|---|---|---|---|
| 343 | 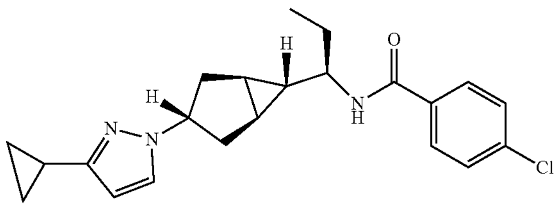 [SMILES: CC[C@@H](NC(=O)c1ccc(Cl)cc1)[C@H]1[C@@H]2C[C@@H](n3ccc(C4CC4)n3)C[C@@H]21] | 383 | 384 | MS |
| 344 | 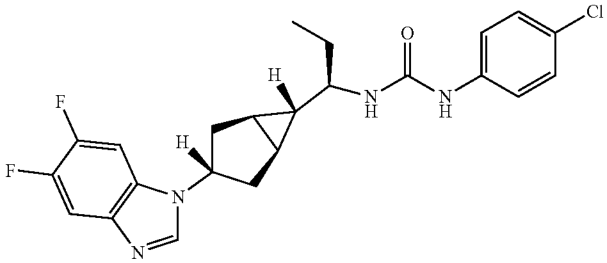 [SMILES: CC[C@@H](NC(=O)Nc1ccc(Cl)cc1)[C@H]1[C@@H]2C[C@@H](n3cnc4cc(F)c(F)cc43)C[C@@H]21] | 444 | 445 | Exemplified |
| 345 | 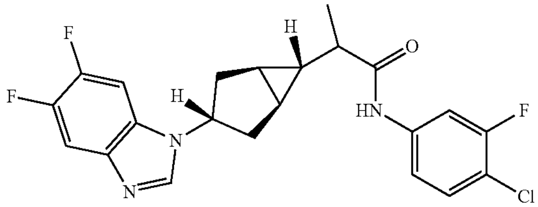 [SMILES: CC(C(=O)Nc1ccc(Cl)c(F)c1)[C@H]1[C@@H]2C[C@@H](n3cnc4cc(F)c(F)cc43)C[C@@H]21] | 433 | 434 | Compound 281 |
| 346 | 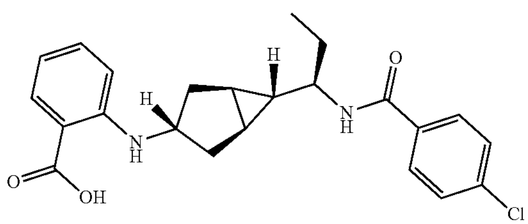 [SMILES: CC[C@@H](NC(=O)c1ccc(Cl)cc1)[C@H]1[C@@H]2C[C@@H](Nc3ccccc3C(=O)O)C[C@@H]21] | 412 | 413 | Exemplified |
| 347 | 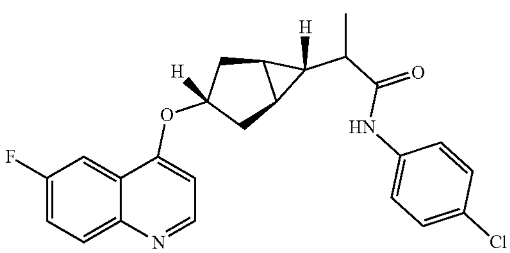 [SMILES: CC(C(=O)Nc1ccc(Cl)cc1)[C@H]1[C@@H]2C[C@@H](Oc3ccnc4ccc(F)cc34)C[C@@H]21] | 424 | 425 | Intermediate per Compound 281 followed by SNAr |
| 348 | 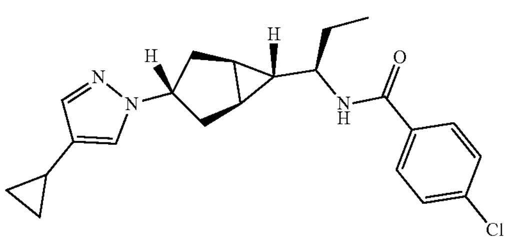 [SMILES: CC[C@@H](NC(=O)c1ccc(Cl)cc1)[C@H]1[C@@H]2C[C@@H](n3cc(C4CC4)cn3)C[C@@H]21] | 383 | 384 | MS |

TABLE 3-continued

| Compound | Structure | Calc. Mass | Mass [M + H]+ | Synthesis as per |
|---|---|---|---|---|
| 349 | 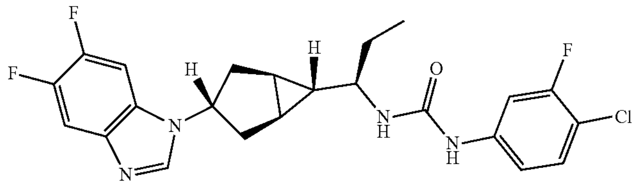 [SMILES: CC[C@@H](NC(=O)Nc1ccc(Cl)c(F)c1)[C@H]1[C@@H]2C[C@@H](n3cnc4cc(F)c(F)cc43)C[C@@H]21] | 462 | 463 | General Urea |
| 350 | 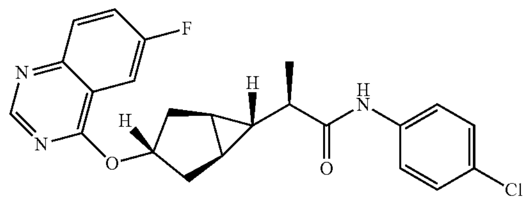 [SMILES: C[C@@H](C(=O)Nc1ccc(Cl)cc1)[C@H]1[C@@H]2C[C@@H](Oc3ncnc4ccc(F)cc34)C[C@@H]21] | 425 | 426 | Compound 339 (SFC separation) |
| 351 | 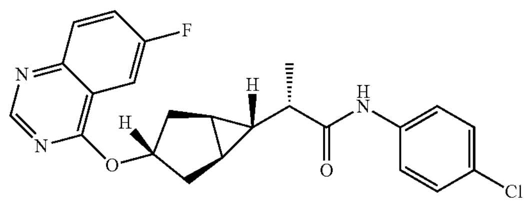 [SMILES: C[C@H](C(=O)Nc1ccc(Cl)cc1)[C@H]1[C@@H]2C[C@@H](Oc3ncnc4ccc(F)cc34)C[C@@H]21] | 425 | 426 | Compound 339 (SFC separation) |
| 352 | 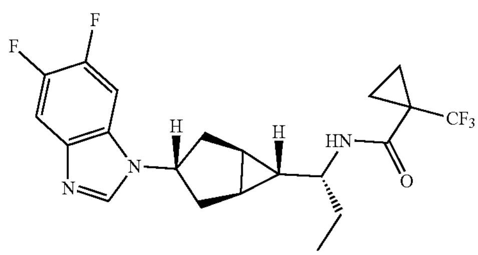 [SMILES: CC[C@@H](NC(=O)C1(C(F)(F)F)CC1)[C@H]1[C@@H]2C[C@@H](n3cnc4cc(F)c(F)cc43)C[C@@H]21] | 427 | 428 | Compound 306 |
| 353 | 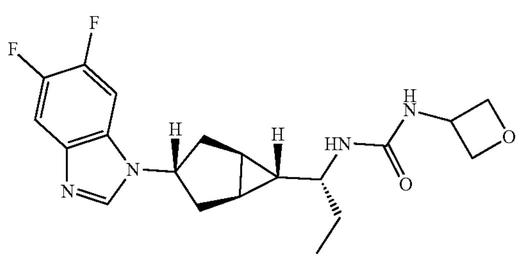 [SMILES: CC[C@@H](NC(=O)NC1COC1)[C@H]1[C@@H]2C[C@@H](n3cnc4cc(F)c(F)cc43)C[C@@H]21] | 390 | 391 | General Urea |
| 354 | 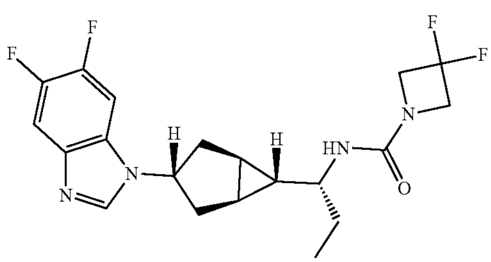 [SMILES: CC[C@@H](NC(=O)N1CC(F)(F)C1)[C@H]1[C@@H]2C[C@@H](n3cnc4cc(F)c(F)cc43)C[C@@H]21] | 410 | 411 | General Urea |

TABLE 3-continued

| Compound | Structure | Calc. Mass | Mass [M + H]+ | Synthesis as per |
|---|---|---|---|---|
| 355 | 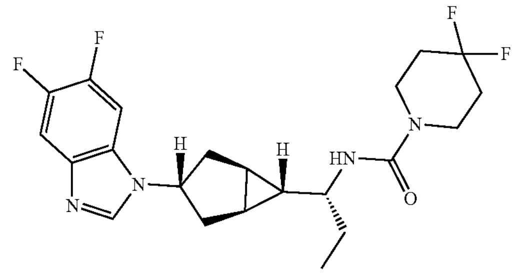 [SMILES: CC[C@@H](NC(=O)N1CCC(F)(F)CC1)[C@H]1[C@@H]2C[C@@H](n3cnc4cc(F)c(F)cc43)C[C@@H]21] | 438 | 439 | General Urea |
| 356 | 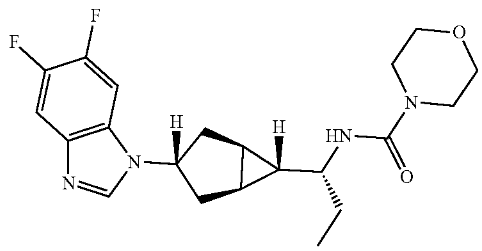 [SMILES: CC[C@@H](NC(=O)N1CCOCC1)[C@H]1[C@@H]2C[C@@H](n3cnc4cc(F)c(F)cc43)C[C@@H]21] | 404 | 405 | General Urea |
| 357 | 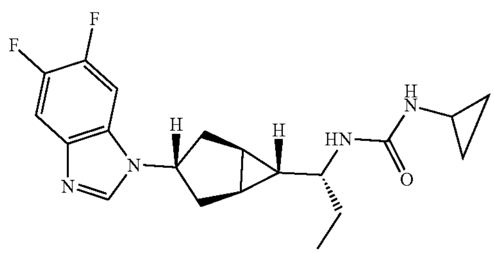 [SMILES: CC[C@@H](NC(=O)NC1CC1)[C@H]1[C@@H]2C[C@@H](n3cnc4cc(F)c(F)cc43)C[C@@H]21] | 374 | 375 | General Urea |

In more detail, the following synthetic schemes were used:

Synthesis of 4-chloro-N—((R)-1-((R, 3S, 5S, 6r)-3-(6-fluoroquinolin-4-yl)bicyclo[3.1.0]hexan-6-yl)propyl)benzamide (Compound 266)

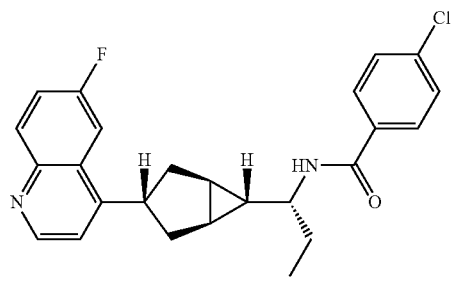 [SMILES: CC[C@@H](NC(=O)c1ccc(Cl)cc1)[C@H]1[C@@H]2C[C@@H](c3ccnc4ccc(F)cc34)C[C@@H]21]

Step 1:

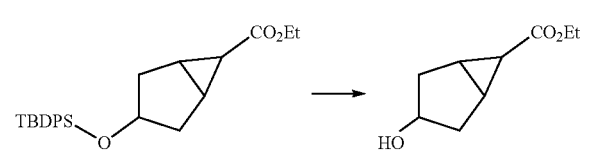

To a solution of ethyl 3-((tert-butyldiphenylsilyl)oxy)bicyclo[3.1.0]hexane-6-carboxylate (10 g, 24.47 mmol) in THF (24.47 mL) was added TBAF (122 mL, 122 mmol) and the resulting mixture was stirred at 25° C. for 18 h. The volatiles were removed under reduced pressure and the residue was purified via silica gel chromatography (0-30% EtOAc in hexanes) to give ethyl 3-hydroxybicyclo[3.1.0]hexane-6-carboxylate (3.2 g, 18.80 mmol, 77% yield) as a colorless liquid. TLC:Rf=0.25 & 0.14 [30% ethyl acetate/hexanes; KMnO$_4$].

Step 2:

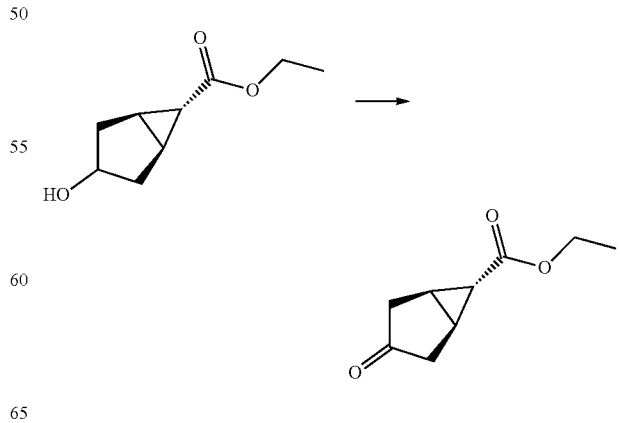

To a cooled 0° C. solution of (1R,5S,6r)-ethyl 3-hydroxybicyclo[3.1.0]hexane-6-carboxylate (187 mg, 1.099 mmol) in DCM (11 mL) was added Dess-Martin Periodinane (699 mg, 1.648 mmol). The resulting mixture was stirred at 25° C. for 2 h. Saturated NaHCO$_3$ (5 mL) and Na$_2$S$_2$O$_3$ (5 mL) were added, and the layers were separated. The aqueous phase was extracted with DCM (3×8 mL), the combined organic layers were washed with sat'd NaCl, dried over Na$_2$SO$_4$, filtered and concentrated under reduced pressure. The residue was purified via silica gel chromatography (0-40% EtOAc in hexanes) to give (1R,5S,6r)-ethyl 3-oxobicyclo[3.1.0]hexane-6-carboxylate (128 mg, 0.761 mmol, 69.3% yield) as a colorless liquid. TLC:Rf=0.65 [50% ethyl acetate/hexanes; KMnO$_4$].

Step 3:

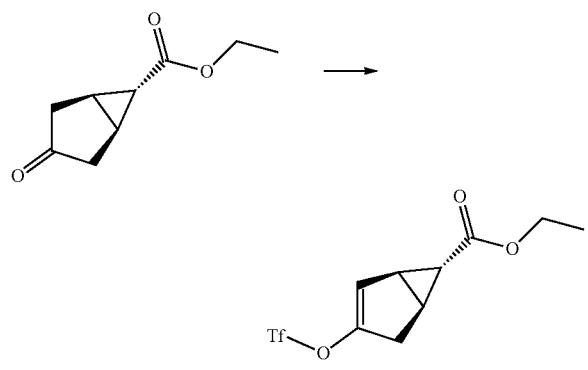

To a solution of (1R,5S,6r)-ethyl 3-oxobicyclo[3.1.0] hexane-6-carboxylate (961 mg, 5.71 mmol) in Toluene (19 mL) was added Hunig's Base (3992 µL, 22.86 mmol) and the resulting mixture was stirred at 45° C. Triflic anhydride (3861 µL, 22.86 mmol) was added, and the temperature rose to 70° C. The reaction was cooled to 45° C. using an ice bath where it remained for an additional 1.5 h. The reaction mixture was diluted with EtOAc (10 mL), sat'd NaHCO$_3$ (10 mL) was added, and the layers were separated. The aqueous phase was extracted with EtOAc (3×5 mL), the combined organic layers were washed with sat'd NaHCO$_3$, water, sat'd NaCl dried over Na$_2$SO$_4$, filtered and concentrated under reduced pressure. The residue was purified via silica gel chromatography (0-10% EtOAc in hexanes) to give (1S,5S,6R)-ethyl 3-(((trifluoromethyl)sulfonyl)oxy)bicyclo[3.1.0]hex-2-ene-6-carboxylate (577 mg, 1.922 mmol, 33.6% yield) as a dark liquid.

Step 4:

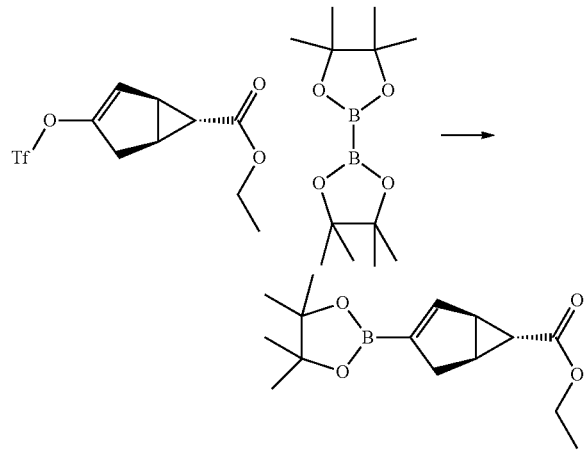

A solution of (1S,5S,6R)-ethyl 3-(((trifluoromethyl)sulfonyl)oxy)bicyclo[3.1.0]hex-2-ene-6-carboxylate (577 mg, 1.92 mmol), 4,4,4',4',5,5,5',5'-octamethyl-2,2'-bi(1,3,2-dioxaborolane) (581 mg, 2.287 mmol) and potassium acetate (566 mg, 5.77 mmol) in Dioxane (6406 µL) was degassed in the sonicator for 2 min. and then purged with N$_2$ for 2 minutes. PdCl$_2$(dppf) (141 mg, 0.192 mmol) was added and the mixture was degassed with N$_2$ for an additional 1 minute. The reaction mixture was heated to 105° C. and stirred for 18 h. The reaction mixture was allowed to cool to room temperature. H$_2$O (50 mL) was added, and the layers were separated. The aqueous phase was extracted with EtOAc (3×50 mL), the combined organic layers were washed with sat'd NaCl, dried over Na$_2$SO$_4$, filtered and concentrated under reduced pressure. The residue was purified via silica gel chromatography (0-20% EtOAc in hexanes) to give (1S,5S,6R)-ethyl 3-(4,4,5,5-tetramethyl-1,3,2-dioxaborolan-2-yl)bicyclo[3.1.0]hex-2-ene-6-carboxylate (343 mg, 1.233 mmol, 64.2% yield) as a yellow liquid. MS (ES$^+$) C$_{15}$H$_{23}$BO$_4$ requires: 278, found: 279 [M+H]$^+$.

Step 5:

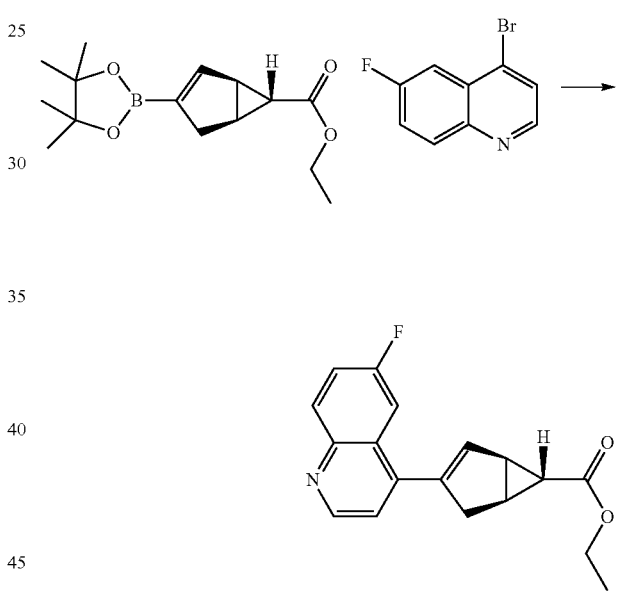

A solution of (1S,5S,6R)-ethyl 3-(4,4,5,5-tetramethyl-1,3,2-dioxaborolan-2-yl)bicyclo[3.1.0]hex-2-ene-6-carboxylate (343 mg, 1.233 mmol), 4-bromo-6-fluoroquinoline (307 mg, 1.356 mmol) and K$_2$CO$_3$ (528 mg, 3.82 mmol) in Dioxane (5605 µL)/Water (561 µL) was degassed with N$_2$ for 2 minutes, PdCl$_2$(dppf)-CH$_2$Cl$_2$ Adduct (201 mg, 0.247 mmol) was added, and the mixture was degassed with N2 for an additional 2 minutes. The reaction mixture was heated to 105° C. and stirred for 6 h. The reaction mixture was allowed to cool to room temperature and filtered through Celite, and the filtrate was concentrated under reduced pressure. The residue was purified via silica gel chromatography (0-70% EtOAc in hexanes) to give (1S,5S,6R)-ethyl 3-(6-fluoroquinolin-4-yl)bicyclo[3.1.0]hex-2-ene-6-carboxylate (138 mg, 0.464 mmol, 37.6% yield) as a colorless liquid. MS (ES$^+$) C$_{18}$H$_{16}$FNO$_2$ requires: 297, found: 298 [M+H]$^+$.

Step 6:

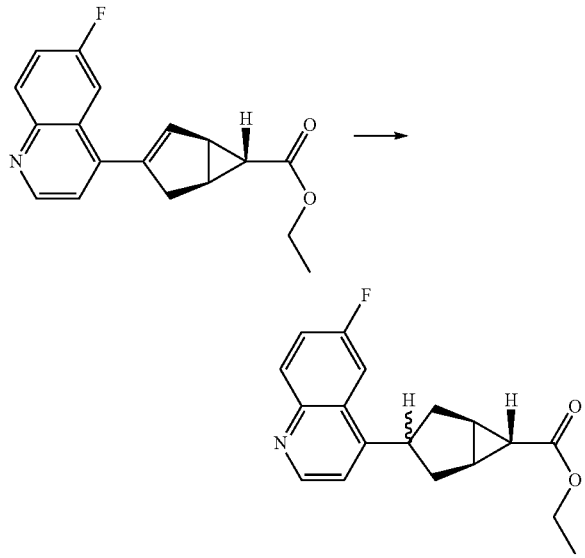

A reaction vessel was charged with (1S,5S,6R)-ethyl 3-(6-fluoroquinolin-4-yl)bicyclo[3.1.0]hex-2-ene-6-carboxylate (138 mg, 0.464 mmol), Pd—C (10%, 49.4 mg, 0.046 mmol) and Ethanol (4641 µL) under an atmosphere of $N_2$. The suspension was degassed with $N_2$ for 2 minutes and purged with $H_2$ for 1 minute. The reaction mixture was stirred under an atmosphere of $H_2$ at 1 atm for 4 h. The reaction mixture was purged with $N_2$, filtered through Celite, and concentrated under reduced pressure to give ethyl (1R,5S,6r)-3-(6-fluoroquinolin-4-yl)bicyclo[3.1.0]hexane-6-carboxylate (117 mg, 0.391 mmol, 84% yield) as a pale yellow liquid. MS (ES) $C_{18}H_{18}FNO_2$ requires: 299, found: 300 [M+H]$^+$.

Step 7:

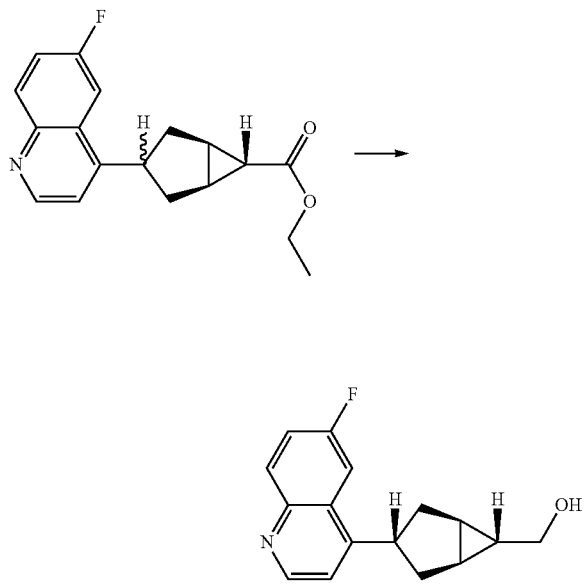

To a cooled −70° C. solution of (1R,3s,5S,6r)-ethyl 3-(6-fluoroquinolin-4-yl) bicyclo[3.1.0]hexane-6-carboxylate (117 mg, 0.391 mmol) and (1R,3r,5S,6r)-ethyl 3-(6-fluoroquinolin-4-yl)bicyclo[3.1.0]hexane-6-carboxylate (117 mg, 0.391 mmol) in Toluene (3909 µL) was added DIBAL-H (1M, Toluene, 821 µL, 0.821 mmol). The resulting mixture was stirred at −70° C. for 1 h. Solid $Na_2SO_4$*$10H_2O$ was added at −70° C. and the reaction mixture was allowed to warm to RT. $H_2O$ (5 mL) was added, and the layers were separated. The aqueous phase was extracted with EtOAc (3×10 mL), the combined organic layers were washed with sat'd NaCl, dried over $Na_2SO_4$, filtered, and concentrated under reduced pressure. The residue was purified via silica gel chromatography (0-5% MeOH in DCM with 1% TEA) to give ((1R,3s,5S,6r)-3-(6-fluoroquinolin-4-yl)bicyclo[3.1.0]hexan-6-yl)methanol (25 mg, 0.097 mmol, 24.86% yield) and ((1R,3r,5S,6r)-3-(6-fluoroquinolin-4-yl)bicyclo[3.1.0]hexan-6-yl)methanol (48 mg, 0.187 mmol, 47.7% yield) as a colorless liquid. MS (ES$^+$) $C_{16}H_{16}FNO$ requires: 257, found: 258 [M+H]$^+$.

Step 8:

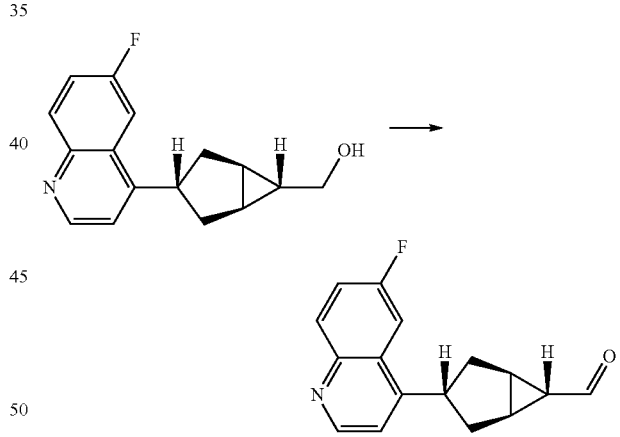

To a solution of ((1R,3s,5S,6r)-3-(6-fluoroquinolin-4-yl) bicyclo[3.1.0]hexan-6-yl)methanol (28 mg, 0.109 mmol) in DCM (1088 µL) was added Dess-Martin Periodinane (50.8 mg, 0.120 mmol) and the resulting mixture was stirred at 25° C. for 2 h. Sat'd $NaHCO_3$ (1 mL) was added, and the layers were separated. The aqueous phase was extracted with DCM (3×5 mL), the combined organic layers were washed with sat'd NaCl, dried over $Na_2SO_4$, filtered and concentrated under reduced pressure. The residue was purified via silica gel chromatography (0-5% MeOH in DCM with 1% TEA) to give (1R,3s,5S,6r)-3-(6-fluoroquinolin-4-yl)bicyclo [3.1.0]hexane-6-carbaldehyde (21 mg, 0.082 mmol, 76% yield) as a yellow liquid. MS (ES$^+$) $C_{16}H_{14}FNO$ requires: 255, found: 256 [M+H]$^+$.

Step 9:

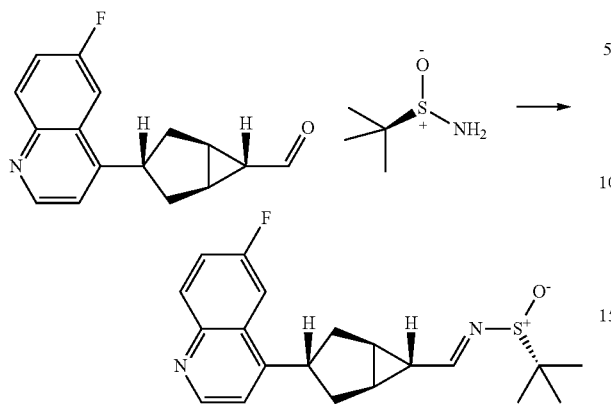

To a solution of (1R,3s,5S,6r)-3-(6-fluoroquinolin-4-yl)bicyclo[3.1.0]hexane-6-carbaldehyde (21 mg, 0.082 mmol) in DCM (823 μL) were added (S)-2-methylpropane-2-sulfinamide (19.9 mg, 0.165 mmol) and copper(II) sulfate (19.7 mg, 0.123 mmol) and the resulting mixture was stirred at 25° C. for 48 h. The reaction mixture was filtered through Celite and the filtrate was concentrated under reduced pressure. The residue was purified via silica gel chromatography (0-5% MeOH in DCM) to give (S,E)-N-(((1R,3R,5S,6r)-3-(6-fluoroquinolin-4-yl)bicyclo[3.1.0]hexan-6-yl)methylene)-2-methylpropane-2-sulfinamide (20 mg, 0.056 mmol, 67.8% yield) as a pale yellow liquid. MS (ES+) $C_{20}H_{23}FN_2OS$ requires: 358, found: 359 [M+H]+.

Step 10:

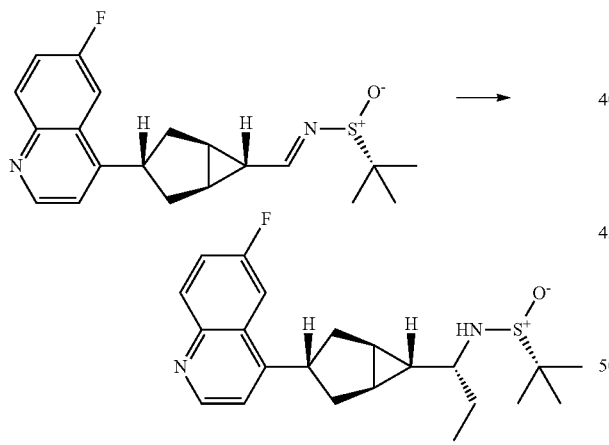

To a cooled 0° C. solution of (S,E)-N-(((1R,3R,5S,6r)-3-(6-fluoroquinolin-4-yl) bicyclo[3.1.0]hexan-6-yl)methylene)-2-methylpropane-2-sulfinamide (20 mg, 0.056 mmol) in THF (279 μL) was added ethylmagnesium bromide (19.5 μL, 0.059 mmol). The resulting mixture was stirred at 25° C. for 12 h. The reaction was cooled to 0° C. and sat'd NH4Cl (0.5 mL) was added, and the layers were separated. The aqueous phase was extracted with EtOAc (3×3 mL), the combined organic layers were washed with sat'd NaCl, dried over Na2SO4, filtered, and concentrated under reduced pressure. The residue was purified via silica gel chromatography (0-5% MeOH in DCM with 1% TEA) to give (S)—N—((R)-1-((1R,3 S,5 S,6r)-3-(6-fluoroquinolin-4-yl)bicyclo[3.1.0]hexan-6-yl)propyl)-2-methylpropane-2-sulfinamide (6 mg, 0.015 mmol, 27.7% yield) as a colorless liquid. MS (ES+)$C_{22}H_{29}FN_2OS$ requires: 388, found: 389 [M+H]+.

Step 11:

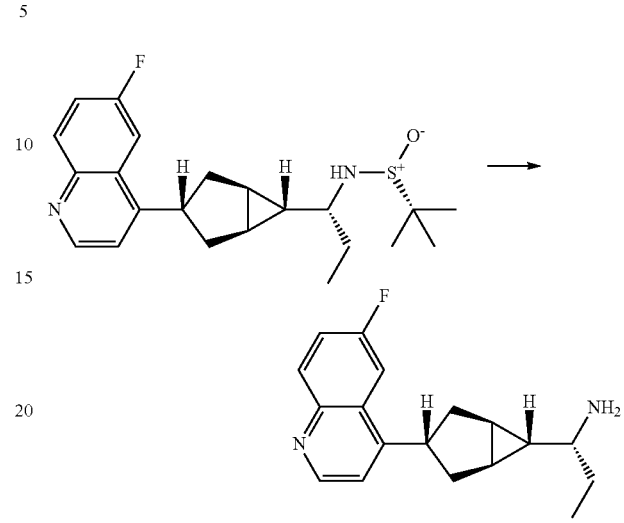

To a solution of (S)—N—((R)-1-((1R,3S,5S,6r)-3-(6-fluoroquinolin-4-yl)bicyclo[3.1.0]hexan-6-yl)propyl)-2-methylpropane-2-sulfinamide (6 mg, 0.015 mmol) in Methanol (154 μL) was added HCl (in Dioxane) (19.3 μL, 0.077 mmol) and the resulting mixture was stirred at 25° C. for 3 h, at which time Hunig's Base (13.5 μL, 0.077 mmol) was added slowly. The reaction mixture was diluted with EtOAc (2 mL) and washed with H2O (3 mL). The layers were separated, and the organic layer was washed with sat'd NaCl (3 mL), dried over Na2SO4, filtered and concentrated under reduced pressure to give (R)-1-((1R,3S,5S,6r)-3-(6-fluoroquinolin-4-yl)bicyclo[3.1.0]hexan-6-yl)propan-1-amine. Product was used without further purification. MS (ES+) $C_{18}H_{21}FN_2$ requires: 284, found: 285 [M+H]+.

Step 12:

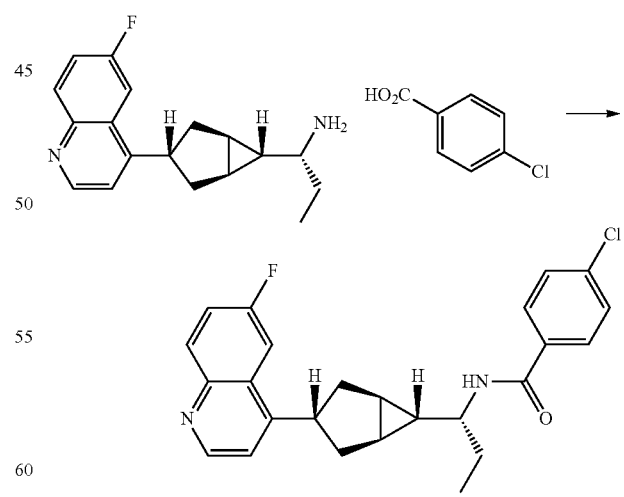

To a solution of the intermediate product from step 11 in DCM (155 μL) was added 4-chlorobenzoic acid (2.7 mg, 0.017 mmol), DIEA (8.11 μL, 0.046 mmol), and HOBT (3.1 mg, 0.020 mmol) and the resulting mixture was stirred at 25° C. for 10 min. EDC (3.26 mg, 0.017 mmol) was then added and the resulting solution was allowed to stir at 25° C. for 18 h. The volatiles were removed under reduced pressure and the residue was purified via silica gel chromatography (0-5% MeOH in DCM) to give 4-chloro-N—((R)-1-((1R, 3S,5S,6r)-3-(6-fluoroquinolin-4-yl)bicyclo[3.1.0]hexan-6-yl)propyl)benzamide (3.9 mg, 9.22 μmol, 59.6% yield) as a colorless liquid. MS (ES+) $C_{25}H_{24}ClFN_2O$ requires: 422, found: 423 [M+H]+. $^1$H NMR (600 MHz, Chloroform-d) δ 8.79 (d, J=4.6 Hz, 1H), 8.11 (dd, J=9.2, 5.7 Hz, 1H), 7.80-7.72 (m, 2H), 7.63 (dd, J=10.5, 2.8 Hz, 1H), 7.52-7.40 (m, 3H), 7.32 (d, J=4.6 Hz, 1H), 6.04 (d, J=8.6 Hz, 1H), 3.52 (dt, J=18.4, 9.1 Hz, 1H), 3.34 (ddd, J=18.4, 11.1, 7.2 Hz, 1H), 2.28 (ddd, J=28.9, 12.8, 7.3 Hz, 2H), 2.03 (dtd, J=46.0, 12.0, 4.8 Hz, 2H), 1.77 (ddt, J=44.7, 14.2, 7.0 Hz, 2H), 1.54 (q, J=6.8, 5.0 Hz, 1H), 1.25 (s, 1H), 1.06 (t, J=7.5 Hz, 4H).

Synthesis of N-(4-chlorophenyl)-2-((1R,3s, 5S, 6r)-3-(5,6-difluoro-1H-benzo[d]imidazol-1-yl)bicyclo[3.1.0]hexan-6-yl)propanamide (Compound 281)

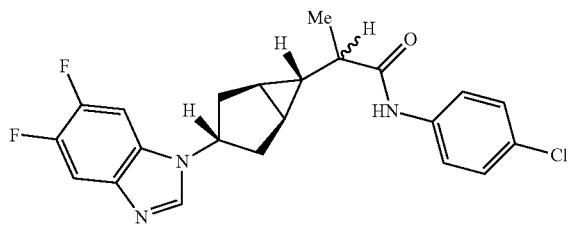 [SMILES: CC(C(=O)Nc1ccc(Cl)cc1)[C@H]1[C@@H]2C[C@@H](n3cnc4cc(F)c(F)cc43)C[C@@H]21]

Step 1:

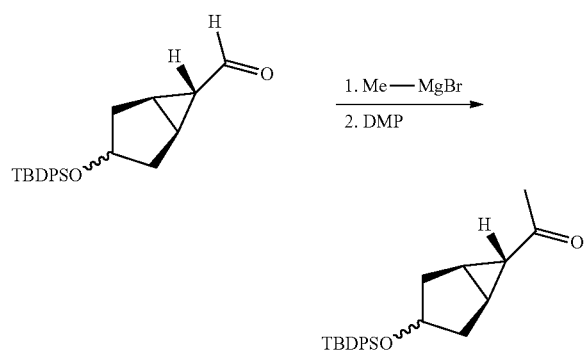

Step A:

To a cooled 0° C. solution of (1R,3r,5S,6r)-3-((tert-butyldiphenylsilyl)oxy) bicyclo[3.1.0]hexane-6-carbaldehyde (100 g, 274 mmol) in THF (300 mL) was added methylmagnesium bromide (110 mL, 3M in diethyl ether, 329 mmol). The resulting mixture was stirred at 0° C. for 3 h. Saturated NH$_4$Cl (200 mL) was added slowly at 0° C., and the layers were separated. The aqueous phase was extracted with EtOAc (3×500 mL), the combined organic layers were washed with sat'd NaCl, dried over Na$_2$SO$_4$, filtered, and concentrated under reduced pressure. The product, a yellow oil, was used without further purification. MS (ES+) $C_{24}H_{32}O_2Si$ requires: 380, found: 363 [M-OH]+.

Step B:

To a cooled 0° C. solution of 1-((1R,3r,5S,6r)-3-((tert-butyldiphenylsilyl)oxy) bicyclo[3.1.0]hexan-6-yl)ethanol (104 g, 273 mmol) in DCM (364 mL) was added DMP (139 g, 328 mmol) portionwise. The resulting mixture was stirred at 25° C. for 3 h. The reaction mixture was cooled to 0° C., sat'd NaHCO$_3$ (200 mL) was added slowly, an equal volume of Na$_2$S$_2$O$_3$ was also added, the mixture was allowed to stir for 30 min., and the layers were separated. The aqueous phase was extracted with DCM (3×300 mL), the combined organic layers were washed with sat'd NaCl, dried over Na$_2$SO$_4$, filtered and concentrated under reduced pressure. The residue was purified via silica gel plug eluting with DCM to give 1-((1R,3r,5S,6r)-3-((tert-butyldiphenylsilyl)oxy)bicyclo[3.1.0]hexan-6-yl)ethanone (83 g, 80%) as a pale orange liquid. MS (ES+) $C_{24}H_{30}O_2Si$ requires: 378, found: 379 [M+H]+.

Step 2:

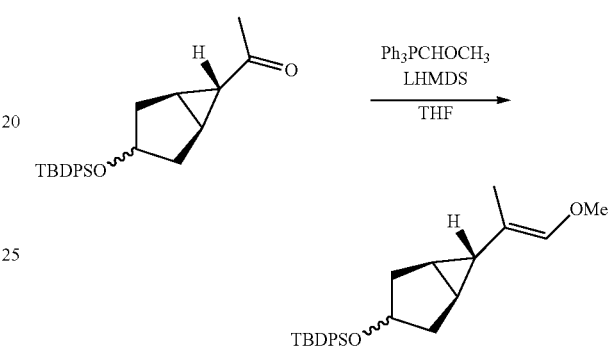

To a −13° C. solution of (methoxymethyl)triphenylphosphonium chloride (5.23 g, 15.25 mmol) in THF (21.79 mL) was added LHMDS (14.82 mL, 14.82 mmol) and the resulting mixture was stirred at 25° C. for 1 h. A solution of 1-((1R,3r,5S,6r)-3-((tert-butyldiphenylsilyl)oxy)bicyclo[3.1.0]hexan-6-yl)ethanone (3.3 g, 8.72 mmol) in THF (7.26 mL) was added dropwise over 30 min. and the reaction was stirred at 25° C. for 12 h. 1M HCl (5 mL) was added, and the layers were separated. The aqueous phase was extracted with EtOAc (3×20 mL), the combined organic layers were washed with sat'd NaCl, dried over Na$_2$SO$_4$, filtered and concentrated under reduced pressure. The residue was purified via silica gel chromatography (5-20% EtOAc in hexanes to give tert-butyl(((1R,3r,5S,6r)-6-((E)-1-methoxyprop-1-en-2-yl)bicyclo[3.1.0]hexan-3-yl)oxy)diphenylsilane (1.96 g, 4.82 mmol, 55.3% yield) as a colorless liquid. MS (ES+) $C_{26}H_{34}O_2Si$ requires: 406, found: 407 [M+H]+.

Step 3:

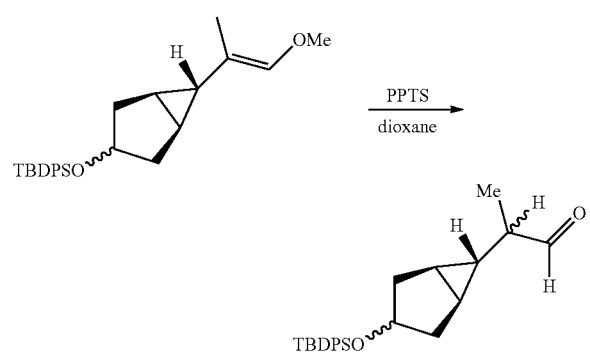

To a solution of tert-butyl(((1R,3r,5 S,6r)-6-((E)-1-methoxyprop-1-en-2-yl)bicyclo[3.1.0]hexan-3-yl)oxy)diphenylsilane (7.5 g, 18.44 mmol) in Dioxane (52.7 mL)

were added PPTS (5.10 g, 20.29 mmol) and Water (8.78 mL) and the resulting mixture was stirred at 70° C. for 12 h. The volatiles were removed under reduced pressure. The reaction mixture was diluted with EtOAc (30 mL) and washed with H₂O (2×50 mL). The layers were separated, and the organic layer was washed with sat'd NaCl (2×50 mL), dried over Na₂SO₄, filtered and concentrated under reduced pressure to give 2-((1R,3r,5S,6r)-3-((tert-butyldiphenylsilyl)oxy)bicyclo[3.1.0]hexan-6-yl)propanal as a pale yellow oil. The product was used without further purification.

Step 4:

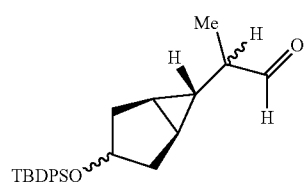

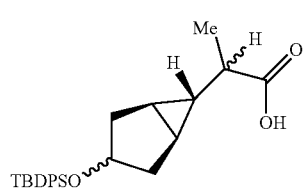

To a cooled 0° C. solution of 2-((1R,3r,5S,6r)-3-((tert-butyldiphenylsilyl)oxy) bicyclo[3.1.0]hexan-6-yl)propanal (7.24 g, 18.44 mmol) in t-Butanol (138 mL)/2-methyl-2-butene (39.1 mL, 369 mmol) was added dropwise a freshly prepared solution of sodium chlorite (3.34 g, 36.9 mmol) and potassium dihydrogenphosphate (5.02 g, 36.9 mmol) in water (46.1 mL). The resulting mixture was stirred at 0° C. for 2 h, then allowed to warm to 25° C. vigorously stirring for 12 h. Sat'd NaCl (150 mL) was added, and the layers were separated. The aqueous phase was extracted with DCM (3×75 mL), the combined organic layers were dried over Na₂SO₄, filtered and concentrated under reduced pressure. The residue was purified via silica gel chromatography (0-5% MeOH in DCM) to give 2-((1R,3r,5S,6r)-3-((tert-butyldiphenylsilyl)oxy)bicyclo[3.1.0]hexan-6-yl)propanoic acid (6.7 g, 16.40 mmol, 89% yield) as a colorless liquid.

Step 5:

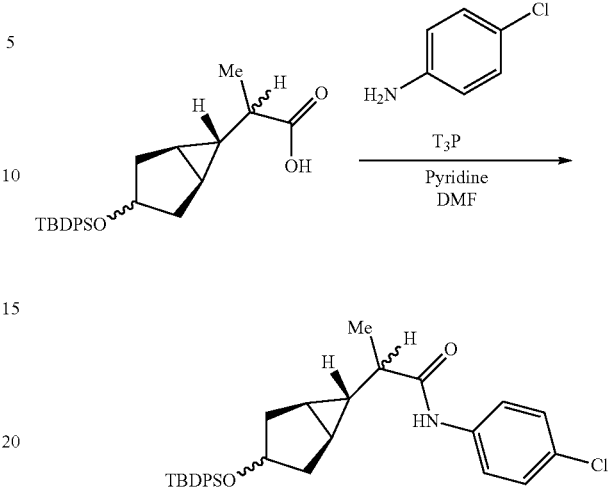

To a solution of 2-((1R,5S,6r)-3-((tert-butyldiphenylsilyl)oxy)bicyclo[3.1.0]hexan-6-yl)propanoic acid (800 mg, 1.95 mmol) and pyridine (0.47 mL, 5.87 mmol) in EtOAc (20 mL) was added 2,4,6-tripropyl-1,3,5,2,4,6-trioxatriphosphinane 2,4,6-trioxide (2.91 mL, 2.9 mmol) and the resulting mixture was stirred at RT for 0.5 h. To this mixture 4-chloroaniline (275 mg, 2.15 mmol) was added and the mixture was stirred at rt for 12 h. The mixture was quenched with 10% Na₂CO₃ (30 mL) and extracted with ethyl acetate (2×50 mL). Combined organics were washed with brine (2×30 mL), dried over MgSO₄, filtered, and concentrated to give the crude product. The residue was purified via silica gel chromatography (2-20% ethylacetate in hexanes) to give 2-((1R,5 S,6r)-3-((tert-butyldiphenylsilyl)oxy) bicyclo[3.1.0]hexan-6-yl)-N-(4-chlorophenyl)propanamide (735 mg, 1.418 mmol, 72.4% yield) as a white solid. MS (ES⁺) $C_{31}H_{36}ClNO_2Si$ requires: 518, found: 519 [M+H]⁺.

Step 6:

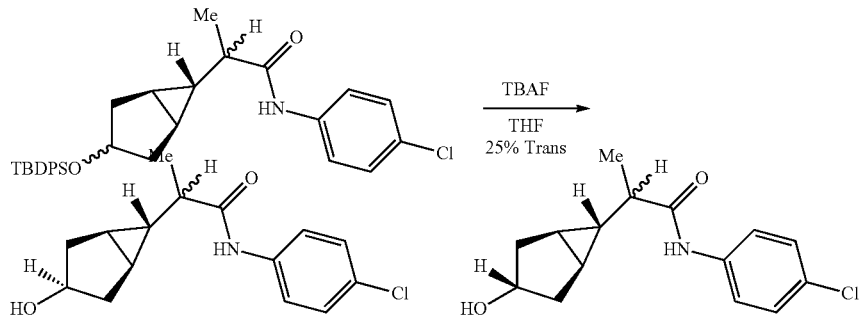

To a solution of 2-((1R,5S,6r)-3-((tert-butyldiphenylsilyl)oxy)bicyclo[3.1.0]hexan-6-yl)-N-(4-chlorophenyl)propanamide (1.6 g, 3.1 mmol) in THF (2 mL) was added a solution of TBAF in THF (1M, 10.00 mL, 10.00 mmol) and the resulting mixture was stirred at 50° C. for 24 h. The reaction mixture was diluted with ethyl acetate (50 mL), 5% HCl (15 mL) was added, and the layers were separated. The aqueous phase was extracted with ethyl acetate (3×10 mL), the combined organic layers were washed with water (20 mL) followed by brine (20 mL), dried over MgSO₄, filtered and concentrated under reduced pressure. The residue was purified via silica gel chromatography (10-80% ethylacetate in hexane) to give N-(4-chlorophenyl)-2-((1R,3r,5S,6r)-3-hydroxybicyclo[3.1.0]hexan-6-yl)propanamide (220 mg, 0.786 mmol, 25.5% yield) as a clear oil. MS (ES$^+$) $C_{15}H_{18}ClNO_2$ requires: 279, found: 280 [M+H]$^+$.

Step 7:

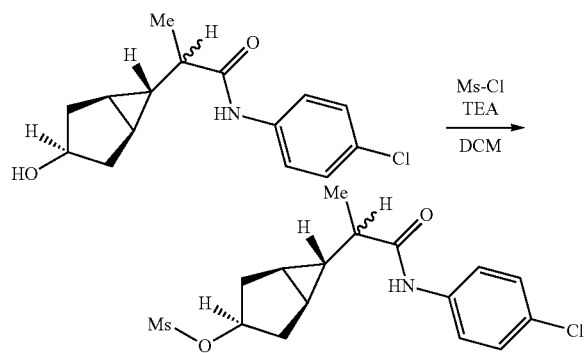

To a solution of N-(4-chlorophenyl)-2-((1R,3r,5S,6r)-3-hydroxybicyclo[3.1.0]hexan-6-yl)propanamide (215 mg, 0.77 mmol) in DCM (5 mL) were added methanesulfonyl chloride (0.12 mL, 1.54 mmol) and TEA (0.32 mL, 2.3 mmol) and the resulting mixture was stirred at 0° C. for 2 h. The reaction mixture was diluted with DCM (20 mL), water (10 mL) was added, and the layers were separated. The aqueous phase was extracted with DCM (3×10 mL), the combined organic layers were washed with 5% HCl (2×10 mL), followed by brine (1×10 mL), dried over MgSO$_4$, filtered and concentrated under reduced pressure. The residue was purified via silica gel chromatography (20-80% ethylacetate in hexane) to give (1R,3r,5S,6r)-6-(1-((4-chlorophenyl)amino)-1-oxopropan-2-yl)bicyclo[3.1.0]hexan-3-yl methanesulfonate (242 mg, 0.676 mmol, 88% yield) as a clear oil. MS (ES$^+$) $C_{16}H_{20}ClNO_4S$ requires: 357, found: 358 [M+H]$^+$.

Step 8:

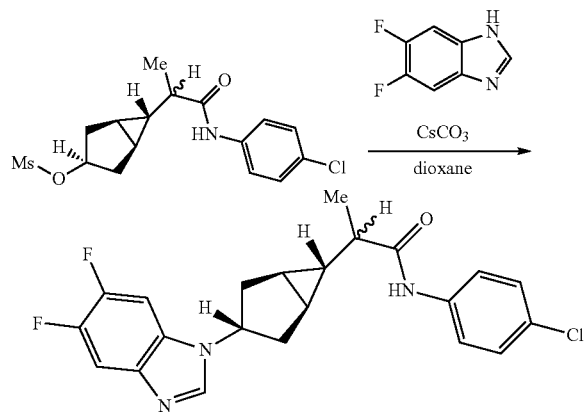

To a solution of (1R,3r,5S,6r)-6-(1-((4-chlorophenyl)amino)-1-oxopropan-2-yl)bicyclo[3.1.0]hexan-3-yl methanesulfonate in 1,4-dioxan (5 mL) were added cesium carbonate and 5,6-difluoro-1H-benzo[d]imidazole and the resulting mixture was stirred at 65° C. for 12 h. The reaction mixture was diluted with ethyl acetate (15 mL), water (10 mL) was added, and the layers were separated. The aqueous phase was extracted with ethyl acetate (3×10 mL), the combined organic layers were washed with brine, dried over MgSO$_4$, filtered and concentrated under reduced pressure. The residue was purified via silica gel chromatography (5-15% 2-propanol in DCM) to give N-(4-chlorophenyl)-2-((1R,3s,5S,6r)-3-(5,6-difluoro-1H-benzo[d]imidazol-1-yl)bicyclo[3.1.0]hexan-6-yl)propanamide (155 mg, 0.373 mmol, 58.0% yield) as a light yellow oil. This was then triturated with ether-hexane (10 mL) to give 70 mg of white solid of the desired material. NMR data and LC-MS confirmed the identity of the compound. The rest of the mother liquor was then concentrated, and the residue was purified by reverse phase preparative HPLC (Mobile phase: A=0.1% NH$_4$OH/H$_2$O, B=0.1% NH$_4$OH/MeCN; Gradient: B=10-100%; 12 min;) to give N-(4-chlorophenyl)-2-((1R,3s,5S,6r)-3-(5,6-difluoro-1H-benzo[d]imidazol-1-yl)bicyclo[3.1.0]hexan-6-yl)propanamide (25 mg) as a white solid. MS (ES) $C_{22}H_{20}ClF_2N_3O$ requires: 415, found: 416 [M+H]$^+$. $^1$H NMR (600 MHz, DMSO-d$_6$) δ 9.90 (s, 1H), 8.43 (s, 1H), 7.89 (dd, J=11.0, 7.3 Hz, 1H), 7.73-7.60 (m, 3H), 7.42-7.31 (m, 2H), 4.73-4.59 (m, 1H), 2.33 (dd, J=12.4, 7.6 Hz, 1H), 2.27-2.12 (m, 3H), 1.86-1.77 (m, 1H), 1.57-1.50 (m, 1H), 1.33 (q, J=6.7, 5.0 Hz, 1H), 1.21-1.19 (m, 4H).

Synthesis of Diethyl 2-((1R,3S,5S, 6r)-6-((R)-1-(4-chlorobenzamido)propyl)bicyclo[3.1.0]hexan-3-yl)malonate (Compound 290)

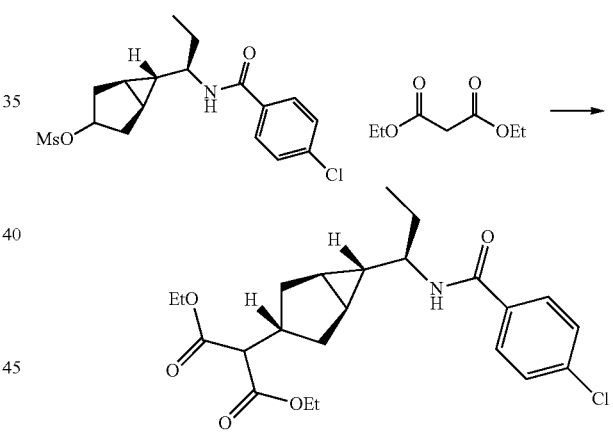

To a cooled 0° C. suspension of NaH (64.5 mg, 1.613 mmol) in THF (6.723 mL) was added diethyl malonate (237 mg, 1.479 mmol). The resulting mixture was stirred at 25° C. for 1 h.

To the reaction solution was added a solution of (1R,5S,6r)-6-((R)-1-(4-chlorobenzamido)propyl)bicyclo[3.1.0]hexan-3-yl methanesulfonate (500 mg, 1.345 mmol) in THF (1 mL) and the resulting solution was heated to 66° C. for 28 h. Saturated NH$_4$Cl (5 mL) was added, and the layers were separated. The aqueous phase was extracted with EtOAc (3×5 mL), the combined organic layers were washed with sat'd NaCl, dried over Na$_2$SO$_4$, filtered, and concentrated under reduced pressure. The residue was purified via silica gel chromatography (0-30% EtOAc in hexanes) to give diethyl 2-((1R,3S,5S,6r)-6-((R)-1-(4-chlorobenzamido)propyl)bicyclo[3.1.0]hexan-3-yl)malonate (258 mg, 0.592 mmol, 44.0% yield) as a white solid. MS (ES) $C_{23}H_{30}ClNO_5$ requires: 435, found: 436 [M+H]$^+$.

Synthesis of 4-chloro-N—((R)-1-((1R, 3S, 5S, 6r)-3-(1,3-dihydroxypropan-2-yl)bicyclo[3.1.0]hexan-6-yl)propyl)benzamide (Compound 291)

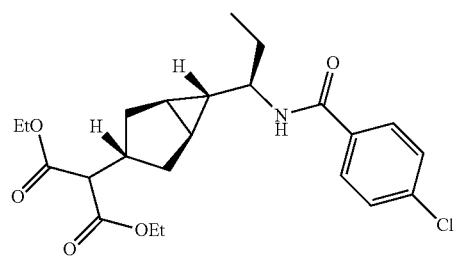

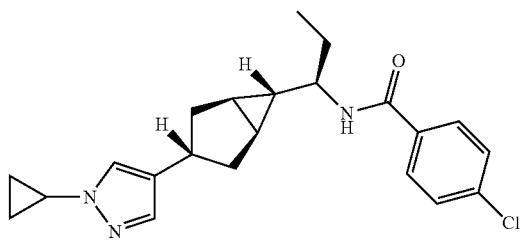 [SMILES: CC[C@@H](NC(=O)c1ccc(Cl)cc1)[C@H]1[C@@H]2C[C@@H](c3cnn(C4CC4)c3)C[C@@H]21]

To a cooled 0° C. suspension of LAH (74.1 mg, 1.953 mmol) in THF (2219 µL) was added Compound 290, diethyl 2-((1R,3S,5S,6r)-6-((R)-1-(4-chlorobenzamido)propyl)bicyclo[3.1.0]hexan-3-yl)malonate, (258 mg, 0.592 mmol) in THF (740 µL) over 10 min. The resulting mixture was stirred at 25° C. for 2 h. The reaction was diluted sequentially with water (260 uL), 10% aqueous sodium hydroxide solution (260 uL), and water (780 uL), then allowed to stir at 0° C. for 20 min. The reaction mixture was filtered through Celite, and the filtrate was concentrated under reduced pressure. The residue was purified via silica gel chromatography (0-10% MeOH in DCM) to give 4-chloro-N—((R)-1-((1R,3S,5S,6r)-3-(1,3-dihydroxypropan-2-yl)bicyclo[3.1.0]hexan-6-yl)propyl)benzamide (96 mg, 0.273 mmol, 46.1% yield) as a white solid. MS (ES+) $C_{19}H_{26}ClNO_3$ requires: 351, found: 352 [M+H]+.

Synthesis of 4-chloro-N—((R)-1-((1R,3S,5S, 6r)-3-(1-cyclopropyl-1H-pyrazol-4-yl)bicyclo[3.1.0]hexan-6-yl)propyl)benzamide (Compound 292)

Step 1:

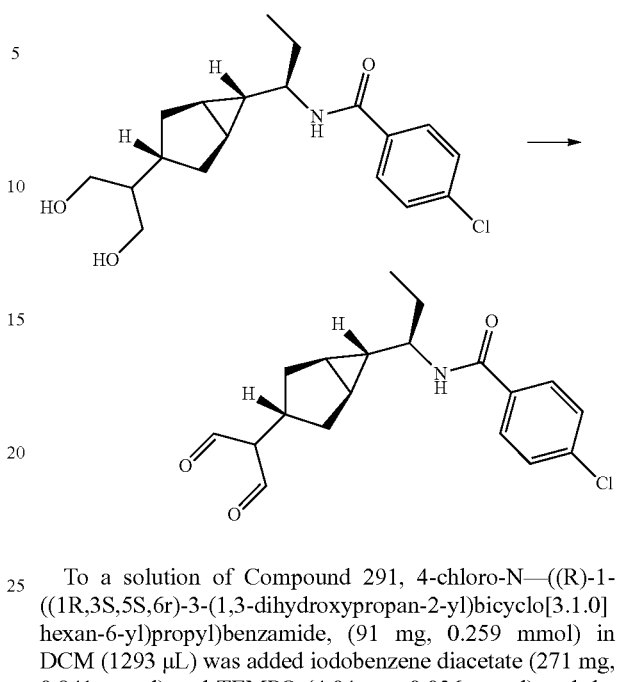

To a solution of Compound 291, 4-chloro-N—((R)-1-((1R,3S,5S,6r)-3-(1,3-dihydroxypropan-2-yl)bicyclo[3.1.0]hexan-6-yl)propyl)benzamide, (91 mg, 0.259 mmol) in DCM (1293 µL) was added iodobenzene diacetate (271 mg, 0.841 mmol) and TEMPO (4.04 mg, 0.026 mmol) and the resulting mixture was stirred at 25° C. for 24 h. Saturated NaHCO₃ (2 mL) and Na₂S₂O₃ (2 mL) were added, stirred for 15 min., and the layers were separated. The aqueous phase was extracted with DCM (3×5 mL), the combined organic layers were washed with sat'd NaCl, dried over Na₂SO₄, filtered, and concentrated under reduced pressure. The residue was purified via silica gel chromatography (0-100% EtOAc in hexanes) to give 4-chloro-N—((R)-1-((1R,3S,5S,6r)-3-(1,3-dioxopropan-2-yl)bicyclo[3.1.0]hexan-6-yl)propyl)benzamide (13 mg, 0.037 mmol, 14.45% yield) as a colorless liquid. MS (ES+) $C_{19}H_{22}ClNO_3$ requires: 347, found: 348 [M+H]+.

Step 2:

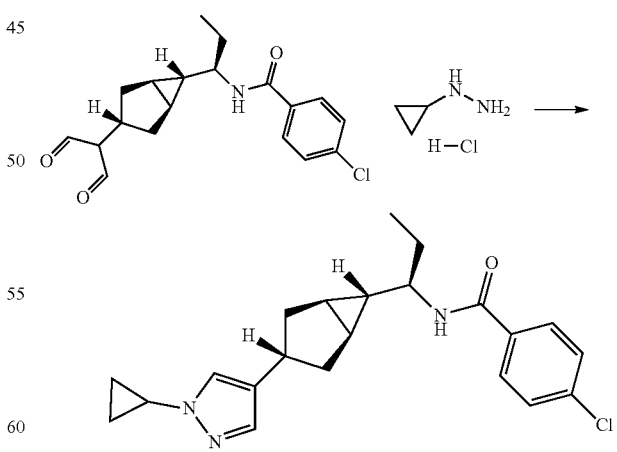

To a solution of 4-chloro-N—((R)-1-((1R,3 S,5S,6r)-3-(1,3-dioxopropan-2-yl)bicyclo[3.1.0]hexan-6-yl)propyl)benzamide (13 mg, 0.037 mmol) in Ethanol (374 µL) was added cyclopropylhydrazine hydrochloride (4.06 mg, 0.037 mmol) and the resulting mixture was stirred at 85° C. for 12 h. The volatiles were removed under reduced pressure and the residue was purified by mass-triggered preparative HPLC (Mobile phase: A=0.1% TFA/H₂O, B=0.1% TFA/MeCN; Gradient: B=50-90%; 12 min; Column: C18) to give 4-chloro-N—((R)-1-((1R,3S,5 S,6r)-3-(1-cyclopropyl-1H-pyrazol-4-yl)bicyclo[3.1.0]hexan-6-yl)propyl)benzamide (0.5 mg, 1.302 μmol, 3.48% yield) as a yellow liquid. MS (ES+)C$_{22}$H$_{26}$ClN$_3$O requires: 383, found: 384 [M+H]$^+$. $^1$H NMR (600 MHz, Methanol-d$_4$) δ 8.33 (d, J=8.7 Hz, 1H), 7.87-7.75 (m, 3H), 7.50-7.44 (m, 3H), 3.53 (tt, J=7.2, 3.9 Hz, 1H), 2.70-2.62 (m, 1H), 2.19-2.05 (m, 3H), 1.76-1.54 (m, 6H), 1.36 (dt, J=31.1, 4.9 Hz, 4H), 1.04-0.98 (m, 4H).

Synthesis of 4-chloro-N-(((1R,3s, 5S, 6r)-3-(5,6-difluoro-1H-benzo[d]imidazol-1-yl)bicyclo[3.1.0]hexan-6-yl)methyl)benzamide (Compound 301)

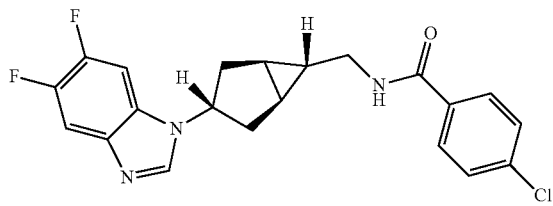 [SMILES: O=C(NC[C@@H]1[C@H]2C[C@H](n3cnc4cc(F)c(F)cc43)C[C@@H]12)c1ccc(Cl)cc1]

Step 1:

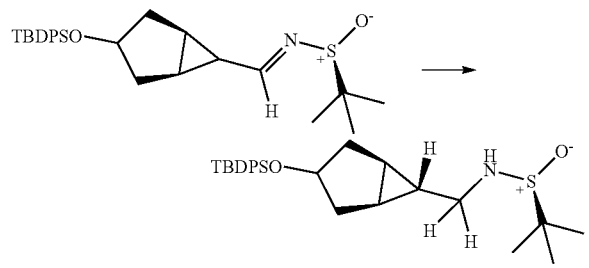

To a solution of (S,E)-N-(((1R,5S)-3-((tert-butyldiphenylsilyl)oxy)bicyclo[3.1.0]hexan-6-yl)methylene)-2-methylpropane-2-sulfinamide (7.1 g, 15.18 mmol) in THF (50.6 mL) cooled in an acetone dry ice bath was added LAH (11.38 mL of 2M THF solution, 22.77 mmol) and the resulting mixture was allowed to warm to RT overnight. The reaction was cooled in an ice bath and quenched following the Fieser and Fieser method (0.9 mL water, 0.9 mL of 15% NaOH, 2.7 mL of water, added MgSO4, stirred for 30 min, and filtered). The resulting filtrate was diluted with water and extracted with EtOAc. The organic layer was washed with brine, dried over MgSO$_4$, filtered, and concentrated to give (S)—N-(((1R,5S,6r)-3-((tert-butyldiphenylsilyl)oxy)bicyclo[3.1.0]hexan-6-yl)methyl)-2-methylpropane-2-sulfinamide (6.35 g, 13.52 mmol, 89% yield) as a clear semi-solid. MS (ES+) C$_{27}$H$_{39}$NO$_2$SSi requires: 469, found: 470 [M+H]$^+$.
Step 2:

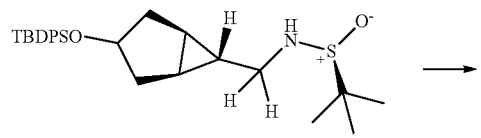

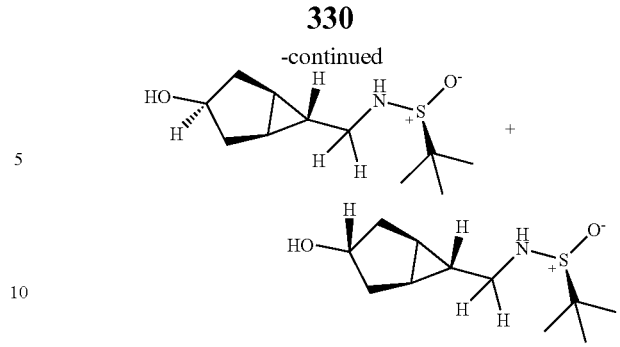

(S)—N-(((1R,5-((tert-butyldiphenylsilyl)oxy)bicyclo[3.1.0]hexan-6-yl)methyl)-2-methylpropane-2-sulfinamide (6.35 g, 13.52 mmol) was dissolved in THF (50.6 mL), cooled in an ice bath and TBAF (30.4 mL of 1M solution in THF, 30.4 mmol) was added dropwise. The reaction was removed from the bath and allowed to warm to RT overnight. The reaction was concentrated, diluted with water, and extracted twice with EtOAc. The organic layers were washed brine, combined, dried over MgSO$_4$, filtered, concentrated, and purified by flash chromatography (10 to 100% of 80:20 EtOAc:IPA in hexanes) to give both isomers.

The first isomer to elute was (S)—N-(((1R,3S,5S,6r)-3-hydroxybicyclo[3.1.0]hexan-6-yl)methyl)-2-methylpropane-2-sulfinamide (1.5 g, 6.48 mmol, 42.7% yield) which was obtained as a white solid. MS (ES+) C$_{11}$H$_{21}$NO$_2$S requires: 231, found: 232 [M+H]$^+$.

The second isomer to elute was (S)—N-(((1R,3R,5S,6r)-3-hydroxybicyclo[3.1.0]hexan-6-yl)methyl)-2-methylpropane-2-sulfinamide (0.3 g, 1.297 mmol, 8.54% yield) which was obtained as white solid. MS (ES+) C$_{11}$H$_{21}$NO$_2$S requires: 231, found: 232 [M+H]$^+$.
Step 3:

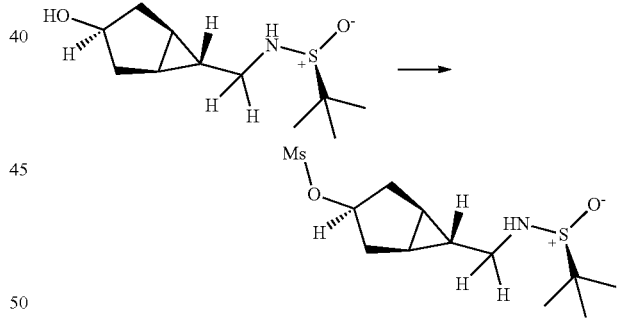

To a cooled 0° C. solution of (S)—N-(((1R,3S,5S,6r)-3-hydroxybicyclo[3.1.0]hexan-6-yl)methyl)-2-methylpropane-2-sulfinamide (1.3 g, 5.62 mmol) in DCM (28.1 mL) was added methanesulfonyl chloride (0.657 mL, 8.43 mmol) and the resulting mixture was stirred and allowed to warm to RT over 3 hr. The reaction was diluted with EtOAc (200 mL) and washed with 0.5 M HCl (100 mL), water (150 mL), 0.5 M NaOH (100 mL), and brine (100 mL). Each aqueous layer was sequentially extracted with EtOAc (100 mL). The two organic layers were combined, dired over MgSO$_4$, filtered, and concentrated to give (1R,3S,5S,6r)-6-(((S)-1,1-dimethylethylsulfinamido)methyl)bicyclo[3.1.0]hexan-3-yl methanesulfonate (1.43 g, 4.62 mmol, 82% yield) as a semi-solid-wax. MS (ES+) C$_{12}$H$_{23}$NO$_4$S$_2$ requires: 309, found: 310 [M+H]$^+$.

Step 4:

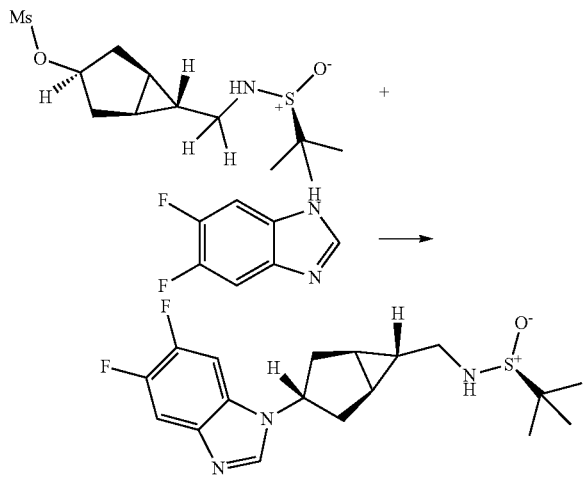

To a solution of (1R,3S,5 S,6r)-6-(((S)-1,1-dimethylethylsulfinamido)methyl) bicyclo[3.1.0]hexan-3-yl methanesulfonate (1.42 g, 4.59 mmol) in THF (15.30 mL) was added cesium carbonate (4.49 g, 13.77 mmol) and 5,6-difluoro-1H-benzo[d]imidazole (0.849 g, 5.51 mmol) and the resulting mixture was stirred at 85° C. for 16 h. The reaction was cooled to RT, concentrated, diluted with water and extracted twice with EtOAc. The organics were washed with brine, combined, dried over MgSO₄, concentrated and purified by flash chromatography (5 to 40% of 80:20:2 EA:EtOH:NH4OH in hexanes) to give (S)—N-(((1R,3R,5 S,6r)-3-(5,6-difluoro-1H-benzo[d]imidazol-1-yl)bicyclo[3.1.0]hexan-6-yl)methyl)-2-methylpropane-2-sulfinamide (1.03 g, 2.80 mmol, 61.1% yield) as a white solid. MS (ES+) $C_{18}H_{23}F_2N_3OS$ requires: 367, found: 368 [M+H]⁺.

Step 5:

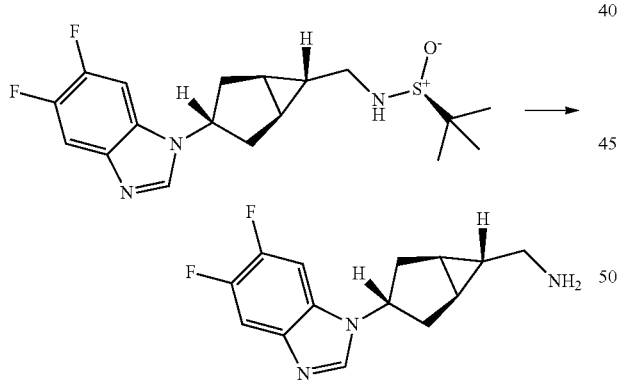

To a cooled 0° C. solution of (S)—N-(((1R,3R,5S,6r)-3-(5,6-difluoro-1H-benzo[d]imidazol-1-yl)bicyclo[3.1.0]hexan-6-yl)methyl)-2-methylpropane-2-sulfinamide (1 g, 2.72 mmol) in MeOH (5.44 mL) was added HCl 4M in Dioxane (2.72 mL, 10.89 mmol) and the resulting mixture was stirred at 0° C. for 5 min then at RT for 3 h. The reaction was concentrated, dried by being azeotroped with ACN and DCM/Hexanes to give ((1R,3s,5S,6r)-3-(5,6-difluoro-1H-benzo[d]imidazol-1-yl)bicyclo[3.1.0]hexan-6-yl)methanamine dihydrochloride (0.9 g, 2.68 mmol, 98% yield) as a white solid. MS (ES⁺) $C_{14}H_{15}F_2N_3$·2ClH requires: 263, found: 264 [M+H]⁺.

Step 6:

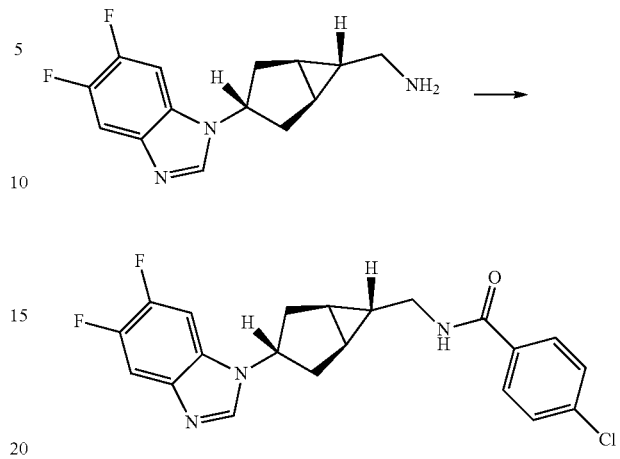

The title compound was synthesized from ((1R,3s,5S,6r)-3-(5,6-difluoro-1H-benzo[d]imidazol-1-yl)bicyclo[3.1.0]hexan-6-yl)methanamine dihydrochloride in a reaction similar to the amide coupling procedure using DIEA, EDC, and HOBt to give 4-chloro-N-(((1R,3s,5S,6r)-3-(5,6-difluoro-1H-benzo[d]imidazol-1-yl)bicyclo[3.1.0]hexan-6-yl)methyl)benzamide (26 mg, 0.065 mmol, 43.5% yield). MS (ES+) $C_{21}H_{18}ClF_2N_3O$ requires: 401, found: 402 [M+H]⁺. ¹H NMR (DMSO-d₆) δ: 8.68 (t, J=5.7 Hz, 1H), 8.43 (s, 1H), 7.88-7.92 (m, 2H), 7.85-7.87 (m, 1H), 7.66-7.70 (m, 1H), 7.53-7.58 (m, 2H), 4.56-4.66 (m, 1H), 3.14-3.18 (m, 2H), 2.30-2.34 (m, 2H), 2.14-2.23 (m, 2H), 1.43 (br. s., 2H), 1.24-1.26 (m, 1H)

Synthesis of N—((R)-1-((3S,6s)-3-(5,6-difluoro-1H-benzo[d]imidazol-1-yl)bicyclo[3.1.0]hexan-6-yl)propyl)-4-fluorobenzamide (Compound 306)

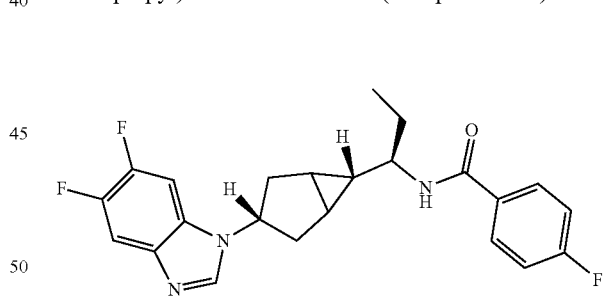

The title compound was synthesized similar to the amide coupling procedure using DIEA, EDC and HOBt from ((1R,3s,5S,6r)-3-(5,6-difluoro-1H-benzo[d]imidazol-1-yl)bicyclo[3.1.0]hexan-6-yl)methanamine (made analogously to the product of Step 5 from the synthesis of Compound 301) and 4-fluorobenzoic acid to give N-((1R)-1-((3S,6s)-3-(5,6-difluoro-1H-benzo[d]imidazol-1-yl)bicyclo[3.1.0]hexan-6-yl)propyl)-4-fluorobenzamide. MS (ES+) $C_{23}H_{22}F_3N_3O$ requires: 413, found: 414 [M+H]⁺. ¹H NMR (CHLOROFORM-d) δ: 9.17 (br. s., 1H), 7.80-7.85 (m, 2H), 7.79-7.74 (m, 1H), 7.46-7.55 (m, 1H), 7.06-7.15 (m, 2H), 6.58 (br d, J=8.7 Hz, 1H), 4.63-4.71 (m, 1H), 3.43-3.55 (m, 1H), 2.47-2.59 (m, 2H), 2.25-2.43 (m, 2H), 1.73-1.83 (m, 2H), 1.35-1.46 (m, 3H), 0.97-1.06 (m, 4H).

Synthesis of 4-chloro-N—((R)-1-((1R,3S,5S, 6r)-3-((2-cyanophenyl)amino)bicyclo[3.1.0]hexan-6-yl)propyl)benzamide (Compound 331)

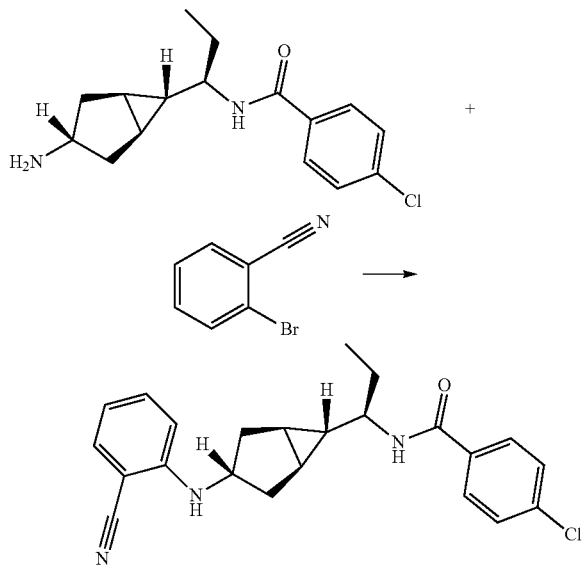

To vial containing N—((R)-1-((1R,3S,5S,6r)-3-aminobicyclo[3.1.0]hexan-6-yl)propyl)-4-chlorobenzamide (40 mg, 0.137 mmol), 2-bromobenzonitrile (24.87 mg, 0.137 mmol), cesium carbonate (89 mg, 0.273 mmol), Xantphos (7.90 mg, 0.014 mmol), and $Pd_2(dba)_3$ (6.25 mg, 6.83 µmol) was added Dioxane (683 µL, previously purged with $N_2$ for 5 min prior to addition) and the resulting mixture was stirred at 95° C. for 5 hr. The reaction was diluted with EtOAc (8 mL) and washed with water and brine (8 mL/each). The aq. layers were extracted once with EtOAc (4 mL). The organic layers combined, dried over $MgSO_4$, filtered, concentrated, and purified by flash chromatography (5 to 50% EtOAc in hexanes) to give 4-chloro-N—((R)-1-((1R,3S,5S,6r)-3-((2-cyanophenyl)amino)bicyclo[3.1.0]hexan-6-yl)propyl) benzamide (13.2 mg, 0.034 mmol, 24.53% yield) as a light yellow solid. MS $(ES^+)C_{23}H_{24}ClN_3O$ requires: 393, found: 394 $[M+H]^+$.

Synthesis of 1-(4-chlorophenyl)-3-((R)-1-((R, 3S, 5S, 6r)-3-(5,6-difluoro-1H-benzo[d]imidazol-1-yl)bicyclo[3.1.0]hexan-6-yl)propyl) urea (Compound 344)

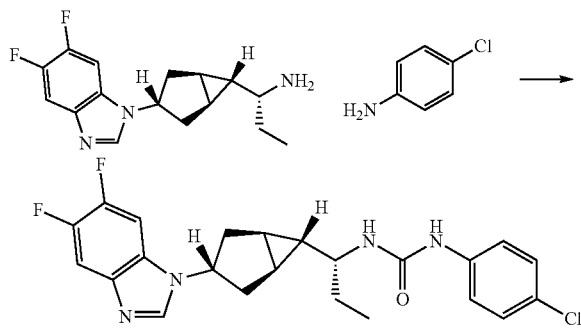

"General Urea" Procedure:

To a solution of (R)-1-((1R,3S,5S,6r)-3-(5,6-difluoro-1H-benzo[d]imidazol-1-yl)bicyclo[3.1.0]hexan-6-yl)propan-1-amine (50.0 mg, 0.172 mmol) and triethylamine (70 µL, 0.516 mmol) in DMF (1.0 mL) was added carbonyldiimidazole (27.9 mg, 0.172 mmol) and the solution stirred at 25° C. for 1 hour. 4-chloroaniline (26.3 mg, 0.206 mmol) was added, and the reaction was heated to 65° C. for 18 hours. The reaction was cooled, diluted with DCM (5 mL), quenched with sat. $NH_4Cl$, and the aqueous layer was extracted with DCM (3×5 mL). The combined organics were then washed with sat'd NaCl, dried over $Na_2SO_4$, filtered, and concentrated under reduced pressure. The crude material was purified by silica gel chromatography (20-100% ethyl acetate in hexanes), affording 1-(4-chlorophenyl)-3-((R)-1-((1R,3S,5S,6r)-3-(5,6-difluoro-1H-benzo[d]imidazol-1-yl)bicyclo[3.1.0]hexan-6-yl)propyl)urea as a white solid (39 mg, 0.087 mmol, 51% yield). MS ($ES^+$) $C_{23}H_{23}ClF_2N_4O$ requires 444, found 445 $[M+H]^+$. $^1H$ NMR (600 MHz, $CDCl_3$) δ 0.73 (m, 1H), 0.96 (t, 3H, J=7.4 Hz), 1.45 (m, 1H), 1.50 (m, 1H), 1.61 (m, 2H), 2.23 (m, 2H), 2.30 (m, 1H), 2.38 (m, 1H), 4.27 (quint, 1H, J=8.5 Hz), 5.45 (d, 1H, J=8.4 Hz), 7.14 (dd, 1H, J=9.7, 7.0 Hz), 7.21 (d, 2H, J=8.7 Hz), 7.31 (d, 2H, J=8.7 Hz), 7.53 (dd, 1H, J=10.3, 7.4 Hz), 7.80 (s, 1H), 7.93 (s, 1H), 8.04 (s, 1H).

Synthesis of 2-(((1R,3S,5S,6r)-6-((R)-1-(4-chlorobenzamido)propyl)bicyclo[3.1.0]hexan-3-yl)amino)benzoic acid (Compound 346)

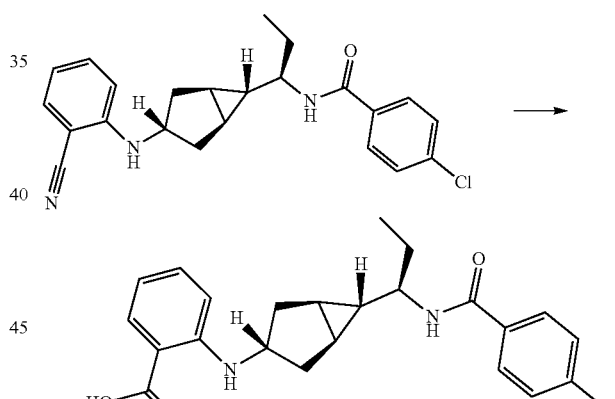

To a suspension of 4-chloro-N—((R)-1-((1R,3 S,5 S,6r)-3-((2-cyanophenyl)amino) bicyclo[3.1.0]hexan-6-yl)propyl)benzamide (10 mg, 0.025 mmol) in Dioxane (203 µL) and Water (50.8 µL) was added conc. HCl (20.98 µL, 0.254 mmol) and the resulting mixture was stirred at 85° C. until complete. The reaction was concentrated, diluted with water and the resulting solid was filtered, and washed with water and hexanes to give 2-(((1R,3S,5S,6r)-6-((R)-1-(4-chlorobenzamido)propyl)bicyclo[3.1.0]hexan-3-yl)amino)benzoic acid (3.2 mg, 7.75 µmol, 30.5% yield) as a white solid. MS (ES+) $C_{23}H_{25}ClN_2O_3$ requires: 412, found: 413 $[M+H]^+$.

Separation of Stereoisomers

Stereoisomers of certain compounds listed above may be separated, e.g. using SFC.

(R)—N-(4-chlorophenyl)-2-((1R,3s,5 S,6r)-3-((6-fluorocinnolin-4-yl)oxy)bicyclo[3.1.0]hexan-6-yl)propanamide (Compound 358) and (S)—N-(4-chlorophenyl)-2-((1R,3s,5S,6r)-3-((6-fluorocinnolin-4-yl)oxy)bicyclo[3.1.0]hexan-6-yl)propanamide (Compound 359) are separated from Compound 340.

(R)—N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide (Compound 360) and (S)—N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide (Compound 361) are separated from Compound 345.

(R)—N-(4-chlorophenyl)-2-((1R,3s,5 S,6r)-3-((6-fluoroquinolin-4-yl)oxy)bicyclo[3.1.0]hexan-6-yl)propanamide (Compound 362) and (S)—N-(4-chlorophenyl)-2-((1R,3s,5S,6r)-3-((6-fluoroquinolin-4-yl)oxy)bicyclo[3.1.0]hexan-6-yl)propanamide (Compound 363) are separated from Compound 347.

Example 17: IDO1 Cell-Based Assay

HeLa cells were obtained from the American Type Culture Collection (ATCC) and maintained in DMEM media containing 10% FBS. Cells (7,000/well) were seeded onto a 384 well plate in 50 μL of media and incubated at 37° C., 5% $CO_2$ overnight. Cell media was aspirated, fresh media containing 10 ng/mL IFNgamma was added, and cells were incubated in absence or presence of various concentrations of test compound (final 0.5% DMSO) for 24 hours. Aliquots of the cell conditioned media were removed from the cell plate, and mixed with an equal volume of 200 mM $ZnSO_4$ to precipitate media containing proteins. Two volumes of acetonitrile were added, mixed, and samples were then centrifuged at 2250G for 20 minutes at 4° C. Aliquots of the supernatant were diluted 1:10 in 0.1% formic acid containing 3 μM of deuterated Tryptophan as an internal standard.

Samples were analyzed via RFMS to quantify N-Formyl Kynurenine (AUC) and L-tryptophan (AUC). A C18 cartridge was used with mobile phases of 0.1% Formic Acid and 80% ACN/0.1% Formic Acid under isocratic conditions. Dose-response curves were analyzed using $IC_{50}$ regression curve fitting (GeneData Screener). Curves were plotted as percent of control and normalized by high controls without inhibitor (100%), and low controls (0%) containing 1 μM of epacadostat, a potent cell-permeable IDO1 inhibitor. Cell viability was also assessed using the Cell Titer Glo Kit (Promega) following manufacturer recommendation.

Table 4 below summarises the results of the IDO1 cell-based assay, in which the $IC_{50}$ values are indicated for each compound as: (A) less than 200 nM; (B) 200 nM to 2 μM; (C) 2 μM to 5 μM; and (D) greater than 5 μM.

TABLE 4

IDO1 cell-based assay

| Compound | $IC_{50}$ |
|---|---|
| 1 | C |
| 2 | A |
| 3 | B |
| 4 | A |
| 5 | A |
| 6 | A |
| 7 | A |
| 8 | C |
| 9 | A |
| 10 | A |
| 11 | D |
| 12 | D |
| 13 | A |

TABLE 4-continued

IDO1 cell-based assay

| Compound | $IC_{50}$ |
|---|---|
| 14 | A |
| 15 | A |
| 16 | D |
| 17 | D |
| 18 | A |
| 19 | A |
| 20 | A |
| 21 | A |
| 22 | A |
| 23 | A |
| 24 | B |
| 25 | D |
| 26 | B |
| 27 | D |
| 28 | D |
| 29 | B |
| 30 | A |
| 31 | B |
| 32 | B |
| 33 | B |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | C |
| 49 | A |
| 50 | A |
| 51 | A |
| 52 | A |
| 53 | A |
| 54 | A |
| 55 | A |
| 56 | A |
| 57 | B |
| 58 | A |
| 59 | A |
| 60 | A |
| 61 | A |
| 62 | C |
| 63 | A |
| 64 | A |
| 65 | B |
| 66 | A |
| 67 | A |
| 68 | C |
| 69 | A |
| 70 | A |
| 71 | A |
| 72 | A |
| 73 | C |
| 74 | B |
| 75 | A |
| 76 | B |
| 77 | B |
| 78 | A |
| 79 | B |
| 80 | A |
| 81 | B |
| 82 | B |
| 83 | B |
| 84 | A |
| 85 | D |
| 86 | C |
| 87 | A |
| 88 | A |
| 89 | A |

TABLE 4-continued

IDO1 cell-based assay

| Compound | IC$_{50}$ |
|---|---|
| 90 | B |
| 91 | A |
| 92 | A |
| 93 | A |
| 94 | D |
| 95 | D |
| 96 | A |
| 97 | B |
| 98 | A |
| 99 | A |
| 100 | A |
| 101 | B |
| 102 | A |
| 103 | A |
| 104 | A |
| 105 | D |
| 106 | D |
| 107 | A |
| 108 | A |
| 109 | D |
| 110 | D |
| 111 | D |
| 112 | D |
| 113 | B |
| 114 | B |
| 115 | A |
| 116 | B |
| 117 | A |
| 118 | A |
| 119 | A |
| 120 | A |
| 121 | A |
| 122 | C |
| 123 | A |
| 124 | A |
| 125 | A |
| 126 | A |
| 127 | A |
| 128 | D |
| 129 | B |
| 130 | A |
| 131 | A |
| 132 | A |
| 133 | A |
| 134 | A |
| 135 | B |
| 136 | B |
| 137 | C |
| 138 | A |
| 139 | B |
| 140 | A |
| 141 | B |
| 142 | D |
| 143 | A |
| 144 | A |
| 145 | A |
| 146 | B |
| 147 | A |
| 148 | D |
| 149 | A |
| 150 | A |
| 151 | A |
| 152 | A |
| 153 | A |
| 154 | A |
| 155 | B |
| 156 | D |
| 157 | B |
| 158 | A |
| 159 | B |
| 160 | B |
| 161 | A |
| 162 | A |
| 163 | A |
| 164 | B |
| 165 | A |
| 166 | A |
| 167 | A |
| 168 | C |
| 169 | B |
| 170 | A |
| 171 | A |
| 172 | B |
| 173 | A |
| 174 | A |
| 175 | A |
| 176 | A |
| 177 | B |
| 178 | A |
| 179 | A |
| 180 | B |
| 181 | A |
| 182 | B |
| 183 | A |
| 184 | A |
| 185 | B |
| 186 | A |
| 187 | B |
| 188 | A |
| 189 | A |
| 190 | B |
| 191 | B |
| 192 | B |
| 193 | B |
| 194 | A |
| 195 | A |
| 196 | A |
| 197 | D |
| 198 | A |
| 199 | A |
| 200 | A |
| 201 | A |
| 202 | B |
| 203 | B |
| 204 | A |
| 205 | A |
| 206 | A |
| 207 | A |
| 208 | A |
| 209 | A |
| 210 | A |
| 211 | A |
| 212 | A |
| 213 | A |
| 214 | A |
| 215 | B |
| 216 | A |
| 217 | D |
| 218 | A |
| 219 | A |
| 220 | A |
| 221 | A |
| 222 | B |
| 223 | A |
| 224 | C |
| 225 | A |
| 226 | A |
| 227 | A |
| 228 | C |
| 229 | A |
| 230 | C |
| 231 | D |
| 232 | D |
| 233 | C |
| 234 | B |
| 235 | B |
| 236 | A |
| 237 | D |
| 238 | A |
| 239 | C |
| 240 | A |
| 241 | A |

TABLE 4-continued

IDO1 cell-based assay

| Compound | IC$_{50}$ |
|---|---|
| 242 | B |
| 243 | B |
| 244 | A |
| 245 | A |
| 246 | A |
| 247 | A |
| 248 | A |
| 249 | D |
| 250 | D |
| 251 | D |
| 252 | D |
| 253 | A |
| 254 | A |
| 255 | B |
| 256 | D |
| 257 | D |
| 258 | B |
| 259 | A |
| 260 | A |
| 261 | A |
| 262 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | B |
| 277 | A |
| 278 | A |
| 279 | A |
| 280 | B |
| 281 | A |
| 282 | A |
| 283 | A |
| 284 | A |
| 285 | A |
| 286 | A |
| 287 | A |
| 288 | A |
| 289 | A |
| 290 | A |
| 291 | B |
| 292 | A |
| 293 | B |
| 294 | A |
| 295 | B |
| 296 | D |
| 297 | D |
| 298 | A |
| 299 | A |
| 300 | A |
| 301 | A |
| 302 | A |
| 303 | A |
| 304 | A |
| 305 | A |
| 306 | A |
| 307 | A |
| 308 | B |
| 309 | B |
| 310 | A |
| 311 | A |
| 312 | A |
| 313 | A |
| 314 | A |
| 315 | A |
| 316 | B |
| 317 | B |
| 318 | B |

TABLE 4-continued

IDO1 cell-based assay

| Compound | IC$_{50}$ |
|---|---|
| 319 | D |
| 320 | B |
| 321 | B |
| 322 | A |
| 323 | B |
| 324 | A |
| 325 | A |
| 326 | A |
| 327 | A |
| 328 | B |
| 329 | A |
| 330 | A |
| 331 | A |
| 332 | A |
| 333 | A |
| 334 | A |
| 335 | A |
| 336 | A |
| 337 | A |
| 338 | A |
| 339 | A |
| 340 | A |
| 341 | C |
| 342 | A |
| 343 | A |
| 344 | A |
| 345 | A |
| 346 | A |
| 347 | A |
| 348 | A |
| 349 | A |
| 352 | B |
| 353 | D |
| 354 | B |
| 355 | A |
| 356 | C |
| 357 | B |

Example 18: Mouse IDO1 Cell-Based Assay (PANC02 Cells)

The murine PANC02 pancreatic ductal adenocarcinoma cell line was routinely maintained in DMEM media containing 10% FBS. Cells (3,000/well) were seeded onto a 384 well plate in 50 μl of media and incubated at 37° C., 5% CO$_2$ overnight. Cell media was aspirated, fresh media containing 30 ng/mL mouse IFNgamma (Gibco Life Technologies, cat #PMC4031) was added, and cells were incubated in absence or presence of various concentrations of compounds (final 0.5% DMSO) for 48 hours at 37° C., 5% CO$_2$. Aliquots of the cell conditioned media was removed from the cell plate, and mixed with equal volume of 200 mM ZnSO$_4$ to precipitate media containing protein. Two volumes of acetonitrile were added by mixing, and samples were then centrifuged at 2250G for 20 minutes at 4° C. Aliquots of the supernatant were diluted 1:10 in 0.1% formic acid containing 3 μM of deuterated Tryptophan as an internal standard.

Samples were analyzed via RFMS to quantify N-Formyl Kynurenine (AUC) and L-tryptophan (AUC). A C18 cartridge was used with mobile phases of 0.1% Formic Acid and 80% ACN/0.1% Formic Acid under isocratic conditions. Dose-response curves were analyzed using IC$_{50}$ regression curve fitting (GeneData Screener). Curves were plotted as percent of control and normalized by high controls without inhibitor (100%), and low controls (0%) containing 1 μM of epacadostat. Cell viability was also assessed using the Cell Titer Glo Kit (Promega) following manufacture recommendation.

Table 5 below summarises the results of the mouse IDO1 cell-based assay, in which the $IC_{50}$ values are indicated for each compound as: (A) less than 500 nM; (B) 500 nM to 2 µM; (C) 2 µM to 5 µM; and (D) greater than 5 µM.

TABLE 5

IDO1 cell-based assay (PANC02 cells)

| Compound | $IC_{50}$ |
|---|---|
| 117 | C |
| 125 | A |
| 130 | A |
| 131 | B |
| 144 | B |
| 145 | D |
| 150 | C |
| 153 | A |
| 158 | B |
| 161 | B |
| 162 | B |
| 163 | A |
| 164 | B |
| 165 | A |
| 166 | A |
| 167 | A |
| 168 | D |
| 171 | B |
| 175 | B |
| 176 | A |
| 177 | D |
| 178 | A |
| 179 | C |
| 180 | B |
| 181 | A |
| 182 | D |
| 183 | B |
| 184 | A |
| 185 | C |
| 186 | A |
| 187 | C |
| 188 | B |
| 189 | B |
| 190 | D |
| 191 | B |
| 192 | B |
| 193 | B |
| 194 | A |
| 195 | A |
| 197 | D |
| 198 | B |
| 200 | B |
| 201 | C |
| 202 | B |
| 203 | A |
| 204 | B |
| 205 | A |
| 206 | B |
| 208 | A |
| 209 | A |
| 210 | B |
| 211 | A |
| 212 | B |
| 213 | B |
| 214 | A |
| 215 | B |
| 216 | A |
| 217 | D |
| 218 | B |
| 219 | B |
| 220 | A |
| 221 | A |
| 222 | B |
| 223 | D |
| 224 | D |
| 225 | C |
| 226 | A |
| 227 | B |
| 228 | C |
| 229 | A |

TABLE 5-continued

IDO1 cell-based assay (PANC02 cells)

| Compound | $IC_{50}$ |
|---|---|
| 230 | B |
| 231 | C |
| 232 | D |
| 233 | D |
| 234 | B |
| 235 | B |
| 236 | B |
| 237 | D |
| 238 | A |
| 239 | D |
| 240 | A |
| 241 | A |
| 242 | D |
| 243 | B |
| 244 | B |
| 245 | A |
| 246 | A |
| 247 | A |
| 248 | A |
| 249 | D |
| 250 | D |
| 251 | D |
| 252 | C |
| 253 | C |
| 254 | A |
| 255 | C |
| 256 | D |
| 257 | D |
| 258 | C |
| 259 | A |
| 260 | A |
| 261 | B |

The teachings of all patents, published applications and references cited herein are incorporated by reference in their entirety.

While the present invention has particularly been shown and described with reference to exemplary embodiments thereof, it will be understood by those skilled in the art that various changes in form and details may be made therein without departing from the sprit and scope of the invention encompassed by the appended claims.

The invention claimed is:

1. A compound of formula (VII),

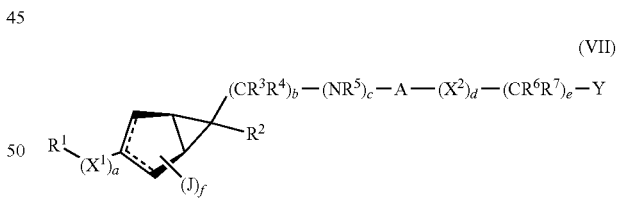

or a pharmaceutically acceptable salt thereof, wherein one but not both of the dashed bonds may optionally be a carbon-carbon double bond, and wherein:
W is selected from C and CH;
a is selected from 0 and 1;
b is selected from 0, 1, and 2;
c is selected from 0 and 1;
d is selected from 0 and 1;
e is selected from 0 and 1;
f is selected from 0, 1, and 2;
A is selected from O, C(O), and $S(O)_2$;
J is in each case independently selected from oxo, OH, CN, halogen, and $C_{1-3}$-alkyl;
$X^1$ is selected from $C(R^8)(R^9)$, $N(R^{10})$, O, and S;

$X^2$ is selected from $C(R^{11})(R^{12})$, $N(R^{13})$ and O;

Y is selected from
- $C_{6-10}$-aryl, and
- 5- to 10-membered heteroaryl comprising 1, 2, 3, or 4 ring heteroatoms selected from N, S, and O,
  wherein said aryl and heteroaryl are optionally substituted by one or more groups independently selected from $R^{14}$;

$R^1$ is selected from
- H,
- $(G)_n$-($C_{1-6}$-alkyl),
- $(G)_n$-($C_{3-8}$-cycloalkyl),
- $N_3$,
- $(G)_n$-heterocycloalkyl, wherein said heterocycloalkyl is a 3- to 6-membered heterocycloalkyl comprising 1, 2, or 3 ring heteroatoms selected from N, S, and O,
- $(G)_n$-($C_{5-8}$-cycloalkenyl),
- $(G)_n$-heterocycloalkenyl, wherein said heterocycloalkenyl is a 5- to 6-membered heterocycloalkenyl comprising 1, 2, or 3 ring heteroatoms selected from N, S, and O,
- $(G)_n$-($C_{6-10}$-aryl), and
- $(G)_n$-heteroaryl, wherein said heteroaryl is a 5- to 10-membered heteroaryl comprising 1, 2, 3, or 4 ring heteroatoms selected from N, S, and O,
  wherein G in each case is independently selected from $C(R^8)(R^9)$, $C(O)$, $S(O)_2$, $C(O)NR^{10}$, and $S(O)_2NR^{10}$; and wherein n in each case is selected from 0 and 1, and
  wherein said alkyl, cycloalkyl, heterocycloalkyl, cycloalkenyl, heterocycloalkenyl, aryl, and heteroaryl are optionally substituted by one or more groups independently selected from $R^{15}$;

$R^2$, $R^3$, $R^4$, $R^6$, $R^7$, $R^8$, $R^9$, $R^{11}$, and $R^{12}$ are in each case independently selected from
- H,
- halogen,
- CN,
- OH,
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$,
- $C_{1-6}$-alkyl,
- O—($C_{1-6}$-alkyl),
- $C_{3-8}$-cycloalkyl,
- 3- to 6-membered heterocycloalkyl comprising 1, 2, or 3 ring heteroatoms selected from N, S, and O,
- $C_{5-8}$-cycloalkenyl,
- 5- to 6-membered heterocycloalkenyl comprising 1, 2, or 3 ring heteroatoms selected from N, S, and O,
- $C_{6-10}$-aryl, and
- 5- to 10-membered heteroaryl comprising 1, 2, 3, or 4 ring heteroatoms selected from N, S, and O, or
- one or both geminal $R^3$ and $R^4$ pairs, taken together with the carbon atom to which they are attached, independently forms a 3- to 6-membered cycloalkyl group or a 3- to 6-membered heterocycloalkyl group which comprises 1, 2, or 3 ring heteroatoms selected from N, S, and O,
  wherein said alkyl, cycloalkyl, heterocycloalkyl, cycloalkenyl, heterocycloalkenyl, aryl, and heteroaryl are optionally substituted by one or more groups independently selected from $R^{16}$;

$R^5$, $R^{10}$ and $R^{13}$ are in each case independently selected from
- H,
- $C_{1-6}$-alkyl,
- $C_{3-8}$-cycloalkyl,
- 3- to 6-membered heterocycloalkyl comprising 1, 2, or 3 ring heteroatoms selected from N, S, and O,
- $C_{5-8}$-cycloalkenyl,
- 5- to 6-membered heterocycloalkenyl comprising 1, 2, or 3 ring heteroatoms selected from N, S, and O,
- $C_{6-10}$-aryl, and
- 5- to 10-membered heteroaryl comprising 1, 2, 3, or 4 ring heteroatoms selected from N, S, and O,
  optionally wherein one of $R^3$ and $R^5$, together with one of $R^{11}$ and $R^{13}$ and the atoms intervening between them, may form a 5- or 6-membered cycloalkyl, cycloalkenyl or aryl group, or a 5- or 6-membered heterocycloalkyl, heterocycloalkenyl or heteroaryl group which comprises 1, 2, 3, or 4 ring heteroatoms selected from N, S, and O;
  wherein said alkyl, cycloalkyl, heterocycloalkyl, cycloalkenyl, heterocycloalkenyl, aryl, and heteroaryl are optionally substituted by one or more groups independently selected from $R^{24}$;

any two $R^{14}$ substituents on adjacent ring atoms may, together with the ring atoms to which they are attached, independently form a 5- or 6-membered cyclic group optionally comprising 1, 2, or 3 ring heteroatoms selected from N, S, and O, which cyclic group is optionally substituted by one or more groups independently selected from halogen, $C_{1-4}$-alkyl, and $C_{1-4}$-haloalkyl, and any remaining $R^{14}$ is in each case independently selected from
- halogen,
- CN,
- OH,
- $C_{1-6}$-alkyl,
- O—($C_{1-6}$-alkyl),
- O—($C_{1-6}$-haloalkyl),
- O—($C_{1-6}$-alkyl-$C_{3-6}$-cycloalkyl),
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$,
- $(C_{0-4}$-alkyl$)$-$NHSO_2R^{20}$,
- $(C_{0-4}$-alkyl$)$-$CON(R^{21})_2$,
- $(C_{0-4}$-alkyl$)$-$CO_2R^{22}$,
- $(C_{0-4}$-alkyl$)$-$SO_2N(R^{23})_2$, and
- $(C_{0-4}$-alkyl$)$-heteroaryl,
  wherein said heteroaryl is a 5- to 10-membered heteroaryl comprising 1, 2, 3, or 4 ring heteroatoms selected from N, S, and O;

$R^{15}$ is in each case independently selected from halogen,
- CN,
- OH,
- oxo,
- $NO_2$,
- $C_{1-6}$-alkyl,
- $C_{2-6}$-alkenyl,
- $C_{2-6}$-alkynyl,
- $(C_{0-4}$-alkyl$)$-O—($C_{1-6}$-alkyl),
- $(C_{0-4}$-alkyl$)$-$SO_2R^{17}$,
- $(C_{0-4}$-alkyl$)$-$N(R^{18})_2$,
- $(C_{0-4}$-alkyl$)$-$NHCOR^{19}$, ($C_{0-4}$-alkyl)-$NHSO_2R^{20}$,
($C_{0-4}$-alkyl)-$CON(R^{21})_2$,
($C_{0-4}$-alkyl)-$CO_2R^{22}$,
($C_{0-4}$-alkyl)-$SO_2N(R^{23})_2$,
($C_{0-4}$-alkyl)-heteroaryl, wherein said heteroaryl is a 5- to 10-membered heteroaryl comprising 1, 2, 3, or 4 ring heteroatoms selected from N, S, and O,
($C_{0-4}$-alkyl)-heterocycloalkenyl, wherein said heterocycloalkenyl is a 5- to 10-membered heterocycloalkenyl comprising 1 or 2 ring heteroatoms selected from N and O,
($C_{0-4}$-alkyl)-heterocycloalkyl, wherein said heterocycloalkyl is a 4- to 6-membered heterocycloalkyl comprising 1 or 2 ring heteroatoms selected from N and O,
($C_{0-4}$-alkyl)-aryl, wherein said aryl is a 6- to 10-membered aryl,
($C_{0-4}$-alkyl)-cycloalkenyl, wherein said cycloalkenyl is a 5- to 8-membered cycloalkenyl, and
($C_{0-4}$-alkyl)-cycloalkyl, wherein said cycloalkyl is a 3- to 8-membered cycloalkyl,
wherein said alkyl, alkenyl, alkynyl, heteroaryl, heterocycloalkenyl, heterocycloalkyl, aryl, cycloalkenyl, and cycloalkyl are optionally substituted by one or more groups independently selected from halogen, OH, O—($C_{1-4}$-alkyl), oxo, C(O)—($C_{1-4}$-alkyl), C(O)O—($C_{1-4}$-alkyl), and $NH_2$;

$R^{16}$ and $R^{24}$ are in each case independently selected from
halogen,
CN,
OH,
$C_{1-6}$-alkyl,
O—($C_{1-6}$-alkyl),
($C_{0-4}$-alkyl)-$SO_2R^{17}$,
($C_{0-4}$-alkyl)-$N(R^{18})_2$,
($C_{0-4}$-alkyl)-$NHCOR^{19}$,
($C_{0-4}$-alkyl)-$NHSO_2R^{20}$,
($C_{0-4}$-alkyl)-$CON(R^{21})_2$,
($C_{0-4}$-alkyl)-$CO_2R^{22}$,
($C_{0-4}$-alkyl)-$SO_2N(R^{23})_2$,
($C_{0-4}$-alkyl)-heteroaryl, wherein said heteroaryl is a 5- to 10-membered heteroaryl comprising 1, 2, 3, or 4 ring heteroatoms selected from N, S, and O,
($C_{0-4}$-alkyl)-heterocycloalkenyl, wherein said heterocycloalkenyl is a 5- to 6-membered heterocycloalkenyl comprising 1 or 2 ring heteroatoms selected from N and O,
($C_{0-4}$-alkyl)-heterocycloalkyl, wherein said heterocycloalkyl is a 4- to 6-membered heterocycloalkyl comprising 1 or 2 ring heteroatoms selected from N and O,
($C_{0-4}$-alkyl)-aryl, wherein said aryl is a 6- to 10-membered aryl,
($C_{0-4}$-alkyl)-cycloalkenyl, wherein said cycloalkenyl is a 5- to 8-membered cycloalkenyl, and
($C_{0-4}$-alkyl)-cycloalkyl, wherein said cycloalkyl is a 3- to 8-membered cycloalkyl,
wherein said alkyl, heteroaryl, heterocycloalkenyl, heterocycloalkyl, aryl, cycloalkenyl, and cycloalkyl are optionally substituted by one or more groups independently selected from halogen; and $R^{17}$ to $R^{23}$ are in each case independently selected from
H,
$C_{1-6}$-alkyl,
$C_{3-8}$-cycloalkyl,
3- to 6-membered heterocycloalkyl comprising 1, 2, or 3 ring heteroatoms selected from N, S, and O,
$C_{5-8}$-cycloalkenyl,
5- to 6-membered heterocycloalkenyl comprising 1, 2, or 3 ring heteroatoms selected from N, S, and O,
$C_{6-10}$-aryl, and
5- to 10-membered heteroaryl comprising 1, 2, 3, or 4 ring heteroatoms selected from N, S, and O,
wherein any pair of $R^{18}$ groups attached to the same nitrogen atom, taken together with the intervening nitrogen atom, may form a 3- to 10-membered heterocycloalkyl or heterocycloalkenyl group comprising 1, 2, or 3 ring heteroatoms selected from N, S, and O,
wherein any pair of $R^{21}$ groups attached to the same nitrogen atom, taken together with the intervening nitrogen atom, may form a 3- to 10-membered heterocycloalkyl or heterocycloalkenyl group comprising 1, 2, or 3 ring heteroatoms selected from N, S, and O,
wherein any pair of $R^{23}$ groups attached to the same nitrogen atom, taken together with the intervening nitrogen atom, may form a 3- to 10-membered heterocycloalkyl or heterocycloalkenyl group comprising 1, 2, or 3 ring heteroatoms selected from N, S, and O,
wherein each said alkyl, cycloalkyl, heterocycloalkyl, cycloalkenyl, heterocycloalkenyl, aryl, and heteroaryl is optionally and independently substituted by one or more groups independently selected from halogen, OH, $C_{1-6}$-alkyl, and $C_{1-6}$-haloalkyl.

2. The compound of claim 1, of formula (I),

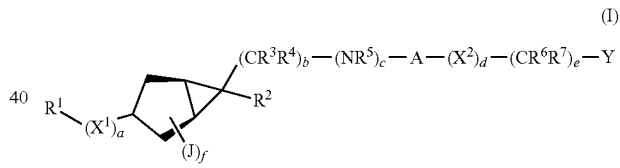

or a pharmaceutically acceptable salt thereof, wherein a, b, c, d, e, f, J, $X^1$, $X^2$, Y, and $R^1$ to $R^7$ are as defined in claim 1, A is C(O), and f is 0.

3. The compound of claim 1, of formula (III),

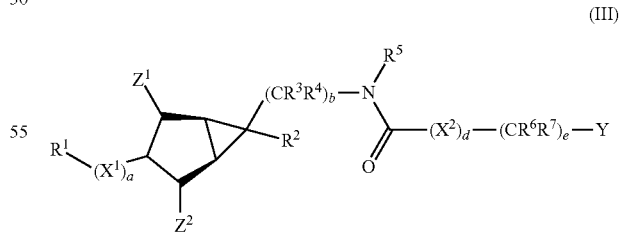

or a pharmaceutically acceptable salt thereof, wherein:
$Z^1$ and $Z^2$ are each independently selected from H;
b is selected from 0 and 1; and
a, d, e, $X^1$, $X^2$, Y, and $R^1$ to $R^7$ are as defined in claim 1.

4. The compound of claim 3, or a pharmaceutically acceptable salt thereof, wherein d is 0.

5. The compound of claim 4, of formula (IV),

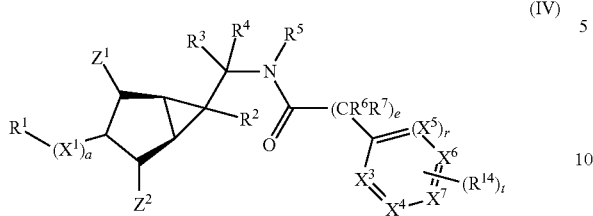
(IV)

or a pharmaceutically acceptable salt thereof, wherein:

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N, a, e, $X^1$, $R^1$ to $R^7$, and $R^{14}$ are as defined in claim 1, and $Z^1$ and $Z^2$ are each independently selected from H.

6. The compound of claim 5, of formula (IVa),

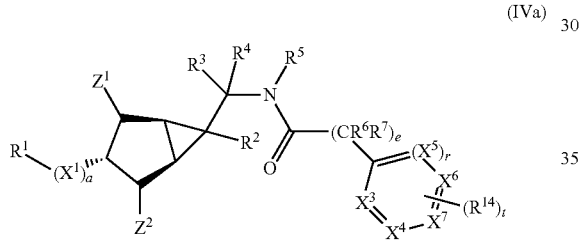
(IVa)

or a pharmaceutically acceptable salt thereof, wherein a, e, $X^1$, $R^1$ to $R^7$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N; and $Z^1$ and $Z^2$ are each independently selected from H.

7. The compound of claim 5, of formula (IVac) or formula (IVbc),

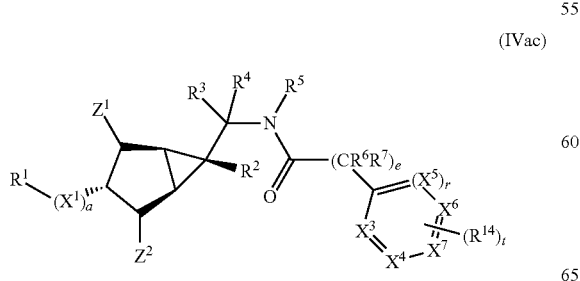
(IVac)

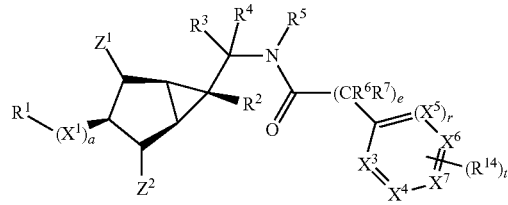
(IVbc)

or a pharmaceutically acceptable salt thereof, wherein a, e, $X^1$, $R^1$ to $R^7$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N; wherein no more than three of $X^3$ to $X^7$ may be N; and $Z^1$ and $Z^2$ are each independently selected from H.

8. The compound of claim 5, of formula (VIII) or formula (IX),

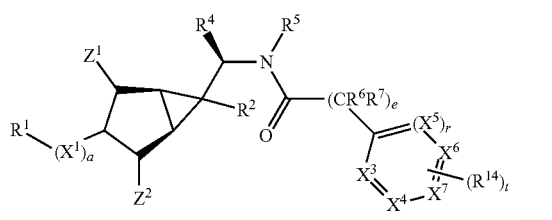
(VIII)

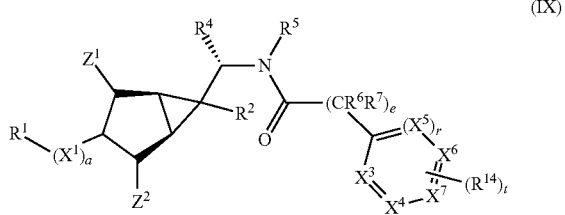
(IX)

or a pharmaceutically acceptable salt thereof, wherein a, e, $X^1$, $R^1$, $R^2$, $R^4$ to $R^7$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N; and $Z^1$ and $Z^2$ are each independently selected from H.

9. The compound of claim 8, of formula (VIIIac),

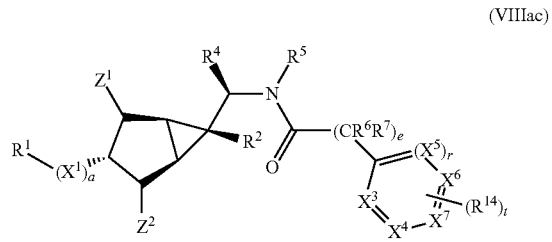
(VIIIac)

or a pharmaceutically acceptable salt thereof, wherein a, e, $X^1$, $R^1$, $R^2$, $R^4$ to $R^7$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N; and $Z^1$ and $Z^2$ are each independently selected from H.

10. The compound of claim 1, of formula (XIII),

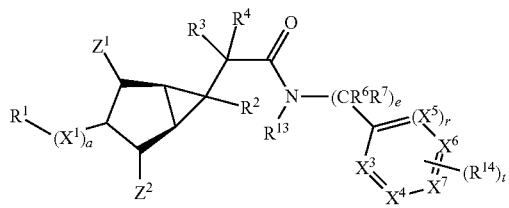

(XIII)

or a pharmaceutically acceptable salt thereof, wherein:

a, e, $X^1$, Y, and $R^1$ to $R^4$, $R^6$, $R^7$, $R^{13}$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N; and $Z^1$ and $Z^2$ are each independently selected from H.

11. The compound of claim 10, of formula (XIIIac),

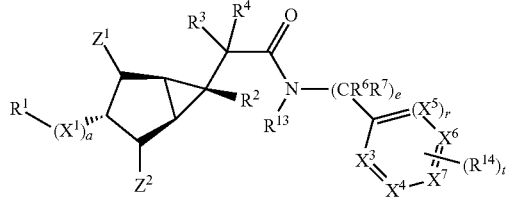

(XIIIac)

or a pharmaceutically acceptable salt thereof, wherein a, e, $X^1$, $R^1$ to $R^4$, $R^6$, $R^7$, $R^{13}$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N; and $Z^1$ and $Z^2$ are each independently selected from H.

12. The compound of claim 10, of formula (XIV) or formula (XV),

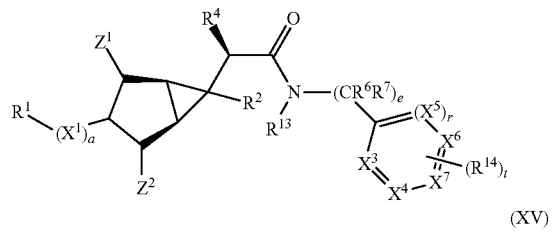

(XIV)

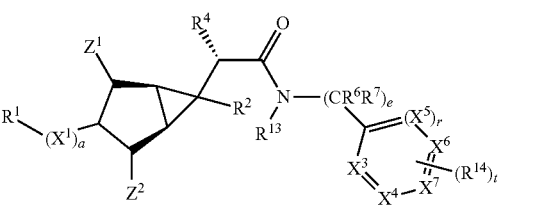

(XV)

or a pharmaceutically acceptable salt thereof, wherein a, e, $X^1$, $R^1$, $R^2$, $R^4$, $R^6$, $R^7$, $R^{13}$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N; and $Z^1$ and $Z^2$ are each independently selected from H.

13. The compound of claim 10, of formula (XIVac),

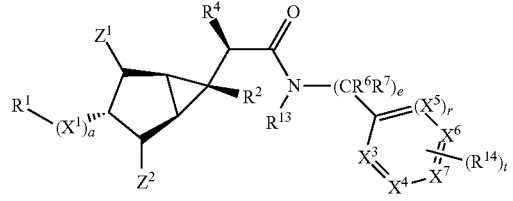

(XIVac)

or a pharmaceutically acceptable salt thereof, wherein a, e, $X^1$, $R^1$, $R^2$, $R^4$, $R^6$, $R^7$, $R^{13}$, and $R^{14}$ are as defined in claim 1;

r is 1;

t is selected from 0, 1, 2, and 3;

$X^7$ is selected from CH and $CR^{14}$;

$X^3$ to $X^6$ are independently selected from CH, $CR^{14}$, and N, wherein no more than three of $X^3$ to $X^7$ may be N; and $Z^1$ and $Z^2$ are each independently selected from H.

14. The compound of claim 1, of formula (V),

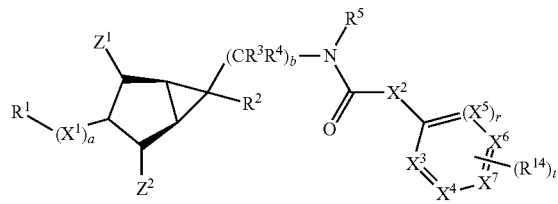

(V)

or a pharmaceutically acceptable salt thereof, wherein a, b, $X^1$ and $X^2$, $R^1$ to $R^5$, and $R^{14}$ are as defined in claim 1;
r is 1;
t is selected from 0, 1, 2, and 3;
$X^7$ is selected from CH and $CR^{14}$;
$X^3$ to $X^6$ are independently selected from CH, $CR^{14}$, and N, wherein no more than three of $X^3$ to $X^7$ may be N; and
$Z^1$ and $Z^2$ are each independently selected from H.

15. The compound of claim 14, of formula (Vac),

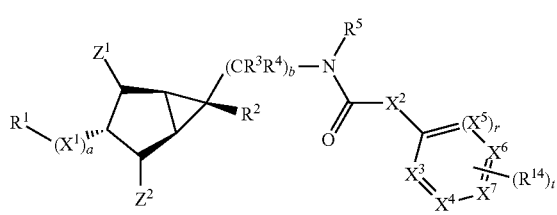

(Vac)

or a pharmaceutically acceptable salt thereof, wherein a, b, $X^1$ and $X^2$, $R^1$ to $R^5$, and $R^{14}$ are as defined in claim 1;
r is 1;
t is selected from 0, 1, 2, and 3;
$X^7$ is selected from CH and $CR^{14}$;
$X^3$ to $X^6$ are independently selected from CH, $CR^{14}$, and N, wherein no more than three of $X^3$ to $X^7$ may be N; and
$Z^1$ and $Z^2$ are each independently selected from H.

16. The compound of claim 15, or a pharmaceutically acceptable salt thereof, wherein $X^2$ is $NR^{13}$.

17. The compound of claim 1, or a pharmaceutically acceptable salt thereof, wherein $R^1$ is selected from $C_{3-8}$-cycloalkyl, 3- to 6-membered heterocycloalkyl comprising 1, 2, or 3 ring heteroatoms selected from N, S, and O, $C_{5-8}$-cycloalkenyl, 5- to 6-membered heterocycloalkenyl comprising 1, 2, or 3 ring heteroatoms selected from N, S, and O, $C_{6-10}$-aryl, and 5- to 10-membered heteroaryl comprising 1, 2, 3, or 4 ring heteroatoms selected from N, S, and O,
wherein said cycloalkyl, heterocycloalkyl, cycloalkenyl, heterocycloalkenyl, aryl, and heteroaryl are optionally substituted by one or more groups independently selected from $R^{15}$ as defined in claim 1.

18. The compound of claim 1, or a pharmaceutically acceptable salt thereof, wherein a is 1; and $X^1$ is selected from O and NH.

19. The compound of claim 1, or a pharmaceutically acceptable salt thereof, wherein a is 0; and $R^1$ is attached to the rest of the molecule via a nitrogen atom of the said $R^1$.

20. The compound of claim 1, or a pharmaceutically acceptable salt thereof, wherein
b is 1;
$R^3$ is independently selected from H, halogen, and $C_{1-6}$-alkyl; and
$R^4$ is independently selected from H, halogen, CN, and $C_{1-6}$-alkyl,
wherein said alkyl is optionally substituted by one or more groups independently selected from $R^{16}$ as defined in claim 1.

21. The compound of claim 1, or a pharmaceutically acceptable salt thereof, wherein Y is selected from:

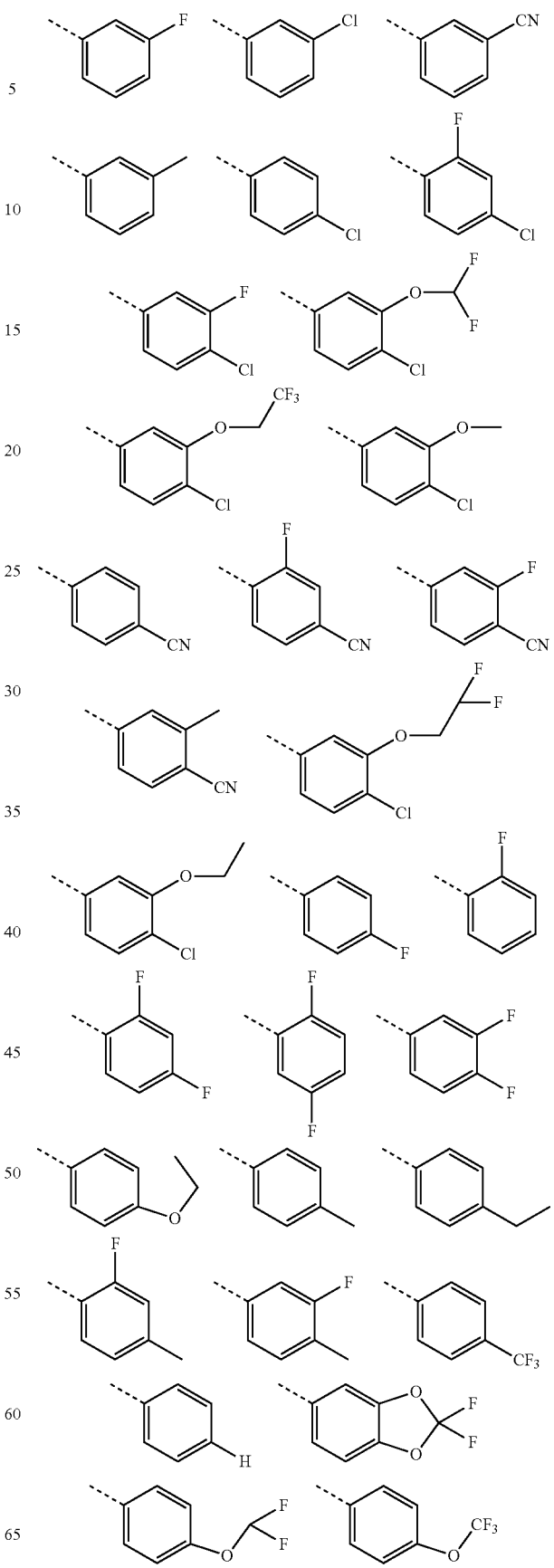

353

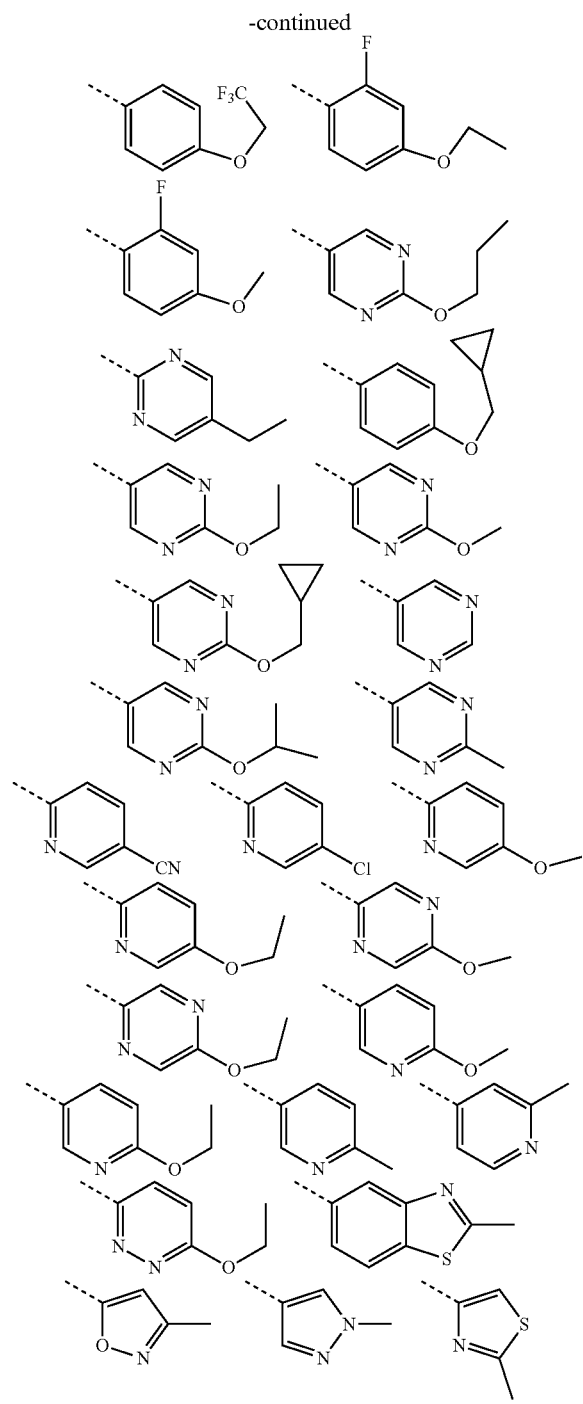

wherein the dashed bonds denotes the point of attachment of Y to the rest of the molecule.

22. The compound of claim 1 or a pharmaceutically acceptable salt thereof, having an inhibitory activity (measured as $IC_{50}$ value) against IDO1 of less than 200 nM.

23. A pharmaceutical composition comprising a compound according to claim 1, or a pharmaceutically acceptable salt thereof, and at least one pharmaceutically acceptable excipient.

24. The pharmaceutical composition of claim 23 comprising a further active agent selected from the group consisting of chemotherapeutic agents and immunotherapeutic agents.

354

25. A method for treating cancer associated with overexpression of IDO1, IDO2, and/or TDO in a subject, the method comprising administering to the subject an effective amount of a compound according to claim 1, or a pharmaceutically acceptable salt thereof.

26. The method of claim 25, wherein the cancer associated with overexpression of IDO1, IDO2, and/or TDO is selected from head and neck cancer, breast cancer (e.g. metastatic breast cancer), prostate cancer (e.g. metastatic prostate cancer), ovarian cancer, endometrial cancer, colon cancer, lung cancer (e.g. non small cell lung cancer), bladder cancer, pancreatic cancer (e.g. metastatic pancreatic cancer), brain tumour (e.g. primary malignant brain tumour), gynecological cancer, peritoneal cancer, skin cancer, thyroid cancer, oesophageal cancer, cervical cancer, gastric cancer, liver cancer, stomach cancer, renal cell cancer, biliary tract cancer, hematologic cancer, and blood cancer.

27. A compound selected from
   4-chloro-N-(1-((1R,3r,5S,6r)-3-hydroxybicyclo[3.1.0]hexan-6-yl)propyl)benzamide;
   4-chloro-N-(1-((1R,3r,5S,6r)-3-(quinolin-4-yloxy)bicyclo[3.1.0]hexan-6-yl)propyl)benzamide;
   4-chloro-N-(1-((1R,3s,5S,6r)-3-hydroxybicyclo[3.1.0]hexan-6-yl)propyl)benzamide;
   4-chloro-N-(1-((1R,3s,5S,6r)-3-(quinolin-4-yloxy)bicyclo[3.1.0]hexan-6-yl)propyl)benzamide;
   4-chloro-N-(1-((1R,3s,5S,6r)-3-((6-fluoroquinazolin-4-yl)oxy)bicyclo[3.1.0]hexan-6-yl)propyl)benzamide;
   4-chloro-N-(1-((1R,3s,5S,6r)-3-(6-fluoro-4-oxoquinazolin-3(4H)-yl)bicyclo[3.1.0]hexan-6-yl)propyl)benzamide
   2-(4-chlorophenyl); —N-((1R,3s,5S,6r)-3-((6-fluoroquinolin-4-yl)oxy)bicyclo[3.1.0]hexan-6-yl)acetamide;
   (1R,5S)—N-(4-chlorophenyl)-3-(quinolin-4-yloxy)bicyclo[3.1.0]hexane-6-carboxamide;
   4-chloro-N-(((1R,3s,5S,6r)-3-((6-fluoroquinolin-4-yl)oxy)bicyclo[3.1.0]hexan-6-yl)methyl)benzamide;
   1-(4-chlorophenyl)-3-((1R,3s,5S,6r)-3-((6-fluoroquinolin-4-yl)oxy)bicyclo[3.1.0]hexan-6-yl)urea;
   2-(4-chlorophenyl)-5-(3-(quinolin-4-yloxy)bicyclo[3.1.0]hexan-6-yl)-1,3,4-oxadiazole;
   4-((6-(2-(4-chlorophenoxy)ethyl)bicyclo[3.1.0]hexan-3-yl)oxy)-6-fluoro-2-(trifluoromethyl)quinoline;
   4-chloro-N-(1-((1R,3s,5S,6r)-3-((6-fluoroquinazolin-4-yl)oxy)bicyclo[3.1.0]hexan-6-yl)ethyl)benzamide;
   4-chloro-N-(1-((1R,3s,5S,6r)-3-(4-fluorophenoxy)bicyclo[3.1.0]hexan-6-yl)propyl)benzamide;
   4-chloro-N-(1-((1R,3s,5S,6r)-3-((2-methylpyridin-4-yl)oxy)bicyclo[3.1.0]hexan-6-yl)propyl)benzamide;
   (1R,5S)—N-(4-chlorobenzyl)-3-(quinolin-4-yloxy)bicyclo[3.1.0]hexane-6-carboxamide;
   (1R,5S)—N-(4-chlorobenzyl)-3-((6-fluoro-2-(trifluoromethyl)quinolin-4-yl)oxy)bicyclo[3.1.0]hexane-6-carboxamide;
   4-chloro-N-(1-((1R,3s,5S,6r)-3-((6-fluoropyridin-3-yl)oxy)bicyclo[3.1.0]hexan-6-yl)propyl)benzamide;
   4-chloro-N-(1-((1R,3s,5S,6r)-3-((6-fluoroquinolin-4-yl)oxy)bicyclo[3.1.0]hexan-6-yl)propyl)benzamide;
   4-chloro-N-(1-((1R,3s,5S,6r)-3-((6-fluoro-2-methylquinolin-4-yl)oxy)bicyclo[3.1.0]hexan-6-yl)propyl)benzamide;
   4-chloro-N-(1-((1R,3s,5S,6r)-3-((7-chloroquinazolin-4-yl)oxy)bicyclo[3.1.0]hexan-6-yl)propyl)benzamide;
   4-chloro-N-(1-((1R,3s,5S,6r)-3-((6-fluoro-2-(trifluoromethyl)quinolin-4-yl)oxy)bicyclo[3.1.0]hexan-6-yl)propyl)benzamide;

4-chloro-N-(((1R,3s,5S,6s)-3-((6-fluoroquinolin-4-yl)oxy)bicyclo[3.1.0]hexan-6-yl)methyl)benzamide;
4-chloro-N-(((1R,3s,5S,6s)-3-((6-fluoro-2-(trifluoromethyl)quinolin-4-yl)oxy)bicyclo[3.1.0]hexan-6-yl)methyl)benzamide;
4-chloro-N-(3-((6-fluoro-2-(trifluoromethyl)quinolin-4-yl)oxy)bicyclo[3.1.0]hexan-6-yl)benzamide;
4-chloro-N-(3-(quinolin-4-yloxy)bicyclo[3.1.0]hexan-6-yl)benzamide;
1-(4-bromophenyl)-N-(3-(quinolin-4-yloxy)bicyclo[3.1.0]hexan-6-yl)methanesulfonamide;
4-chloro-N-(3-(quinolin-4-yloxy)bicyclo[3.1.0]hexan-6-yl)benzenesulfonamide;
1-(4-chlorophenyl)-3-((1R,3r,5S,6r)-3-((6-fluoroquinolin-4-yl)oxy)bicyclo[3.1.0]hexan-6-yl)urea;
2-(4-chlorophenyl)-N-((1R,5S)-3-(quinolin-4-yloxy)bicyclo[3.1.0]hexan-6-yl)acetamide;
2-(4-chlorophenyl)-N-((1R,3r,5S)-3-((6-fluoroquinolin-4-yl)oxy)bicyclo[3.1.0]hexan-6-yl)acetamide;
4-chloro-N-(((1R,3r,5S,6r)-3-((6-fluoroquinolin-4-yl)oxy)bicyclo[3.1.0]hexan-6-yl)methyl)benzamide;
4-chloro-N-(((1R,3r,5S,6r)-3-((4-chloroquinolin-6-yl)oxy)bicyclo[3.1.0]hexan-6-yl)methyl)benzamide;
4-chloro-N-(1-((1R,3s,5S,6r)-3-(7-fluoro-4-oxoquinazolin-3(4H)-yl)bicyclo[3.1.0]hexan-6-yl)propyl)benzamide;
4-chloro-N-(1-((1R,3s,5S,6r)-3-((7-fluoroquinazolin-4-yl)oxy)bicyclo[3.1.0]hexan-6-yl)propyl)benzamide;
4-chloro-N-(1-((1R,3s,5S,6r)-3-((5-fluoro-4-oxoquinazolin-3(4H)-yl)bicyclo[3.1.0]hexan-6-yl)propyl)benzamide;
4-chloro-N-(1-((1R,3s,5S,6r)-3-((5-fluoroquinazolin-4-yl)oxy)bicyclo[3.1.0]hexan-6-yl)propyl)benzamide;
N-(1-((1R,3s,5S,6r)-3-((1,5-naphthyridin-4-yl)oxy)bicyclo[3.1.0]hexan-6-yl)propyl)-4-chlorobenzamide;
4-chloro-N-(1-((1R,3s,5S,6r)-3-((3-fluoropyridin-2-yl)oxy)bicyclo[3.1.0]hexan-6-yl)propyl)benzamide;
4-chloro-N-(1-((1R,3s,5S,6r)-3-((6-methylpyridin-2-yl)oxy)bicyclo[3.1.0]hexan-6-yl)propyl)benzamide;
4-chloro-N-(1-((1R,3s,5S,6r)-3-((3-methylpyridin-2-yl)oxy)bicyclo[3.1.0]hexan-6-yl)propyl)benzamide;
4-chloro-N-(1-((1R,3s,5S,6r)-3-(2,5-difluorophenoxy)bicyclo[3.1.0]hexan-6-yl)propyl)benzamide;
4-chloro-N-(1-((1R,3s,5S,6r)-3-(quinolin-8-yloxy)bicyclo[3.1.0]hexan-6-yl)propyl)benzamide;
4-chloro-N-(1-((1R,3s,5S,6r)-3-(2,6-difluorophenoxy)bicyclo[3.1.0]hexan-6-yl)propyl)benzamide;
N-(1-((1R,3s,5S,6r)-3-(2-(2-amino-2-oxoethyl)phenoxy)bicyclo[3.1.0]hexan-6-yl)propyl)-4-chlorobenzamide;
4-chloro-N-(1-((1R,3s,5S,6r)-3-(cinnolin-4-yloxy)bicyclo[3.1.0]hexan-6-yl)propyl)benzamide;
4-chloro-N-(1-((1R,3s,5S,6r)-3-(4-oxocinnolin-1(4H)-yl)bicyclo[3.1.0]hexan-6-yl)propyl)benzamide;
4-chloro-N-(1-((1R,3s,5S,6r)-3-(2-((dimethylamino)methyl)phenoxy)bicyclo[3.1.0]hexan-6-yl)propyl)benzamide;
4-chloro-N-(1-((1R,3s,5S,6r)-3-(quinolin-3-yloxy)bicyclo[3.1.0]hexan-6-yl)propyl)benzamide;
4-chloro-N-(1-((1R,3s,5S,6r)-3-((1-methyl-2-oxo-1,2-dihydroquinolin-4-yl)oxy)bicyclo[3.1.0]hexan-6-yl)propyl)benzamide;
N-(1-((1R,3s,5S,6r)-3-(1H-pyrazolo[4,3-c]pyridin-1-yl)bicyclo[3.1.0]hexan-6-yl)propyl)-4-chlorobenzamide;
4-chloro-N-(1-((1R,3s,5S,6r)-3-((5-fluoro-2-methylpyrimidin-4-yl)oxy)bicyclo[3.1.0]hexan-6-yl)propyl)benzamide;
4-chloro-N-(1-((1R,3s,5S,6r)-3-(7-chloro-4-oxoquinazolin-3(4H)-yl)bicyclo[3.1.0]hexan-6-yl)propyl)benzamide;
4-chloro-N-(1-((1R,3s,5S,6r)-3-((5-fluoropyrimidin-4-yl)oxy)bicyclo[3.1.0]hexan-6-yl)propyl)benzamide;
N-(1-((1R,3s,5S,6r)-3-((1,6-naphthyridin-4-yl)oxy)bicyclo[3.1.0]hexan-6-yl)propyl)-4-chlorobenzamide;
4-chloro-N-(1-((1R,3s,5S,6r)-3-((7-fluoroquinolin-4-yl)oxy)bicyclo[3.1.0]hexan-6-yl)propyl)benzamide;
4-chloro-N-(1-((1R,3s,5S,6r)-3-((4-chloroquinolin-7-yl)oxy)bicyclo[3.1.0]hexan-6-yl)propyl)benzamide;
4-chloro-N-(1-((1R,3s,5S,6r)-3-((5-fluoropyridin-3-yl)oxy)bicyclo[3.1.0]hexan-6-yl)propyl)benzamide;
4-chloro-N-(1-((1R,3s,5S,6r)-3-(quinazolin-4-yloxy)bicyclo[3.1.0]hexan-6-yl)propyl)benzamide;
4-chloro-N-(1-((1R,3s,5S,6r)-3-((2-chloropyridin-3-yl)oxy)bicyclo[3.1.0]hexan-6-yl)propyl)benzamide;
2-(4-chlorophenyl)-N-((1R,3s,5S,6r)-3-((6-fluoroquinazolin-4-yl)oxy)bicyclo[3.1.0]hexan-6-yl)acetamide;
2-(4-chlorophenyl)-N-((1R,3s,5S,6r)-3-(6-fluoro-4-oxoquinazolin-3(4H)-yl)bicyclo[3.1.0]hexan-6-yl)acetamide;
4-chloro-N-(1-((1R,3s,5S,6r)-3-(6-fluoro-4-oxoquinazolin-3(4H)-yl)bicyclo[3.1.0]hexan-6-yl)ethyl)benzamide;
4-chloro-N-(1-((1R,3s,5S,6r)-3-((6-fluoroquinazolin-4-yl)oxy)bicyclo[3.1.0]hexan-6-yl)ethyl)benzamide;
4-chloro-N-(((1R,3s,5S,6r)-3-(6-fluoro-4-oxoquinazolin-3(4H)-yl)bicyclo[3.1.0]hexan-6-yl)methyl)benzamide;
4-cyano-N-(1-((1R,3s,5S,6r)-3-((6-fluoroquinazolin-4-yl)oxy)bicyclo[3.1.0]hexan-6-yl)propyl)benzamide;
4-cyano-N-(1-((1R,3s,5S,6r)-3-(6-fluoro-4-oxoquinazolin-3(4H)-yl)bicyclo[3.1.0]hexan-6-yl)propyl)benzamide;
N-(1-((1R,3s,5S,6r)-3-((6-fluoroquinazolin-4-yl)oxy)bicyclo[3.1.0]hexan-6-yl)propyl)-2-methoxypyrimidine-5-carboxamide;
2,2-difluoro-N-(1-((1R,3s,5S,6r)-3-((6-fluoroquinazolin-4-yl)oxy)bicyclo[3.1.0]hexan-6-yl)propyl)benzo[d][1,3]dioxole-5-carboxamide;
4-chloro-N-(1-((1R,3s,5S,6r)-3-((7-fluoroquinazolin-4-yl)oxy)bicyclo[3.1.0]hexan-6-yl)ethyl)benzamide;
4-chloro-N-(1-((1R,3s,5S,6r)-3-((3-methylpyridin-2-yl)oxy)bicyclo[3.1.0]hexan-6-yl)ethyl)benzamide;
4-chloro-N-(1-((1R,3s,5S,6r)-3-(phthalazin-1-yloxy)bicyclo[3.1.0]hexan-6-yl)propyl)benzamide;
4-chloro-N-(1-((1R,3s,5S,6r)-3-morpholinobicyclo[3.1.0]hexan-6-yl)propyl)benzamide;
N-(1-((1R,3s,5S,6r)-3-(6-fluoro-4-oxoquinazolin-3(4H)-yl)bicyclo[3.1.0]hexan-6-yl)propyl)-6-methoxynicotinamide;
5-chloro-N-(1-((1R,3s,5S,6r)-3-(6-fluoro-4-oxoquinazolin-3(4H)-yl)bicyclo[3.1.0]hexan-6-yl)propyl)picolinamide;
5-cyano-N-(1-((1R,3s,5S,6r)-3-(6-fluoro-4-oxoquinazolin-3(4H)-yl)bicyclo[3.1.0]hexan-6-yl)propyl)picolinamide;
5-chloro-N-(1-((1R,5S)-3-(cinnolin-4-yloxy)bicyclo[3.1.0]hexan-6-yl)propyl)picolinamide;
N-(1-((1R,3s,5S,6r)-3-((6-fluoroquinazolin-4-yl)oxy)bicyclo[3.1.0]hexan-6-yl)propyl)-6-methoxynicotinamide;
2-(4-chlorophenyl)-N-((1R,3s,5S,6r)-3-(cinnolin-4-yloxy)bicyclo[3.1.0]hexan-6-yl)acetamide;
N-(1-((1R,3s,5S,6r)-3-(cinnolin-4-yloxy)bicyclo[3.1.0]hexan-6-yl)propyl)-4-cyanobenzamide;

N-(1-((1R,3s,5S,6r)-3-(1H-1,2,4-triazol-1-yl)bicyclo[3.1.0]hexan-6-yl)propyl)-4-chlorobenzamide;
N-(1-((1R,3s,5S,6r)-3-(cinnolin-4-yloxy)bicyclo[3.1.0]hexan-6-yl)propyl)-5-cyanopicolinamide;
5-cyano-N-(1-((1R,3s,5S,6r)-3-(4-oxocinnolin-1(4H)-yl)bicyclo[3.1.0]hexan-6-yl)propyl)picolinamide;
ethyl 3-(4-chlorobenzamido)-3-((1R,3s,5S,6r)-3-(cinnolin-4-yloxy)bicyclo[3.1.0]hexan-6-yl)propanoate;
2-(4-chlorophenyl)-N-((1R,3s,5S,6r)-3-(4-oxocinnolin-1(4H)-yl)bicyclo[3.1.0]hexan-6-yl)acetamide;
2-(4-chlorophenyl)-N-((1R,3s,5S,6r)-3-(cinnolin-4-yloxy)bicyclo[3.1.0]hexan-6-yl)-N-methylacetamide;
4-cyano-N-(2-((1R,5S)-3-(4-oxocinnolin-1(4H)-yl)bicyclo[3.1.0]hexan-6-yl)propan-2-yl)benzamide;
N-(2-((1R,5S)-3-(cinnolin-4-yloxy)bicyclo[3.1.0]hexan-6-yl)propan-2-yl)-4-cyanobenzamide;
N-(1-((1R,3s,5S,6r)-3-(1H-benzo[d]imidazol-1-yl)bicyclo[3.1.0]hexan-6-yl)propyl)-4-chlorobenzamide;
N-(1-((1R,3s,5S,6r)-3-azidobicyclo[3.1.0]hexan-6-yl)propyl)-4-chlorobenzamide;
4-chloro-N-(1-((1R,3s,5S,6r)-3-(4-cyclopropyl-1H-1,2,3-triazol-1-yl)bicyclo[3.1.0]hexan-6-yl)propyl)benzamide;
4-chloro-N-(1-((1R,3s,5S,6r)-3-((4-chloro-2-methylpyridin-3-yl)oxy)bicyclo[3.1.0]hexan-6-yl)propyl)benzamide;
4-chloro-N-(1-((1R,3s,5S,6r)-3-((3-fluoro-2-methylpyridin-4-yl)oxy)bicyclo[3.1.0]hexan-6-yl)propyl)benzamide;
1-((1R,3s,5S,6r)-6-(1-(4-chlorobenzamido)propyl)bicyclo[3.1.0]hexan-3-yl)-1H-1,2,3-triazole-4-carboxylic acid;
1-((1R,3s,5S,6r)-6-(1-(4-chlorobenzamido)propyl)bicyclo[3.1.0]hexan-3-yl)-1H-1,2,3-triazole-4-carboxamide;
4-chloro-N-(1-((1R,3s,5S,6r)-3-((tetrahydro-2H-pyran-4-yl)methoxy)bicyclo[3.1.0]hexan-6-yl)propyl)benzamide;
4-chloro-N-(1-((1R,3s,5S,6r)-3-(4-(2-hydroxypropan-2-yl)-1H-1,2,3-triazol-1-yl)bicyclo[3.1.0]hexan-6-yl)propyl)benzamide;
4-chloro-N-(1-((1R,3s,5S,6r)-3-(4-(pyrrolidine-1-carbonyl)-1H-1,2,3-triazol-1-yl)bicyclo[3.1.0]hexan-6-yl)propyl)benzamide;
N-(1-((1R,3s,5S,6r)-3-(1H-benzo[d][1,2,3]triazol-1-yl)bicyclo[3.1.0]hexan-6-yl)propyl)-4-chlorobenzamide;
N-(1-((1R,3s,5S,6r)-3-(2H-benzo[d][1,2,3]triazol-2-yl)bicyclo[3.1.0]hexan-6-yl)propyl)-4-chlorobenzamide;
4-chloro-N-(1-((1R,3s,5S,6r)-3-((tetrahydro-2H-pyran-4-yl)oxy)bicyclo[3.1.0]hexan-6-yl)propyl)benzamide;
4-cyano-N-(1-((1R,3s,5S,6r)-3-((7-fluoroquinazolin-4-yl)oxy)bicyclo[3.1.0]hexan-6-yl)ethyl)benzamide;
4-chloro-N—(S)-1-((1R,3R,5S,6r)-3-(cinnolin-4-yloxy)bicyclo[3.1.0]hexan-6-yl)propyl)benzamide;
4-chloro-N—(R)-1-((1R,3S,5S,6r)-3-(cinnolin-4-yloxy)bicyclo[3.1.0]hexan-6-yl)propyl)benzamide;
4-cyano-N-(1-((1R,3r,5S,6r)-3-hydroxybicyclo[3.1.0]hexan-6-yl)ethyl)benzamide;
4-cyano-N-(1-((1R,3s,5S,6r)-3-hydroxybicyclo[3.1.0]hexan-6-yl)ethyl)benzamide;
4-cyano-N-(1-((1R,3s,5S,6r)-3-((6-fluoroquinazolin-4-yl)oxy)bicyclo[3.1.0]hexan-6-yl)ethyl)benzamide;
4-cyano-N-(1-((1R,3s,5S,6r)-3-(6-fluoro-4-oxoquinazolin-3(4H)-yl)bicyclo[3.1.0]hexan-6-yl)ethyl)benzamide;
N-(1-((1R,5S,6R)-bicyclo[3.1.0]hex-2-en-6-yl)propyl)-4-chlorobenzamide;
4-chloro-N-(1-((1R,3s,5S,6r)-3-(2,3-dioxoindolin-1-yl)bicyclo[3.1.0]hexan-6-yl)propyl)benzamide;
N-(1-((1R,3s,5S,6r)-3-((6-fluoroquinazolin-4-yl)oxy)bicyclo[3.1.0]hexan-6-yl)ethyl)-6-methoxynicotinamide;
4-chloro-N-(1-((1R,3s,5S,6r)-3-(phenylsulfonamido)bicyclo[3.1.0]hexan-6-yl)propyl)benzamide;
N-((1R,3s,5S,6r)-6-(1-(4-chlorobenzamido)propyl)bicyclo[3.1.0]hexan-3-yl)picolinamide;
N-((1R,3s,5S,6r)-6-(1-(4-chlorobenzamido)propyl)bicyclo[3.1.0]hexan-3-yl)quinoline-2-carboxamide;
4-chloro-N-(1-((1R,3s,5S,6r)-3-(3,3-difluoro-2-oxoindolin-1-yl)bicyclo[3.1.0]hexan-6-yl)propyl)benzamide;
4-cyano-N-(1-((1R,3s,5S,6r)-3-(7-fluoro-4-oxoquinazolin-3(4H)-yl)bicyclo[3.1.0]hexan-6-yl)ethyl)benzamide;
4-chloro-N-(1-((1R,3s,5S,6r)-3-(5-fluoro-2-oxoindolin-1-yl)bicyclo[3.1.0]hexan-6-yl)propyl)benzamide;
4-chloro-N-(1-((1R,3s,5S,6r)-3-(3,3-dimethyl-2,5-dioxopyrrolidin-1-yl)bicyclo[3.1.0]hexan-6-yl)propyl)benzamide;
4-chloro-N-(1-((1R,3s,5S,6r)-3-((6-fluoroquinazolin-4-yl)amino)bicyclo[3.1.0]hexan-6-yl)propyl)benzamide;
N-(1-((1R,3s,5S,6r)-3-((7-fluoroquinazolin-4-yl)oxy)bicyclo[3.1.0]hexan-6-yl)ethyl)-6-methoxynicotinamide;
4-chloro-N-(1-((1R,3s,5S,6r)-3-(6-fluoro-1H-benzo[d]imidazol-1-yl)bicyclo[3.1.0]hexan-6-yl)propyl)benzamide;
4-chloro-N-(1-((1R,3r,5S,6r)-3-((6-fluoroquinolin-4-yl)oxy)bicyclo[3.1.0]hexan-6-yl)propyl)benzamide;
4-chloro-N-(1-((1R,3r,5S,6r)-3-((4-chloroquinolin-6-yl)oxy)bicyclo[3.1.0]hexan-6-yl)propyl)benzamide;
N-(1-((1R,3s,5S,6r)-3-hydroxybicyclo[3.1.0]hexan-6-yl)ethyl)-6-methoxynicotinamide;
4-cyano-N-(1-((1R,3s,5S,6r)-3-(4-cyclopropyl-1H-1,2,3-triazol-1-yl)bicyclo[3.1.0]hexan-6-yl)ethyl)benzamide;
4-cyano-N—((R)-1-((1R,3S,5S,6r)-3-((6-fluoroquinazolin-4-yl)oxy)bicyclo[3.1.0]hexan-6-yl)ethyl)benzamide;
4-cyano-N—((S)-1-((1R,3R,5S,6r)-3-((6-fluoroquinazolin-4-yl)oxy)bicyclo[3.1.0]hexan-6-yl)ethyl)benzamide;
4-cyano-N—((R)-1-((1R,3S,5S,6r)-3-((7-fluoroquinazolin-4-yl)oxy)bicyclo[3.1.0]hexan-6-yl)ethyl)benzamide;
4-cyano-N—((S)-1-((1R,3R,5S,6r)-3-((7-fluoroquinazolin-4-yl)oxy)bicyclo[3.1.0]hexan-6-yl)ethyl)benzamide;
Ethyl 3-(4-chlorobenzamido)-3-((1R,3s,5S,6r)-3-((6-fluoroquinazolin-4-yl)oxy)bicyclo[3.1.0]hexan-6-yl)propanoate;
N-(1-((1R,3s,5S,6r)-3-(cinnolin-4-yloxy)bicyclo[3.1.0]hexan-6-yl)ethyl)-4-cyanobenzamide;
4-cyano-N-(1-((1R,3s,5S,6r)-3-(4-oxocinnolin-1(4H)-yl)bicyclo[3.1.0]hexan-6-yl)ethyl)benzamide;
4-chloro-N-(1-((1R,3s,5S,6r)-3-((6-fluoroquinazolin-4-yl)oxy)bicyclo[3.1.0]hexan-6-yl)-3-hydroxypropyl)benzamide;
4-chloro-N-(1-((1R,3r,5S,6r)-3-(cinnolin-4-yloxy)bicyclo[3.1.0]hexan-6-yl)propyl)benzamide;
4-chloro-N-(1-((1R,3s,5S,6r)-3-(cinnolin-4-yloxy)bicyclo[3.1.0]hexan-6-yl)-3-hydroxypropyl)benzamide;
4-chloro-N-(3-hydroxy-1-((1R,3s,5S,6r)-3-(4-oxocinnolin-1(4H)-yl)bicyclo[3.1.0]hexan-6-yl)propyl)benzamide;

4-chloro-N—((R)-1-((1R,3S,5S,6r)-3-(4-(2-hydroxypropan-2-yl)-1H-1,2,3-triazol-1-yl)bicyclo[3.1.0]hexan-6-yl)propyl)benzamide;
4-chloro-N—((S)-1-((1R,3R,5S,6r)-3-(4-(2-hydroxypropan-2-yl)-1H-1,2,3-triazol-1-yl)bicyclo[3.1.0]hexan-6-yl)propyl)benzamide;
N-((1R,3s,5S,6r)-6-(1-(4-cyanobenzamido)ethyl)bicyclo[3.1.0]hexan-3-yl)picolinamide;
N-((1R,3s,5S,6r)-6-(1-(4-chlorobenzamido)propyl)bicyclo[3.1.0]hexan-3-yl)-5-fluoropicolinamide;
N-((1R,3s,5S,6r)-6-(1-(4-chlorobenzamido)propyl)bicyclo[3.1.0]hexan-3-yl)nicotinamide;
4-chloro-N-(1-((1R,3s,5S,6r)-3-(4-(hydroxymethyl)-1H-1,2,3-triazol-1-yl)bicyclo[3.1.0]hexan-6-yl)propyl)benzamide;
4-chloro-N-(1-((1R,3s,5S,6r)-3-(4-(prop-1-en-2-yl)-1H-1,2,3-triazol-1-yl)bicyclo[3.1.0]hexan-6-yl)propyl)benzamide;
3-(4-chlorobenzamido)-3-((1R,3s,5S,6r)-3-((6-fluoroquinazolin-4-yl)oxy)bicyclo[3.1.0]hexan-6-yl)propanoic acid;
N-((1R,3s,5S,6r)-6-(1-(4-chlorobenzamido)propyl)bicyclo[3.1.0]hexan-3-yl)pyrimidine-4-carboxamide;
6-chloro-N-((1R,3s,5S,6r)-6-(1-(4-chlorobenzamido)propyl)bicyclo[3.1.0]hexan-3-yl)pyrazine-2-carboxamide;
N-((1R,3s,5S,6r)-6-(1-(4-chlorobenzamido)propyl)bicyclo[3.1.0]hexan-3-yl)pyridazine-3-carboxamide;
N-((1R,3s,5S,6r)-6-(1-(4-chlorobenzamido)propyl)bicyclo[3.1.0]hexan-3-yl)pyrazine-2-carboxamide;
4-chloro-N-(1-((1R,3s,5S,6r)-3-(5-cyclopropyl-1H-1,2,3-triazol-1-yl)bicyclo[3.1.0]hexan-6-yl)propyl)benzamide;
4-chloro-N-(1-((1R,3s,5S,6r)-3-(5-(2-hydroxypropan-2-yl)-1H-1,2,3-triazol-1-yl)bicyclo[3.1.0]hexan-6-yl)propyl)benzamide;
4-chloro-N-(1-((1R,3s,5S,6r)-3-(5-(hydroxymethyl)-1H-1,2,3-triazol-1-yl)bicyclo[3.1.0]hexan-6-yl)propyl)benzamide;
N-((1R,3s,5S,6r)-6-(1-(4-chlorobenzamido)propyl)bicyclo[3.1.0]hexan-3-yl)piperazine-1-carboxamide;
N-((1R,3s,5S,6r)-6-(1-(4-chlorobenzamido)propyl)bicyclo[3.1.0]hexan-3-yl)morpholine-4-carboxamide;
3-chloro-N-((1R,3s,5S,6r)-6-(1-(4-chlorobenzamido)propyl)bicyclo[3.1.0]hexan-3-yl)-4-(trifluoromethyl)picolinamide;
4-chloro-N-(1-((1R,3s,5S,6r)-3-(methylsulfonamido)bicyclo[3.1.0]hexan-6-yl)propyl)benzamide;
4-chloro-N-(1-((1R,3s,5S,6r)-3-((1-methylcyclopropane)-1-sulfonamido)bicyclo[3.1.0]hexan-6-yl)propyl)benzamide;
4-chloro-N-(1-((1R,3s,5S,6r)-3-(1,3-dioxoisoindolin-2-yl)bicyclo[3.1.0]hexan-6-yl)propyl)benzamide;
4-chloro-N-(1-((1R,3s,5S,6r)-3-(6-fluoro-1H-indazol-1-yl)bicyclo[3.1.0]hexan-6-yl)propyl)benzamide;
4-chloro-N-(1-((1R,3s,5S,6r)-3-(6-fluoro-2H-indazol-2-yl)bicyclo[3.1.0]hexan-6-yl)propyl)benzamide;
N-((1R,3s,5S,6r)-6-(1-(4-chlorobenzamido)propyl)bicyclo[3.1.0]hexan-3-yl)-5-methoxypicolinamide;
4-chloro-N-(1-((1R,3s,5S,6r)-3-(5-ethyl-1H-1,2,3-triazol-1-yl)bicyclo[3.1.0]hexan-6-yl)propyl)benzamide;
4-chloro-N-(1-((1R,3s,5S,6r)-3-(cyano(phenyl)methyl)bicyclo[3.1.0]hexan-6-yl) propyl)benzamide;
4-chloro-N-(1-((1R,3s,5S,6r)-3-(4-ethyl-1H-1,2,3-triazol-1-yl)bicyclo[3.1.0]hexan-6-yl)propyl)benzamide;
4-chloro-N-(1-((1R,3s,5S,6r)-3-(4-cyclopropyl-1H-1,2,3-triazol-1-yl)bicyclo[3.1.0]hexan-6-yl)-2-hydroxyethyl)benzamide;
Methyl 2-(4-chlorobenzamido)-2-((1R,3s,5S,6r)-3-(4-cyclopropyl-1H-1,2,3-triazol-1-yl)bicyclo[3.1.0]hexan-6-yl)acetate;
N-((1R,3s,5S,6r)-6-(1-(4-chlorobenzamido)propyl)bicyclo[3.1.0]hexan-3-yl)-5-fluoronicotinamide;
N-((1R,3s,5S,6r)-6-(1-(4-chlorobenzamido)propyl)bicyclo[3.1.0]hexan-3-yl)-3,5-difluoropicolinamide;
4-chloro-N-(1-((1R,3s,5S,6r)-3-(3-cyclopropyl-4H-1,2,4-triazol-4-yl)bicyclo[3.1.0]hexan-6-yl)propyl)benzamide;
4-chloro-N-(1-((1R,3s,5S,6r)-3-(4-cyclopropyl-1H-1,2,3-triazol-1-yl)bicyclo[3.1.0]hexan-6-yl)-2-methoxyethyl)benzamide;
N-(1-((1R,3s,5S,6r)-3-(1H-pyrazolo[3,4-c]pyridin-1-yl)bicyclo[3.1.0]hexan-6-yl)propyl)-4-chlorobenzamide;
4-chloro-N-(1-((1R,3s,5S,6r)-3-(1-oxoisoindolin-2-yl)bicyclo[3.1.0]hexan-6-yl)propyl)benzamide;
4-chloro-N-(1-((1R,3s,5S,6r)-3-(5,6-dichloro-1H-benzo[d]imidazol-1-yl)bicyclo[3.1.0]hexan-6-yl)propyl)benzamide;
N-((1R,3s,5S,6r)-6-(1-(4-chlorobenzamido)propyl)bicyclo[3.1.0]hexan-3-yl)-1H-pyrazole-4-carboxamide;
N-(1-((1R,3s,5S,6r)-3-(6-bromo-1H-benzo[d][1,2,3]triazol-1-yl)bicyclo[3.1.0]hexan-6-yl)propyl)-4-chlorobenzamide;
N-(1-((1R,3s,5S,6r)-3-(5-bromo-2H-benzo[d][1,2,3]triazol-2-yl)bicyclo[3.1.0]hexan-6-yl)propyl)-4-chlorobenzamide;
4-chloro-N-(1-((1R,3s,5S,6r)-3-(2-oxo-2,3-dihydro-1H-benzo[d]imidazol-1-yl)bicyclo[3.1.0]hexan-6-yl)propyl)benzamide;
4-chloro-N-(1-((1R,3s,5S,6r)-3-(3-methyl-2-oxo-2,3-dihydro-1H-benzo[d]imidazol-1-yl)bicyclo[3.1.0]hexan-6-yl)propyl)benzamide;
N-(1-((1R,3s,5S,6r)-3-(4H-imidazo[4,5-b]pyridin-4-yl)bicyclo[3.1.0]hexan-6-yl)propyl)-4-chlorobenzamide;
N-(1-((1R,3s,5S,6r)-3-(1H-imidazo[4,5-b]pyridin-1-yl)bicyclo[3.1.0]hexan-6-yl)propyl)-4-chlorobenzamide;
N-(1-((1R,3s,5S,6r)-3-(3H-imidazo[4,5-b]pyridin-3-yl)bicyclo[3.1.0]hexan-6-yl)propyl)-4-chlorobenzamide;
4-chloro-N-(1-((1R,3s,5S,6r)-3-(2-oxooxazolidin-3-yl)bicyclo[3.1.0]hexan-6-yl)propyl)benzamide;
4-chloro-N-(1-((1R,3r,5S,6r)-3-(4-cyclopropyl-1H-1,2,3-triazol-1-yl)bicyclo[3.1.0]hexan-6-yl)propyl)benzamide;
4-chloro-N-(1-((1R,3r,5S,6r)-3-(4-(hydroxymethyl)-1H-1,2,3-triazol-1-yl)bicyclo[3.1.0]hexan-6-yl)propyl)benzamide;
N-((1R,3s,5S,6r)-6-(1-(4-chlorobenzamido)propyl)bicyclo[3.1.0]hexan-3-yl)-3-fluoropicolinamide;
4-chloro-N-(1-((1R,3s,5S,6r)-3-(3-methyl-3-(pyridin-2-yl)ureido)bicyclo[3.1.0]hexan-6-yl)propyl)benzamide;
Ethyl 2-(((1R,3s,5S,6r)-6-(1-(4-chlorobenzamido)propyl)bicyclo[3.1.0]hexan-3-yl)amino)-2-phenylacetate;
4-chloro-N-(1-((1R,3r,5S,6r)-3-(5-cyclopropyl-1H-1,2,3-triazol-1-yl)bicyclo[3.1.0]hexan-6-yl)propyl)benzamide;
4-chloro-N-(1-((1R,3s,5S,6r)-3-(5-fluoro-2-oxo-2,3-dihydro-1H-benzo[d]imidazol-1-yl)bicyclo[3.1.0]hexan-6-yl)propyl)benzamide;
4-chloro-N-(1-((1R,3s,5S,6r)-3-((6-fluoro-1H-benzo[d]imidazol-2-yl)oxy)bicyclo[3.1.0]hexan-6-yl)propyl)benzamide;
4-chloro-N-(1-((1R,3s,5S,6r)-3-(4-fluoro-1H-benzo[d]imidazol-1-yl)bicyclo[3.1.0]hexan-6-yl)propyl)benzamide;

4-chloro-N-(1-((1R,3s,5S,6r)-3-(7-fluoro-1H-benzo[d]
imidazol-1-yl)bicyclo[3.1.0]hexan-6-yl)propyl)benz-
amide
N-(1-((1R,3s,5S,6r)-3-(1H-imidazo[4,5-c]pyridin-1-yl)
bicyclo[3.1.0]hexan-6-yl)propyl)-4-chlorobenzamide;
N-(1-((1R,3s,5S,6r)-3-(3H-imidazo[4,5-c]pyridin-3-yl)
bicyclo[3.1.0]hexan-6-yl)propyl)-4-chlorobenzamide;
N-(1-((1R,3s,5S,6r)-3-(5H-imidazo[4,5-c]pyridin-5-yl)
bicyclo[3.1.0]hexan-6-yl)propyl)-4-chlorobenzamide;
4-chloro-N-(1-((1R,3s,5S,6r)-3-(5-fluoro-1H-benzo[d]
imidazol-1-yl)bicyclo[3.1.0]hexan-6-yl)propyl)benz-
amide;
4-chloro-N-(1-((1R,3s,5S,6r)-3-(4-phenyl-1H-imidazol-
1-yl)bicyclo[3.1.0]hexan-6-yl)propyl)benzamide;
4-chloro-N-(1-((1R,3s,5S,6r)-3-(2-methyl-1H-imidazol-
1-yl)bicyclo[3.1.0]hexan-6-yl)propyl)benzamide;
methyl (S/R)-2-((1R,3S,5S,6S)-6-((R/S)-1-(4-chloroben-
zamido)propyl)bicyclo [3.1.0]hexan-3-yl)-2-phenylac-
etate;
methyl (S/R)-2-((1R,3R,5S,6S)-6-((S/R)-1-(4-chloroben-
zamido)propyl)bicyclo[3.1.0]hexan-3-yl)-2-phenylac-
etate;
4-chloro-N-(1-((1R,3s,5S,6r)-3-(4-phenyl-2H-1,2,3-tri-
azol-2-yl)bicyclo[3.1.0]hexan-6-yl)propyl)benzamide;
4-chloro-N-(1-((1R,3s,5S,6r)-3-(7-fluoro-2H-indazol-2-
yl)bicyclo[3.1.0]hexan-6-yl)propyl)benzamide;
4-chloro-N-(1-((1R,3s,5S,6r)-3-(7-fluoro-1H-indazol-1-
yl)bicyclo[3.1.0]hexan-6-yl)propyl)benzamide;
4-chloro-N-(1-((1R,3s,5S,6r)-3-(5-fluoro-2H-indazol-2-
yl)bicyclo[3.1.0]hexan-6-yl)propyl)benzamide;
4-chloro-N-(1-((1R,3s,5S,6r)-3-(5-fluoro-1H-indazol-1-
yl)bicyclo[3.1.0]hexan-6-yl)propyl)benzamide;
4-chloro-N-(1-((1R,3s,5S,6r)-3-(4-fluoro-2H-indazol-2-
yl)bicyclo[3.1.0]hexan-6-yl)propyl)benzamide;
4-chloro-N-(1-((1R,3s,5S,6r)-3-(4-fluoro-1H-indazol-1-
yl)bicyclo[3.1.0]hexan-6-yl)propyl)benzamide;
N-(1-((1R,3s,5S,6r)-3-(2H-pyrazolo[3,4-b]pyridin-2-yl)
bicyclo[3.1.0]hexan-6-yl)propyl)-4-chlorobenzamide;
N-(1-((1R,3s,5S,6r)-3-(1H-pyrazolo[3,4-b]pyridin-1-yl)
bicyclo[3.1.0]hexan-6-yl)propyl)-4-chlorobenzamide;
4-chloro-N-(1-((1R,3s,5S,6r)-3-(4,6-difluoro-2H-benzo
[d][1,2,3]triazol-2-yl)bicyclo[3.1.0]hexan-6-yl)propyl)
benzamide
4-chloro-N-(1-((1R,3r,5S,6r)-3-(4-(methoxymethyl)-1H-
1,2,3-triazol-1-yl)bicyclo[3.1.0]hexan-6-yl)propyl)
benzamide;
4-chloro-N-(1-((1R,3r,5S,6r)-3-(4-((2-methoxyethoxy)
methyl)-1H-1,2,3-triazol-1-yl)bicyclo[3.1.0]hexan-6-
yl)propyl)benzamide;
4-chloro-N-(1-((1R,3r,5S,6r)-3-(4-(ethoxymethyl)-1H-1,
2,3-triazol-1-yl)bicyclo[3.1.0]hexan-6-yl)propyl)benz-
amide;
2-(((1R,3s,5S,6r)-6-(1-(4-chlorobenzamido)propyl)bicy-
clo[3.1.0]hexan-3-yl)amino)-2-phenylacetic acid;
3-chloro-N-((1R,3s,5S,6r)-6-(1-(4-chlorobenzamido)pro-
pyl)bicyclo[3.1.0]hexan-3-yl)picolinamide;
N-((1R,3s,5S,6r)-6-(1-(4-chlorobenzamido)propyl)bicy-
clo[3.1.0]hexan-3-yl)-4-(trifluoromethyl)nicotinamide;
N-((1R,3r,5S,6r)-6-(1-(4-chlorobenzamido)propyl)bicy-
clo[3.1.0]hexan-3-yl)-3-fluoropicolinamide;
N-((1R,3r,5S,6r)-6-(1-(4-chlorobenzamido)propyl)bicy-
clo[3.1.0]hexan-3-yl)-5-fluoropicolinamide;
3-chloro-N-((1R,3r,5S,6r)-6-(1-(4-chlorobenzamido)pro-
pyl)bicyclo[3.1.0]hexan-3-yl)-4-(trifluoromethyl)pi-
colinamide;
N-((1R,3s,5S,6r)-6-(1-(4-chlorobenzamido)propyl)bicy-
clo[3.1.0]hexan-3-yl)-2-methylnicotinamide;

4-chloro-N-(1-((1R,3s,5S,6r)-3-((2-(methylamino)-2-
oxo-1-phenylethyl)amino)bicyclo[3.1.0]hexan-6-yl)
propyl)benzamide;
N-((1R,3s,5S,6r)-6-(1-(4-chlorobenzamido)propyl)bicy-
clo[3.1.0]hexan-3-yl)-4-(trifluoromethyl)picolinamide;
4-chloro-N-(1-((1R,3s,5S,6r)-3-(pyridin-2-ylamino)bicy-
clo[3.1.0]hexan-6-yl)propyl)benzamide;
4-chloro-N-(1-((1R,3s,5S,6r)-3-((5-fluoropyridin-2-yl)
amino)bicyclo[3.1.0]hexan-6-yl)propyl)benzamide;
2-((1R,3s,5S,6r)-6-(1-(4-chlorobenzamido)propyl)bicy-
clo[3.1.0]hexan-3-yl)-2-phenylacetic acid;
4-chloro-N-(1-((1R,3s,5S,6r)-3-(5-fluoro-1H-indol-1-yl)
bicyclo[3.1.0]hexan-6-yl)propyl)benzamide;
4-chloro-N—((R/S)-1-((1R,3S,5S,6S)-3-((S/R)-2-(meth-
ylamino)-2-oxo-1-phenylethyl) bicyclo[3.1.0]hexan-6-
yl)propyl)benzamide;
4-chloro-N—((R/S)-1-((1R,3S,5S,6S)-3-((R/S)-2-(meth-
ylamino)-2-oxo-1-phenylethyl) bicyclo[3.1.0]hexan-6-
yl)propyl)benzamide;
4-chloro-N-(1-((1R,3s,5S,6r)-3-(4-(1,3-dioxoisoindolin-
2-yl)-1H-1,2,3-triazol-1-yl)bicyclo[3.1.0]hexan-6-yl)
propyl)benzamide;
3-(1-((1R,3s,5S,6r)-6-(1-(4-chlorobenzamido)propyl)bi-
cyclo[3.1.0]hexan-3-yl)-1H-1,2,3-triazol-4-yl)azeti-
dine-1-carboxylate;
4-chloro-N-(1-((1R,3s,5S,6r)-3-(6-cyano-3H-imidazo[4,
5-b]pyridin-3-yl)bicyclo[3.1.0]hexan-6-yl)propyl)ben-
zamide;
4-chloro-N-(1-((1R,3s,5S,6r)-3-(6-cyano-1H-imidazo[4,
5-b]pyridin-1-yl)bicyclo[3.1.0]hexan-6-yl)propyl)ben-
zamide;
4-chloro-N-(1-((1R,3s,5S,6r)-3-((5-fluoro-3-nitropyri-
din-2-yl)amino)bicyclo[3.1.0]hexan-6-yl)propyl)benz-
amide;
N-(1-((1R,3s,5S,6r)-3-(4-(azetidin-3-yl)-1H-1,2,3-tri-
azol-1-yl)bicyclo[3.1.0]hexan-6-yl)propyl)-4-chlo-
robenzamide;
4-chloro-N-(1-((1R,3s,5S,6r)-3-(4-(dimethylamino)-1H-
1,2,3-triazol-1-yl)bicyclo[3.1.0]hexan-6-yl)propyl)
benzamide;
N-(1-((1R,3s,5S,6r)-3-(4-amino-1H-1,2,3-triazol-1-yl)bi-
cyclo[3.1.0]hexan-6-yl)propyl)-4-chlorobenzamide;
4-chloro-N-(1-((1R,3s,5S,6r)-3-(6-fluoro-3H-imidazo[4,
5-b]pyridin-3-yl)bicyclo[3.1.0]hexan-6-yl)propyl)ben-
zamide;
4-chloro-N-(1-((1R,3s,5S,6r)-3-(5,6-difluoro-1H-benzo
[d]imidazol-1-yl)bicyclo[3.1.0]hexan-6-yl)propyl)ben-
zamide;
4-cyano-N-(1-((1R,3s,5S,6r)-3-(4-(methoxymethyl)-1H-
1,2,3-triazol-1-yl)bicyclo[3.1.0]hexan-6-yl)ethyl)benz-
amide;
4-chloro-N-(1-((1R,3s,5S,6r)-3-((3,5-difluoro-2-nitrop-
henyl)amino)bicyclo[3.1.0]hexan-6-yl)propyl)benz-
amide;
4-chloro-N-(1-((1R,3s,5S,6r)-3-((2,3-difluoro-6-nitrop-
henyl)amino)bicyclo[3.1.0]hexan-6-yl)propyl)benz-
amide;
4-chloro-N-(1-((1R,3s,5S,6r)-3-(6,7-difluoro-1H-benzo
[d]imidazol-1-yl)bicyclo[3.1.0]hexan-6-yl)propyl)ben-
zamide;
4-chloro-N-(1-((1R,3s,5S,6r)-3-(4,6-difluoro-1H-benzo
[d]imidazol-1-yl)bicyclo[3.1.0]hexan-6-yl)propyl)ben-
zamide;
4-chloro-N—((R)-1-((1R,3S,5S,6r)-3-(6-fluoro-1H-
benzo[d]imidazol-1-yl)bicyclo[3.1.0]hexan-6-yl)pro-
pyl)benzamide;

4-chloro-N—((S)-1-((1R,3S,5S,6r)-3-(6-fluoro-1H-benzo[d]imidazol-1-yl)bicyclo[3.1.0]hexan-6-yl)propyl)benzamide;
4-chloro-N-(1-((1R,3s,5S,6r)-3-((7-chloroquinazolin-4-yl)oxy)bicyclo[3.1.0]hexan-6-yl)propyl)benzamide;
4-chloro-N-(1-((1R,5R,6S)-3-(5-(trifluoromethyl)pyridin-3-yl)bicyclo[3.1.0]hex-2-en-6-yl)propyl)benzamide;
4-chloro-N-(1-((1R,5R,6S)-3-(7-fluoroquinazolin-4-yl)bicyclo[3.1.0]hex-2-en-6-yl)propyl)benzamide;
N-(1-((1R,3s,5S,6r)-3-(4-acetamido-1H-1,2,3-triazol-1-yl)bicyclo[3.1.0]hexan-6-yl)propyl)-4-chlorobenzamide;
N-(1-((1R,3s,5S,6r)-3-(4-(1-acetylazetidin-3-yl)-1H-1,2,3-triazol-1-yl)bicyclo[3.1.0]hexan-6-yl)propyl)-4-chlorobenzamide;
4-chloro-N-(1-((1R,3s,5S,6r)-3-(5-cyclopropyl-1H-1,2,4-triazol-1-yl)bicyclo[3.1.0]hexan-6-yl)propyl)benzamide;
4-chloro-N-(1-((1R,3s,5S,6r)-3-(3-cyclopropyl-1H-1,2,4-triazol-1-yl)bicyclo[3.1.0]hexan-6-yl)propyl)benzamide;
4-chloro-N—((R)-1-((1R,3S,5S,6r)-3-(5,6-difluoro-1H-benzo[d]imidazol-1-yl)bicyclo[3.1.0]hexan-6-yl)propyl)benzamide;
4-chloro-N-(1-((1R,3s,5S,6r)-3-(4-cyclopropyl-1H-imidazol-1-yl)bicyclo[3.1.0]hexan-6-yl)propyl)benzamide;
4-chloro-N-(1-((1R,3S,5S,6r)-3-(4-(propen-2-yl)-1H-1,2,3-triazol-1-yl)bicyclo[3.1.0]hexan-6-yl)propyl)benzamide;
4-chloro-N-(1-((1R,3s,5S,6r)-3-(pyrazol-1-yl)bicyclo[3.1.0]hexan-6-yl)ethyl)benzamide;
4-chloro-N-(1-((1R,3s,5S,6r)-3-((2,4-difluoro-6-nitrophenyl)amino)bicyclo[3.1.0]hexan-6-yl)propyl)benzamide;
4-chloro-N—(R)-1-((1R,3S,5S,6r)-3-(5,6-difluoro-1H-benzo[d]imidazol-1-yl)bicyclo[3.1.0]hexan-6-yl)ethyl)benzamide;
4-chloro-N—((R)-1-((1R,3S,5S,6r)-3-(6-fluoroquinolin-4-yl)bicyclo[3.1.0]hexan-6-yl)propyl)benzamide;
4-chloro-N-(1-((1R,3s,5S,6r)-3-(5,7-difluoro-1H-benzo[d]imidazol-1-yl)bicyclo[3.1.0]hexan-6-yl)propyl)benzamide;
4-cyano-N—((R)-1-((1R,3S,5S,6r)-3-(5,6-difluoro-1H-benzo[d]imidazol-1-yl)bicyclo[3.1.0]hexan-6-yl)propyl)benzamide;
4-chloro-N-(1-((1R,3s,5S,6r)-3-((4-cyano-2-nitrophenyl)amino)bicyclo[3.1.0]hexan-6-yl)propyl)benzamide;
4-chloro-N-(1-((1R,3s,5S,6r)-3-((4-chloro-2-nitrophenyl)amino)bicyclo[3.1.0]hexan-6-yl)propyl)benzamide;
4-chloro-N-(1-((1R,3s,5S,6r)-3-(5-cyano-1H-benzo[d]imidazol-1-yl)bicyclo[3.1.0]hexan-6-yl)propyl)benzamide;
4-chloro-N-(1-((1R,3s,5S,6r)-3-(5-chloro-1H-benzo[d]imidazol-1-yl)bicyclo[3.1.0]hexan-6-yl)propyl)benzamide;
4-chloro-N—((R)-1-((1R,3S,5S,6r)-3-(6-chloro-1H-benzo[d]imidazol-1-yl)bicyclo[3.1.0]hexan-6-yl)propyl)benzamide;
4-cyano-N—((R)-1-((1R,3S,5S,6r)-3-(5,6-difluoro-1H-benzo[d]imidazol-1-yl)bicyclo[3.1.0]hexan-6-yl)ethyl)benzamide;
4-chloro-N—((R)-1-((1R,3S,5S,6r)-3-(6-fluoro-2-methyl-1H-benzo[d]imidazol-1-yl)bicyclo[3.1.0]hexan-6-yl)propyl)benzamide;
4-chloro-N—((R)-1-((1R,3S,5S,6r)-3-(6-fluoro-2-(trifluoromethyl)-1H-benzo[d]imidazol-1-yl)bicyclo[3.1.0]hexan-6-yl)propyl)benzamide;
4-cyano-N—((R)-1-((1R,3S,5S,6r)-3-(6-fluoroquinolin-4-yl)bicyclo[3.1.0]hexan-6-yl)propyl)benzamide;
4-cyano-N—((R)-1-((1R,3S,5S,6r)-3-(6-fluoroquinolin-4-yl)bicyclo[3.1.0]hexan-6-yl)ethyl)benzamide;
4-chloro-N—((R)-1-((1R,3S,5S,6r)-3-(6-fluoroquinazolin-4-yl)bicyclo[3.1.0]hexan-6-yl)propyl)benzamide;
N-(4-chlorophenyl)-2-((1R,3s,5S,6r)-3-(5,6-difluoro-1H-benzo[d]imidazol-1-yl)bicyclo[3.1.0]hexan-6-yl)propanamide;
4-chloro-N—((R)-1-((1R,3S,5S,6r)-3-(6-cyano-1H-benzo[d]imidazol-1-yl)bicyclo[3.1.0]hexan-6-yl)propyl)benzamide;
N-((1R)-1-((1R,5S,6r)-3-azidobicyclo[3.1.0]hexan-6-yl)propyl)-4-cyanobenzamide;
4-chloro-N—((R)-1-((1R,3S,5S,6r)-3-((5-chloro-2-nitrophenyl)amino)bicyclo[3.1.0]hexan-6-yl)propyl)benzamide;
4-chloro-N—((R)-1-((1R,3S,5S,6r)-3-(6-fluoroquinolin-4-yl)bicyclo[3.1.0]hexan-6-yl)ethyl)benzamide;
4-chloro-N—((R)-1-((1R,3R,5S,6r)-3-(6-fluoroquinolin-4-yl)bicyclo[3.1.0]hexan-6-yl)propyl)benzamide;
4-chloro-N-(2-((1R,3s,5S,6r)-3-(5,6-difluoro-1H-benzo[d]imidazol-1-yl)bicyclo[3.1.0]hexan-6-yl)propan-2-yl)benzamide;
4-cyano-N—((R)-1-((1R,3S,5S,6r)-3-(6-cyano-1H-benzo[d]imidazol-1-yl)bicyclo[3.1.0]hexan-6-yl)propyl)benzamide;
N—((R)-1-((1R,3S,5S,6r)-3-(6-chloro-1H-benzo[d]imidazol-1-yl)bicyclo[3.1.0]hexan-6-yl)propyl)-4-cyanobenzamide;
diethyl 2-((1R,3S,5S,6r)-6-((R)-1-(4-chlorobenzamido)propyl)bicyclo[3.1.0]hexan-3-yl)malonate;
4-chloro-N—((R)-1-((1R,3S,5S,6r)-3-(1,3-dihydroxypropan-2-yl)bicyclo[3.1.0]hexan-6-yl)propyl)benzamide;
4-chloro-N—((R)-1-((1R,3S,5S,6r)-3-(1-cyclopropyl-1H-pyrazol-4-yl)bicyclo[3.1.0]hexan-6-yl)propyl)benzamide;
4-cyano-N—((R)-1-((1R,3S,5S,6r)-3-(6-cyano-2-methyl-1H-benzo[d]imidazol-1-yl)bicyclo[3.1.0]hexan-6-yl)propyl)benzamide;
N—((R)-1-((1R,3S,5S,6r)-3-(6-chloro-2-methyl-1H-benzo[d]imidazol-1-yl)bicyclo[3.1.0]hexan-6-yl)propyl)-4-cyanobenzamide;
4-cyano-N-((1R)-1-((1R,3S,5S,6r)-3-(4-(tetrahydrofuran-3-yl)-1H-1,2,3-triazol-1-yl)bicyclo[3.1.0]hexan-6-yl)propyl)benzamide;
4-cyano-N—((R)-1-((1R,3R,5S,6r)-3-hydroxybicyclo[3.1.0]hexan-6-yl)ethyl)benzamide;
4-cyano-N—((R)-1-((1R,3S,5S,6r)-3-hydroxybicyclo[3.1.0]hexan-6-yl)ethyl)benzamide;
(R)—N-(4-chlorophenyl)-2-((1R,3S,5S,6r)-3-(5,6-difluoro-1H-benzo[d]imidazol-1-yl)bicyclo[3.1.0]hexan-6-yl)propanamide;
(S)—N-(4-chlorophenyl)-2-((1R,3R,5S,6r)-3-(5,6-difluoro-1H-benzo[d]imidazol-1-yl)bicyclo[3.1.0]hexan-6-yl)propanamide;
dimethyl 1-((1R,3S,5S,6r)-6-((R)-1-(4-cyanobenzamido)propyl)bicyclo[3.1.0]hexan-3-yl)-1H-1,2,3-triazole-4,5-dicarboxylate;
4-chloro-N-(((1R,3s,5S,6r)-3-(5,6-difluoro-1H-benzo[d]imidazol-1-yl)bicyclo[3.1.0]hexan-6-yl)methyl)benzamide;

4-cyano-N-(((1R,3s,5S,6r)-3-(5,6-difluoro-1H-benzo[d]imidazol-1-yl)bicyclo[3.1.0]hexan-6-yl)methyl)benzamide;
4-chloro-N—(R)-1-((1R,3R,5S,6r)-3-(5-cyclopropylpyridin-3-yl)bicyclo[3.1.0]hexan-6-yl)propyl)benzamide;
4-chloro-N—(R)-1-((1R,3S,5S,6r)-3-(4-iodo-1H-pyrazol-1-yl)bicyclo[3.1.0]hexan-6-yl)propyl)benzamide;
4-chloro-N—(R)-1-((1R,3S,5S,6r)-3-(4-vinyl-1H-pyrazol-1-yl)bicyclo[3.1.0]hexan-6-yl)propyl)benzamide;
N—(R)-1-((1R,3S,5S,6r)-3-(5,6-difluoro-1H-benzo[d]imidazol-1-yl)bicyclo[3.1.0]hexan-6-yl)propyl)-4-fluorobenzamide;
4-chloro-N—(R)-1-((1R,3S,5S,6r)-3-(5,6-difluoro-1H-benzo[d]imidazol-1-yl)bicyclo[3.1.0]hexan-6-yl)propyl)-3-fluorobenzamide;
N—(R)-1-((1R,3S,5S,6r)-3-(5,6-difluoro-1H-benzo[d]imidazol-1-yl)bicyclo[3.1.0]hexan-6-yl)propyl)-2-methylisonicotinamide;
N—(R)-1-((1R,3S,5S,6r)-3-(5,6-difluoro-1H-benzo[d]imidazol-1-yl)bicyclo[3.1.0]hexan-6-yl)propyl)-2-methylthiazole-4-carboxamide;
3-chloro-N—(R)-1-((1R,3S,5S,6r)-3-(5,6-difluoro-1H-benzo[d]imidazol-1-yl)bicyclo[3.1.0]hexan-6-yl)propyl)benzamide;
N—(R)-1-((1R,3S,5S,6r)-3-(5,6-difluoro-1H-benzo[d]imidazol-1-yl)bicyclo[3.1.0]hexan-6-yl)propyl)-6-methylnicotinamide;
N—(R)-1-((1R,3S,5S,6r)-3-(5,6-difluoro-1H-benzo[d]imidazol-1-yl)bicyclo[3.1.0]hexan-6-yl)propyl)-3-fluorobenzamide;
3-cyano-N—(R)-1-((1R,3S,5S,6r)-3-(5,6-difluoro-1H-benzo[d]imidazol-1-yl)bicyclo[3.1.0]hexan-6-yl)propyl)benzamide;
N-(((1R,3s,5S,6r)-3-(5,6-difluoro-1H-benzo[d]imidazol-1-yl)bicyclo[3.1.0]hexan-6-yl)methyl)-4-fluorobenzamide;
4-chloro-N-(((1R,3s,5S,6r)-3-(5,6-difluoro-1H-benzo[d]imidazol-1-yl)bicyclo[3.1.0]hexan-6-yl)methyl)-3-fluorobenzamide;
3-chloro-N-(((1R,3s,5S,6r)-3-(5,6-difluoro-1H-benzo[d]imidazol-1-yl)bicyclo[3.1.0]hexan-6-yl)methyl)benzamide;
N-(((1R,3s,5S,6r)-3-(5,6-difluoro-1H-benzo[d]imidazol-1-yl)bicyclo[3.1.0]hexan-6-yl)methyl)-6-methylnicotinamide;
N-(((1R,3s,5S,6r)-3-(5,6-difluoro-1H-benzo[d]imidazol-1-yl)bicyclo[3.1.0]hexan-6-yl)methyl)-6-methoxynicotinamide;
N-(((1R,3s,5S,6r)-3-(5,6-difluoro-1H-benzo[d]imidazol-1-yl)bicyclo[3.1.0]hexan-6-yl)methyl)-1-methyl-1H-pyrazole-4-carboxamide;
N-(((1R,3s,5S,6r)-3-(5,6-difluoro-1H-benzo[d]imidazol-1-yl)bicyclo[3.1.0]hexan-6-yl)methyl)-3-fluorobenzamide;
3-cyano-N-(((1R,3s,5S,6r)-3-(5,6-difluoro-1H-benzo[d]imidazol-1-yl)bicyclo[3.1.0]hexan-6-yl)methyl)benzamide;
N-(((1R,3s,5S,6r)-3-(5,6-difluoro-1H-benzo[d]imidazol-1-yl)bicyclo[3.1.0]hexan-6-yl)methyl)-4-methylbenzamide;
N-(((1R,3s,5S,6r)-3-(5,6-difluoro-1H-benzo[d]imidazol-1-yl)bicyclo[3.1.0]hexan-6-yl)methyl)-3-methylbenzamide;
N—(R)-1-((1R,3S,5S,6r)-3-(1H-pyrazol-1-yl)bicyclo[3.1.0]hexan-6-yl)propyl)-4-chlorobenzamide;
4-chloro-N—(R)-1-((1R,3S,5S,6r)-3-(4-cyano-1H-pyrazol-1-yl)bicyclo[3.1.0]hexan-6-yl)propyl)benzamide;
methyl 1-((1R,3S,5S,6r)-6-((R)-1-(4-chlorobenzamido)propyl)bicyclo[3.1.0]hexan-3-yl)-1H-pyrazole-4-carboxylate;
N-((1R,3S,5S,6r)-6-((R)-1-(4-chlorobenzamido)propyl)bicyclo[3.1.0]hexan-3-yl)-3-fluoropicolinamide;
1-((1R,3S,5S,6r)-6-((R)-1-(4-chlorobenzamido)propyl)bicyclo[3.1.0]hexan-3-yl)-1H-pyrazole-4-carboxylic acid;
N—(R)-1-((1R,3S,5S,6r)-3-(4-bromo-1H-pyrazol-1-yl)bicyclo[3.1.0]hexan-6-yl)propyl)-4-chlorobenzamide;
4-chloro-N—(R)-1-((1R,3S,5S,6r)-3-(4-methyl-1H-pyrazol-1-yl)bicyclo[3.1.0]hexan-6-yl)propyl)benzamide;
4-chloro-N—(R)-1-((1R,3S,5S,6r)-3-((2-cyanophenyl)amino)bicyclo[3.1.0]hexan-6-yl)propyl)benzamide;
4-chloro-N—(R)-1-((1R,3S,5S,6r)-3-(4-(trifluoromethyl)-1H-pyrazol-1-yl)bicyclo[3.1.0]hexan-6-yl)propyl)benzamide;
N-((1R,3S,5S,6r)-6-((R)-1-(4-chlorobenzamido)propyl)bicyclo[3.1.0]hexan-3-yl)picolinamide;
N-((1R,3S,5S,6r)-6-((R)-1-(4-chlorobenzamido)propyl)bicyclo[3.1.0]hexan-3-yl)-5-fluoronicotinamide;
N-((1R,3S,5S,6r)-6-((R)-1-(4-chlorobenzamido)propyl)bicyclo[3.1.0]hexan-3-yl)nicotinamide;
4-chloro-N—(R)-1-((1R,3S,5S,6r)-3-((6-fluoroquinazolin-4-yl)amino)bicyclo[3.1.0]hexan-6-yl)propyl)benzamide;
4-chloro-N—(R)-1-((1R,3S,5S,6r)-3-((6-ethynylquinazolin-4-yl)amino)bicyclo[3.1.0]hexan-6-yl)propyl)benzamide;
4-chloro-N—(R)-1-((1R,3S,5S,6r)-3-((6-methylquinazolin-4-yl)amino)bicyclo[3.1.0]hexan-6-yl)propyl)benzamide;
N-(4-chlorophenyl)-2-((1R,3s,5S,6r)-3-((6-fluoroquinazolin-4-yl)oxy)bicyclo[3.1.0]hexan-6-yl)propanamide;
N-(4-chlorophenyl)-2-((1R,3s,5S,6r)-3-((6-fluorocinnolin-4-yl)oxy)bicyclo[3.1.0]hexan-6-yl)propanamide;
4-chloro-2-(((1R,3S,5S,6r)-6-((R)-1-(4-chlorobenzamido)ethyl)bicyclo[3.1.0]hexan-3-yl)oxy)benzoic acid;
4-chloro-N—(R)-1-((1R,3S,5S,6r)-3-(5-cyclopropyl-1H-pyrazol-1-yl)bicyclo[3.1.0]hexan-6-yl)propyl)benzamide;
4-chloro-N—(R)-1-((1R,3S,5S,6r)-3-(3-cyclopropyl-1H-pyrazol-1-yl)bicyclo[3.1.0]hexan-6-yl)propyl)benzamide;
1-(4-chlorophenyl)-3-((R)-1-((1R,3S,5S,6r)-3-(5,6-difluoro-1H-benzo[d]imidazol-1-yl)bicyclo[3.1.0]hexan-6-yl)propyl)urea;
N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide;
2-(((1R,3S,5S,6r)-6-((R)-1-(4-chlorobenzamido)propyl)bicyclo[3.1.0]hexan-3-yl)amino)benzoic acid;
N-(4-chlorophenyl)-2-((1R,3s,5S,6r)-3-((6-fluoroquinolin-4-yl)oxy)bicyclo[3.1.0]hexan-6-yl)propanamide;
4-chloro-N—(R)-1-((1R,3S,5S,6r)-3-(4-cyclopropyl-1H-pyrazol-1-yl)bicyclo[3.1.0]hexan-6-yl)propyl)benzamide;
1-(4-chloro-3-fluorophenyl)-3-((R)-1-((1R,3S,5S,6r)-3-(5,6-difluoro-1H-benzo[d]imidazol-1-yl)bicyclo[3.1.0]hexan-6-yl)propyl)urea;

(R)—N-(4-chlorophenyl)-2-((1R,3S,5S,6r)-3-((6-fluoro-quinazolin-4-yl)oxy)bicyclo[3.1.0]hexan-6-yl)propanamide;

(S)—N-(4-chlorophenyl)-2-((1R,3R,5S,6r)-3-((6-fluoro-quinazolin-4-yl)oxy)bicyclo[3.1.0]hexan-6-yl)propanamide;

N—((R)-1-((1R,3S,5S,6r)-3-(5,6-difluoro-1H-benzo[d]imidazol-1-yl)bicyclo[3.1.0]hexan-6-yl) propyl)-1-(trifluoromethyl)cyclopropane-1-carboxamide;

1-((R)-1-((1R,3S,5S,6r)-3-(5,6-difluoro-1H-benzo[d]imidazol-1-yl)bicyclo[3.1.0]hexan-6-yl) propyl)-3-(oxetan-3-yl)urea;

N—((R)-1-((1R,3S,5S,6r)-3-(5,6-difluoro-1H-benzo[d]imidazol-1-yl)bicyclo[3.1.0]hexan-6-yl) propyl)-3,3-difluoroazetidine-1-carboxamide;

N—((R)-1-((1R,3S,5S,6r)-3-(5,6-difluoro-1H-benzo[d]imidazol-1-yl)bicyclo[3.1.0]hexan-6-yl) propyl)-4,4-difluoropiperidine-1-carboxamide;

N—((R)-1-((1R,3S,5S,6r)-3-(5,6-difluoro-1H-benzo[d]imidazol-1-yl)bicyclo[3.1.0]hexan-6-yl) propyl)morpholine-4-carboxamide;

1-cyclopropyl-3-((R)-1-((1R,3S,5S,6r)-3-(5,6-difluoro-1H-benzo[d]imidazol-1-yl)bicyclo[3.1.0]hexan-6-yl)propyl)urea;

(R)—N-(4-chlorophenyl)-2-((1R,3s,5S,6r)-3-((6-fluoro-cinnolin-4-yl)oxy)bicyclo[3.1.0]hexan-6-yl)propanamide;

(S)—N-(4-chlorophenyl)-2-((1R,3s,5S,6r)-3-((6-fluoro-cinnolin-4-yl)oxy)bicyclo[3.1.0]hexan-6-yl)propanamide;

(R)—N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide;

(S)—N-(4-chloro-3-fluorophenyl)-2-((1R,3s,5S,6r)-3-(5,6-difluoro-1H-benzo[d]imidazol-1-yl)bicyclo[3.1.0]hexan-6-yl)propanamide;

(R)—N-(4-chlorophenyl)-2-((1R,3s,5S,6r)-3-((6-fluoro-quinolin-4-yl)oxy)bicyclo[3.1.0]hexan-6-yl)propanamide; and (S)—N-(4-chlorophenyl)-2-((1R,3s,5S,6r)-3-((6-fluoro-quinolin-4-yl)oxy)bicyclo[3.1.0]hexan-6-yl)propanamide;

or a pharmaceutically acceptable salt thereof.

\* \* \* \* \*